(12) United States Patent
Anderson et al.

(10) Patent No.: US 12,065,464 B2
(45) Date of Patent: *Aug. 20, 2024

(54) 2,2-DIFLUOROPROPIONAMIDE DERIVATIVES OF BARDOXOLONE METHYL, POLYMORPHIC FORMS AND METHODS OF USE THEREOF

(71) Applicant: REATA PHARMACEUTICALS HOLDINGS, LLC, Plano, TX (US)

(72) Inventors: Eric Anderson, Southlake, TX (US);
Xiaofeng Liu, Coppell, TX (US);
Andrea Decker, Basel (CH)

(73) Assignee: REATA PHARMACEUTICALS HOLDINGS, LLC, Plano, TX (US)

( * ) Notice: Subject to any disclaimer, the term of this patent is extended or adjusted under 35 U.S.C. 154(b) by 24 days.

This patent is subject to a terminal disclaimer.

(21) Appl. No.: 17/304,778

(22) Filed: Jun. 25, 2021

(65) Prior Publication Data
US 2021/0355156 A1 Nov. 18, 2021

Related U.S. Application Data

(63) Continuation of application No. 15/622,568, filed on Jun. 14, 2017, now Pat. No. 11,078,230, which is a continuation of application No. 14/625,829, filed on Feb. 19, 2015, now Pat. No. 9,701,709, which is a continuation of application No. 13/869,833, filed on Apr. 24, 2013, now Pat. No. 8,993,640.

(60) Provisional application No. 61/780,444, filed on Mar. 13, 2013, provisional application No. 61/775,288, filed on Mar. 8, 2013, provisional application No. 61/687,669, filed on Apr. 27, 2012.

(51) Int. Cl.
C07J 63/00 (2006.01)
A61K 31/277 (2006.01)
C07C 255/47 (2006.01)

(52) U.S. Cl.
CPC ........... *C07J 63/008* (2013.01); *A61K 31/277* (2013.01); *C07C 255/47* (2013.01)

(58) Field of Classification Search
CPC ..... C07J 63/008; C07C 255/47; A61K 31/277
See application file for complete search history.

(56) References Cited

U.S. PATENT DOCUMENTS

| | | | |
|---|---|---|---|
| 4,395,423 A | 7/1983 | Neumann | |
| 5,064,823 A | 11/1991 | Lee et al. | |
| 6,025,395 A | 2/2000 | Breitner et al. | |
| 6,326,507 B1 | 12/2001 | Gribble et al. | |
| 6,369,101 B1 | 4/2002 | Carlson | |
| 6,552,075 B2 | 4/2003 | Gribble et al. | |
| 6,642,217 B2 | 11/2003 | Krasutsky et al. | |
| 6,649,654 B1 | 11/2003 | Karin et al. | |
| 6,951,847 B2 | 10/2005 | Gibson et al. | |
| 6,974,801 B2 | 12/2005 | Honda et al. | |
| 7,053,119 B2 | 5/2006 | Karin et al. | |
| 7,144,875 B2 | 12/2006 | Gibson et al. | |
| 7,176,237 B2 | 2/2007 | Honda et al. | |
| 7,288,568 B2 | 10/2007 | Gribble et al. | |
| 7,399,606 B2 | 7/2008 | Karin et al. | |
| 7,410,958 B2 | 8/2008 | Krasutsky et al. | |
| 7,435,755 B2 | 10/2008 | Konopleva et al. | |
| 7,678,830 B2 | 3/2010 | Honda et al. | |
| 7,714,012 B2 | 5/2010 | Honda et al. | |
| 7,795,305 B2 | 9/2010 | Konopleva et al. | |
| 7,863,327 B2 | 1/2011 | Gribble et al. | |
| 7,915,402 B2 | 3/2011 | Anderson et al. | |
| 7,943,778 B2 | 5/2011 | Jiang et al. | |
| 8,034,955 B2 | 10/2011 | Gribble et al. | |
| 8,067,394 B2 | 11/2011 | Honda et al. | |
| 8,067,465 B2 | 11/2011 | Honda et al. | |
| 8,071,632 B2 | 12/2011 | Jiang et al. | |
| 8,088,824 B2 | 1/2012 | Walling et al. | |
| 8,124,656 B2 | 2/2012 | Anderson et al. | |
| 8,124,799 B2 | 2/2012 | Anderson et al. | |
| 8,129,429 B2 | 3/2012 | Sporn et al. | |
| 8,258,329 B2 | 9/2012 | Anderson et al. | |
| 8,299,046 B2 | 10/2012 | Sporn et al. | |
| 8,309,601 B2 | 11/2012 | Walling et al. | |
| 8,314,137 B2 | 11/2012 | Honda et al. | |
| 8,338,618 B2 | 12/2012 | Jiang et al. | |
| 8,394,967 B2 | 3/2013 | Jiang et al. | |
| 8,440,820 B2 | 5/2013 | Anderson et al. | |
| 8,440,854 B2 | 5/2013 | Anderson et al. | |
| 8,455,544 B2 | 6/2013 | Sporn et al. | |
| 8,513,436 B2 | 8/2013 | Anderson et al. | |
| 8,586,775 B2 | 11/2013 | Gribble et al. | |
| 8,747,901 B2 | 6/2014 | Zhang et al. | |
| RE45,288 E | 12/2014 | Anderson et al. | |

(Continued)

FOREIGN PATENT DOCUMENTS

| | | |
|---|---|---|
| CN | 102070697 | 5/2011 |
| CN | 102079772 | 6/2011 |

(Continued)

OTHER PUBLICATIONS

"Alzheimer's Disease" CNN Health, Obtained Oct. 9, 2010, URL:http://www.cnn.com/2003/HEALTH/conditions/09/24/alzheimers.drug.ap/index.html.

(Continued)

*Primary Examiner* — Barbara P Badio
(74) *Attorney, Agent, or Firm* — Parker Highlander PLLC

(57) ABSTRACT

The present invention relates generally to the compound: N-((4aS,6aR,6bS,8aR,12aS,14aR,14bS)-11-cyano-2,2,6a, 6b,9,9,12a-heptamethyl-10,14-dioxo-1,2,3,4,4a,5,6,6a, 6b,7,8,8a,9,10,12a,14,14a,14b-octadecahydropicen-4a-yl)-2,2-difluoropropanamide, polymorphic forms thereof, methods for preparation and use thereof, pharmaceutical compositions thereof, and kits and articles of manufacture thereof.

18 Claims, 139 Drawing Sheets
Specification includes a Sequence Listing.

(56) References Cited

U.S. PATENT DOCUMENTS

| | | |
|---|---|---|
| 8,921,419 B2 | 12/2014 | Gribble et al. |
| RE45,325 E | 1/2015 | Anderson et al. |
| 8,993,640 B2 | 3/2015 | Anderson et al. |
| 9,000,188 B2 | 4/2015 | Honda et al. |
| 9,090,574 B2 | 7/2015 | Anderson et al. |
| 9,102,681 B2 | 8/2015 | Anderson et al. |
| 9,174,941 B2 | 11/2015 | Anderson et al. |
| 9,233,998 B2 | 1/2016 | Anderson et al. |
| 9,249,089 B2 | 2/2016 | Jiang et al. |
| 9,278,912 B2 | 3/2016 | Jiang et al. |
| 9,278,913 B2 | 3/2016 | Gribble et al. |
| 9,290,536 B2 | 3/2016 | Anderson et al. |
| 9,464,082 B2 | 10/2016 | Donner et al. |
| 9,512,094 B2 | 12/2016 | Jiang et al. |
| 9,556,222 B2 | 1/2017 | Anderson et al. |
| 9,593,074 B2 | 3/2017 | Bender et al. |
| 9,670,147 B2 | 6/2017 | Anderson et al. |
| 9,701,709 B2 | 7/2017 | Anderson et al. |
| 9,757,359 B2 | 9/2017 | Sporn et al. |
| 9,856,286 B2 | 1/2018 | Sheikh et al. |
| 9,889,143 B2 | 2/2018 | Jiang et al. |
| 10,093,614 B2 | 10/2018 | Anderson et al. |
| 10,105,372 B2 | 10/2018 | Meyer et al. |
| 10,398,711 B2 | 9/2019 | Jiang et al. |
| 10,501,489 B2 | 12/2019 | Bender et al. |
| 10,556,858 B2 | 2/2020 | Anderson et al. |
| 11,078,230 B2 | 8/2021 | Anderson et al. |
| 2002/0042535 A1 | 4/2002 | Gribble et al. |
| 2003/0119732 A1 | 6/2003 | Konopleva et al. |
| 2003/0232786 A1 | 12/2003 | Honda et al. |
| 2003/0236303 A1 | 12/2003 | Gribble et al. |
| 2004/0002463 A1 | 1/2004 | Honda et al. |
| 2004/0097436 A1 | 5/2004 | Krasutsky et al. |
| 2005/0208151 A1 | 9/2005 | Hurez et al. |
| 2005/0288363 A1 | 12/2005 | Gribble et al. |
| 2006/0258752 A1 | 11/2006 | Vander Jagt et al. |
| 2007/0155742 A1 | 7/2007 | Honda et al. |
| 2007/0232577 A1 | 10/2007 | Xu et al. |
| 2007/0244081 A1 | 10/2007 | Krasutsky et al. |
| 2007/0249561 A1 | 10/2007 | Taylor |
| 2007/0259839 A1 | 11/2007 | Krasutsky et al. |
| 2007/0259842 A1 | 11/2007 | Krasutsky et al. |
| 2008/0220057 A1 | 9/2008 | Gribble et al. |
| 2008/0233195 A1 | 9/2008 | Sporn et al. |
| 2008/0234368 A9 | 9/2008 | Gribble et al. |
| 2008/0254055 A1 | 10/2008 | Oblong et al. |
| 2008/0261985 A1 | 10/2008 | Honda et al. |
| 2009/0048204 A1 | 2/2009 | Walling et al. |
| 2009/0048205 A1 | 2/2009 | Meyer et al. |
| 2009/0060873 A1 | 3/2009 | Sporn et al. |
| 2009/0093447 A1 | 4/2009 | Konopleva et al. |
| 2009/0326063 A1 | 12/2009 | Sporn et al. |
| 2010/0041904 A1 | 2/2010 | Jiang et al. |
| 2010/0048887 A1 | 2/2010 | Anderson et al. |
| 2010/0048892 A1 | 2/2010 | Anderson et al. |
| 2010/0048911 A1 | 2/2010 | Jiang et al. |
| 2010/0056777 A1 | 3/2010 | Anderson et al. |
| 2010/0261930 A1 | 10/2010 | Honda et al. |
| 2011/0009363 A1 | 1/2011 | Honda et al. |
| 2011/0196007 A1 | 8/2011 | Honda et al. |
| 2011/0245206 A1 | 10/2011 | Jiang et al. |
| 2011/0245233 A1 | 10/2011 | Anderson et al. |
| 2011/0250300 A1 | 10/2011 | Biswal et al. |
| 2011/0281955 A1 | 11/2011 | Meyer et al. |
| 2012/0022156 A1 | 1/2012 | Zhang et al. |
| 2012/0071684 A1 | 3/2012 | Walling et al. |
| 2012/0101149 A1 | 4/2012 | Honda et al. |
| 2012/0196880 A1 | 8/2012 | Anderson et al. |
| 2012/0214814 A1 | 8/2012 | Anderson et al. |
| 2012/0220652 A1 | 8/2012 | Sporn et al. |
| 2012/0238767 A1 | 9/2012 | Jiang et al. |
| 2012/0245374 A1 | 9/2012 | Anderson et al. |
| 2012/0252776 A1 | 10/2012 | Anderson et al. |
| 2012/0283450 A1 | 11/2012 | Anderson et al. |
| 2013/0237721 A1 | 9/2013 | Gribble et al. |
| 2013/0274480 A1 | 10/2013 | Honda et al. |
| 2013/0303607 A1 | 11/2013 | Gribble et al. |
| 2013/0303797 A1 | 11/2013 | Gribble et al. |
| 2013/0317007 A1 | 11/2013 | Anderson et al. |
| 2013/0324599 A1 | 12/2013 | Anderson et al. |
| 2013/0345276 A1 | 12/2013 | Sporn et al. |
| 2014/0051739 A1 | 2/2014 | Anderson et al. |
| 2014/0066408 A1 | 3/2014 | Jiang et al. |
| 2014/0073700 A1 | 3/2014 | Wagner et al. |
| 2014/0088163 A1 | 3/2014 | Jiang et al. |
| 2014/0088188 A1 | 3/2014 | Jiang et al. |
| 2014/0100227 A1 | 4/2014 | Bender et al. |
| 2014/0179928 A1 | 6/2014 | Anderson et al. |
| 2014/0275618 A1 | 9/2014 | Gribble et al. |
| 2014/0323579 A1 | 10/2014 | Sheikh et al. |
| 2015/0011627 A1 | 1/2015 | Gribble et al. |
| 2015/0080465 A1 | 3/2015 | Chin et al. |
| 2015/0148384 A1 | 5/2015 | Anderson et al. |
| 2015/0152071 A1 | 6/2015 | Jiang et al. |
| 2015/0225397 A1 | 8/2015 | Donner et al. |
| 2015/0259377 A1 | 9/2015 | Anderson et al. |
| 2015/0376121 A1 | 12/2015 | Anderson et al. |
| 2017/0165278 A1 | 6/2017 | Jiang et al. |
| 2018/0094020 A1 | 4/2018 | Sheikh et al. |
| 2018/0127380 A1 | 5/2018 | Jiang et al. |
| 2019/0153022 A1 | 5/2019 | Visnick et al. |

FOREIGN PATENT DOCUMENTS

| | | |
|---|---|---|
| CN | 102093462 | 6/2011 |
| CN | 102153613 | 8/2011 |
| CN | 102250189 | 11/2011 |
| CN | 102875634 | 10/2012 |
| CN | 102887936 | 10/2012 |
| CN | 103665087 | 8/2013 |
| JP | 55-055153 | 4/1980 |
| JP | 2005-314381 | 11/2005 |
| JP | 2008-110962 | 5/2008 |
| JP | 2008-247898 | 10/2008 |
| JP | 2001-240573 | 9/2011 |
| WO | WO 1999/065478 | 12/1999 |
| WO | WO 2000/073253 | 12/2000 |
| WO | WO 2002/003996 | 1/2002 |
| WO | WO 2002/026761 | 4/2002 |
| WO | WO 2002/026762 | 4/2002 |
| WO | WO 2002/032410 | 4/2002 |
| WO | WO 2002/047611 | 6/2002 |
| WO | WO 2002/092768 | 11/2002 |
| WO | WO 2003/059339 | 7/2003 |
| WO | WO 2003/062260 | 7/2003 |
| WO | WO 2004/064723 | 8/2004 |
| WO | WO 2004/089357 | 10/2004 |
| WO | WO 2005/042002 | 5/2005 |
| WO | WO 2005/046732 | 5/2005 |
| WO | WO 2006/029221 | 3/2006 |
| WO | WO 2007/005879 | 6/2007 |
| WO | WO 2007/112043 | 10/2007 |
| WO | WO 2007/127791 | 11/2007 |
| WO | WO 2008/000068 | 1/2008 |
| WO | WO 2008/000070 | 1/2008 |
| WO | WO 2008/016095 | 2/2008 |
| WO | WO 2008/064132 | 5/2008 |
| WO | WO 2008/064133 | 5/2008 |
| WO | WO 2008/097596 | 8/2008 |
| WO | WO 2008/111497 | 9/2008 |
| WO | WO 2008/136838 | 11/2008 |
| WO | WO 2009/023232 | 2/2009 |
| WO | WO 2009/023845 | 2/2009 |
| WO | WO 2009/058849 | 5/2009 |
| WO | WO 2009/089545 | 7/2009 |
| WO | WO 2009/129545 | 10/2009 |
| WO | WO 2009/129546 | 10/2009 |
| WO | WO 2009/129548 | 10/2009 |
| WO | WO 2009/146216 | 12/2009 |
| WO | WO 2009/146218 | 12/2009 |
| WO | WO 2010/011782 | 12/2009 |
| WO | WO 2010/053817 | 5/2010 |
| WO | WO 2010/059245 | 5/2010 |
| WO | WO 2010/093944 | 8/2010 |

(56) References Cited

FOREIGN PATENT DOCUMENTS

| | | |
|---|---|---|
| WO | WO 2010/127029 | 11/2010 |
| WO | WO 2011/130302 | 10/2011 |
| WO | WO 2011/140078 | 11/2011 |
| WO | WO 2012/009171 | 1/2012 |
| WO | WO 2012/083306 | 6/2012 |
| WO | WO 2012/106190 | 8/2012 |
| WO | WO 2012/125488 | 9/2012 |
| WO | WO 2012/154554 | 11/2012 |
| WO | WO 2013/163344 | 10/2013 |
| WO | WO 2013/169553 | 11/2013 |
| WO | WO 2013/169740 | 11/2013 |
| WO | WO 2013/188818 | 12/2013 |
| WO | WO 2014/011085 | 1/2014 |
| WO | WO 2014/040052 | 3/2014 |
| WO | WO 2014/040056 | 3/2014 |
| WO | WO 2014/040060 | 3/2014 |
| WO | WO 2014/040073 | 3/2014 |
| WO | WO 2014/048033 | 4/2014 |
| WO | WO 2014/176415 | 1/2015 |
| WO | WO 2015/027206 | 2/2015 |
| WO | WO 2015/112792 | 7/2015 |
| WO | WO 2017/053868 | 3/2017 |
| WO | WO 2018/089539 | 5/2018 |
| WO | WO 2018/111315 | 6/2018 |

OTHER PUBLICATIONS

Abraham and Kappas, "Heme oxygenase and the cardiovascular-renal system," *Free Radic. Biol. Med.*, 2005, 39(1):1-25.

Ahmad et al., "Combining the FLT3 Inhibitor PKC412 and the Triterpenoid CDDO-Me Synergistically Induces Apoptosis in Acute Myeloid Leukemia with the Internal Tandem Duplication Mutation," *Mol. Cancer Res.*, 8(7):986-993, 2010.

Ahmad et al., "Triterpenoid CDDO-Me blocks the NF-κB pathway by direct inhibition of IKKβ on Cys-179," *J. Biol. Chem.*, 2006, 281:35764-35769.

Ahmad et al., "Triterpenoid CDDO-methyl ester inhibits the Janus-activated kinase-1 (JAK1) signal transducer and activator of transcription-3 (STAT3) pathway by direct inhibition of JAK1 and STAT3," *Cancer Res.*, 2008, 68(8): 2920-2926.

Akiyama et al., "Cell mediators of inflammation in the Alzheimer disease brain," *Alzheimer Dis. Assoc. Disord.*, 2000, 14(1): S47-S53.

Alabran et al., "Human neuroblastoma cells rapidly enter cell cycle arrest and apoptosis following exposure to C-28 derivatives of the synthetic triterpenoid CDDO," *Cancer Biology & Therapy*, 7(5):709-717, 2008.

Albini and Sporn, "Opinion: the tumour microenvironment as a target for chemoprevention," *Nature Reviews Cancer*, 2002, Abstract 501:149.

Alexeev et al., "Radiation Protection of the Gastrointestinal Tract and Growth Inhibition of Prostate Cancer Xenografts," *Molecular Cancer Therapeutics*, 13(12):2968-2977, 2014.

Ames et al., "The triterpenoid CDDO-Me Promotes Hematopoietic Progenitor Expansion and Myelopoiesis in Mice," *Biology of Blood and Marrow Transportation*, 18(3):396-405, 2012.

Auletta et al., "The Synthetic Triterpenoid, CDDO-Me, Modulates the Proinflammatory Response to In Vivo Lipopolysaccharide Challenge," *J. Interferon Cytokine Res.*, 30(7):497-508, 2010.

Bagasra et al., "Activation of the inducible form of nitric oxide synthase in the brains of patients with multiple sclerosis," *Proc. Natl. Acad. Sci. USA*, 1995, 92:12041-12045.

Bai et al., "Modified compounds from ursolic acid and their antitumor activities," *Huaxi Yaoxue Zazhi*, 18(2):87-90, 2003 (Chinese, English Abstract).

Baird and Dinkova-Kostova, "The cytoprotective role of the Keap1-Nrf2 pathway", *Arch. Toxicol.*, 85:241-272, 2011.

Ballesta-Acosta et al., "A new 24-nor-oleanane triterpenoid from *Salvia carduacea,*" *J. Nat. Prod.*, 2002, 65(10):1513-1515.

Barton et al., "The synthesis of β-amyrin," *J. Chem. Soc.*, 1031-1040, 1968.

Baud and Karin, "Is NF-κB a good target for cancer therapy? Hopes and pitfalls", *Nat. Rev. Drug Discov.*, 8:33-40, 2009.

Bensasson et al., "Potency ranking of triterpenoids as inducers of a cytoprotective enzyme and as inhibitors of a cellular inflammatory response via their electron affinity and their electrophilicity index," *Chem. Biol. Interact.*, 186(2):118-126, 2010.

Berridge et al., "The biochemical and cellular basis of cell proliferation assays that use tetrazolium salts," *Biochemica*, 1996, 4:14-19.

Bore et al., "The anti-inflammatory triterpenoid methyl 2-cyano-3,12-dioxoolean 1,9(11)-dien-28-oate methanol solvate hydrate," *Acta Crystallorg C.*, 2002, 58(Pt 3):o199-o200.

Bowden et al., "Constituents of the fruit of *Pseudopanax arboretum* (Araliaceae)," *Australian Journal of Chemistry*, 1975, 28(1):91-107.

Brookes et al., "The triterpenoid 2-cyano-3,12-dioxooleana-1,9-dien-28-oic acid and its derivatives elicit human lymphoid cell apoptosis through a novel pathway involving the unregulated mitochondrial permeability transition pore," *Cancer Res.*, 67:1793-18.

Brown and Dubois, "COX-2: a molecular target for colorectal cancer prevention," *J. Clin. Oncol.*, 2005, 23(12):2840-2855.

Buchanan et al., "The conversion of turraeanthin and turraeanthin A into simple melaiacins by a route involving an oxidative rearrangement of probable biogenetic importance," *J. Chem. Soc. C*, 1970, 17:2280-2284.

Burton et al., "In vivo modulation of the Parkinsonian phenotype by Nrf2", *Neurotoxicology*, 27:1094-1100, 2006.

Cai et al., "Local and systemic insulin resistance resulting from hepatic activation of IKKβ and NF-κB," *Nature Medicine*, 2005, 11(2):183-190.

Caira, "Crystalline Polymorphism of Organic Compounds", In: Topics in Current Chemistry, 198:163-208, 1998.

Calkins et al., "Protection from mitochondrial complex II inhibition in vitro and in vivo by Nrf2-mediated transcription", *Proc. Natl. Acad. Sci. USA*, 102:244-249, 2005.

Calkins et al., "The Nrf2/ARE pathway as a potential therapeutic target in neurodegenerative disease," *Antioxid. Redox. Signal.*, 11(3):497-508, 2009.

Chadalapaka et al., "Structure-dependent inhibition of bladder and pancreatic cancer cell growth by 2-substituted glycyrrhetinic and ursolic acid derivatives," *Bioorganic & Medicinal Chemistry Letters*, 18:2633-2639, 2008.

Chauhan et al., "The bortezomib/proteasome inhibitor PS-341 and triterpenoid CDDO-Im induce synergistic anti-multiple myeloma (MM) activity and overcome bortezomib resistance," *Blood*, 2004, 103:3158-3166.

Chen et al., "Chondrogenesis in chick limb bud mesodermal cells: reciprocal modulation by activin and inhibin," *Exp. Cell. Res.*, 1993, 206:119-27.

Chen et al., "Nrf2-mediated neuroprotection in the MPTP mouse model of Parkinson's disease: Critical role for the astrocyte", *Proc. Natl. Acad. Sci. USA*, 106:2933-2938, 2009.

Chintharlapalli et al., "2-Cyano-3,12-dioxoolean-1,9-dien-28-oic acid and related compounds inhibit growth of colon cancer cells through peroxisome proliferator-activated receptor γ-dependent and -independent pathways," Mol. Pharmacol., 2005, 68:119-128.

Chintharlapalli et al., "2-Cyano-lup-1-en-3-oxo-20-oic acid, a cyano derivative of betulinic acid, activates peroxisome proliferator-activated receptor γ in colon and pancreatic cancer cells," *Carcinogenesis*, 2007, 28(11):2337-2346.

Chintharlapalli et al., "Structure-dependent activity of glycyrrhetinic acid derivatives as peroxisome proliferator-activated receptor γ agonists in colon cancer cells," *Molecular Cancer Therapeutics*, 2007, 6(5):1588-1598.

Clinicaltrials.gov Study Record, NCT 00352040, "CDDO in treating patients with metastatic or unresectable solid tumors or lymphoma conditions: lymphoma; small intestine cancer; unspecified adult solid tumor, protocol specifc," update of Jul. 6, 2009.

(56) References Cited

OTHER PUBLICATIONS

Clinicaltrials.gov Study Record, NCT 00508807, "RTA 402 in advanced solid tumors or lymphoid malignancies," update as of Sep. 7, 2008.
Clinicaltrials.gov Study Record, NCT 00508807, "RTA 402 in advanced solid tumors or lymphoid malignancies conditions: lymphoid malignancies; solid tumors," update of Aug. 27, 2008.
Clinicaltrials.gov Study Record, NCT 00508807, "RTA 402 in advanced solid tumors or lymphoid malignancies conditions: lymphoid malignancies; solid tumors," update of Oct. 5, 2010.
Clinicaltrials.gov Study Record, NCT 00529113, "Study with gemcitabine and RTA 402 for patients with unresectable pancreatic cancer," update of Dec. 1, 2010.
Clinicaltrials.gov Study Record, NCT 00529113, "Study with gemcitabine and RTA 402 for patients with unresectable pancreatic cancer," update of Jun. 12, 2008.
Clinicaltrials.gov Study Record, NCT 00529438, "RTA 402 in patients with advanced solid tumors or lymphoid malignancies conditions: advanced solid tumors; lymphoid malignancies," update of Dec. 21, 2008.
Clinicaltrials.gov Study Record, NCT 00550849, "Study to assess the safety, tolerability, and pharmacodynamics of RTA 402 in patients with hepatic dysfunction," update as of Nov. 29, 2007.
Clinicaltrials.gov Study Record, NCT 00550849, "Study to assess the safety, tolerability, and pharmacodynamics of RTA 402 in patients with hepatic dysfunction condition: liver disease," update of Nov. 6, 2007.
Clinicaltrials.gov Study Record, NCT 00664027, "Phase IIa trail to determine the effects of bardoxolone methyl on renal function in patients with diabetic nephropathy," update as of Dec. 21, 2008.
Clinicaltrials.gov Study Record, NCT 00664027, "Phase IIa trial to determine the effects of bardoxolone methyl on renal function in patients with diabetic nephropathy condition: diabetic nephropathy," update of Feb. 18, 2009.
Clinicaltrials.gov Study Record, NCT 00664027, "Phase IIa trial to determine the effects of bardoxolone methyl on renal function in patients with diabetic nephropathy condition: diabetic nephropathy," update of Jun. 25, 2011.
Clinicaltrials.gov Study Record, NCT 00811889, "Trial to determine the effects of bardoxolone methyl on eGFR in patients with type 2 diabetes and chronic kidney disease conditions: chronic kidney disease; type 2 diabetes; diabetic nephropathy," update as Jun. 4, 2009.
Clinicaltrials.gov Study Record, NCT0352040, "CDDO in treating patients with metastatic or unresectable solid tumors or lymphoma," update as of Dec. 11, 2008.
Cock et al., "Mitochondrial dysfunction associated with neuronal death following status epilepticus in rat", *Epilepsy Res.*, 48:157-168, 2002.
Cohen et al., "A general method for removal of a 4-methyl group from triterpenoids. Synthesis of 4β-demethylgylycyrrhetinic acid," *J. Chem. Soc. Perkin Trans. 1*, 1973, 19:2076-2082.
Connolly et al., "Grandiofolione: a novel tetranortriterpenoid," *Chemical Communications*, 1966, 23:567-568.
Couch et al., "2-cyano-3,12-dioxooleana-1,9(11)-diene-28-oic Acid Disrupts Microtubule Polymerization: A Possible Mechanism Contributing to Apoptosis," *Molecular Pharmacology*, 2006, 69:1158-1165.
Couch et al., "Studies on the reactivity of CDDO, a promising new chemopreventive and chemotherapeutic agent: implications for a molecular mechanism of action," *Bioorganic and Medicinal Chemistry Letters*, 2005, 15(9):2215-2219.
Cuadrado, "NRF2 in neurodegenerative diseases," *Curr. Opin. Toxicol.*, 1:46-53, 2016.
Cui, Yong, "A material science perspective of pharmaceutical solids," *Int. J. Pharmaceuticals*, 2007, 339:3-18.
Damasio, "Alzheimer's disease and related dementias", Cecil Textbook of Medicine, 20th Edition, 2: 1992-1996, 1996.
Damsté et al., "A sedimentary tetrahydrophenanthrene derivative of tetrahymanol," *Tetrahedron Letters*, 1999, 40(20):3949-3952.

De Mico et al., "A Versatile and Highly Selective Hypervalent Iodine (III)/2,2,6,6-Tetramethyl-1-piperidinyloxyl-Mediated Oxidation of Alcohols to Carbonyl Compounds," *J. Org. Chem.*, 1997, 62:6974.
De Zeeuw et al., "Bardoxolone methyl in type 2 diabetes and stage 4 chronic kidney disease," *New Engl. J. Med.*, 369(26):2492-2503, 2013.
Dean et al., "Halogenolysis of methyl glycyrrhetate with lithium iodidedimethylformamide," *J. Chem. Soc.*, 1965, 6655-6659.
Deeb et al., "CDDO-Me Induces Apoptosis and Inhibits Akt, mTOR, and NF-κB Signaling Proteins in Prostate Cancer Cells," *Anticancer Research*, 27:3035-3044, 2007.
Deeb et al., "CDDO-Me inhibits proliferation, induces apoptosis, down-regulates Akt, mTOR, NF-κB and NF-κB-regulated antiapoptotic and proangiogenic proteins in TRAMP prostate cancer cells," *J. of Experimental Therapeutics and Oncology*, 7:31-39, 2008.
Deeb et al., "CDDO-Me: a novel synthetic triterpenoid for the treatment of pancreatic cancer," *Cancers*, 2:1779-1793, 2010.
Deeb et al., "Oleanane triterpenoid CDDO-Me inhibits growth and induces apoptosis in prostate cancer cells through a ROS-dependent mechanism," *Biochem. Pharmacol.*, 79(3):350-360, 2010.
Deeb et al., "Oleanane triterpenoid CDDO-Me inhibits growth and induces apoptosis in prostate cancer cells by independently targeting pro-survival Akt and mTOR," *Prostate*, 69(8):851-860, 2009.
Deng and Synder, "Preparation of a 24-Nor-1,4-dien-3-one triterpene derivative from betulin: a new route to 24-nortriterpene analogues," *J. of Organic Chemistry*, 2002, 67(9):2864-2873.
Dezube et al., "Interim results of a phase I trial with a novel orally administered synthetic triterpenoid RTA 402 (CDDO-Me) in patients with solid tumors and lymphoid malignancies," *J. Clin. Oncol.*, 2007 ASCO Annual Meeting Proceedings, 2007, 25(18S):14101.
DiDonato et al., "NF-κB and the link between inflammation and cancer," *Immunol. Rev.*, 246:379-400, 2012.
Ding et al., "The synthetic triterpenoid, RTA 405, increases the glomerular filtration rate and reduces angiotensin II-induced contraction of glomerular mesangial cells," *Kidney International*, 83(5):845-854, 2013.
Dinkova-Kostova et al., "Direct evidence that sulfhydryl groups of Keap1 are the sensors regulating induction of phase 2 enzymes that protect against carcinogens and oxidants," *Proc. Natl. Acad. Sci.*, 2002, 99(18):11908-11913.
Dinkova-Kostova et al., "Extremely potent triterpenoid inducers of the phase 2 response: correlations of protection against oxidant and inflammatory stress," *Proc. Natl. Acad. Sci.*, 2005, 102(12):4584-4589.
Dinkova-Kostova et al., "Protection against UV-light-induced skin carcinogenesis in SKH-1 high-risk mice by sulforaphane-containing broccoli sprout extracts", *Cancer Lett.*, 240:243-252, 2006.
Dirsch et al., "The triterpenoid quinomethide pristimerin inhibits induction of inducible nitric oxide synthase in murine macrophages," *Eur. J. Pharmacol.*, 1997, 336(2-3):211-217.
Dračinský et al., "Preparation and Conformational Study of 19β,28-Epoxy-18α-olean-5-ene derivatives," *Collection of Czechoslovak Chemical Communications*, 2006, 71(3):387-410.
Dragnev et al., "Specific chemopreventive agents trigger proteasomal degradation of $G_1$ cyclins: implications for combination therapy," *Clin. Cancer Research*, 2004, 10(7): 2570-2577.
Duan et al., "CDDO-Me, a synthetic triterpenoid, inhibits expression of IL-6 and Stat3 phosphory lation in multi-drug resistant ovarian cancer cells," *Cancer Chemother. Pharmacol.*, 63(4):681-689, 2009.
Duan et al., "Di- and triterpenoids from *Triptergium hypoglaucum*," *Phytochemistry*, 1997, 46(3):535-543.
Duan et al., "Immunosuppressive terpenoids from extracts of *Tripterygium wilfordii*," *Tetrahedron*, 2001, 57(40): 8413-8424.
Elliot et al., "The triterpenoid CDDO inhibits expression of matrix metalloproteinase-1, matrix metalloproteinase-13 and Bcl-3 in primary human chondrocytes," *Arthritis Res. Ther.*, 2003, 5:R285-R291.
Elsawa et al., "CDDO-imidazolide mediated inhibition of malignant cell growth in Waldenstroem macroglobulinemia," *Leukemia Res.*, 32(12):1895-1902, 2008.

(56) References Cited

OTHER PUBLICATIONS

Elsawa et al., "Preferential Inhibition of Malignant Cell Growth by CDDO in Waldenstrom Macroglobulinemia," *Blood*, 2006, 108(11):2528.

Eskiocak et al., "CDDO-Me protects against space radiation-induced transformation of human colon epithelial cells," *Radiat. Res.*, 174(1):27-36, 2010.

Favaloro, Jr. et al., "Design and Synthesis of Tricyclic Compounds with Enone Functionalities in Rings A and C: A Novel Class of Highly Active Inhibitors of Nitric Oxide Production in Mouse Macrophages," *J. Med Chem.*, 2002, 45(22):4801-4805.

Finlay et al., "Novel A-ring cleaved analogs of oleanolic and ursolic acids which affect growth regulation in NRP.152 prostate cells," *Bioorg. Med. Chem. Lett.*, 1997, 7(13):1769-1772.

Finlay et al., "The Effect of A and C Ring Modification of Oleanolic and Ursolic Acid on the Inhibition of Nitric Oxide Formation in Mouse Macrophages," 213th American Chemical Society National Meeting, Abstract:084, 1997.

Frey et al., "Protection from carcinogenic effects of space radiation," *Aviation, Space, and Environmental Medicine*, 84(7):748-749, 2013.

Ganguly et al., "Chemical constituents of *Glochidion hohenackeri*," *Tetrahedron*, 22:1513-1519, 1966.

Gao et al., "Immunomodulatory Activity of Synthetic Triterpenoids: Inhibition of Lymphocyte Proliferation, Cell-Mediated Cytotoxicity, and Cytokine Gene Expression Through Suppression of NF-κB," *Immunopharmacol. Immunotoxicol.*, 30(3):581-600, 2008.

Gao et al., "Powerful and prolonged protection of human retinal pigment epithelial cells, keratinocytes, and mouse leukemia cells against oxidative damage: The indirect antioxidant effects of sulforaphane", *Proc. Natl. Acad. Sci. USA*, 98:15221-15226, 2001.

Gao et al., "Synthetic triterpenoids inhibit growth and induce apoptosis in human glioblastoma and neuroblastoma cells through inhibition of prosurvival Akt, NF-κB and Notch1 signaling," *J. of Neurooncology*, 2007, 84(2):147-157.

Gao et al., "Synthetic triterpenoids inhibit growth, induce apoptosis and suppress pro-survival Akt, mTOR and NF-κB signaling protein in colorectal cancer cells," *Anticancer Res.*, 30(3):785-792, 2010.

Gheeya et al., "Screening a panel of drugs with diverse mechanisms of action yields potential therapeutic agents against neuroblastoma," *Cancer Biol. Ther.*, 8(24):2386-2395, 2009.

Goldman et al., "The triterpenoid RTA 408 is a robust mitigator of hematopoietic acute radiation syndrome of mice," *Radiation Research*, 183(3):338-344, 2015.

Grant et al., "Boron trifluoride catalyzed rearrangements of novel epoxide derivatives of manool and manoyl oxide," *Australian Journal of Chemistry*, 1993, 46(8):1125-1145.

Greco et al., "Sulforaphane inhibits mitochondrial permeability transition and oxidative stress", *Free Radic. Biol. Med.*, 51:2164-2171, 2011.

Greten et al., "IKKβ links inflammation and tumorigenesis in a mouse model of colitis-associated cancer," *Cell*, 2004, 118(3):285-296.

Grieco and Speake et al., "Synthetic Studies on Quassinoids: Total Synthesis and Biological Evaluation of (+)-Des-D-chaparrinone," *J. Org. Chem.*, 1998, 63:5929-5936.

Grivennikov and Karin, "Dangerous Liaisons: STAT3 and NF-κB collaboration and crosstalk in cancer," *Cytokine Growth Factor Rev.*, 2010, 21(1):11-19.

Hail et al., "Evidence supporting a role for calcium in apoptosis induction by the synthetic triterpenoid 2-cyano-3,12-dioxooleana-1,9-dien-28-oic acid (CDDO)," *J. Biol. Chem.*, 2004, 279:11179-11187.

Han et al., "CDDO-Imidazolide inhibits growth and survival of c-Myc-induced mouse B cell and plasma cell neoplasms," *Molecular Cancer*, 2006, 5:22.

Haskew-Layton et al., "15-Deoxy-Δ12,14-prostaglandin J2 (15d-PGJ2) protects neurons from oxidative death via an Nrf2 astrocyte-specific mechanism independent of PPARγ," *J. Neurochem.*, 124:536-547, 2013.

He and Karin, "NF-κB and STAT3—key players in liver inflammation and cancer," *Cell Research*, 2011, 21:159-168.

Heather E. Ferguson, "PPARγ ligands have potent anti-fibrotic activity: mechanism of action and implications for therapy of pulmonary fibrosis," Dissertation, University of Rochester, 2008.

Heiss et al., "Active NF-E2-related factor (Nrf2) contributes to keep endothelial NO synthase (eNOS) in the coupled state: role of reactive oxygen species (ROS), eNOS, and heme oxygenase (HO-1) levels," *J. Biol. Chem.*, 2009, 284:31579-31586.

Hill et al., "Synthetical approaches to the pristimerin chromophore," *J. of the Chemical Society*, 1965, 361-375.

Hirota et al., "Suppression of tumor promoter-induced inflammation of mouse ear by ursolic acid and 4,4-dimethycholestane derivatives," *Agric. Biol. Chem.*, 1990, 54:1073-1075.

Hirota et al., "Total synthesis of (±)-amarolide, a quassinoid bitter principle," *J. Org. Chem.*, 1991, 56:1119-1127.

Honda et al., "2-Cyano-3,10-dioxooleana-1,9(11)-dien-28-oic acid anhydride. A novel and highly potent anti-inflammatory and cytoprotective agent," *Bioorg. Med. Chem. Lett.*, 20(7):2275-2278, 2010.

Honda et al., "A novel dicyanotriterpenoid, 2-cyano-3,12-dioxooleana-1,9(11)-dien-28-onitrile, active at picomolar concentrations for inhibition of nitric oxide production," *Bioorg. Med. Chem. Lett.*, 2002, 12:1027-1030.

Honda et al., "An efficient synthesis of tricyclic compounds (±)—(4aβ, 8aβ, 10βaa)—1,2,3,4,4a,6,7,8,8a,9,1-,10a-Dodecahydro-1,1,4a-Trimethyl-2-Oxophenanthrene-8a-Carboxolic acid, its methyl ester, and (±)-(4aβ,8aβ, 10aα)-3,4,4a,6,7,8,8a,9,10,10a-Decahydro-8a-Hydroxymethy-1,1,4a-Trimethylphenanthren-2(1H)-one," *Org. Prep. Proced Int.*, 2005, 37(6):546-550.

Honda et al., "Design and synthesis of 23,24-dinoroleanolic acid derivatives, novel triterpenoid-steroid hybrid molecules," *J. Org. Chem.*, 1998, 63:4846-4849.

Honda et al., "Design and synthesis of 2-cyano-3,12-dioxoolean-1,9-dien-28-oic acid, a Novel and highly active inhibitor of nitric oxide production in mouse macrophages," *Bioorg Med Chem Lett.*, 1998, 8(19):2711-2714.

Honda et al., "Design, synthesis, and biological evaluation of biotin conjugates of 2-cyano-3,12-dioxooleana-1,9(11)-dien-28-oic acid for the isolation of the protein targets," *J. Med. Chem.*, 2004, 47(20):4923-4932.

Honda et al., "Efficient synthesis of (−)- and (+)-tricyclic compounds with enome functionalities in rings A and C. A novel class of orally active anti-inflammatory and cancer chemopreventive agents," *Org Biomol Chem.*, 2003, 1:4384-4391.

Honda et al., "New enone derivatives of oleanolic acid and ursolic acid as inhibitors of nitric oxide production in mouse macrophages," *Bioorg. Med. Chem. Lett.*, 1997, 7:1623-1628.

Honda et al., "New synthetic oleanane and ursane triterpenoids as inhibitors of nitric oxide production in mouse macrophages," The Fifth Chemical Congress of North America, Cancun, Mexico, Abstract 552 and slides for oral presentation, Nov. 1997.

Honda et al., "Novel synthetic oleanane and ursane triterpenoids with various enone functionalities in ring A as inhibitors of nitric oxide production in mouse macrophages," *J. of Medicinal Chemistry*, 2000, 43(9):1866-1877.

Honda et al., "Novel synthetic oleanane triterpenoids: a series of highly active inhibitors of nitric oxide production in mouse macrophages," *Bioorg. Med. Chem. Lett.*, 1999, 9(24):3429-3434.

Honda et al., "Novel tricyclic compounds having acetylene groups at C-8a and cyano enones in rings A and C: highly potent anti-inflammatory and cytoprotective agents," *J. Med. Chem.*, 2007, 50:1731-1734.

Honda et al., "Revision and confirmation of the regiochemistry of isoxazoles derived from methyl oleanonate and lanost-8-en-3-one. Synthesis of a new lanostane triterpenoid with a cyano-enone functionality in ring A," *J. Org. Chem.*, 2003, 68:4991-4993.

Honda et al., "Synthesis of (±)-3,3-ethylenedioxy-14α-hydroxy-5-picrasene-11,16-dione, a 14αH-picrasane derivative," *Chem. Lett.*, 1981, 299-302.

Honda et al., "Synthesis of a novel dicyano abietane analogue: a potential antiinflammatory agent," *J. Org. Chem.*, 2006, 71:3314-3316.

(56) References Cited

OTHER PUBLICATIONS

Honda et al., "Synthetic oleanane and ursane triterpenoids with modified rings A and C: A series of highly active inhibitors of nitric oxide production in mouse macrophages," *J. Med. Chem.*, 2000, 43:4233-4246.

Hong et al., "A Phase I First in-Human Trial of Bardoxolone Methyl in Patients with Advanced Solid Tumors and Lymphomas," *Clin. Cancer. Res.*, 18:3396-3406, 2012.

Hong et al., "Phase I trial of a novel oral NF-κB/pSTAT3 inhibitor RTA-402 in patients with solid tumors and lymphoid malignancies," 44th Annual Meeting of the American Society of Clinical Oncology, 2008.

Hughes et al., "The synthetic triterpenoid CDDO-Im inhibits fatty acid synthase expression and has antiproliferative and proapoptotic effects in human liposarcoma cells," *Cancer Investigation*, 26:118-127, 2008.

Hybertson et al., "Oxidative stress in health and disease: The therapeutic potential of Nrf2 activation," *Molecular Aspects of Medicine*, 2011, 32:234-246.

Hyer et al., "Apoptotic activity and mechanism of 2-cyano-3,12-dioxoolean-1,9-dien-28-oic acid and related synthetic triterpenoids in prostate cancer," *Cancer Res.*, 68:2927-2933, 2008.

Hyer et al., "Synthetic triterpenoids cooperate with tumor necrosis factor-related apoptosis-inducing ligand to induce apoptosis of breast cancer cells," *Cancer Res.*, 2005, 65:4799-4808.

Ikeda et al., "Induction of redox imbalance and apoptosis in multiple myeloma cells by the novel triterpenoid 2-cyano-3, 12-dioxoolean-1,9-dien-28-oic acid," *Mol. Cancer Ther.*, 2004, 3:39-45.

Ikeda et al., "The novel triterpenoid CDDO and its derivatives induce apoptosis by disruption of intracellular redox balance," *Cancer Res.*, 2003, 63:5551-5558.

Ikeda et al., "Triterpenoid CDDO-Im downregulates PML/RARα expression in acute promyelocytic leukemia cell," *Cell Death and Differentiation*, 2005, 12(5):523-531.

Innamorato et al., "Different susceptibility to the Parkinson's toxin MPTP in mice lacking the redox master regulator Nrf2 or its target gene heme oxygenase-1", *PLoS One*, 5:e11838, 2010.

Innamorato et al., "The transcription factor Nrf2 is a therapeutic target against brain inflammation", *J. Immunol.* 181:680-689, 2008.

Inoue et al., "CDDO induces apoptosis via the intrinsic pathway in lymphoid cells," *Leukemia*, 2004, 18(5):948-952.

Ito et al., "Involvement of caspase-8 in the induction of osteosarcoma cell apoptosis by the novel triterpenoid CDDO," 47th Annual Meeting, Orthopaedic Research Society, Feb. 25-28, 2001, San Francisco, California, 2001, p. 0863, Poster Session.

Ito et al., "The novel triterpenoid 2-cyano-3,12-dioxoolean-1,9-dien-28-oic acid induces apoptosis of human myeloid leukemia cells by a caspase-8-dependent mechanism," *Cell Growth & Differentiation*, 2000, 11(5):261-267.

Ito et al., "The novel triterpenoid CDDO induces apoptosis and differentiation of human osteosarcoma cells by a caspase-8 dependent mechanism," *Mol. Pharmacol.*, 2001, 59:1094-1099.

Jakel et al., "Nrf2-mediated protection against 6-hydroxydopamine", *Brain Res.*, 1144:192-201, 2007.

Jang et al., "24-nor-ursane type triterpenoids from the stems of *Rumex japonicus*," *Chem. Pharm. Bull* (Tokyo), 2005, 53(12):1594-1596.

Ji et al., "The synthetic triterpenoid CDDO-imidazolide induces monocytic differentiation by activating the Smad and ERK signaling pathways in HL60 leukemia cells," *Molecular Cancer Therapeutics*, 2006, 5(6):1452-1458.

Johansen et al., "Pharmacology and preclinical pharmacokinetics of the triterpenoid CDDO methyl ester," *Proc. Amer. Assoc. Cancer. Res.*, 2003, 44:1728.

Johnson et al., "The absence of the pro-antioxidant transcription factor Nrf2 exacerbates experimental autoimmune encephalomyelitis", *Toxicol. Sci.*, 114:237-246, 2010.

Johnson et al., "The Nrf2-ARE pathway: an indicator and modulator of oxidative stress in neurodegeneration", *Ann. N.Y. Acad. Sci.*, 1147:61-69, 2008.

Jung and Kwak, "The Nrf2 system as a potential target for the development of indirect antioxidants," *Molecules*, 15:7266-91, 2010.

Jutooru et al., "Methyl 2-cyano-3,12-dioxooleana-1,9-dien-28-oate decreases specificity protein transcription factors and inhibits pancreatic tumor growth: role of microRNA-27a," *Mol. Pharmacol.*, 78(2):226-236, 2010.

Kahne and Collum, "Kinetic Cyanation of Ketone Enolates," *Tetrahedron Lett.*, 1981, 22:5011-5014.

Kaltschmidt et al., "Transcription factor NF-κB is activated in primary neurons by amyloid beta peptides and in neurons surrounding early plaques from patients with Alzheimer disease," *Proc. Natl. Acad. Sci. USA*, 1997, 94:2642-2647.

Kamal et al., "23-oxoisopristimerin III: an new natural phenolic (9→8)-24-nor-D:A-friedo-oleanane triterpene," *Tetrahedron Letters*, 1983, 24(27):2799-2800.

Kamal et al., "Structures of two new phenolic 24-nor-D:A-friedoleananes related to zeylasterone: a partial synthesis of trimethylzeylasterone," *Tetrahedron Letters*, 1983, 24(19):2025-2028.

Kamal et al., "The structure of zeylasterone, the first of a new series of phenolic 24-nor-D: A friedo-oleanane triterpenes," *Tetrahedron Letters*, 1980, 21(49):4749-4752.

Kanninen et al., "Nuclear factor erythroid 2-related factor 2 protects against beta amyloid", *Mol. Cell. Neurosci.*, 39:302-313, 2008.

Kansanen et al., "Regulation of Nrf2-dependent gene expression by 15-deoxy-Δ12,14-prostaglandin J2," *Free Radic. Biol. Med.*, 2009, 47(9):1310-1317.

Kaplan, "Friedrich's ataxia is a mitochondrial disorder," *Proc. Natl. Acad. Sci. USA*, 96:10948-10949, 1999.

Karin et al., "NF-κB in cancer: From innocent bystander to major culprit," *Nature Reviews*, 2002, 2:301-303.

Karin et al., "Nuclear factor-kB in cancer development and progression," *Nature*, 2006, 441(7092):431-436.

Khalid et al., "Isolation and characterization of pristimerin as the antiplasmodial and antileishmanial agent of *Maytenus senegalensis* (Lam.) Exell," *ARKIVOC*, 2007, 129-134.

Kim et al., "A protective role of nuclear factor-erythroid 2-related factor-2 (Nrf2) in inflammatory disorder," *Mutation Res.*, 690:12-23, 2010.

Kim et al., "An inducible Pathway for Degradation of FLIP protein Sensitizes Tumor Cells to TRAIL-induced Apoptosis," *J. Biological Chemistry*, 2002, 277(25):22320-22329.

Kim et al., "Caspase-3 activation is Involved in Apoptosis Induced by a Synthetic Triterpenoid in Non-small Cell Lung Cancer (NSCLC) cells," *Proc. Amer. Assoc. Cancer. Res.*, 2000, 41:770, Abstract #4894.

Kim et al., "Identification of a Novel Synthetic Triterpenoid, methyl-2-cyano-3,12-dioxooleana-1,9-dien-28-oate, that Potently Induces Caspace-mediated apoptosis in Human Lung Cancer Cells," *Molecular Cancer Therapeutics*, 2002, 1:177-184.

Kim et al., "Mitigation of radiation-induced damage by targeting EGFR in noncancerous human epithelial cells," *Radiation Research*, 180(3):259-267, 2013.

Kim et al., "Targeting of Nrf2 induces DNA damage signaling and protects colonic epithelial cells from ionizing radiation," *Proc. Natl. Acad. Sci., USA*, 109(43):E2949-E2955, 2012.

Kim et al., "The role of oxidative stress in neurodegenerative diseases," *Exp. Neurobio.*, 24(4):325-340, 2015.

Kircher, "Triterpenees, in organ pipe cactus," *Phytochemistry*, 1980, 19:2707-2712.

Klyne et al., "The molecular rotations of polycyclic compounds. III. Polycyclic alochols and their derivatives," *J. Chem. Soc.*, 1954, 1979-1988.

Kobayahsi et al., "The antioxidant defense system Keap1-Nrf2 comprises a multiple sensing mechanism for responding to a wide range of chemical compounds," *Mol. Cell Biol.*, 2009, 29(2):493-502.

Kolak et al., "Antioxidant and anticholinesterase constituents of *Salvia poculata*," *Turkish Journal of Chemistry*, 2009, 33(6):813-823.

(56) References Cited

OTHER PUBLICATIONS

Kong et al., "Synthetic triterpenoids have cytotoxicity in pediatric acute lymphoblastic leukemia cell lines but cytotoxicity is independent of induced ceramide increase in MOL T-4 cells," *Leukemia*, 22(6): 1258-1262, 2008.
Konopleva et al., "Activation of nuclear transcription factor PPARγ by the novel triterpenoid CDDO as targeted therapy in breast cancer," 2002 Keystone Symposium, 2002, Abstract No. 539.
Konopleva et al., "Mechanisms and Activity of PPARγ-Active Triterpenoids CDDO and CDDO-Me in Leukemias," *Blood*, 2005, 106:2460.
Konopleva et al., "Novel synthetic triterpenoid CDDO-Me: potent antiproliferative, proapoptotic and differentiating agent in AML," *Blood*, 2000, 96(11), Part 1:121A, abstract #522.
Konopleva et al., "Novel synthetic triterpenoid, CDDO, and its methyl ester: Potent antiproliferative, proapoptotic and differentiating agent in AML," *Blood*, 1999, 94(Suppl 1):479a, Abstract #2140.
Konopleva et al., "Novel triterpenoid CDDO-Me is a potent inhibitor of apoptosis and differentiation in acute myelogenous leukema," *Blood*, 2002, 99(1):326-335.
Konopleva et al., "Peroxisome proliferator-activated receptor γ and retinoid X receptor ligands are potent inducers of differentiation and apoptosis in leukemias," *Mol. Cancer Ther.*, 2004, 3:1249-1262.
Konopleva et al., "PPARγ Ligand CDDO Induces Apoptosis in Leukemias Via Multiple Apoptosis Pathways," Abstracts of the 44th Annual Meeting of the American Society of Hematology, 2002, Abstract No. 2209.
Konopleva et al., "PPARγ Ligands Are Potent Induces of Apoptosis in Leukemias and Lymphomas," American Society of Hematology 43rd Annual Meeting and Exposition, 2001, Abstract No. 501.
Konopleva et al., "PPARγ Nuclear Receptor as a Novel Molecular Target in Leukemia Therapy," *Proc. Amer. Assoc. Cancer Res.*, 2002, 43:4730.
Konopleva et al., "PPARγ nuclear receptor as a novel therapeutic target in AML," *Proc. of the AACR*, 2001, 42, Abstract #4458.
Konopleva et al., "PPARγ nuclear receptor as a novel therapeutic target in AML," *Blood*, 2000, 96(11):460a, Abstract #1982.
Konopleva et al., "Suppression of ERK Activation is Required for Triterpenoid Methyl-CDDO-Induced Apoptosis in AML," *Blood*, 2003, 102(110):1404.
Konopleva et al., "Synthetic triterpenoid 2-cyano-3,12-dioxooleana-1,9-dien-28-oic acid induces growth arrest in HER2-overexpressing breast cancer cells," *Mol. Cancer. Ther.*, 2006, 5:317-328.
Konopleva et al., "Synthetic triterpenoid CDDO as a novel therapy for resistant breast cancer," *Proc. Amer. Assoc. Cancer Res.*, 2003, 44:2726.
Konopleva et al., "The novel triterpenoid CDDO-Me suppresses MAPK pathways and promotes p38 activation in acute myeloid leukemia cells," *Leukemia*, 2005, 19:1350-1354.
Konopleva et al., "The synthetic triterpenoid 2-cyano-3,12-dioxoolean-1,9-dien-28-oic acid Induces caspase-dependent and -independent apoptosis in acute myelogenous leukemia," *Exp. Opin. Inv. Drug*, 1999, 8:2027-2057.
Konopleva et al., "Triterpenoid methyl-CDDO is a potent inducer of apoptosis in CD34+ AML progenitor cells via activation of SAPK pathways and inhibition of MAPK cascades," *Blood*, 2004, 104:2533.
Korovin and Tkachev, "Synthesis of quinoxalines fused with triterpenes, ursolic acid and betulin derivatives," *Russian Chemical Bulletin*, (Translation of Izvestiya Akademii Nauk, Seriya Khimicheskaya), 2001, 20(2):304-310.
Koschmieder et al., "CDDO induces granulocytic differentiation of myeloid leukemic blasts through translational up-regulation of p42 CCAAT enhanced-binding protein α," Blood, 2007, 110(10):3695-3705.
Kovac et al., "Prolonged seizure activity impairs mitochondrial bioenergetics and induces cell death", *J. Cell Sci.*, 125:1796-1806, 2012.
Kraft et al., "Neuronal sensitivity to kainic acid is dependent on the Nrf2-mediated actions of the antioxidant response element", *J. Neurochem.*, 98:1852-1865, 2006.
Kress et al., "Triterpenoids display single agent activity in a mouse model of CLL/SBL," *Blood*, 2006, 108(11):2530.
Kress et al., "Triterpenoids display single agent anti-tumor activity in a transgenic mouse model of chronic lymphocytic leukemia and small B cell lymphoma," *PLoS One*, 2007, 6(e559):1-11.
Kurinna et al., "The novel triterpenoid CDDO-Me promotes apoptosis in Gleevec-resistant chronic meyloid leukemia cells by caspase-independent mechanisms," *Proc. Amer. Assoc. Cancer Res.*, 2005, 46:2240.
Kutschabsky et al., "Natural products from Vietnamese plants. Part XV. Molecular and crystal structure of a new 24-nor triterpenoid carboxylic acid from *Acanthopanax trifoliatus*," *Croatica Chemica Acta*, 1986, 58(4):427-434.
Lapillonne et al., "Activation of peroxisome proliferator-activated receptor γ by a novel synthetic triterpenoid 2-cyano-3,12-dioxooleana-1,9-dien-28-oic acid induces growth arrest and apoptosis in breast cancer cells," *Cancer Res.*, 2003, 63:5926-5939.
Lavie et al., "Studies on epoxides. IV. Rearrangments in triterpenoids," *Tetrahedron Letters*, 1968, 17:2097-2100.
Lavie et al., "Tetranortriterpenoids from *Melia azadirachta*," *Chem. Comm.*, 1967, 6:278-280.
Le Brocq et al., "Endothelial Dysfunction: From Molecular Mechanisms to Measurement, Clinical Implications, and Therapeutic Opportunities", *Antioxid. Redox Signal.*, 10(9):1631-1673, 2008.
Lee et al., "Nrf2, a multi-organ protector?" *FASEB J.*, 19:1061-66, 2005.
Li et al., "Activation of Nrf2-antioxidant signaling attenuates NFκB-inflammatory response and elicits apoptosis", *Biochem. Pharmacol.*, 76(11):1485-1489, 2008.
Li et al., "Terpenoids from *Tripterygium wilfordii*," *Phytochemistry*, 1997, 45(4):791-796.
Li et al., "The triterpenoid CDDO-Me delays murine acute graft-versus-host disease with the preservation of graft-versus-tumor effects after allogeneic bone marrow transplantation," *Biol. Blood Marrow Transplant.*, 16(6):739-750, 2010.
Liby et al., "A novel acetylenic tricyclic bis-(cyano enone) potently induces phase 2 cytoprotective pathways and blocks liver carcinogenesis induced by aflatoxin," *Cancer Res.*, 2008, 68:6727-6733.
Liby et al., "Novel semisynthetic analogues of betulinic acid with diverse cytoprotective, antiproliferative, and proapoptotic activities," *Mol. Cancer Ther.*, 2007, 6(7):2113-2119.
Liby et al., "Prevention and Treatment of Experimental Estrogen Receptor-Negative Mammary Carcinogenesis by the Synthetic Triterpenoid CDDO-Methyl Ester and the Rexinoid LG100268," *Clin. Cancer Res.*, 14(14):4556-4563, 2008.
Liby et al., "Synthetic triterpenoids prolong survival in a transgenic mouse model of pancreatic cancer," *Cancer Prevent. Res.*, 3(11):1427-1434, 2010.
Liby et al., "The rexinoid LG100268 and the synthetic triterpenoid CDDO-methyl amide are more potent than erlotinib for prevention of mouse lung carcinogenesis," *Mol. Cancer Ther.*, 2008, 7:1251-1257.
Liby et al., "The synthetic triterpenoid CDDO-Imidazolide suppresses STAT phosphorylation and induces apoptosis in myeloma and lung cancer cells," *Clinical Cancer Research*, 2006, 12(14 Part 1):4288-4293.
Liby et al., "The synthetic triterpenoids CDDO and CDDO-imidazole, are potent induces of heme oxygenase-1 and Nrf2/ARE signaling," *Cancer Research*, 2005, 65(11):4789-4798.
Liby et al., "The synthetic triterpenoids CDDO-Methyl ester and CDDO-ethyl amide prevent lung cancer induced by vinyl carbamate in A/J mice," *Cancer Research*, 2007, 67(6):1-7.
Liby et al., "Triterpenoids and rexinoids as multifunctional agents for the prevention and treatment of cancer," *Nature Review Cancer*, 2007, 7(5):357-369.
Liby et al., "Triterpenoids CDDO-methyl ester or CDDO-ethyl amide and rexinoids LG100268 or NRX194204 for prevention and treatment of lung cancer in mice," *Cancer Prev. Res.*, 2(12):1050-1058, 2009.

(56) References Cited

OTHER PUBLICATIONS

Ling et al., "The novel triterpenoid C-28 methyl ester of 2-cyano-3,12-dioxoolen-1,9-dien-28-oic acid inhibits metastatic murine breast tumor tissue growth through inactivation of STAT3 signaling," *Cancer Research*, 2007, 67:4210-4218.

Ling et al., "The novel triterpenoid C-28 methyl ester of 2-cyano-3,12-dioxoolen-1,9-dien-28-oic acid inhibits metastatic murine breast tumor growth through inactivation of STAT3 signaling," [Erratum to document cited in CA 147:157653], *Cancer Res.*, 68(12):4958, 2008.

Ling et al., "The novel triterpenoid CDDO-Me inhibits metastatic murine breast tumor through inhibition of STAT3 signaling," 2007 AACR Annual Meeting, Abstract No. 301, 2007.

Liu et al., "Chemical constitutents from root of *Rubus irenaeus*," *Zhongcaoyao*, 2003, 34(5):394-396 (Chinese, English Abstract).

Liu et al., "Coordinate regulation of enzyme markers for inflammation and for protection against oxidants and electrophiles," *Proc. Natl. Acad. Sci.*, 105(41):15926-15931, 2008.

Liu et al., "New lupane-type triterpenoid saponins from leaves of *Oplopanax horridus* (Devil's Club)," *Nat. Prod. Comm.*, 2010, 5(7):1019-1022.

Liu et al., "The novel triterpenoid RTA 408 protects human retinal pigment epithelial cells against H2O2-induced cell injury via NF-E2-related factor 2 (Nrf2) activation," *Redox Biol.*, 8:98-109, 2016.

Ma et al., "Multiorgan Autoimmune Inflammation, Enhanced Lymphoproliferation, and Impaired Homeostasis of Reactive Oxygen Species in Mice Lacking the Antioxidant-Activated Transcription Factor Nrf2", *Am. J. Pathol.*, 168:1960-1974, 2006.

Magesh et al., "Small molecule modulators of Keap1-Nrf2-ARE pathway as potential preventive and therapeutic agents," *Med. Res. Rev.*, 32:687-726, 2012.

Marples and Spilling, "Ene reactions of unsaturated acyloins," *Tetrahedron Letters*, 1985, 26(52):6515-6518.

Marples and Spilling, "Facile intramolecular ene reactions of steroidal unsaturated acyloins," *Tetrahedron*, 1992, 48(19):4017-4026.

Marty et al., "RTA 402 (CDDO-Me) increases survival of mice administered high doses of cytotoxic chemotherapy," *European Organization for Research and Treatment of Cancer, American Association for Cancer Research and National Cancer Institute International Conference*, Nov. 2005, Poster presentation.

Melichar et al., "Growth-inhibitory effect of a novel synthetic triterpenoid, 2-cyano-3,12-dioxoolean-1,9-dien-28-oic acid, on ovarian carcinoma cell lines not dependent on peroxisome proliferator-activated receptor-γ expression," *Gynecologic Oncology*, 2004, 93:149-154.

Mencherini et al., "Triterpenoid constituents from the roots of the *Paeonia rockii* ssp. *rockii*," *J. Nat. Prod.*, 2011, 74(10):2116-2121.

Minns et al., "A novel triterpenoid induces transforming growth factor β production by intraepithelial lymphocytes to prevent ileitis," *Gastroenterology*, 2004, 127:119-126.

Mix et al., "A synthetic triterpenoid selectively inhibits the induction of matrix metalloproteinases 1 and 13 by inflammatory cytokines," *Arthritis Rheum.*, 2001, 44:1096-1104.

Mix et al., "Peroxisome proliferator-activated receptor-gamma-independent repression of collagenase gene expression by 2-cyano-3,12-dioxooleana-1,9-dien-28-oic acid and prostaglandin 15-deoxy-Δ(12,14) J2: a role in Smad signaling," *Mol. Pharmacol.*, 2004, 65(2):309-318.

Murphy et al., "Immunomodulatory Effects of the Triterpenoid CDDO after Allogeneic Bone Marrow Transplantation in Mice: Reduction of Acute Graft-Versus-Host Disease Lethality," *Blood*, 2005, 106:1316.

Murray and Zweifel, "Preparation of Phenyl Cyanate and Its Utilization for the Synthesis of α, β-Unsaturated Nitriles," *Synthesis*, 1980, 150-151.

Muzart, "Synthesis of unsaturated carbonyl compounds via chromium-mediated allylic oxidation by 70% tert-butylhydroperoxide," *Tetrahedron Lett.*, 1987, 28:4665-4668.

Na and Surh et al., "Transcriptional regulation via cysteine thiol modification: a novel molecular strategy for chemoprevention and cytoprotection," *Mol. Carcinog.*, 2006, 45(6):368-380.

Nagaraj et al., "Anti-inflammatory Triterpenoid Blocks Immune Suppressive Function of MDSCs and Improves Immune Response in Cancer," *Clin. Cancer Res.*, 16(6):1812-1823, 2010.

Nair et al., "Triterpenes. XLVII. Oxidation rates of triterpenoid secondary alcohols with chromic acid," *Collection of Czechoslovak Chemical Communications*, 1976, 41(3):770-779.

Nanduri et al., "Biological investigation and structure-activity relationship studies on azadirone from *Azadirachta indica* A. juss," *Bioorganic and Medicinal Chemistry*, 2003, 13(22):4111-4115.

Nathan et al., "Protection from Alzheimer's-like disease in the mouse by genetic ablation of inducible nitric oxide synthase," *The Journal of Experimental Medicine*, 202:1163-1169, 2005.

Nelson et al., "Oxidative demethylation at C-4 of a steroid via nitroxide photolysis," *J. of the American Chemical Society*, 1975, 97(3):648-649.

Neurath and Finotto, "IL-6 signaling in autoimmunity, chronic inflammation and inflammation-associated cancer," *Cytokine Growth Factor Rev.*, 22:83-89, 2011.

Neymotin et al., "Neuroprotective effect of Nrf2/ARE Activators, CDDO-ethylamide and CDDO-trifluoroethylamide in a Mouse Model of Amyotrophic Lateral Sclerosis", *Free Rad. Biol. Med.*, 51(1):88-96, 2011.

Niikura et al., "The effects of synthetic triterpenoids on superficial zone protein synthesis in articular chondrocytes," Abstract, Orthopedic Research Society, San Diego, 2007.

Niikura et al., "The effects of synthetic triterpenoids on szp synthesis in articular chondrocytes," Abstract P197, *Osteoarthritis and Cartilage*, 2006, 14(Suppl B):S112-S113.

Nishimura et al., "Activity-guided isolation of triterpenoid acyl CoA cholesteryl acyl transferase (ACAT) inhibitors from *Ilex kudincha*," *J. Nat. Prod.*, 1999, 62(7):1061-1064.

Nishino et al., "Inhibition of the tumor-promoting action of 12-O tetradecanoylphorbol-13-acetate by some oleanane-type triterpenoid compounds," *Cancer Res.*, 1988, 48:5210-5215.

Notice of Allowance issued in U.S. Appl. No. 13/869,833, filed Apr. 24, 2013.

Oekinghaus and Ghosh, "The NF-κB family of transcription factors and its regulation", *Cold Spring Harb. Perspect. Biol.*, 1:a000034, 2009.

Office Communication issued in corresponding U.S. Appl. No. 16/786,429, mailed on Nov. 11, 2020.

Olsen et al., "Fatty acid synthesis is a therapeutic target in human liposarcoma," *Int. J. Oncol.*, 36(5):1309-1314, 2010.

Osburn et al., "Genetic of pharmacologic amplification of Nrf2 signaling inhibits acute inflammatory liver injury in mice," *Toxicology Sciences*, 2008, 104:218-227.

Overnell and Whitehurts, "Reactions of steroid A-ring lactones with Grignard reagents," *J. of the Chemical Society [Section C: Organic]*, 1971, 2:378-384.

Pappas et al., "Photoisomerization of phenalen-1-one oxide. New course of light-induced α,β-epoxy ketone rearrangement," *J. of the American Chemical Society*, 1970, 92(19):5797-5798.

Pareek et al., "Triterpenoid modulation of IL-17 and Nrf-2 expression ameliorates neuroinflammation and promotes remyelination in autoimmune encephalomyelitis", *Sci. Rep.*, 1:201, 2011.

PCT International Search Report and Written Opinion issued in International Application No. PCT/US2013/038064 dated Jul. 10, 2013.

Peakman et al., "Characterization of 24-nor-triterpenoids occurring in sediments and crude oils by comparison with synthesized standards," *Tetrahedron*, 1991, 47(23):3779-3786.

Pedersen et al., "The triterpenoid CDDO induces apoptosis in refractory CLL B cells," *Blood*, 2002, 100:2965-2972.

Pergola et al., "Bardoxolone Methyl and Kidney Function in CKD with Type 2 diabetes," *New England Journal of Medicine*, 2011, 365:327-336.

Place et al., "The novel synthetic triterpenoid, CDDO-imidazolide, inhibits inflammatory response and tumor growth in vivo," *Clin. Cancer Res.*, 2003, 9:2798-2806.

(56) References Cited

OTHER PUBLICATIONS

Place, "Pre-clinical evaluation of the novel synthetic triterpenoid CDDO-Imidazolide," Thesis, Dartmouth College, May 5, 2004.
Probst et al., "RTA 408, a novel synthetic triterpenoid with broad anticancer and anti-inflammatory activity," *PLoS One*, 10(4):e0122942/1-e0122942/16, 2015.
Prochaska and Santamaria, "Direct measurement of NAD(P)H:Quinone reductase from cells culttured in microtiter wells: a screening assay for anticarcinogenic enzyme inducers", *Anal. Biochem.*, 1988, 169:328-336.
Ramsey et al., "Expression of Nrf2 in neurodegenerative diseases," *J. Neuropathol. Exp. Neurol.*, 66(1):75-85, 2007.
Rasmusson et al., "Azasteroids: structure-activity relationships for inhibition of 5 α-reductase and of androgen receptor binding," *J. Med. Chem.*, 1986, 29(11):2298.
Ray, Denise M. et al., "The novel triterpenoid 2-cyano-3,12-dioxooleana-1,9-dien-28-oic acid (CDDO) Induces Apoptosis of Human Diffuse Large B-cell Lymphoma Cells through a Peroxisome Proliferator-activated Receptor γ-independent Pathway," *Experimental Hematology*, 2006, 34:1201-1210.
Reisman et al., "CDDO-9,11-dihydro-trifluoroethyl amide (CDDO-dhTFEA) induces hepatic cytoprotective genes and increases bile flow in rats," *Xenobiotica*, 43(7):571-578, 2013.
Reisman et al., "Topical administration of the synthetic triterpenoid RTA 408 protects mice from radiation-induced dermatitis," *Radiation Research Society*, 181(5):512-520, 2014.
Reisman et al., "Topical application of RTA 408 lotion activates Nrf2 in human skin and is well-tolerated by healthy human volunteers," *BMC Dermatology*, 15(10):1-11, 2015.
Reisman et al., "Topical application of the synthetic triterpenoid RTA 408 activates Nrf2 and induces cytoprotective genes in rat skin," *Archives of Dermatological Research*, 306(5):447-454, 2014.
Ribo et al., "Synthesis of methyl 1,11-dioxooleanan-2,12-dien-30-oate and its 24-nor derivative", *Afinidad*, 1981, 38(373):197-200.
Riccioni et al., "Resistance of acute myeloid leukemic cells to the triterpenoid CDDO-Imidazolide is associated with low caspase-8 and FADD levels," *Leukemia Research*, 32:1244-1258, 2008.
Rodríguez-Spong et al., "General principles of pharmaceutical solid polymorphism: a supramolecular perspective," *Advanced Drug Delivery Reviews*, 2004, 56:241-274.
Rossi et al., "Anti-inflammatory cyclopentenone prostaglandins are direct inhibitors of IκB kinase," *Nature*, 2000, 403:103-108.
Rouquette et al., "A ring-D functionalized nor-triterpenoid of the lupane series as a key intermediate in the formation of widespread hydrocarbon derivatives of higher plant origin in petroleum," *Organic Geochemistry*, 2005, 36(9):1227-1233.
Ruiz et al., "Targeting the transcription factor Nrf2 to ameliorate oxidative stress and inflammation in chronic kidney disease," *Kidney Int.*, 83(6):1029-1041, 2013.
Rushworth et al., "TNF mediates the sustained activation of Nrf2 in human monocytes", *J. Immunol.*, 187(2):702-717, 2011.
Ruvolo et al., "The novel triterpenoid methyl-CDDO inhibits Bc12 phosphorylation and potently kills U937 cells," *Blood*, 1999, 94(10), Suppl. 1, Part 1: 280A, abstract #1251.
Ryu et al., "Activation of signal transducer and activator of transcription 3 (Stat3) pathway in osteosarcoma cells and overexpression of phosphorylated-Stat3 correlates with poor prognosis," *J. Orthop. Res.*, 28(7):971-978, 2010.
Ryu et al., "Oleanane triterpenoid CDDO-Me induces apoptosis in multidrug resistant osteosarcoma cells through inhibition of Stat3 pathway," *BMC Cancer*, 10:187, 2010.
Saha et al., "The triterpenoid 2-cyano-3,12-dioxooleana-1,9-dien-28-oic acid methyl ester has potent anti-diabetic effects in diet-induced diabetic mice and Lepr$^{db/db}$ mice," *J. Biol. Chem.*, 2010, 285:40581-92.
Samudio et al., "2-cyano-3,12-dioxoolean-1,9-diene-28-imidazolide induces apoptosis in pancreatic cancer via redox-dependent cytoplasmic stress," *Proc. Amer. Assoc. Cancer Res.*, 2005, 46:Abstract No. 5899.
Samudio et al., "2-cyano-3,12-dioxooleana-1,9-dien-28-imidazolide (CDDO-Im) directly targets mitochondrial glutathione to induce apoptosis in pancreatic cancer," *J. Biol. Chem.*, 2005, 280:36273-36282.
Samudio et al., "A novel mechanism of action of methyl-2-cyano-3,12-dioxoolean-1,9-diene-28-oate (CDDO-Me): Direct permeabilization of the inner mitochondrial membrane to inhibit electron transport and induce apoptosis," *Proc. Am. Assoc. Cancer Res.*, 2006, 47:Abstract #4693.
Samudio et al., "A novel mechanism of action of methyl-2-cyano-3,12-dioxoolean-1,9-diene-28-oate: direct permeabilization of the inner mitochondrial membrane to inhibit electron transport and induce apoptosis," *Mol. Pharmacol.*, 2006, 69:1182-1193.
Samudio et al., "Inhibition of mitochondrial metabolism by methyl-2-cyano-3,12-dioxoolean-1,9-diene-28-oate induces apoptotic or autophagic cell death in chronic myelogenous leukemia cells," *Mol. Cancer Ther.*, 7(5):1130-1139, 2008.
Samudio et al., "The novel triterpenoid CDDOme potently synergizes with inhibition of bcl-2 function to induce apoptosis in AML via disruption of intracellular redox homeostasis," *Proc. Amer. Assoc. Cancer Res.*, 2005, 46:Abstract No. 4955.
Satoh et al., "Activation of the Keap1/Nrf2 pathway for neuroprotection by electrophillic phase II inducers," *PNAS*, 2006, 103(3):768-773.
Scholtz et al., "Sensitive and specific methods for the determination of CDDO methyl ester in mouse, rat, dog, monkey, and human plasma by LC-tandem mass spectrometry," *Proc. Amer. Assoc. Cancer Res.*, 2003, 4:Abstract No. 6321.
Sharpless et al., "Electrophilic and nucleophilic organoselenium reagents. New routes to α,β-unsaturated carbonyl compounds," *J. Am. Chem. Soc.*, 1973, 95:6137.
Shekh-Ahmad et al., "KEAP1 inhibition is neuroprotective and suppresses the development of epilepsy," *Brain*, 141(5):1390-1403, 2018.
Shelton et al., "Role of Nrf2 in protection against acute kidney injury," *Kidney Int.*, 84(6):1090-1095, 2013.
Shin et al., "Nrf2 modulates aryl hydrocarbon receptor signaling: influence on adipogenesis," *Molecular and Cellular Biology*, 2007, 27(20):7188-7197.
Shin et al., "Role of Nrf2 in prevention of high-fat diet-induced obesity by synthetic triterpenoid CDDO-imidazolium," *Eur. J. Pharmacol.*, 2009, 620(1-3):138-144.
Shin, "Inhibitory roles of Nrf2 and an oleanolic triterpenoid on adipocyte differentiation and obesity," dissertation submitted to John Hopkins University in conformity with the requirements for the degree of Doctor of Philosophy, Mar. 2009.
Shishodia et al., "A synthetic triterpenoid, CDDO-Me, inhibits IKBα kinase and enhances apoptosis induced by THF and chemotherapuetic agents through down-regulation of expression of nuclear factor κB-regulated gene products in human leukemic cells," *Clinical Cancer Research*, 2006, 12(6):1828-1838.
Siddiqui et al., "Kanerin and 12,13-dihydroursolic acid, two new pentacyclic triterpenes from the leaves of Nerium oleander," *J. Nat. Prod.*, 1989, 52(1):57-62.
Simonian and Coyle, "Oxidative stress in neurodegenerative diseases," *Annu. Rev. Pharmacol. Toxicol.*, 36:83-106, 1996.
Simonsen et al., "Tetracyclic hydroxy acids," In the Terpenes, Cambridge University, Cambridge, 1957, 5:221-285.
Singh et al., "Anti-inflammatory activity of oleanolic acid in rats and mice," *J. Pharm. Pharmacol.*, 1992, 44:456-458.
Slides by Reata Pharmaceuticals, "RTA 402, Therapeutic Properties III," podium presentation at BIO 2006 conference, Apr. 9-12, 2006, Chicago, Illinois.
Slides/Handouts by Reata Pharmaceuticals, "RTA 402, Therapeutic Properties I," Private partnering meetings at BioSquare 2006 conference, Mar. 8-10, 2006, Geneva, Switzerland.
Slides/Handouts by Reata Pharmaceuticals, "RTA 402, Therapeutic Properties II," Private partnering meetings at BIO 2006 conference, Apr. 9-12, 2006, Chicago, Illinois.
Slides/Handouts by Reata Pharmaceuticals, "RTA 402, Therapeutic Properties IV," Private partnering meetings at BioPartnering Europe 2006 conference, Oct. 8-10, 2006, London, England.

(56) References Cited

OTHER PUBLICATIONS

Slides/Handouts by Reata Pharmaceuticals, "RTA 402, Therapeutic Properties IX," Private partnering meeting at BIO Europe 2007 conference, Nov. 12-14, 2007, Hamburg, Germany.
Slides/Handouts by Reata Pharmaceuticals, "RTA 402, Therapeutic Properties V," Private partnering meetings at BIO 2007 conference, May 6-9, 2007, Boston, Massachusetts.
Slides/Handouts by Reata Pharmaceuticals, "RTA 402, Therapeutic Properties VI," Private partnering meetings at BIO 2007 conference, May 6-9, 2007, Boston, Massachusetts.
Slides/Handouts by Reata Pharmaceuticals, "RTA 402, Therapeutic Properties VII," Podium presentation at BIO 2007 conference, May 6-9, 2007, Boston, Massachusetts.
Slides/Handouts by Reata Pharmaceuticals, "RTA 402, Therapeutic Properties VIII," Private partnering meetings at BIO Europe 2007 conference, Nov. 12-14, 2007, Hamburg, Germany.
Sporn and Roberts, "Peptide growth factors and inflammation, tissue repair, and cancer," *J. Clin. Invest.*, 1986, 78:329-332.
Sporn et al., "New synthetic triterpenoids: potent agents for prevention and treatment of tissue injury caused by inflammatory and oxidative stress," *J. Nat. Prod.*, 74(3):537-545, 2011.
Sporn et al., "Prospects for prevention and treatment of cancer with selective PPARγ modulators (SPARMs)," *Trends in Molecular Medicine*, 2001, 7(9):395-400.
Stack et al., "Triterpenoids CDDO-ethyl amide and CDDO-trifluoroethyl amide improve the behavioral phenotype and brain pathology in a transgenic mouse model of Huntington's disease", *Free Radic. Biol. Med.*, 49:147-158, 2010.
Stadheim et al., "The novel triterpenoid 2-cyano-3,12-dioxooleana-1,9-dien-28-oic acid (CDDO) potently enhances apoptosis induced by tumor necrosis factor in human leukemia cells," *J. Biol. Chem.*, 2002, 277:16448-16455.
Subba Rao et al., "Chemical modifications of natural triterpenes—glycyrrhetinic and boswellic acids: evaluation of their biological activity," *Tetrahedron*, 64(51):11541-11548, 2008.
Suh et al., "A novel synthetic oleanane triterpenoid, 2-cyano-3,12-dioxooleanan-1,9-dien-28-oic acid (CDDO), induces cell differentiation in human myeloid leukemias," Proceedings of the American Association for Cancer Research Annual Meeting, 40:300 abstract 1988, 1999.
Suh et al., "A novel synthetic oleanane triterpenoid, 2-cyano-3,12-dioxooleanan-1,9-dien-28-oic acid, with potent differentiating, antiproliferative, and anti-inflammatory activity," *Cancer Res.*, 1999, 59(2):336-341.
Suh et al., "New triterpenoids as cancer preventive and anti-inflammatory agents," Proceedings of the American Association for Cancer Research, 1997, Abstract No. 1457, 38:216.
Suh et al., "Novel triterpenoids suppress inducible nitric oxide synthase (iNOS) and inducible cyclooxygenase (COX-2)," Proceedings of the American Association for Cancer Research Annual Meeting, 1998, 39:Abstract No. 1821.
Suh et al., "Novel triterpenoids suppress inducible nitric oxide synthase (iNOS) and inducible cyclooxygenase (COX-2) in mouse macrophages," *Cancer Res.*, 1998, 58:717-723.
Suh et al., "Synthetic triterpenoids activate a pathway for apoptosis in AML cells involving downregulation of FLIP and sensitization to TRAIL," *Leukemia*, 2003, 17:2122-2129.
Suh et al., "Triterpenoids CDDO and CDDO-Me Down-Regulate FLIP Expression and Sensitize AML cells to Trail-Induced Apoptosis," American Society of Hematology 43rd Annual Meeting and Exposition, 2001, Abstract No. 498.
Suh, "Synthetic triterpenoids enhance transforming growth factor β/Smad signaling," *Cancer Res.*, 2003, 63:1371-1376.
Sultana et al., "Phytochemical studies on *Alstonia scholaris*," Zeitschrift für Naturforschung B, *A Journal of Chemical Sciences*, 2010, 65(2):203-210.
Sun et al., "Structure-activity relationships of olean- and ursane-type triterpenoids," *Botanical Studies*, 2006, 47:339-368.

Sun et al., "The synthetic triterpenoid, CDDO, suppresses alloreactive T cell responses and reduces murine early acute graft-versus-host disease mortality," *Biology of Blood and Marrow Transplantation*, 2007, 13(5):521-529.
Sun et al., "Therapeutic potential of synthetic triterpenoids in neuroblastoma," *Cancer Biology & Therapy*, 7(5):720-722, 2008.
Sussan et al., "Targeting Nrf2 with the triterpenoid CDDO-imidazolide attenuates cigarette smoke-induced emphysema and cardiac dysfunction in mice," *Proc. Nat. Sci. Acad. USA*, 2009, 106:250-255.
Tabe et al., "Chromatin-Mediated Transcriptional Activation with Novel Peroxisome Proliferator-Activated Receptor gamma(PPARγ) Ligand 2-cyano-1,9-dien-28-oic acid (CDDO) in Acute Promyelocytic leukemia cells," Abstracts of the 44th Annual Meeting of the American Society of Hematology, 2002.
Takaishi et al., "Triterpenoid inhibitors of interleukin-1 secretion and tumor-promotion from *Tripterygium wilfordii* var. regelii," *Phytochemistry*, 1997, 45(5):969-974.
Talalay et al., "Sulforaphane mobilizes cellular defenses that protect skin against damage by UV radiation", *Proc. Natl. Acad. Sci. USA*, 104:17500-17505, 2007.
Tanaka et al., "A new triterpenoid from the leaves of *Eucommia ulmoides Oliv.*," *Chem. Pharm. Bull* (Tokyo), 1997, 45(8):1379-1380.
Ten Haven et al., "Early diagenetic transformation of higher-plant triterpenoids in deep-sea sediments from Baffin Bay," *Geochimicha et Cosmochimica Acta*, 1992, 56(5):2001-2024.
Thimmulappa et al., "Identification of Nrf2-regulated genes induced by the chemopreventive agent sulforaphane by oligonucleotide microarray," *Cancer Research*, 2002, 62:5196-5203.
Thimmulappa et al., "Nrf2 is a critical regulator of the innate immune response and survival during experimental sepsis," *J. Clinical Investigations*, 2006, 116(4):984-995.
Thimmulappa et al., "Nrf2-dependent protection from LPS induced inflammatory response and mortality by CDDO-imidazole," *Biochem. Biophys. Res. Commun.*, 351:883-889, 2006.
Thimmulappa et al., "Preclinical evaluation of targeting the Nrf2 pathway by triterpenoids (CDDO-Im and CDDO-Me) for protection from LPS-induced inflammatory response and reactive oxygen species in human peripheral blood mononuclear cells and neutrophils," *Antioxidants & Redox Signaling*, 9(11):1-8, 2007.
To et al., "Synthetic Triterpenoids Target the Arp2/3 Complex and Inhibit Branched Actin Polymerization," *J. Biol. Chem.*, 285(36):27944-27957, 2010.
To et al., "The synthetic triterpenoid 2-cyano-3,12-dioxooleana-1,9-dien-28-oic acid-imidazolide alters transforming growth factor β-dependent signaling and cell migration by affecting the cytoskeleton and the polarity complex," *J. Biol. Chem.*, 283:11700-11713, 2008.
Tran et al., "The synthetic triterpenoid CDDO-methyl ester modulates microglial activities, inhibits THF production, and provides dopaminergic neuroprotection," *Journal of Neuroinflammation*, 2008, 5:1-14.
Tsao et al., "DRIP205 co-activator overexpression enhances PPARγ-mediated differentiation of leukemia cells by CDDO," *Proc. Amer. Assoc. Cancer Res.*, 2005, 46:Abstract No. 1855.
Tsao et al., "Targeted Induction of Apoptosis in Leukemias by PPARγ Ligation," American Society of Hematology 43rd Annual Meeting and Exposition, 2001, Abstract No. 2381.
Urban et al., "Influence of esterification and modification of A-ring in a group of lupane acids on their cytotoxicity," *Bioorganic and Medicinal Chemistry*, 2005, 13(19):5527-5535.
Urban et al., "Synthesis of A-seco derivatives of betulinic acid with cytotoxic activity," *J. of Natural Products*, 2004, 67(7):1100-1105.
Uskoković et al., "D-Homosteroids. I. 3β-hydroxy-17a,17a-dimethyl-D-homoandrostane-17-one and related compounds," *J. of the American Chemical Society*, 1959, 81:4561-4566.
Van Kiem et al., "A new 24-nor-lupane-gylcoside of *Acanthopanax trifoliatus*," *Arch. Pharm. Res.*, 2003, 26(9):706-708.
Van Muiswinkel and Kuiperij, "The Nrf2-ARE Signalling Pathway: Promising Drug Target to Combat Oxidative Stress in Neurodegenerative Disorders," *Current Drug Targets—CNS & Neurological Disorders*, 4:267-281, 2005.

(56) References Cited

OTHER PUBLICATIONS

Vannini et al., "The synthetic oleanane triterpenoid, CDDO-methyl ester, is a potent antiangiogenic agent," *Molecular Cancer Therapeutics*, 2007, 6(12 Part 1):3139-3146.

Vargas et al., "Nrf2 activation in astrocytes protects against neurodegeneration in mouse models of familial amyotrophic lateral sclerosis", *J. Neurosci.*, 28:13574-13581, 2008.

Vazquez et al., "Human immunodeficiency virus type 1-induced macrophage gene expression includes the p21 gene, a target for viral regulation," *J. Virol.*, 2005, 79:4479-4491.

Venè et al., "Glycogen synthase kinase 3β regulates cell death induced by synthetic triterpenoids," *Cancer Res.*, 68:6987-6996, 2008.

Vilayur and Harris, "Emerging therapies for chronic kidney disease: what is their role?", *Nature Reviews*, 2009, 5:375-383.

Vincenti et al., "The synthetic triterpenoid TP-222 inhibits RANKL induction of differentiation and MMP-9 gene expression in osteoclasts," Abstract 1385, American College of Rheumatology Annual Scientific Meeting, 2006.

Wada and Tanaka, "Synthetic lanostane-type triterpenoids as inhibitors of DNA topoisomerase II," *Bioorganic and Medicinal Chemistry Letters*, 2005, 15(12):2966-2969.

Wang et al., "A novel synthetic triterpenoid, 2-cyano-3,12-dioxoolean-1,9-dien-28-oic acid (CDDO) induces adipocyte differentiation in 3T3-L1 cells," Proceedings of the American Association for Cancer Research Annual Meeting, 1999, 40:300 abstract No. 1989.

Wang et al., "A synthetic triterpenoid, 2-cyano-3,12-dioxooleana-1,9-dien-28-oic acid (CDDO), is a ligand for the peroxisome proliferator-activated receptor γ," *Mol. Endocrin.*, 2000, 14(10):1550-1556.

Wang et al., "Synthetic triterpenoid CDDO and its derivatives increase ceramides and are cytotoxic to pediatric acute lymphoblastic leukemia cell lines," *Proc. Am. Assoc. Cancer Res.*, 2006, 47:4643.

Wang, "Differentiating and anti-inflammatory activities of the triterpenoid, CDDO," Thesis, Dartmouth College, May 4, 2001.

Waratchareeyakul et al., "2,19-dihydroxy-3-oxo-(2,4,19)-24-nor-olean-12-en-28-oic acid monohydrate," *Acta. Cryst.*, 2007, E63, o4062-o4063.

Wardle et al., "Nuclear factor κB for the nephrologist," *Nephrol. Dial. Transplant.*, 2001, 16(9):1764-68.

Wen et al., "Naturally occurring pentacyclic triterpenes as inhibitors of glycogen phosphorylase: synthesis, structure-activity relationships, and X-ray crystallographic studies," *J. Med. Chem.*, 51:3540-3554, 2008.

Wen et al., "Pentacyclic triterpenes. Part 2: Synthesis and Biological evaluation of maslinic acid derivatives as glycogen phosphorylase inhibitors," *Bioorganic and Medicinal Chemistry Letters*, 2006, 16(3):722-726.

White et al., "A novel demethylated oxygenated triterpenoid in crude oils from the Canadian Beaufort sea and northeast Alaska," *Tetrahedron Letters*, 1998, 39(19):3031-3034.

Wu et al., "Beneficial role of Nrf2 in regulating NADPH generation and consumption," *Toxicological Sciences*, 2011, 123(2):590-600.

Xie et al., "ARE- and TRE-mediated regulation of gene expression response to xenobiotics and antioxidants," *J. Biol. Chem.*, 1995, 270(12):6894-6900.

Xing et al., "Triterpenoid dihydro-CDDO-trifluoroethyl amide protects against maladaptive cardiac remodeling and dysfunction in mice: a critical role of Nrf2," *PLoS One*, 2012, 7:344899.

Xu et al., "Inhibition of the signal transducer and activator of transcription-3 (STAT3) signaling pathway by 4-oxo-1-phenyl-1,4-dihydroquinoline-3-carboxylic acid esters," *J. Med. Chem.*, 51:4115-4121, 2008.

Xu et al., "The role of nitric oxide in cancer", *Cell Res.*, 12:311-320, 2002.

Yang et al., "Neuroprotective effects of the triterpenoid, CDDO methyl amide, a potent inducer of Nrf2-mediated transcription", *PLoS One*, 4:e5757, 2009.

Yates et al., "Pharmacodynamic characterization of chemopreventive triterpenoids as exceptionally potent inducers of Nrf2-regulated genes," *Mol. Cancer Ther.*, 2007, 6:154-162.

Yates et al., "Potent protection against aflatoxin-induced tumorigenesis through induction of Nrf2-regulated pathways by the triterpenoid 1-[2-cyano-3,12-dioxooleana-1,9(11)-dien-28-oyl]imidazole," *Cancer Res.*, 2007, 66(4):2488-2494.

Yoh et al., "Nrf2-deficient female mice develop lupus-like autoimmune nephritis", *Kidney Int.*, 60:1343-1353, 2001.

Yore et al., "The synthetic triterpenoid 1-[2-cyano-3,12-dioxooleana-1,9(11)-dien-28-oyl]imidazole blocks nuclear factor-κB activation through direct inhibition of IKB kinase β," *Mol. Cancer Ther.*, 2006, 5(12):3232-3239.

You et al., "Synthesis and cytotoxic activity of a-ring modified betulinic acid derivatives," *Bioorganic and Medicinal Chemistry Letters*, 2003, 13(19):3137-3140.

Yue et al., "Depletion of intracellular glutathione contributes to JNK-mediated death receptor 5 upregulation and apoptosis induction by the novel synthetic triterpenoid methyl-2-cyano-3,12-dioxooleana-1,9-dien-28-oate (CDDO-Me)," *Cancer & Biology Therapy*, 2006, 5(5):492-497.

Zapata et al., "CDDO and CDDO-Im reduce tumor burden in a transgenic mouse model of CLL," *Blood*, 2004, 104:3477.

Zapata et al., "Trterpenoids show activity against leukemic cells in a transgenic mouse model of CLL," *Proc. Amer. Assoc. Cancer Res.*, 2005, 46:Abstract No. 5179.

Zhang et al., "Synthetic triterpenoid CDDO as effective therapy for HER2-expressing resistant breast cancer," *Proc. Amer. Assoc. Cancer Res.*, 2004, Abstract No. 3799.

Zhang et al., "The novel synthetic oleanane triterpenoid CDDO (2-cyano-3,12-dioxoolean-1,9-dien-28-oic acid) induces apoptosis in Mycosis fungoides/Sézary syndrome cells," *J. Invest. Dermatol.*, 2004, 123:380-387.

Zhou et al., "A new triterpenoid from the roots of *Tripterygium wildfordii*," *Chinese Chemical Letters*, 2010, 21(5):600-602.

Zhou et al., "Physical stability of amorphous pharmaceuticals: Importance of configurational thermodynamic quantities and molecule mobility," *J. Pharmaceutical Sciences*, 2002, 91(8):1863-1872.

Zou et al., "c-FLIP downregulation contributes to apoptosis induction by the novel synthetic triterpenoid methyl-2-cyano-3,12-dioxooleana-1,9-dien-28-oate (CDDO-Me) in human lung cancer cells," *Cancer Biology & Therapy*, 6(10):1614-1620, 2007.

Zou et al., "c-Jun NH2-terminal kinase-mediated up-regulation of death receptor 5 contributes to induction of apoptois by the novel synthetic triterpenoid methyl-2-cyano-3,12-dioxooleana-1,9-dien-28-oate in human lung cancer cells," *Cancer Res.*, 2004, 64:7570.

Zou et al., "Coupling of endoplasmic reticulum stress to CDDO-Me-induced up-regulation of death receptor 5 via a CHOP-dependent mechanism involving JNK activation," *Cancer Res.*, 68:7484-7492, 2008.

Ichikawa et al., "Dihydro-CDDO-Trifluoroethyl Amide (dh404), a Novel Nrf2 Activator, Suppresses Oxidative Stress in Cardiomyocytes", PLoS One, 4(12):e8391, 2009.

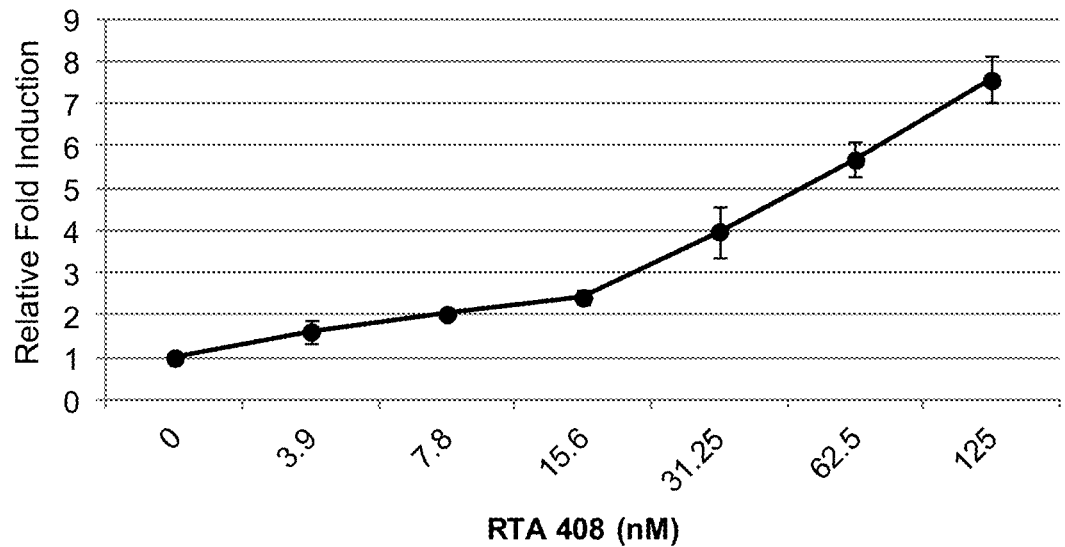
(a)
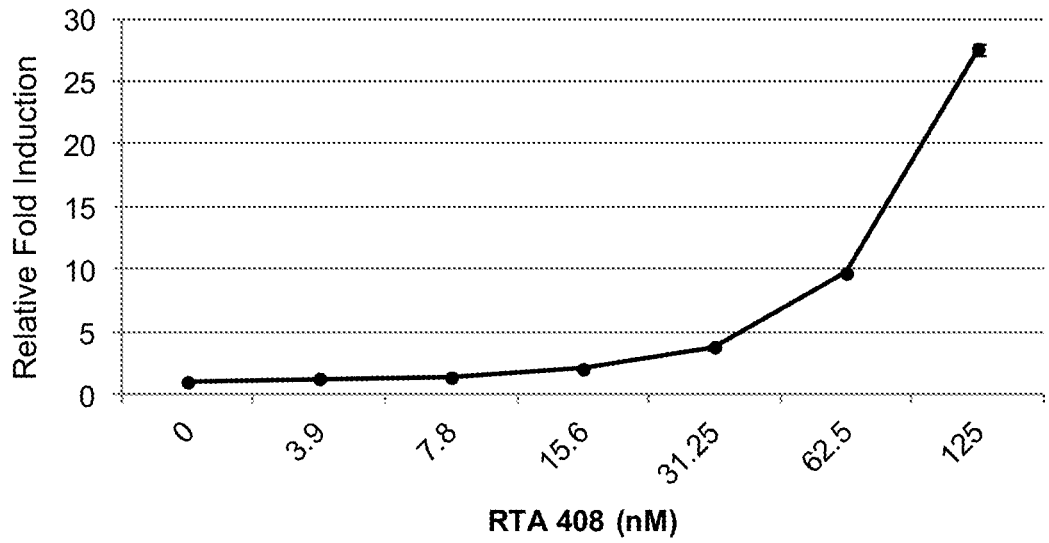
(b)
FIGS. 2a & b

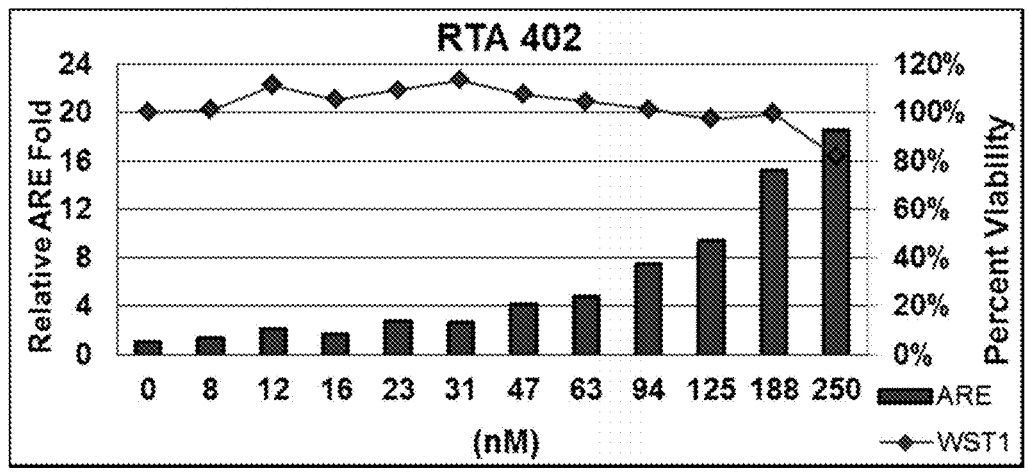
(a)
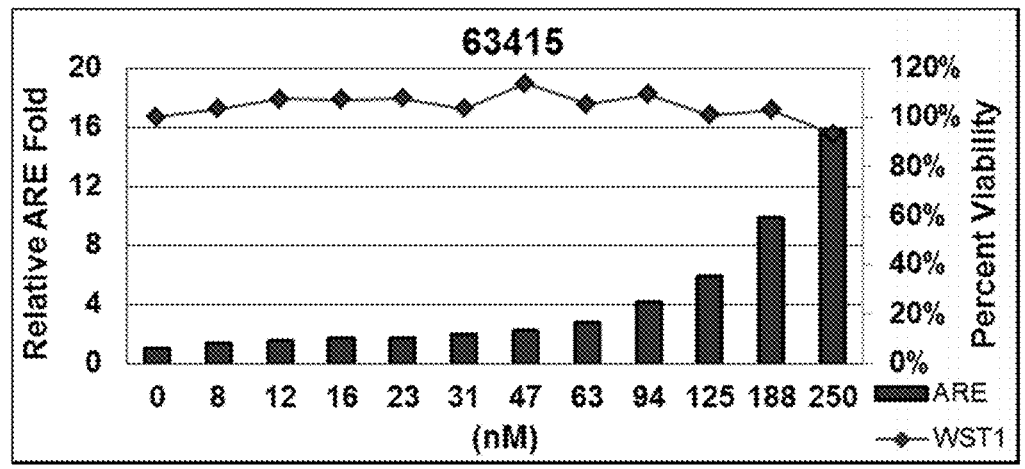
(b)
FIGS. 3a & b

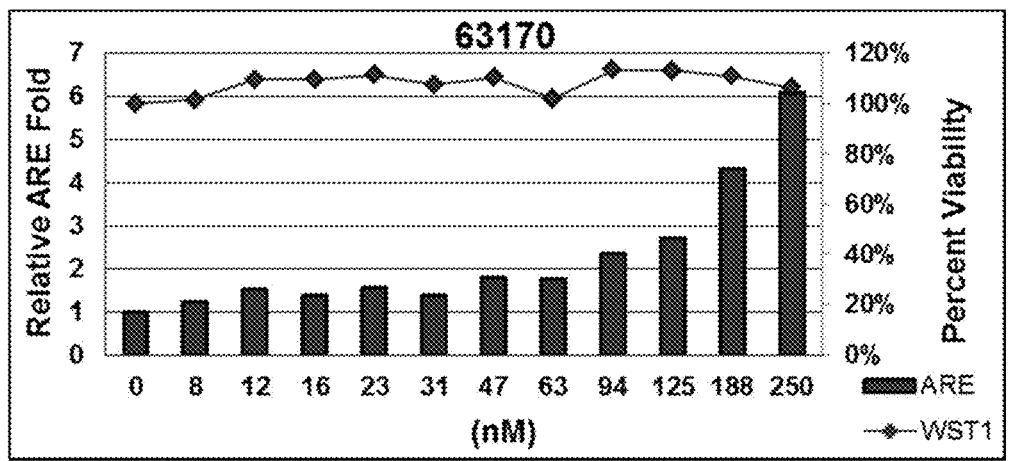
(c)
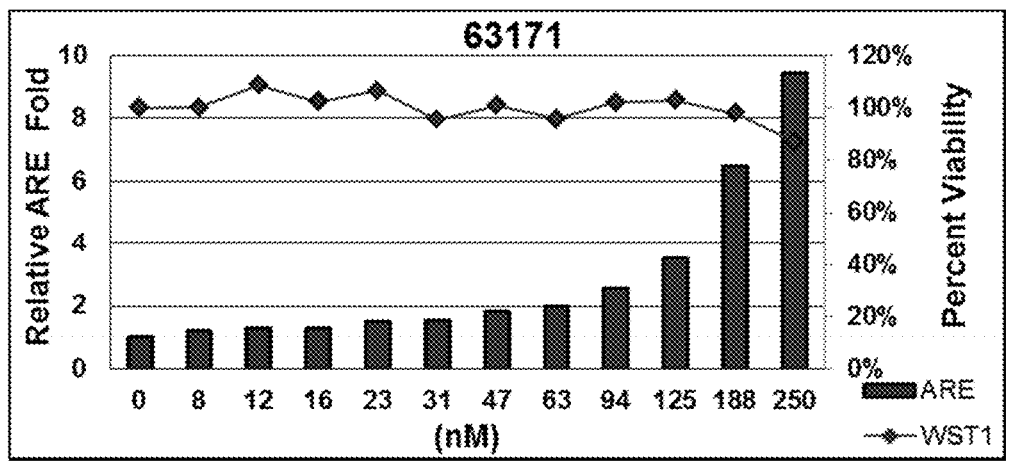
(d)
FIGS. 3c & d

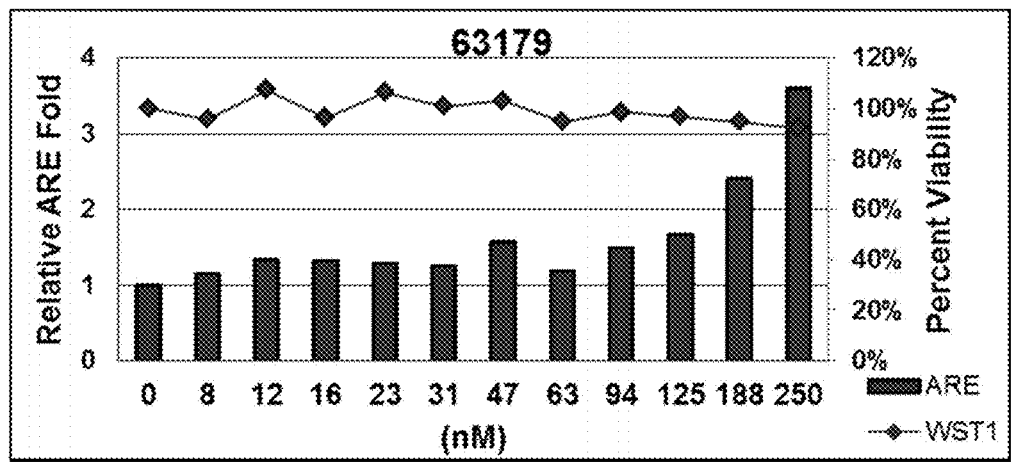
(e)
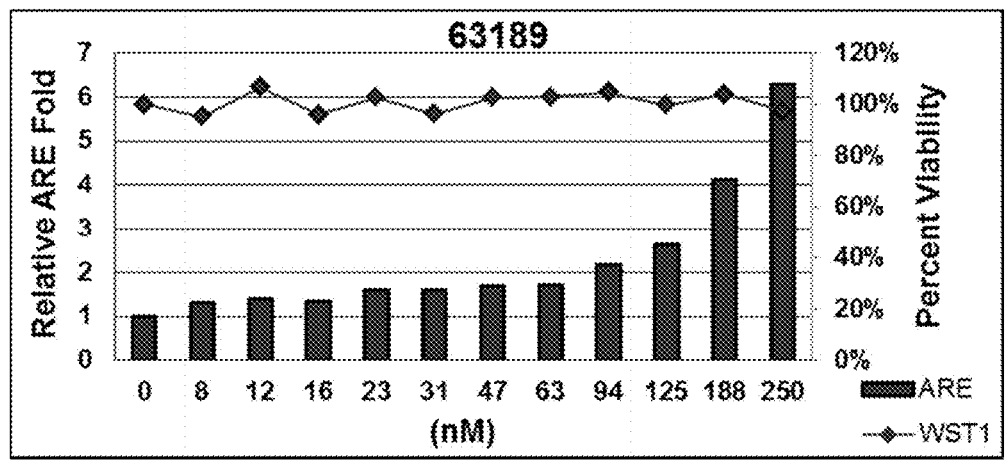
(f)
FIGS. 3e & f

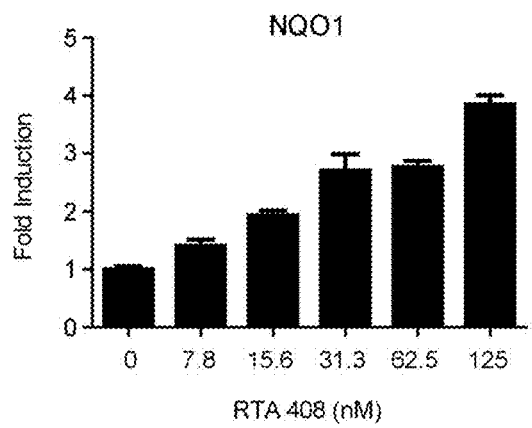
(a)
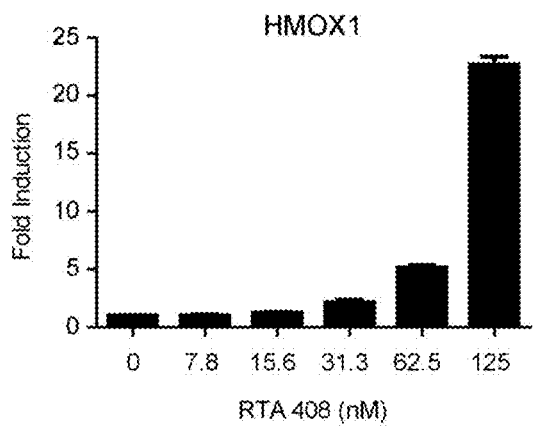
(b)
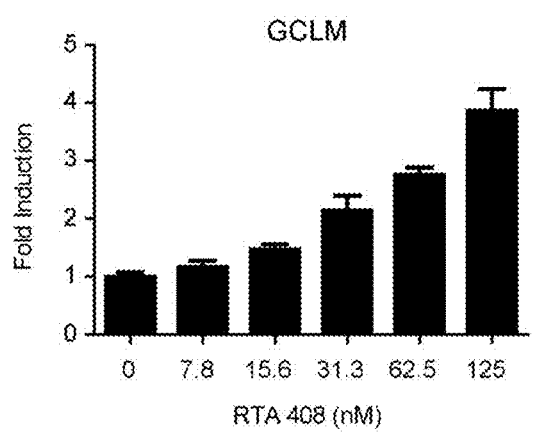
(c)
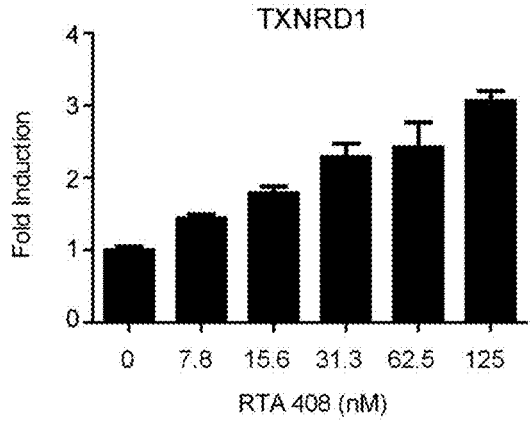
(d)
FIGS. 4a – d

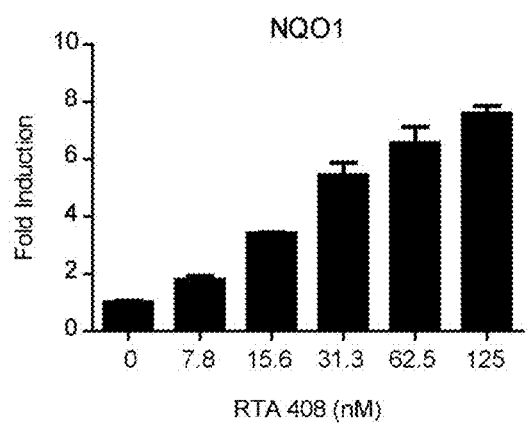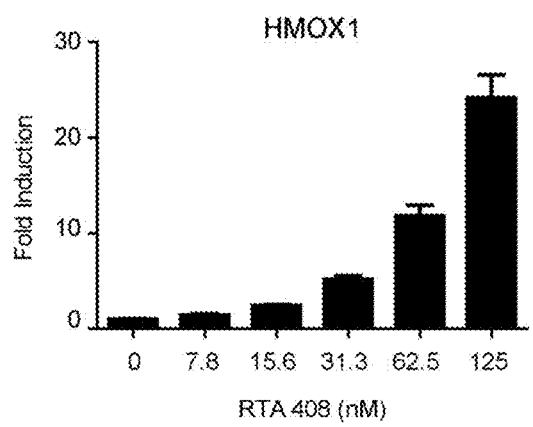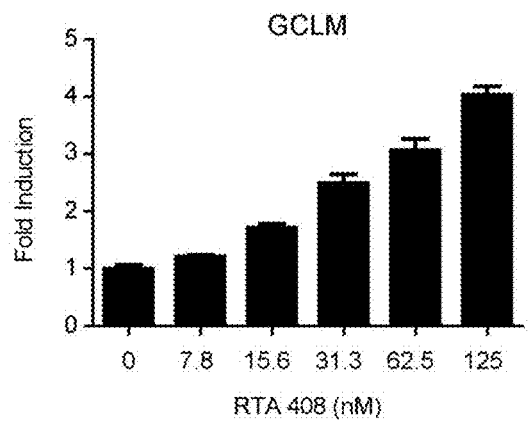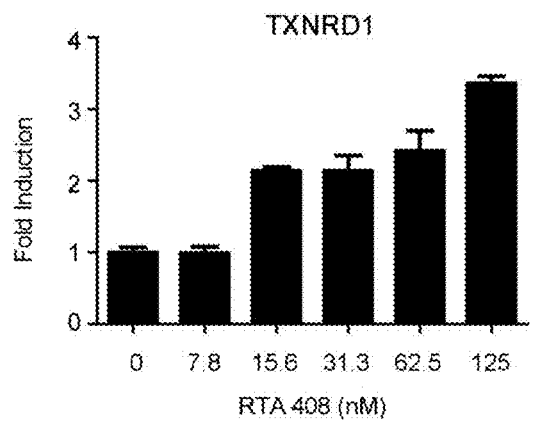
FIGS. 5a – d

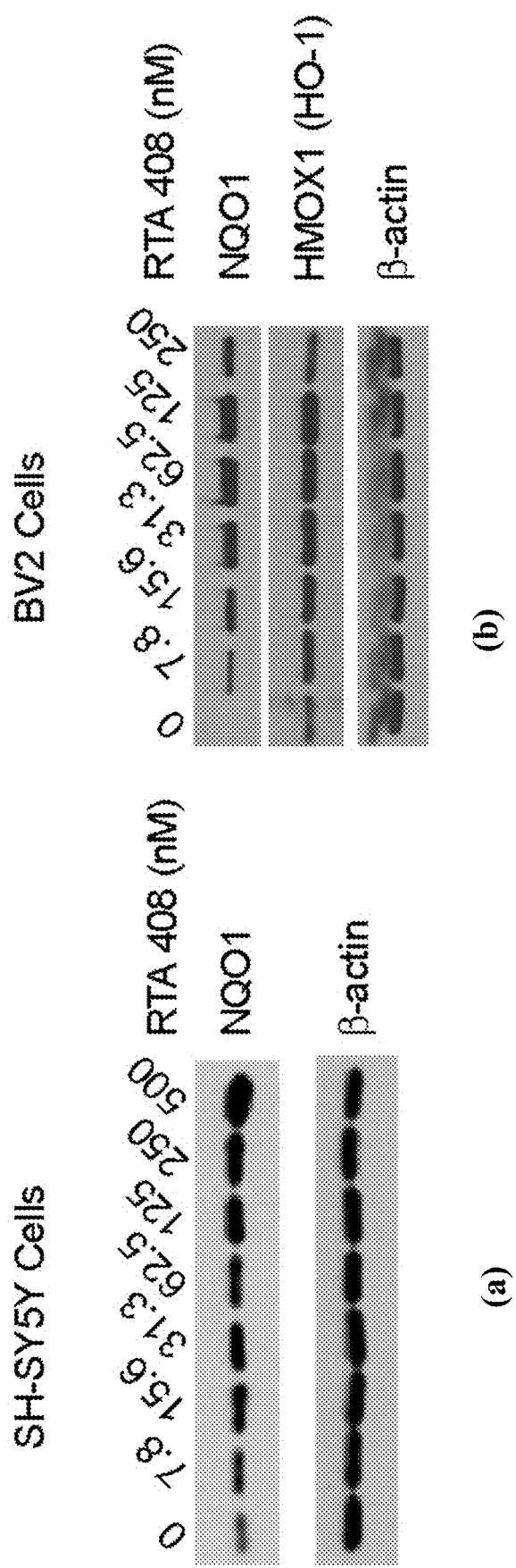
FIGS. 6a & b

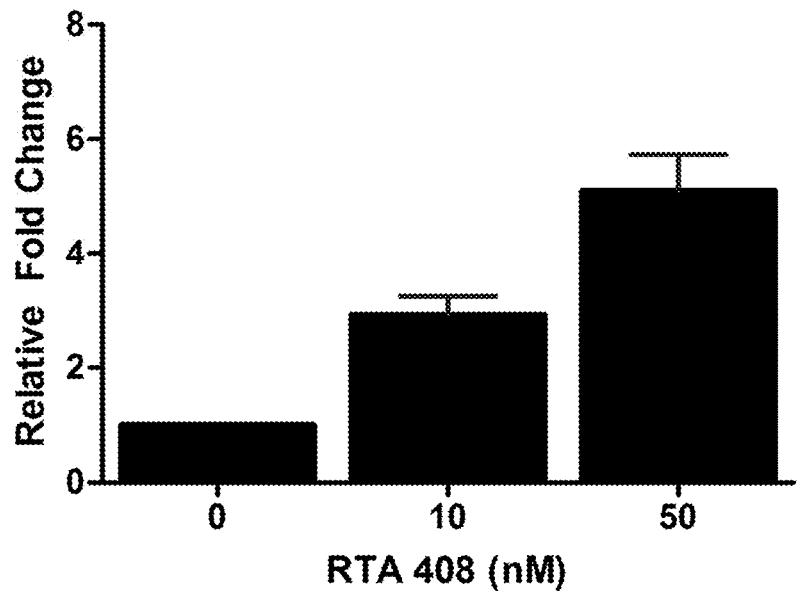
(a)
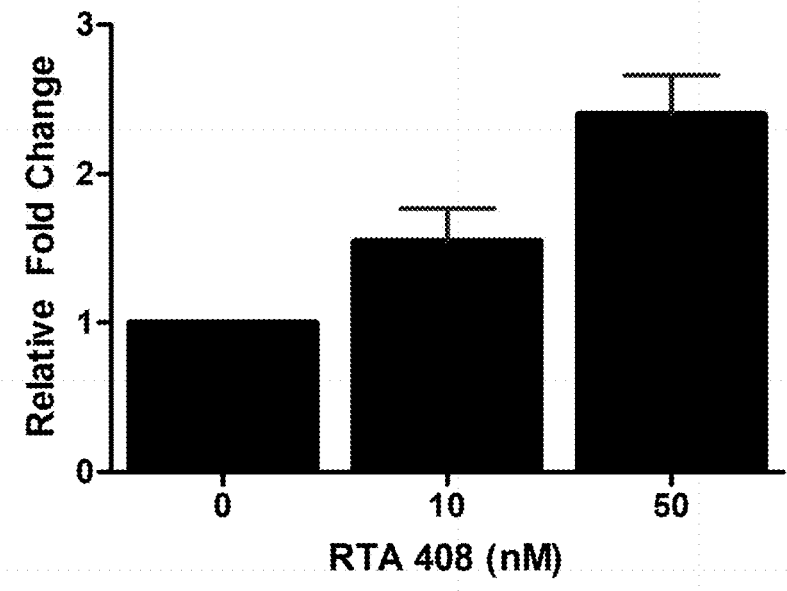
(b)
FIGS. 10a & b

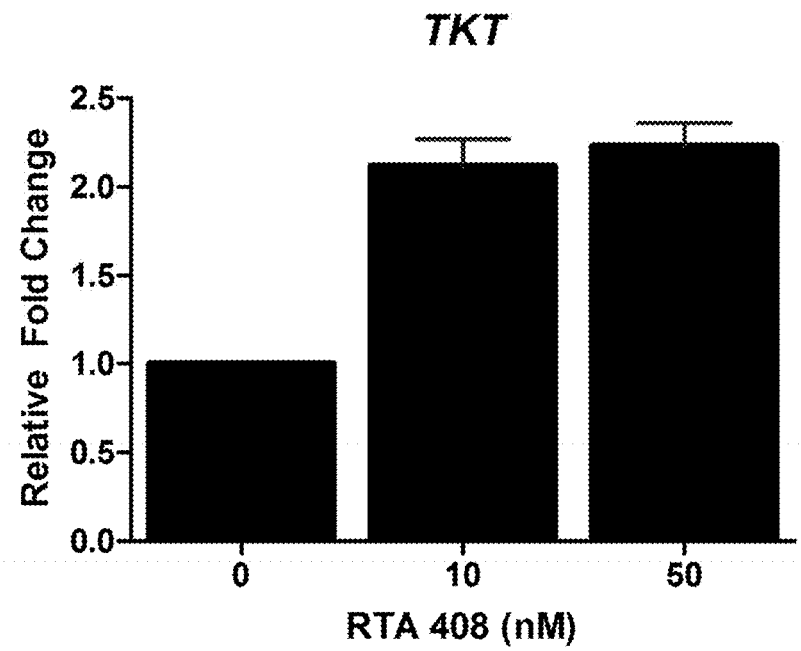
(c)
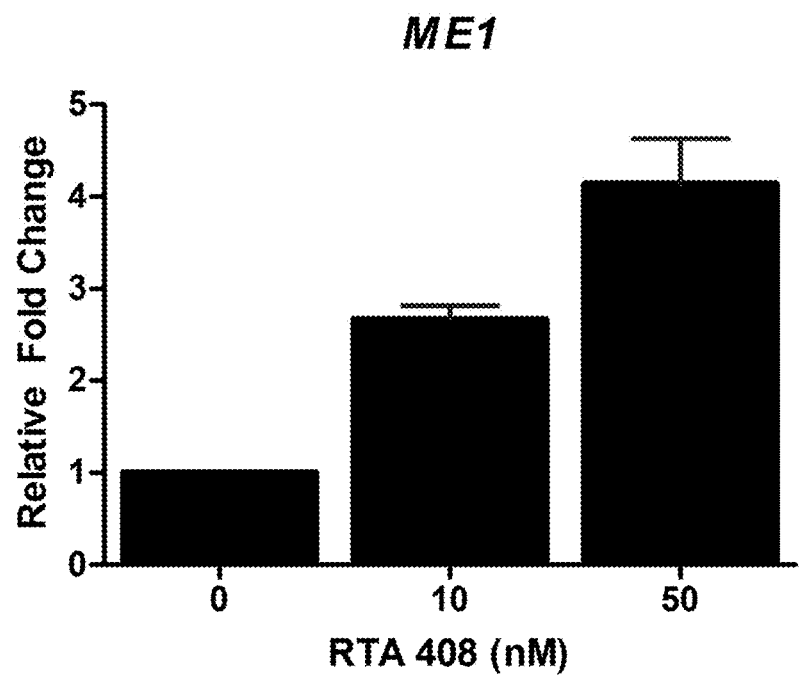
(d)
FIGS. 10c & d

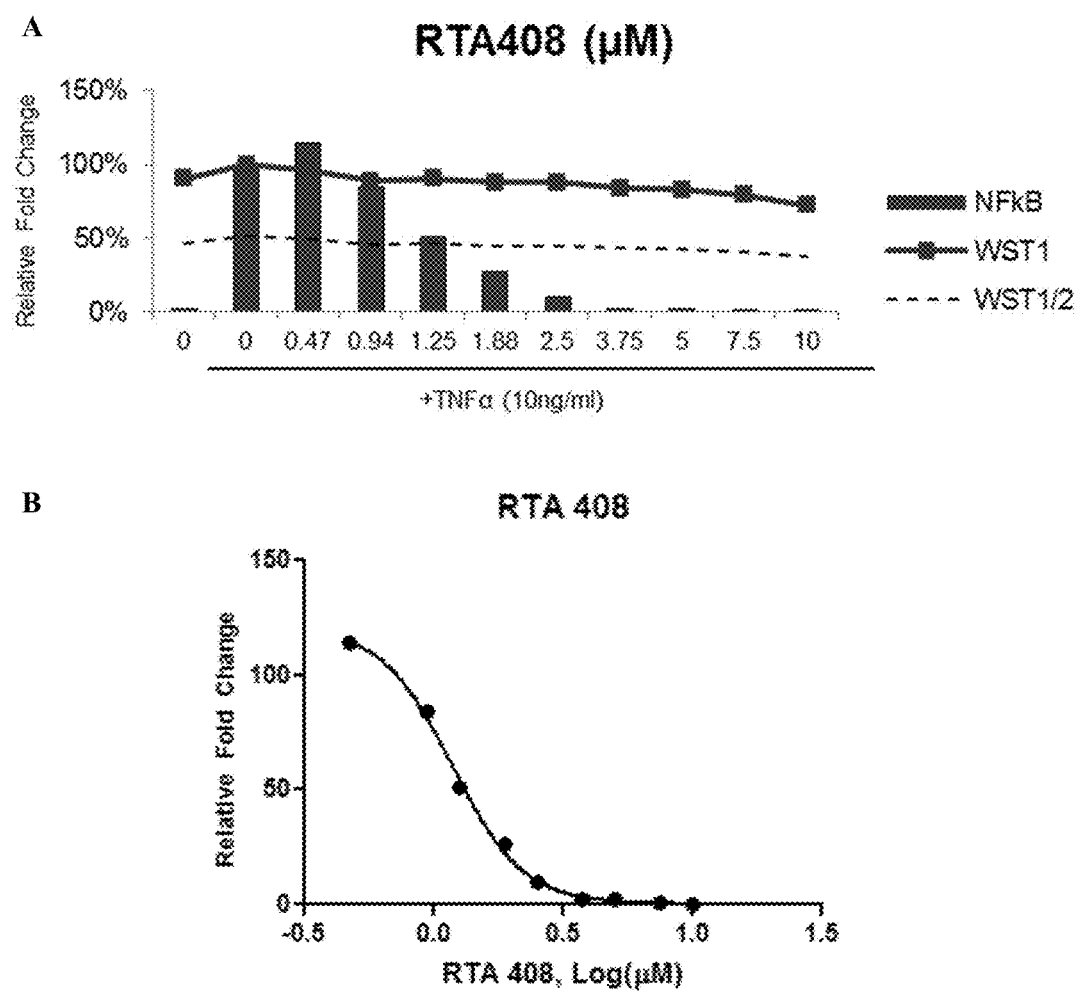
FIGS. 11a & b

FIGS. 13a & b

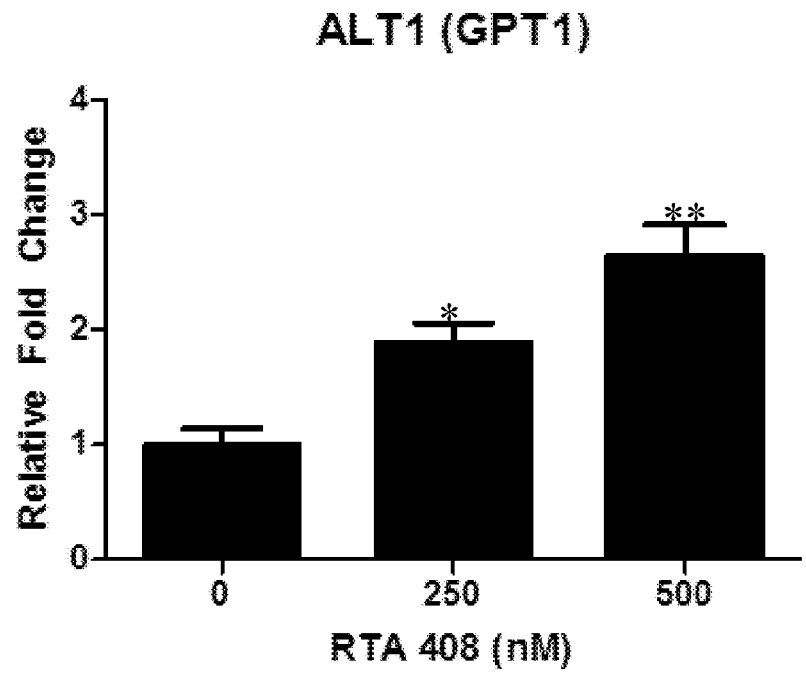
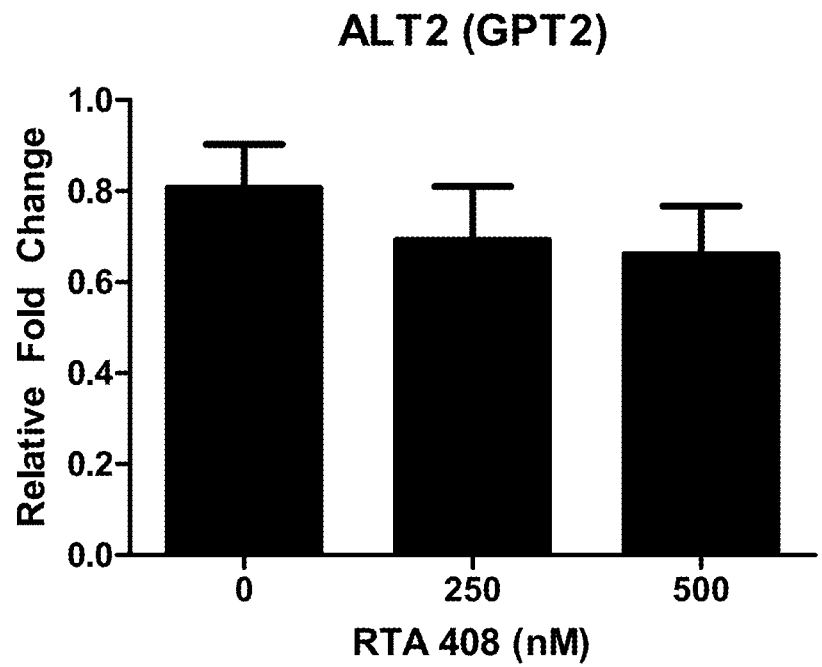
FIGS. 15a & b

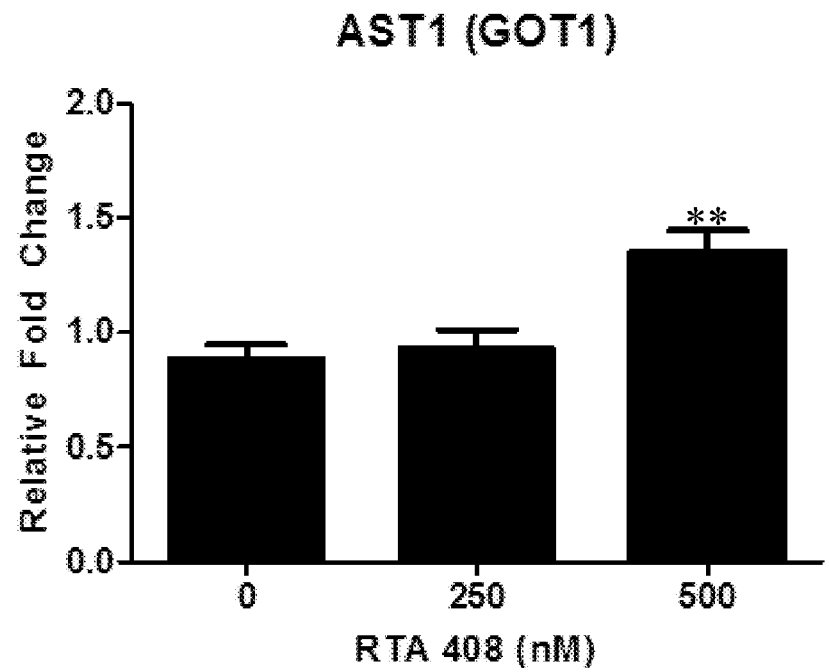
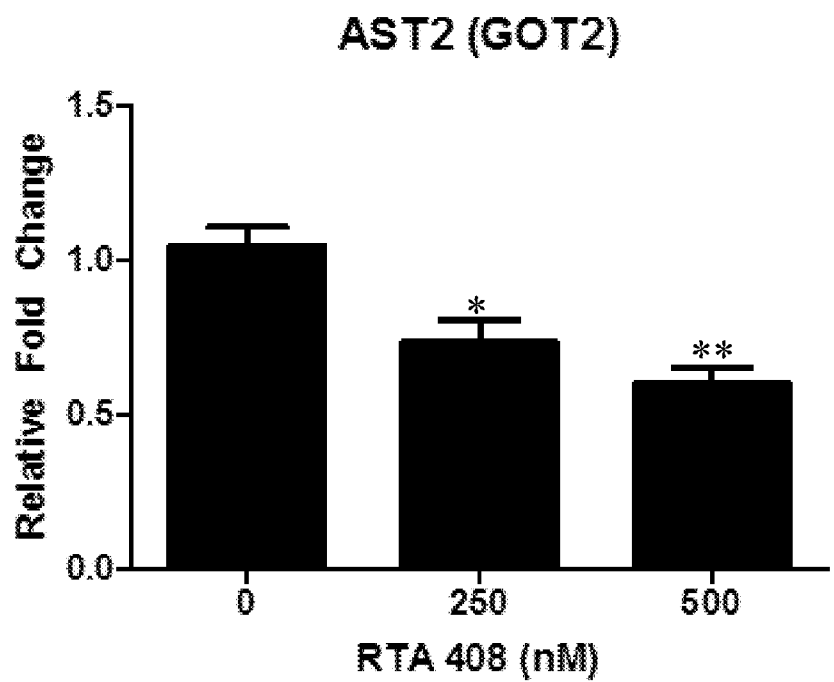
FIGS. 15c & d

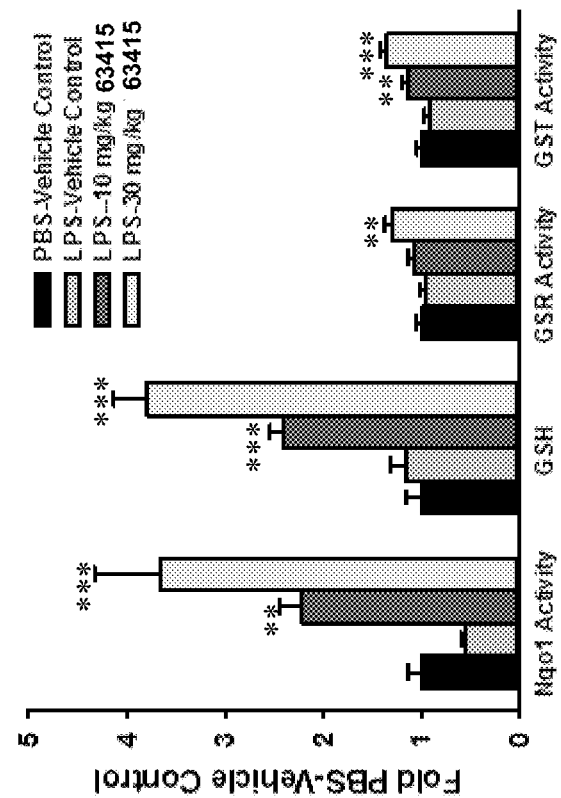
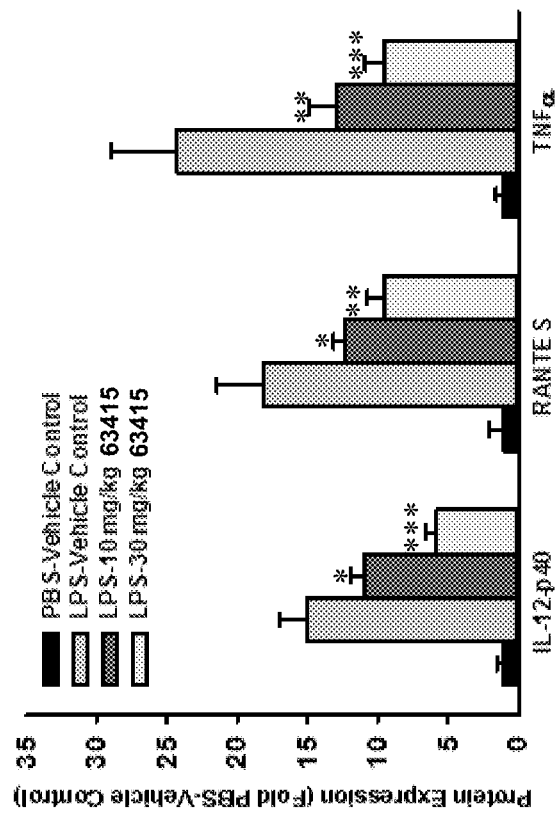
FIGS. 18a & b

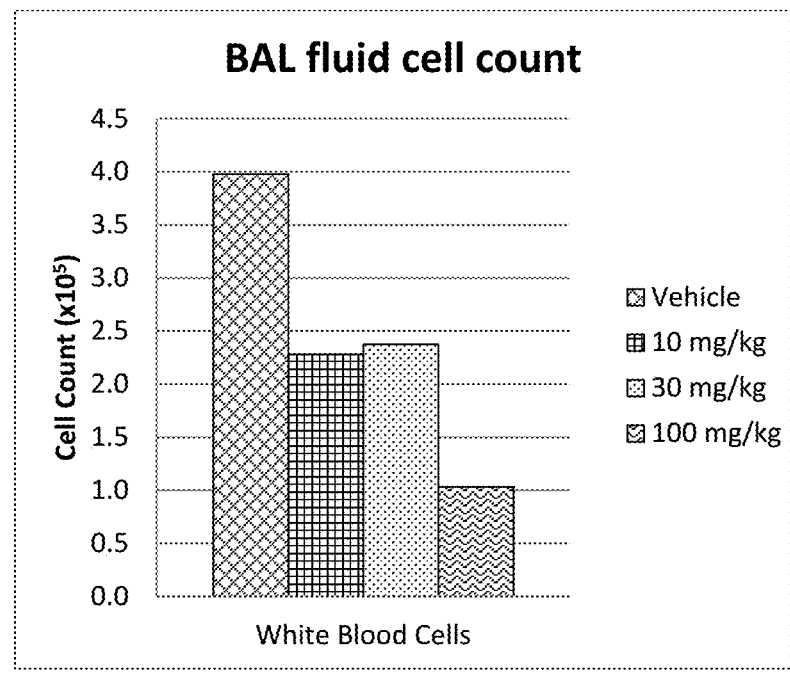
(a)
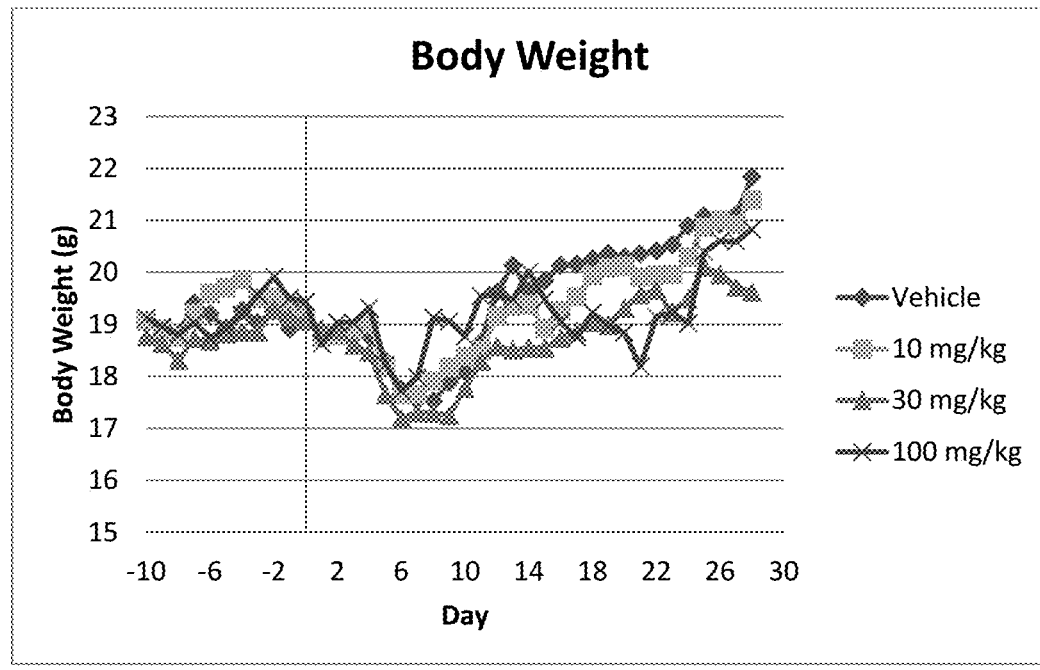
(b)
FIGS. 19a & b

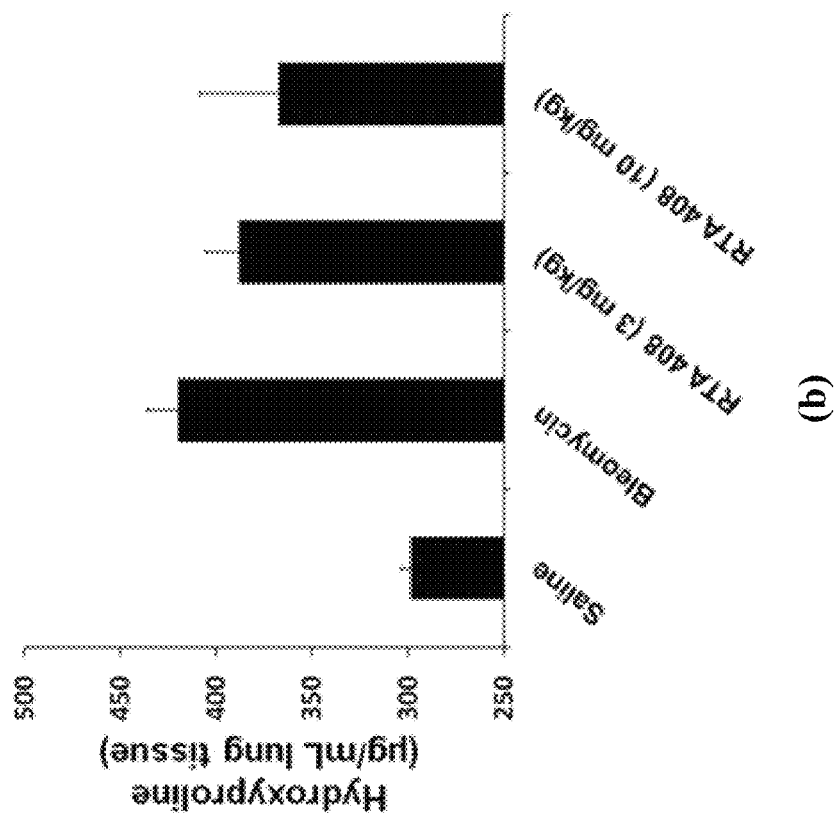
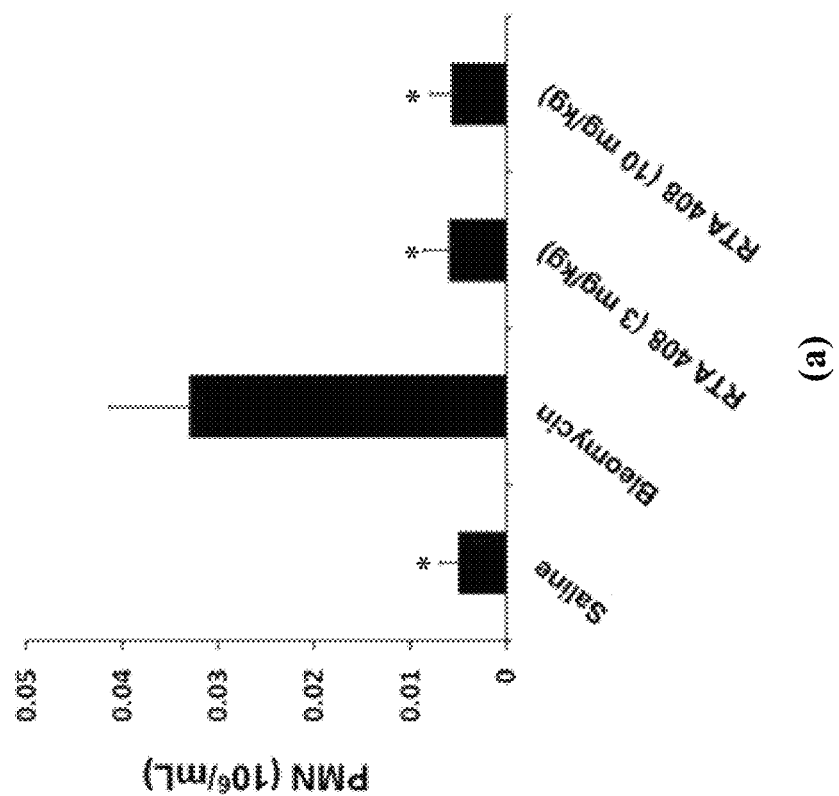
FIGS. 20a & b

FIGS. 22a – e

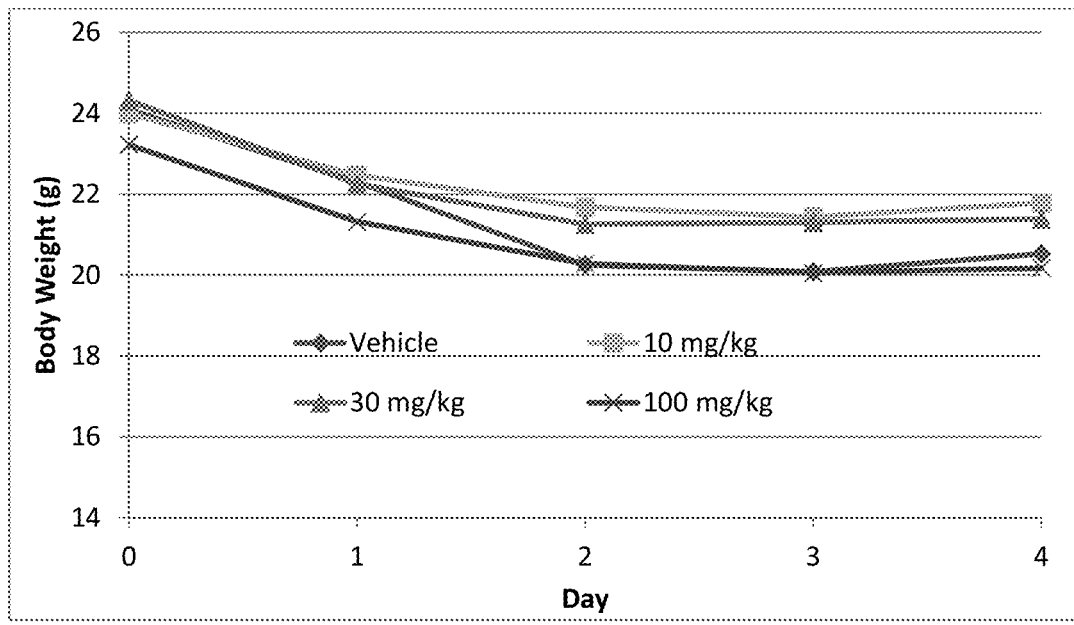
(a)
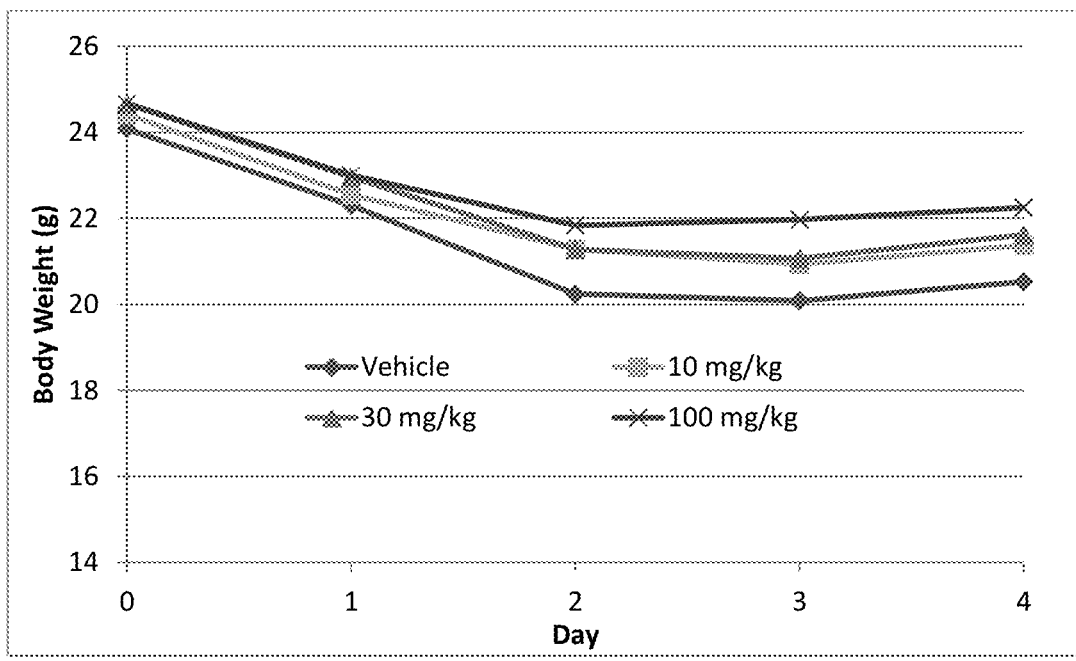
(b)
FIGS. 24a & b

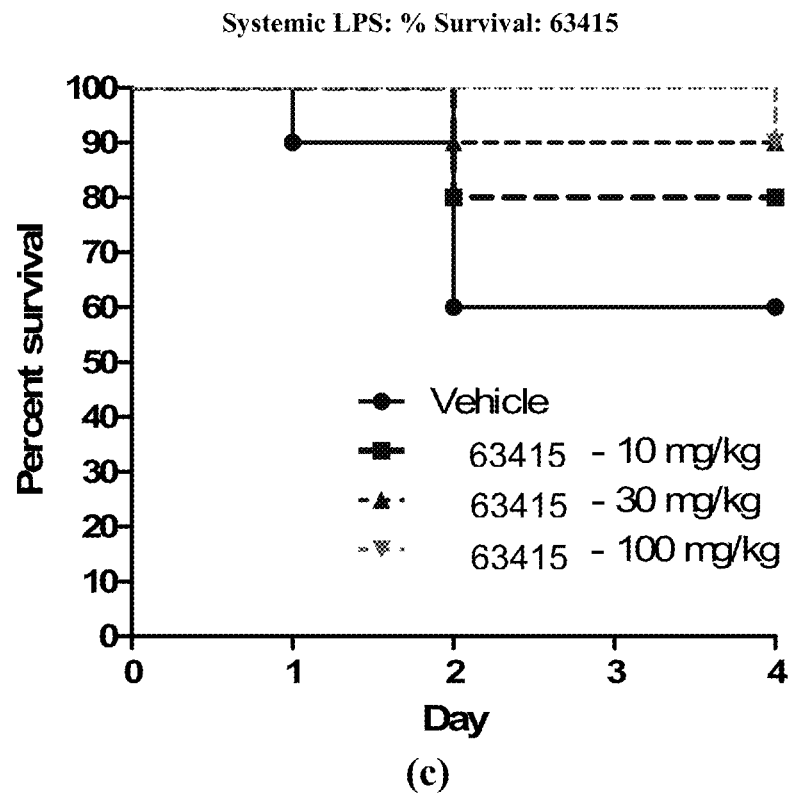
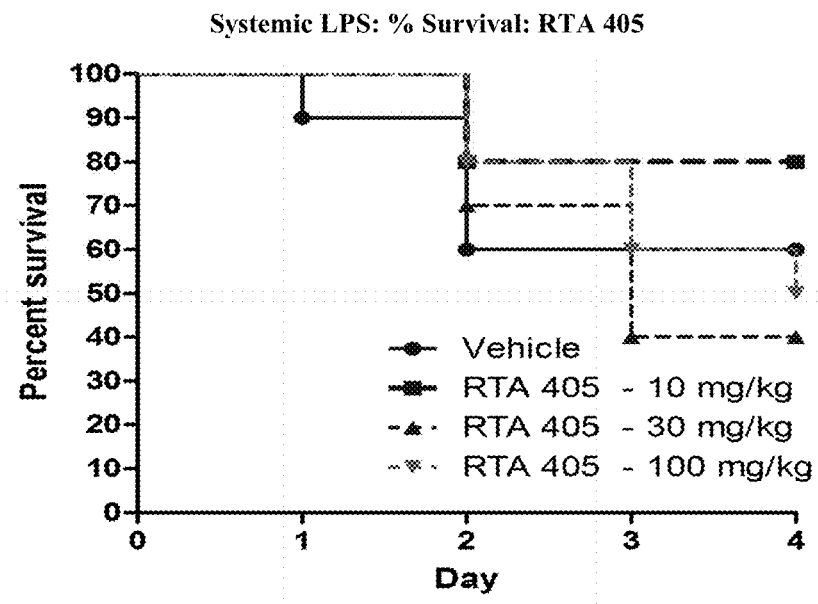
FIGS. 24c & d

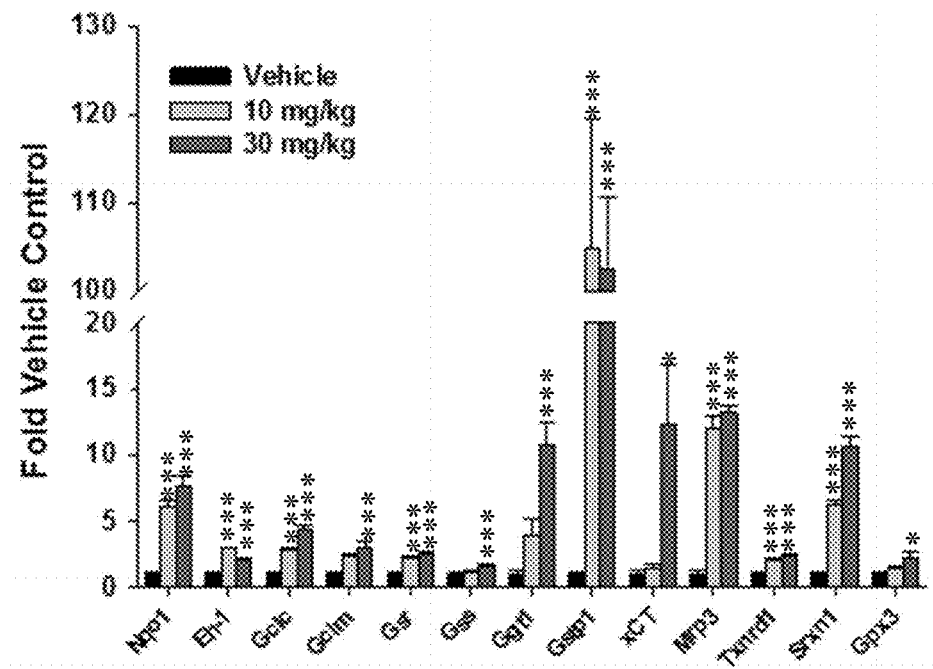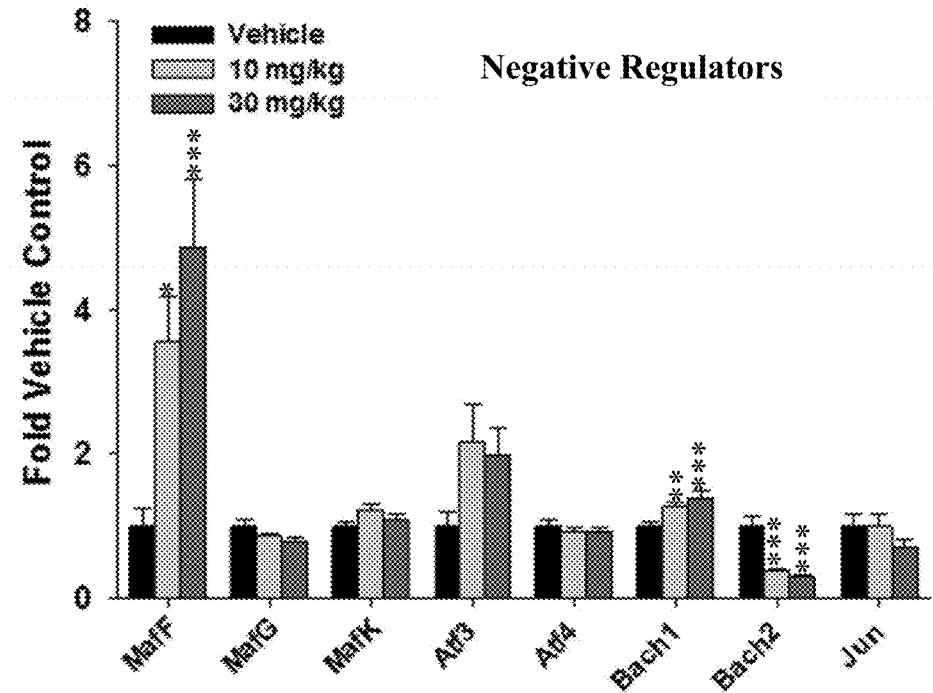
FIGS. 27a & b

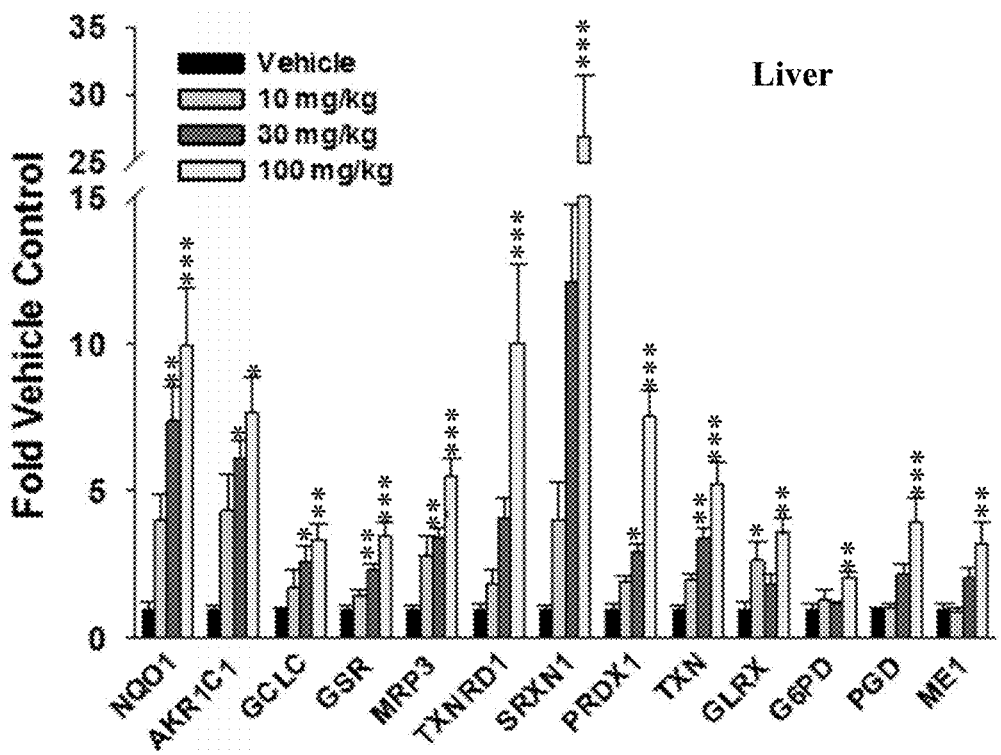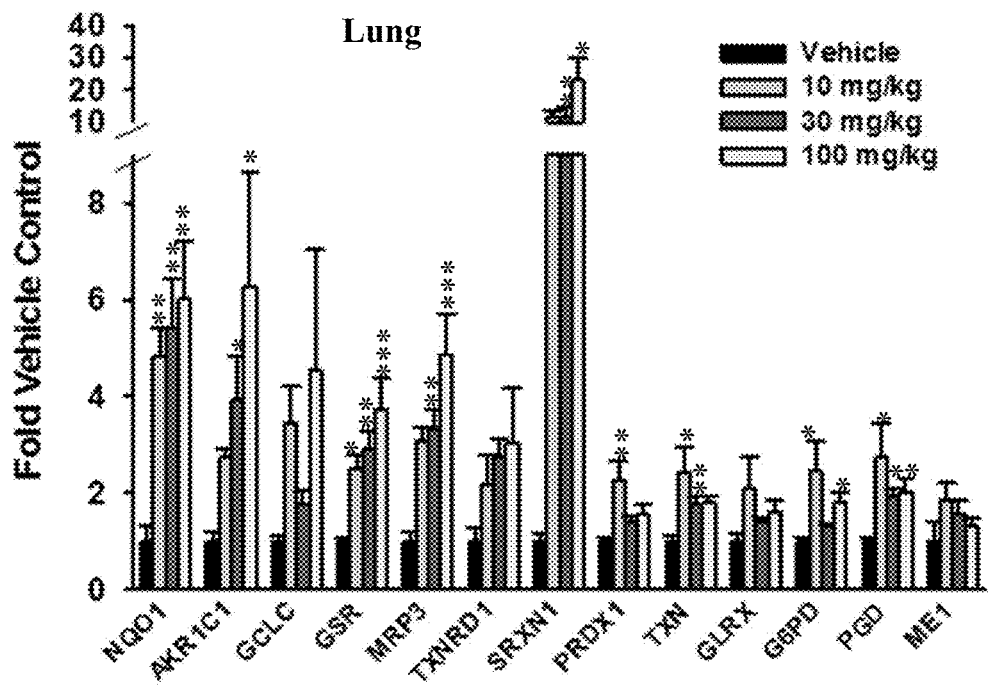
FIGS. 28a & b

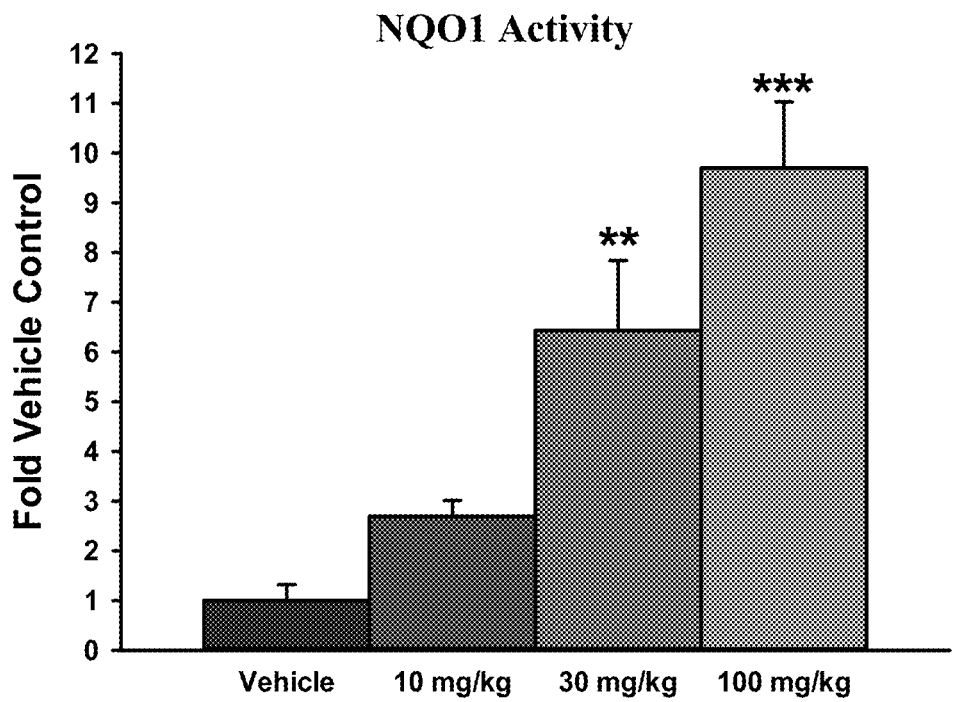
(a)
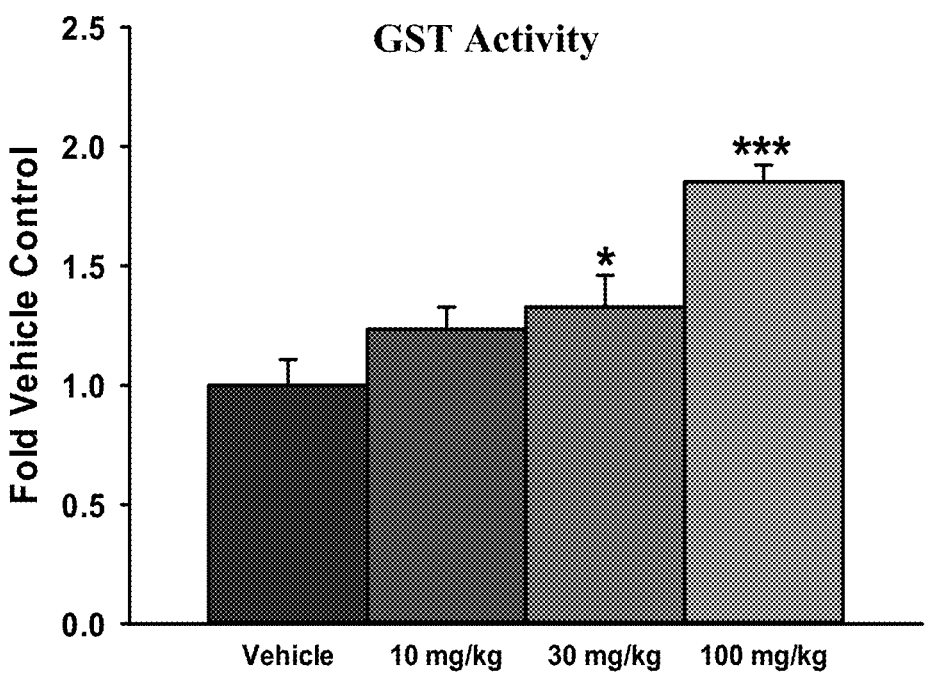
(b)
FIGS. 29a & b

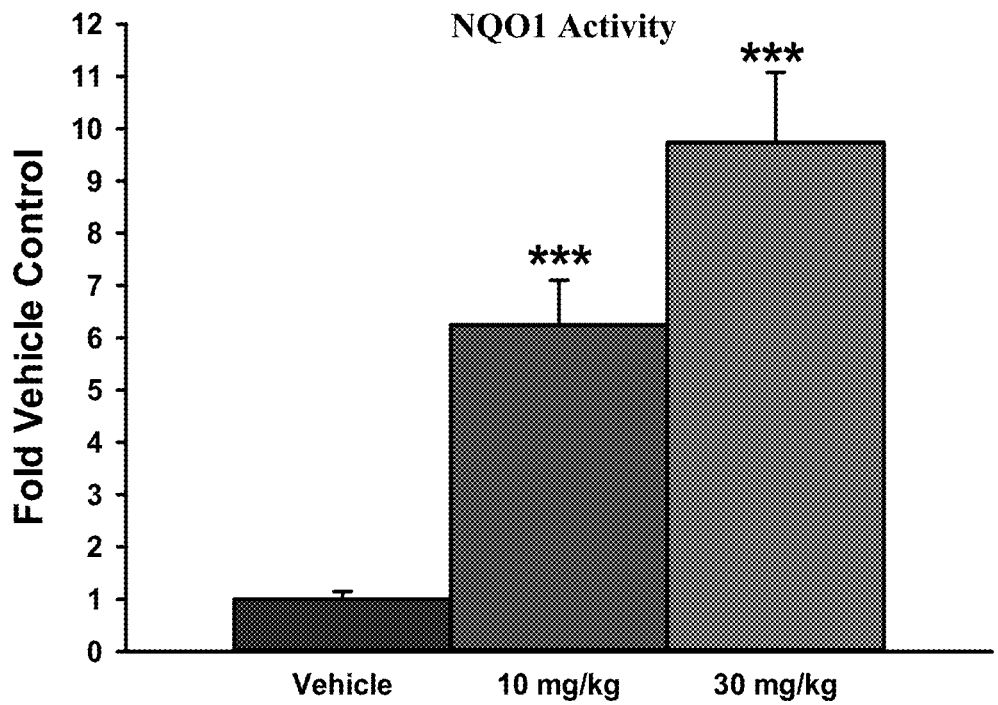
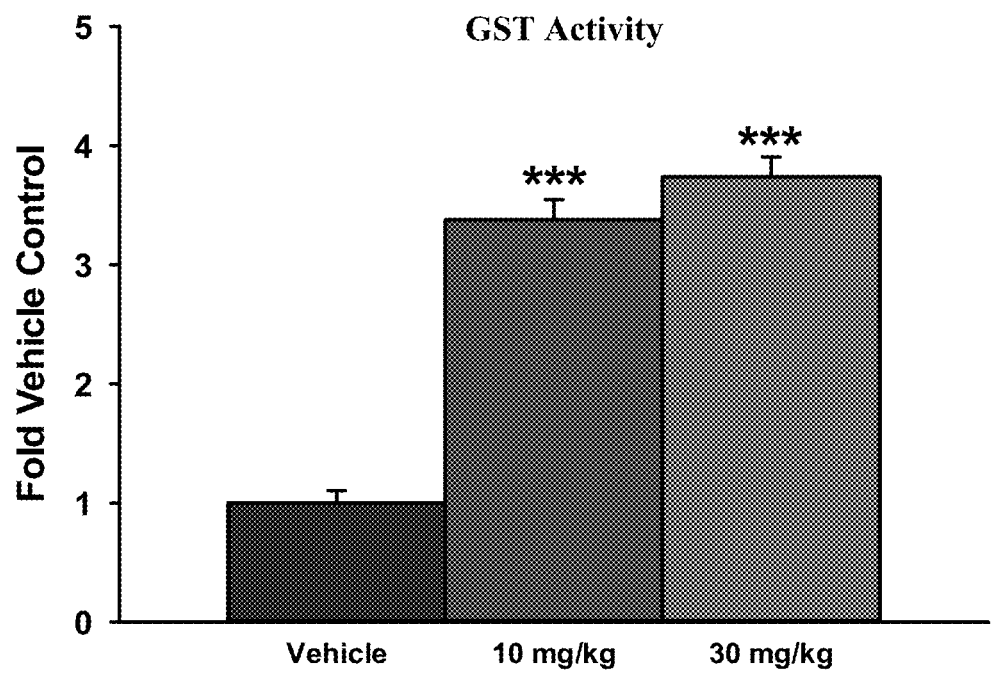
FIGS. 30a & b

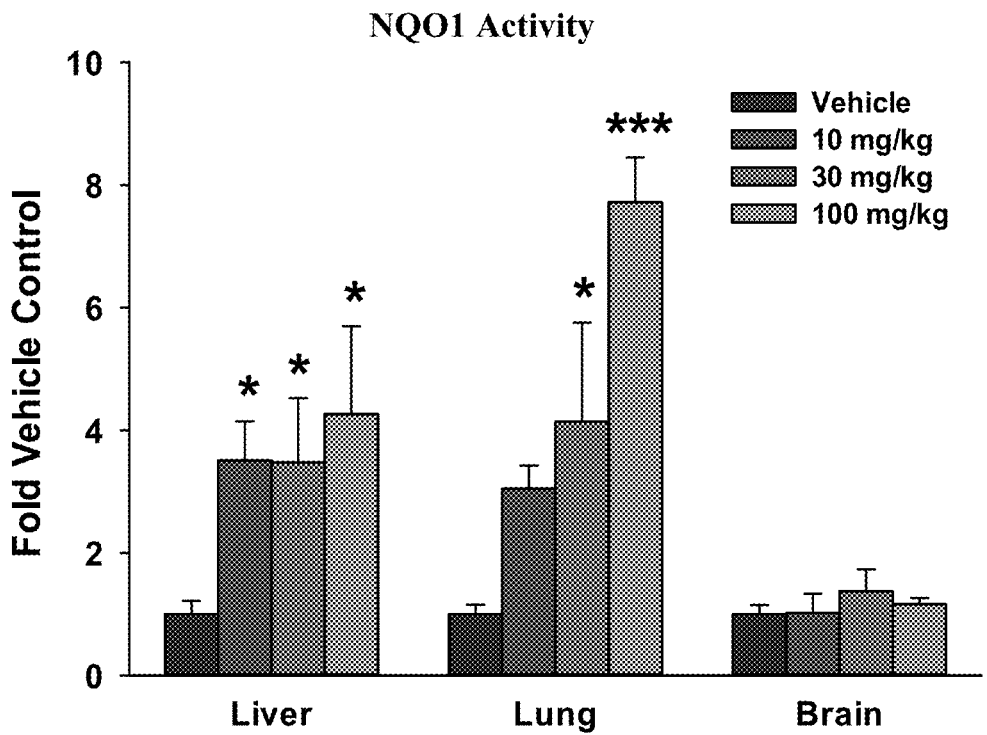
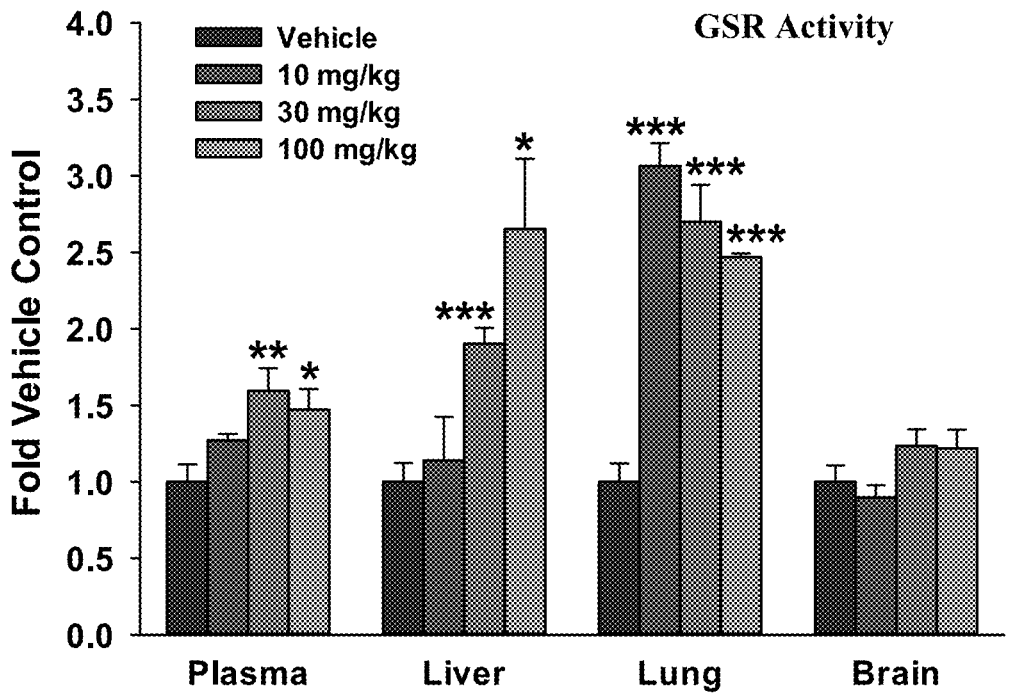
FIGS. 31a & b

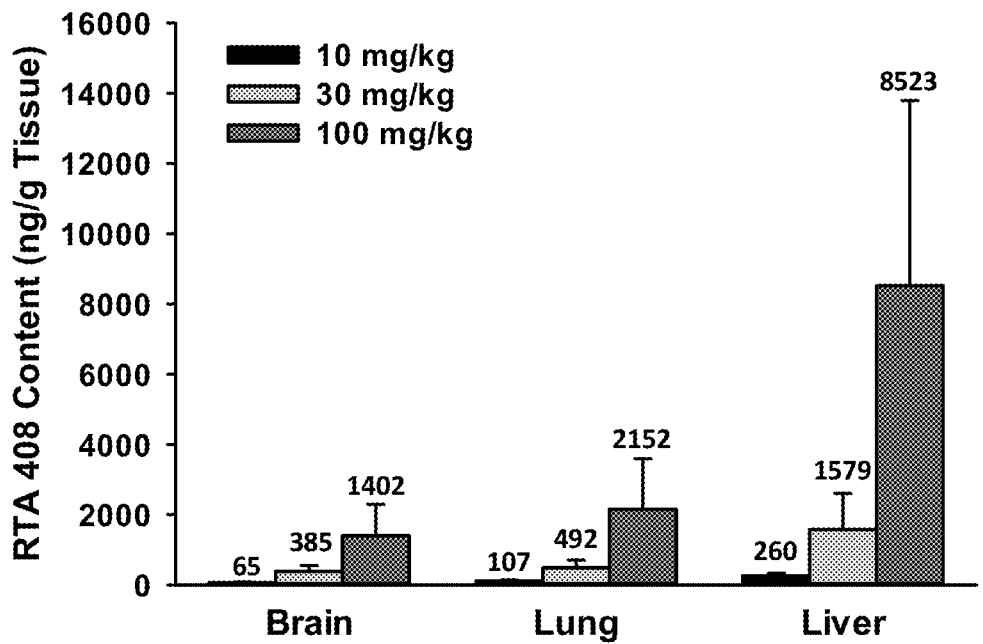
(a)
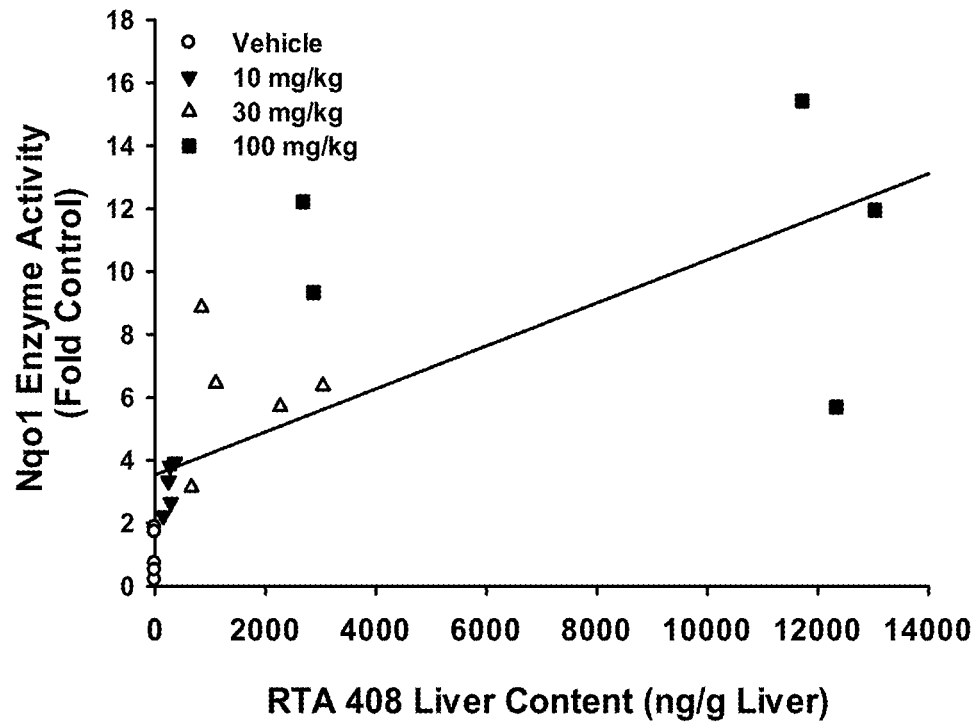
(b)
FIGS. 32a & b

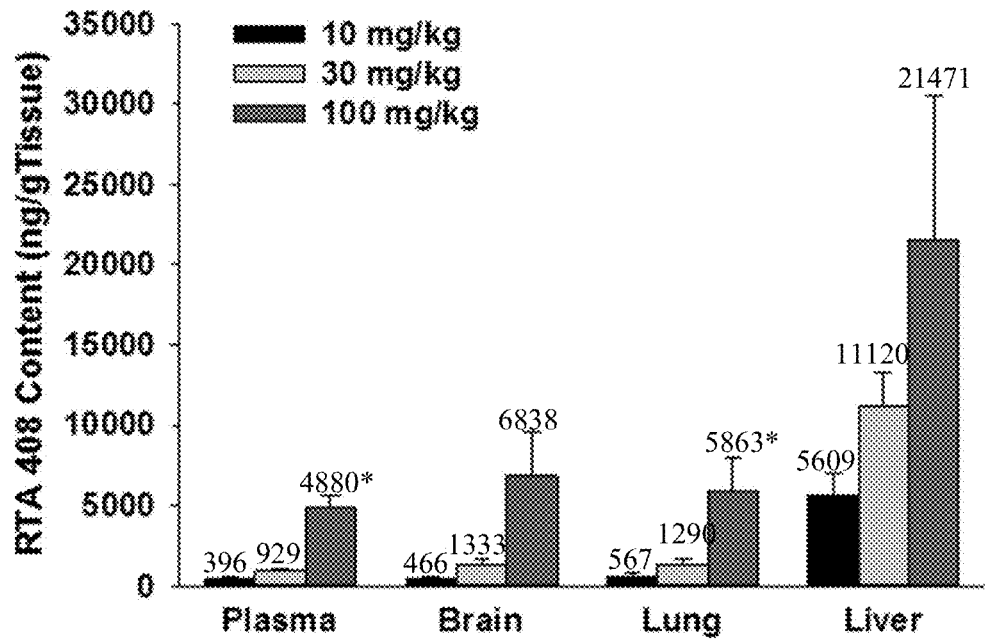
(a)
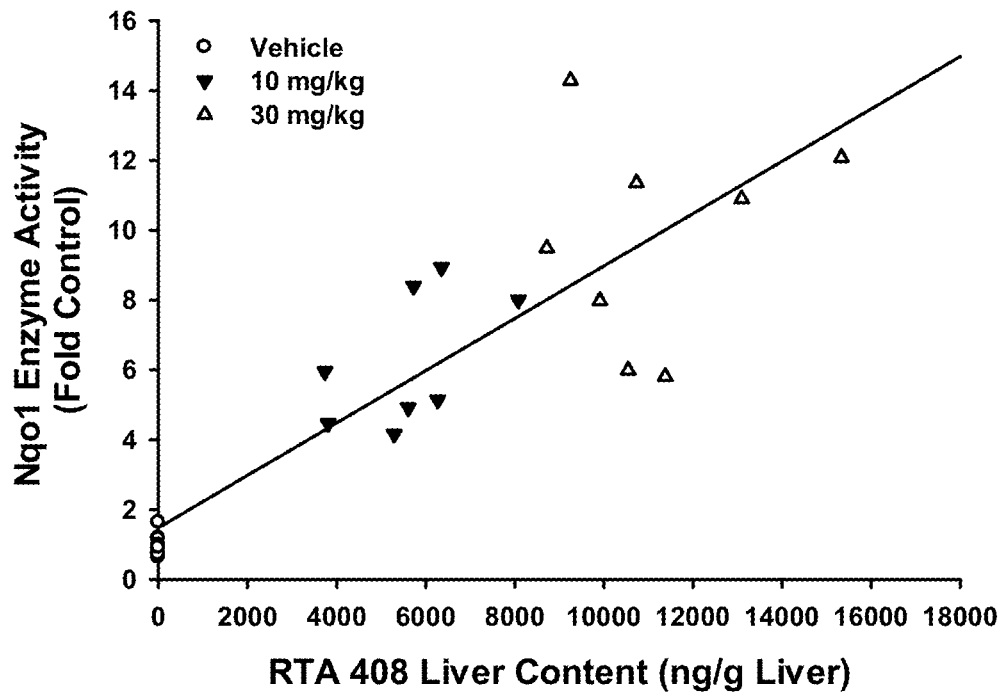
(b)
FIGS. 33a & b

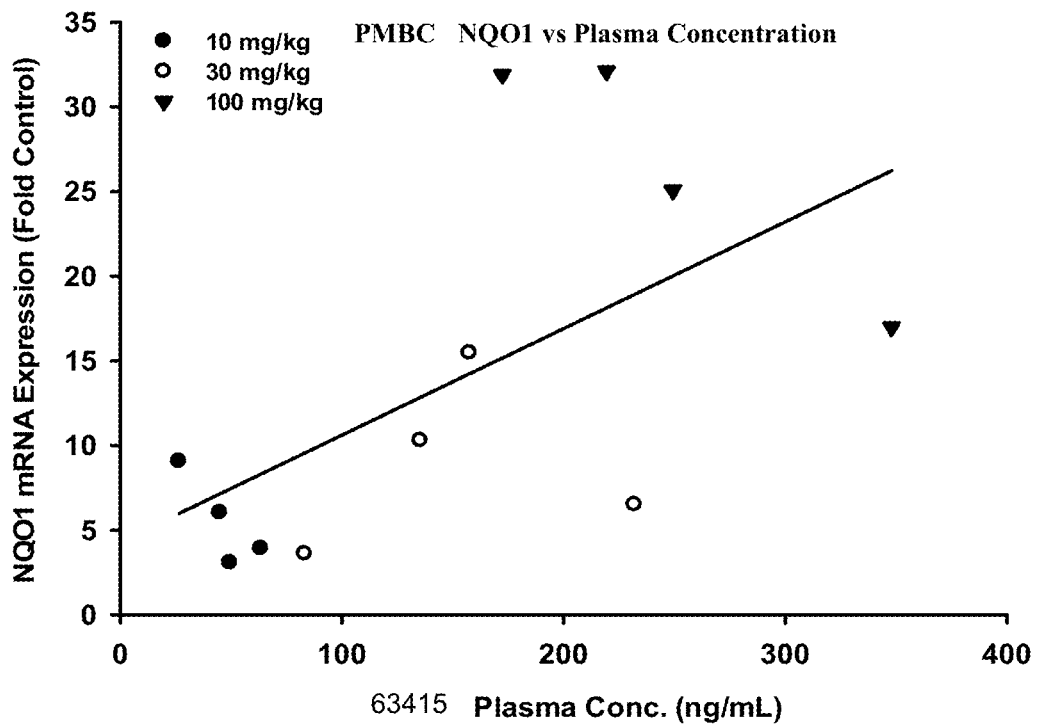
(a)
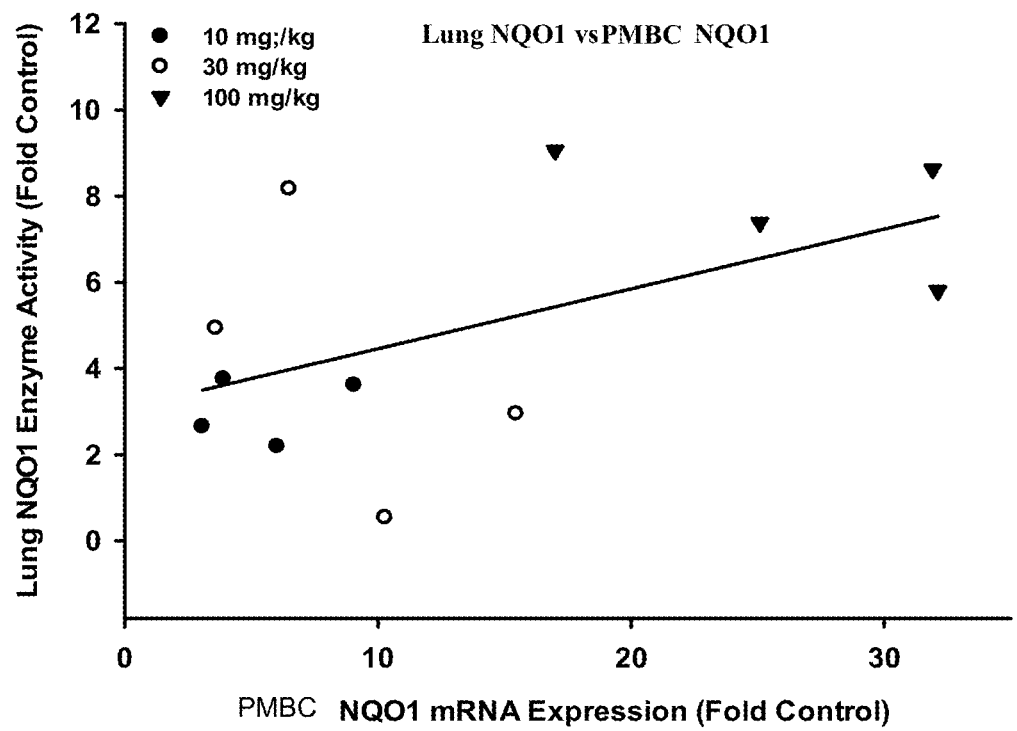
(b)
FIGS. 34a & b

FIGS. 37a & b

2,2-DIFLUOROPROPIONAMIDE DERIVATIVES OF BARDOXOLONE METHYL, POLYMORPHIC FORMS AND METHODS OF USE THEREOF

The present application is a continuation application of U.S. patent application Ser. No. 15/622,568, filed Jun. 14, 2017, which is a continuation application of U.S. patent application Ser. No. 14/625,829, filed Feb. 19, 2015, now U.S. Pat. No. 9,701,709, which is a continuation of U.S. patent application Ser. No. 13/869,833, filed Apr. 24, 2013, now U.S. Pat. No. 8,993,640, which claims the benefit of priority to U.S. Provisional Application No. 61/780,444, filed on Mar. 13, 2013, U.S. Provisional Application No. 61/775,288, filed on Mar. 8, 2013, and U.S. Provisional Application No. 61/687,669, filed on Apr. 27, 2012; the entire contents of each are herein incorporated by reference.

Pursuant to 37 C.F.R. 1.821(c), a sequence listing is submitted herewith as an ASCII compliant text file named "REATP0073USC3_ST25," created on Jun. 24, 2021 and having a size of ~7 kilobytes. The content of the aforementioned file is hereby incorporated by reference in its entirety.

BACKGROUND OF THE INVENTION

I. Field of the Invention

The present invention relates generally to the compound: N-((4aS,6aR,6bS,8aR,12aS,14aR,14bS)-11-cyano-2,2,6a, 6b,9,9,12a-heptamethyl-10,14-dioxo-1,2,3,4,4a,5,6,6a, 6b,7,8,8a,9,10,12a,14,14a,14b-octadecahydropicen-4a-yl)-2,2-difluoropropanamide, also referred to herein as RTA 408, 63415, or PP415. The present invention also relates to polymorphic forms thereof, methods for preparation and use thereof, pharmaceutical compositions thereof, and kits and articles of manufacture thereof.

II. Description of Related Art

The anti-inflammatory and anti-proliferative activity of the naturally occurring triterpenoid, oleanolic acid, has been improved by chemical modifications. For example, 2-cyano-3,12-dioxooleana-1,9(11)-dien-28-oic acid (CDDO) and related compounds have been developed. See Honda et al., 1997; Honda et al., 1998; Honda et al., 1999; Honda et al., 2000a; Honda et al., 2000b; Honda et al., 2002; Suh et al., 1998; Suh et al., 1999; Place et al., 2003; Liby et al., 2005; and U.S. Pat. Nos. 8,129,429, 7,915,402, 8,124,799, and 7,943,778, all of which are incorporated herein by reference. The methyl ester, bardoxolone methyl (CDDO-Me), has been evaluated in phase II and III clinical trials for the treatment and prevention of diabetic nephropathy and chronic kidney disease. See Pergola et al., 2011, which is incorporated herein by reference.

Synthetic triterpenoid analogs of oleanolic acid have also been shown to be inhibitors of cellular inflammatory processes, such as the induction by IFN-γ of inducible nitric oxide synthase (iNOS) and of COX-2 in mouse macrophages. See Honda et al, (2000a), Honda et al. (2000b), Honda et al. (2002), and U.S. Pat. Nos. 8,129,429, 7,915,402, 8,124,799, and 7,943,778, which are all incorporated herein by reference. Compounds derived from oleanolic acid have been shown to affect the function of multiple protein targets and thereby modulate the activity of several important cellular signaling pathways related to oxidative stress, cell cycle control, and inflammation (e.g., Dinkova-Kostova et al., 2005; Ahmad et al., 2006; Ahmad et al., 2008; Liby et al., 2007a, and U.S. Pat. Nos. 8,129,429, 7,915,402, 8,124, 799, and 7,943,778).

Given that the biological activity profiles of known triterpenoid derivatives vary, and in view of the wide variety of diseases that may be treated or prevented with compounds having potent antioxidant and anti-inflammatory effects, and the high degree of unmet medical need represented within this variety of diseases, it is desirable to synthesize new compounds with different biological activity profiles for the treatment or prevention of one or more indications.

SUMMARY OF THE INVENTION

In some aspects of the present invention, there is provided a compound of the formula (also referred to herein as RTA 408, 63415, or PP415):

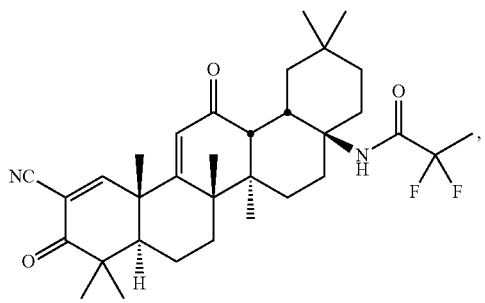

or a pharmaceutically acceptable salt thereof.

In some embodiments, the compound is in the form of a pharmaceutically acceptable salt. In some embodiments, the compound is not in the form of a salt.

In another aspect of the present invention, there are provided polymorphic forms of the above compound. In some embodiments, the polymorphic form has an X-ray powder diffraction pattern (CuKα) comprising a halo peak at about 14° 2θ. In some embodiments, the X-ray powder diffraction pattern (CuKα) further comprises a shoulder peak at about 8° 2θ. In some embodiments, the X-ray powder diffraction pattern (CuKα) is substantially as shown in FIG. 59. In some embodiments, the polymorphic form has a $T_g$ from about 150° C. to about 155° C., including, for example, a $T_g$ of about 153° C. or a $T_g$ of about 150° C. In some embodiments, the polymorphic form has a differential scanning calorimetry (DSC) curve comprising an endotherm centered from about 150° C. to about 155° C. In some embodiments, the endotherm is centered at about 153° C. In some embodiments, the endotherm is centered at about 150° C. In some embodiments, the differential scanning calorimetry (DSC) curve is substantially as shown in FIG. 62.

In some embodiments, the polymorphic form is a solvate having an X-ray powder diffraction pattern (CuKα) comprising peaks at about 5.6, 7.0, 10.6, 12.7, and 14.6°2θ.

In some embodiments, the X-ray powder diffraction pattern (CuKα) is substantially as shown in FIG. 75, top pattern.

In some embodiments, the polymorphic form is a solvate having an X-ray powder diffraction pattern (CuKα) comprising peaks at about 7.0, 7.8, 8.6, 11.9, 13.9 (double peak), 14.2, and 16.0° 2θ. In some embodiments, the X-ray diffraction pattern (CuKα) is substantially as shown in FIG. 75, second pattern from top.

In some embodiments, the polymorphic form is an acetonitrile hemisolvate having an X-ray powder diffraction pattern (CuKα) comprising peaks at about 7.5, 11.4, 15.6 and 16.6° 2θ. In some embodiments, the X-ray diffraction pattern (CuKα) is substantially as shown in FIG. 75, second pattern from bottom. In some embodiments, the polymorphic form has a $T_g$ of about 196° C. In some embodiments, the polymorphic form has a differential scanning calorimetry (DSC) curve comprising an endotherm centered at about 196° C. In some embodiments, the differential scanning calorimetry (DSC) curve is substantially as shown in FIG. 116.

In some embodiments, the polymorphic form is a solvate having an X-ray powder diffraction pattern (CuKα) comprising peaks at about 6.8, 9.3, 9.5, 10.5, 13.6, and 15.6° 2θ. In some embodiments, the X-ray diffraction pattern (CuKα) is substantially as shown in FIG. 75, bottom pattern.

In another aspect of the present invention, there are provided pharmaceutical compositions comprising an active ingredient consisting of the above compound or a polymorphic form thereof (such as, e.g., any one of the polymorphic forms described herein above and below), and a pharmaceutically acceptable carrier. In some embodiments, the pharmaceutical composition is formulated for administration: orally, intraadiposally, intraarterially, intraarticularly, intracranially, intradermally, intralesionally, intramuscularly, intranasally, intraocularly, intrapericardially, intraperitoneally, intrapleurally, intraprostatically, intrarectally, intrathecally, intratracheally, intratumorally, intraumbilically, intravaginally, intravenously, intravesicularlly, intravitreally, liposomally, locally, mucosally, parenterally, rectally, subconjunctival, subcutaneously, sublingually, topically, transbuccally, transdermally, vaginally, in crèmes, in lipid compositions, via a catheter, via a lavage, via continuous infusion, via infusion, via inhalation, via injection, via local delivery, or via localized perfusion. In some embodiments, the pharmaceutical composition is formulated for oral, intraarterial, intravenous, or topical administration. In some embodiments, the pharmaceutical composition is formulated for oral administration.

In some embodiments, the pharmaceutical composition is formulated as a hard or soft capsule, a tablet, a syrup, a suspension, an emulsion, a solution, a solid dispersion, a wafer, or an elixir. In some embodiments, the pharmaceutical composition according to the invention further comprises an agent that enhances solubility and dispersibility. (For example, agents that enhance solubility and dispersibility include, but are not limited to, PEGs, cyclodextrans, and cellulose derivatives.) In some embodiments, the compound or polymorphic form is suspended in sesame oil.

In other embodiments, the pharmaceutical composition is formulated for topical administration. In other embodiments, the pharmaceutical composition is formulated as a lotion, a cream, a gel, an oil, an ointment, a salve, an emulsion, a solution, or a suspension. In some embodiments, the pharmaceutical composition is formulated as a lotion, as a cream, or as a gel. In some embodiments, the amount of the active ingredient is from about 0.01% to about 5% by weight, about 0.01% to about 3% by weight, or 0.01%, 0.1%, 1%, or 3% by weight.

In another aspect of the present invention there are provided methods of treating or preventing a condition associated with inflammation or oxidative stress in a patient in need thereof, comprising administering to the patient a therapeutically effective amount of the pharmaceutical composition as described above or below. The invention likewise relates to the compound N-((4aS,6aR,6bS,8aR,12aS,14aR,14bS)-11-cyano-2,2,6a,6b,9,9,12a-heptamethyl-10,14-dioxo-1,2,3,4,4a,5,6,6a,6b,7,8,8a,9,10,12a,14,14a,14b-octadecahydropicen-4a-yl)-2,2-difluoropropanamide (or RTA 408) or a pharmaceutically acceptable salt thereof, or a polymorphic form of that compound (such as, e.g., any one of the polymorphic forms described herein above or below), or a pharmaceutical composition comprising any of the aforementioned entities and a pharmaceutically acceptable carrier (including, e.g., the pharmaceutical compositions described above), for use in treating or preventing a condition associated with inflammation or oxidative stress. The invention also relates to the use of the aforementioned compound, polymorphic form or pharmaceutical composition for the preparation of a medicament for the treatment or prevention of a condition associated with inflammation or oxidative stress. In some embodiments, the condition is associated with inflammation. In other embodiments, the condition is associated with oxidative stress. In some embodiments, the condition is a skin disease or disorder, sepsis, dermatitis, osteoarthritis, cancer, inflammation, an autoimmune disease, inflammatory bowel disease, a complication from localized or total-body exposure to ionizing radiation, mucositis, acute or chronic organ failure, liver disease, pancreatitis, an eye disorder, a lung disease or diabetes.

The present invention furthermore relates to the compound N-((4aS,6aR,6bS,8aR,12aS,14aR,14bS)-11-cyano-2,2,6a,6b,9,9,12a-heptamethyl-10,14-dioxo-1,2,3,4,4a,5,6,6a,6b,7,8,8a,9,10,12a,14,14a,14b-octadecahydropicen-4a-yl)-2,2-difluoropropanamide (or RTA 408) or a pharmaceutically acceptable salt thereof, or a polymorphic form of that compound (such as, e.g., any one of the polymorphic forms described herein above or below), or a pharmaceutical composition comprising any of the aforementioned entities and a pharmaceutically acceptable carrier (including, e.g., the pharmaceutical compositions described above), for use in treating or preventing a condition selected from a skin disease or disorder, sepsis, dermatitis, osteoarthritis, cancer, inflammation, an autoimmune disease, inflammatory bowel disease, a complication from localized or total-body exposure to ionizing radiation, mucositis, acute or chronic organ failure, liver disease, pancreatitis, an eye disorder, a lung disease, or diabetes. Accordingly, the invention relates to the use of the aforementioned compound, polymorphic form or pharmaceutical composition for the preparation of a medicament for the treatment or prevention of a condition selected from a skin disease or disorder, sepsis, dermatitis, osteoarthritis, cancer, inflammation, an autoimmune disease, inflammatory bowel disease, a complication from localized or total-body exposure to ionizing radiation, mucositis, acute or chronic organ failure, liver disease, pancreatitis, an eye disorder, a lung disease, or diabetes. The invention also relates to a method of treating or preventing a condition selected from a skin disease or disorder, sepsis, dermatitis, osteoarthritis, cancer, inflammation, an autoimmune disease, inflammatory bowel disease, a complication from localized or total-body exposure to ionizing radiation, mucositis, acute or chronic organ failure, liver disease, pancreatitis, an eye disorder, a lung disease, or diabetes in a patient in need thereof, the method comprising administering to the patient a therapeutically effective amount of the aforementioned compound, polymorphic form or pharmaceutical composition. In some embodiments, the condition is a skin disease or disorder such as dermatitis, a thermal or chemical burn, a chronic wound, acne, alopecia, other disorders of the hair follicle, epidermolysis bullosa, sunburn, complications of sunburn, disorders of skin pigmentation, an aging-related skin condition; a post-surgical wound, a scar from a skin injury or burn, psoriasis, a dermatological manifestation of an autoimmune disease or a graft-versus host disease, skin cancer, or a disorder involving hyperproliferation of skin cells. In some embodiments, the skin disease or disorder is dermatitis. In some embodiments, the dermatitis is allergic dermatitis, atopic dermatitis, dermatitis due to chemical exposure, or radiation-induced dermatitis. In other embodiments, the skin disease or disorder is a chronic wound. In some embodiments, the chronic wound is a diabetic ulcer, a pressure sore, or a venous ulcer. In other embodiments, the skin disease or disorder is alopecia. In some embodiments, the alopecia is selected from baldness or drug-induced alopecia. In other embodiments, the skin disease or disorder is a disorder of skin pigmentation. In some embodiments, the disorder of skin pigmentation is vitiligo. In other embodiments, the skin disease or disorder is a disorder involving hyperproliferation of skin cells. In some embodiments, the disorder involving hyperproliferation of skin cells is hyperkeratosis.

In other embodiments, the condition is an autoimmune disease, such as rheumatoid arthritis, lupus, Crohn's disease, or psoriasis. In other embodiments, the condition is a liver disease, such as fatty liver disease or hepatitis.

In other embodiments, the condition is an eye disorder, such as uveitis, macular degeneration, glaucoma, diabetic macular edema, blepharitis, diabetic retinopathy, a disease or disorder of the corneal endothelium, post-surgical inflammation, dry eye, allergic conjunctivitis or a form of conjunctivitis. In some embodiments, the eye disorder is macular degeneration. In some embodiments, the macular degeneration is the dry form. In other embodiments, the macular degeneration is the wet form. In some embodiments, the disease or disorder of the corneal endothelium is Fuchs endothelial corneal dystrophy.

In other embodiments, the condition is a lung disease, such as pulmonary inflammation, pulmonary fibrosis, COPD, asthma, cystic fibrosis, or idiopathic pulmonary fibrosis. In some embodiments, the COPD is induced by cigarette smoke.

In other embodiments, the condition is sepsis. In other embodiments, the condition is mucositis resulting from radiation therapy or chemotherapy. In some embodiments, the mucositis presents orally. In other embodiments, the condition is associated with exposure to radiation. In some embodiments, the radiation exposure leads to dermatitis. In some embodiments, the radiation exposure is acute. In other embodiments, the radiation exposure is fractionated.

In other embodiments, the condition is cancer. In some embodiments, the cancer is a carcinoma, sarcoma, lymphoma, leukemia, melanoma, mesothelioma, multiple myeloma, or seminoma. In other embodiments, the cancer is of the bladder, blood, bone, brain, breast, central nervous system, cervix, colon, endometrium, esophagus, gall bladder, genitalia, genitourinary tract, head, kidney, larynx, liver, lung, muscle tissue, neck, oral or nasal mucosa, ovary, pancreas, prostate, skin, spleen, small intestine, large intestine, stomach, testicle, or thyroid.

In some embodiments, the pharmaceutical composition is administered before or immediately after a subject is treated with a radiation therapy or a chemotherapy wherein the chemotherapy does not comprise RTA 408 or its polymorphic forms. In some embodiments, the pharmaceutical composition is administered both before and after the subject is treated with radiation therapy, chemotherapy or both. In some embodiments, the treatment reduces a side effect of the radiation therapy or the chemotherapy. In some embodiments, the side effect is mucositis and dermatitis. In some embodiments, the treatment enhances the efficacy of the radiation therapy or the chemotherapy. In some embodiments, the chemotherapy comprises administering to the patient a therapeutically effective amount of 5-fluorouracil or docetaxel.

Additional combination treatment therapy is also contemplated by the present disclosure. For example, in some embodiments, the methods of treating cancer in a subject, comprising administering to the subject a pharmaceutically effective amount of a compound of the present disclosure, the methods may further comprise one or more treatments selected from the group consisting of administering a pharmaceutically effective amount of a second drug, radiotherapy, immunotherapy, gene therapy, and surgery. In some embodiments, the methods may further comprise (1) contacting a tumor cell with the compound prior to contacting the tumor cell with the second drug, (2) contacting a tumor cell with the second drug prior to contacting the tumor cell with the compound, or (3) contacting a tumor cell with the compound and the second drug at the same time. The second drug may, in certain embodiments, be an antibiotic, anti-inflammatory, anti-neoplastic, anti-proliferative, anti-viral, immunomodulatory, or immunosuppressive. In other embodiments, the second drug may be an alkylating agent, androgen receptor modulator, cytoskeletal disruptor, estrogen receptor modulator, histone-deacetylase inhibitor, HMG-CoA reductase inhibitor, prenyl-protein transferase inhibitor, retinoid receptor modulator, topoisomerase inhibitor, or tyrosine kinase inhibitor. In certain embodiments, the second drug is 5-azacitidine, 5-fluorouracil, 9-cis-retinoic acid, actinomycin D, alitretinoin, all-trans-retinoic acid, annamycin, axitinib, belinostat, bevacizumab, bexarotene, bosutinib, busulfan, capecitabine, carboplatin, carmustine, CD437, cediranib, cetuximab, chlorambucil, cisplatin, cyclophosphamide, cytarabine, dacarbazine, dasatinib, daunorubicin, decitabine, docetaxel, dolastatin-10, doxifluridine, doxorubicin, doxorubicin, epirubicin, erlotinib, etoposide, gefitinib, gemcitabine, gemtuzumab ozogamicin, hexamethylmelamine, idarubicin, ifosfamide, imatinib, irinotecan, isotretinoin, ixabepilone, lapatinib, LBH589, lomustine, mechlorethamine, melphalan, mercaptopurine, methotrexate, mitomycin, mitoxantrone, MS-275, neratinib, nilotinib, nitrosourea, oxaliplatin, paclitaxel, plicamycin, procarbazine, semaxanib, semustine, sodium butyrate, sodium phenylacetate, streptozotocin, suberoylanilide hydroxamic acid, sunitinib, tamoxifen, teniposide, thiopeta, tioguanine, topotecan, TRAIL, trastuzumab, tretinoin, trichostatin A, valproic acid, valrubicin, vandetanib, vinblastine, vincristine, vindesine, or vinorelbine.

Methods of treating or preventing a disease with an inflammatory component in a subject, comprising administering to the subject a pharmaceutically effective amount of a compound of the present disclosure are also contemplated. In some embodiments, the disease may be, for example, lupus or rheumatoid arthritis. In other embodiments, the disease may be an inflammatory bowel disease, such as Crohn's disease or ulcerative colitis. In other embodiments, the disease with an inflammatory component may be a cardiovascular disease. In other embodiments, the disease with an inflammatory component may be diabetes, such as type 1 or type 2 diabetes. In other embodiments, RTA 408, its polymorphs, and pharmaceutical compositions may also be used to treat complications associated with diabetes. Such complications are well-known to a person of skill in the art and include but are not limited to, for example, obesity, hypertension, atherosclerosis, coronary heart disease, stroke, peripheral vascular disease, hypertension, nephropathy, neuropathy, myonecrosis, retinopathy and metabolic syndrome (syndrome X). In other embodiments, the disease with an inflammatory component may be a skin disease, such as psoriasis, acne, or atopic dermatitis. Administration of RTA 408, its polymorphs, and pharmaceutical compositions in treatment methods of such skin diseases may be but are not limited to, for example, topical or oral.

In other embodiments, the disease with an inflammatory component may be metabolic syndrome (syndrome X). A patient having this syndrome is characterized as having three or more symptoms selected from the following group of five symptoms: (1) abdominal obesity; (2) hypertriglyceridemia; (3) low high-density lipoprotein cholesterol (HDL); (4) high blood pressure; and (5) elevated fasting glucose, which may be in the range characteristic of Type 2 diabetes if the patient is also diabetic. Each of these symptoms is defined in the Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670, which is incorporated herein by reference. Patients with metabolic syndrome, whether or not they have or develop overt diabetes mellitus, have an increased risk of developing the macrovascular and microvascular complications that are listed above that occur with type 2 diabetes, such as atherosclerosis and coronary heart disease.

Another general method of the present disclosure entails a method of treating or preventing a cardiovascular disease in a subject, comprising administering to the subject a pharmaceutically effective amount of a compound of the present disclosure. In some embodiments, the cardiovascular disease may be but not limited to, for example, atherosclerosis, cardiomyopathy, congenital heart disease, congestive heart failure, myocarditis, rheumatic heart disease, valve disease, coronary artery disease, endocarditis, or myocardial infarction. Combination therapy is also contemplated for methods of treating or preventing a cardiovascular disease in a subject. For example, such methods may further comprise administering a pharmaceutically effective amount of one or more cardiovascular drugs. The cardiovascular drug may be but not limited to, for example, a cholesterol lowering drug, an anti-hyperlipidemic, a calcium channel blocker, an anti-hypertensive, or an HMG-CoA reductase inhibitor. In some embodiments, non-limiting examples of cardiovascular drugs include amlodipine, aspirin, ezetimibe, felodipine, lacidipine, lercanidipine, nicardipine, nifedipine, nimodipine, nisoldipine or nitrendipine. In other embodiments, other non-limiting examples of cardiovascular drugs include atenolol, bucindolol, carvedilol, clonidine, doxazosin, indoramin, labetalol, methyldopa, metoprolol, nadolol, oxprenolol, phenoxybenzamine, phentolamine, pindolol, prazosin, propranolol, terazosin, timolol or tolazoline. In other embodiments, the cardiovascular drug may be, for example, a statin, such as atorvastatin, cerivastatin, fluvastatin, lovastatin, mevastatin, pitavastatin, pravastatin, rosuvastatin or simvastatin.

Methods of treating or preventing a neurodegenerative disease in a subject, comprising administering to the subject a pharmaceutically effective amount of a compound of the present disclosure are also contemplated. In some embodiments, the neurodegenerative disease may be selected, for example, from the group consisting of Parkinson's disease, Alzheimer's disease, multiple sclerosis (MS), Huntington's disease and amyotrophic lateral sclerosis. In particular embodiments, the neurodegenerative disease is Alzheimer's disease. In particular embodiments, the neurodegenerative disease is MS, such as primary progressive, relapsing-remitting secondary progressive or progressive relapsing MS. In some embodiments, the subject may be, for example, a primate. In some embodiments, the subject may be a human.

In particular embodiments of methods of treating or preventing a neurodegenerative disease in a subject, comprising administering to the subject a pharmaceutically effective amount of a compound of the present disclosure, the treatment suppresses the demyelination of neurons in the subject's brain or spinal cord. In certain embodiments, the treatment suppresses inflammatory demyelination. In certain embodiments, the treatment suppresses the transection of neuron axons in the subject's brain or spinal cord. In certain embodiments, the treatment suppresses the transection of neurites in the subject's brain or spinal cord. In certain embodiments, the treatment suppresses neuronal apoptosis in the subject's brain or spinal cord. In certain embodiments, the treatment stimulates the remyelination of neuron axons in the subject's brain or spinal cord. In certain embodiments, the treatment restores lost function after an MS attack. In certain embodiments, the treatment prevents a new MS attack. In certain embodiments, the treatment prevents a disability resulting from an MS attack.

One general aspect of the present disclosure contemplates a method of treating or preventing a disorder characterized by overexpression of iNOS genes in a subject, comprising administering to the subject a pharmaceutically effective amount of RTA 408, polymorphic forms, or a pharmaceutical composition of the present disclosure.

Another general aspect of the present disclosure contemplates a method of inhibiting IFN-γ-induced nitric oxide production in cells of a subject, comprising administering to said subject a pharmaceutically effective amount of RTA 408, polymorphic forms, or a pharmaceutical composition of the present disclosure.

Yet another general method of the present disclosure contemplates a method of treating or preventing a disorder characterized by overexpression of COX-2 genes in a subject, comprising administering to the subject a pharmaceutically effective amount of RTA 408, polymorphic forms, or a pharmaceutical composition of the present disclosure.

Methods of treating renal/kidney disease (RKD) in a subject, comprising administering to the subject a pharmaceutically effective amount of a compound of the present disclosure are also contemplated. See U.S. Pat. No. 8,129,429, which is incorporated by reference herein. The RKD may result from, for example, a toxic insult.

The toxic insult may result from but not limited to, for example, an imaging agent or a drug. The drug may be a chemotherapeutic, for example. The RKD may result from ischemia/reperfusion injury, in certain embodiments. In certain embodiments, the RKD results from diabetes or hypertension. In some embodiments, the RKD may result from an autoimmune disease. The RKD may be further defined as chronic RKD or acute RKD.

In certain methods of treating renal/kidney disease (RKD) in a subject, comprising administering to the subject a pharmaceutically effective amount of a compound of the present disclosure, the subject has undergone or is undergoing dialysis. In certain embodiments, the subject has undergone or is a candidate to undergo kidney transplant. The subject may be a primate. The primate may be a human. The subject in this or any other method may be, for example, a cow, horse, dog, cat, pig, mouse, rat or guinea pig.

Also contemplated by the present disclosure is a method for improving glomerular filtration rate or creatinine clearance in a subject, comprising administering to the subject a pharmaceutically effective amount of RTA 408, polymorphic forms, or a pharmaceutical composition of the present disclosure.

In some embodiments, the pharmaceutical composition is administered in a single dose per day. In other embodiments, the pharmaceutical composition is administered in more than one dose per day. In some embodiments, the pharmaceutical composition is administered in a pharmaceutically effective amount.

In some embodiments, the dose is from about 1 mg/kg to about 2000 mg/kg. In other embodiments, the dose is from about 3 mg/kg to about 100 mg/kg. In other embodiments, the dose is about 3, 10, 30, or 100 mg/kg.

In other embodiments, the pharmaceutical composition is administered topically. In some embodiments, the topical administration is administered to the skin. In other embodiments, the topical administration is administered to the eye.

In other embodiments, the pharmaceutical composition is administered orally. In other embodiments, the pharmaceutical composition is administered intraocularly.

Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description. Note that simply because a particular compound is ascribed to one particular generic formula does not mean that it cannot also belong to another generic formula.

BRIEF DESCRIPTION OF THE DRAWINGS

The following drawings form part of the present specification and are included to further demonstrate certain aspects of the present disclosure. One or more German words can be found in the drawings, including "Masseänderung" and "temperatur", which mean "change in mass" and "temperature", respectively. The invention may be better understood by reference to one of these drawings in combination with the detailed description of specific embodiments presented herein.

FIGS. 2a & b—Effect of RTA 408 on antioxidant response element (ARE) activation: (a) NQO1-ARE luciferase activity; (b) GSTA2-ARE luciferase activity.

FIGS. 3a-f—Relative Nrf2 GST ARE fold increase after cellular treatment with (a) RTA 402; (b) 63415 (RTA 408); (c) 63170; (d) 63171; (e) 63179; and (f) 63189. The graphs also show the viability of the cells as assayed using the WST1 cell proliferation reagent and measuring the absorbance after 1 hour. All drugs were administered in DMSO and cells were grown at 10,000 cells/well in 384-well plates in DMEM low glucose supplemented with 10% FBS, 1% Penicillin Streptomycin, and 0.8 mg/mL Geneticin.

FIGS. 4a-d—Effect of RTA 408 on Nrf2 target gene expression in HFL1 lung fibroblasts. (a) NQO1; (b) HMOX1; (c) GCLM; (d) TXNRD1.

FIGS. 5a-d—Effect of RTA 408 on Nrf2 target gene expression in BEAS-2B bronchial epithelial cells. (a) NQO1; (b) HMOX1; (c) GCLM; (d) TXNRD1.

FIGS. 6a & b—Effect of RTA 408 on Nrf2 target protein levels. (a) SH-SY5Y cells; (b) BV2 cells.

FIGS. 10a-d—Effect of RTA 408 on expression of genes involved in NADPH synthesis. (a) H6PD; (b) PGD; (c) TKT; (d) ME1.

FIGS. 11a & b—(a) Effect of RTA 408 on TNF-α-induced activation of an NF-κB luciferase reporter in the mouse NIH3T3 cell line with WST1 viability and WST1/2 viability overlaid. (b) TNF-α-induced activation of an NF-κB luciferase reporter in the mouse NIH3T3 cell line. The graph shows relative fold change as a function of log change in RTA 408 concentration.

FIGS. 15a-d—Effect of RTA 408 on transaminase gene expression: (a) ALT1 (GPT1); (b) ALT2 (GPT2); (c) AST1 (GOT1); (d) AST1 (GOT2). Asterisks indicate a statistically-significant difference from the control group (*P<0.05; **P<0.01).

FIGS. 18a & b—Effect of RTA 408 on LPS-induced pulmonary inflammation in mice. (a) inflammatory cytokines; (b) Nrf2 targets. RTA 408 was administered to female BALB/c mice (n=10) QD×6 at Time 0, 24, 48, 72, 96, and 120 h followed by LPS at 121 h with animals sacrificed at 141 h. Pro-inflammatory cytokine protein expression assayed in BALF. Nrf2 biomarkers assayed in lung. Asterisks indicate a statistically significant difference from the saline control group (*P<0.05; P<0.01; *P<0.001).

FIGS. 19a & b—Effect of 63415 on BALF infiltrates in bleomycin-induced pulmonary inflammation: (a) BAL fluid cell count; (b) body weight. Compound 63415 was administered QD×39 on Days −10 to 28 in C57BL/6 mice. Bleomycin was given on Day 0. Daily weights were measured. BALF cell counts were obtained at sacrifice. A notable reduction in inflammatory infiltrate was observed. No significant improvements in chronic inflammation score, interstitial fibrosis, or number of fibrotic foci were observed.

FIGS. 20a & b—Effect of RTA 408 on bleomycin-induced pulmonary fibrosis in rats: (a) PMN; (b) Hydroxyproline. Asterisks indicate a statistically significant difference from the bleomycin control group (*P<0.05).

FIGS. 24a-d—Effects of 63415 (RTA 408) on body weight in a BALB/c mouse model of sepsis. LPS was administered to all animals on Day 0. (a) Body Weight: 63415 (RTA 408); (b) Body Weight: RTA 405; (c) Systemic LPS: % Survival: 63415 (RTA 408); (d) Systemic LPS: % Survival: RTA 405. Both RTA 405 and 63415 (RTA 408) were administered QD×5 on Days −2 to 2. 63415 (RTA 408) improved survival. Body weight as a function of time in 63415-treated BALB/c mice serves as a model for sepsis.

FIGS. 27a & b—Effect of 63415 on Nrf2 target gene induction in rat livers: (a) Target genes; (b) Negative regulators. mRNAs of Nrf2 target genes were assessed in livers of rats treated PO QD×14.

FIGS. 28a & b—Effect of 63415 on Nrf2 target genes in monkey tissues: (a) Liver; (b) Lung. mRNAs of Nrf2 target genes were assessed in monkeys treated PO QD×14 using Panomics QuantiGene® 2.0 Plex technology.

FIGS. 29a & b—Effect of 63415 on Nrf2 target enzyme activity in mouse liver: (a) NQO1 activity; (b) GST activity. Nrf2 target enzyme activity was assessed in livers of mice treated PO QD×14. NQO1 and GST enzyme activities were induced in a dose-dependent manner.

FIGS. 30a & b—Effect of 63415 on Nrf2 target enzyme activity in rat liver: (a) NQO1 activity; (b) GST activity. Nrf2 target enzyme activity was assessed in livers of rats treated PO QD×14. NQO1 and GST enzyme activities were induced in a dose dependent manner.

FIGS. 31a & b—Effects of 63415 on Nrf2 target enzyme activity induction in various tissues of cynomolgus monkeys: (a) NQO1 activity; (b) GSR activity.

FIGS. 32a & b—RTA 408 concentration in mouse liver, lung, and brain, and NQO1 activity in mouse liver after 14 days of daily oral administration. (a) Tissue distribution of RTA 408 in mice after 14 days of daily oral administration. Data represent the mean±SD of RTA 408 concentrations in tissue collected 4 h after the final dose of the study. Numbers above the error bars are representative of the mean. (b) Correlation of mouse liver RTA 408 content with NQO1 enzyme activity. Individual mouse liver RTA 408 liver content was plotted against individual enzyme activity from this report.

FIGS. 33a & b—RTA 408 concentration in rat plasma, liver, lung, and brain, and NQO1 activity in rat liver after 14 days of daily oral administration. (a) Tissue distribution of RTA 408 in rats after 14 days of daily oral administration. Data represent the mean±SD of RTA 408 concentrations in tissue collected 4 h after the final dose of the study. Numbers above the error bars are representative of the mean. *Two values were excluded from the mean calculation due to being outliers, defined as values causing the set of data to fail the Shapiro-Wilk normality test. (b) Correlation of rat liver RTA 408 content with NQO1 enzyme activity. Individual rat liver RTA 408 content was plotted against individual enzyme activity from this report. The tissues from the 100 mg/kg RTA 408 dose group were collected on Day 6, and the observed toxicities in this group precluded liver NQO1 enzyme activity evaluations.

FIGS. 34a & b—Effect of 63415 treatment on Nrf2 activation in monkey PBMC: (a) PBMC NQO1 vs. Plasma Concentration; (b) Lung NQO1 vs. PBMC NQO1.

Figure 119:
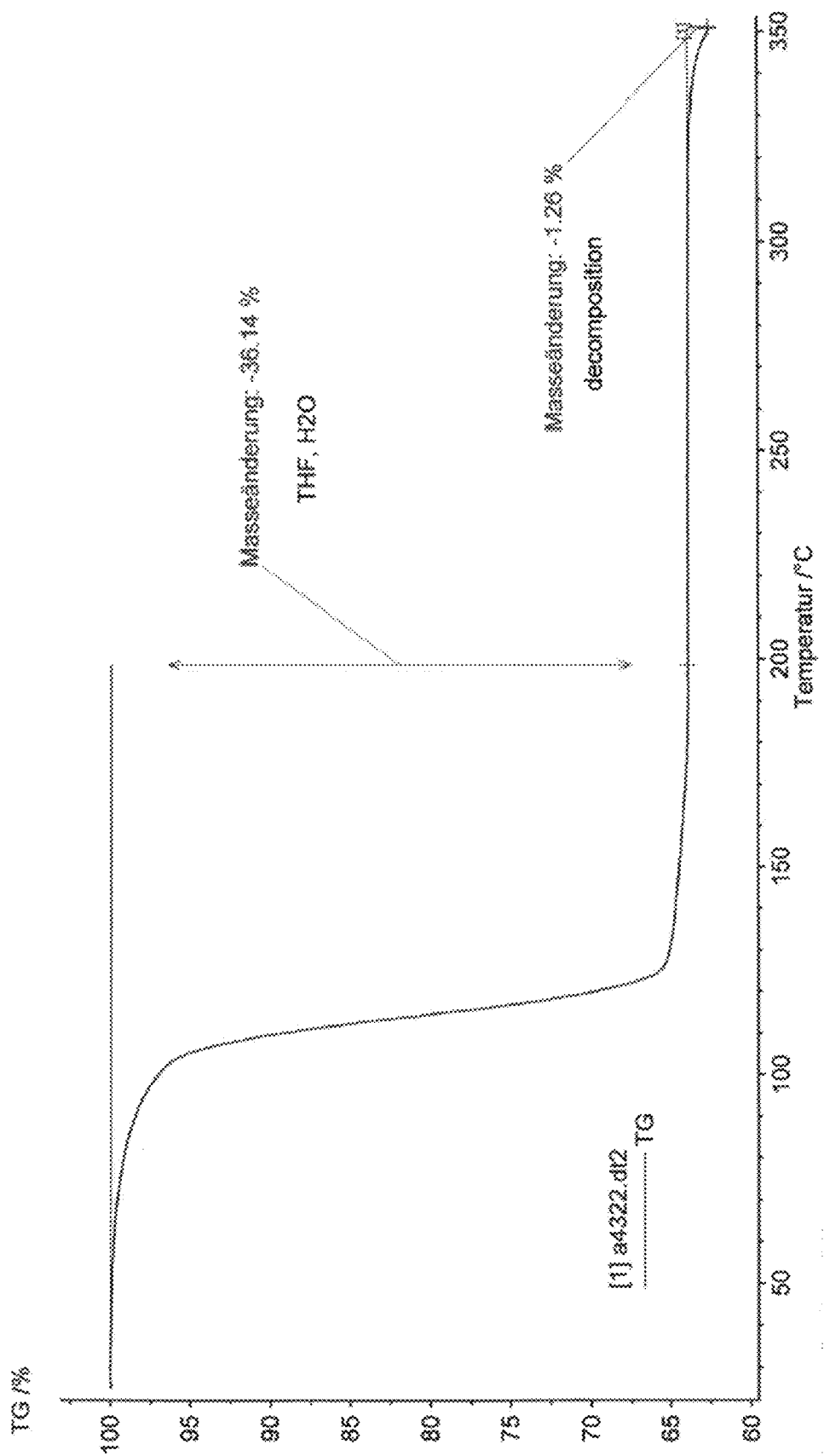

FIG. 119—TG-FTIR thermogram of the sample PP415-P14, which corresponds to a THF solvate form (Class 5).

Figure 120:
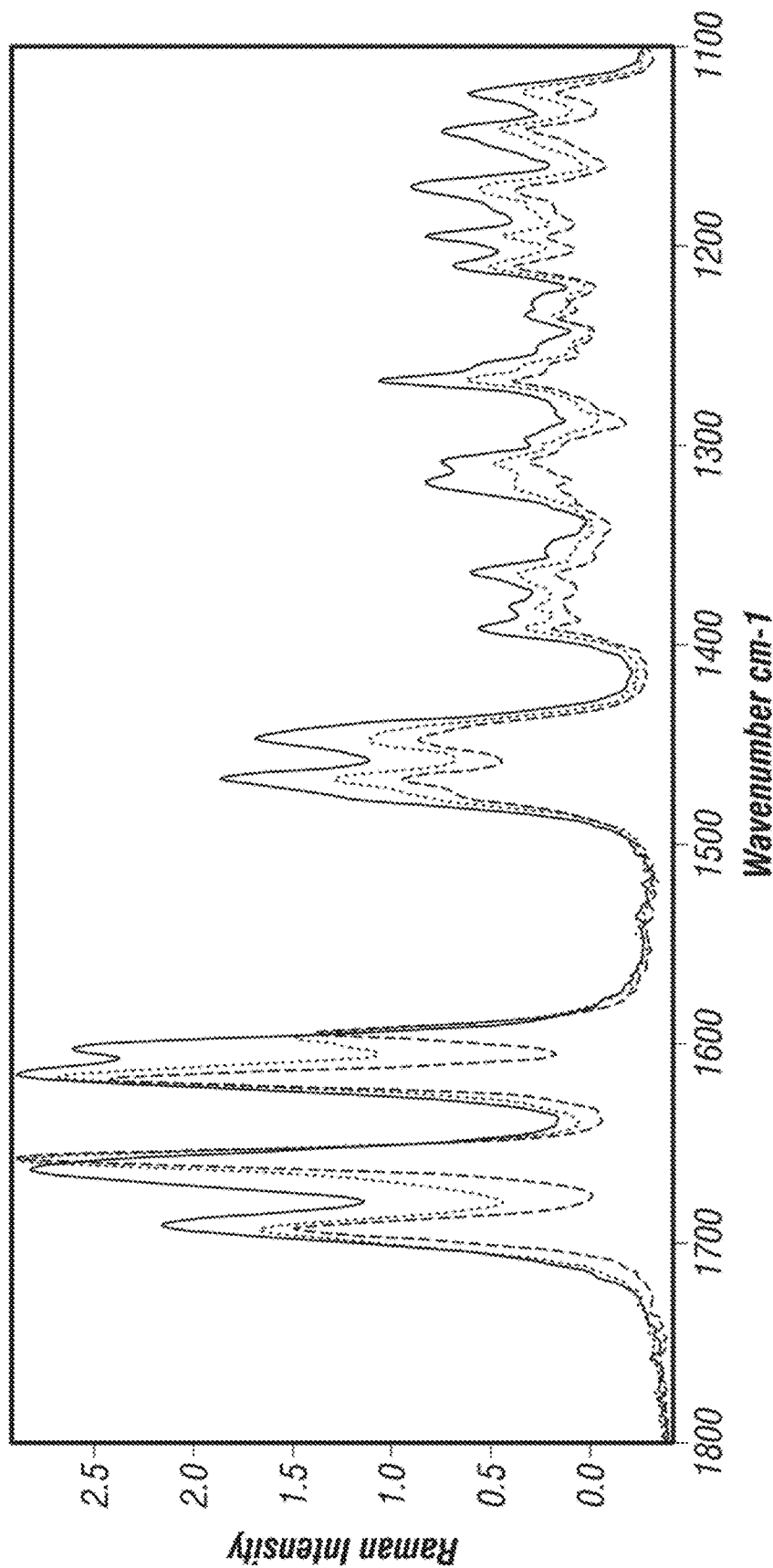

FIG. 120—FT-Raman spectra (1800-1100 cm$^1$) of a THF solvate form (Class 5) (dashed line, sample PP415-P14), dried material of a THF solvate form (Class 5) (dotted line, sample PP415-P27), and of the amorphous form (Class 1) (solid line, sample PP415-P1). The spectra have been scaled for the purpose of comparison and show small changes in magnitude but little corresponding change in spectral shape.

Figure 121:
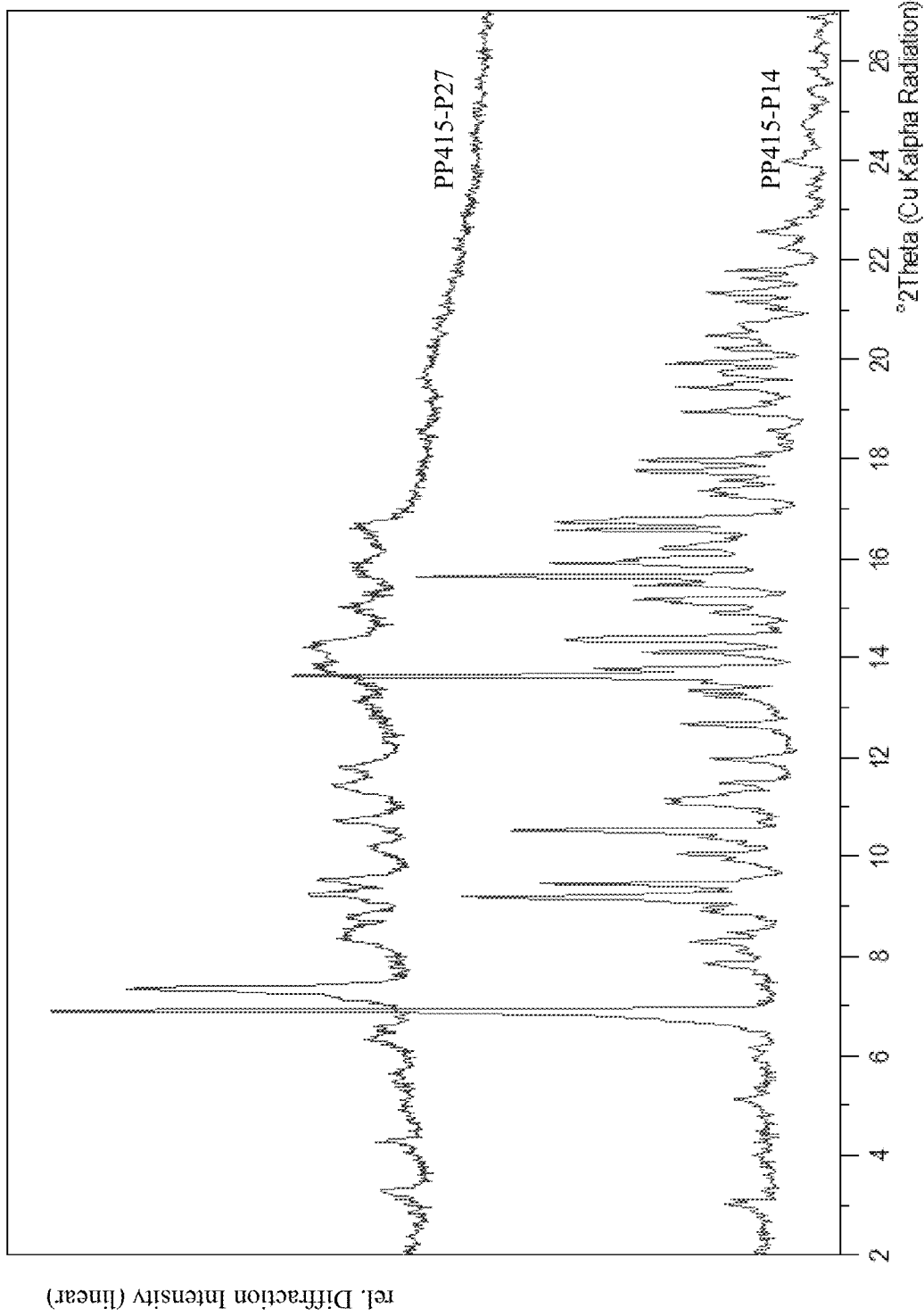

FIG. 121—PXRD pattern of the dried THF solvate form (Class 5), sample PP415-P27 (top) in comparison to the pattern of the THF solvate form (Class 5), sample PP415-P14 (bottom). The patterns have not been scaled but are offset in the y-direction for the purpose of comparison.

Figure 122:
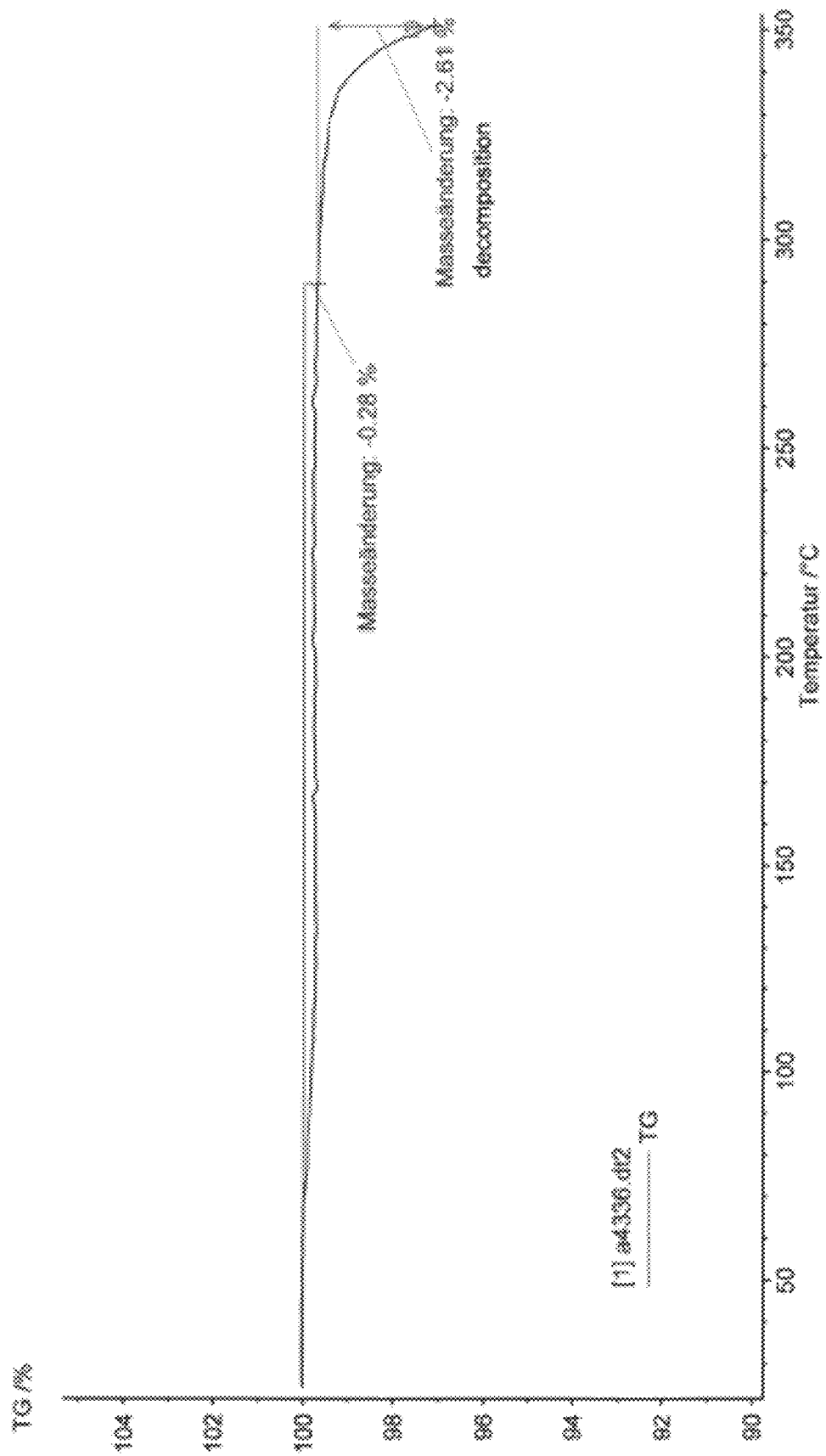

FIG. 122—TG-FTIR thermogram of the sample PP415-P27, which corresponds to a dried THF solvate (Class 5).

Figure 123:
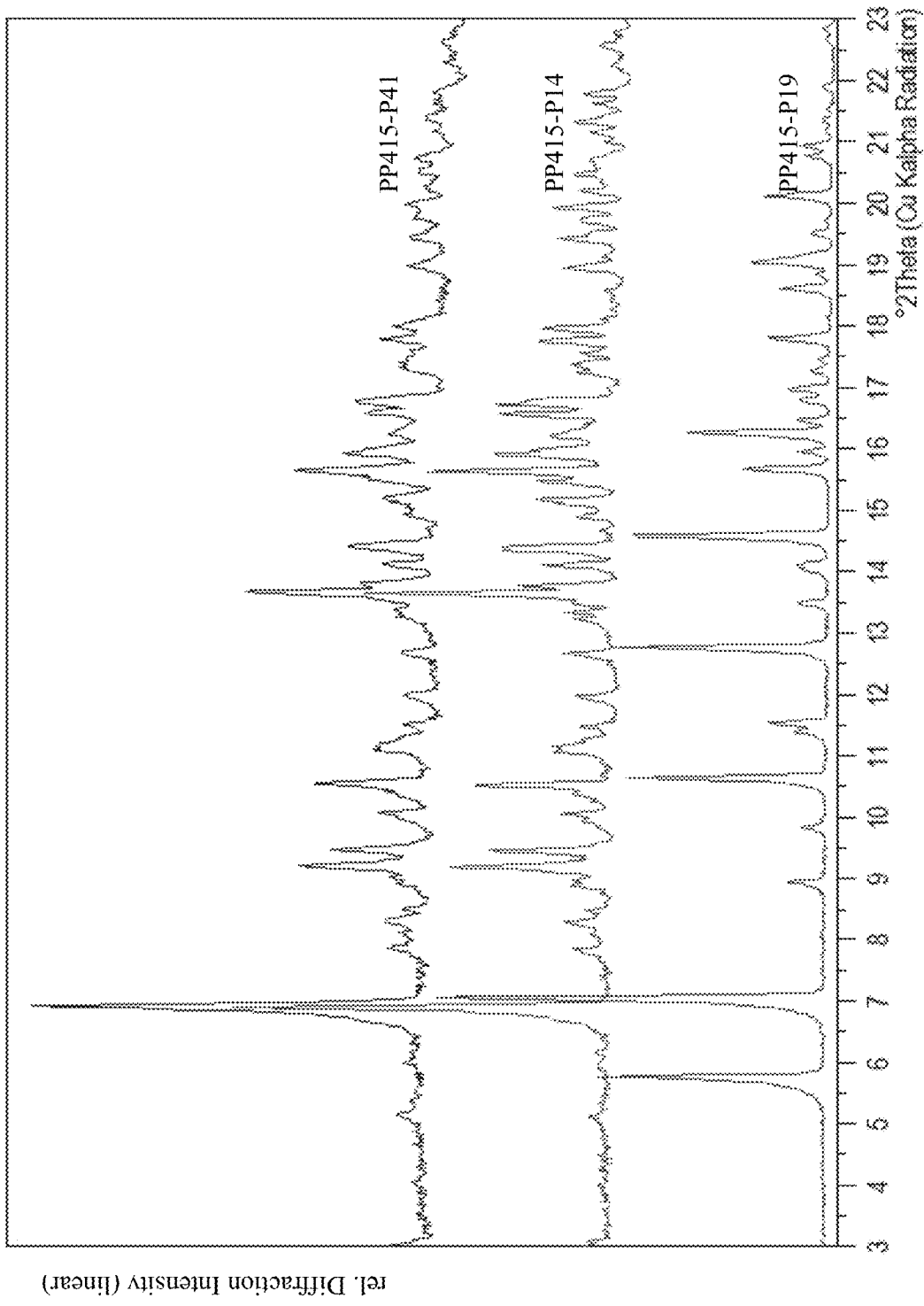

FIG. 123—PXRD pattern of sample PP415-P41 (top) corresponds to the pattern of the THF solvate form (Class 5) (middle, sample PP415-P14) and not to the pattern of the heptane solvate form, (Class 2) (bottom, sample PP415-P19). The patterns have been scaled and offset in the y-direction for purposes of comparison.

Figure 124:
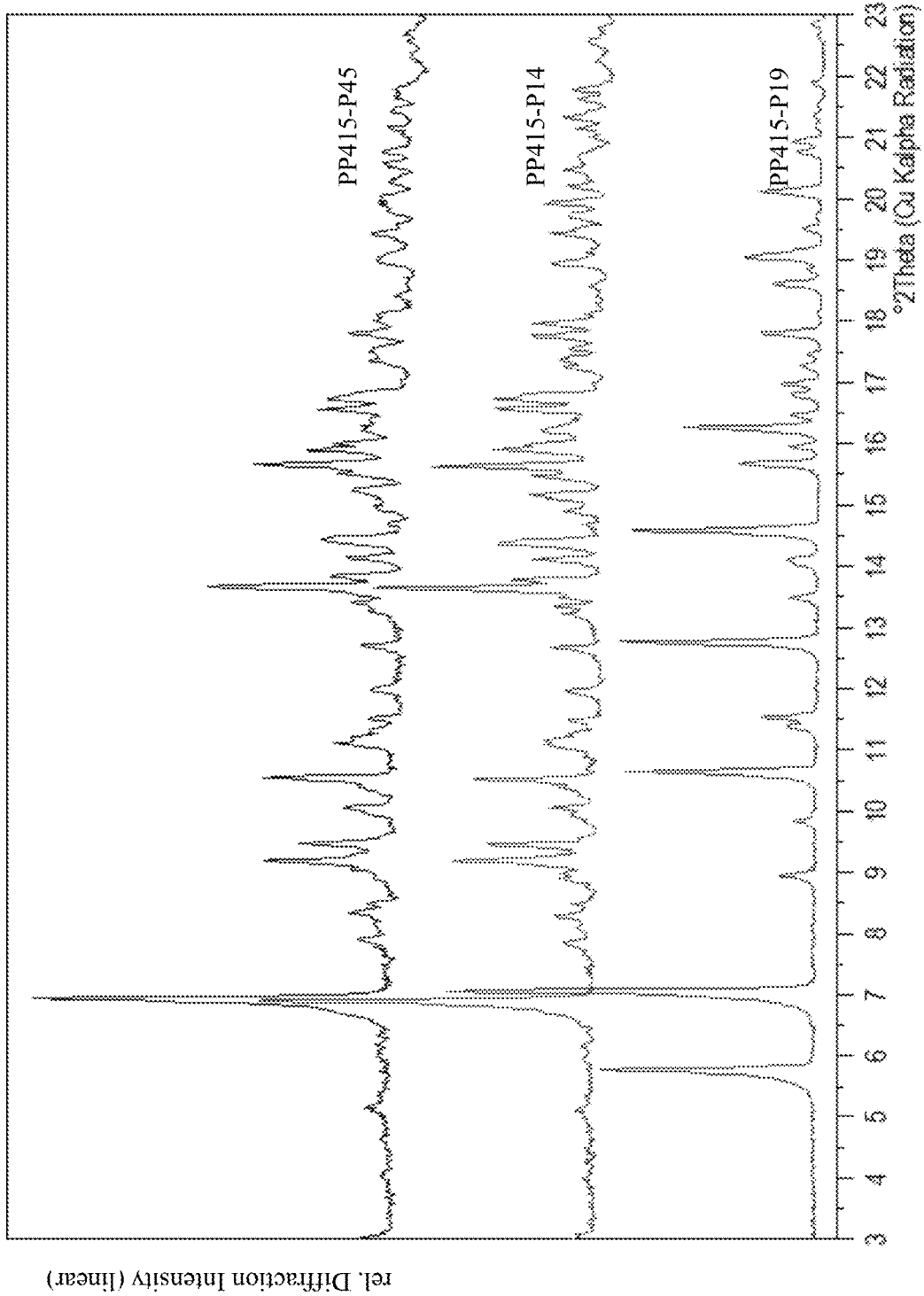

FIG. 124—PXRD pattern of sample PP415-P45 (top) corresponds to the pattern of the THF solvate form (Class 5) (middle, sample PP415-P14) and not to the pattern of the heptane solvate form (Class 2) (bottom, sample PP415-P19). The patterns have been scaled and offset in the y-direction for the purpose of comparison.

Figure 125:
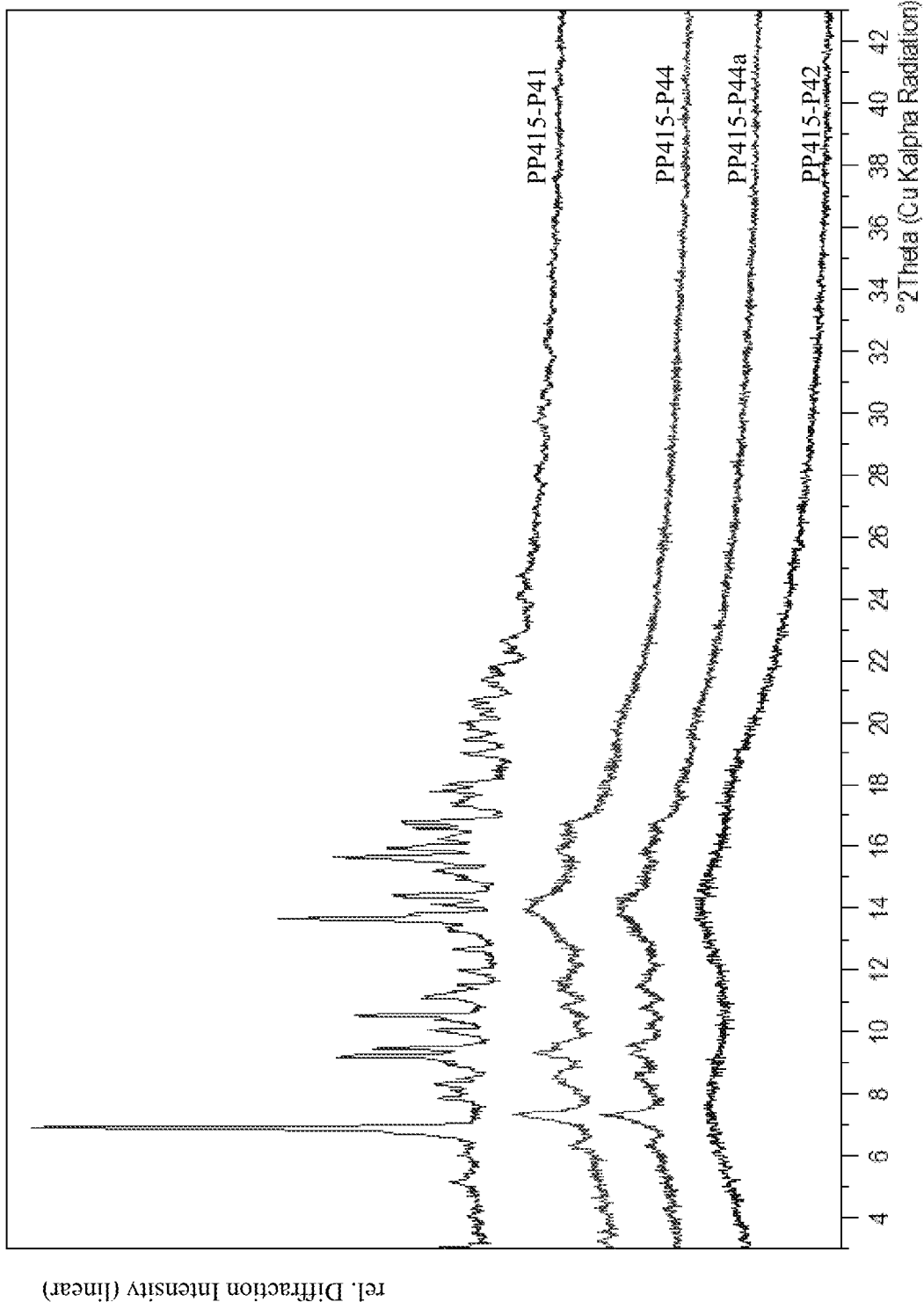

FIG. 125—PXRD pattern of sample PP415-P41 (top) corresponds to a THF solvate form (Class 5). After drying sample PP415-P41 for 1 day (2$^{nd}$ from top, sample: PP415-P44), the material is mainly amorphous. Some broad peaks with low intensity remain. After further drying overnight (2$^{nd}$ from bottom, sample PP415-P44a) the intensity of these broad peaks is further reduced. The amorphous form (Class 1) is shown as a reference (bottom, sample: PP415-P42). The patterns have not been scaled but are offset in the y-direction for the purpose of comparison.

Figure 126:
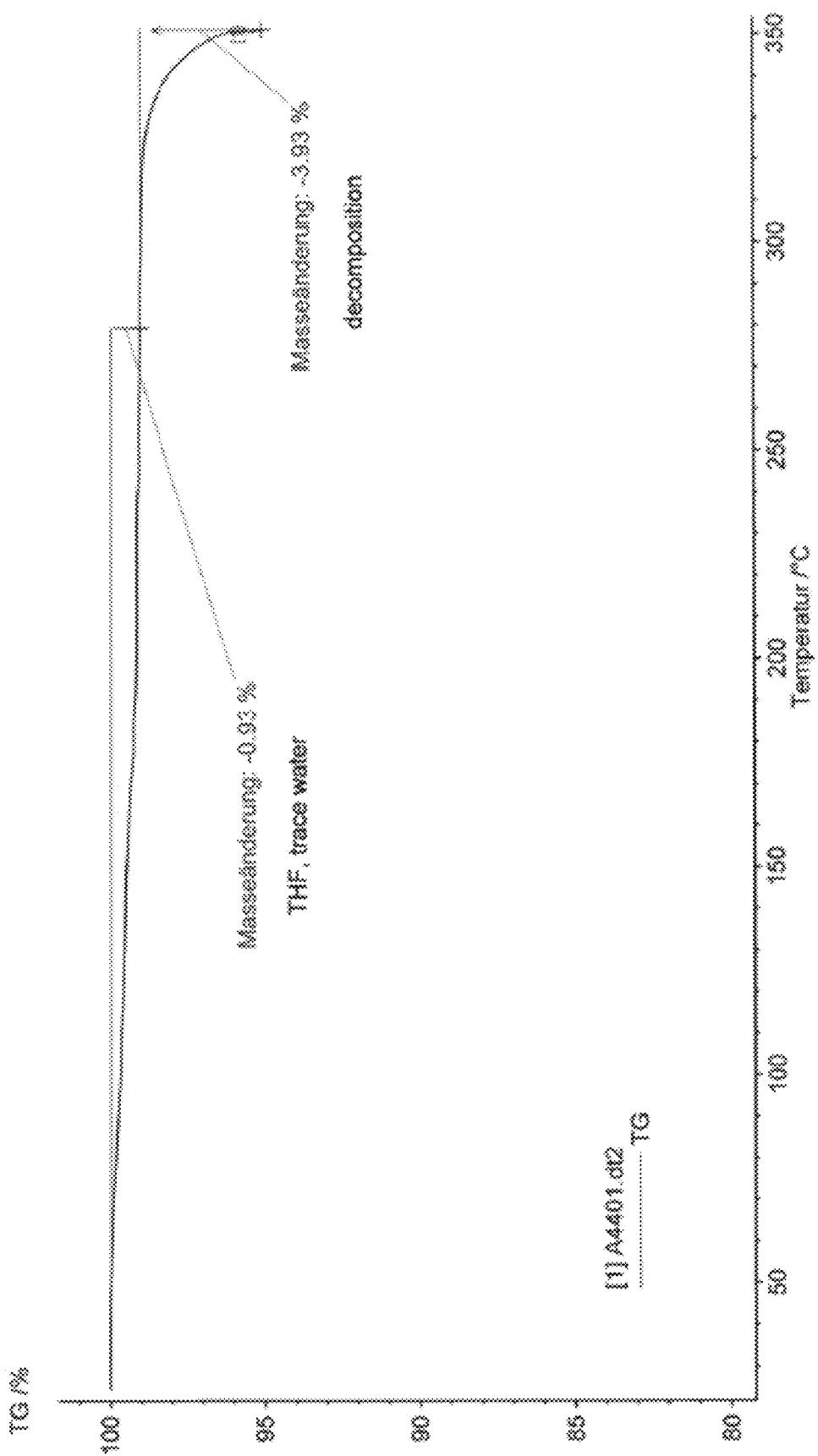

FIG. 126—TG-FTIR thermogram of the sample PP415-P44a, which corresponds to the amorphous form (Class 1).

Figure 127:
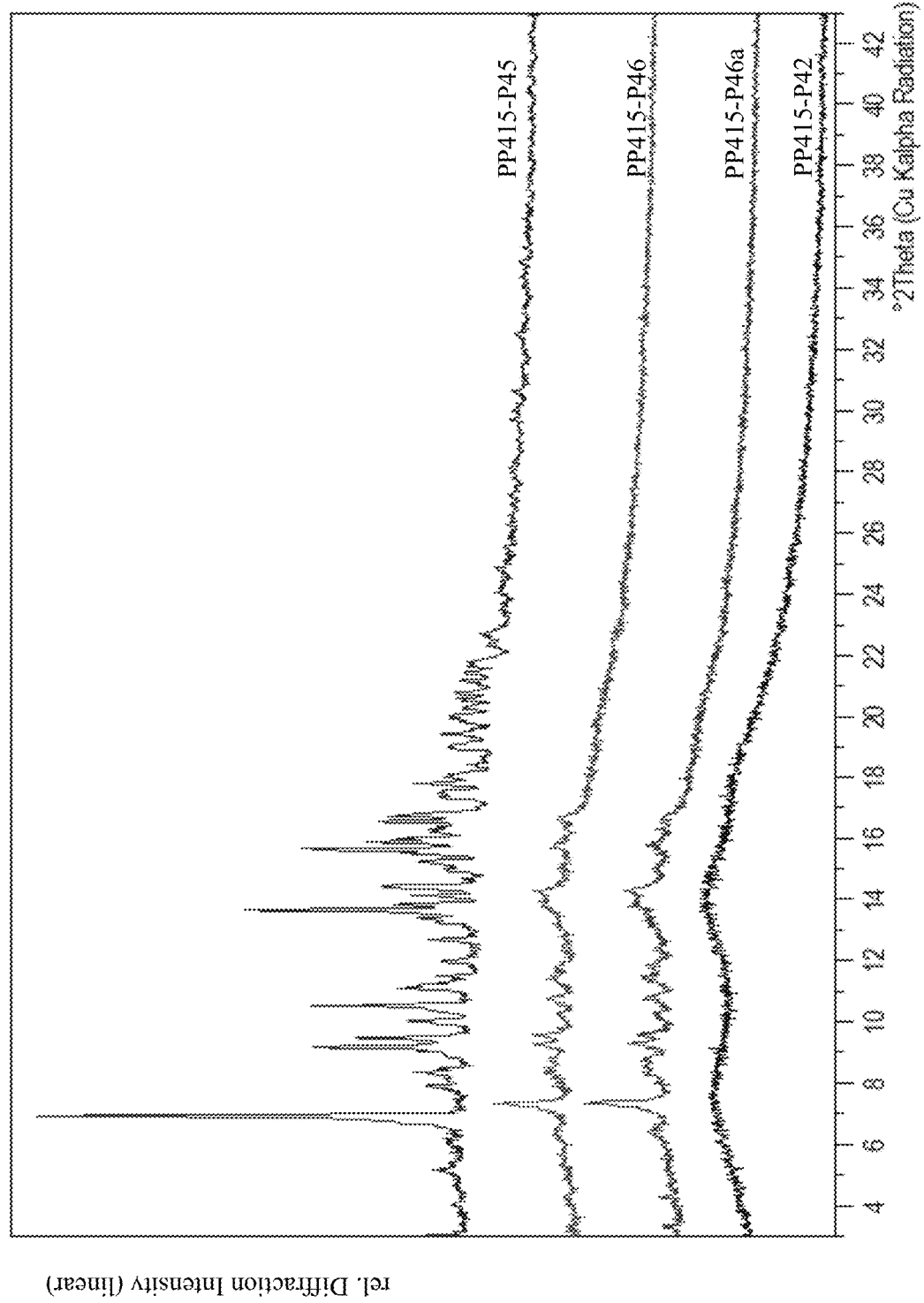

FIG. 127—PXRD pattern of sample PP415-P45 (top) corresponds to a THF solvate form (Class 5). After drying sample PP415-P45 for 1 day (2$^{nd}$ from top, sample PP415-P46), the material is mainly amorphous. Some broad peaks with low intensity remain. After a total of 4 days of drying (2$^{nd}$ from bottom, sample PP415-P46a), the pattern remains unchanged. The amorphous form (Class 1) is shown as reference (bottom, sample PP415-P42). The patterns have not been scaled but are offset in the y-direction for the purpose of comparison.

Figure 128:
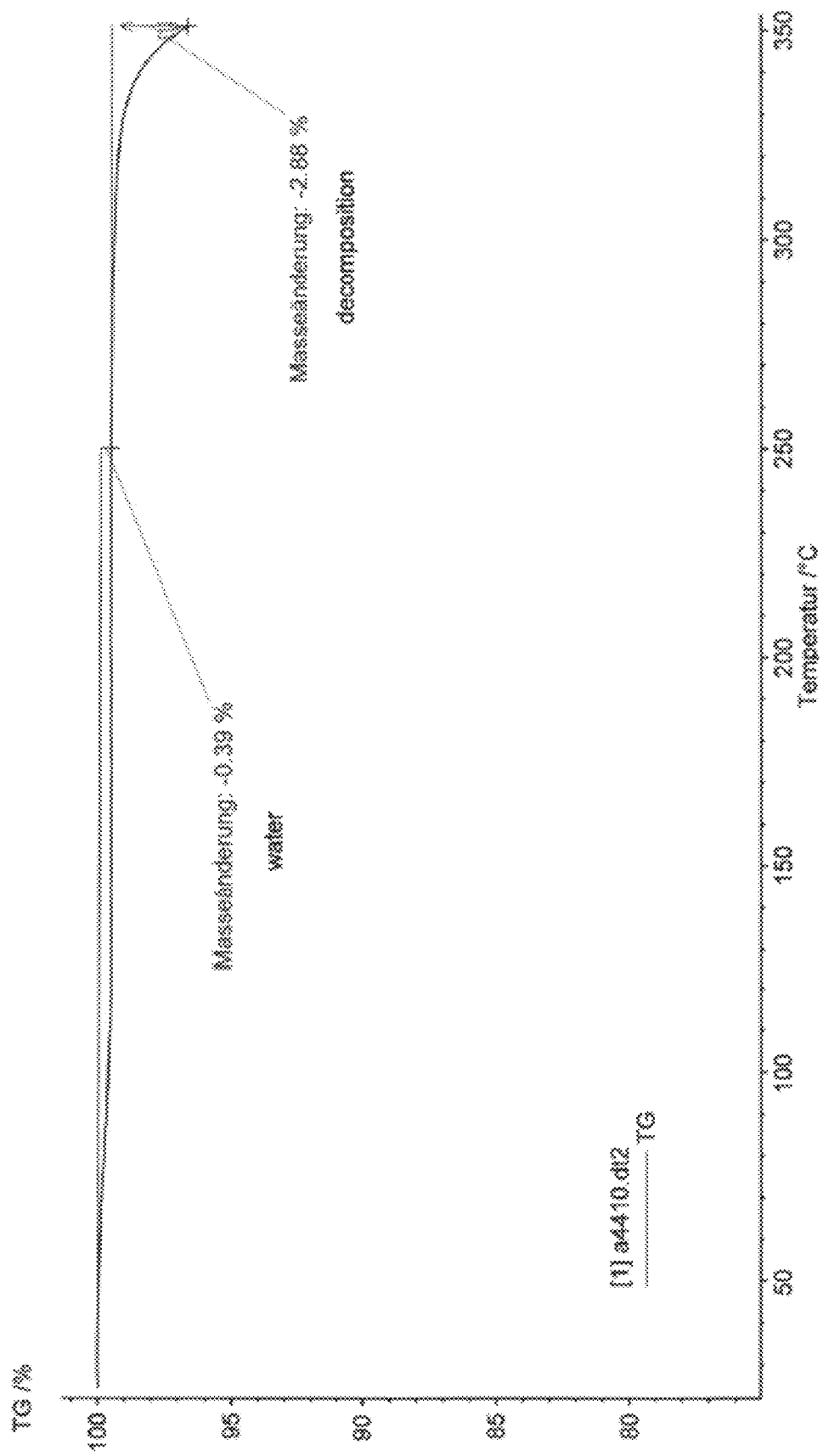

FIG. 128—TG-FTIR thermogram of the sample PP415-P46a, which corresponds to the amorphous form (Class 1).

Figure 129:
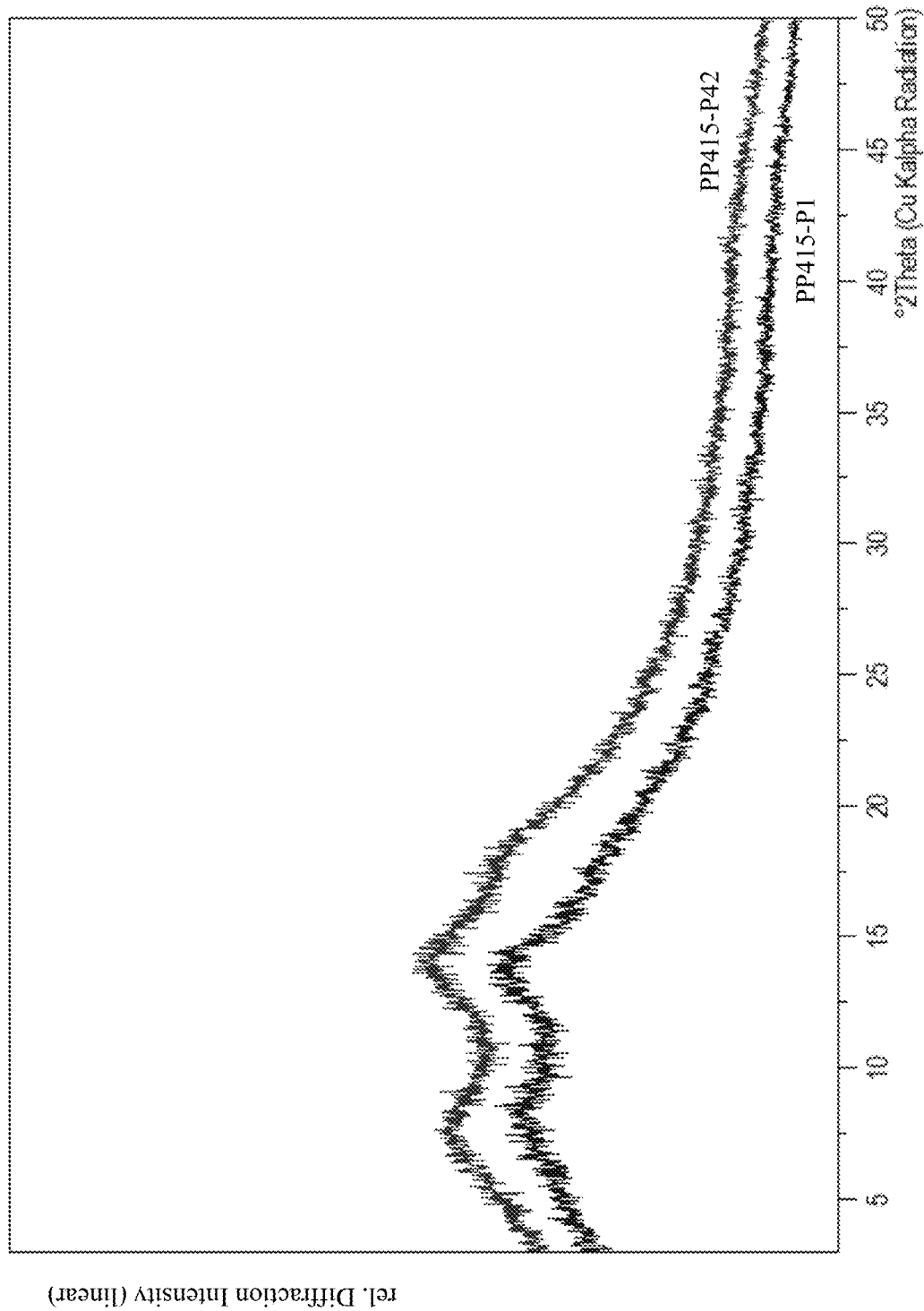

FIG. 129—PXRD pattern of sample PP415-P42 (top) corresponds to the pattern of the amorphous form (Class 1) (bottom, sample PP415-P1). The patterns have been scaled and offset in the y-direction for the purpose of comparison.

Figure 130:
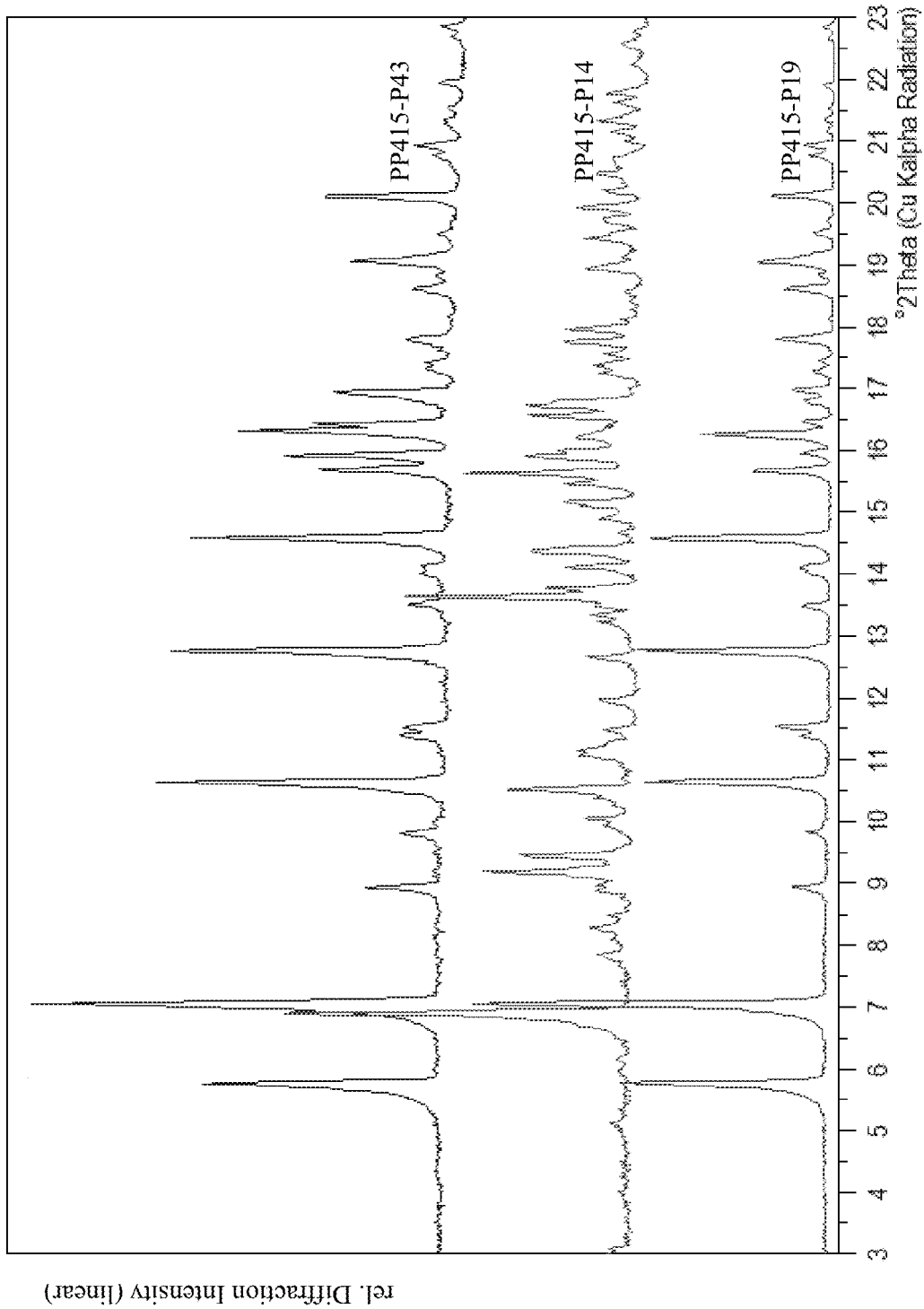

FIG. 130—PXRD pattern of sample PP415-P43 (top) corresponds to the pattern of the isostructural solvate form (Class 2) (bottom, sample PP415-P19) and not to the pattern of the THF solvate form (Class 5) (middle, sample PP415-P14). The patterns have been scaled and offset in the y-direction for the purpose of comparison.

Figure 131:
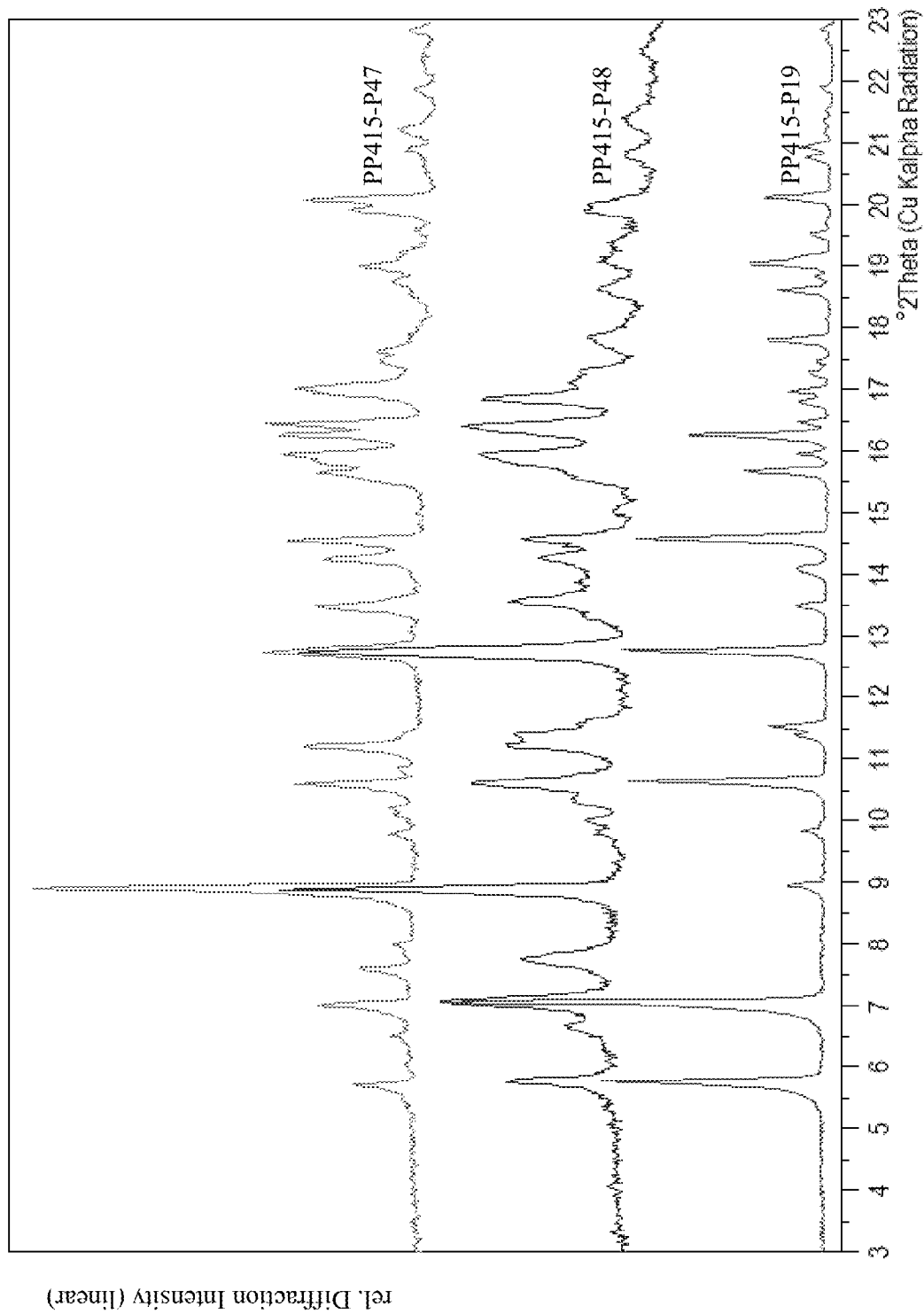

FIG. 131—PXRD patterns of samples PP415-P47 (top) and PP415-P48 (middle) correspond essentially to the pattern of the isostructural solvate forms (Class 2) (bottom, sample PP415-P19), although there are some differences. The patterns have been scaled and offset in the y-direction for the purpose of comparison.

Figure 132:
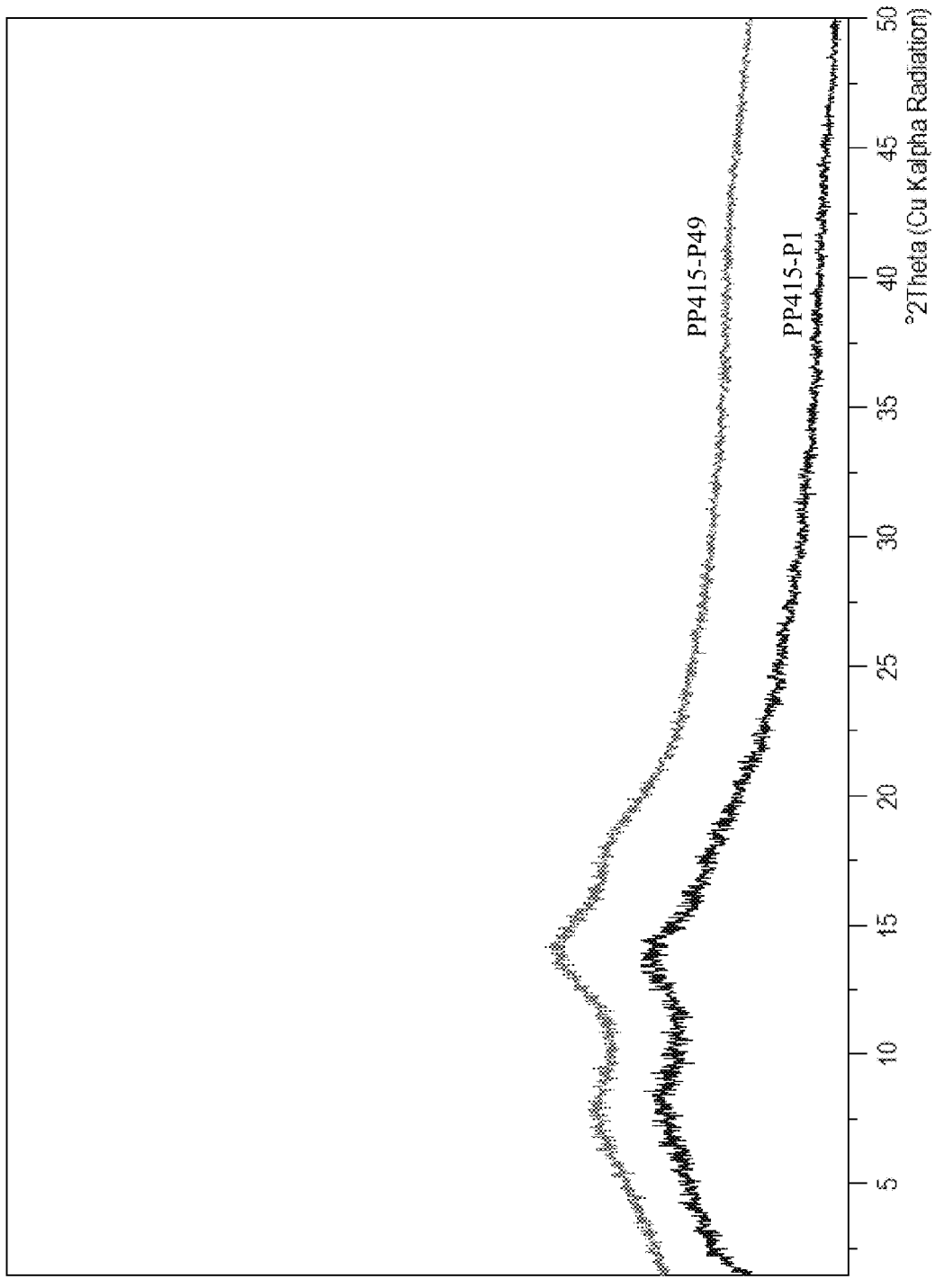

FIG. 132—PXRD pattern of sample PP415-P49 (top) corresponds to the pattern of the amorphous form (Class 1) (bottom, sample PP415-P1). The patterns have been scaled and offset in the y-direction for the purpose of comparison.

DESCRIPTION OF ILLUSTRATIVE EMBODIMENTS

The present invention provides in one aspect the compound:

N-((4aS,6aR,6bS,8aR,12aS,14aR,14bS)-11-cyano-2,2,6a,6b,9,9,12a-heptamethyl-10,14-dioxo-1,2,3,4,4a,5,6,6a,6b,7,8,8a,9,10,12a,14,14a,14b-octadecahydropicen-4a-yl)-2,2-difluoropropanamide, which is also referred to herein as RTA 408, 63415, or PP415. In other non-limiting aspects, the present invention also provides polymorphic forms thereof, including solvates thereof. In other non-limiting aspects, the invention also provides pharmaceutically acceptable salts thereof. In other non-limiting aspects, there are also provided methods for preparation, pharmaceutical compositions, and kits and articles of manufacture of these compounds and polymorphic forms thereof.

I. Definitions

When used in the context of a chemical group: "hydrogen" means —H; "hydroxy" means —OH; "oxo" means=O; "carbonyl" means —C(=O)—; "carboxy" means —C(=O)OH (also written as —COOH or —CO$_2$H); "halo" means independently —F, —Cl, —Br or —I; "amino" means —NH$_2$; "hydroxyamino" means —NHOH; "nitro" means —NO$_2$; imino means=NH; "cyano" means —CN; "isocyanate" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; and "thio" means=S; "sulfonyl" means —S(O)$_2$—; and "sulfinyl" means —S(O)—. Any undefined valency on an atom of a structure shown in this application implicitly represents a hydrogen atom bonded to the atom.

In the context of this disclosure, the formulas:

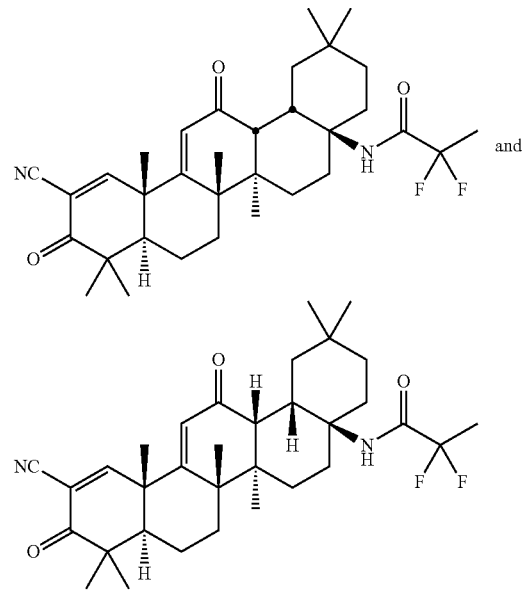

represent the same structures. When a dot is drawn on a carbon, the dot indicates that the hydrogen atom attached to that carbon is coming out of the plane of the page.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects. When used in the context of X-ray powder diffraction, the term "about" is used to indicate a value of ±0.2° 2θ from the reported value, preferably a value of ±0.1° 2θ from the reported value. When used in the context of differential scanning calorimetry or glass transition temperatures, the term "about" is used to indicate a value of ±10° C. relative to the maximum of the peak, preferably a value of 2° C. relative to the maximum of the peak. When used in other contexts, the term "about" is used to indicate a value of 10% of the reported value, preferably a value of ±5% of the reported value. It is to be understood that, whenever the term "about" is used, a specific reference to the exact numerical value indicated is also included.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result. "Effective amount," "Therapeutically effective amount" or "pharmaceutically effective amount" when used in the context of treating a patient or subject with a compound means that amount of the compound which, when administered to a subject or patient for treating a disease, is sufficient to effect such treatment for the disease.

The term "halo peak" in the context of X-ray powder diffraction would mean a broad peak, often spanning >10° 2θ in an X-ray powder diffractogram, typically characteristic of an amorphous solid or system.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

As used herein, the term "$IC_{50}$" refers to an inhibitory dose that is 50% of the maximum response obtained. This quantitative measure indicates how much of a particular drug or other substance (inhibitor) is needed to inhibit a given biological, biochemical, or chemical process (or component of a process, i.e. an enzyme, cell, cell receptor or microorganism) by half.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a non-human animal. In certain embodiments, the patient or subject is a primate. In certain embodiments, the patient or subject is a human. Non-limiting examples of human subjects are adults, juveniles, infants and fetuses.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2] oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

"Prodrug" means a compound that is convertible in vivo metabolically into an inhibitor according to the present invention. The prodrug itself may or may not also have activity with respect to a given target protein. For example, a compound comprising a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, propionates, succinates, fumarates, maleates, methylene-bis-β-hydroxynaphthoate, gentisates, isethionates, di-p-toluoyltartrates, methane-sulfonates, ethanesulfonates, benzenesulfonates, p-toluenesulfonates, cyclohexylsulfamates, quinates, esters of amino acids, and the like. Similarly, a compound comprising an amine group may be administered as an amide that is converted by hydrolysis in vivo to the amine compound.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed $2^n$, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably 5%, or most preferably ≤1% of another stereoisomer(s).

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

The above definitions supersede any conflicting definition in any of the reference that is incorporated by reference herein. The fact that certain terms are defined, however, should not be considered as indicative that any term that is undefined is indefinite.

Rather, all terms used are believed to describe the invention in terms such that one of ordinary skill can appreciate the scope and practice the present invention.

II. RTA 408 and Synthetic Methods

RTA 408 can be prepared according to the methods described in the Examples section below. These methods can be further modified and optimized using the principles and techniques of organic chemistry as applied by a person skilled in the art. Such principles and techniques are taught, for example, in *March's Advanced Organic Chemistry: Reactions, Mechanisms, and Structure* (2007), which is incorporated by reference herein.

It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

RTA 408 may also exist in prodrug form. Since prodrugs are known to enhance numerous desirable qualities of pharmaceuticals, e.g., solubility, bioavailability, manufacturing, etc., the compounds employed in some methods of the invention may, if desired, be delivered in prodrug form. Thus, the invention contemplates prodrugs of compounds of the present invention as well as methods of delivering prodrugs. Prodrugs of the compounds employed in the invention may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a patient, cleaves to form a hydroxy, amino, or carboxylic acid, respectively.

RTA 408 may contain one or more asymmetrically-substituted carbon or nitrogen atoms, and may be isolated in optically active or racemic form. Thus, all chiral, diastereomeric, racemic form, epimeric form, and all geometric isomeric forms of a structure are intended, unless the specific stereochemistry or isomeric form is specifically indicated. RTA 408 may occur as racemates and racemic mixtures, single enantiomers, diastereomeric mixtures and individual diastereomers. In some embodiments, a single diastereomer is obtained. The chiral centers of RTA 408 according to the present invention can have the S or the R configuration.

In addition, atoms making up RTA 408 of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$. Similarly, it is contemplated that one or more carbon atom(s) of a compound of the present invention may be replaced by a silicon atom(s). Furthermore, it is contemplated that one or more oxygen atom(s) of RTA 408 may be replaced by a sulfur or selenium atom(s).

RTA 408 and polymorphic form thereof may also have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical advantages over, compounds known in the prior art for use in the indications stated herein.

III. Polymorphic Forms of RTA 408

In some embodiments, the present invention provides different solid forms of RTA 408, including solvates thereof. A preformulation and preliminary polymorphism study was performed, and RTA 408 was found to have a high tendency for solvate formation. Crystalline forms of classes 2, 3, 4, and 5 are consistent with solvates. For a description of the classes, see Table 1 below. Attempts to dry classes 2 and 3 (two groups of isostructural solvates) were not successful, which is consistent with tightly bound solvent molecules. In some embodiments, drying of a class 4 solid (acetonitrile solvate) led to an isostructural desolvated form. In some embodiments, drying of a class 5 solid (THF solvate) resulted in the amorphous form class 1. Non-solvated forms of RTA 408 include the amorphous form (class 1) and the crystalline desolvated solvate of class 4 (isostructural to the class 4 acetonitrile solvate). In some embodiments, the amorphous form has a high glass transition with $T_g \approx 153°$ C. ($\Delta Cp=0.72$ J/g° C.) and is only slightly hygroscopic ($\Delta m=+0.4\%$ 50%→85% r.h.). In some embodiments, the amorphous form is stable for at least four weeks under elevated temperature and humidity conditions (i.e., open at 40° C./~75% r.h. or closed at 80° C.). In some embodiments, the amorphous form (class 1) was successfully prepared from class 2 material in a two-step process (transformation into class 5 and subsequent drying of class 5 to obtain the amorphous form), as well as in a direct one-step method (precipitation from an acetone solution in a cold water bath). The crystalline desolvated solvate of class 4 (isostructural to the class 4 solvate) is slightly hygroscopic (mass gain of ~0.7 wt.-% from 50% r.h. to 85% r.h.) and has a possible melting point at 196.1° C. ($\Delta H=29.31$ J/g).

A sample of the amorphous form of 63415, class 1, was characterized by FT-Raman spectroscopy, PXRD, TG-FTIR, Karl Fischer titration, $^1$H-NMR, DSC, and DVS (see Examples section for additional details). The sample was found to contain ~0.9 wt.-% EtOH with traces of $H_2O$ (according to the TG-FTIR). A water content of 0.5 wt.-% was determined by Karl Fischer titration. DSC shows a high glass transition temperature with $T_g \approx 153°$ C. ($\Delta Cp=0.72$ J/g° C.). According to DVS, the material is slightly hygroscopic ($\Delta m=+0.4\%$ 50%→85% r.h.). No crystallization was observed in the DSC or DVS experiments.

The chemical stability of the amorphous form was investigated in organic solvents, including acetone, EtOAc, MeOH, and MeCN, as well as different aqueous media (e.g., 1% aq. Tween 80, 1% aq. SDS, 1% aq. CTAB) at a concentration of 1 mg/mL at time points 6 h, 24 h, 2 d, and 7 d. Decomposition ≥1% was observed only for solutions in MeCN after 7 days and for suspensions in the 1% aqueous Tween 80 medium (at all times points at 254 nm and after 24 h, 2 d, and 7 d at 242 nm).

In addition, the stability of the amorphous form was investigated by storage under elevated temperature and humidity conditions (open at 25° C./62% r.h. and 40° C./75% r.h. and closed at 60° C. and 80° C.). After one week, two weeks, and four weeks, the stored samples were analyzed by PXRD. None of the samples differed from the amorphous starting material.

More than 30 crystallization and drying experiments were carried out, including suspension equilibration, slow cooling, evaporation, and precipitation. Four new crystalline forms were obtained (classes 2, 3, 4, and 5) in addition to the amorphous form (class 1).

The four new forms (classes 2, 3, 4, and 5) were characterized by FT-Raman spectroscopy, PXRD, and TG-FTIR. All forms correspond to solvates (Table 1). Drying experiments under vacuum or $N_2$ flow were carried out with the aim to obtain a crystalline, non-solvated form of 63415.

TABLE 1

Summary of Obtained Classes

| Class | Characteristics | Result of Drying Experiments |
| --- | --- | --- |
| Class 1 | amorphous form | — |
| Class 2 | isostructural solvates (e.g., heptane) | drying not successful |
| Class 3 | isostructural solvates (e.g., ethanol) | drying not successful |
| Class 4 | MeCN solvate & desolvated solvate | drying successful, structure unchanged |
| Class 5 | THF solvate | drying resulted in amorphous form |

Class 2: Most crystallization experiments that were conducted resulted in solid material of class 2 (see Examples section below). Its members may correspond to isostructural, non-stoichiometric (<0.5 eq.) solvates (of heptane, cyclohexane, isopropyl ether, 1-butanol, triethylamine, and possibly other solvents, such as hexane, other ethers, etc.) with tightly bound solvent molecules. The Raman spectra and PXRD patterns within this class are very similar to each other, thus the structures might be essentially identical with only small differences due to the different solvents that were incorporated.

Drying experiments on class 2 samples have not resulted in a crystalline, non-solvated form. Even elevated temperatures (80° C.) and a high vacuum (<$1\times10^{-3}$ mbar) could not remove the tightly bound solvent molecules completely; a solvent content of >2 wt.-% always remained. The crystallinity of these partially dried samples is reduced, but neither transformation into a different structure nor substantial amorphization was observed.

Class 3: Solid material of class 3 may be obtained from several crystallizations (see Examples section below). The samples of class 3 are likely isostructural solvates of 2PrOH, EtOH, and probably acetone with tightly bound solvent molecules. They could correspond to either stoichiometric hemisolvates or non-stoichiometric solvates with a solvent content of ~0.5 eq. As with class 2, the Raman spectra and PXRD patterns within this class are very similar to each other, indicating similar structures that incorporate different solvents.

Similar to class 2, drying experiments were not successful. The very tightly bound solvent molecules could only partially be removed (i.e., ~5.4 wt.-% to ~4.8 wt.-% after up to 3 d at $1\times10^{-3}$ mbar and 80° C.). The PXRD patterns remained unchanged.

Class 4 may be obtained from a 7:3 MeCN/$H_2O$ solvent system (see Examples section below). It most likely corresponds to a crystalline acetonitrile hemisolvate. By drying (under vacuum or $N_2$ flow at elevated temperatures) most of the solvent molecules could be removed without changing or destroying the crystal structure (PXRD remained unchanged). Thus, a crystalline, non-solvated form (or rather desolvated solvate) was obtained. It is slightly hygroscopic (mass gain of ~0.7 wt.-% from 50% r.h. to 85% r.h.) and has a possible melting point at 196.1° C. (ΔH=29.31 J/g).

Class 5 may be obtained from an ~1:1 THF/$H_2O$ solvent system. Class 5 contains bound THF (and may be $H_2O$). As the content of the two components cannot be readily quantified separately, the exact nature of this crystalline solvate has not been determined.

Drying of class 5 resulted in significant desolvation and transformation in the direction of the amorphous form (class 1). In some embodiments, the amorphous form of RTA 408 may be prepared by suspending class 2 heptane solvate in 1:1 THF/$H_2O$ to form a class 5 solid, followed by drying and amorphization.

Experiments with the aim of preparing the amorphous form (class 1) were carried out using class 2 starting material. Mainly amorphous material (class 1) was prepared starting from class 2 material in a two-step process via class 5 on a 100-mg and 3-g scale (drying at 100 mbar, 80° C., several days). The preparation of fully amorphous material (class 1) was found to be possible in a one-step process avoiding the solvent THF by direct precipitation of the amorphous form (class 1) from an acetone solution of class 2 material in a cold water bath.

IV. Diseases Associated with Inflammation and/or Oxidative Stress

Inflammation is a biological process that provides resistance to infectious or parasitic organisms and the repair of damaged tissue. Inflammation is commonly characterized by localized vasodilation, redness, swelling, and pain, the recruitment of leukocytes to the site of infection or injury, production of inflammatory cytokines, such as TNF-α and IL-1, and production of reactive oxygen or nitrogen species, such as hydrogen peroxide, superoxide, and peroxynitrite. In later stages of inflammation, tissue remodeling, angiogenesis, and scar formation (fibrosis) may occur as part of the wound healing process. Under normal circumstances, the inflammatory response is regulated, temporary, and is resolved in an orchestrated fashion once the infection or injury has been dealt with adequately. However, acute inflammation can become excessive and life-threatening if regulatory mechanisms fail. Alternatively, inflammation can become chronic and cause cumulative tissue damage or systemic complications. Based at least on the evidence presented herein, RTA 408 can be used in the treatment or prevention of inflammation or diseases associated with inflammation.

Many serious and intractable human diseases involve dysregulation of inflammatory processes, including diseases such as cancer, atherosclerosis, and diabetes, which were not traditionally viewed as inflammatory conditions. In the case of cancer, the inflammatory processes are associated with processes that include tumor formation, progression, metastasis, and resistance to therapy. In some embodiments, RTA 408 may be used in the treatment or prevention of cancers including a carcinoma, sarcoma, lymphoma, leukemia, melanoma, mesothelioma, multiple myeloma, or seminoma, or cancer of the bladder, blood, bone, brain, breast, central nervous system, cervix, colon, endometrium, esophagus, gall bladder, genitalia, genitourinary tract, head, kidney, larynx, liver, lung, muscle tissue, neck, oral or nasal mucosa, ovary, pancreas, prostate, skin, spleen, small intestine, large intestine, stomach, testicle, or thyroid. Atherosclerosis, long viewed as a disorder of lipid metabolism, is now understood to be primarily an inflammatory condition, with activated macrophages playing an important role in the formation and eventual rupture of atherosclerotic plaques. Activation of inflammatory signaling pathways has also been shown to play a role in the development of insulin resistance, as well as in the peripheral tissue damage associated with diabetic hyperglycemia. Excessive production of reactive oxygen species and reactive nitrogen species, such as superoxide, hydrogen peroxide, nitric oxide, and peroxynitrite, is a hallmark of inflammatory conditions. Evidence of dysregulated peroxynitrite production has been reported in a wide variety of diseases (Szabo et al., 2007; Schulz et al., 2008; Forstermann, 2006; Pall, 2007).

Autoimmune diseases such as rheumatoid arthritis, lupus, psoriasis, and multiple sclerosis involve inappropriate and chronic activation of inflammatory processes in affected tissues, arising from dysfunction of self vs. non-self recognition and response mechanisms in the immune system. In neurodegenerative diseases such as Alzheimer's and Parkinson's diseases, neural damage is correlated with activation of microglia and elevated levels of pro-inflammatory proteins, such as inducible nitric oxide synthase (iNOS). Chronic organ failure, such as renal failure, heart failure, liver failure, and chronic obstructive pulmonary disease, is closely associated with the presence of chronic oxidative stress and inflammation, leading to the development of fibrosis and eventual loss of organ function. Oxidative stress in vascular endothelial cells, which line major and minor blood vessels, can lead to endothelial dysfunction and is believed to be an important contributing factor in the development of systemic cardiovascular disease, complications of diabetes, chronic kidney disease and other forms of organ failure, and a number of other aging-related diseases, including degenerative diseases of the central nervous system and the retina.

Many other disorders involve oxidative stress and inflammation in affected tissues, including inflammatory bowel disease; inflammatory skin diseases; mucositis and dermatitis related to radiation therapy and chemotherapy; eye diseases, such as uveitis, glaucoma, macular degeneration, and various forms of retinopathy; transplant failure and rejection; ischemia-reperfusion injury; chronic pain; degenerative conditions of the bones and joints, including osteoarthritis and osteoporosis; asthma and cystic fibrosis; seizure disorders; and neuropsychiatric conditions, including schizophrenia, depression, bipolar disorder, post-traumatic stress disorder, attention deficit disorders, autism-spectrum disorders, and eating disorders, such as anorexia nervosa. Dysregulation of inflammatory signaling pathways is believed to be a major factor in the pathology of muscle wasting diseases, including muscular dystrophy and various forms of cachexia.

A variety of life-threatening acute disorders also involve dysregulated inflammatory signaling, including acute organ failure involving the pancreas, kidneys, liver, or lungs, myocardial infarction or acute coronary syndrome, stroke, septic shock, trauma, severe burns, and anaphylaxis.

Many complications of infectious diseases also involve dysregulation of inflammatory responses. Although an inflammatory response can kill invading pathogens, an excessive inflammatory response can also be quite destructive and in some cases can be a primary source of damage in infected tissues. Furthermore, an excessive inflammatory response can also lead to systemic complications due to overproduction of inflammatory cytokines, such as TNF-α and IL-1. This is believed to be a factor in mortality arising from severe influenza, severe acute respiratory syndrome, and sepsis.

The aberrant or excessive expression of either iNOS or cyclooxygenase-2 (COX-2) has been implicated in the pathogenesis of many disease processes. For example, it is clear that NO is a potent mutagen (Tamir and Tannebaum, 1996), and that nitric oxide can also activate COX-2 (Salvemini et al., 1994). Furthermore, there is a marked increase in iNOS in rat colon tumors induced by the carcinogen, azoxymethane (Takahashi et al., 1997). A series of synthetic triterpenoid analogs of oleanolic acid have been shown to be powerful inhibitors of cellular inflammatory processes, such as the induction by IFN-γ of inducible nitric oxide synthase (iNOS) and of COX-2 in mouse macrophages. See Honda et al. (2000a), Honda et al. (2000b), and Honda et al. (2002), which are all incorporated herein by reference.

In one aspect, RTA 408 disclosed herein is in part characterized by its ability to inhibit the production of nitric oxide in macrophage-derived RAW 264.7 cells induced by exposure to γ-interferon. RTA 408 is further characterized by the ability to induce the expression of antioxidant proteins, such as NQO1, and reduce the expression of pro-inflammatory proteins, such as COX-2 and inducible nitric oxide synthase (iNOS). These properties are relevant to the treatment of a wide array of diseases and disorders involving oxidative stress and dysregulation of inflammatory processes, including cancer, complications from localized or total-body exposure to ionizing radiation, mucositis and dermatitis resulting from radiation therapy or chemotherapy, autoimmune diseases, cardiovascular diseases, including atherosclerosis, ischemia-reperfusion injury, acute and chronic organ failure, including renal failure and heart failure, respiratory diseases, diabetes and complications of diabetes, severe allergies, transplant rejection, graft-versus-host disease, neurodegenerative diseases, diseases of the eye and retina, acute and chronic pain, degenerative bone diseases, including osteoarthritis and osteoporosis, inflammatory bowel diseases, dermatitis and other skin diseases, sepsis, burns, seizure disorders, and neuropsychiatric disorders.

In another aspect, RTA 408 may be used for treating a subject having a condition such as eye diseases. For example, uveitis, macular degeneration (both the dry form and wet form), glaucoma, diabetic macular edema, blepharitis, diabetic retinopathy, diseases and disorders of the corneal endothelium such as Fuchs endothelial corneal dystrophy, post-surgical inflammation, dry eye, allergic conjunctivitis and other forms of conjunctivitis are non-limiting examples of eye diseases that could be treated with RTA 408.

In another aspect, RTA 408 may be used for treating a subject having a condition such as skin diseases or disorders.

For example, dermatitis, including allergic dermatitis, atopic dermatitis, dermatitis due to chemical exposure, and radiation-induced dermatitis; thermal or chemical burns; chronic wounds including diabetic ulcers, pressure sores, and venous ulcers; acne; alopecia including baldness and drug-induced alopecia; other disorders of the hair follicle; epidermolysis bullosa; sunburn and its complications; disorders of skin pigmentation including vitiligo; aging-related skin conditions; post-surgical wound healing; prevention or reduction of scarring from skin injury, surgery, or burns; psoriasis; dermatological manifestations of autoimmune diseases or graft-versus host disease; prevention or treatment of skin cancer; disorders involving hyperproliferation of skin cells such as hyperkeratosis is a non-limiting example of skin diseases that could be treated with RTA 408.

Without being bound by theory, the activation of the antioxidant/anti-inflammatory Keap1/Nrf2/ARE pathway is believed to be implicated in both the anti-inflammatory and anti-carcinogenic properties of the compound disclosed herein.

In another aspect, RTA 408 may be used for treating a subject having a condition caused by elevated levels of oxidative stress in one or more tissues. Oxidative stress results from abnormally high or prolonged levels of reactive oxygen species, such as superoxide, hydrogen peroxide, nitric oxide, and peroxynitrite (formed by the reaction of nitric oxide and superoxide). The oxidative stress may be accompanied by either acute or chronic inflammation. The oxidative stress may be caused by mitochondrial dysfunction, by activation of immune cells, such as macrophages and neutrophils, by acute exposure to an external agent, such as ionizing radiation or a cytotoxic chemotherapeutic agent (e.g., doxorubicin), by trauma or other acute tissue injury, by ischemia/reperfusion, by poor circulation or anemia, by localized or systemic hypoxia or hyperoxia, by elevated levels of inflammatory cytokines and other inflammation-related proteins, and/or by other abnormal physiological states, such as hyperglycemia or hypoglycemia.

In animal models of many such conditions, stimulating expression of inducible heme oxygenase (HO-1), a target gene of the Nrf2 pathway, has been shown to have a significant therapeutic effect including in models of myocardial infarction, renal failure, transplant failure and rejection, stroke, cardiovascular disease, and autoimmune disease (e.g., Sacerdoti et al., 2005; Abraham & Kappas, 2005; Bach, 2006; Araujo et al., 2003; Liu et al., 2006; Ishikawa et al., 2001; Kruger et al., 2006; Satoh et al., 2006; Zhou et al., 2005; Morse and Choi, 2005; Morse and Choi, 2002). This enzyme breaks free heme down into iron, carbon monoxide (CO), and biliverdin (which is subsequently converted to the potent antioxidant molecule, bilirubin).

In another aspect, RTA 408 may be used in preventing or treating tissue damage or organ failure, acute and chronic, resulting from oxidative stress exacerbated by inflammation. Examples of diseases that fall in this category include heart failure, liver failure, transplant failure and rejection, renal failure, pancreatitis, fibrotic lung diseases (cystic fibrosis, COPD, and idiopathic pulmonary fibrosis, among others), diabetes (including complications), atherosclerosis, ischemia-reperfusion injury, glaucoma, stroke, autoimmune disease, autism, macular degeneration, and muscular dystrophy. For example, in the case of autism, studies suggest that increased oxidative stress in the central nervous system may contribute to the development of the disease (Chauhan and Chauhan, 2006).

Evidence also links oxidative stress and inflammation to the development and pathology of many other disorders of the central nervous system, including psychiatric disorders, such as psychosis, major depression, and bipolar disorder; seizure disorders, such as epilepsy; pain and sensory syndromes, such as migraine, neuropathic pain, or tinnitus; and behavioral syndromes, such as the attention deficit disorders. See, e.g., Dickerson et al., 2007; Hanson et al., 2005; Kendall-Tackett, 2007; Lencz et al., 2007; Dudhgaonkar et al., 2006; Lee et al., 2007; Morris et al., 2002; Ruster et al., 2005; McIver et al., 2005; Sarchielli et al., 2006; Kawakami et al., 2006; Ross et al., 2003, which are all incorporated by reference herein. For example, elevated levels of inflammatory cytokines, including TNF-α, interferon-γ, and IL-6, are associated with major mental illness (Dickerson et al., 2007). Microglial activation has also been linked to major mental illness. Therefore, downregulating inflammatory cytokines and inhibiting excessive activation of microglia could be beneficial in patients with schizophrenia, major depression, bipolar disorder, autism-spectrum disorders, and other neuropsychiatric disorders.

Accordingly, in pathologies involving oxidative stress alone or oxidative stress exacerbated by inflammation, treatment may comprise administering to a subject a therapeutically effective amount of a compound of this invention, such as those described above or throughout this specification. Treatment may be administered preventively, in advance of a predictable state of oxidative stress (e.g., organ transplantation or the administration of radiation therapy to a cancer patient), or it may be administered therapeutically in settings involving established oxidative stress and inflammation. In some embodiments, when a compound of the present invention is used for treating a patient receiving radiation therapy and/or chemotherapy, the compound of the invention may be administered before, at the same time, and/or after the radiation or chemotherapy, or the compound may be administered in combination with the other therapies. In some embodiments, the compound of the invention may prevent and/or reduce the severity of side effects associated with the radiation therapy or chemotherapy (using a different agent) without reducing the anticancer effects of the radiation therapy or chemotherapy. Because such side effects may be dose-limiting for the radiation therapy and/or chemotherapy, in some embodiments, the compound of the present invention may be used to allow for higher and/or more frequent dosing of the radiation therapy and/or chemotherapy, for example, resulting in greater treatment efficacy. In some embodiments, the compound of the invention when administered in combination with the radiation therapy and/or chemotherapy may enhance the efficacy of a given dose of radiation and/or chemotherapy. In some embodiments, the compound of the invention when administered in combination with the radiation therapy and/or chemotherapy may enhance the efficacy of a given dose of radiation and/or chemotherapy and reduce (or, at a minimum, not add to) the side effects of the radiation and/or chemotherapy. In some embodiments, and without being bound by theory, this combinatorial efficacy may result from inhibition of the activity of the pro-inflammatory transcription factor NF-κB by the compound of the invention. NF-κB is often chronically activated in cancer cells, and such activation is associated with resistance to therapy and promotion of tumor progression (e.g., Karin, 2006; Aghajan et al., 2012). Other transcription factors that promote inflammation and cancer, such as STAT3 (e.g., He and Karin 2011; Grivennikov and Karin, 2010), may also be inhibited by the compound of the invention in some embodiments.

RTA 408 may be used to treat or prevent inflammatory conditions, such as sepsis, dermatitis, autoimmune disease, and osteoarthritis. RTA 408 may also be used to treat or prevent inflammatory pain and/or neuropathic pain, for example, by inducing Nrf2 and/or inhibiting NF-κB.

RTA 408 may also be used to treat or prevent diseases, such as cancer, inflammation, Alzheimer's disease, Parkinson's disease, multiple sclerosis, autism, amyotrophic lateral sclerosis, Huntington's disease, autoimmune diseases, such as rheumatoid arthritis, lupus, Crohn's disease, and psoriasis, inflammatory bowel disease, all other diseases whose pathogenesis is believed to involve excessive production of either nitric oxide or prostaglandins, and pathologies involving oxidative stress alone or oxidative stress exacerbated by inflammation. RTA 408 may be used in the treatment or prevention of cancers include a carcinoma, sarcoma, lymphoma, leukemia, melanoma, mesothelioma, multiple myeloma, or seminoma, or cancer of the bladder, blood, bone, brain, breast, central nervous system, cervix, colon, endometrium, esophagus, gall bladder, genitalia, genitourinary tract, head, kidney, larynx, liver, lung, muscle tissue, neck, oral or nasal mucosa, ovary, pancreas, prostate, skin, spleen, small intestine, large intestine, stomach, testicle, or thyroid.

Another aspect of inflammation is the production of inflammatory prostaglandins, such as prostaglandin E. RTA 408 may be used to promote vasodilation, plasma extravasation, localized pain, elevated temperature, and other symptoms of inflammation. The inducible form of the enzyme COX-2 is associated with their production, and high levels of COX-2 are found in inflamed tissues. Consequently, inhibition of COX-2 may relieve many symptoms of inflammation and a number of important anti-inflammatory drugs (e.g., ibuprofen and celecoxib) act by inhibiting COX-2 activity. It has been demonstrated that a class of cyclopentenone prostaglandins (cyPGs) (e.g., 15-deoxy prostaglandin J2, a.k.a. PGJ2) plays a role in stimulating the orchestrated resolution of inflammation (e.g., Rajakariar et al., 2007). COX-2 is also associated with the production of cyclopentenone prostaglandins. Consequently, inhibition of COX-2 may interfere with the full resolution of inflammation, potentially promoting the persistence of activated immune cells in tissues and leading to chronic, "smoldering" inflammation. This effect may be responsible for the increased incidence of cardiovascular disease in patients using selective COX-2 inhibitors for long periods of time.

In one aspect, RTA 408 may be used to control the production of pro-inflammatory cytokines within the cell by selectively activating regulatory cysteine residues (RCRs) on proteins that regulate the activity of redox-sensitive transcription factors. Activation of RCRs by cyPGs has been shown to initiate a pro-resolution program in which the activity of the antioxidant and cytoprotective transcription factor Nrf2 is potently induced and the activities of the pro-oxidant and pro-inflammatory transcription factors NF-κB and the STATs are suppressed. In some embodiments, RTA 408 may be used to increase the production of antioxidant and reductive molecules (NQO1, HO-1, SOD1, γ-GCS) and decrease oxidative stress and the production of pro-oxidant and pro-inflammatory molecules (iNOS, COX-2, TNF-α). In some embodiments, RTA 408 may be used to cause the cells that host the inflammatory event to revert to a non-inflammatory state by promoting the resolution of inflammation and limiting excessive tissue damage to the host.

A. Cancer

In some embodiments, RTA 408, the polymorphic forms, and methods of the present disclosure may be used to induce apoptosis in tumor cells, to induce cell differentiation, to inhibit cancer cell proliferation, to inhibit an inflammatory response, and/or to function in a chemopreventative capacity. For example, the invention provides new polymorphic forms that have one or more of the following properties: (1) an ability to induce apoptosis and differentiate both malignant and non-malignant cells, (2) an activity at sub-micromolar or nanomolar levels as an inhibitor of proliferation of many malignant or premalignant cells, (3) an ability to suppress the de novo synthesis of the inflammatory enzyme inducible nitric oxide synthase (iNOS), (4) an ability to inhibit NF-κB activation, and (5) an ability to induce the expression of heme oxygenase-1 (HO-1).

The levels of iNOS and COX-2 are elevated in certain cancers and have been implicated in carcinogenesis and COX-2 inhibitors have been shown to reduce the incidence of primary colonic adenomas in humans (Rostom et al., 2007; Brown and DuBois, 2005; Crowel et al., 2003). iNOS is expressed in myeloid-derived suppressor cells (MDSCs) (Angulo et al., 2000) and COX-2 activity in cancer cells has been shown to result in the production of prostaglandin $E_2$ ($PGE_2$), which has been shown to induce the expression of arginase in MDSCs (Sinha et al., 2007). Arginase and iNOS are enzymes that utilize L-arginine as a substrate and produce L-ornithine and urea, and L-citrulline and NO, respectively. The depletion of arginine from the tumor microenvironment by MDSCs, combined with the production of NO and peroxynitrite has been shown to inhibit proliferation and induce apoptosis of T cells (Bronte et al., 2003). Inhibition of COX-2 and iNOS has been shown to reduce the accumulation of MDSCs, restore cytotoxic activity of tumor-associated T cells, and delay tumor growth (Sinha et al., 2007; Mazzoni et al., 2002; Zhou et al., 2007).

Inhibition of the NF-κB and JAK/STAT signaling pathways has been implicated as a strategy to inhibit proliferation of cancer epithelial cells and induce their apoptosis. Activation of STAT3 and NF-κB has been shown to result in suppression of apoptosis in cancer cells, and promotion of proliferation, invasion, and metastasis. Many of the target genes involved in these processes have been shown to be transcriptionally regulated by both NF-κB and STAT3 (Yu et al., 2007).

In addition to their direct roles in cancer epithelial cells, NF-κB and STAT3 also have important roles in other cells found within the tumor microenvironment. Experiments in animal models have demonstrated that NF-κB is required in both cancer cells and hematopoeitic cells to propagate the effects of inflammation on cancer initiation and progression (Greten et al., 2004). NF-κB inhibition in cancer and myeloid cells reduces the number and size, respectively, of the resultant tumors. Activation of STAT3 in cancer cells results in the production of several cytokines (IL-6, IL-10) which suppress the maturation of tumor-associated dendritic cells (DC). Furthermore, STAT3 is activated by these cytokines in the dendritic cells themselves. Inhibition of STAT3 in mouse models of cancer restores DC maturation, promotes antitumor immunity, and inhibits tumor growth (Kortylewski et al., 2005). In some embodiments, RTA 408 and its polymorphic forms can be used to treat cancer, including, for example, prostate cancer. In some embodiments, RTA 408 and its polymorphic forms can be used in a combination therapy to treat cancer including, for example, prostate cancer. See, e.g., Example H below.

B. Multiple Sclerosis and Other Neurodegenerative Conditions

In some embodiments, RTA 408, the polymorphic forms, and the methods of this invention may be used for treating patients for multiple sclerosis (MS) or other neurodegenerative conditions such as Alzheimer's disease, Parkinson's disease, or amyotrophic lateral sclerosis. MS is known to be an inflammatory condition of the central nervous system (Williams et al., 1994; Merrill and Benvenist, 1996; Genain and Nauser, 1997). Based on several investigations, evidence suggests that inflammatory, oxidative, and/or immune mechanisms are involved in the pathogenesis of Alzheimer's disease (AD), Parkinson's disease (PD), amyotrophic lateral sclerosis (ALS), and MS (Bagasra et al., 1995; McGeer and McGeer, 1995; Simonian and Coyle, 1996; Kaltschmidt et al., 1997). Epidemiologic data indicate that chronic use of NSAIDs which block synthesis of prostaglandins from arachidonate, markedly lowers the risk for development of AD (McGeer et al., 1996; Stewart et al., 1997). Thus, agents that block formation of NO and prostaglandins, may be used in approaches to prevent and treat neurodegenerative diseases. Successful therapeutic candidates for treating such a disease typically require an ability to penetrate the blood-brain barrier. See, for example, U.S. Patent Publication 2009/0060873, which is incorporated by reference herein.

C. Neuroinflammation

In some embodiments, RTA 408, the polymorphic forms, and methods of this invention may be used for treating patients with neuroinflammation. Neuroinflammation encapsulates the idea that microglial and astrocytic responses and actions in the central nervous system have a fundamentally inflammation-like character, and that these responses are central to the pathogenesis and progression of a wide variety of neurological disorders. These ideas have been extended from Alzheimer's disease to other neurodegenerative diseases (Eikelenboom et al., 2002; Ishizawa and Dickson, 2001), to ischemic/toxic diseases (Gehrmann et al., 1995; Touzani et al., 1999), to tumor biology (Graeber et al., 2002) and even to normal brain development. Neuroinflammation incorporates a wide spectrum of complex cellular responses that include activation of microglia and astrocytes and induction of cytokines, chemokines, complement proteins, acute phase proteins, oxidative injury, and related molecular processes, and the events may have detrimental effects on neuronal function, leading to neuronal injury, further glial activation, and ultimately neurodegeneration.

D. Renal Diseases

In some embodiments, RTA 408, as well as polymorphic forms thereof, may be used for treating patients with renal diseases and disorders, including renal failure and chronic kidney disease (CKD), based, for example, on the methods taught by U.S. Pat. No. 8,129,429, which is incorporated by reference herein. Renal failure, resulting in inadequate clearance of metabolic waste products from the blood and abnormal concentrations of electrolytes in the blood, is a significant medical problem throughout the world, especially in developed countries. Diabetes and hypertension are among the most important causes of chronic renal failure, also known as chronic kidney disease (CKD), but it is also associated with other conditions such as lupus. Acute renal failure may arise from exposure to certain drugs (e.g., acetaminophen) or toxic chemicals, or from ischemia-reperfusion injury associated with shock or surgical procedures such as transplantation, and may result in chronic renal failure. In many patients, renal failure advances to a stage in which the patient requires regular dialysis or kidney transplantation to continue living. Both of these procedures are highly invasive and associated with significant side effects and quality of life issues. Although there are effective treatments for some complications of renal failure, such as hyperparathyroidism and hyperphosphatemia, no available treatment has been shown to halt or reverse the underlying progression of renal failure. Thus, agents that can improve compromised renal function would represent a significant advance in the treatment of renal failure.

Inflammation contributes significantly to the pathology of CKD. There is also a strong mechanistic link between oxidative stress and renal dysfunction. The NF-κB signaling pathway plays an important role in the progression of CKD as NF-κB regulates the transcription of MCP-1, a chemokine that is responsible for the recruitment of monocytes/macrophages resulting in an inflammatory response that ultimately injures the kidney (Wardle, 2001). The Keap1/Nrf2/ARE pathway controls the transcription of several genes encoding antioxidant enzymes, including heme oxygenase-1 (HO-1). Ablation of the Nrf2 gene in female mice results in the development of lupus-like glomerular nephritis (Yoh et al., 2001). Furthermore, several studies have demonstrated that HO-1 expression is induced in response to renal damage and inflammation and that this enzyme and its products—bilirubin and carbon monoxide—play a protective role in the kidney (Nath et al., 2006).

Acute kidney injury (AKI) can occur following ischemia-reperfusion, treatment with certain pharmacological agents, such as cisplatin and rapamycin, and intravenous injection of radiocontrast media used in medical imaging. As in CKD, inflammation and oxidative stress contribute to the pathology of AKI. The molecular mechanisms underlying radiocontrast-induced nephropathy (RCN) are not well understood; however, it is likely that a combination of events including prolonged vasoconstriction, impaired kidney autoregulation, and direct toxicity of the contrast media all contribute to renal failure (Tumlin et al., 2006). Vasoconstriction results in decreased renal blood flow and causes ischemia-reperfusion and the production of reactive oxygen species. HO-1 is strongly induced under these conditions and has been demonstrated to prevent ischemia-reperfusion injury in several different organs, including the kidney (Nath et al., 2006). Specifically, induction of HO-1 has been shown to be protective in a rat model of RCN (Goodman et al., 2007). Reperfusion also induces an inflammatory response, in part though activation of NF-κB signaling (Nichols, 2004). Targeting NF-κB has been proposed as a therapeutic strategy to prevent organ damage (Zingarelli et al., 2003).

E. Cardiovascular Disease

In some embodiments, RTA 408, the polymorphic forms and methods of this invention may be used for treating patients with cardiovascular disease. The etiology of CV disease is complex, but the majority of causes are related to inadequate or completely disrupted supply of blood to a critical organ or tissue. Frequently such a condition arises from the rupture of one or more atherosclerotic plaques, which leads to the formation of a thrombus that blocks blood flow in a critical vessel.

In some incidences, atherosclerosis may be so extensive in critical blood vessels that stenosis (narrowing of the arteries) develops and blood flow to critical organs (including the heart) is chronically insufficient. Such chronic ischemia can lead to end-organ damage of many kinds, including the cardiac hypertrophy associated with congestive heart failure.

Atherosclerosis, the underlying defect leading to many forms of cardiovascular disease, occurs when a physical defect or injury to the lining (endothelium) of an artery triggers an inflammatory response involving the proliferation of vascular smooth muscle cells and the infiltration of leukocytes into the affected area. Ultimately, a complicated lesion known as an atherosclerotic plaque may form, composed of the above-mentioned cells combined with deposits of cholesterol-bearing lipoproteins and other materials (e.g., Hansson et al., 2006). Despite the significant benefits offered by current therapeutic treatments, mortality from cardiovascular disease remains high and significant unmet needs in the treatment of cardiovascular disease remain.

Induction of HO-1 has been shown to be beneficial in a variety of models of cardiovascular disease, and low levels of HO-1 expression have been clinically correlated with elevated risk of CV disease. RTA 408, the polymorphic forms and methods of the invention, therefore, may be used in treating or preventing a variety of cardiovascular disorders including but not limited to atherosclerosis, hypertension, myocardial infarction, chronic heart failure, stroke, subarachnoid hemorrhage, and restenosis. In some embodiments, RTA 408, the polymorphic forms and methods of the invention may be used as a combination therapy with other known cardiovascular therapies such as but not limited to anticoagulants, thrombolytics, streptokinase, tissue plasminogen activators, surgery, coronary artery bypass grafting, balloon angioplasty, the use of stents, drugs which inhibit cell proliferation, or drugs which lower cholesterol levels.

F. Diabetes

In some embodiments, RTA 408, as well as polymorphic forms thereof, may be used for treating patients with diabetes, based, for example, on the methods taught by U.S. Pat. No. 8,129,429, which is incorporated by reference herein. Diabetes is a complex disease characterized by the body's failure to regulate circulating levels of glucose. This failure may result from a lack of insulin, a peptide hormone that regulates both the production and absorption of glucose in various tissues. Deficient insulin compromises the ability of muscle, fat, and other tissues to absorb glucose properly, leading to hyperglycemia (abnormally high levels of glucose in the blood). Most commonly, such insulin deficiency results from inadequate production in the islet cells of the pancreas. In the majority of cases this arises from autoimmune destruction of these cells, a condition known as type 1 or juvenile-onset diabetes, but may also be due to physical trauma or some other cause.

Diabetes may also arise when muscle and fat cells become less responsive to insulin and do not absorb glucose properly, resulting in hyperglycemia. This phenomenon is known as insulin resistance, and the resulting condition is known as type 2 diabetes. Type 2 diabetes, the most common type, is highly associated with obesity and hypertension. Obesity is associated with an inflammatory state of adipose tissue that is thought to play a major role in the development of insulin resistance (e.g., Hotamisligil, 2006; Guilherme et al., 2008).

Diabetes is associated with damage to many tissues, largely because hyperglycemia (and hypoglycemia, which can result from excessive or poorly timed doses of insulin) is a significant source of oxidative stress. Because of their ability to protect against oxidative stress, particularly by the induction of HO-1 expression, RTA 408, the polymorphic forms, and methods of the current invention may be used in treatments for many complications of diabetes. As noted above (Cai et al., 2005), chronic inflammation and oxidative stress in the liver are suspected to be primary contributing factors in the development of type 2 diabetes. Furthermore, $PPAR_\gamma$ agonists such as thiazolidinediones are capable of reducing insulin resistance and are known to be effective treatments for type 2 diabetes. In some embodiments, RTA 408, the polymorphic forms, and methods of the current invention may be used as combination therapies with $PPAR_\gamma$ agonists such as thiazolidinediones.

G. Arthritis

In some embodiments, RTA 408, the polymorphic forms, and methods of this invention may be used for treating patients with a form of arthritis. In some embodiments, the forms of arthritis that could be treated with RTA 408 and the polymorphic forms of this invention are rheumatoid arthritis (RA), psoriatic arthritis (PsA), spondyloarthropathies (SpAs) including ankylosing spondylitis (AS), reactive arthritis (ReA), and enteropathic arthritis (EA), juvenile rheumatoid arthritis (JRA), and early inflammatory arthritis.

For rheumatoid arthritis, the first signs typically appear in the synovial lining layer, with proliferation of synovial fibroblasts and their attachment to the articular surface at the joint margin (Lipsky, 1998). Subsequently, macrophages, T cells and other inflammatory cells are recruited into the joint, where they produce a number of mediators, including the cytokines interleukin-1 (IL-1), which contributes to the chronic sequelae leading to bone and cartilage destruction, and tumor necrosis factor (TNF-α), which plays a role in inflammation (Dinarello, 1998; Arend and Dayer, 1995; van den Berg, 2001). The concentration of IL-1 in plasma is significantly higher in patients with RA than in healthy individuals and, notably, plasma IL-1 levels correlate with RA disease activity (Eastgate et al., 1988). Moreover, synovial fluid levels of IL-1 are correlated with various radiographic and histologic features of RA (Kahle et al., 1992; Rooney et al., 1990).

Other forms of arthritis include psoriatic arthritis (PsA), which is a chronic inflammatory arthropathy characterized by the association of arthritis and psoriasis. Studies have revealed that PsA shares a number of genetic, pathogenic and clinical features with other spondyloarthropathies (SpAs), a group of diseases that comprise ankylosing spondylitis, reactive arthritis and enteropathic arthritis (Wright, 1979). The notion that PsA belongs to the SpA group has recently gained further support from imaging studies demonstrating widespread enthesitis in PsA but not RA (McGonagle et al., 1999; McGonagle et al., 1998). More specifically, enthesitis has been postulated to be one of the earliest events occurring in the SpAs, leading to bone remodeling and ankylosis in the spine, as well as to articular synovitis when the inflamed entheses are close to peripheral joints. Increased amounts of TNF-α have been reported in both psoriatic skin (Ettehadi et al., 1994) and synovial fluid (Partsch et al., 1997). Recent trials have shown a positive benefit of anti-TNF treatment in both PsA (Mease et al., 2000) and ankylosing spondylitis (Brandt et al., 2000).

Juvenile rheumatoid arthritis (JRA), a term for the most prevalent form of arthritis in children, is applied to a family of illnesses characterized by chronic inflammation and hypertrophy of the synovial membranes. The term overlaps, but is not completely synonymous, with the family of illnesses referred to as juvenile chronic arthritis and/or juvenile idiopathic arthritis in Europe.

Polyarticular JRA is a distinct clinical subtype characterized by inflammation and synovial proliferation in multiple joints (four or more), including the small joints of the hands (Jarvis, 2002). This subtype of JRA may be severe, because of both its multiple joint involvement and its capacity to progress rapidly over time. Although clinically distinct, polyarticular JRA is not homogeneous, and patients vary in disease manifestations, age of onset, prognosis, and therapeutic response. These differences very likely reflect a spectrum of variation in the nature of the immune and inflammatory attack that can occur in this disease (Jarvis, 1998).

Ankylosing spondylitis (AS) is a disease subset within a broader disease classification of spondyloarthropathy. Patients affected with the various subsets of spondyloarthropathy have disease etiologies that are often very different, ranging from bacterial infections to inheritance. Yet, in all subgroups, the end result of the disease process is axial arthritis.

AS is a chronic systemic inflammatory rheumatic disorder of the axial skeleton with or without extraskeletal manifestations. Sacroiliac joints and the spine are primarily affected, but hip and shoulder joints, and less commonly peripheral joints or certain extra-articular structures such as the eye, vasculature, nervous system, and gastrointestinal system may also be involved. The disease's etiology is not yet fully understood (Wordsworth, 1995; Calin and Taurog, 1998). The etiology is strongly associated with the major histocompatibility class I (MHC I) HLA-B27 allele (Calin and Taurog, 1998). AS affects individuals in the prime of their life and is feared because of its potential to cause chronic pain and irreversible damage of tendons, ligaments, joints, and bones (Brewerton et al., 1973a; Brewerton et al., 1973b; Schlosstein et al., 1973).

H. Ulcerative Colitis

In some embodiments, RTA 408, the polymorphic forms and methods of this invention may be used for treating patients with ulcerative colitis. Ulcerative colitis is a disease that causes inflammation and sores, called ulcers, in the lining of the large intestine. The inflammation usually occurs in the rectum and lower part of the colon, but it may affect the entire colon. Ulcerative colitis may also be called colitis or proctitis. The inflammation makes the colon empty frequently, causing diarrhea. Ulcers form in places where the inflammation has killed the cells lining the colon and the ulcers bleed and produce pus.

Ulcerative colitis is an inflammatory bowel disease (IBD), the general name for diseases that cause inflammation in the small intestine and colon. Ulcerative colitis can be difficult to diagnose because its symptoms are similar to other intestinal disorders and to another type of IBD, Crohn's disease. Crohn's disease differs from ulcerative colitis because it causes inflammation deeper within the intestinal wall. Also, Crohn's disease usually occurs in the small intestine, although the disease can also occur in the mouth, esophagus, stomach, duodenum, large intestine, appendix, and anus.

I. Crohn's Disease

In some embodiments, RTA 408, the polymorphic forms, and methods of this invention may be used for treating patients with Crohn's disease. Crohn's disease symptoms include intestinal inflammation and the development of intestinal stenosis and fistulas; neuropathy often accompanies these symptoms. Anti-inflammatory drugs, such as 5-aminosalicylates (e.g., mesalamine) or corticosteroids, are typically prescribed, but are not always effective (reviewed in Botoman et al., 1998). Immunosuppression with cyclosporine is sometimes beneficial for patients resistant to or intolerant of corticosteroids (Brynskov et al., 1989).

In active cases of Crohn's disease, elevated concentrations of TNF-α and IL-6 are secreted into the blood circulation, and TNF-α, IL-1, IL-6, and IL-8 are produced in excess locally by mucosal cells (id.; Funakoshi et al., 1998). These cytokines can have far-ranging effects on physiological systems including bone development, hematopoiesis, and liver, thyroid, and neuropsychiatric function. Also, an imbalance of the IL-1β/IL-1ra ratio, in favor of pro-inflammatory IL-1β, has been observed in patients with Crohn's disease (Rogler and Andus, 1998; Saiki et al., 1998; Dionne et al., 1998; but see Kuboyama, 1998).

Treatments that have been proposed for Crohn's disease include the use of various cytokine antagonists (e.g., IL-1ra), inhibitors (e.g., of IL-1β converting enzyme and antioxidants) and anti-cytokine antibodies (Rogler and Andus, 1998; van Hogezand and Verspaget, 1998; Reimund et al., 1998; Lugering et al., 1998; McAlindon et al., 1998). In particular, monoclonal antibodies against TNF-α have been tried with some success in the treatment of Crohn's disease (Targan et al., 1997; Stack et al., 1997; van Dullemen et al., 1995). These compounds may be used in combination therapy with RTA 408, the polymorphic forms, and methods of the present disclosure.

J. Systemic Lupus Erythematosus

In some embodiments, RTA 408, the polymorphic forms and methods of this invention may be used for treating patients with SLE. Systemic lupus erythematosus (SLE) is an autoimmune rheumatic disease characterized by deposition in tissues of autoantibodies and immune complexes leading to tissue injury (Kotzin, 1996). In contrast to autoimmune diseases, such as MS and type 1 diabetes mellitus, SLE potentially involves multiple organ systems directly, and its clinical manifestations are diverse and variable (reviewed by Kotzin and O'Dell, 1995). For example, some patients may demonstrate primarily skin rash and joint pain, show spontaneous remissions, and require little medication. At the other end of the spectrum are patients who demonstrate severe and progressive kidney involvement that requires therapy with high doses of steroids and cytotoxic drugs such as cyclophosphamide (Kotzin, 1996).

One of the antibodies produced by SLE, IgG anti-dsDNA, plays a major role in the development of lupus glomerulonephritis (GN) (Hahn and Tsao, 1993; Ohnishi et al., 1994). Glomerulonephritis is a serious condition in which the capillary walls of the kidney's blood purifying glomeruli become thickened by accretions on the epithelial side of glomerular basement membranes. The disease is often chronic and progressive and may lead to eventual renal failure.

K. Irritable Bowel Syndrome

In some embodiments, RTA 408, the polymorphic forms, and methods of this invention may be used for treating patients with irritable bowel syndrome (IBS). IBS is a functional disorder characterized by abdominal pain and altered bowel habits. This syndrome may begin in young adulthood and can be associated with significant disability. This syndrome is not a homogeneous disorder. Rather, subtypes of IBS have been described on the basis of the predominant symptom—diarrhea, constipation, or pain. In the absence of "alarm" symptoms, such as fever, weight loss, and gastrointestinal bleeding, a limited workup is needed.

Increasingly, evidence for the origins of IBS suggests a relationship between infectious enteritis and subsequent development of IBS. Inflammatory cytokines may play a role. In a survey of patients with a history of confirmed bacterial gastroenteritis (Neal et al., 1997), 25% reported persistent alteration of bowel habits. Persistence of symptoms may be due to psychological stress at the time of acute infection (Gwee et al., 1999).

Recent data suggest that bacterial overgrowth in the small intestine may also have a role in IBS symptoms. In one study (Pimentel et al., 2000), 157 (78%) of 202 IBS patients referred for hydrogen breath testing had test findings that were positive for bacterial overgrowth. Of the 47 subjects who had follow-up testing, 25 (53%) reported improvement in symptoms (i.e., abdominal pain and diarrhea) with antibiotic treatment.

L. Sjögren's Syndrome

In some embodiments, RTA 408, the polymorphic forms, and methods of this invention may be used for treating patients with Sjögren's syndrome. Primary Sjögren's syndrome (SS) is a chronic, slowly progressive, systemic autoimmune disease, which affects predominantly middle-aged women (female-to-male ratio 9:1), although it can be seen in all ages including childhood (Jonsson et al., 2002). The disease is characterized by lymphocytic infiltration and destruction of the exocrine glands, which are infiltrated by mononuclear cells including CD4+, CD8+ lymphocytes, and B-cells (Jonsson et al., 2002). In addition, extraglandular (systemic) manifestations are seen in one-third of patients (Jonsson et al., 2001).

In other systemic autoimmune diseases, such as RA, factors critical for ectopic germinal centers (GCs) have been identified. Rheumatoid synovial tissues with GCs were shown to produce chemokines CXCL13, CCL21, and lymphotoxin (LT)-β (detected on follicular center and mantle zone B cells). Multivariate regression analysis of these analytes identified CXCL13 and LT-β as the solitary cytokines predicting GCs in rheumatoid synovitis (Weyand and Goronzy, 2003). Recently CXCL13 and CXCR5 in salivary glands has been shown to play an essential role in the inflammatory process by recruiting B and T cells, therefore contributing to lymphoid neogenesis and ectopic GC formation in SS (Salomonsson et al., 2002).

M. Psoriasis

In some embodiments, RTA 408, the polymorphic forms, and methods of this invention may be used for treating patients with psoriasis. Psoriasis is a chronic skin disease of scaling and inflammation that affects 2 to 2.6 percent of the United States population, or between 5.8 and 7.5 million people. Psoriasis occurs when skin cells quickly rise from their origin below the surface of the skin and pile up on the surface before they have a chance to mature. Usually this movement (also called turnover) takes about a month, but in psoriasis turnover may occur in only a few days. In its typical form, psoriasis results in patches of thick, red (inflamed) skin covered with silvery scales. These patches, which are sometimes referred to as plaques, usually itch or feel sore. The plaques most often occur on the elbows, knees, other parts of the legs, scalp, lower back, face, palms, and soles of the feet, but they can occur on skin anywhere on the body. The disease may also affect the fingernails, the toenails, and the soft tissues of the genitals and inside the mouth.

Psoriasis is a skin disorder driven by the immune system, especially involving a type of white blood cell called a T cell. Normally, T cells help protect the body against infection and disease. In the case of psoriasis, T cells are put into action by mistake and become so active that they trigger other immune responses, which lead to inflammation and to rapid turnover of skin cells.

N. Infectious Diseases

In some embodiments, RTA 408, the polymorphic forms, and methods of the present disclosure may be useful in the treatment of infectious diseases, including viral and bacterial infections. As noted above, such infections may be associated with severe localized or systemic inflammatory responses. For example, influenza may cause severe inflammation of the lung and bacterial infection can cause the systemic hyperinflammatory response, including the excessive production of multiple inflammatory cytokines, which is the hallmark of sepsis. In addition, compounds of the invention may be useful in directly inhibiting the replication of viral pathogens. Previous studies have demonstrated that related compounds such as CDDO can inhibit the replication of HIV in macrophages (Vazquez et al., 2005). Other studies have indicated that inhibition of NF-κB signaling may inhibit influenza virus replication, and that cyclopentenone prostaglandins may inhibit viral replication (e.g., Mazur et al., 2007; Pica et al., 2000).

The present invention relates to the treatment or prevention of each of the diseases/disorders/conditions referred to above in section IV using the compound RTA 408 or a pharmaceutically acceptable salt thereof, or a polymorphic form of that compound (such as, e.g., any one of the polymorphic forms described herein above or below), or a pharmaceutical composition comprising any of the aforementioned entities and a pharmaceutically acceptable carrier (including, e.g., the pharmaceutical compositions described above).

V. Pharmaceutical Formulations and Routes of Administration

RTA 408 may be administered by a variety of methods, e.g., orally or by injection (e.g., subcutaneous, intravenous, intraperitoneal, etc.). Depending on the route of administration, the active compounds may be coated in a material to protect the compound from the action of acids and other natural conditions which may inactivate the compound. They may also be administered by continuous perfusion/infusion of a disease or wound site.

To administer RTA 408 by other than parenteral administration, it may be necessary to coat the compound with, or co-administer the compound with, a material to prevent its inactivation. For example, the therapeutic compound may be administered to a patient in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al., 1984).

RTA 408 may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

Sterile injectable solutions can be prepared by incorporating RTA 408 in the required amount in an appropriate solvent with one or a combination of ingredients enumerated above, as required, followed by filtered sterilization. Generally, dispersions are prepared by incorporating the therapeutic compound into a sterile carrier that contains a basic dispersion medium and the required other ingredients from those enumerated above. In the case of sterile powders for the preparation of sterile injectable solutions, the preferred methods of preparation are vacuum drying and freeze-drying, which yields a powder of the active ingredient (i.e., the therapeutic compound) plus any additional desired ingredient from a previously sterile-filtered solution thereof.

RTA 408 may be rendered fully amorphous using a direct spray drying procedure. RTA 408 can be orally administered, for example, with an inert diluent or an assimilable edible carrier. The therapeutic compound and other ingredients may also be enclosed in a hard or soft shell gelatin capsule, compressed into tablets, or incorporated directly into the patient's diet. For oral therapeutic administration, the therapeutic compound may be incorporated, for example, with excipients and used in the form of ingestible tablets, buccal tablets, troches, capsules including hard or soft capsules, elixirs, emulsions, solid dispersions, suspensions, syrups, wafers, and the like. The percentage of the therapeutic compound in the compositions and preparations may, of course, be varied. The amount of the therapeutic compound in such therapeutically useful compositions is such that a suitable dosage will be obtained.

It is especially advantageous to formulate parenteral compositions in dosage unit form for ease of administration and uniformity of dosage. Dosage unit form as used herein refers to physically discrete units suited as unitary dosages for the patients to be treated, each unit containing a predetermined quantity of therapeutic compound calculated to produce the desired therapeutic effect in association with the required pharmaceutical carrier. The specification for the dosage unit forms of the invention are dictated by and directly dependent on (a) the unique characteristics of the therapeutic compound and the particular therapeutic effect to be achieved, and (b) the limitations inherent in the art of compounding such a therapeutic compound for the treatment of a selected condition in a patient.

RTA 408 may also be administered topically to the skin, eye, or mucosa. In some embodiments, the compound may be prepared in a lotion, cream, gel, oil, ointment, salve, solution, suspension, or emulsion. Alternatively, if local delivery to the lungs is desired the therapeutic compound may be administered by inhalation in a dry-powder or aerosol formulation.

RTA 408 will typically be administered at a therapeutically effective dosage sufficient to treat a condition associated with a given patient. For example, the efficacy of a compound can be evaluated in an animal model system that may be predictive of efficacy in treating the disease in humans, such as the model systems shown in the examples and drawings.

The actual dosage amount of RTA 408 or composition comprising RTA 408 administered to a patient may be determined by physical and physiological factors, such as age, sex, body weight, severity of condition, the type of disease being treated, previous or concurrent therapeutic interventions, idiopathy of the patient, and the route of administration. These factors may be determined by a skilled artisan. The practitioner responsible for administration will typically determine the concentration of active ingredient(s) in a composition and appropriate dose(s) for the individual patient. The dosage may be adjusted by the individual physician in the event of any complication.

An effective amount typically will vary from about 0.001 mg/kg to about 1000 mg/kg, from about 0.01 mg/kg to about 750 mg/kg, from about 100 mg/kg to about 500 mg/kg, from about 1.0 mg/kg to about 250 mg/kg, from about 10.0 mg/kg to about 150 mg/kg in one or more dose administrations daily, for one or several days (depending of course of the mode of administration and the factors discussed above). Other suitable dose ranges include 1 mg to 10000 mg per day, 100 mg to 10000 mg per day, 500 mg to 10000 mg per day, and 500 mg to 1000 mg per day. In some particular embodiments, the amount is less than 10,000 mg per day with a range of 750 mg to 9000 mg per day.

The effective amount may be less than 1 mg/kg/day, less than 500 mg/kg/day, less than 250 mg/kg/day, less than 100 mg/kg/day, less than 50 mg/kg/day, less than 25 mg/kg/day, or less than 10 mg/kg/day. It may alternatively be in the range of 1 mg/kg/day to 200 mg/kg/day. In some embodiments, the amount could be 10, 30, 100, or 150 mg/kg formulated as a suspension in sesame oil as described below in Example C1. In some embodiments, the amount could be 3, 10, 30 or 100 mg/kg administered daily via oral gavage as described below in Examples C2 and C3. In some embodiments, the amount could be 10, 30, or 100 mg/kg administered orally as described below in Example C6. For example, regarding treatment of diabetic patients, the unit dosage may be an amount that reduces blood glucose by at least 40% as compared to an untreated patient. In another embodiment, the unit dosage is an amount that reduces blood glucose to a level that is ±10% of the blood glucose level of a non-diabetic patient.

In other non-limiting examples, a dose may also comprise from about 1 μg/kg body weight, about 5 μg/kg body weight, about 10 μg/kg body weight, about 50 μg/kg body weight, about 100 μg/kg body weight, about 200 μg/kg body weight, about 350 μg/kg body weight, about 500 μg/kg body weight, about 1 mg/kg body weight, about 5 mg/kg body weight, about 10 mg/kg body weight, about 50 mg/kg body weight, about 100 mg/kg body weight, about 200 mg/kg body weight, about 350 mg/kg body weight, about 500 mg/kg body weight, to about 1000 mg/kg body weight or more per administration, and any range derivable therein. In non-limiting examples of a derivable range from the numbers listed herein, a range of about 5 mg/kg body weight to about 100 mg/kg body weight, about 5 μg/kg body weight to about 500 mg/kg body weight, etc., can be administered, based on the numbers described above.

In certain embodiments, a pharmaceutical composition of the present disclosure may comprise, for example, at least about 0.01% of RTA 408. In other embodiments, RTA 408 may comprise between about 0.01% to about 75% of the weight of the unit, or between about 0.01% to about 5%, for example, and any range derivable therein. In some embodiments, RTA 408 may be used in a formulation such as a suspension in sesame oil of 0.01%, 0.1%, or 1% as described below in Examples F and G. In some embodiments, RTA 408 may be formulated for topical administration to the skin or eye, using a pharmaceutically suitable carrier or as a suspension, emulsion, or solution in concentrations ranging from about 0.01% to 10%. In some embodiments the concentration ranges from about 0.1% to about 5%. The optimal concentration may vary depending upon the target organ, the specific preparation, and the condition to be treated.

Single or multiple doses of the agent comprising RTA 408 are contemplated. Desired time intervals for delivery of multiple doses can be determined by one of ordinary skill in the art employing no more than routine experimentation. As an example, patients may be administered two doses daily at approximately 12 hour intervals. In some embodiments, the agent is administered once a day. The agent(s) may be administered on a routine schedule. As used herein a routine schedule refers to a predetermined designated period of time. The routine schedule may encompass periods of time that are identical or that differ in length, as long as the schedule is predetermined. For instance, the routine schedule may involve administration twice a day, every day, every two days, every three days, every four days, every five days, every six days, a weekly basis, a monthly basis, or any set number of days or weeks there-between. Alternatively, the predetermined routine schedule may involve administration on a twice daily basis for the first week, followed by a daily basis for several months, etc. In other embodiments, the invention provides that the agent(s) may be taken orally and that the timing of which is or is not dependent upon food intake. Thus, for example, the agent can be taken every morning and/or every evening, regardless of when the patient has eaten or will eat.

VI. Combination Therapy

In addition to being used as a monotherapy, RTA 408 and the polymorphic forms described in the present invention may also find use in combination therapies. Effective combination therapy may be achieved with a single composition or pharmacological formulation that includes both agents, or with two distinct compositions or formulations, administered at the same time, wherein one composition includes RTA 408 or its polymorphic forms, and the other includes the second agent(s). The other therapeutic modality may be administered before, concurrently with, or following administration of RTA 408 or its polymorphic forms. The therapy using RTA 408 or its polymorphic forms may precede or follow administration of the other agent(s) by intervals ranging from minutes to weeks. In embodiments where the other agent and RTA 408 or its polymorphic forms are administered separately, one would generally ensure that a significant period of time did not expire between the time of each delivery, such that each agent would still be able to exert an advantageously combined effect. In such instances, it is contemplated that one would typically administer RTA 408 or the polymorphic forms and the other therapeutic agent within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of RTA 408 or its polymorphic forms, or the other agent will be desired. In this regard, various combinations may be employed. By way of illustration, where RTA 408 or its polymorphic forms is "A" and the other agent is "B", the following permutations based on 3 and 4 total administrations are exemplary:

A/B/A B/A/B B/B/A A/A/B B/A/A A/B/B B/B/B/A B/B/ A/B A/A/B/B A/B/A/B A/B/B/A B/B/A/A B/A/B/A B/A/A/B B/B/B/A A/A/A/B B/A/A/A A/B/A/A A/A/ B/A A/B/B/B B/A/B/B B/B/A/B

Other combinations are likewise contemplated. Non-limiting examples of pharmacological agents that may be used in the present invention include any pharmacological agent known to be of benefit in the treatment of a cancer. In some embodiments, combinations of RTA 408 or its polymorphic forms with a cancer targeting immunotherapy, gene therapy, radiotherapy, chemotherapeutic agent, or surgery are contemplated. Also contemplated is a combination of RTA 408 or its polymorphic forms with more than one of the above mentioned methods including more than one type of a specific therapy. In some embodiments, the immunotherapy can be other cancer targeting antibodies such as but not limited to trastuzumab (HERCEPTIN®), alemtuzumab (CAMPATH®), bevacizumab (AVASTIN®), cetuximab (ERIBITUX®), and panitumumab (VECTIBIX®) or conjugated antibodies such as ibritumomab tiuxetan (ZEVALIN®), tositumomab (BEXXAR®), brentuximab vedotin (ADCETRIS®), ado-trastuzumab emtansine (KADCYLA™), or denileukin dititox (ONTAK®). Furthermore, in some embodiments, RTA 408 or its polymorphic forms are envisioned to be used in combination therapies with dendritic cell-based immunotherapies such as Sipuleucel-T (PROVENGE®) or adoptive T-cell immunotherapies.

Furthermore, it is contemplated that RTA 408 or its polymorphic forms are used in combination with a chemotherapeutic agent such as but not limited to anthracyclines, taxanes, methotrexate, mitoxantrone, estramustine, doxorubicin, etoposide, vinblastine, carboplatin, vinorelbine, 5-fluorouracil, cisplatin, topotecan, ifosfamide, cyclophosphamide, epirubicin, gemcitabine, vinorelbine, irinotecan, etoposide, vinblastine, pemetrexed, melphalan, capecitabine, and oxaliplatin. In some embodiments, RTA 408 or its polymorphic forms are used in combination with radiation therapy including but not limited to the use of ionizing radiation. In some embodiments, the effects of the cancer therapeutic agent are synergistically enhanced through administration with RTA 408 and its polymorphic forms. In some embodiments, combination therapies which included RTA 408 are used to treat cancer including for example, prostate cancer. See, e.g., Example H below.

In some embodiments, the methods may further comprise (1) contacting a tumor cell with the compound prior to contacting the tumor cell with the second chemotherapeutic agent, (2) contacting a tumor cell with the second chemotherapeutic agent prior to contacting the tumor cell with the compound, or (3) contacting a tumor cell with the compound and the second chemotherapeutic agent at the same time. The second chemotherapeutic agent may, in certain embodiments, be an antibiotic, anti-inflammatory, anti-neoplastic, anti-proliferative, anti-viral, immunomodulatory, or immunosuppressive. In other embodiments, the second chemotherapeutic agent may be an alkylating agent, androgen receptor modulator, cytoskeletal disruptor, estrogen receptor modulator, histone-deacetylase inhibitor, HMG-CoA reductase inhibitor, prenyl-protein transferase inhibitor, retinoid receptor modulator, topoisomerase inhibitor, or tyrosine kinase inhibitor. In certain embodiments, the second chemotherapeutic agent is 5-azacitidine, 5-fluorouracil, 9-cis-retinoic acid, actinomycin D, alitretinoin, all-trans-retinoic acid, annamycin, axitinib, belinostat, bevacizumab, bexarotene, bosutinib, busulfan, capecitabine, carboplatin, carmustine, CD437, cediranib, cetuximab, chlorambucil, cisplatin, cyclophosphamide, cytarabine, dacarbazine, dasatinib, daunorubicin, decitabine, docetaxel, dolastatin-10, doxifluridine, doxorubicin, doxorubicin, epirubicin, erlotinib, etoposide, gefitinib, gemcitabine, gemtuzumab ozogamicin, hexamethylmelamine, idarubicin, ifosfamide, imatinib, irinotecan, isotretinoin, ixabepilone, lapatinib, LBH589, lomustine, mechlorethamine, melphalan, mercaptopurine, methotrexate, mitomycin, mitoxantrone, MS-275, neratinib, nilotinib, nitrosourea, oxaliplatin, paclitaxel, plicamycin, procarbazine, semaxanib, semustine, sodium butyrate, sodium phenylacetate, streptozotocin, suberoylanilide hydroxamic acid, sunitinib, tamoxifen, teniposide, thiopeta, tioguanine, topotecan, TRAIL, trastuzumab, tretinoin, trichostatin A, valproic acid, valrubicin, vandetanib, vinblastine, vincristine, vindesine, or vinorelbine.

Additionally, combination therapies for the treatment of cardiovascular disease utilizing RTA 408, polymorphic forms, and pharmaceutical compositions of the present disclosure are contemplated. For example, such methods may further comprise administering a pharmaceutically effective amount of one or more cardiovascular drugs in addition to RTA 408, polymorphic forms, and pharmaceutical compositions of the present disclosure. The cardiovascular drug may be but not limited to, for example, a cholesterol lowering drug, an anti-hyperlipidemic, a calcium channel blocker, an anti-hypertensive, or an HMG-CoA reductase inhibitor. In some embodiments, non-limiting examples of cardiovascular drugs include amlodipine, aspirin, ezetimibe, felodipine, lacidipine, lercanidipine, nicardipine, nifedipine, nimodipine, nisoldipine or nitrendipine. In other embodiments, other non-limiting examples of cardiovascular drugs include atenolol, bucindolol, carvedilol, clonidine, doxazosin, indoramin, labetalol, methyldopa, metoprolol, nadolol, oxprenolol, phenoxybenzamine, phentolamine, pindolol, prazosin, propranolol, terazosin, timolol or tolazoline. In other embodiments, the cardiovascular drug may be, for example, a statin, such as atorvastatin, cerivastatin, fluvastatin, lovastatin, mevastatin, pitavastatin, pravastatin, rosuvastatin or simvastatin.

VI. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

A. Synthesis of RTA 408 (63415)

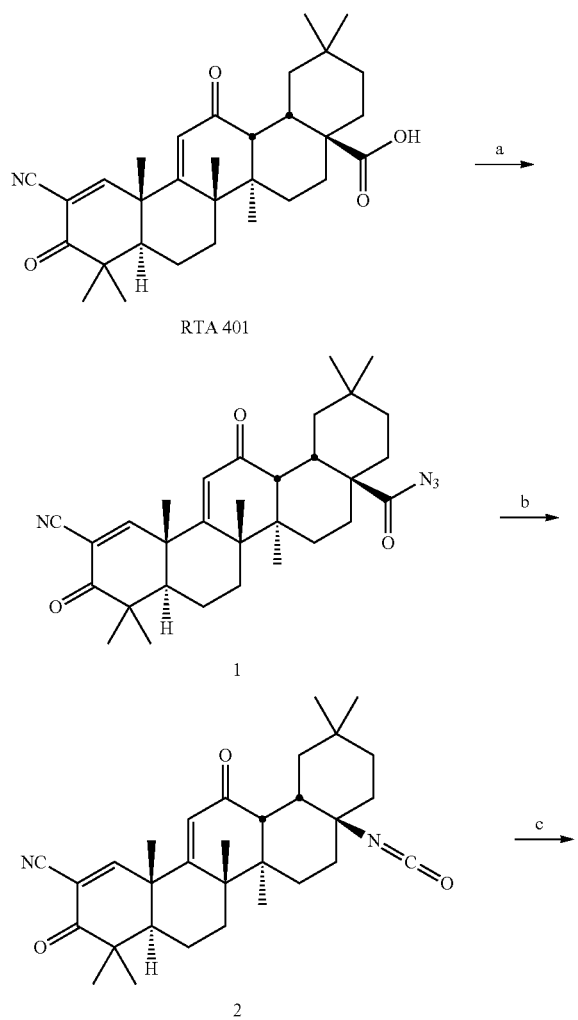

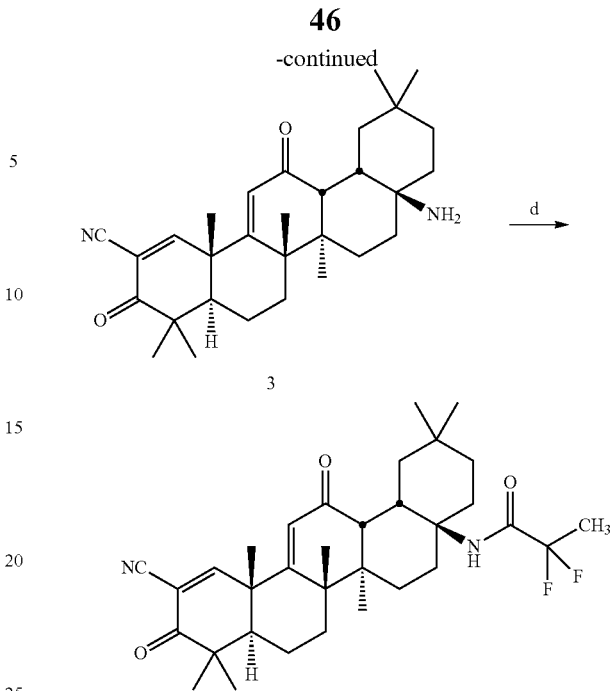

RTA 408 (63415)

Reagents and conditions: (a) (PhO)$_2$PON$_3$ (DPPA), Et$_3$N, toluene, 0° C. for 5 min, then r.t. overnight, ~94%; (b) benzene, 80° C. for 2 h; (c) HCl, CH$_3$CN, r.t. for 1 h; (d) CH$_3$CF$_2$CO$_2$H, DCC, DMAP, CH$_2$Cl$_2$, r.t. overnight, 73% from RTA 401 (4 steps).

Compound 1: To a solution of toluene (400 mL), RTA 401 (which can be prepared according to the methods taught, for example, by Honda, et al., 1998; Honda et al., 2000b; Honda et al., 2002; Yates et al., 2007; and U.S. Pat. Nos. 6,326,507 and 6,974,801, which are incorporated herein by reference) (20.0 g, 40.6 mmol) and Et$_3$N (17.0 mL, 122.0 mmol) were added into a reactor and cooled to 0° C. with stirring. Diphenyl phosphoryl azide (DPPA) (13.2 mL, 61.0 mmol) was added with stirring at 0° C. over 5 min and the mixture was continually stirred at room temperature overnight (HPLC-MS check shows no RTA 401 left). The reaction mixture was directly loaded on a silica gel column and purified by column chromatography (silica gel, 0% to 5% EtOAc in CH$_2$Cl$_2$) to give compound 1 (19.7 g, ~94%, partially converted into compound 2) as a white foam.

Compound 2: Compound 1 (19.7 g, ~38.1 mmol) and benzene (250 mL) were added into a reactor and heated to 80° C. with stirring for 2 h (HPLC-MS check shows no compound 1 left). The reaction mixture was concentrated at reduced pressure to afford crude compound 2 as a solid residue, which was used for the next step without purification.

Compound 3: Crude compound 2 (≤38.1 mmol) and CH$_3$CN (200 mL) were added into a reactor and cooled to 0° C. with stirring. HCl (12 N, 90 mL) was added at 0° C. over 1 min and the mixture was continually stirred at room temperature for 1 h (HPLC-MS check shows no compound 2 left). The reaction mixture was cooled to 0° C. and 10% NaOH (~500 mL) was added with stirring. Then, saturated NaHCO$_3$ (1 L) was added with stirring. The aqueous phase was extracted by EtOAc (2×500 mL). The combined organic phase was washed by H$_2$O (200 mL), saturated NaCl (200 mL), dried over Na$_2$SO$_4$, and concentrated to afford crude compound 3 (16.62 g) as a light yellow foam, which was used for the next step without purification.

RTA 408: Crude amine 3 (16.62 g, 35.9 mmol), CH₃CF₂CO₂H (4.7388 g, 43.1 mmol), and CH₂Cl₂ (360 mL) were added into a reactor with stirring at room temperature. Then, dicyclohexylcarbodiimide (DCC) (11.129 g, 53.9 mmol) and 4-(dimethylamino)-pyridine (DMAP) (1.65 g, 13.64 mmol) were added and the mixture was continually stirred at room temperature overnight (HPLC-MS check shows no compound 3 left). The reaction mixture was filtered to remove solid by-products and the filtrate was directly loaded on a silica gel column and purified by column chromatography (silica gel, 0% to 20% EtOAc in Hexanes) twice to give compound RTA 408 (16.347 g, 73% from RTA 401 over 4 steps) as a white foam: ¹H NMR (400 MHz, CD₃Cl) δ 8.04 (s, 1H), 6.00 (s, 1H), 5.94 (s, br, 1H), 3.01 (d, 1H, J=4.8 Hz), 2.75-2.82 (m, 1H), 1.92-2.18 (m, 4H), 1.69-1.85 (m, 7H), 1.53-1.64 (m, 1H), 1.60 (s, 3H), 1.50 (s, 3H), 1.42 (s, 3H), 1.11-1.38 (m, 3H), 1.27 (s, 3H), 1.18 (s, 3H), 1.06 (s, 3H), 1.04 (s, 3H), 0.92 (s, 3H); m/z 555 (M+1).

B. Pharmacodynamics

A summary of the in vitro and in vivo studies to evaluate the primary pharmacodynamic effects of RTA 408 is provided below.

1. Effects of RTA 408 on Keap1-Nrf2 and NF-κB In Vitro

Figure 1:
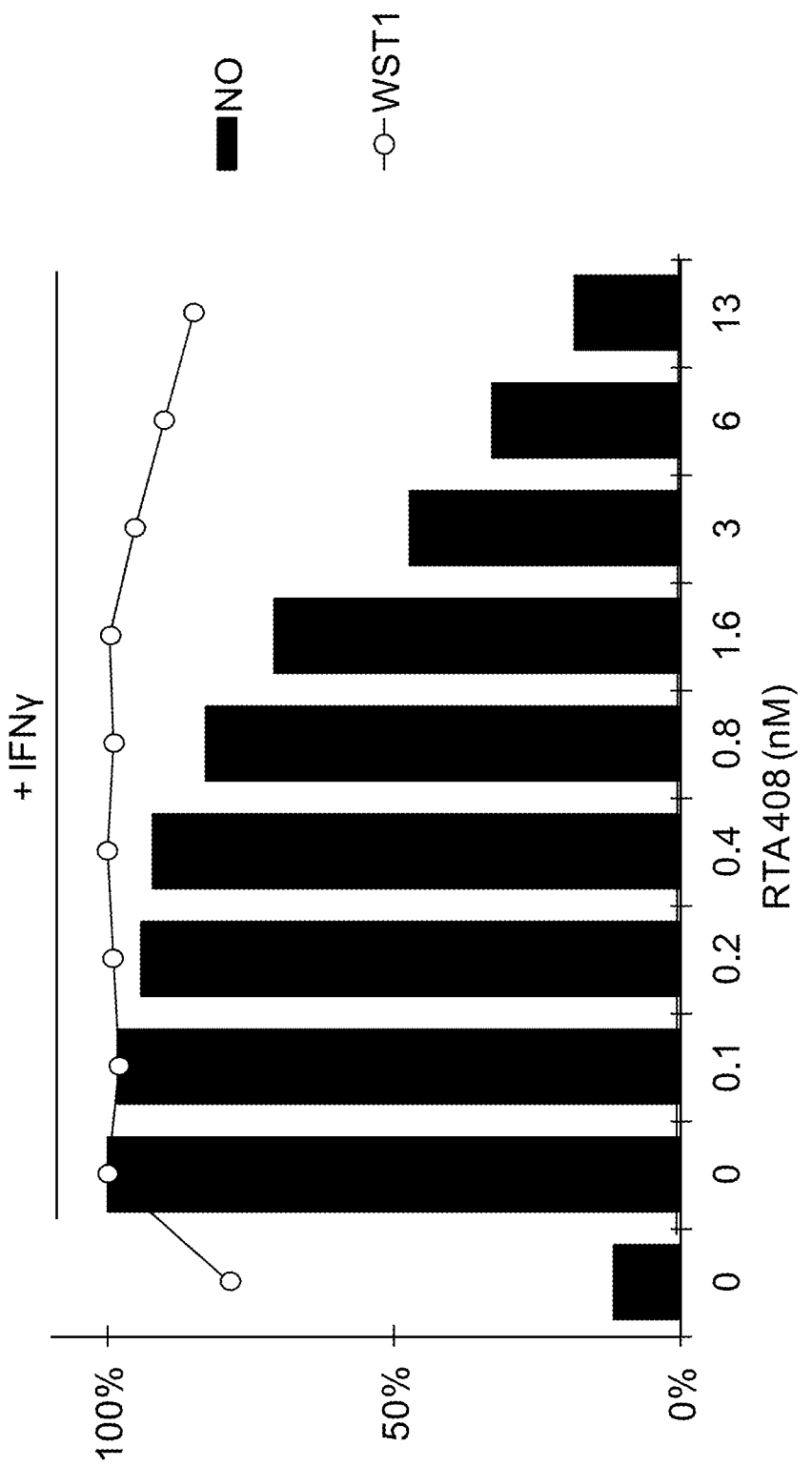
FIG. 1—Effect of RTA 408 on IFNγ-induced nitric oxide production and cell viability in RAW264.7 cells.

Inhibition of IFNγ-induced NO production by AIMs is Nrf2-dependent (Dinkova-Kostova, 2005). RAW264.7 mouse macrophages were plated in 96-well plates at 30,000 cells/well in triplicated in RPMI 1640 supplemented with 0.5% FBS and incubated at 37° C. with 5% CO₂. On the next day, cells were pre-treated with DMSO (vehicle) or RTA 408 for 2 h, followed by treatment with 20 ng/mL of mouse IFNγ for 24 h. Nitrite (NO₂⁻) levels in the media were measured as a surrogate for nitric oxide using the Griess Reagent System (cat #G2930, Promega), according to the manufacturer's instructions, since nitrite is a primary, stable breakdown product of NO. Cell viability was assessed using the WST-1 Cell Proliferation Reagent (cat #11644807001, Roche Applied Science) according to the manufacturer's instructions. IC₅₀ values were determined based on the suppression of IFNγ-induced nitric oxide production normalized to cell viability. Treatment with RTA 408 resulted in a dose-dependent suppression of IFNγ-induced NO production, with an average IC₅₀ value of 3.8±1.2 nM. Results from a representative experiment are shown in FIG. 1. The IC₅₀ value for RTA 408 was found to be 45%-65% lower than the IC₅₀ values for compounds 63170 (8±3 nM), 63171 (6.9±0.6 nM), 63179 (11±2 nm), and 63189 (7±2 nM). 63170, 63171, 63179, and 63189 are compounds of the formulas:

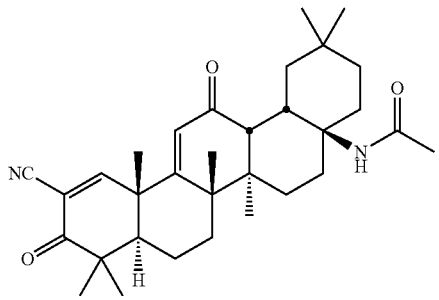
63170

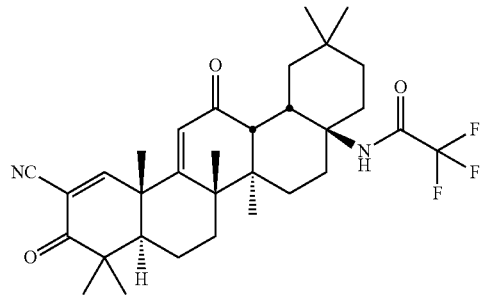
63171

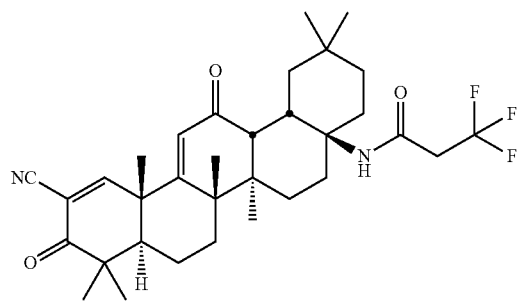
63179

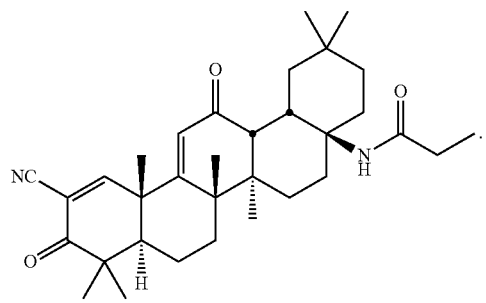
63189

2. Effect of RTA 408 on Nrf2 Target Genes

RTA 408 was tested in two different luciferase reporter assays to assess activation of the ARE. The first luciferase reporter tested was under the control of a single ARE derived from the promoter of the human NQO1 gene, which allows for quantitative assessment of the endogenous activity of the Nrf2 transcription factor in cultured mammalian cells. Expression of Firefly luciferase from NQO1-ARE luciferase reporter plasmid is controlled by binding of Nrf2 to a specific enhancer sequence corresponding to the antioxidant response element (ARE) that was identified in the promoter region of the human NADPH:quinone oxidoreductase 1 (NQO1) gene (Xie et al., 1995). The NQO1-ARE-luciferase reporter plasmid was constructed by inserting the human NQO1-ARE (5'-CAGTCACAGTGACTCAGCAGAATCTG-3') (SEQ ID NO: 31) into the pLuc-MCS vector using HindIII/XhoI cloning sites (GenScript Corp., Piscataway, NJ). The HuH-7 human hepatoma cell line, maintained in DMEM (Invitrogen) supplemented with 10% FBS and 100 U/mL (each) of penicillin and streptomycin, was transiently transfected using Lipofectamine 2000 (Invitrogen) with the NQO1-ARE luciferase reporter plasmid and the pRL-TK plasmid, which constitutively expresses Renilla luciferase and is used as an internal control for normalization of transfection levels. Thirty hours of transfection, cells were treated with RTA 408 for 18 h.

Firefly and Renilla luciferase activity was assayed by Dual-Glo Luciferase Assay (cat #E2920, Promega), and the luminescence signal was measured on an L-Max II luminometer (Molecular Devices). Firefly luciferase activity was normalized to the Renilla activity, and fold induction over a vehicle control (DMSO) of normalized Firefly activity was calculated. FIG. 2a shows a dose-dependent induction of luciferase activity by RTA 408 in this cell line. Values represent the average of three independent experiments. Twenty percent less RTA 408 (12 nM) than 63189 (14.9 nM) was required to increase transcription from the NQO1 ARE in HuH-7 cells by 2-fold. Likewise, 2.1-2.4 fold less RTA 408 than 63170 (25.2 nM) and 63179 (29.1 nM), respectively, was required to increase transcription from the NQO1 ARE in HuH-7 cells by 2-fold.

The effect of RTA 408 on luciferase reporter activation was also assessed in the AREc32 reporter cell line. This cell line is derived from human breast carcinoma MCF-7 cells and is stably transfected with a Firefly luciferase reporter gene under the transcriptional control of eight copies of the rat GSTA2 ARE sequence (Wang, et al., 2006, which is incorporated herein by reference). Following treatment with RTA 408 for 18 h, Firefly luciferase activity was measured using the ONE-Glo Luciferase Assay System (Promega, Catalog #E6110) according to the manufacturer's instructions. A dose-dependent response was observed in the AREc32 reporter cell line (FIG. 2b). A ~2-fold induction of luciferase activity was evident following treatment with 15.6 nM RTA 408 in both the NQO1-ARE and GSTA2-ARE reporter assay system. When looking at the results from the GSTA2-ARE (AREc32) luciferase activity study, the effects of 63415 (RTA 408) on GSTA2-ARE induction can be directly compared to that of RTA 402, 63170, 63171, 63179, and 63189 along with WST1 viability studies (FIGS. 3a-f). Compared to the values of RTA 402, 63415 showed the quickest induction of GSTA2-ARE-mediated transcription of the five comparison compounds with a concentration of 93 nM needed to reach 4-fold induction in the luciferase reporter assay. All other compounds showed a similar induction only with much higher concentrations with 63170 needing a concentration of 171 nM, 63171 needing a concentration of 133 nM, 63179 needing a concentration of 303 nM and 63189 needing a concentration of 174 nM to achieve a 4 fold induction of luciferase activity. These values correspond to a 1.86 (63415), 3.40 (63170), 2.65 (63171), 6.05 (63179) and 3.47 (63189) fold increase in the amount of the active compound needed compared to RTA 402 to lead to the same amount of activity.

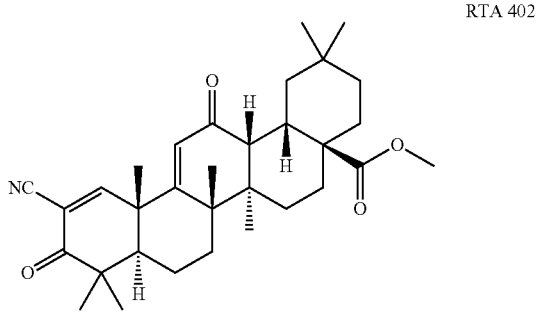

RTA 402

RTA 408 was also shown to increase transcript levels of known Nrf2 target genes in the HFL1 human fetal lung fibroblast and BEAS-2B human bronchial epithelial cell lines. HFL1 cells were cultured in F-12K media supplemented with 10% fetal bovine serum and 1% penicillin-streptomycin. BEAS-2B cells were cultured in DMEM/F-12 media supplemented with 10% fetal bovine serum and 1% penicillin-streptomycin. Cells were plated in 6-well dishes at a density of $2.5 \times 10^5$ cells/well. The following day, cells were treated with DMSO (vehicle) or RTA 408 (7.8, 15.6, 31.3, 62.5, or 125 nM) for 18 h. Each well received the same amount of vehicle. Following treatment, media was removed and cells were harvested using RLT buffer (Qiagen). Lysates were homogenized using QIAShredder columns (Qiagen, Catalog #79654) and RNA was isolated using RNeasy Mini kits (Qiagen, Catalog #74104). For reverse transcription, RNA (1 μg) was combined with Oligo(dT)$_{12-18}$ primer and $H_2O$ in a final volume of 23.25 μL. The mixture was heated to 70° C. for 10 min and then placed on ice. A master mix containing 8 μL $5\times1^{st}$ strand buffer, 2 μL 1 mg/mL BSA, 2 μL 20 mM DTT, 4 μL 5 mM dNTP mix, 0.25 μL RNase-OUT™ and 0.5 μL SUPERSCRIPT® II reverse transcriptase was added to the RNA mixture and incubated at 42° C. for 1 h. The reaction was inactivated by heating to 70° C. for 10 min. The reaction mixture was diluted 1:3 with $H_2O$ prior to use in qPCR. 2.5 μL of the diluted reverse transcription reaction was combined with one set of PCR primers (0.36 μM final concentration), 2×iQ™ SYBR® Green Supermix (Bio-Rad, Catalog #170-8885) and $H_2O$ to a final volume of 20 μL Sequences for PCR primers are as follows: Glutamate-cysteine ligase, modifier subunit (GCLM), forward primer 5'-GCTGTGGCTACTGCGGT-ATT-3' (SEQ ID NO: 1) reverse primer 5'-ATCTGCCT-CAATGACACCAT-3' (SEQ ID NO: 2); Heme oxygenase-1 (HMOX1) forward primer 5'-TCCGATGGGTCCTTA-CACTC-3' (SEQ ID NO: 3), reverse primer 5'-TAGGCTCCTTCCTCCTTTCC-3' (SEQ ID NO: 4); NAD(P)H dehydrogenase, quinone 1 (NQO1) forward primer 5'-AAAACACTGCCCTCTTGTGG-3' (SEQ ID NO: 5), reverse primer 5'-GTGCCAGTCAGCATCTGGTA-3' (SEQ ID NO: 6); Ribosomal protein S9 (RPS9) forward primer 5'-GATGAGAAGGACCCCACGGCGTCTG-3' (SEQ ID NO: 7), reverse primer 5'-GA-GACAATCCAGCAGCCCAGGAGGG-3' (SEQ ID NO: 8); Thioredoxin Reductase I (TXNRD1) forward primer 5'-AT-TGCCACTGGTGAAAGACC-3' (SEQ ID NO: 9), reverse primer 5'-ACCAATTTTGTTGGCCATGT-3' (SEQ ID NO: 10). All primers had previously been validated for specificity and amplification efficiency. cDNA was amplified using the following cycle conditions: (95° C. for 3 min, 44 cycles of 95° C. for 30 sec, 60° C. for 15 sec, 72° C. for 15 sec, followed by a melt curve of 55° C. to 95° C. in increments of 0.5° C.). The relative abundance of each Nrf2 target gene was determined using the comparative $C_T$ method ($\Delta\Delta C_T$). PCR reactions were run in triplicate wells for each sample. Two independent experiments were performed using the conditions described above. Treatment of HFL1 lung fibroblasts with RTA 408 for 18 h resulted in increased expression of several Nrf2 target genes, including NQO1, HMOX1, GCLM, and TXNRD1, as measured by quantitative PCR (FIGS. 4a-d). For all genes tested, induction by RTA 408 was dose-dependent and evident at concentrations as low as 15.6 nM. Treatment of BEAS-2B bronchial epithelial cells with RTA 408 for 18 h resulted in a similar dose-dependent increase of all Nrf2 target genes evaluated (FIGS. 5a-d). RTA 408 also increased expression of Nrf2 target genes in normal human mesangial cells (nHMC), the mouse BV2 microglial cell line, and the human SH-SY5Y neuroblastoma cell line at similar concentrations.

Protein levels of Nrf2 targets NQO1 and HMOX1 were measured in SH-5Y5Y and BV-2 cells by Western blot following treatment with RTA 408. SH-SY5Y cells were plated in 6-well plates at a density of $4 \times 10^5$ cells per well. BV-2 cells were plated in 6-well plates at a density of $2.5 \times 10^4$ cells per well. Twenty-four (BV-2) or 48 (SH-SY5Y) h after plating, cells were treated with RTA 408 for 24 hours. Following treatment, cells were washed twice with cold PBS and harvested in lysis buffer. Cells were sonicated and debris was cleared by centrifugation (10 min @ 18,000 rcf, Beckman Coulter, microfuge 18 centrifuge). Total protein in supernatant was quantified using Bio-Rad protein reagent with BSA as a standard. Equal amounts of total cellular protein were separated on SDS-PAGE, and proteins were transferred to nitrocellulose membrane. Membranes were blocked for 1 hour in TBST (1×TBS with 0.1% Tween-20) containing 5% milk, washed 3 times with TBST, and incubated with primary antibodies overnight at 4° C. NQO1 antibody was from Abcam (#AB2346); HMOX1 (HO-1) antibody was from Santa Cruz (#sc-10789); actin antibody was from Millipore (#MAB 1501). After washing with TBST, secondary antibodies were added in TBST+5% milk for 1 h at room temperature. AffiniPure goat anti-rabbit or anti-mouse IgG secondary antibodies were from Jackson ImmunoResearch (catalog #111-035-144 and #115-035-146, respectively). Membranes were washed in TBST, developed using ECL, and exposed to X-ray film. Treatment with RTA 408 also increased NQO1 protein levels in SH-SY5Y cells in a dose-dependent manner (FIG. 6a). HMOX1 protein was not detected in untreated or RTA 408-treated SH-SY5Y cells. In BV2 cells, treatment with RTA 408 increased NQO1 and HMOX1 protein levels at concentrations up to 125 nM (FIG. 6b). The $EC_{50}$ value for induction of Nrf2 protein expression in SK—N—SH cells by RTA 408 (56.4 nM) was 45%-65% lower than the $EC_{50}$ values for 63171 (122 nM), 63189 (102 nM), and 63179 (126 nM). The same amount of 63170 (54.6 nM) was required.

The $EC_{50}$ was measured using an in-cell western NQO1 assay where the cells were incubated with the compound under evaluation for three days. After incubation with the compound of interest, the cells were reacted with mouse NQO1 antibody and then the next day the cells were reacted with IRDye-800CW-anti-mouse IgG antibody. The target signals were visualized and then analyzed.

Figure 7:
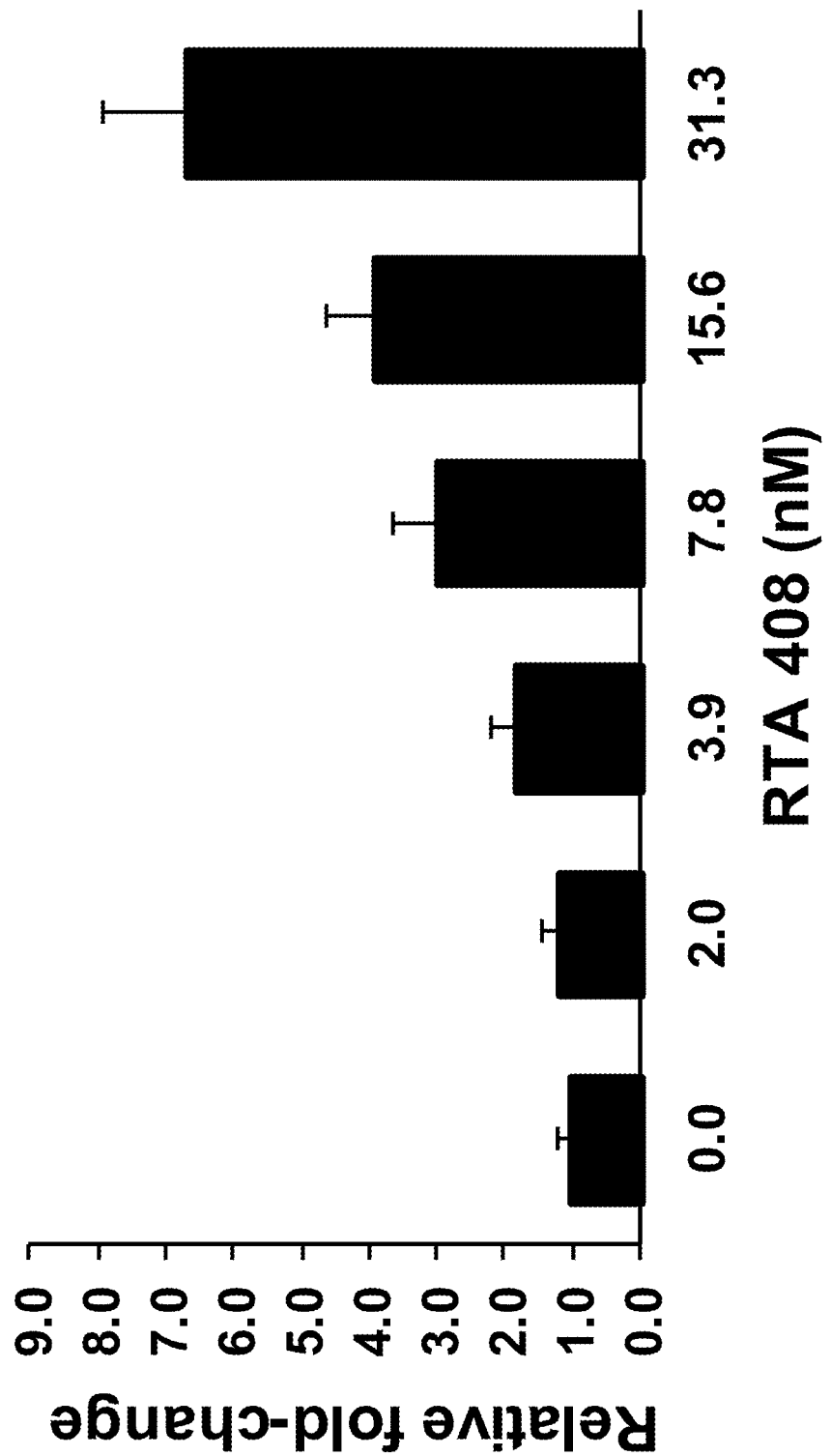
FIG. 7—Effect of RTA 408 on NQO1 enzymatic activity in RAW264.7 cells.

Consistent with induction of Nrf2 target genes and corresponding protein products, treatment of RAW264.7 mouse macrophage cells for 24 h increased NQO1 enzymatic activity in a dose-dependent manner, with increases evident at 7.8 nM (FIG. 7). NQO1 enzymatic activity was measured by a modified Prochaska assay (Prochaska and Santamaria, *Anal Biochem.* 169:328-336, 1988, which is incorporated herein by reference).

Taken together, these data from multiple cell lines demonstrate that treatment with RTA 408 increases transcriptional activity controlled by antioxidant response elements, increases expression of Nrf2 target genes, and increases the activity of NQO1, an Nrf2 target gene product.

3. Effect of RTA 408 on Markers of Cellular Redox Capacity

Figure 8:
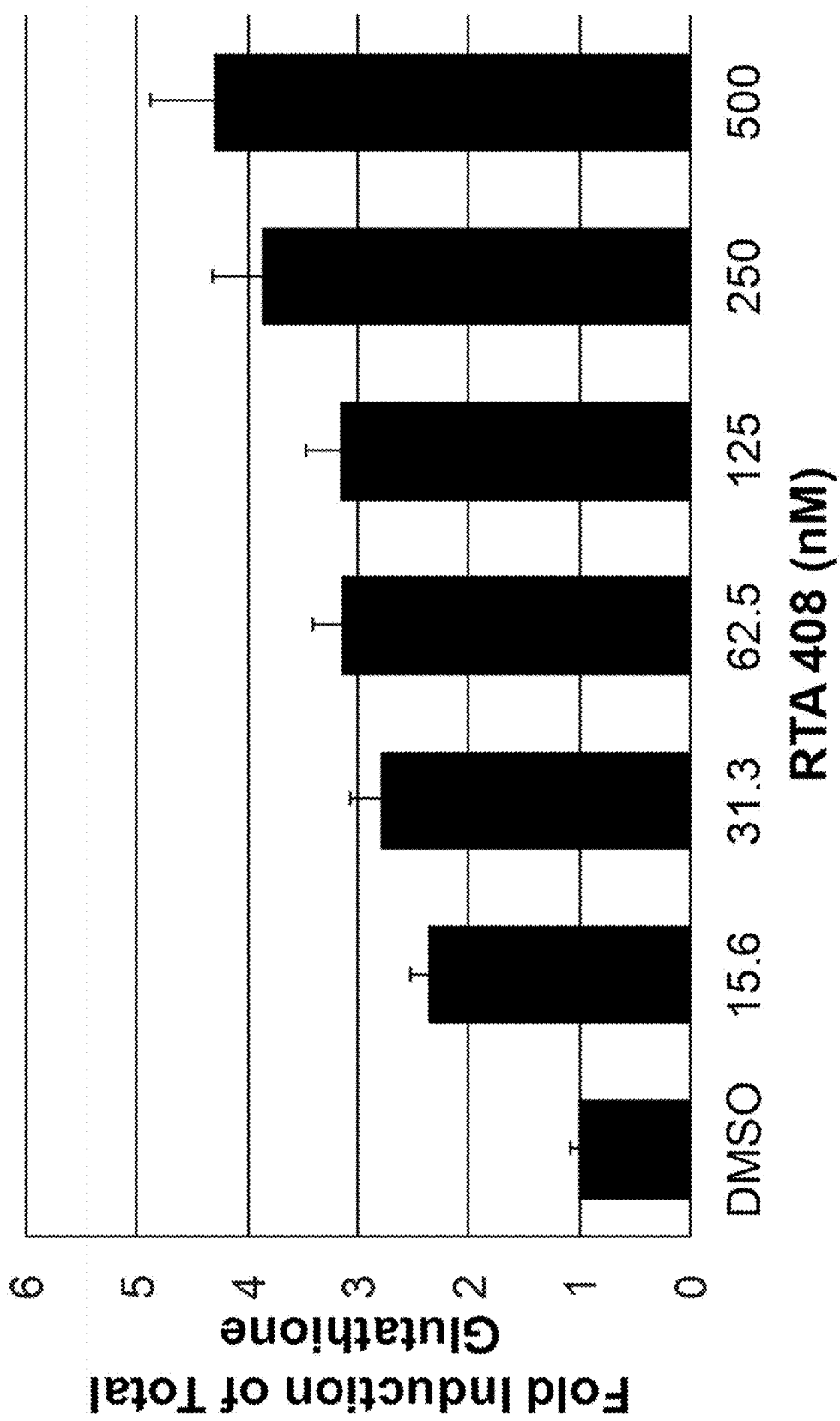
FIG. 8—Effect of RTA 408 on total glutathione levels in the AML-12 hepatocyte cell line.

Glutathione and NADPH are critical factors required for the maintenance of cellular redox capacity. Several genes involved in the synthesis of glutathione (e.g., GCLC and GLCM) and NADPH [e.g., hexose-6-phosphate dehydrogenase (H6PD) and malic enzyme 1 (ME1)] have been demonstrated to be regulated by Nrf2 (Wu, 2011). The effect of RTA 408 treatment on total glutathione levels was evaluated in the mouse AML-12 hepatocyte cell line using the GSH-GLO™ Glutathione Assay kit (Promega, Catalog #V6912) according to the manufacturer's instructions. Treatment of AML-12 cells for 24 h with RTA 408 increased total cellular glutathione levels in a dose-dependent manner (FIG. 8). Data shown are representative of two independent experiments. A >2-fold increase in total glutathione was observed at RTA 408 concentrations as low as 15.6 nM. The $EC_{50}$ value using a RAW264.7 mouse model for induction of glutathione levels by RTA 408 (9.9 nM) was 22%-57% lower than the $EC_{50}$ values for 63170 (12.1 nM), 63171 (23.2 nM), and 63189 (16 nM).

Figure 9:
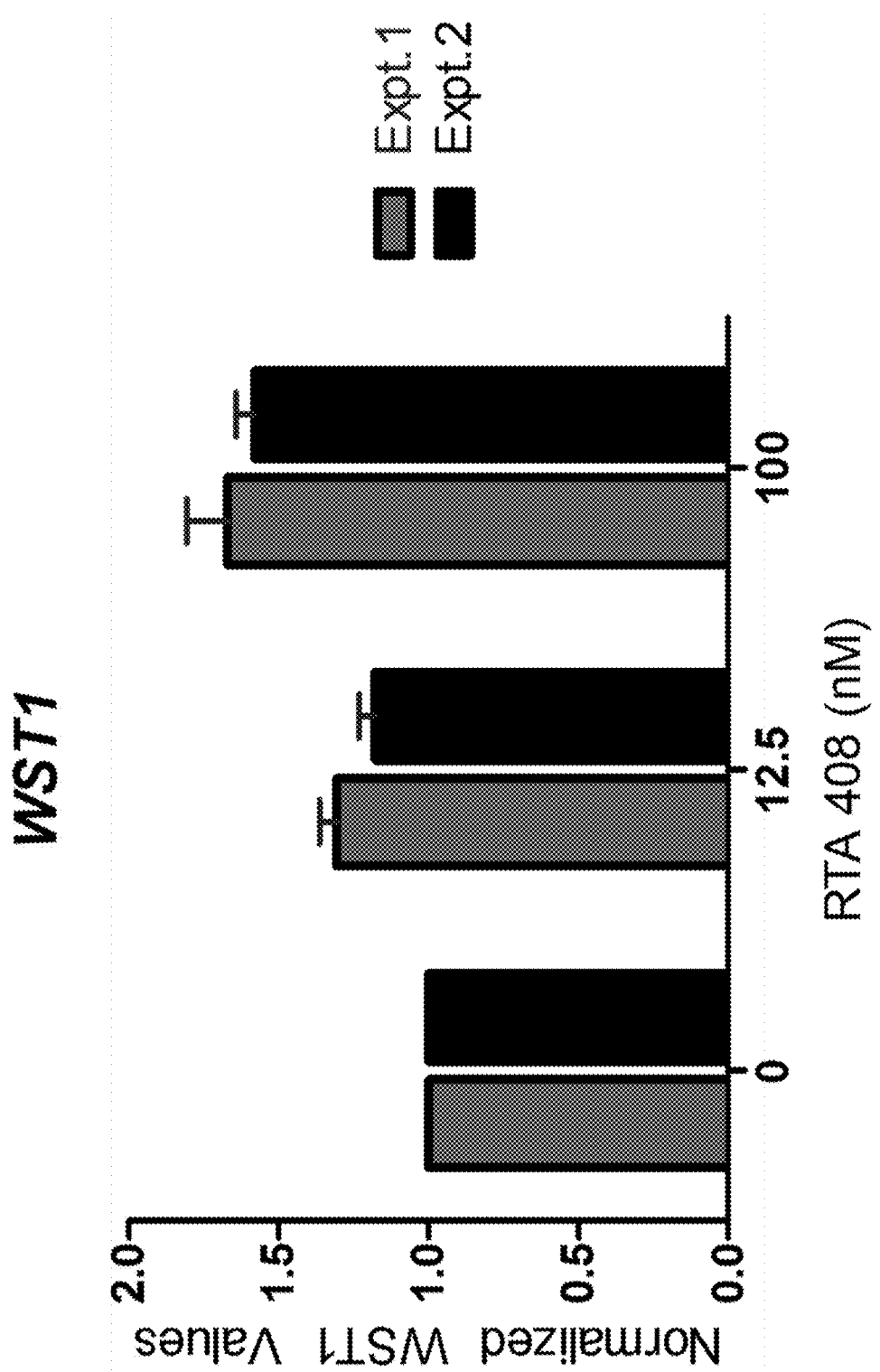
FIG. 9—Effect of RTA 408 on WST-1 absorbance as a marker of NADPH.

The effect of RTA 408 treatment on the levels of NADPH, as measured by the absorbance of a redox-sensitive dye, WST-1 (Roche Applied Science, Catalog #11644807001), was evaluated in HCT-116 cells. WST-1 absorbance is commonly used to assess cell viability by measuring glycolytic production of NAD(P)H by viable cells. Therefore, in situations where NADPH production increases in the absence of any effect on cell viability, WST-1 absorbance also increases (Berridge et al., *Biochemica*, 4:14-19 1996, which is incorporated herein by reference). Several key genes involved in NADPH production have also been shown to be regulated by Nrf2 (Thimmulappa et al., 2002; Wu, et al., 2011, which are both incorporated herein by reference). RTA 408 treatment for 24 h increased WST-1 absorbance in a dose-dependent manner (FIG. 9), suggesting that NADPH levels were increased.

The effect of RTA 408 on the expression of genes involved in NADPH synthesis pathways was also evaluated in this study. HCT-116 cells were treated with RTA 408 for 24 h, and mRNA levels of H6PD, phosphogluconate dehydrogenase (PGD), transketolase (TKT), and ME1 were measured using quantitative PCR. HCT-116 cells were plated in 6-well dishes at a density of $3 \times 10^5$ cells/well. The following day, cells were treated with DMSO (vehicle), 10 nM RTA 408, or 50 nM RTA 408 for 24 h. Each well received the same amount of vehicle. Following treatment, media was removed and cells were harvested using RLT buffer (Qiagen). Lysates were homogenized using QIAShredder columns (Qiagen, Catalog #79654) and RNA was isolated using RNeasy Mini kits (Qiagen, Catalog #74104). For reverse transcription, RNA (1 µg) was combined with Oligo(dT)12-18 primer and $H_2O$ in a final volume of 23.25 µL. The mixture was heated to 70° C. for 10 min and then placed on ice. A master mix containing 8 µL 5×1st strand buffer, 2 µL 1 mg/mL BSA, 2 µL 20 mM DTT, 4 µL 5 mM dNTP mix, 0.25 µL RNASEOUT™ and 0.5 µL SUPERSCRIPT® II reverse transcriptase was added to the RNA mixture and incubated at 42° C. for 1 h. The reaction was inactivated by heating to 70° C. for 10 min. The reaction mixture was diluted 1:3 with $H_2O$ prior to use in qPCR. 2.5 µL of the diluted reverse transcription reaction was combined with one set of PCR primers (0.36 µM final concentration), 2×iQ™ SYBR® Green Supermix (Bio-Rad, Catalog #170-8885) and $H_2O$ to a final volume of 20 µL. Sequences for PCR primers are as follows: Ribosomal protein S9 (RPS9) forward primer 5'-GAT-GAGAAGGACCCCACGGCGTCTG-3' (SEQ ID NO: 7), reverse primer 5'-GAGACAATCCAGCAGCCCAG-GAGGG-3' (SEQ ID NO: 8); Hexose-6-phosphate dehydrogenase (H6PD) forward primer 5'-GAGGCCGTGTACAC-CAAGAT-3' (SEQ ID NO: 11), reverse primer 5'-AGCAGTGGGGTGAAAATACG-3' (SEQ ID NO: 12), Phosphogluconate dehydrogenase (PGD) forward primer 5'-AAGGCACTCTACGCTTCCAA-3' (SEQ ID NO: 13), reverse primer 5'-AGGAGTCCTGGCAGTTTTCA-3' (SEQ ID NO: 14), Transketolase (TKT) forward primer 5'-CATCTCCGAGAGCAACATCA-3' (SEQ ID NO: 15), reverse primer 5'-TTGTATTGGCGGCTAGTTCC-3' (SEQ ID NO: 16); Malic enzyme 1 (ME1) forward primer 5'-TATATCCTGGCCAAGGCAAC-3' (SEQ ID NO: 17) reverse primer 5'-GGATAAAGCCGACCCTCTTC-3' (SEQ ID NO: 18). All primers had previously been validated for specificity and amplification efficiency. cDNA was amplified using the following cycle conditions: (95° C. for 3 min, 44 cycles of 95° C. for 30 sec, 60° C. for 15 sec, 72° C. for 15 sec, followed by a melt curve of 55° C. to 95° C. in increments of 0.5° C.). The relative abundance of each target gene was determined using the comparative CT method ($\Delta\Delta$CT). PCR reactions were run in triplicate wells for each sample. Two independent experiments were performed using the conditions described above. Treatment with RTA 408 resulted in a dose-dependent increase in expression of genes involved in NADPH synthesis (FIGS. 10a-d).

In summary, treatment with RTA 408 increased total glutathione levels in AML-12 hepatocytes and increased WST-1 absorbance, a marker of NADPH production, in HCT-116 cells. This observation correlated with an increase in the expression of several key genes encoding enzymes involved in NADPH synthesis.

4. Effect of RTA 408 on TNFα-Induced NF-κB Signaling

Figure 12:
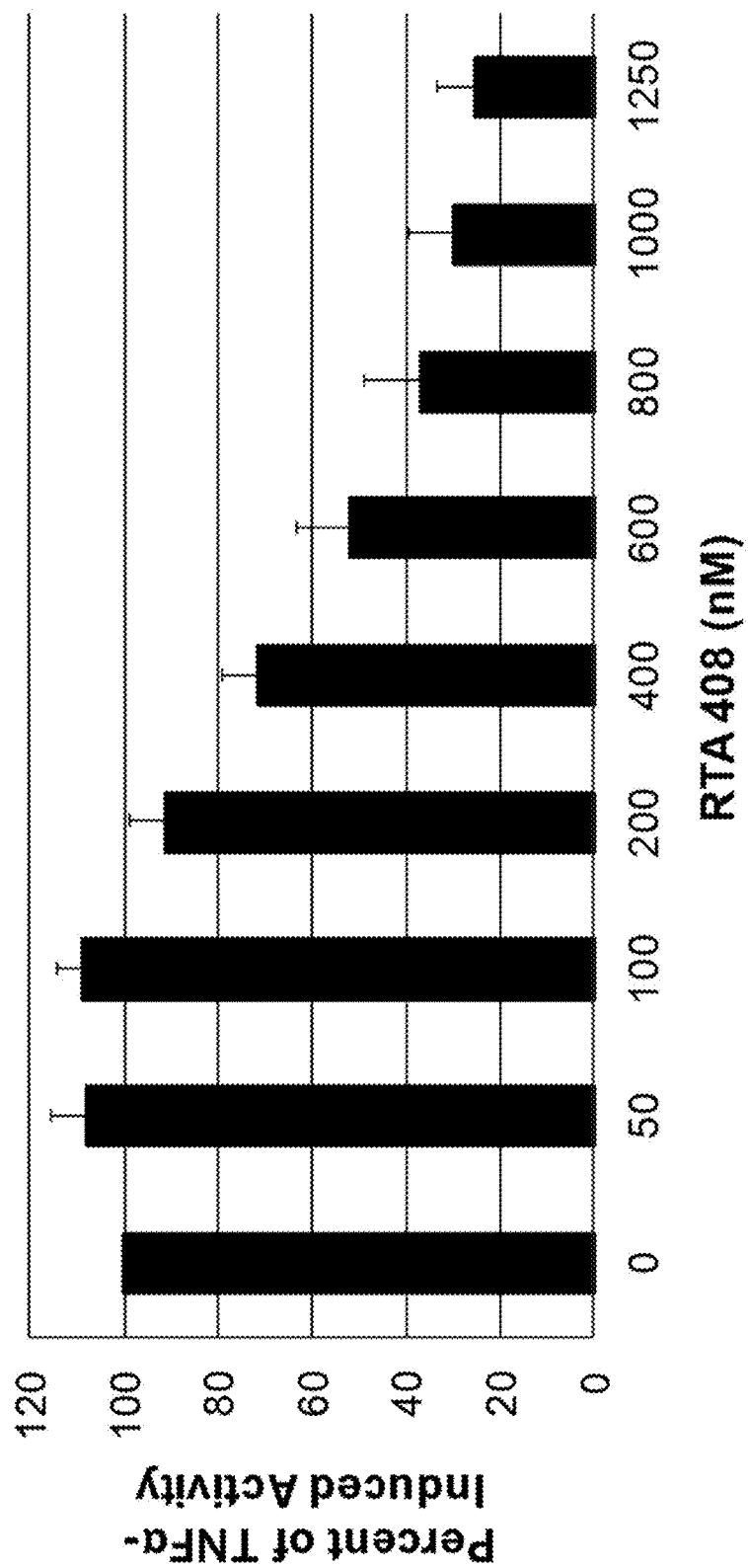
FIG. 12—Effect of RTA 408 on TNF-α-induced activation of a NF-κB luciferase reporter construct.
Figure 13:
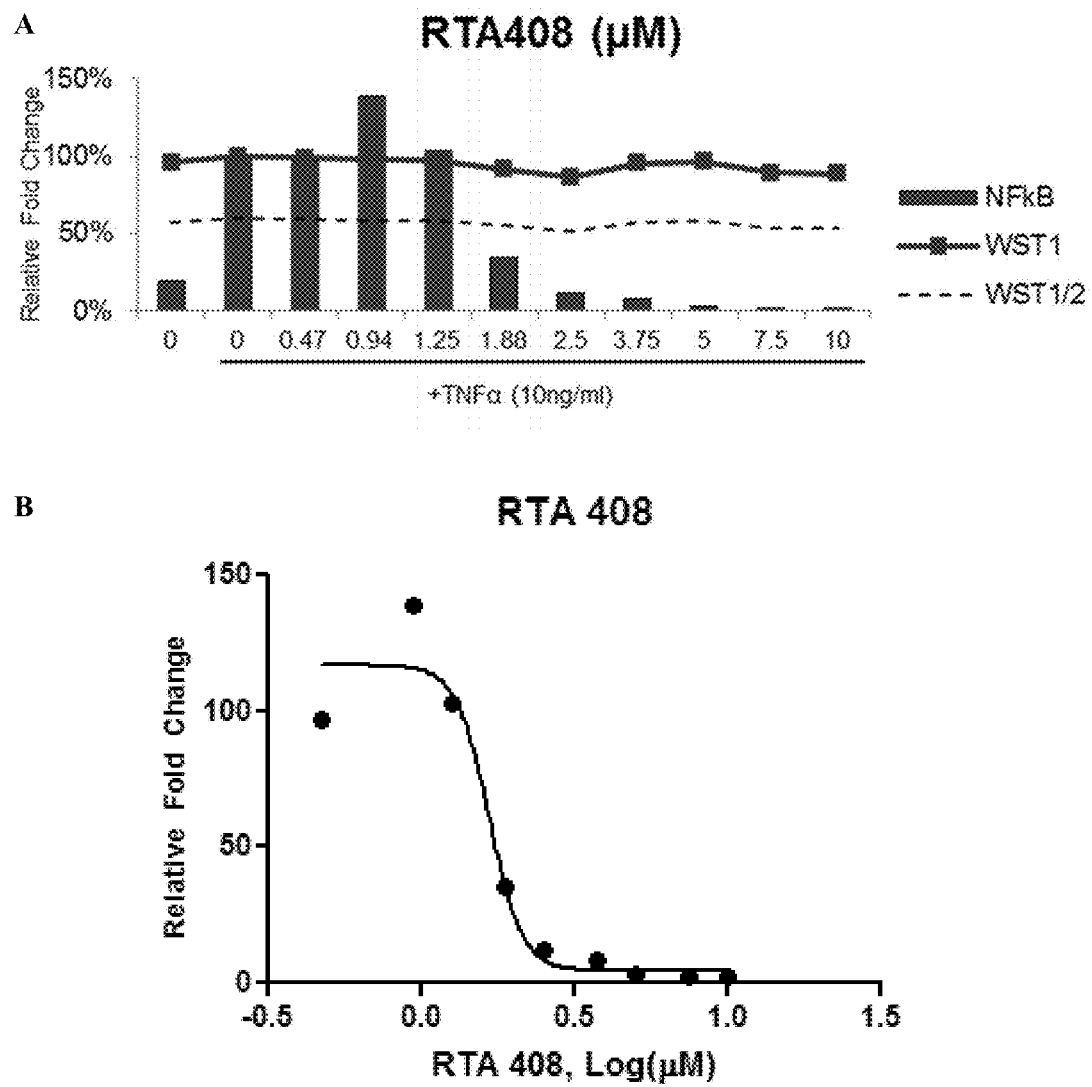
FIGS. 13a & b—(a) Effect of RTA 408 on TNF-α-induced activation of an NF-κB luciferase reporter in the human A549 cell line with WST1 viability and WST1/2 viability overlaid. (b) TNF-α-induced activation of an NF-κB luciferase reporter in the human A549 cell line. The graph shows relative fold change as a function of log change in RTA 408 concentration.

NF-κB is a transcription factor that plays a central role in the regulation of many immune and inflammatory responses. RTA 402 and other AIMs have been shown to inhibit pro-inflammatory NF-κB signaling in a variety of cell lines (Shishodia, 2006; Ahmad, 2006; Yore, 2006). Using the mouse NIH3T3/NF-κB-luc cell line (Panomics), the effects of RTA 408 and the compounds 63171, 63179, 63170, and 63189 on the NF-κB-Luc reporter were explored. The NIH3T3/NF-κB-luc cell line maintains a chromosomal integration of a Firefly luciferase reporter construct regulated by eight copies of the NF-κB response element. The effects of these compounds can be quantified by measuring the value of the NF-κB $IC_{50}$. RTA 408 showed a 1.2 µM $IC_{50}$, which when normalized for viability showed an $IC_{50}$ of 1.4 µM. The other four compounds showed NIH3T3/NF-κB $IC_{50}$ values of 1.7, 0.2, 1.1, and 1.1 µM, which when viability normalized showed $IC_{50}$ values of 1.8, 0.6, 1.1, and 1.0 µM, respectively. RTA 408 and its effects on NF-κB are plotted as a function of dosing and relative fold change as well as WST1 and WST1/2 are shown in FIGS. 11a & b. The effect of RTA 408 on TNFα-induced NF-κB signaling was evaluated in HeLa/NF-κB-Luc cells, a human cervical adenocarcinoma cell line stably transfected with a luciferase reporter construct under the control of multiple NF-κB transcriptional response elements. HeLa/NF-κB-Luc cells were pretreated for 1 h with RTA 408, followed by treatment with TNF-α (10 ng/mL) for an additional 5 h. After treatment, luminescence was measured, and the effect of RTA 408 pretreatment on TNF-α-induced luciferase activity was determined. The average results and standard deviations from three independent experiments are shown in FIG. 12. RTA 408 dose-dependently inhibited TNF-α-induced NF-κB activation with an $IC_{50}$ value of 517±83 nM. Similar results were observed in another NF-κB reporter cell line (A549/NF-κB-Luc) where RTA 408 inhibited TNF-α-induced NF-κB activation with an $IC_{50}$ value of 627 nM (range 614-649 nM). RTA 408 was 1.6-1.8 fold more efficient at reducing expression from the NF-κB promoter reporter in HeLa/NF-κB-Luc cells than 63189 (854 nM) and 63170 (953 nM), respectively. Further experimentation with the human A549 cell line showed an $IC_{50}$ for RTA 408 as 1.7 µM and a value that has been viability normalized to 1.7 µM. The $IC_{50}$ of RTA 408 showed similar activity to 63189, 63179, 63171, and 63170 which showed $IC_{50}$ values of 1.1, 1.4, 2.0, and 1.0, respectively. When those values were viability normalized, the assay showed 1.2, 1.5, 2.1 and 1.1 µM $IC_{50}$, respectively. The fold change for NF-κB as a function of RTA 408 concentration along with WST1 and WST1/2 curves were plotted and are shown in FIGS. 13a&b.

Figure 14:
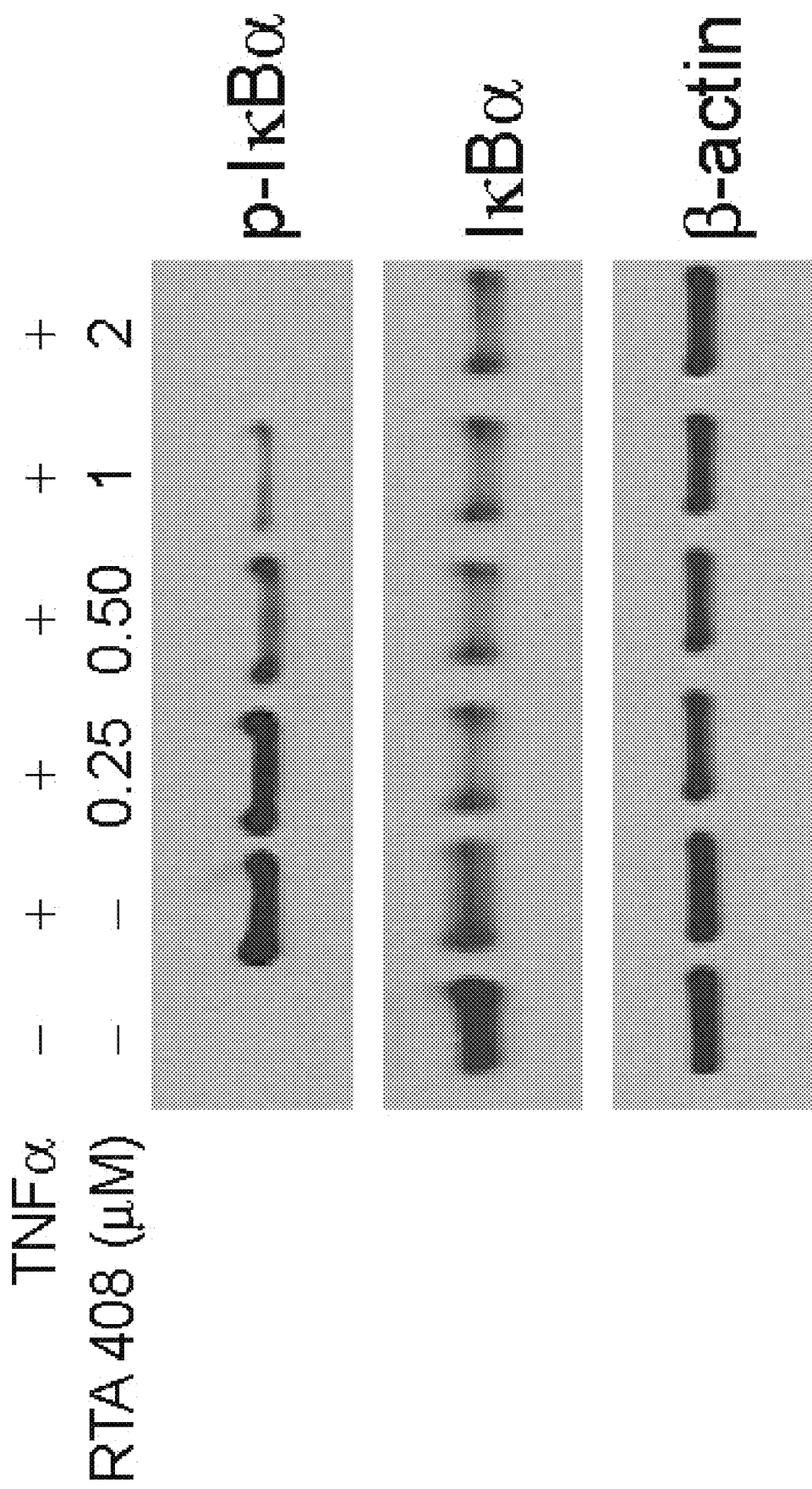
FIG. 14—Effect of RTA 408 on TNF-α-induced phosphorylation of IκBα.

The effect of RTA 408 on TNF-α-induced phosphorylation of IκBα, a key step in activation of the NF-κB pathway, was also evaluated in HeLa cells. HeLa cells were pretreated with RTA 408 for 6 h, followed by treatment with TNF-α (20 ng/mL) for 5 min. Total and phosphorylated levels of IκBa were evaluated by Western blot. Primary IκBa antibodies were from Santa-Cruz (sc-371), pIκBα antibody was from Cell Signaling (9246), actin antibody was from Millipore (MAB 1501). Peroxidase-conjugated affini-pure Goat anti-Rabbit (IgG) and peroxidase-conjugated affini-pure Goat anti-Mouse IgG secondary antibodies were purchased from Jackson ImmunoResearch. Protein blots were developed using ECL, and exposed to X-ray film. Consistent with the results from the luciferase reporter assay, RTA 408 inhibited TNF-α-induced phosphorylation of IκBa in a dose-dependent manner (FIG. 14).

RTA 408 has also been demonstrated to inhibit other pro-inflammatory signaling pathways, such as IL-6-induced signal transducer and activator of transcription 3 (STAT3) phosphorylation and receptor activator of NF-κB ligand (RANKL)-induced osteoclastogenesis. In HeLa cells, pretreatment with 1 µM RTA 408 for 6 h inhibited phosphorylation of STAT3 induced by IL-6. STAT3 (124H6) and phospho-STAT3 (Tyr705) monoclonal antibodies were from Cell Signaling Technology. Peroxidase-conjugated Affini-pure Goat anti-Rabbit IgG and Peroxidase-conjugated Affini-pure Goat anti-Mouse IgG were from Jackson ImmunoResearch. Osteoclastogenesis is a multi-step differentiation process that results from the binding of RANKL to its receptor, RANK, on cells of hematopoietic origin. This results in the activation of NF-κB and MAPK, which in turn increase transcription of osteoclast-specific target genes, including tartrate-resistant acid phosphatase (TRAP). The effect of RTA 408 on RANKL-induced osteoclastogenesis was evaluated in the mouse macrophage cell line RAW264.7. RAW 264.7 cells were plated in 24-well plates at a density of 5,000 cells/well. The next day, cells were treated with RTA 408 for 2 h and then treated with 50 ng/mL recombinant mouse RANKL (R&D systems). The treated cells were incubated for four days to allow differentiation into osteoclasts. Differentiation into osteoclasts was assessed by measuring TRAP activity. In brief, 90 µL of conditioned cell culture media was removed from each test well and aliquoted into triplicate wells (30 µL/well) of a 96-well plate. 170 µL of TRAP Assay buffer (Kamiya Biomedical) was then added to each well and the plate was incubated at 37° C. for 3 hours. Following the incubation, absorbance at 540 nm was determined using a Spectramax M2 plate reading spectrophotometer. RTA 408 dose-dependently inhibited RANKL-induced TRAP activity and the formation of osteoclasts, with an $IC_{50}$ of ~5-10 nM.

5. Effect of RTA 408 on Expression of Genes Encoding Transaminase Enzymes

Transaminase elevations were observed in the 28-day toxicity studies with RTA 408 in rats and, to a much lower extent, in monkeys. Similar findings have been observed following oral administration of a related AIM (bardoxolone methyl) in humans (Pergola, 2011). One hypothesis for this effect is that AIMs directly or indirectly increase transaminase gene expression in the absence of cellular toxicity. To assess whether treatment with RTA 408 affects transaminase mRNA levels, mouse AML-12 hepatocytes were treated with RTA 408 for 18 h, and the mRNA levels of genes encoding transaminases were measured using quantitative PCR. AML-12 cells were plated in 6-well culture dishes at $3 \times 10^5$ cells per well using 2 mL of media per well. The following day cells were treated with DMSO (vehicle) or 250 nM and 500 nM RTA 408 for 18 h at 37° C. Each well received 0.1% DMSO. Three independent replicate experiments were performed. Following treatment, media was removed and cells were harvested using RLT buffer (Qiagen). Lysates were homogenized using QIAShredder columns (Qiagen, Catalog #79654) and RNA was isolated using RNeasy Mini kits (Qiagen, Catalog #74104). For reverse transcription, RNA (1 µg) was combined with Oligo (dT)12-18 primer and $H_2O$ in a final volume of 23.25 µL. The mixture was heated to 70° C. for 10 min and then placed on ice. A master mix containing 8 µL 5×1st strand buffer, 2 µL 1 mg/mL BSA, 2 µL 20 mM DTT, 4 µL 5 mM dNTP mix, 0.25 µL RNASEOUT™ and 0.5 µL SUPERSCRIPT® II reverse transcriptase was added to the RNA mixture and incubated at 42° C. for 1 h. The reaction was inactivated by heating to 70° C. for 10 min. The reaction mixture was diluted 1:3 with $H_2O$ prior to use in qPCR. 2.5 µL of the diluted reverse transcription reaction was combined with one set of PCR primers (0.36 µM final concentration), 2×iQ™ SYBR® Green Supermix (Bio-Rad, Catalog #170-8885) and $H_2O$ to a final volume of 20 µL. Sequences for PCR primers are as follows: Ribosomal protein L19 (Rpl19) forward primer 5'-TCAGGCTACAGAAGAGGCTTGC-3' (SEQ ID NO: 19), reverse primer 5'-ACAGTCACAGGCTTGCGGATG-3' (SEQ ID NO: 20); NAD(P)H dehydrogenase, quinone 1 (Nqo1) forward primer 5'-TCGGGCTAGTCCCAGTTAGA-3' (SEQ ID NO: 21), reverse primer 5'-AAAGAGCTGGAGAGCCAACC-3' (SEQ ID NO: 22); Glutamic pyruvic transaminase 1 (Gpt1 or Alt1) forward primer 5'-CACGGAGCAGGTCTTCAACG-3' (SEQ ID NO: 23), reverse primer 5'-AGAATGGTCATCCGGAAATG-3' (SEQ ID NO: 24); Glutamic pyruvic transaminase 2 (Gpt2 or Alt2) forward primer 5'-CGCGGTGCAGGTCAACTACT-3' (SEQ ID NO: 25), reverse primer 5'-CCTCATCAGCCAGGAGAAAA-3' (SEQ ID NO: 26); Glutamate oxaloacetate transaminase 1 (Got1 or Ast1) forward primer 5'-GGCTATTCGCTATTTTGTGT-3' (SEQ ID NO: 27), reverse primer 5'-GACCAGGTGATTCGTACAAT-3' (SEQ ID NO: 28); Glutamate oxaloacetate transaminase 2 (Got2 or Ast2) forward primer 5'-AGAGTCCTCTTCAGTCATTG-3' (SEQ ID NO: 29), reverse primer 5'-ATGATTAGAGCAGATGGTGG-3' (SEQ ID NO: 30). All primers had previously been validated for specificity and amplification efficiency. cDNA was amplified using the following cycle conditions: (95° C. for 3 min, 44 cycles of 95° C. for 30 sec, 60° C. for 15 sec, 72° C. for 15 sec, followed by a melt curve of 55° C. to 95° C. in increments of 0.5° C.). The relative abundance of each target gene was determined using the comparative CT method (ΔΔCT). PCR reactions were run in triplicate wells for each sample. Treatment with RTA 408 increased mRNA levels of alanine transaminase 1 (Alt1 or Gpt1) and aspartate transaminase 1 (Ast1 or Got1) (FIGS. 15a,c). RTA 408 had no effect on alanine transaminase 2 (Alt2 or Gpt2) mRNA levels and reduced mRNA levels of aspartate transaminase 2 (Ast2 or Got2) (FIGS. 15b,d). These results demonstrate that RTA 408, at the concentrations tested (250 nM or 500 nM), affects transaminase gene expression in vitro.

6. Effect of RTA 408 on Levels of Glycolytic Intermediates

Studies in diabetic mice have demonstrated that bardoxolone methyl increases muscle-specific insulin-stimulated glucose uptake (Saha, 2010). In humans, a higher percentage of patients receiving bardoxolone methyl reported experiencing muscle cramps compared with patients receiving placebo (Pergola, 2011). Muscle spasms have also been reported in diabetic patients following insulin administration, suggesting a possible association with muscle glucose metabolism. The effect of RTA 408 on glycolytic metabolism was evaluated through the assessment of lactate and pyruvate levels in cultured rodent C2C12 muscle cells. To measure lactate levels, differentiated C2C12 myotubes were treated with 1 µM or 2 µM RTA 408 or insulin for 3 h at 37° C. Buffer was removed and saved for measurement of extracellular lactate levels. Cell debris was pelleted by centrifugation (10 min at 14,000 rpm) prior to measurement of lactate. To measure intracellular lactate, cells were suspended in 0.1% Triton X-100 in PBS and lysed by shearing with a 25 gauge needle. Cell lysate was centrifuged (10 min at 14,000 rpm, 4° C.) and lactate was measured in the supernatant. Intracellular and extracellular lactate was measured using the Lactate Assay Kit (BioVision, Catalog #K607-100). Similar to treatment with insulin, treatment of differentiated C2C12 myotubes with 1 µM or 2 µM RTA 408 for 3 h significantly increased intracellular and extracellular lactate levels in a dose-dependent manner.

Figure 16:
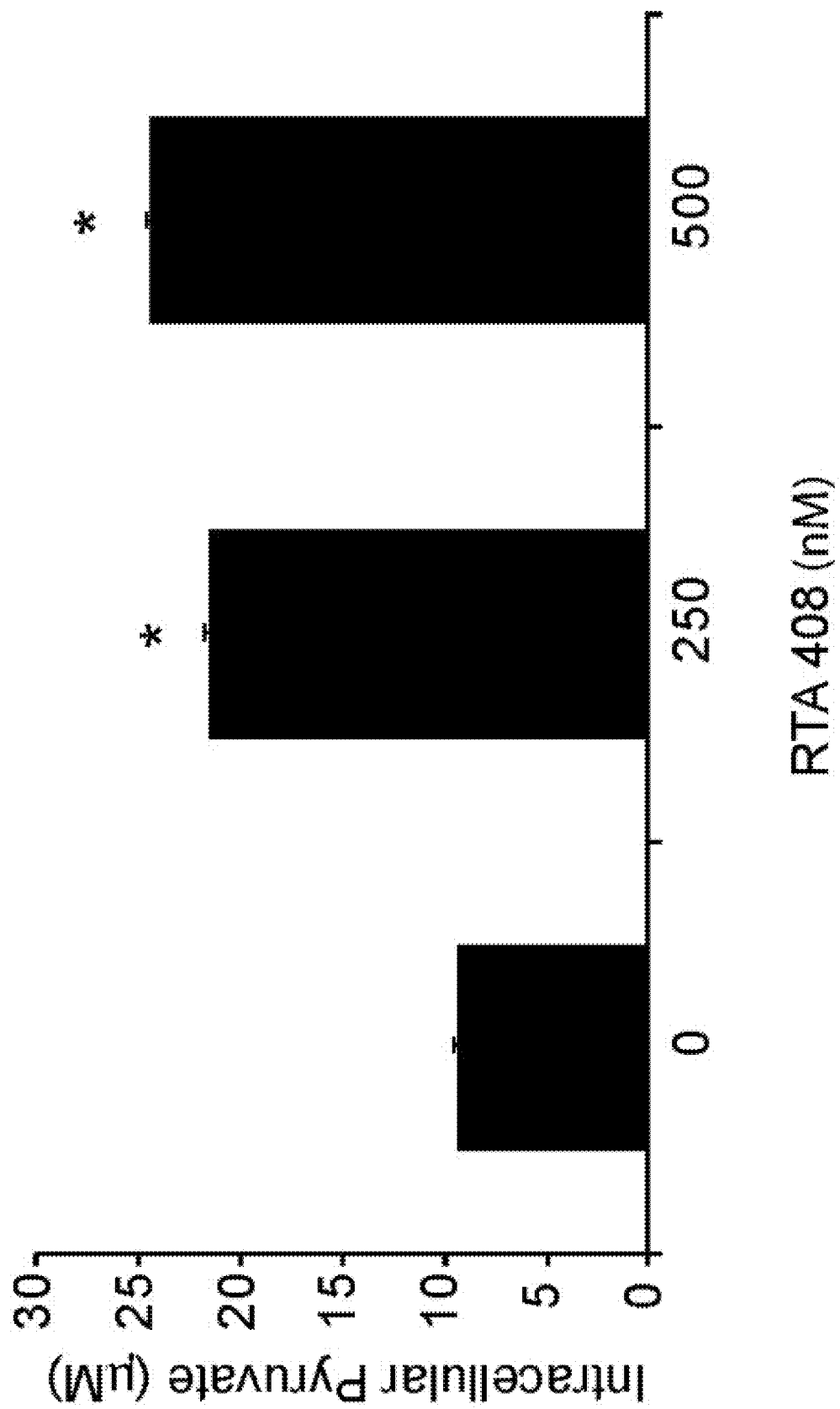
FIG. 16—Effect of RTA 408 on pyruvate levels in cultured muscle cells (*P<0.05).

To measure pyruvate levels, differentiated C2C12 myotubes were treated with 250 or 500 nM RTA 408 or 100 nM insulin for 18 h. Following drug treatment, media was removed and cells were washed with PBS. Cells were lysed in Pyruvate Assay Buffer (Pyruvate Assay Kit, BioVision, Catalog #K609-100). Cell lysates were centrifuged (10 min at 14,000 rpm, 4° C.) and pyruvate levels were measured in the supernatant. Treatment of C2C12 differentiated myotubes with 250 nM or 500 nM RTA 408 for 18 h also significantly ($P<0.0001$, noted by asterisks) increased intracellular pyruvate levels in a dose-dependent manner (FIG. 16). Together, these results demonstrate that RTA 408, at the concentrations tested, can affect muscle glycolytic intermediates in vitro; however, it is unclear how the results from this in vitro system at the RTA 408 concentrations tested relate to the potential effects on glucose metabolism at clinically-relevant dose levels in humans.

7. In Vitro Evaluation of RTA 408 Efflux by MRP-1

One of characteristic of a drug candidate is the compound's efflux ratio. The efflux ratio measures how easily the compound is transported across a membrane. The MRP-1 protein, or the multidrug resistance-assistance protein 1, is one of a family of proteins which help to facilitate the transport of organic anions and other small molecules through cellular membranes. A larger efflux ratio typically means that the drug candidate is more readily transported out of the membrane and less available to modulate intracellular processes. Similar proteins also regulate the transport of compounds across the blood-brain barrier. The efflux ratio MRP-1 for RTA 408 (1.3) was experimentally determined to be approximately ten-fold lower than 63170 (10) and 63171 (11.2) and over 40-fold lower than 63179 (56.5) and 63189 (57.1). Without being bound by theory, RTA 408 may not be a good substrate for MRP-1 and/or a candidate for p-glycoprotein mediated efflux at the blood-brain barrier. In some embodiments, RTA 408 may be used for treating disorders of the central nervous system (CNS).

C. Protective Effects of RTA 408 in Animal Models of Lung Disease

RTA 408 was tested in several animal models of pulmonary disease to evaluate its potential efficacy in the lung. For all studies, RTA 408 was orally administered daily in sesame oil at dose levels in the range of 3 to 150 mg/kg. In most cases, RTA 408 was administered starting several days prior to the induction of the lung injury response.

1. LPS-Induced Pulmonary Inflammation in Mice

Figure 17:
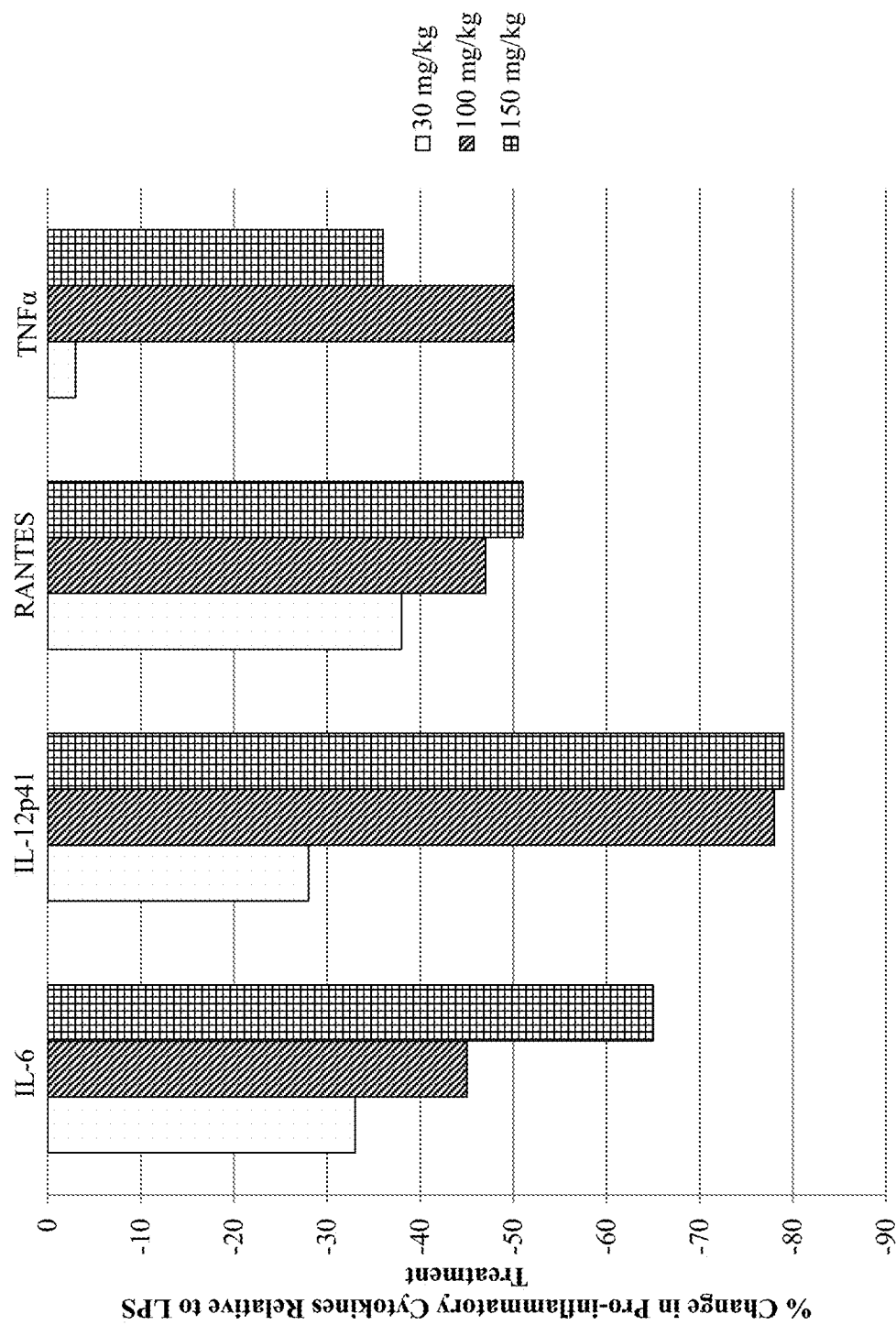
FIG. 17—Effect of 63415 in a model of pulmonary LPS-mediated inflammation (% change in pro-inflammatory cytokines relative to LPS treatment). Compound 63415 was administered QD×3 at Time 0, 24, and 48 h followed by LPS one h after the last dose of 63415 in female BALB/c mice. Animals were sacrificed 20 h after LPS administration. BALF was examined for pro-inflammatory cytokine expression. Compound 63415 reduced pro-inflammatory cytokines in a dose-dependent manner, with peak reductions ranging from 50%-80% in TNF-α, IL-6, and IL-12.

RTA 408 was tested in two studies of LPS-induced pulmonary inflammation in mice. In the first study, intended to be a preliminary dose-range finder, RTA 408 (30, 100, or 150 mg/kg) was administered orally once daily for three days, followed by LPS administration 1 h after the final dose. Bronchoalveolar lavage fluid (BALF) was collected 20 h after LPS administration (21 h after the final dose of RTA 408) and evaluated for levels of pro-inflammatory markers (i.e., IL-6, IL-12p40, TNF-α, and RANTES) using LUMINEX™ technology. RTA 408 treatment resulted in a significant reduction in IL-12p40 at all doses and in TNF-α at the 100 and 150 mg/kg doses (FIG. 17). In the second study, RTA 408 (10, 30, or 100 mg/kg) was administered daily for six days, followed by LPS administration 1 h after the final dose. In this study, significant decreases in body weight were observed at the 100 mg/kg dose level starting on Day 3. Significant reductions in TNF-α were observed at the 10 mg/kg dose, and significant reductions in IL-12p40, TNF-α, and RANTES were observed at the 30 mg/kg dose (FIG. 18a). Further evaluation of lungs from mice in this study revealed meaningful engagement of relevant Nrf2 target genes, including significant induction of NQO1 enzyme activity (by measurement of rate of reduction of 2,6-dicholorphenol-indophenol) and increases in total GSH (GSH-GLO™, Promega, Madison, WI) at 10 and 30 mg/kg (FIG. 18b).

2. Bleomycin-Induced Pulmonary Fibrosis

The effect of RTA 408 was also evaluated in models of bleomycin-induced pulmonary fibrosis in mice and rats. In the first preliminary study, RTA 408 (10, 30, or 100 mg/kg) was administered to mice daily via oral gavage for 39 days, with bleomycin challenge (intranasal) on day 10. On the last day of dosing, lung tissue was collected and histology was performed to evaluate the extent of inflammation and interstitial fibrosis. In this model, no statistically significant effects were observed at the RTA 408 doses tested (FIGS. 19a & b). Additional evaluation was performed using a rat model of pulmonary fibrosis that has been extensively characterized at the Lovelace Respiratory Research Institute. In this study, rats were challenged with bleomycin or saline by intratracheal administration on day 0. Following the challenge, animals received RTA 408 (3, 10, or 30 mg/kg) daily via oral gavage for 28 days. Administration of the 30-mg/kg dose was stopped on day 14 due to excessive dehydration and diarrhea in the animals. For the remaining animals, bronchoalveolar lavage fluid was collected on day 28 for assessment of pro-inflammatory infiltrates by flow cytometry, and lung tissue was analyzed for hydroxyproline levels by LC-MS and histopathology. Challenge with bleomycin sulfate induced a substantial release of neutrophils and an increase in soluble collagen in the BALF, as well as an increase in hydroxyproline in the lung. Treatment with 3 and 10 mg/kg RTA 408 significantly suppressed polymorphonuclear (PMN) cell infiltration into the lungs and also produced a meaningful reduction (~10%-20%) in hydroxyproline deposition (FIGS. 20a & b).

Importantly, histopathological evaluation revealed a significant decrease in collagen deposition, as assessed by trichrome staining, in rats treated with RTA 408. Whereas bleomycin control animals primarily exhibited moderate staining, animals treated with 10 mg/kg RTA 408 had predominantly minimal to mild staining (Table 2).

TABLE 2

Effect of RTA 408 on collagen deposition in rat lungs as assessed by intensity of trichrome staining

| Staining Intensity[a] | Bleomycin Control | RTA 408 (3 mg/kg) | RTA 408 (10 mg/kg) |
|---|---|---|---|
| Minimal | 0 | 0 | 3 |
| Mild | 1 | 0 | 4 |
| Moderate | 7 | 7 | 1 |

[a]Values represent intensity of staining in animals with interstitial trichrome staining in areas of bleomycin-induced lung alterations.

Figure 21:
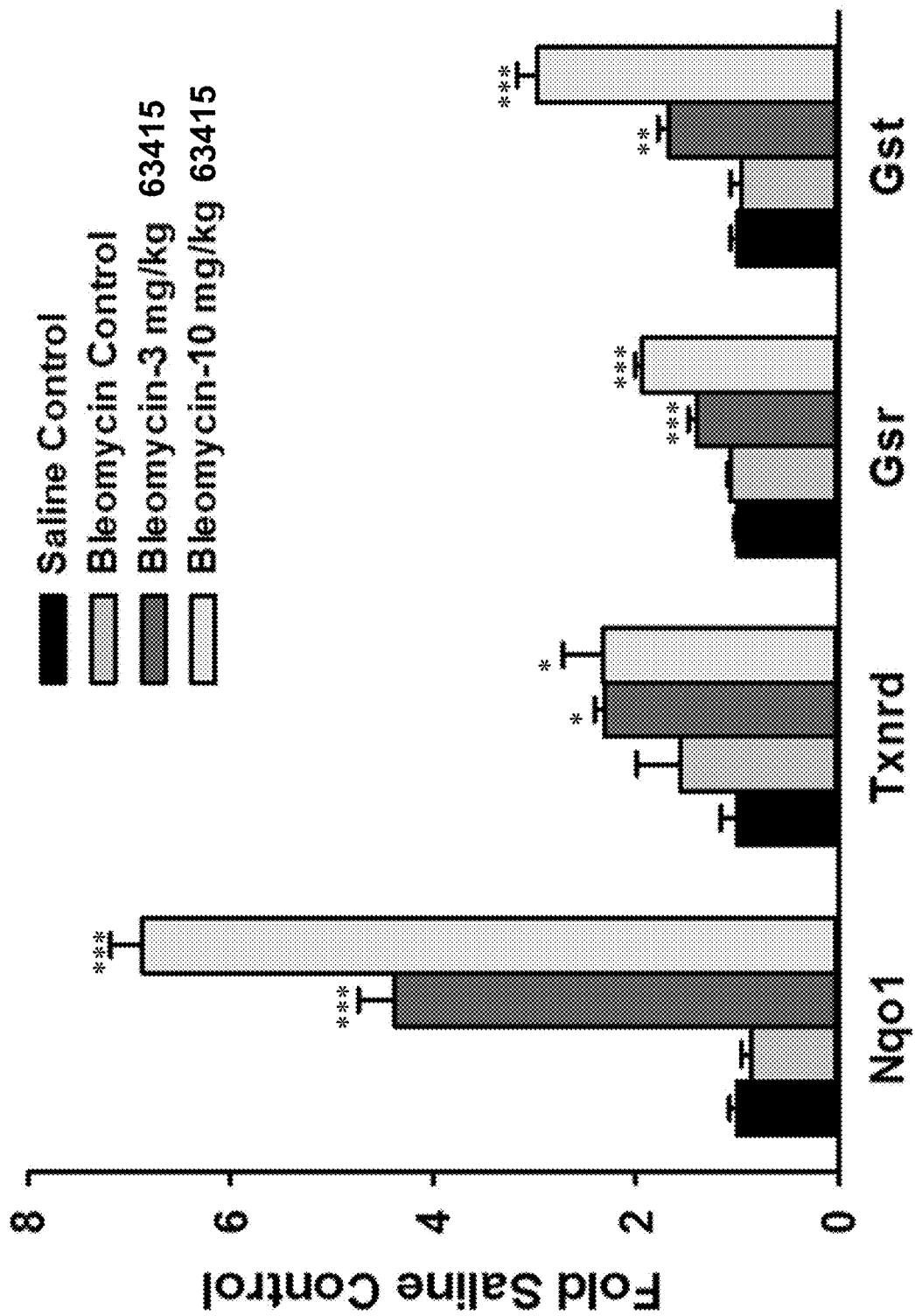
FIG. 21—Effect of RTA 408 on Nrf2 target enzymes in lungs from rats with bleomycin-induced pulmonary fibrosis. Asterisks indicate a statistically significant difference from the saline control group (*P<0.05; P<0.01; *P<0.001).
Figure 22:
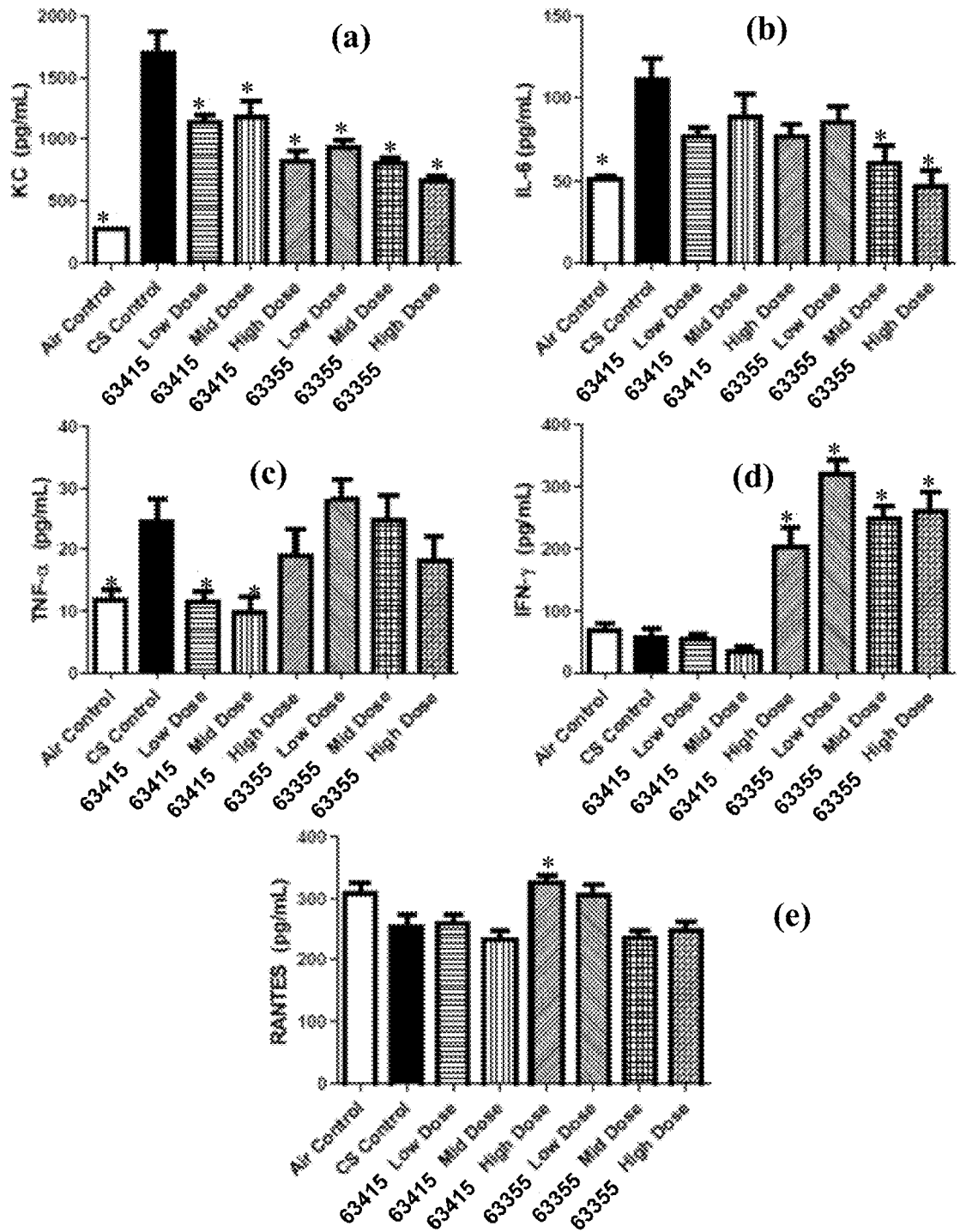
FIGS. 22a-e—Effect of RTA 408 on cigarette smoke-induced COPD in mice. (a) KC; (b) IL-6; (c) TNF-α; (d) IFN-7; (e) RANTES. RTA 408 (63415) was tested at dose levels of 3 mg/kg (low), 10 mg/kg (mid), and 30 mg/kg (high). An AIM analog (63355) was tested in the same study for comparison. Asterisks indicate a statistically significant difference form the CS control group.

Further evaluation of lungs from rats in this study also revealed meaningful engagement of relevant Nrf2 target genes as assayed by Quantigene Plex 2.0 Multiplex assay (Affymetrix, Santa Clara, CA) (FIG. 21). RTA 408 significantly and dose-dependently increased NQO1, Txnrd, Gsr, and Gst enzyme activity in the lungs of rats exposed to bleomycin, demonstrating Nrf2 activation by RTA 408 in this disease setting. NQO1 enzyme activity was assessed by measuring the rate of reduction of DCPIP. Txnrd, Gst, and Gst enzyme activities were measured using commercially available kits from Cayman Chemical (Ann Arbor, MI).

3. Cigarette Smoke-Induced COPD in Mice

RTA 408 was also tested in a mouse model of cigarette smoke-induced COPD. Mice received RTA 408 (3, 10, or 30 mg/kg) daily via oral gavage for two weeks and were exposed to cigarette smoke five days per week during the RTA 408 dosing period. At the end of the study, lung tissue and BALF were collected for analysis of inflammatory infiltrates and cytokines. In this experiment, multiple-dose administration of RTA 408 at doses as low as 3 mg/kg RTA 408 resulted in significant suppression of pro-inflammatory cytokines, including KC (functional mouse homolog of human IL-8) and TNF-α as measured using LUMINEX™ Technology. A summary of results from this study is presented in FIGS. 22a-e. An AIM analog (63355) was tested in the same study for comparison. 63355 is a compound of the formula:

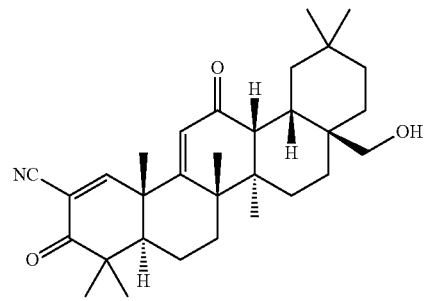

Figure 23:
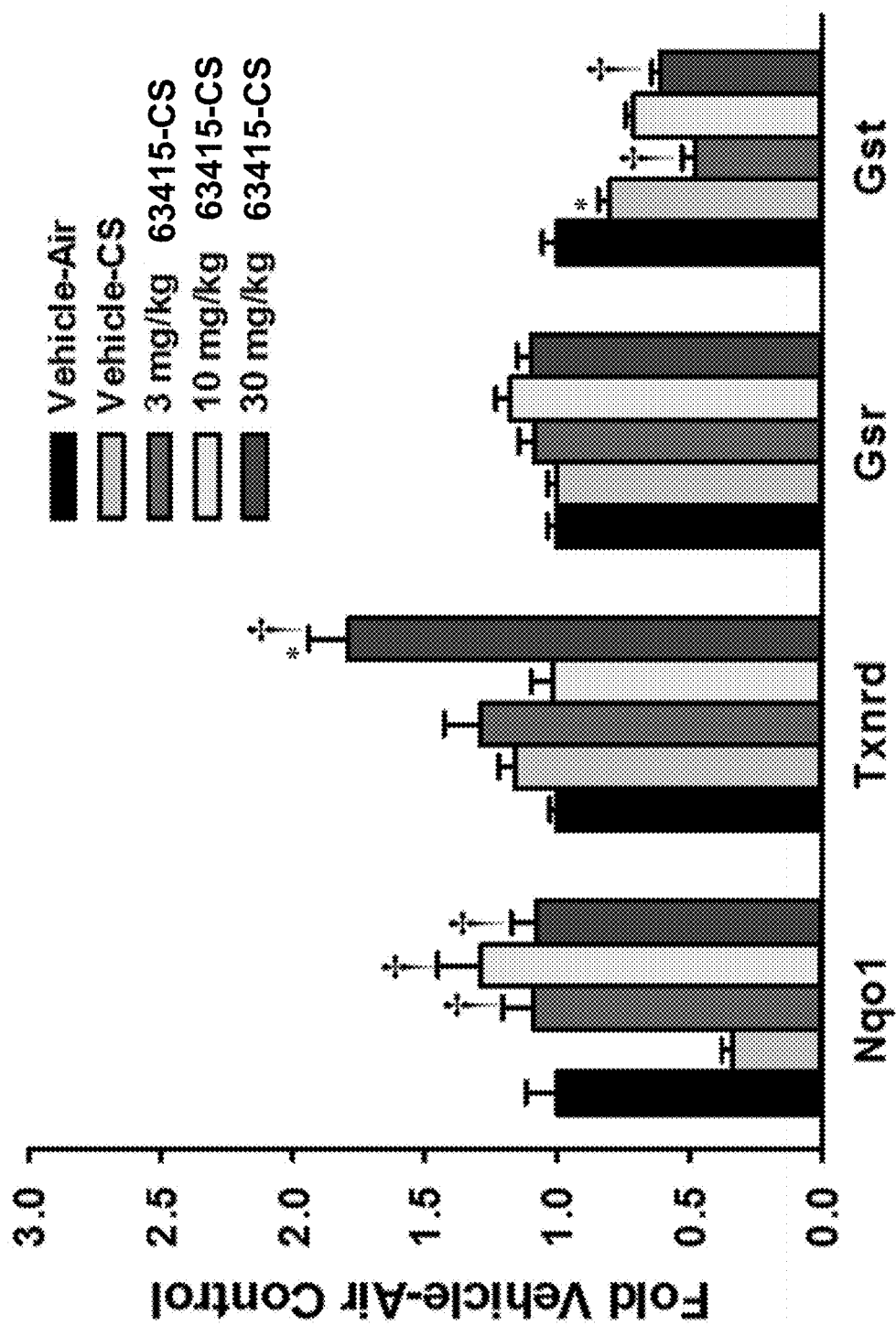
FIG. 23—Effect of RTA 408 on Nrf2 target enzymes in lungs from mice with cigarette smoke-induced COPD. Asterisks indicate a statistically significant difference from the saline control group (*P<0.05; P<0.01; *P<0.001). Daggers represent a statistically significant difference from mice expose to cigarette smoke and administered vehicle (†P<0.05).

Further evaluation of lungs from mice in this study also revealed meaningful engagement of relevant Nrf2 target genes (FIG. 23). NQO1 enzyme activity in the lung, measured as the rate of reduction of DCPIP, was significantly decreased by cigarette smoke exposure; administration of RTA 408 rescued this loss. Txnrd enzyme activity was also induced by the 30 mg/kg dose of RTA 408. In general Gsr enzyme activity was not altered, and Gst enzyme activity was decreased with treatment—both of which were likely the consequence of a temporal response for these enzymes. Txnrd, Gst, and Gst enzyme activities were measured using commercially available kits from Cayman Chemical (Ann Arbor, MI).

4. Ovalbumin-Induced Asthma in Mice

The potential activity of RTA 408 was also evaluated in a pilot study in a mouse model of ovalbumin-induced asthma. Mice were sensitized with an IP injection of ovalbumin and aluminum hydroxide on Day 0 and Day 14 and challenged intranasally with ovalbumin in saline on Days 14, 25, 26, and 27. Mice received RTA 408 (3, 10, or 30 mg/kg) daily via oral gavage on Days 1-13 and 15-27. Following sensitization and challenge with ovalbumin, vehicle-treated mice had a significant increase in the total number of leukocytes compared with positive control (dexamethasone)-treated mice. An increase in the number of T cells and B cells was also observed in the vehicle-treated mice. Treatment with RTA 408 at 30 mg/kg significantly reduced the number and percentage of B cells within the airways. RTA 408 (3 and 30 mg/kg) also significantly reduced the number of macrophages, but not the mean percentage of macrophages, detected in the airways. These observations are suggestive of potential efficacy in this model.

5. Effects of RTA 408 on LPS-Induced Sepsis in Mice

Sepsis was induced on Day 0 with an IP injection of LPS (21 mg/kg), and survival was followed until Day 4. RTA 408 (10, 30, or 100 mg/kg) was administered daily via oral gavage from Day −2 to Day 2. In the vehicle control group, 60% of the animals survived until Day 4 (higher than the ~40% survival rate expected in this model). In the RTA 408 treatment groups, 80% of the animals in the 10 mg/kg dose group and 90% of the animals in the 30 mg/kg dose group survived until Day 4 (FIGS. 24c & d). For the 100 mg/kg dose group, 90% of the animals survived until Day 4, with only a single death occurring on Day 4. Although these RTA 408-induced effects are indicative of profound efficacy in this model, the relatively high survival rate in the vehicle control group precluded a statistically-significant difference between the control and RTA 408-treated groups. Results obtained using the compound RTA 405 are also presented (FIGS. 24a & b). RTA 405 is a compound of the formula:

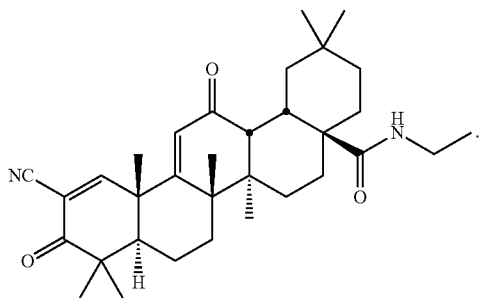

6. Effects of RTA 408 Against Radiation-Induced Oral Mucositis

Figure 25:
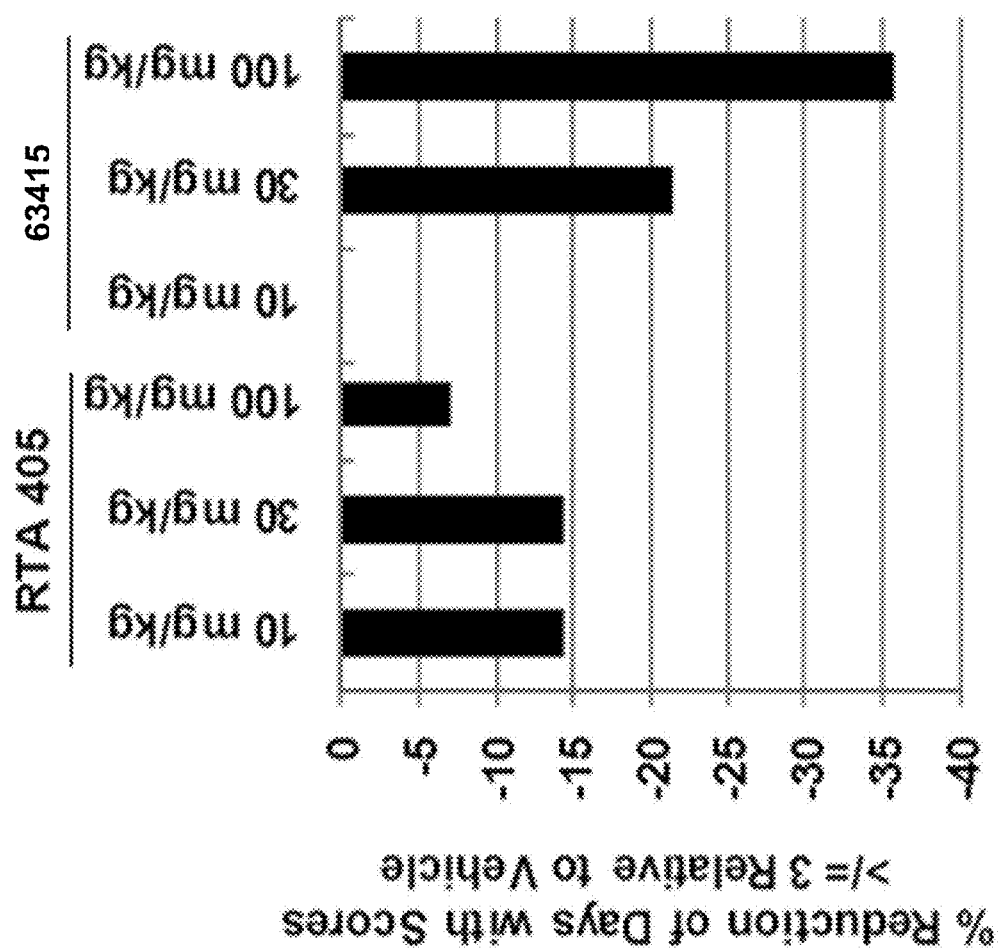
FIG. 25—Effect of 63415 in a model of radiation-induced oral mucositis. RTA 405 or 63415 (RTA 408) was administered BID×20 on Days −5 to −1 and Days 1 to 15 to male Syrian Golden Hamsters. Radiation occurred on Day 0. Mucositis scores range from 0 to 5 based on clinical manifestations (0: completely healthy; 1-2: light to severe erythema; 3-5: varying degrees of ulceration). 63415 improved mucositis at 30 mg/kg and 100 mg/kg with up to a 36% reduction in ulceration.

Exposure to acute radiation directed to the buccal cheek pouch of hamsters produces effects similar to those observed in oral ulcerative mucositis in humans. These effects include moderate to severe mucositis characterized by severe erythema and vasodilation, erosion of the superficial mucosa, and formation of ulcers. A single study was conducted to evaluate the effects of RTA 408 in this model. On Day 0, each hamster was given an acute radiation dose of 40 Gy directed to the left buccal cheek pouch. RTA 408 (10, 30, or 100 mg/kg) was orally administered twice daily from Day −5 to Day −1, and Day 1 to Day 15. Beginning on Day 6 and continuing until Day 28 on alternate days, oral mucositis was evaluated using a standard 6-point scoring scale. Both the 30 and 100 mg/kg doses of RTA 408 caused a significant reduction in the duration of ulcerative mucositis (FIG. 25). Furthermore, a dose-dependent decrease in the percentage of animals with mucositis scores ≥3 was also observed. However, administration of RTA 408 at 30 or 100 mg/kg caused significant dose-dependent reductions in weight gain in irradiated hamsters. Due to weight loss in excess of 20%, two out of eight hamsters in the 100 mg/kg dose group were euthanized on Day 2.

7. Effect of RTA 408 on the Induction of Nrf2 Biomarkers In Vivo

As described above, a key molecular target of RTA 408 is Nrf2, a central transcriptional regulator of antioxidative cellular protection. Activation of Nrf2 induces upregulation of a battery of cytoprotective genes, including NQO1, enzymes involved in GSH synthesis [i.e., glutamate-cysteine ligase catalytic and modifier subunits (Gclc and Gclm)], enzymes involved in detoxification (i.e., glutathione S-transferases [Gsts]), and efflux transporters [i.e., multidrug resistance-associated proteins (Mrps)]. Induction of these genes results in a coordinated cellular effort to protect against oxidative insult, highlighted by increased antioxidative capacity, induction of glutathione synthesis, and conjugation and export of potentially harmful molecules from the cell. In addition to the efficacy endpoints and Nrf2 target gene expression evaluated in the various animal models described above, the ability of RTA 408 to induce expression of Nrf2 target genes was also assessed using tissues collected from healthy RTA 408-treated mice, rats, and monkeys.

As part of the non-GLP 14-day toxicity studies of RTA 408 in mice, rats, and monkeys, tissues were collected for the purposes of measuring mRNA and enzyme activity levels of selected Nrf2 target genes. For mice and rats, liver samples were collected 4 h after the final dose on Day 14. For monkeys, blood (for PBMC isolation), liver, lung, and brain tissue were collected 24 h after the final dose on Day 14. Enzyme activity for NQO1, Gst, and glutathione reductase (Gsr), as described above, were measured in tissue homogenates. Levels of mRNA were determined using Quantigene Plex 2.0 technology according to the manufacturer's protocol, which involves a hybridization-based assay using xMAP® LUMINEX® magnetic beads for direct quantification of mRNA targets. In addition, RTA 408 concentrations were measured in plasma and tissues by LC/MS/MS methods on a TQD mass spectrometer (Waters, Milford, MA).

Figure 26:
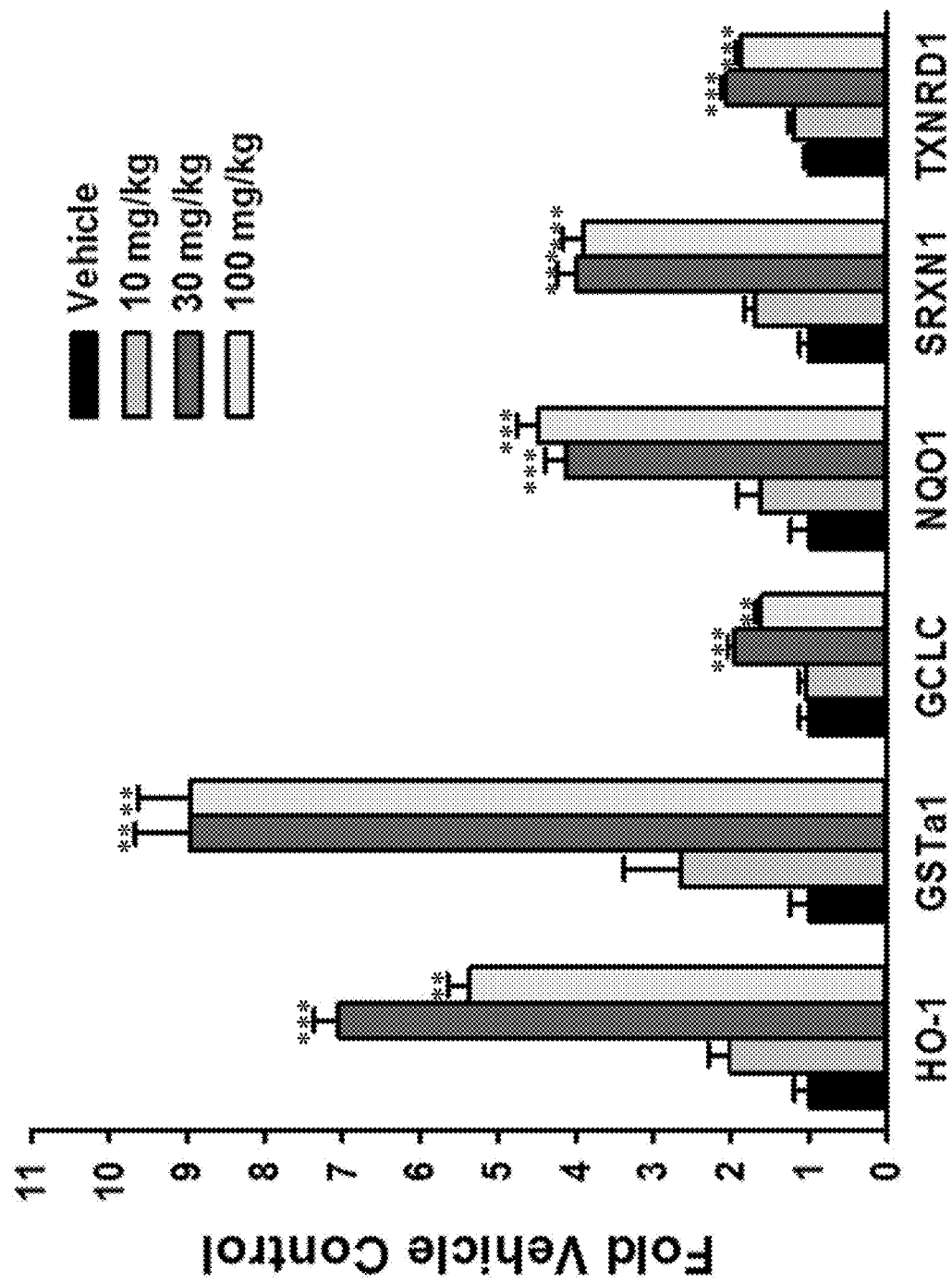
FIG. 26—Effect of 63415 on Nrf2 target gene induction in a 14-day mouse toxicity study in C57BL/6 mice. mRNAs of Nrf2 target genes were assessed in livers of mice treated PO QD×14. Substantial increases in mRNA expression for multiple Nrf2 target genes were observed and were consistent with tissue exposure.
Figure 37:
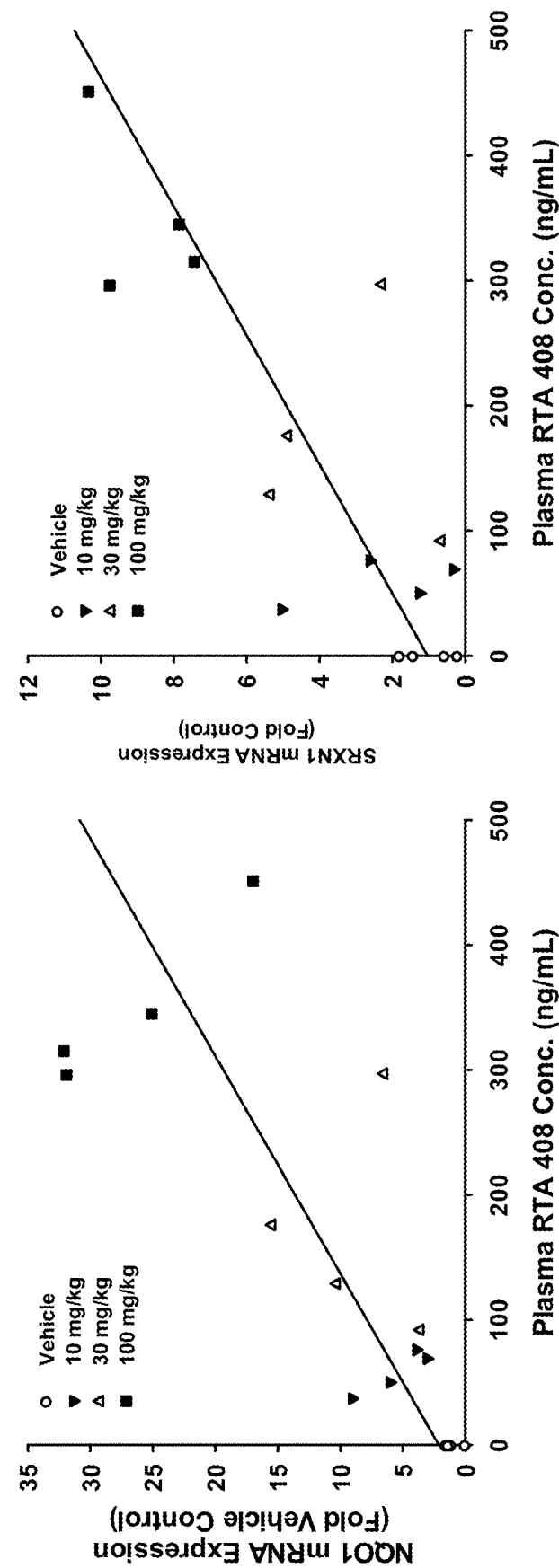
FIGS. 37a & b—Correlation of exposure to RTA 408 in monkey plasma with NQO1 and SRXN1 mRNA expression in PBMCs: (a) NQO1; (b) SRXN1.

RTA 408 generally increased the expression of various Nrf2 target genes in a dose-dependent manner at doses of 10, 30, and 100 mg/kg (FIG. 26, FIG. 27a, FIGS. 28a & b). Transcriptional upregulation of Nrf2 target genes by RTA 408 also resulted in functional increases in the antioxidant response, as manifested by dose-dependent increases in NQO1, Gst, and Gsr enzyme activity in rodent liver, as well as monkey liver and lung (FIGS. 29a & b, FIGS. 30a & b, FIGS. 31a & b). Furthermore, in rodents, liver exposure of RTA 408 correlated with the level of enzyme activity of NQO1, the prototypical target gene for Nrf2 (FIG. 32b, FIG. 33b). In monkeys, the level of mRNA expression in PBMCs of both NQO1 and sulfiredoxin 1 (SRXN1) correlated with plasma exposure to RTA 408 (FIGS. 37a & b). Overall, RTA 408 increased mRNA levels and activity of Nrf2 targets, and such increases generally correlated with tissue and plasma exposures, suggesting Nrf2 targets may serve as feasible biomarkers for Nrf2 activation (FIGS. 34a & b) and may be useful for assessing pharmacological activity of RTA 408 in healthy human subjects.

D. Safety Pharmacology

A GLP-compliant safety pharmacology program was completed using RTA 408. This included in vitro and in vivo (monkey) studies on the cardiovascular system, as well as studies on the respiratory system and central nervous system in rats.

1. Evaluation of the Effects of RTA 408 on Cloned hERG Channels Expressed in HEK293 Cells This study was conducted to assess the effects of RTA 408 on the rapidly activating inward rectifying potassium current ($I_{Kr}$) conducted by hERG (human ether-a-go-go-related gene) channels stably expressed in the human embryonic kidney (HEK293) cell line. The effects of RTA 408 on the hERG-related potassium current were assessed using whole-cell patch clamp electrophysiology methods. RTA 408 was determined to have $IC_{50}$ value of 12.4 µM in a hERG QPatch_Kv11.1 assay. This value was 2.5-3 fold higher than the values for 63170 (4.9 µM) and 63189 (3.8 µM), respectively. The RTA 408 $IC_{50}$ value was similar to the 63171 value (15.7 µM).

2. Cardiovascular Evaluation of RTA 408 in the Cynomolgus Monkey

A single study was conducted to evaluate the potential cardiovascular effects of RTA 408 in conscious freely moving cynomolgus monkeys. The same four male and four female cynomolgus monkeys were administered the vehicle (sesame oil) and RTA 408 at dose levels of 10, 30, and 100 mg/kg according to a Latin square design, with one animal/sex/treatment dosed each week followed by a 14-day washout period between administrations, until each animal received all treatments. Vehicle and RTA 408 were administered to all animals via oral gavage at a dose volume of 5 mL/kg.

Animals were instrumented with telemetry transmitters for measurement of body temperature, blood pressure, heart rate, and electrocardiogram (ECG) evaluation. Body temperature, systolic, diastolic, and mean arterial blood pressure, heart rate, and ECG parameters (QRS duration and RR, PR, and QT intervals) were monitored continuously from at least 2 h pre-dose until at least 24 h post-dose. ECG tracings were printed at designated time points from the cardiovascular monitoring data and were qualitatively evaluated by a board-certified veterinary cardiologist. Prior to the first administration on study, untreated animals were continuously monitored for cardiovascular endpoints for at least 24 h, and these data were used in the calculation of the corrected QT interval throughout the study.

Observations for morbidity, mortality, injury, and availability of food and water were conducted at least twice daily for all animals. Clinical observations were conducted pre-dose, approximately 4 h post-dose, and following completion of the cardiovascular monitoring period. Body weights were measured and recorded on the day prior to each treatment administration.

Figure 35:
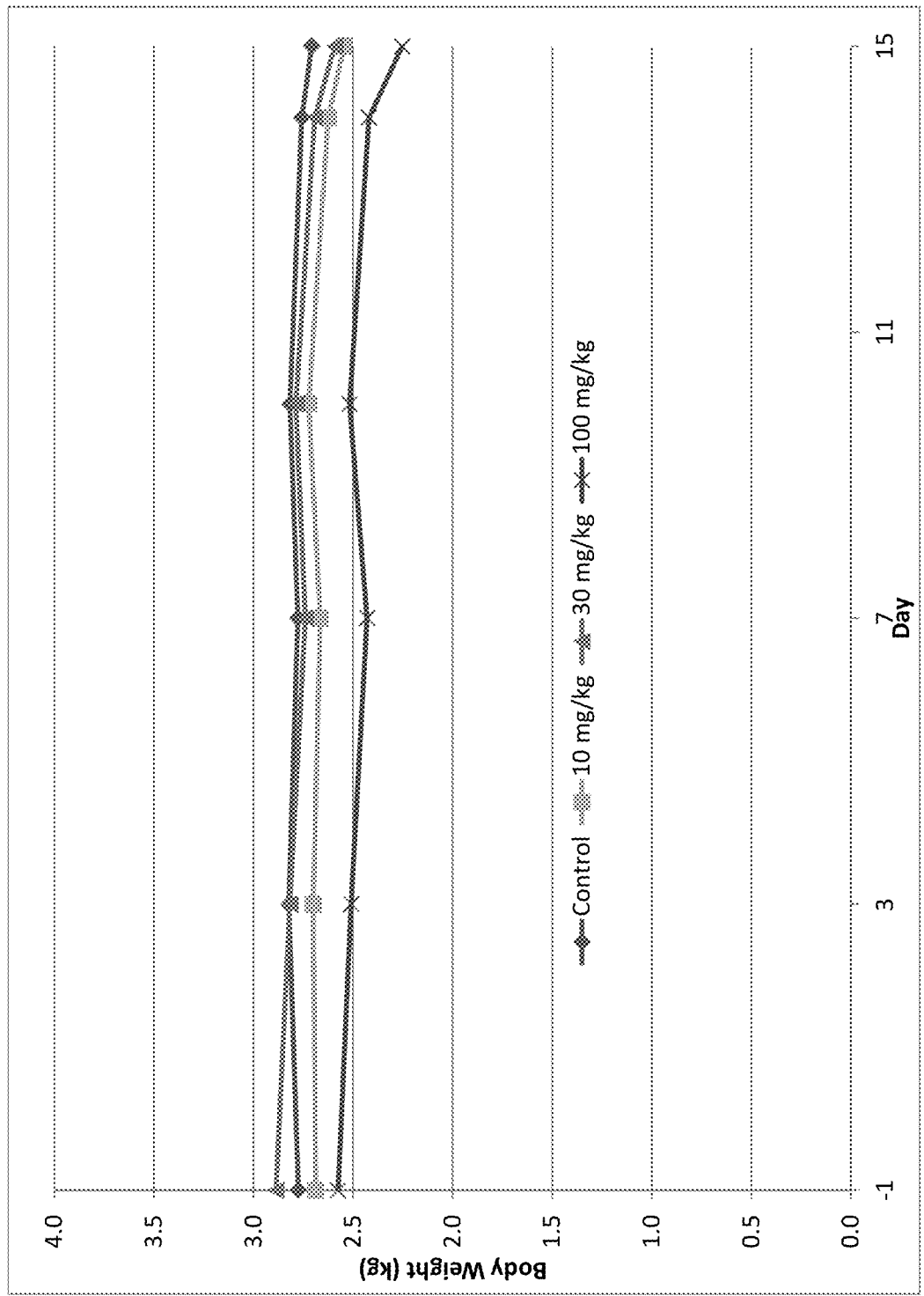
FIG. 35—Summary of 63415 14-day monkey toxicity study. All doses were well-tolerated without adverse clinical signs. Clinical chemistry data suggested no obvious toxicity.

RTA 408 at dose levels of 10, 30, and 100 mg/kg did not produce mortality, adverse clinical signs, or result in meaningful changes in body weight, body temperature, blood pressure, or qualitative or quantitative (PR, RR, QRS, QT intervals) ECG parameters (FIG. 35; Table 45). In the 100 mg/kg dose group, a small (1.6% on average) but statistically significant increase in the corrected QT interval was observed; however, individual animal data did not show consistent increases in QTc that would indicate a test article related effect. Consequently, due to the small magnitude of change and lack of a consistent response in individual animals, these slight increases in QTc were not considered to be related to RTA 408 treatment. Therefore, oral administration of RTA 408 produced no effects on cardiovascular function in cynomolgus monkeys at doses up to and including 100 mg/kg.

3. Neurobehavioral Evaluation of RTA 408 in Rats

The potential acute neurobehavioral toxicity of RTA 408 was evaluated in rats. Three treatment groups of 10 male and 10 female CD® [Crl:CD® (SD)] rats received RTA 408 at dose levels of 3, 10, or 30 mg/kg. One additional group of 10 animals/sex served as the control and received vehicle (sesame oil). Vehicle or RTA 408 was administered to all groups via oral gavage once on Day 1 at a dose volume of 10 mL/kg.

Observations for morbidity, mortality, injury, and availability of food and water were conducted twice daily for all animals. Observations for clinical signs were conducted prior to dosing on Day 1 and following each functional observational battery (FOB) evaluation. FOB evaluations were conducted pre-dose (Day −1) and at approximately 4 and 24 h post-dose. Body weights were measured and recorded pre-dose on Day 1.

RTA 408 at doses of 3, 10, and 30 mg/kg did not produce mortality, adverse clinical observations, or effects on any of the neurobehavioral measures tested. Slight decreases in body weight gain were observed approximately 24 h after dosing in the 30 mg/kg group that may potentially be test article-related. With respect to the basic neurobehavioral endpoints evaluated in this study, RTA 408 did not produce any adverse effects in rats at doses up to and including 30 mg/kg.

4. Pulmonary Evaluation of RTA 408 in Rats

The potential effect of RTA 408 on pulmonary function was evaluated in rats. Three treatment groups of eight male and eight female CD® [Crl:CD® (SD)] rats received RTA 408 at dose levels of 3, 10, or 30 mg/kg. One additional group of 8 animals/sex served as the control and received vehicle (sesame oil). Vehicle or RTA 408 was administered to all groups via oral gavage once on Day 1 at a dose volume of 10 mL/kg.

Observations for mortality, morbidity, injury, and availability of food and water were conducted twice daily for all animals. Clinical observations were conducted prior to dosing, approximately 4 h post-dose, and following completion of the 8-h pulmonary monitoring period. Body weights were measured and recorded on the day of RTA 408 administration. Pulmonary function (respiratory rate, tidal volume, and minute volume) was monitored for at least 1 h prior to dosing to establish a baseline and for at least 8 h post-dose.

RTA 408 at doses of 3, 10, and 30 mg/kg did not produce mortality, adverse clinical observations, or effects on any of the pulmonary parameters evaluated. Therefore, with respect to the basic pulmonary endpoints evaluated in this study, RTA 408 did not produce any adverse effects in rats at doses up to and including 30 mg/kg.

E. Nonclinical Overview

1. Pharmacokinetics

RTA 408 has been investigated both in vitro and in vivo to assess its PK and metabolism properties. In vitro studies have been conducted to determine RTA 408 plasma protein binding and blood/plasma partitioning, cytochrome P450 (CYP450) inhibition and induction, and to identify metabolites formed by liver microsomes of mice, rats, monkeys, and humans. Data pertaining to the in vivo absorption and distribution following repeated administration of RTA 408 has been obtained primarily through monitoring of drug levels in plasma and select tissues from toxicology studies. Sensitive and selective liquid chromatography-mass spectrometry-based bioanalytical methods (LC/MS/MS) have been used to measure concentrations of RTA 408 in plasma, blood, and tissues with appropriate accuracy and precision. Measurements were performed on TQD and QToF mass spectrometers (Waters).

a. Absorption

The absorption and systemic pharmacokinetic behavior of RTA 408 was studied in mice, rats, and monkeys following single and repeated (daily) oral administration. Following oral administration of a suspension formulation at doses of 10 to 100 mg/kg, maximal concentrations were observed within 1 to 2 h in mice, and within 1 to 24 h in rats and monkeys. Systemic exposure to RTA 408 tended to be highest in rats, with lower levels observed in mice and monkeys. Estimates of the apparent terminal half-life of RTA 408 observed after oral administration were generally in the 6- to 26-h range, though the apparent prolonged absorption phase in some instances precluded calculation of a definitive half-life estimate.

Systemic exposure to RTA 408 was generally similar in males and females. Exposure to RTA 408 following repeated daily oral administration tended to be slightly higher (≤2-fold) than the exposure observed after a single dose. Administration of RTA 408 over a dose range from 3 to 100 mg/kg in a suspension formulation generally resulted in dose-proportional increases in systemic exposure. However, administration of higher doses (100 to 800 mg/kg in monkeys; 500 to 2000 mg/kg in rats) did not result in similar increases in exposure, suggesting saturation of absorption at doses above 100 mg/kg. Following oral administration of an unoptimized (loose-filled) capsule formulation of RTA 408 (3 mg/kg) to monkeys, dose-normalized systemic exposure tended to be somewhat lower than that observed with a suspension formulation.

The absorption and systemic pharmacokinetic behavior of RTA 408 was studied in rats using single and repeated topical administration. The administration of RTA 408 over a range of 0.01% to 3% showed lower plasma concentrations relative to similar oral dosing. The systemic exposure to RTA 408 generally increased in a dose dependent manner. The topical administration was formulated as a suspension in sesame oil.

Figure 36:
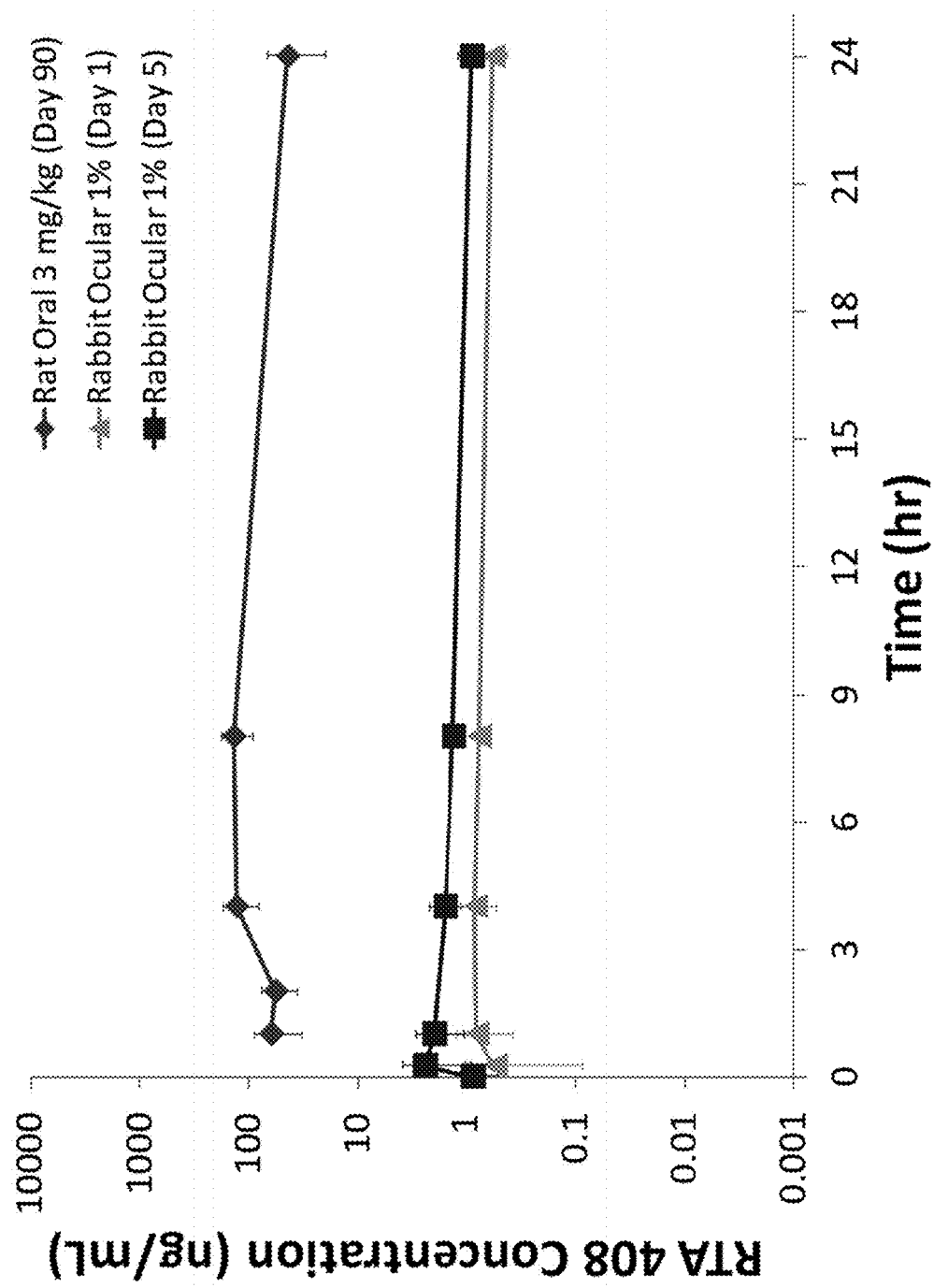
FIG. 36—Effect of dosing time on plasma concentration of RTA 408 after topical ocular and oral administration. The plasma concentration of RTA 408 was also measured after 5 days of daily topical ocular administration of RTA 408 and determined to remain relatively consistent from the measurements taken after the first day.

Using rabbits, the ocular absorption and systemic pharmacokinetic behavior of RTA 408 was evaluated. RTA 408 was administered topically to the eye once per day for five days. The ocular administration showed lower plasma concentration of RTA 408 relative to when RTA 408 is administered orally (FIG. 36). The amount of RTA 408 in the plasma even after five consecutive days showed only a small change compared to the concentration after the first dose relative to when RTA 408 was administered orally, where plasma concentrations were almost 100-fold higher (FIG. 36).

b. Distribution

Plasma protein binding of RTA 408 was evaluated in mouse, rat, rabbit, dog, minipig, monkey, and human plasma at RTA 408 concentrations of 10-2000 ng/mL using ultracentrifugation methodology. RTA 408 was extensively bound to plasma proteins. Plasma protein binding in the nonclinical species ranged from 93% (mouse) to >99% (minipig), with binding of 95% in the toxicology species (rat and monkey) and 97% in human. There was no evidence of concentration-dependent protein binding in any species tested. Results from blood-to-plasma partitioning experiments indicate that RTA 408 tended to distribute primarily in the plasma fraction of blood in a linear manner, with blood:plasma ratios <1.0 for all species and all concentrations tested.

The distribution of RTA 408 into tissues has been investigated after oral administration to mice, rats, and monkeys. In the 14-day non-GLP toxicity studies, select tissues (liver, lung, and brain) were collected at a single time point (4 h for rat and mouse; 24 h for monkey) after the final dose of the study was administered and were analyzed for RTA 408 content using LC/MS/MS. RTA 408 readily distributes into lung, liver, and brain. In lung, RTA 408 concentrations at 4 h in mice and rats were similar to or slightly higher (<2-fold) than concentrations in plasma, while at 24 h in monkeys, RTA 408 concentrations in lung were 6- to 16-fold higher than plasma concentrations. A similar pattern was observed for brain. In contrast, RTA 408 concentrations in liver were 5- to 17-fold higher than plasma for mice and rats at 4 h, and 2- to 5-fold higher than plasma at 24 h in monkeys.

The pharmacodynamic effects of RTA 408 in tissues were assessed in mice, rats, and monkeys, by monitoring the induction of Nrf2 target genes in the same tissues collected for drug exposure from the 14-day toxicity studies. Induction of Nrf2 target genes by RTA 408 resulted in increases in the antioxidant response as manifested by dose-dependent increases in NQO1, glutathione S-transferase (Gst), and glutathione reductase (Gsr) enzyme activity in the examined tissues. Enzyme activities were measured as described above. Furthermore, in rodents, RTA 408 liver content correlated with the level of enzyme activity for NQO1, the prototypical target gene for Nrf2. In monkeys, the level of mRNA expression in peripheral blood mononuclear cells (PBMCs) for both NQO1 and sulfiredoxin 1 (SRXN1) correlated with plasma exposure of RTA 408 (FIGS. 37a & b). Overall, RTA 408 induced biomarkers of Nrf2 in rodents and monkeys, and such inductions generally correlated well with tissue and plasma exposure to RTA 408.

Figure 38:
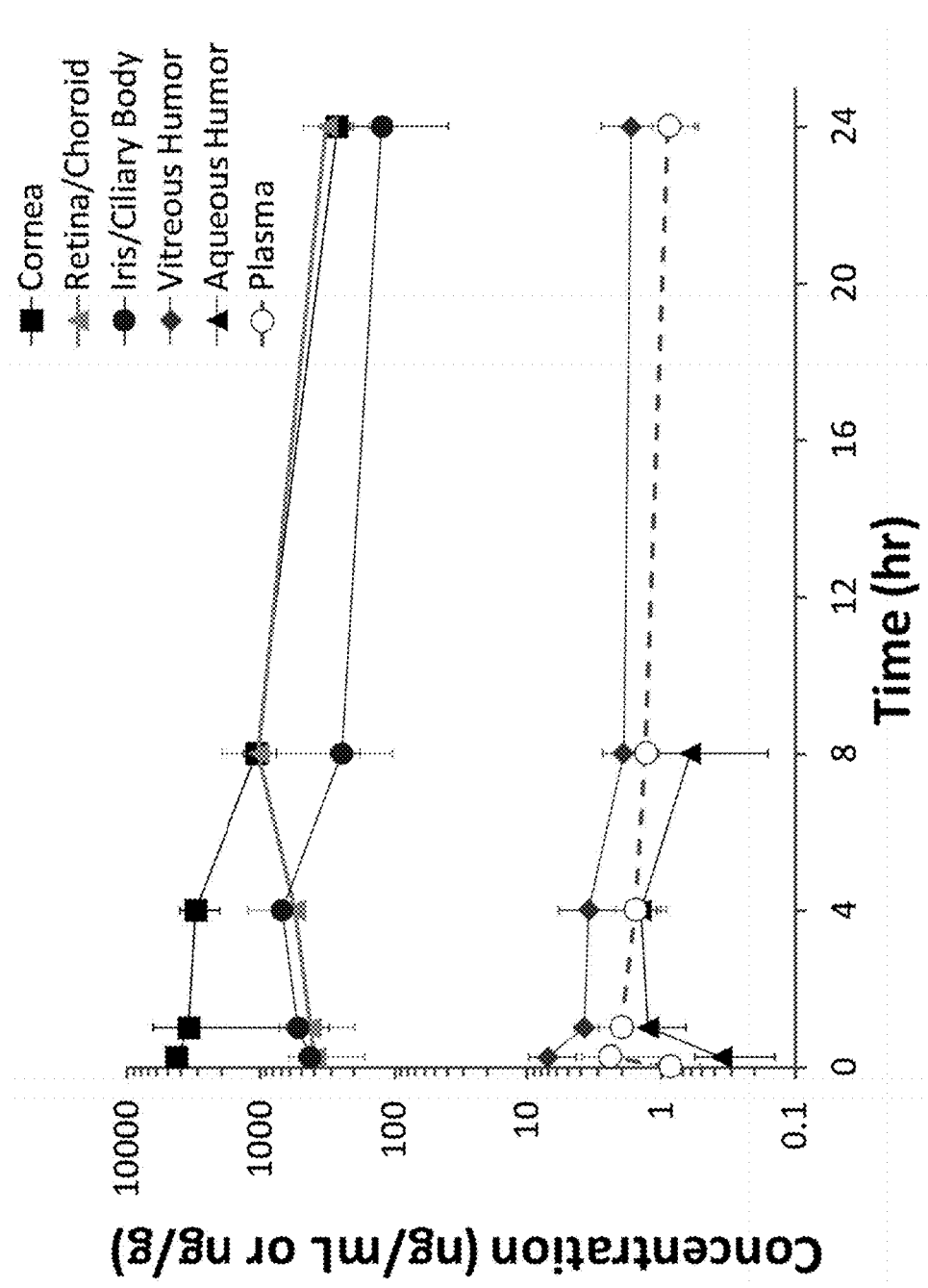
FIG. 38—Concentration of RTA 408 in various tissues or fluids within the eye as a function of time after 5 days of topical ocular dosing. RTA 408 concentration in plasma was also measured after topical ocular administration.
Figure 39:
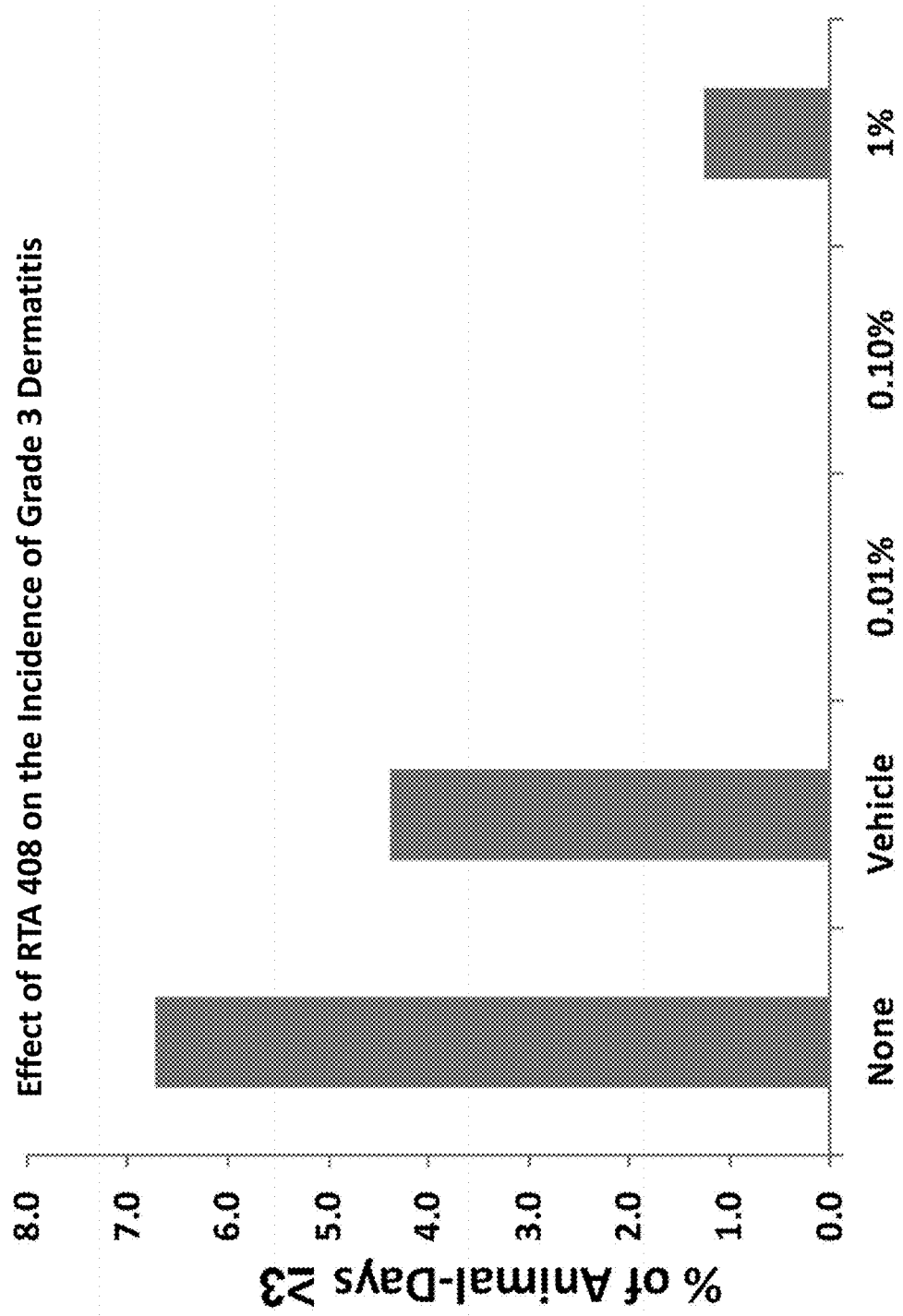
FIG. 39—Effect of RTA 408 on the incidence of grade 3 dermatitis caused by acute radiation exposure for different concentrations of topically administered RTA 408.
Figure 40:
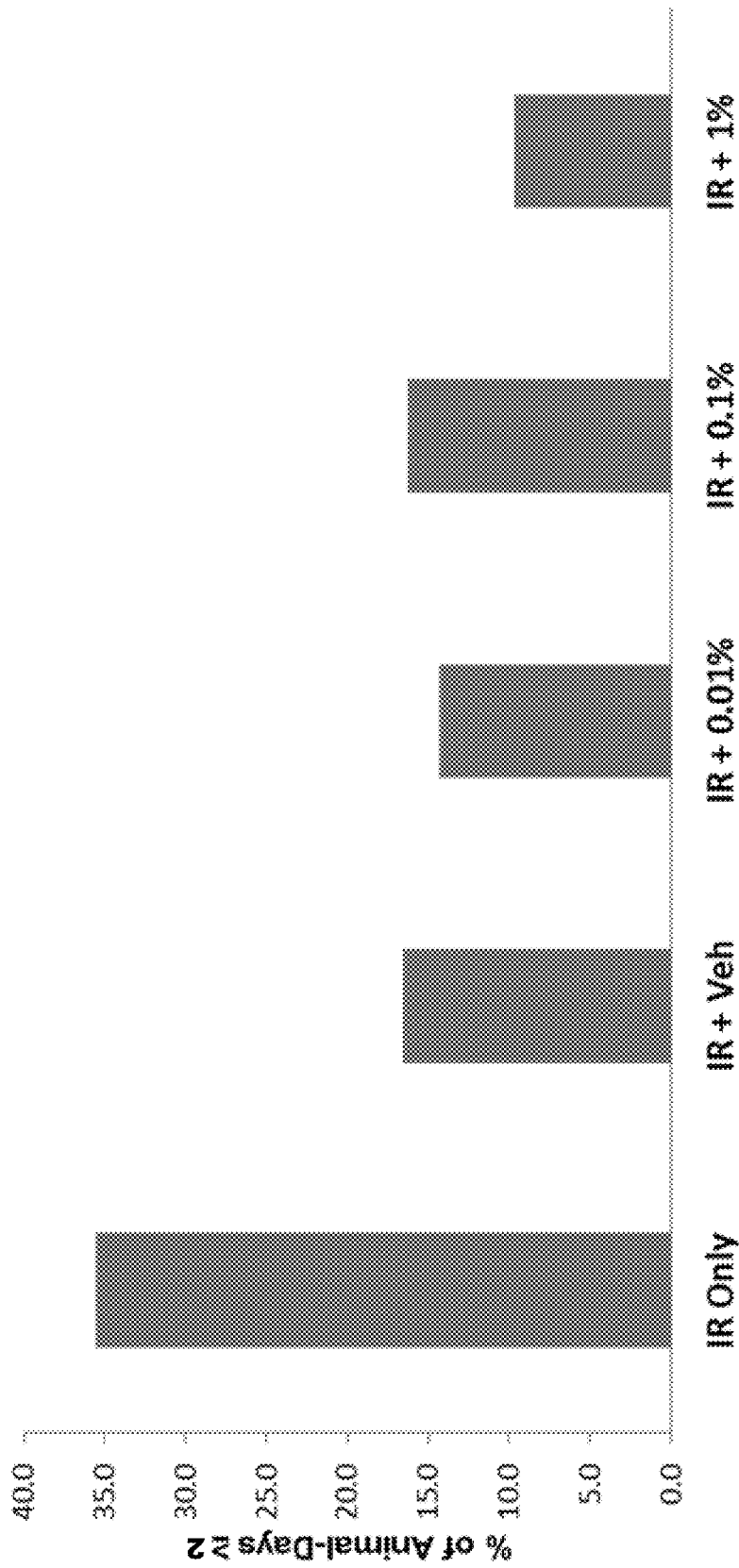
FIG. 40—Effect of RTA 408 on the incidence of grade 2 dermatitis caused by acute radiation exposure over a 30 day treatment course for different concentrations of topically administered RTA 408.
Figure 41:
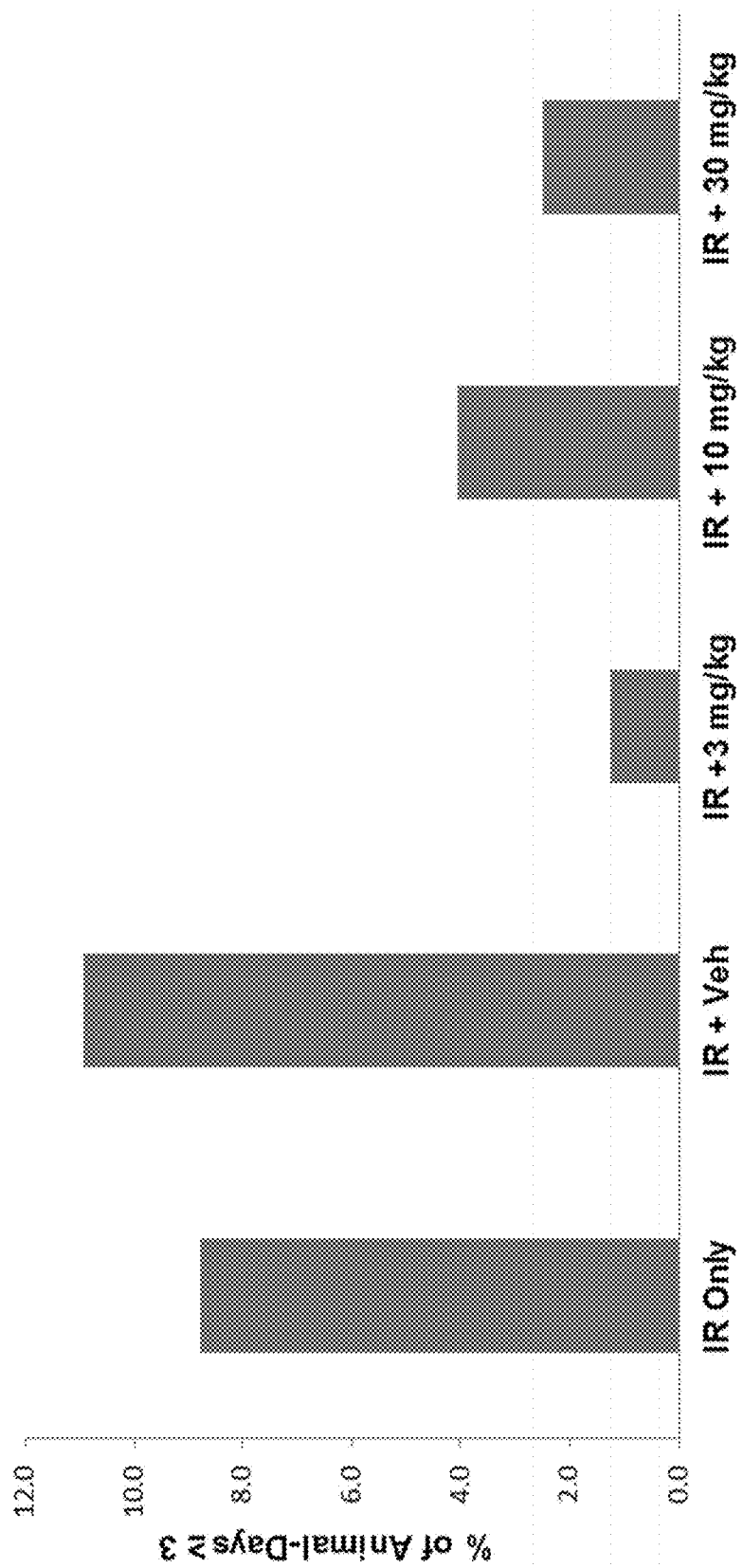
FIG. 41—Effect of RTA 408 on the incidence of grade 2 dermatitis caused by acute radiation exposure over a 28 day treatment course for different concentrations of orally administered RTA 408.
Figure 42A:
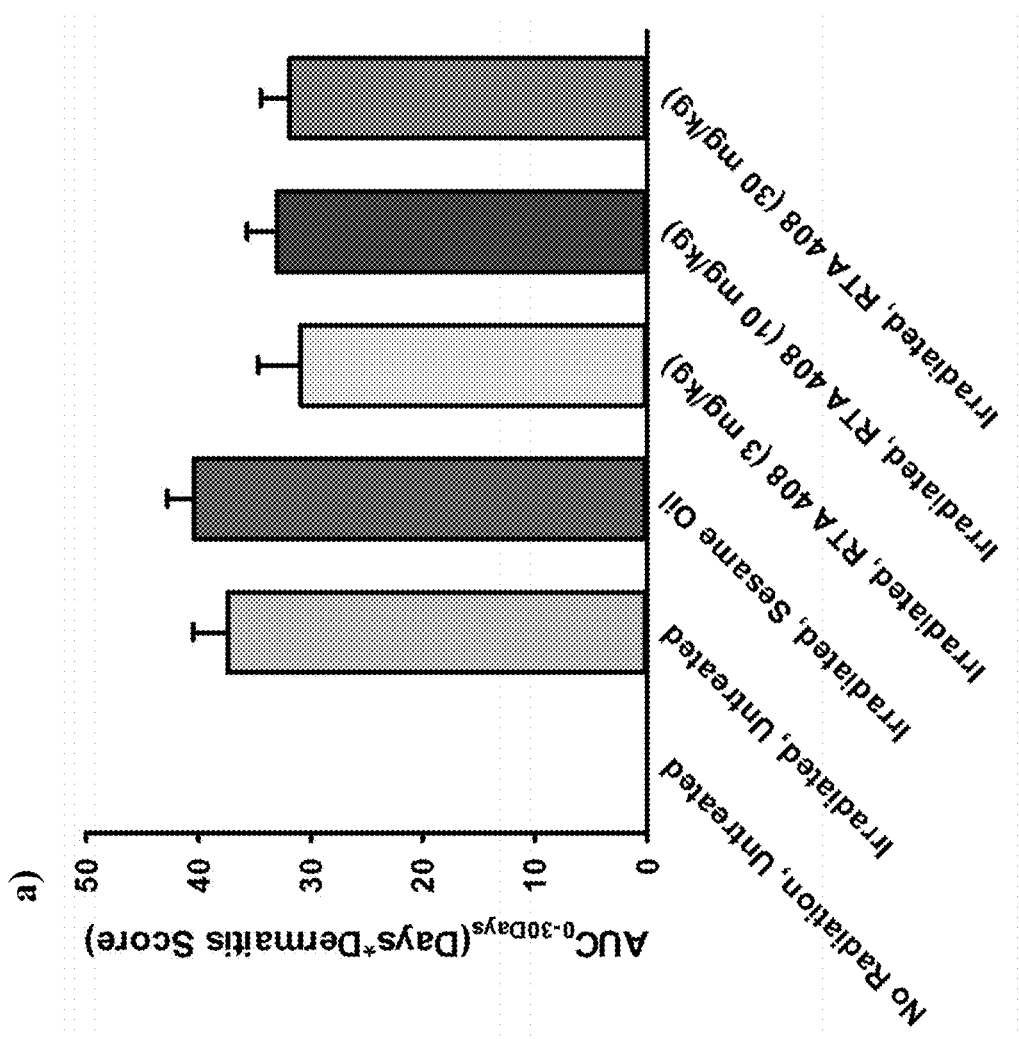
FIGS. 42a & b—(a) Area under the curve analysis of clinical score of the dermatitis as a function of time for each of the different control groups including all of the animals used in the test. (b) Area under the curve analysis of the clinical score of the dermatitis as a function of the duration of that score for each of the different control groups including only animals that completed the entire 30 days in the trial.
Figure 42B:
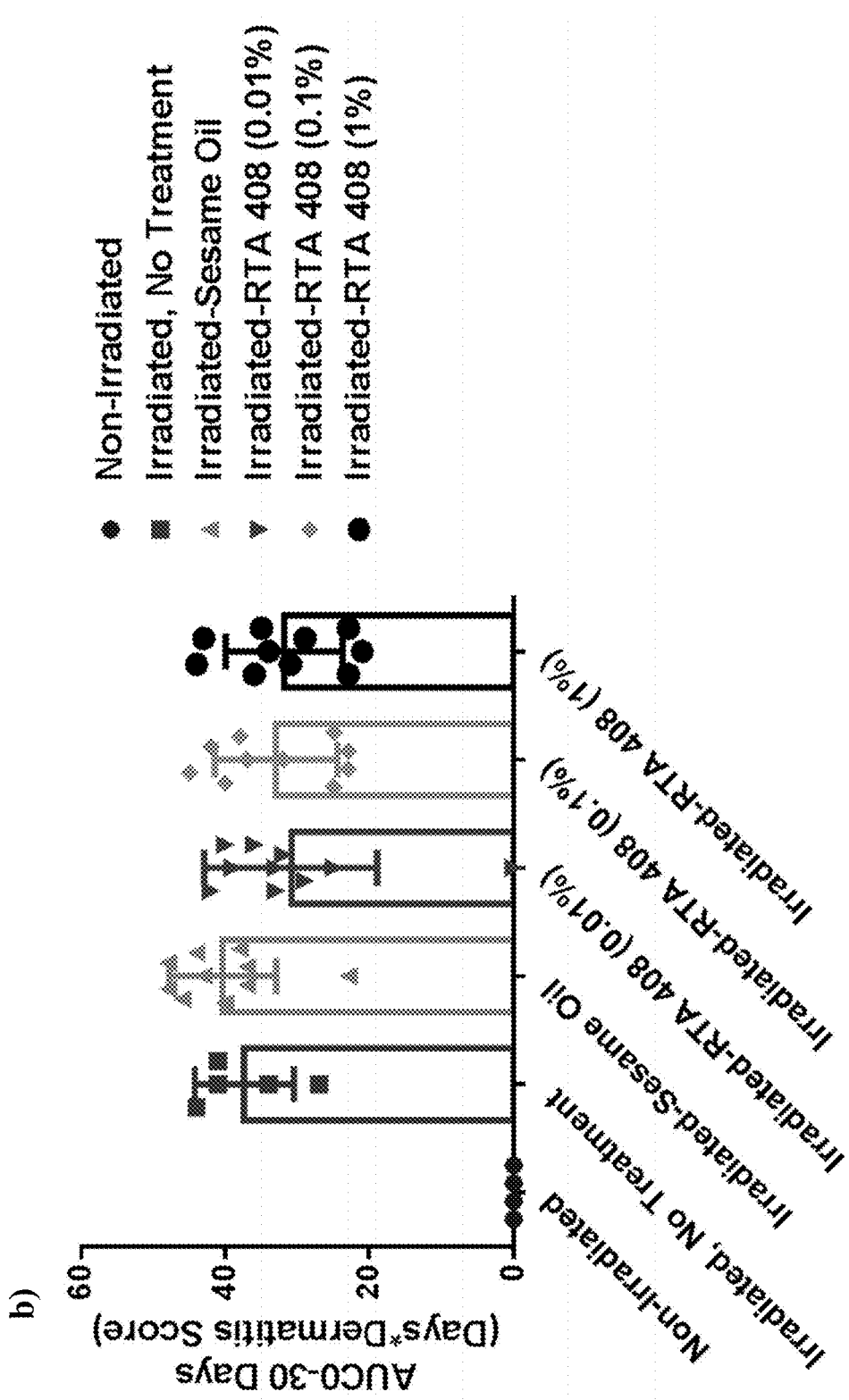

When RTA 408 was administered to rabbits via ocular topical administration, the highest concentrations of the compound were found in the cornea, retina, or iris while the vitreous humor, aqueous humor, and plasma showed significantly lower concentrations of RTA 408 (FIG. 38).

c. Metabolism

The metabolism of RTA 408 has been investigated after in vitro incubation of RTA 408 for 60 min with liver microsomes from mice, rats, monkeys, and humans in the presence of a nicotinamide adenine dinucleotide phosphate (NADPH)-regenerating system and a uridine diphosphate glucuronosyltransferase (UGT) reaction mixture. Extensive turnover of RTA 408 was observed with primate microsomes, with <10% of the parent molecule remaining at the end of the 60-min incubation in both monkey and human microsomes. In contrast, the extent of metabolism was lower in rodent microsomes, with >65% of the parent molecule remaining at the end of the incubation. The lack of available authentic standards for the various potential metabolites of RTA 408 precluded quantitative evaluation of the observed metabolites. From a qualitative perspective, a similar pattern of RTA 408 metabolites was observed across species, and included peaks with masses consistent with reduction and hydroxylation of RTA 408 as well as glucuronidation of RTA 408 or of its reduction/hydroxylation metabolites. No unique human metabolites were observed, with all peaks in the human microsome incubations also being observed in one or more of the preclinical species. In particular, based on in vitro microsome data, all human metabolites were present in rat or monkey, the selected rodent and non-rodent toxicity species.

d. Pharmacokinetic Drug Interactions

The potential for RTA 408 to inhibit cytochrome P450 (CYP450)-mediated metabolism was evaluated using pooled human liver microsomes and standard substrates for specific CYP450 enzymes. RTA 408 directly inhibited CYP2C8 and CYP3A4/5 with Ki values of approximately 0.5 µM for each enzyme. No meaningful inhibition was observed for the other enzymes tested (CYP1A2, CYP2B6, CYP2C9, CYP2C19, or CYP2D6), with inhibition <50% at the highest concentration tested (3 µM). In addition, there was little or no evidence of metabolism-dependent inhibition of any of the enzymes tested. Future studies investigating the potential for CYP3A4/5-mediated drug-drug interactions may be warranted based on these data, and the potentially high concentrations that may be achieved locally in the gastrointestinal (GI) tract after oral administration.

The potential for RTA 408 to induce CYP450 enzyme expression was evaluated using cultured human hepatocytes. Under conditions where prototypical inducers caused the expected increases in CYP activity, RTA 408 (up to 3 µM) was not an inducer of CYP1A2, CYP2B6, or CYP3A4 enzyme activity in cultured human hepatocytes. Enzyme activity was measured by monitoring substrate conversion of phenacetin, bupropion, and testosterone for CYP1A2, CYP2B6, and CYP3A4, respectively, in isolated microsomes.

F. Effects of RTA 408 on Acute Radiation Dermatitis

The effects of RTA 408 as a topical or oral preventative for acute radiation dermatitis have been examined. Using male BALB/c mice, a 30 Gy dose of radiation was administered on day 0 (Table 3). The sesame oil vehicle or RTA 408 was administered to the rats on day −5 to −1 and days 1 to 30. RTA 408 was administered both orally in 3, 10, and 30 mg/kg in sesame oil and topically in percentage composition of 0.01%, 0.1%, and 1% in sesame oil. The dermatitis was blindly evaluated every other day from day 4 to day 30. On day 12, the typical peak of dermatitis was observed and 4 mice were sacrificed 4 hours after administration of the dose. The remaining mice were sacrificed on day 30 at 4 h post-dose. Plasma was collected on days 12 and 30 as well as irradiated skin samples for mRNA and histological examination.

TABLE 3

Study Design for Acute Radiation Dermatitis Model

| Group | Number of Animals | Radiation (Day 0) | Treatment | Treatment Schedule |
|---|---|---|---|---|
| 1 | 9 males | — | Untreated | — |
| 2 | 10 males | 30 Gy | Untreated | — |
| 3 | 14 males | 30 Gy | Vehicle Control (sesame oil) | Day −5 to −1 & Day 1 to 30 |
| 4 | 14 males | 30 Gy | RTA 408—0.01% or 3 mg/kg | Day −5 to −1 & Day 1 to 30 |
| 5 | 14 males | 30 Gy | RTA 408—0.1% or 10 mg/kg | Day −5 to −1 & Day 1 to 30 |
| 6 | 14 males | 30 Gy | RTA 408—1% or 30 mg/kg | Day −5 to −1 & Day 1 to 30 |

Figure 43:
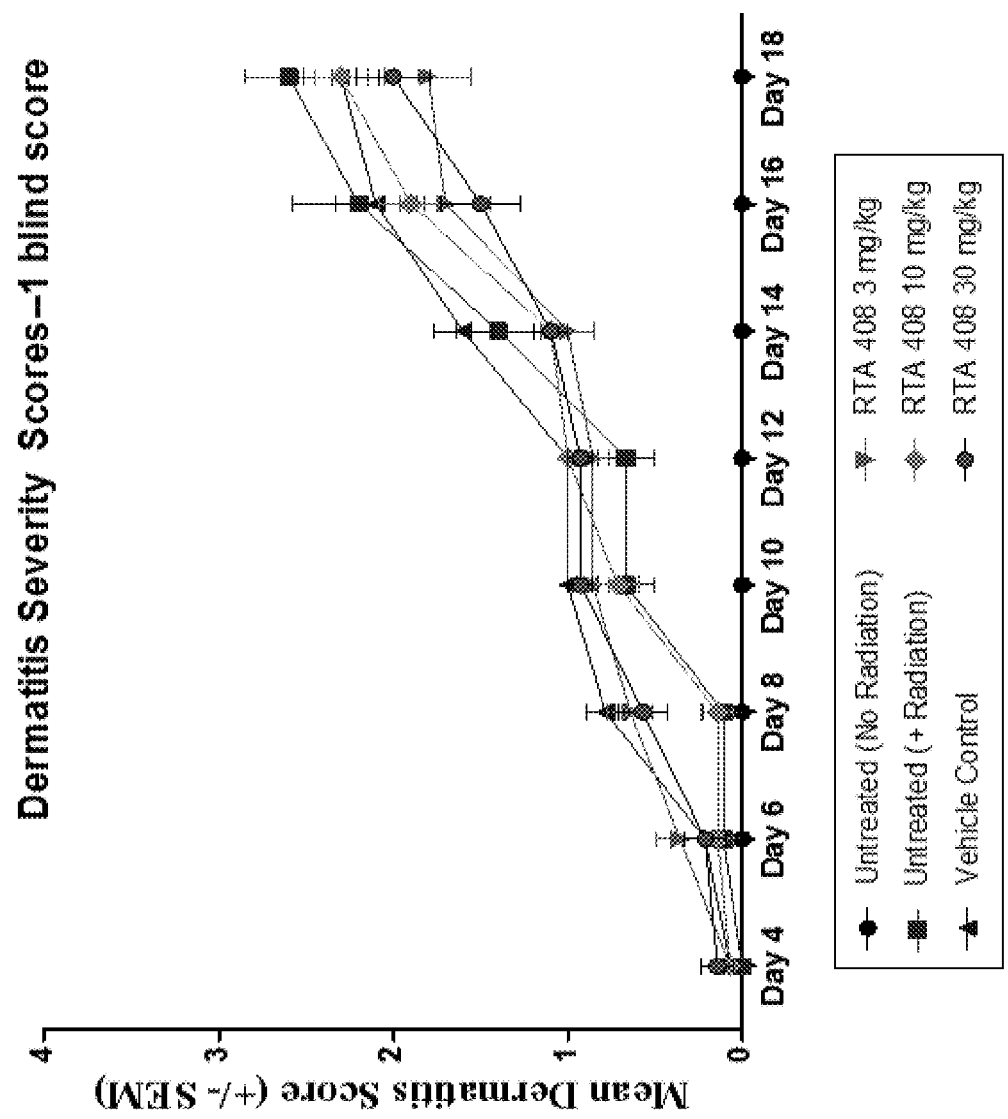
FIG. 43—Average $1^{st}$ blind score of acute radiation dermatitis as a function of time for untreated, untreated with no radiation exposure, vehicle only and three oral amounts of RTA 408 at 3, 10, and 30 mg/kg. The dermatitis score was based upon a scale that 0 was completely healthy, 1-2 exhibited mild to moderate erythema with minimal to slight desquamation, 3-4 exhibited moderate to severe erythema and desquamation, and 5 exhibited a frank ulcer.
Figure 44:
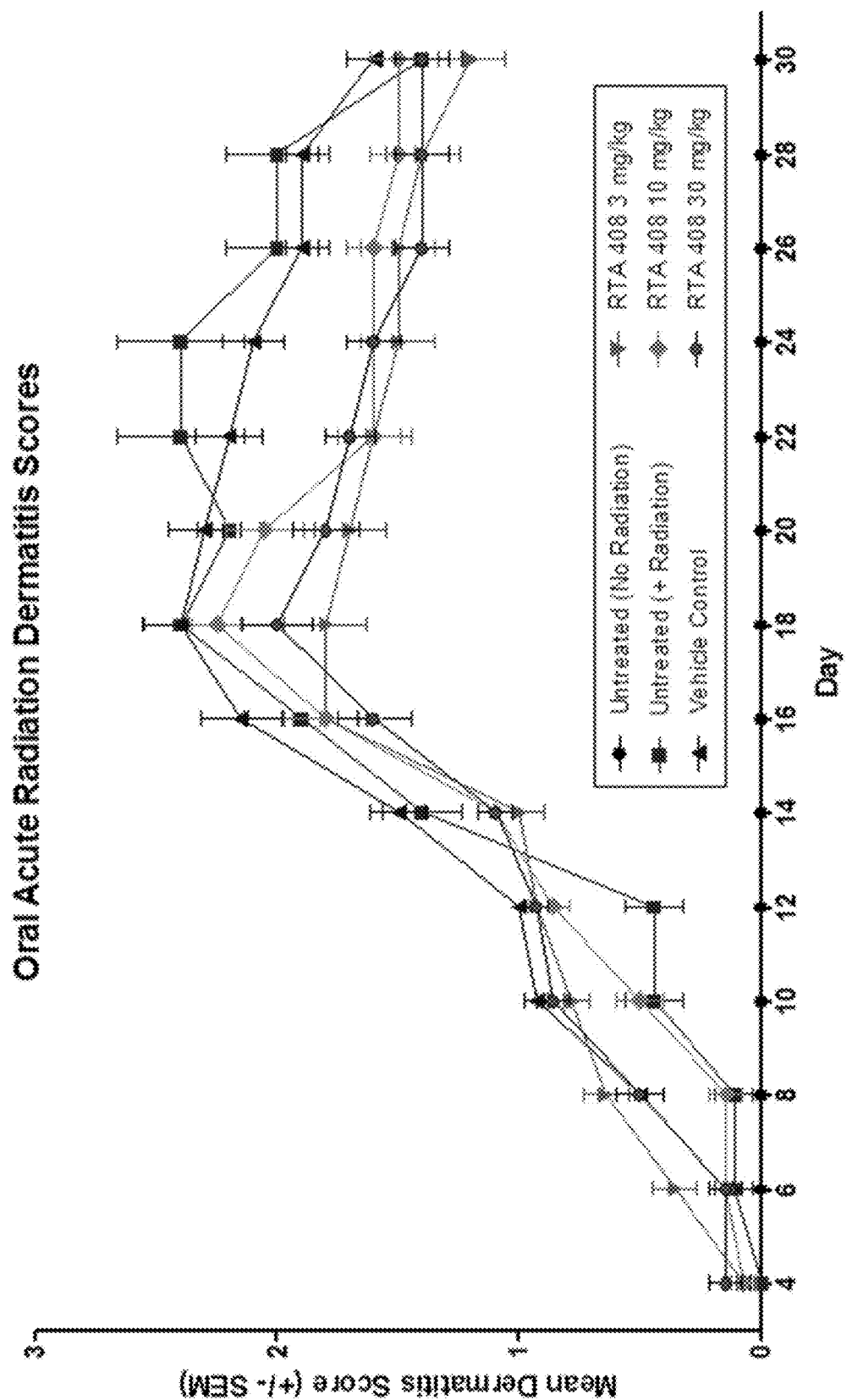
FIG. 44—Mean score of the acute radiation dermatitis as a function of time for untreated, untreated with no radiation exposure, vehicle only, and three oral amounts of RTA 408 at 3, 10, and 30 mg/kg measured every other day from day 4 to day 30. The dermatitis score was based upon a scale that 0 was completely healthy, 1-2 exhibited mild to moderate erythema with minimal to slight desquamation, 3-4 exhibited moderate to severe erythema and desquamation, and 5 exhibited a frank ulcer.
Figure 45:
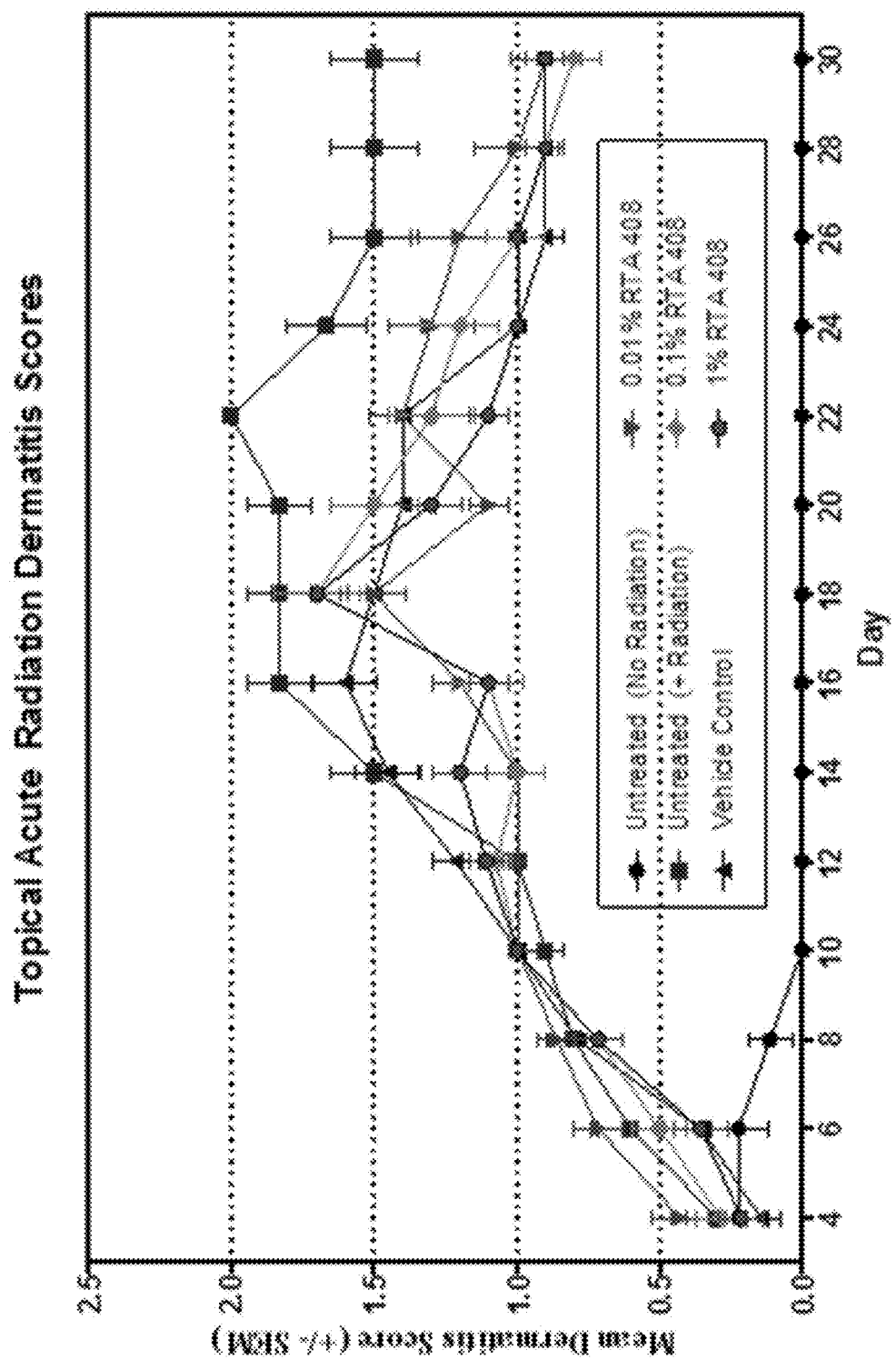
FIG. 45—Mean score of the acute radiation dermatitis as a function of time for untreated, untreated with no radiation exposure, vehicle only, and three topical amounts of RTA 408 at 0.01%, 0.1%, and 1% measured every other day from day 4 to day 30. The dermatitis score was based upon a scale that 0 was completely healthy, 1-2 exhibited mild to moderate erythema with minimal to slight desquamation, 3-4 exhibited moderate to severe erythema and desquamation, and 5 exhibited a frank ulcer.

In the test groups where the mice were treated with RTA 408, the incidence of dermatitis appeared to be slightly diminished in severity when RTA 408 was given in either an oral or topical administration (FIGS. 39-42). Furthermore, curves plotting the average dermatitis clinic score for the test groups as a function of time show some change with the administration of RTA 408 either in oral or topical form from the untreated test groups (FIGS. 43-45) particularly in the case where RTA 408 was given through an oral administration. Furthermore, as can be seen in Tables 4 and 5 below, the percentage of mice suffering from dermatitis with a clinical score above 3 was significantly lower for mice treated with RTA 408 through an oral administration while the percentage of mice suffering from dermatitis with a clinical score above 2 was slightly lower for test groups who were given a topical administration of RTA 408.

TABLE 4

Percentage of mice per testing group which scored above 2 in their clinical dermatitis exam and given a topical treatment containing RTA 408

| | | Day 12 | Day 14 | Day 16 | Day 18 | Day 20 | Day 22 | Day 24 | Day 26 | Day 28 | Day 30 | % animal-days >=2 | % animal-days >=3 |
|---|---|---|---|---|---|---|---|---|---|---|---|---|---|
| 1 | no radiation, untreated | 0.0 | 0.0 | 0.0 | 0.0 | 0.0 | 0.0 | 0.0 | 0.0 | 0.0 | 0.0 | 0.0 | 0.0 |
| 2 | irradiated, untreated | 0.0 | 50.0 | 83.3 | 83.3 | 83.3 | 100.0 | 66.7 | 50.0 | 50.0 | 50.0 | 35.6 | 0.0 |
| 3 | irradiated, sesame oil | 21.4 | 45.0 | 60.0 | 50.0 | 40.0 | 40.0 | 0.0 | 0.0 | 0.0 | 0.0 | 16.6 | 0.0 |
| 4 | irradiated, RTA 408-0.01% | 0.0 | 0.0 | 20.0 | 50.0 | 10.0 | 40.0 | 40.0 | 40.0 | 20.0 | 10.0 | 14.4 | 0.0 |
| 5 | irradiated, RTA 408-0.1% | 7.1 | 10.0 | 20.0 | 80.0 | 60.0 | 40.0 | 30.0 | 10.0 | 0.0 | 0.0 | 16.3 | 0.0 |
| 6 | irradiated, RTA 408-1.0% | 10.7 | 20.0 | 10.0 | 70.0 | 30.0 | 10.0 | 0.0 | 0.0 | 0.0 | 0.0 | 9.7 | 0.0 |

TABLE 5

Percentage of mice per testing group which scored above 3 in their clinical dermatitis exam and given an oral treatment containing RTA 408

| | | Day 16 | Day 18 | Day 20 | Day 22 | Day 24 | Day 26 | Day 28 | % animal-days >=2 | % animal-days >=3 |
|---|---|---|---|---|---|---|---|---|---|---|
| 1 | no radiation, untreated | 0 | 0 | 0 | 0 | 0 | 0 | 0 | 0.0 | 0.0 |
| 2 | irradiated, untreated | 20 | 40 | 20 | 20 | 20 | 20 | 20 | 39.0 | 8.8 |
| 3 | irradiated, sesame oil | 35 | 50 | 40 | 30 | 20 | 0 | 0 | 45.6 | 10.9 |
| 4 | irradiated, RTA 408-3 mg/kg | 10 | 10 | 0 | 0 | 0 | 0 | 0 | 32.5 | 1.3 |
| 5 | irradiated, RTA 408-10 mg/kg | 10 | 25 | 30 | 0 | 0 | 0 | 0 | 33.8 | 4.1 |
| 6 | irradiated, RTA 408-30 mg/kg | 10 | 20 | 10 | 0 | 0 | 0 | 0 | 28.8 | 2.5 |

G. Effects of RTA 408 on Fractionated Radiation Dermatitis

Figure 46:
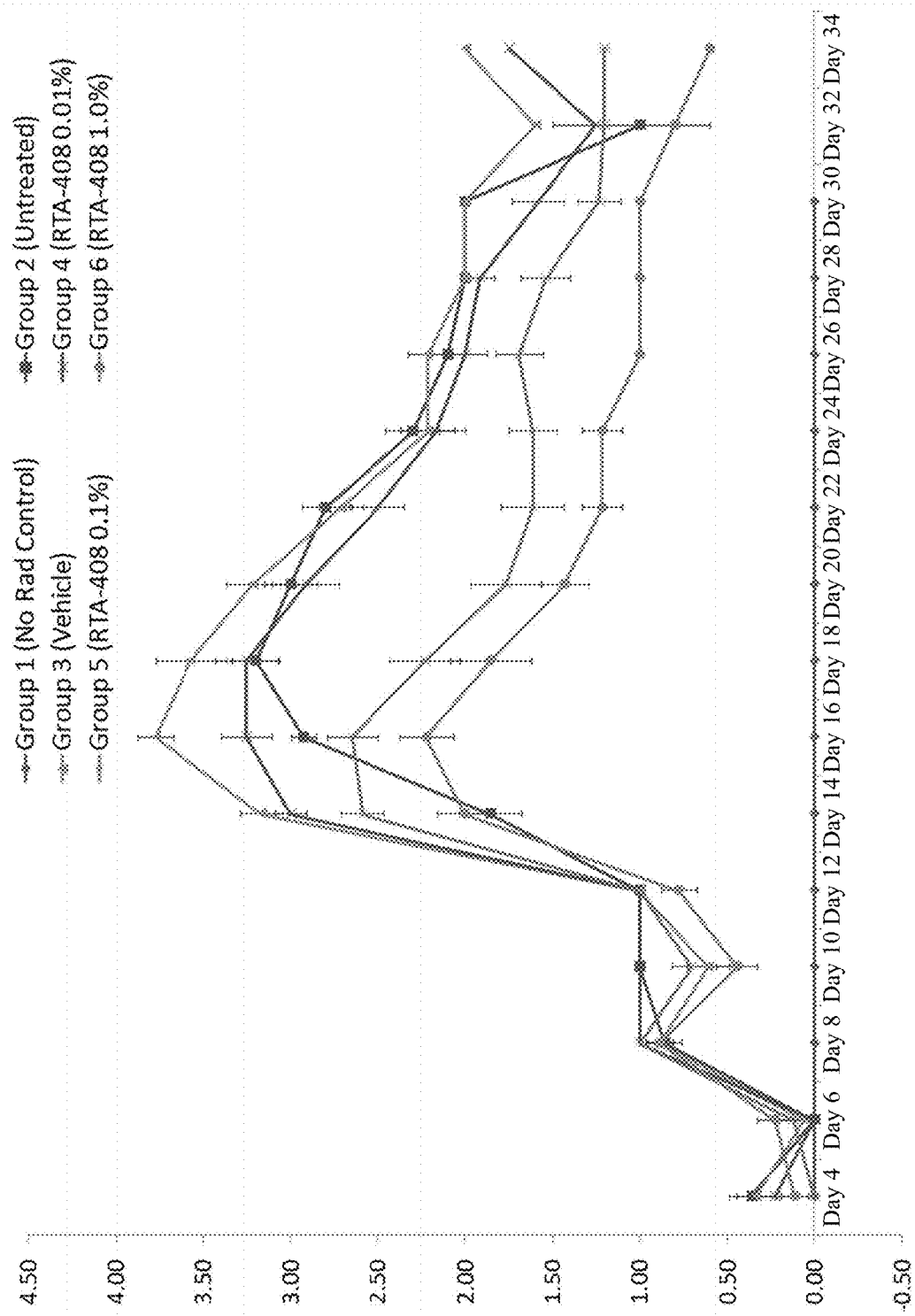
FIG. 46—Clinical scores of fractional radiation dermatitis plotted versus time and changes in dermatitis score for each testing group. The dermatitis score was based upon a scale that 0 was completely healthy, 1-2 exhibited mild to moderate erythema with minimal to slight desquamation, 3-4 exhibited moderate to severe erythema and desquamation, and 5 exhibited a frank ulcer.

Utilizing RTA 408 through topical administration, the effects of RTA 408 towards ameliorating the effects of fractionated radiation dermatitis were measured. Using Balb/c mice, RTA 408 in a topical preparation was administered to the mice daily from day −5 to day 30 in three doses ranging from 0.01% to 1%. The mice were irradiated on days 0-2 and 5-7 with six 10-Gy doses per day. Clinical dermatitis scores for the mice were evaluated blindly every two days from day 4 until the end of the study. In FIG. 46, the graph shows the change in the average clinical score for each group were plotted as a function of time. The graph shows a statistically significant improvement in the scores for mice treated with 0.1% to 1% topical formulations of RTA 408. Study and treatment parameters can be found in Table 6.

TABLE 6

Study Conditions for Fractionated Radiation-Induced Dermatitis

| Group | Number of Animals | Radiation (Days 0-2, 5-7) | Treatment | Treatment Schedule |
|---|---|---|---|---|
| 1 | 9 males | — | Untreated | — |
| 2 | 14 males | 6x 10 Gy | Untreated | — |
| 3 | 18 males | 6x 10 Gy | Vehicle Control (sesame oil) | QD Days −5 to 30 |
| 4 | 18 males | 6x 10 Gy | RTA 408—0.01% | QD Days −5 to 30 |
| 5 | 18 males | 6x 10 Gy | RTA 408—0.1% | QD Days −5 to 30 |
| 6 | 18 males | 6x 10 Gy | RTA 408—1% | QD Days −5 to 30 |

Figure 47:
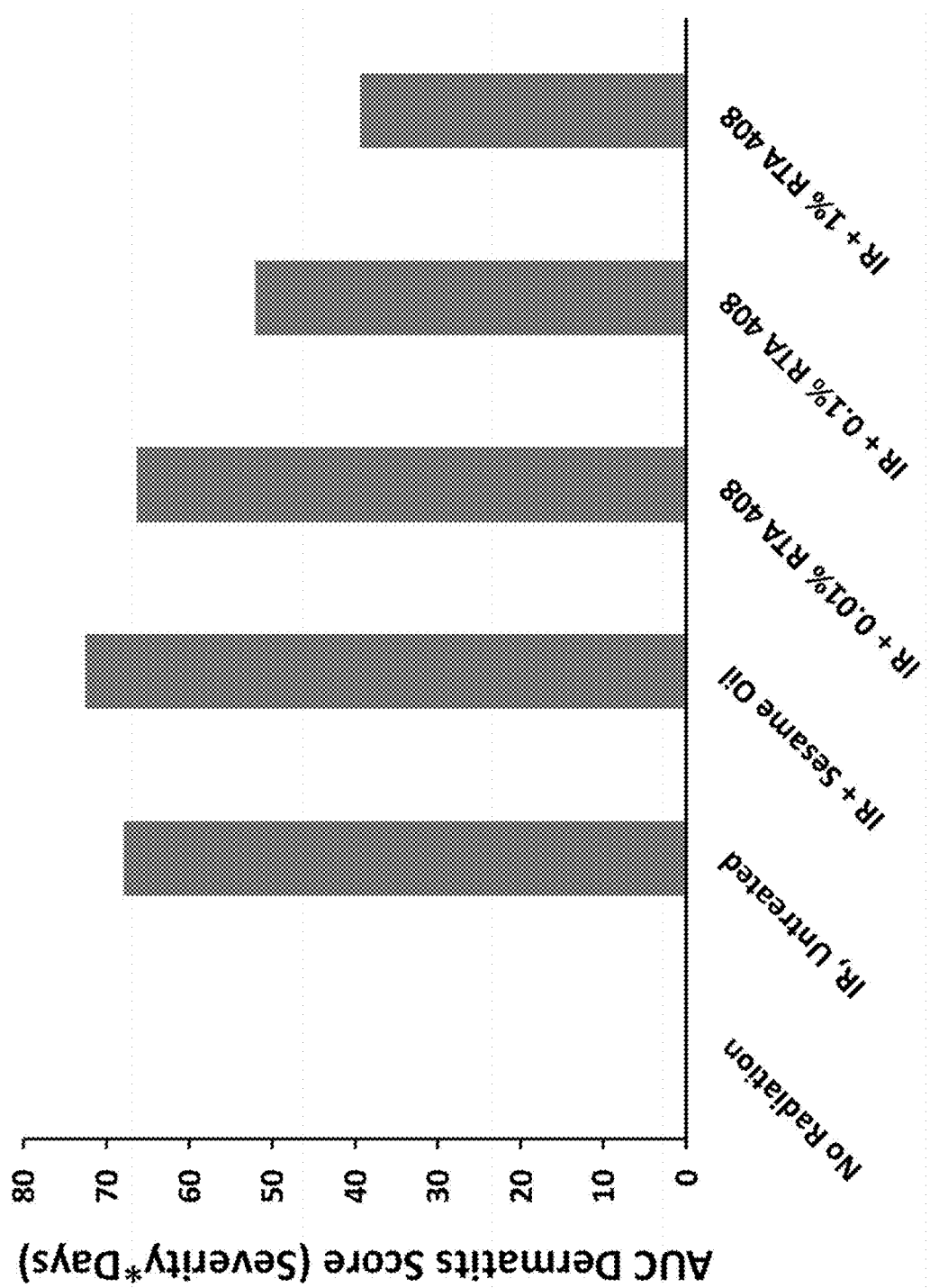
FIG. 47—Graph of the AUC analysis showing the dermatitis score (severity×days) for each of the testing groups over the entire observation period. The dermatitis scores were assessed every two days from day 4 to day 30 of the study.

By analyzing the average clinical scores that were shown in FIG. 46, an area under the curve (AUC) analysis was performed, which yielded the severity of the dermatitis relative to how long the dermatitis persisted. This AUC analysis allowed for direct comparison between the different groups of mice and the effect of the different percentage compositions of RTA 408 (FIG. 47 and Table 7). Administration of topical RTA 408 formulations reduced Grade 2 and Grade 3 lesions from 60% and 33% when the mice were only exposed to the vehicle to 21% and 6% with RTA 408 at 1%, concentration, respectively. The other RTA composition showed some activity but was not as significant as that shown by the 1% formulation.

TABLE 7

Percentage of Dermatitis Score for Each Treatment Group

| Group | % Days ≥2 | % Days ≥3 |
|---|---|---|
| No Rad, No Tx | 0% | 0% |
| Rad, No Tx | 66% | 31% |
| Rad, Sesame Oil | 60% | 33% |
| Rad, RTA 408 (0.01%) | 54% | 29% |
| Rad, RTA 408 (0.1%) | 40% | 13% |
| Rad, RTA 408 (1%) | 21% | 6% |

H. Synergistic Effects of RTA 408 and Cancer Therapeutic Agents on Tumor Growth

Figure 48A:
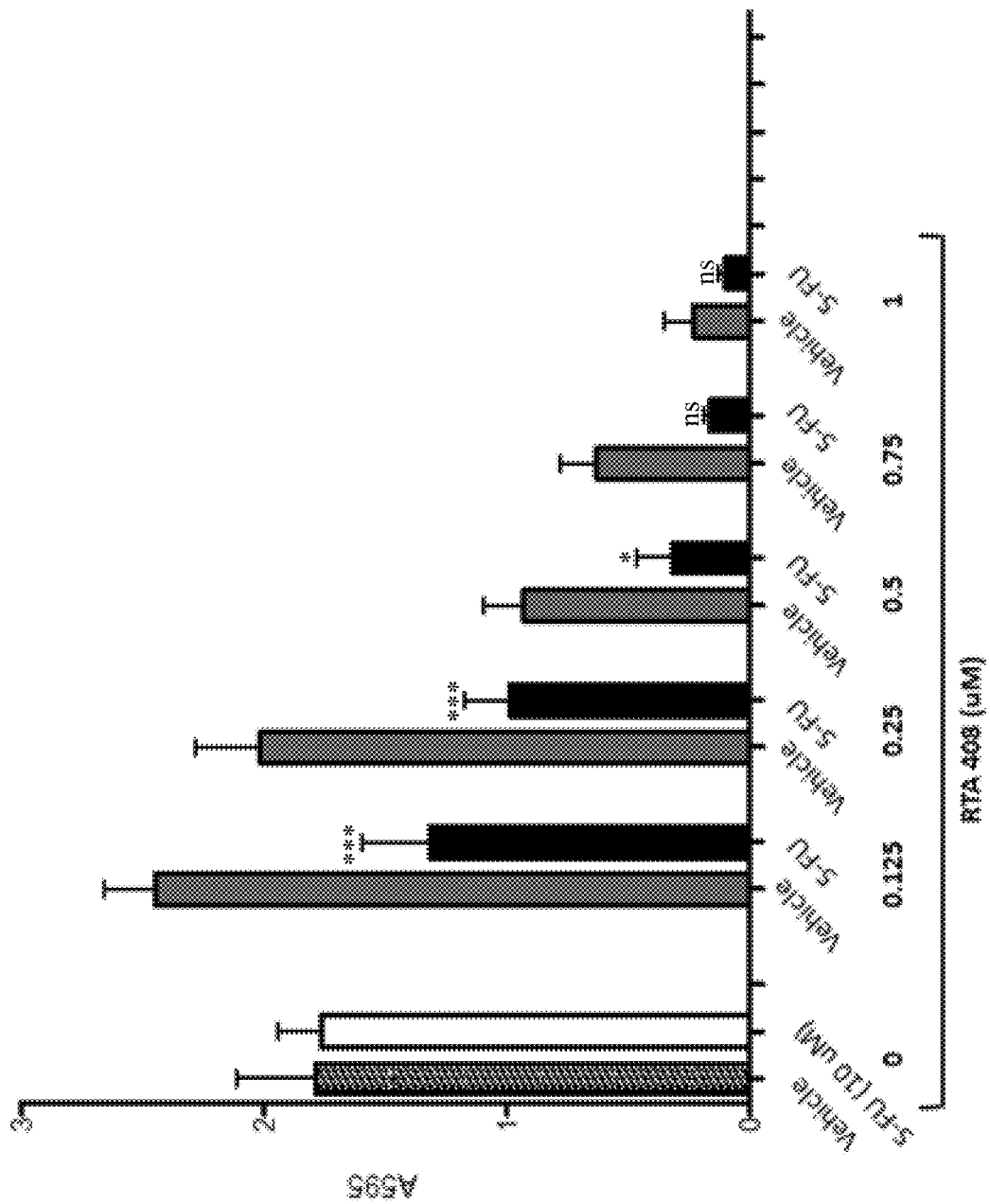
FIGS. 48a & b—(a) Graph of the absorbance at 595 nm for treated prostate cancer cell line LNCaP showing relative cytotoxic effect on cells treated with a chemotherapeutic agent and RTA 408 versus RTA 408 alone. (b) Graph of the absorbance at 595 nm for treated prostate cancer cell line DU-145 showing relative cytotoxic effect on cells treated with a chemotherapeutic agent and RTA 408 versus RTA 408 alone.
Figure 48B:
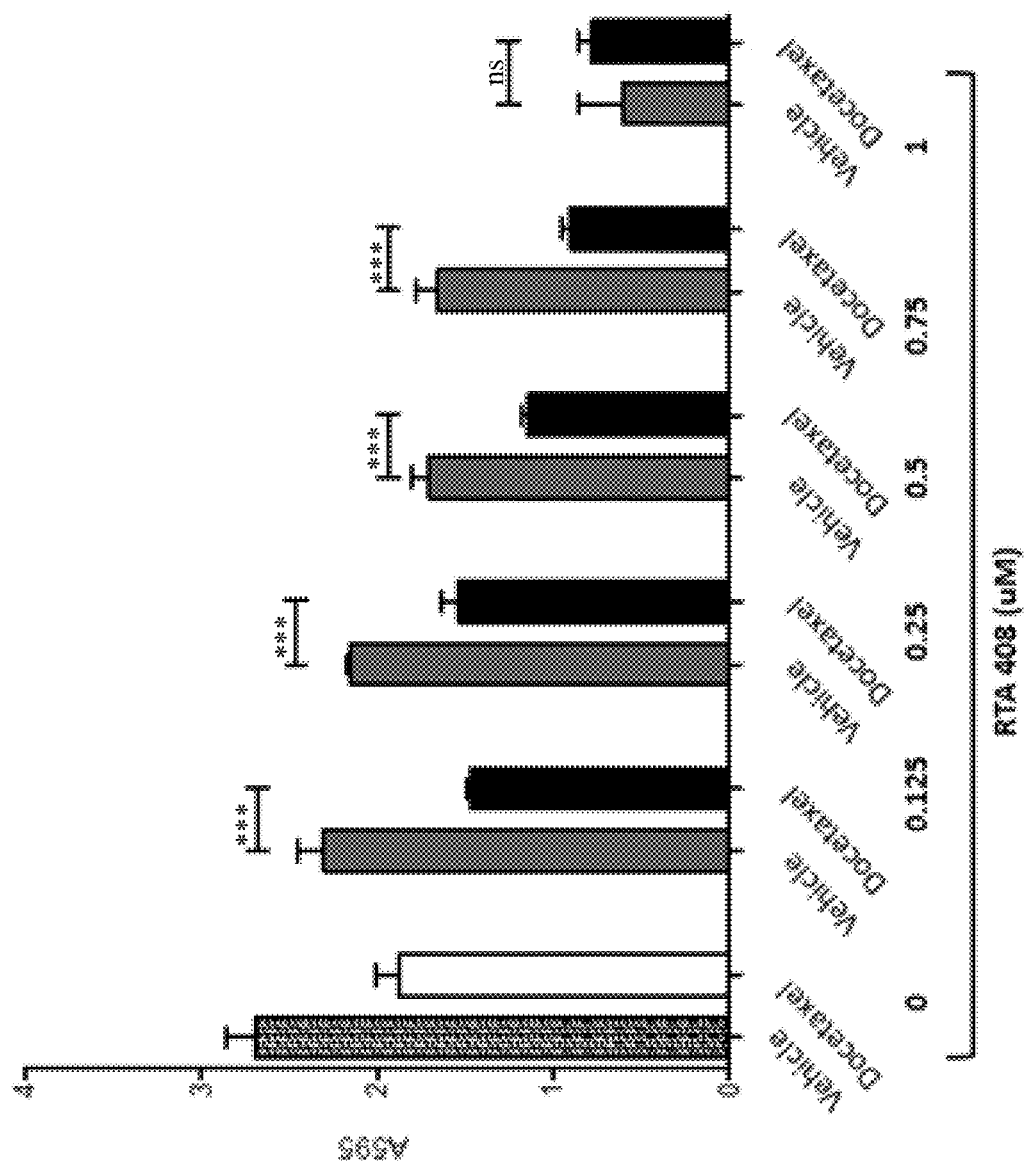

A study of the effects of RTA 408 used in combination with traditional chemotherapeutic agents was carried out to determine the efficacy of the potential treatment. In vitro studies were carried out to determine the effects of RTA 408 on two different prostate cancer cell lines, LNCaP and DU-145. As can be seen in FIG. 48a, the treatment of the prostate cancer cell lines (LNCaP) in vitro with 5-fluorouracil shows a statistically significant increase in cytotoxicity when combined with RTA 408 at doses from ranging from 0.125 to 0.5 µM. Using the prostate cell line DU-145 and docetaxel, RTA 408 amplified the cytotoxicity of the chemotherapeutic agent in a statistically significant fashion for dosing of RTA 408 from 0.125 to 0.75 µM as shown in FIG. 48b. This evidence supports the concept that RTA 408 could act synergistically with cancer therapeutic agents and may be used in some embodiments to provide greater efficacy in treating cancer patients.

Figure 49:
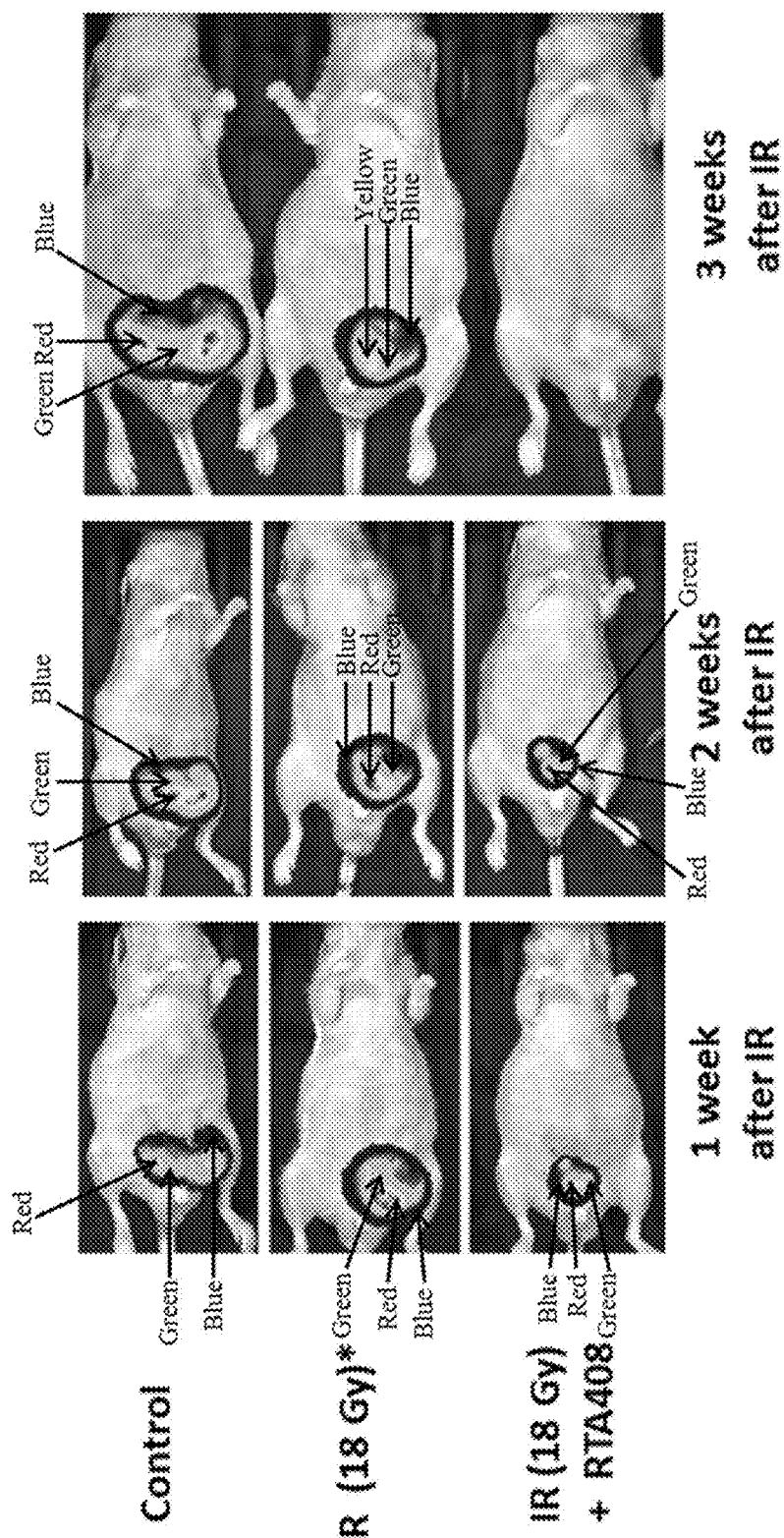
FIG. 49—Black and white versions of color photographs of imaged mice showing the luciferase activity of tumors for three mice: a control animal with no treatment, an animal subjected only to ionizing radiation (single dose, 18 Gy), and an animal given both ionizing radiation (single dose, 18 Gy, day 0) and RTA 408 (17.5 mg/kg i.p., once daily on days −3 to −1, then single doses on days 1, 3, and 5). The colors indicated by the arrows are indicative of intensity with the intensities being represented by red, yellow, green, and blue in order from highest to lowest intensity.

After the successful results of the in vitro assay, a pilot in vivo assay was carried out using LNCaP/C4-2B and DU145 human prostate cancer engineered to express firefly luciferase (hereafter referred to as C4-2B-Luc and DU145-Luc, respectively). Of note, both of these cell lines grow in an androgen-independent fashion. Cells were cultured in RPMI 1640 supplemented with 10% FBS. Cells were harvested using TrypLE Express (Invitrogen) and washed in PBS and counted. Cells were reconstituted in PBS to arrive at a final concentration of 3×10⁶ cells per 30 µL (unless otherwise stated) and aliquoted in separate tubes. Growth factor-reduced Matrigel (BD Bioscience) was thawed overnight at +4° C. and transferred into the tubes in 30 µL aliquots. The cell/Matrigel solutions were transferred to the vivarium and mixed right before injection at a 1:1 ratio. Each mouse (n=1 per group for a total of three animals) received a single subcutaneous injection of the tumor cells. Tumors were pre-established for 4 weeks. Then, one animal was treated with RTA 408 (17.5 mg/kg, i.p.) once a day for 3 days (Days −3 to −1). On the following day (Day 0), the RTA 408 treated animals and one other animal were treated with a single dose of 18 Gy IR, localized to the pelvic region where the tumors were implanted. The mouse that was pre-treated with RTA 408 received three additional doses of RTA 408 (17.5 mg/kg, i.p.), once every other day, over the following week. The third animal received no treatment and served as a positive control. Tumor progression was monitored weekly via live imaging. To detect luciferase-expressing tumor cells, mice were IP injected with D-Luciferin 5 min prior to imaging according to the manufacturer's protocol (Caliper Life-Science). Prior to imaging mice were anesthetized by isoflurane inhalation and imaged on the IVIS Lumina XR system (Caliper LifeScience). For standardization, minimal exposure time necessary to image control tumor was determined and all animals were imaged under these conditions. On Day 7, no apparent reduction in tumor size was visible in the TR treated animal compared to the control, whereas the animal receiving both RTA 408 and IR showed a smaller tumor image. On Day 14 and Day 21, the control animal showed continued tumor development and growth while the animal treated with ionizing radiation showed some improvement, most notably at Day 21. On the other hand, the animal treated with RTA 408 and ionizing radiation showed no progression from Day 7 to Day 14 and had no visible tumor on Day 21. The progress of the tumor per week can be seen in FIG. 49. Both the in vitro and in vivo data show that RTA 408 appears to complement the activity of different cancer therapeutic agents thus increasing the agent's efficacy.

I. Effects of RTA 408 on a Model of Ocular Inflammation

Figure 50:
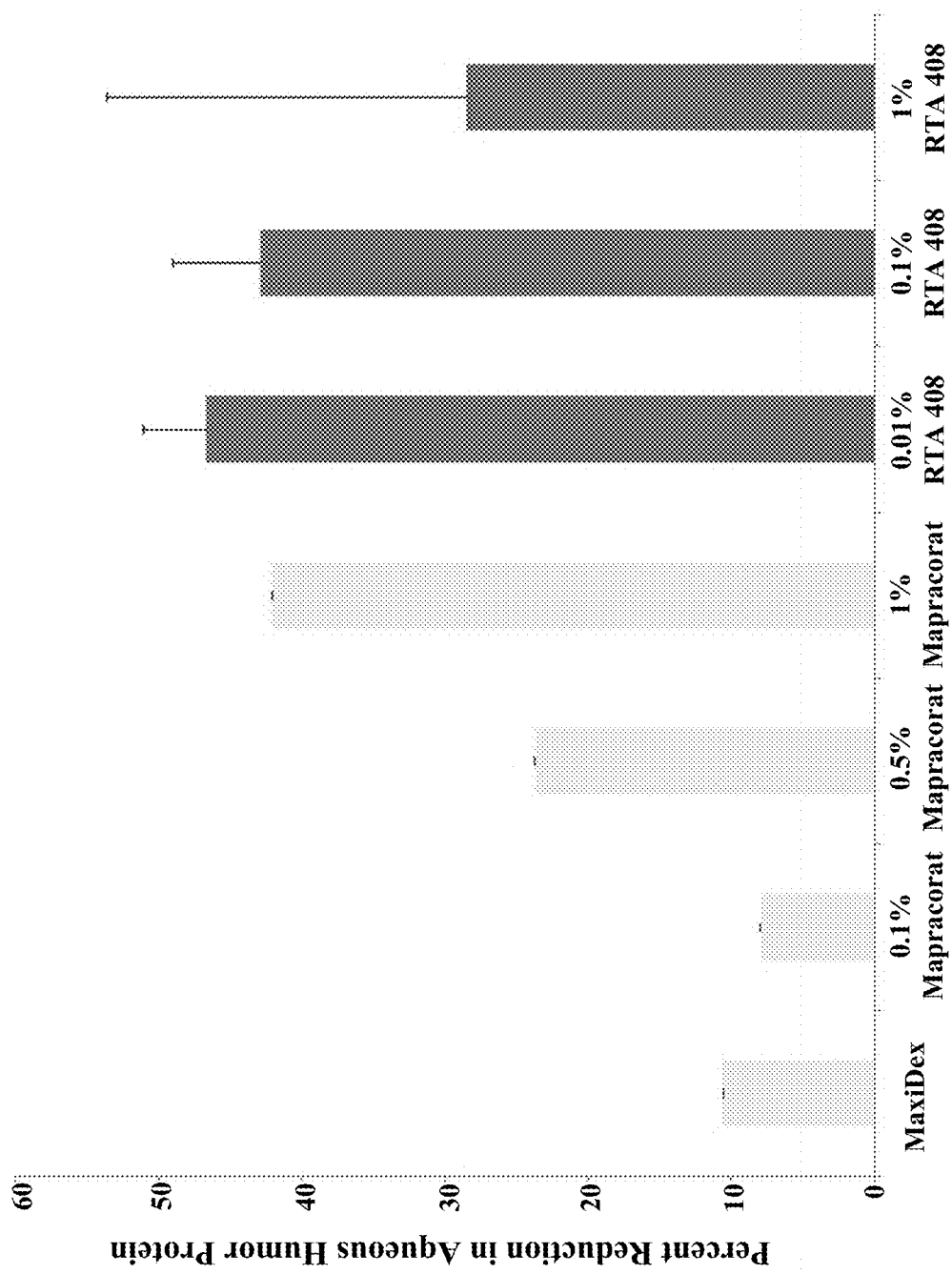
FIG. 50—Reduction of aqueous humor protein concentrations for different formulations of RTA 408 (dark bars) compared to literature values for MaxiDex® (0.1% dexamethasone) and mapracorat (light bars) after induction of paracentesis.

A study of the effects of RTA 408 on ocular inflammation was carried out using rabbits of the New Zealand albino strain. The rabbits were divided into 5 groups of 12 rabbits which were given three different concentrations of RTA 408 (0.01%, 0.1%, and 1%), Voltarene® collyre at 0.1% and the vehicle (sesame oil). Each rabbit was given three instillations within 60 min before induction of paracentesis and two instillations within 30 min after induction of paracentesis. Each instillation was 50 µL and given in both eyes. Aqueous humor for 6 animals per time-point was collected 30 min and again 2 h after induction of paracentesis. The amount of inflammation was determined by protein concentration in the aqueous humor. As shown in FIG. 50, RTA 408 showed a reduction in aqueous humor protein similar to that of the highest concentration of any of the other reference compounds (MaxiDex or mapracorat) at only 0.01% RTA 408 in the formulation. The effects of increasing concentration of RTA 408 appeared to be negligible as all concentrations of RTA 408 appeared to show relatively similar effects within error in reducing aqueous humor protein concentration.

J. Polymorph Screen

A preformulation and polymorphism study was performed for compound 63415. As part of this study, a preliminary polymorphism program was carried out with the aim to identify the most stable anhydrous form at room temperature and possible hydrates with a reasonably high probability. A total of 30 crystallization experiments, including phase equilibrations, drying experiments and other techniques, were carried out. All obtained solids were characterized by FT-Raman spectroscopy. All new forms were characterized by PXRD and TG-FTIR, and optionally by DSC and DVS.

In addition, the amorphous form was prepared and characterized. Several experiments using different techniques and approaches were carried out to prepare the amorphous form. The amorphous form was characterized by FT-Raman spectroscopy, PXRD, TG-FTIR, DSC, DVS, and Karl-Fischer titration. The stability of the amorphous form was tested at elevated humidity and temperature conditions over the course of four weeks.

1. Starting Material and Nomenclature

Two batches of 63415 were used as starting materials (Table 8). 63415 is also referred to as PP415 in this disclosure. All samples received or generated during this project received a unique identification code of the form PP415-Px, where Px refers to the sample/experiment number (x=1, 2, . . . , n).

TABLE 8

Starting materials

| Sample | Material | Amount | Received |
|---|---|---|---|
| PP415-P1 | 63415, batch #: 0141-66-1; MW = 554.7 g/mol, $C_{33}H_{44}F_2N_2O_3$ | 5.0 g | Mar. 25, 2011 |
| PP415-P40 | 63415, batch #: 2083-69-DC; MW = 554.7 g/mol, $C_{33}H_{44}F_2N_2O_3$ | 5.0 g | May 27, 2011 |

2. Compound 63415, Batch #0414-66-1 (PP415-P1): The Amorphous Form

The 63415, batch #0414-66-1, starting material was characterized by FT-Raman spectroscopy, PXRD, TG-FTIR, Karl-Fischer titration, $^1$H-NMR, DSC, DVS, and approximate solubility measurements. The results are summarized in Table 9.

TABLE 9

Characterization of the 63415 starting material (PP415-P1)

| Method | Results |
|---|---|
| FT-Raman | will be used as the reference |
| PXRD | no sharp peak pattern, material is amorphous |
| TG-FTIR | ~0.9 wt.-% (~0.1 eq.) EtOH with traces of $H_2O$ from 25° C. to 200° C., decomposition at T > 290° C. |
| Karl-Fischer | 0.5 wt.-% $H_2O$ |
| $^1$H-NMR | agrees with structure, ~0.08 eq. EtOH |
| DSC | $1^{st}$ heating scan: glass transition $T_g$ = 152.7° C. ($\Delta C_p$ = 0.72 J/g° C.); $2^{nd}$ heating scan: glass transition $T_g$ = 149.7° C. ($\Delta C_p$ = 0.45 J/g° C.) |
| DVS | slightly hygroscopic; $\Delta m$ = +0.4% (50%→85% r.h.); FT-Raman and PXRD unchanged |

Figure 58:
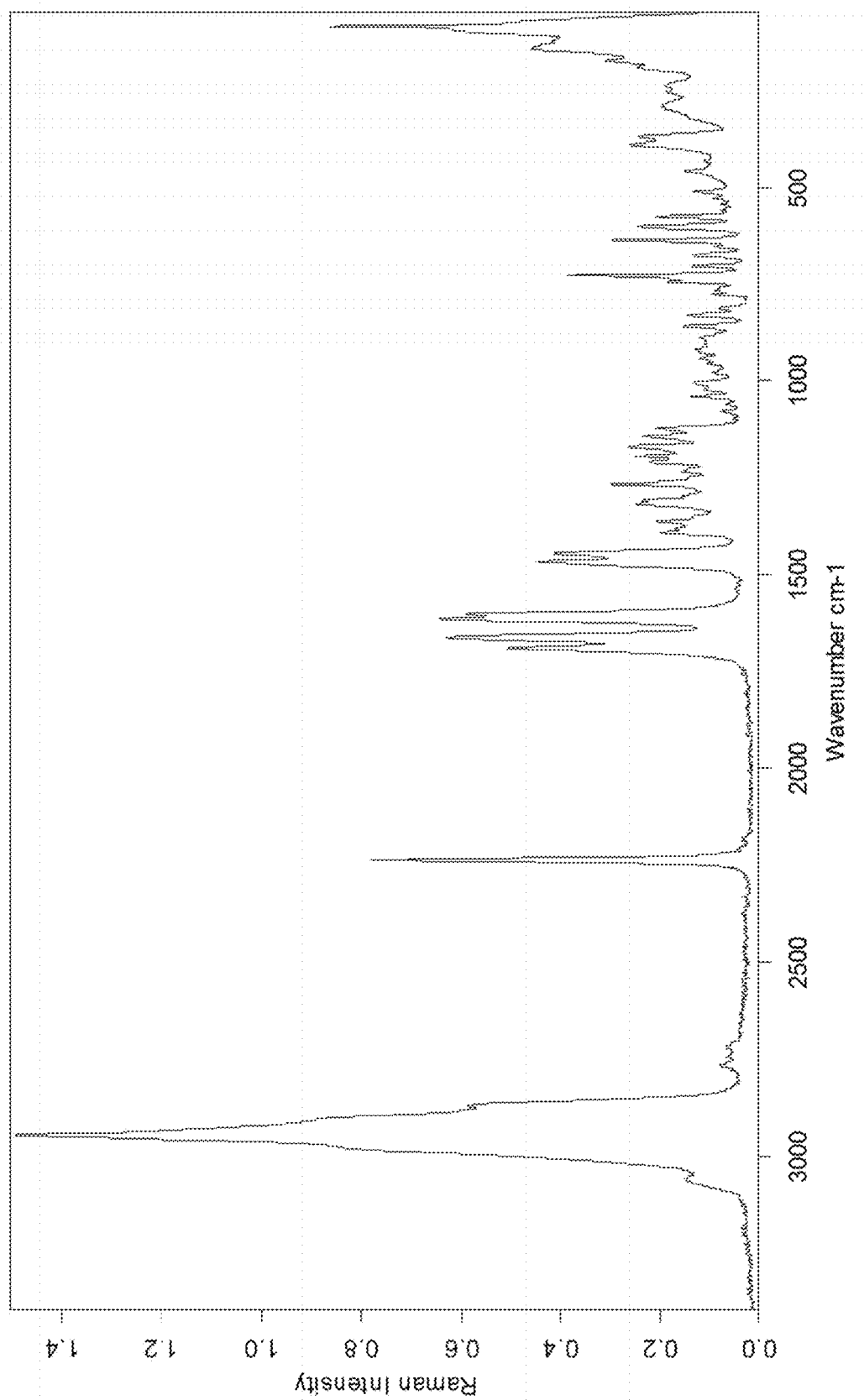
FIG. 58—FT-Raman spectrum (3400-50 $cm^{-1}$) of the sample PP415-P1, which corresponds to the amorphous form (Class 1).

The FT-Raman spectrum (FIG. 58) will be used as the reference spectrum for the starting material. PXRD (FIG. 59) shows no sharp peak pattern. The broad halo at ~10-20° 2θ is characteristic for amorphous materials.

Figure 60:
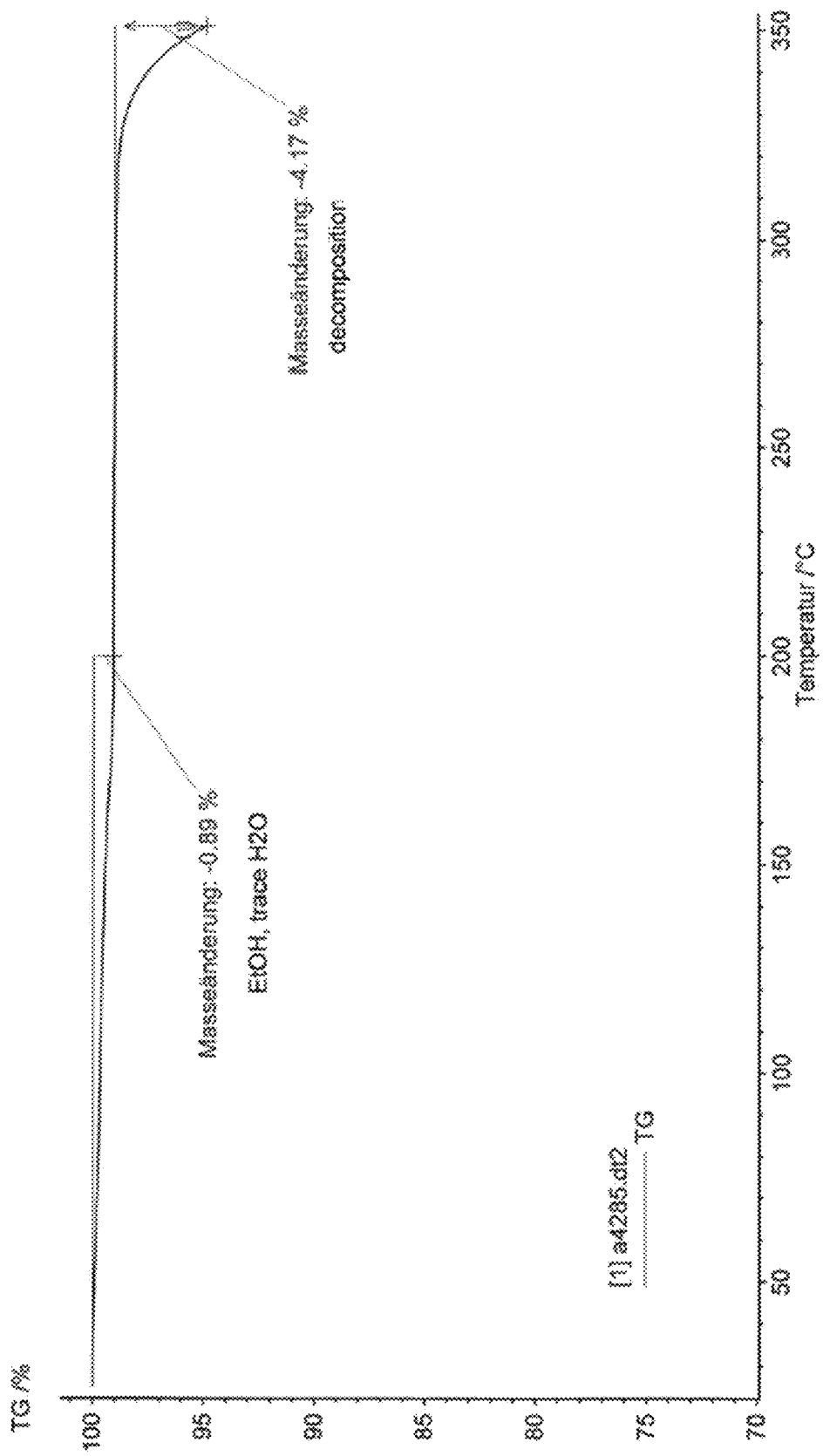
FIG. 60—TG-FTIR thermogram (25-350° C.) of the sample PP415-P1, which corresponds to the amorphous form (Class 1).

The TG-FTIR thermogram (FIG. 60) shows the gradual loss of ~0.9 wt.-% EtOH (i.e., ~0.1 eq.) with traces of $H_2O$ between 25 and 200° C. Decomposition starts at T>290° C.

A water content of 0.5 wt.-% was determined by Karl-Fischer titration.

Figure 61:
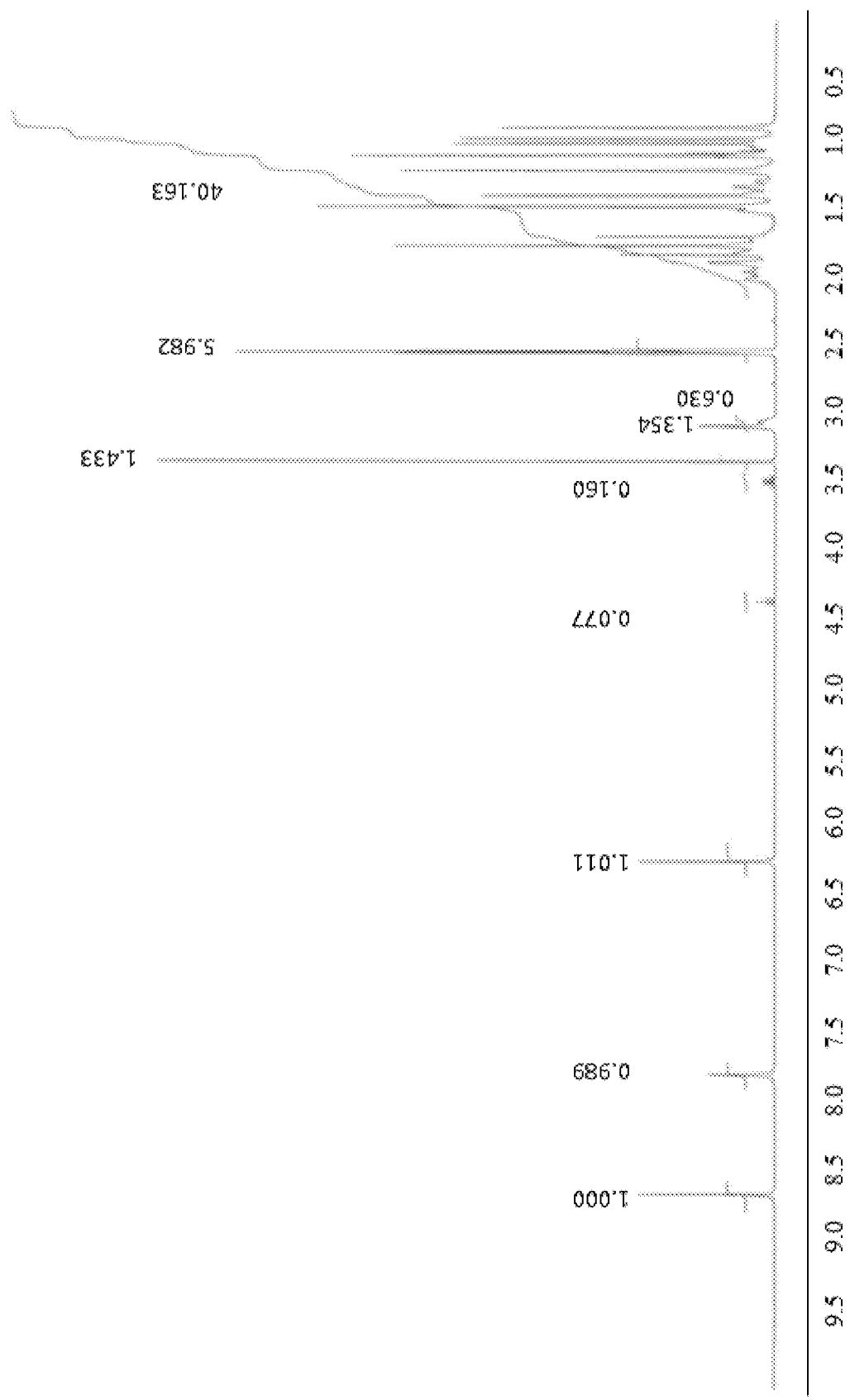
FIG. 61—$^1$H-NMR spectrum in DMSO-$d_6$ of the sample PP415-P1, which corresponds to the amorphous form (Class 1).

The $^1$H-NMR spectrum (FIG. 61) agrees with the structure and shows ~0.08 eq. EtOH, in agreement with the TG-FTIR thermogram.

The DSC thermogram (FIG. 62) shows in a first heating scan a glass transition of the amorphous material at $T_g$=152.7° C. ($\Delta C_p$=0.72 J/g° C.). In a second scan after quench cooling, the glass transition occurs at $T_g$=149.7° C. ($\Delta C_p$=0.45 J/g° C.).

Figure 63:
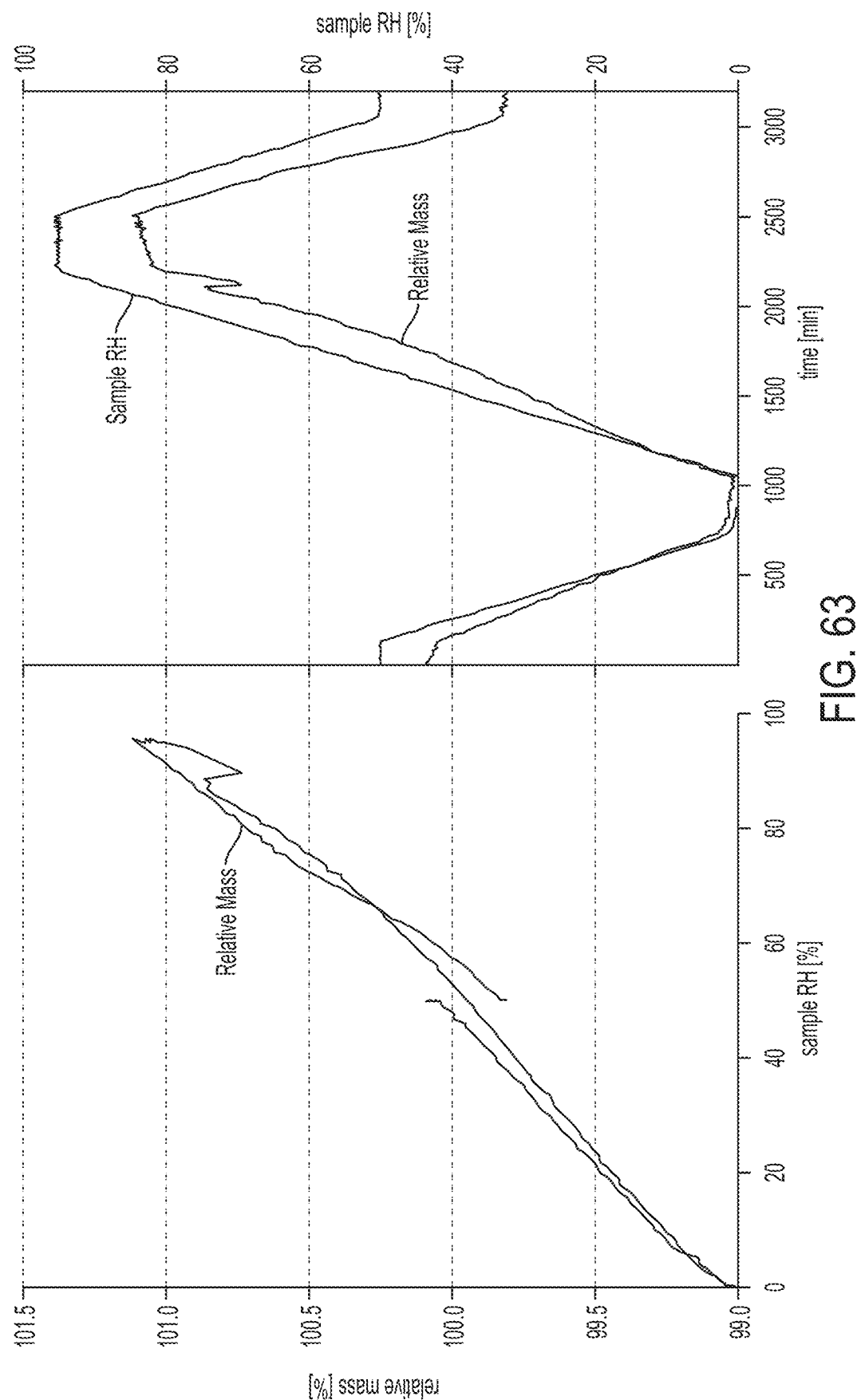
FIG. 63—DVS isotherm of the sample PP415-P1, which corresponds to the amorphous form (Class 1).

The DVS isotherm (FIG. 63) shows that a gradual mass loss of 1.0 wt.-% occurred upon lowering the relative humidity from 50% r.h. to 0% r.h.; equilibrium was reached at 0% r.h. Upon increasing the relative humidity to 95% r.h.

a gradual mass gain of 2.1 wt.-% (relative to the mass at 0% r.h.) occurred; equilibrium was reached at 95% r.h. Upon lowering the relative humidity from 95% r.h. to 50% r.h. the final mass was 0.2 wt.-% below the starting mass. The mass increase of 0.4 wt.-% at 85% r.h. (relative to the starting mass) classifies the sample as slightly hygroscopic.

Figure 64:
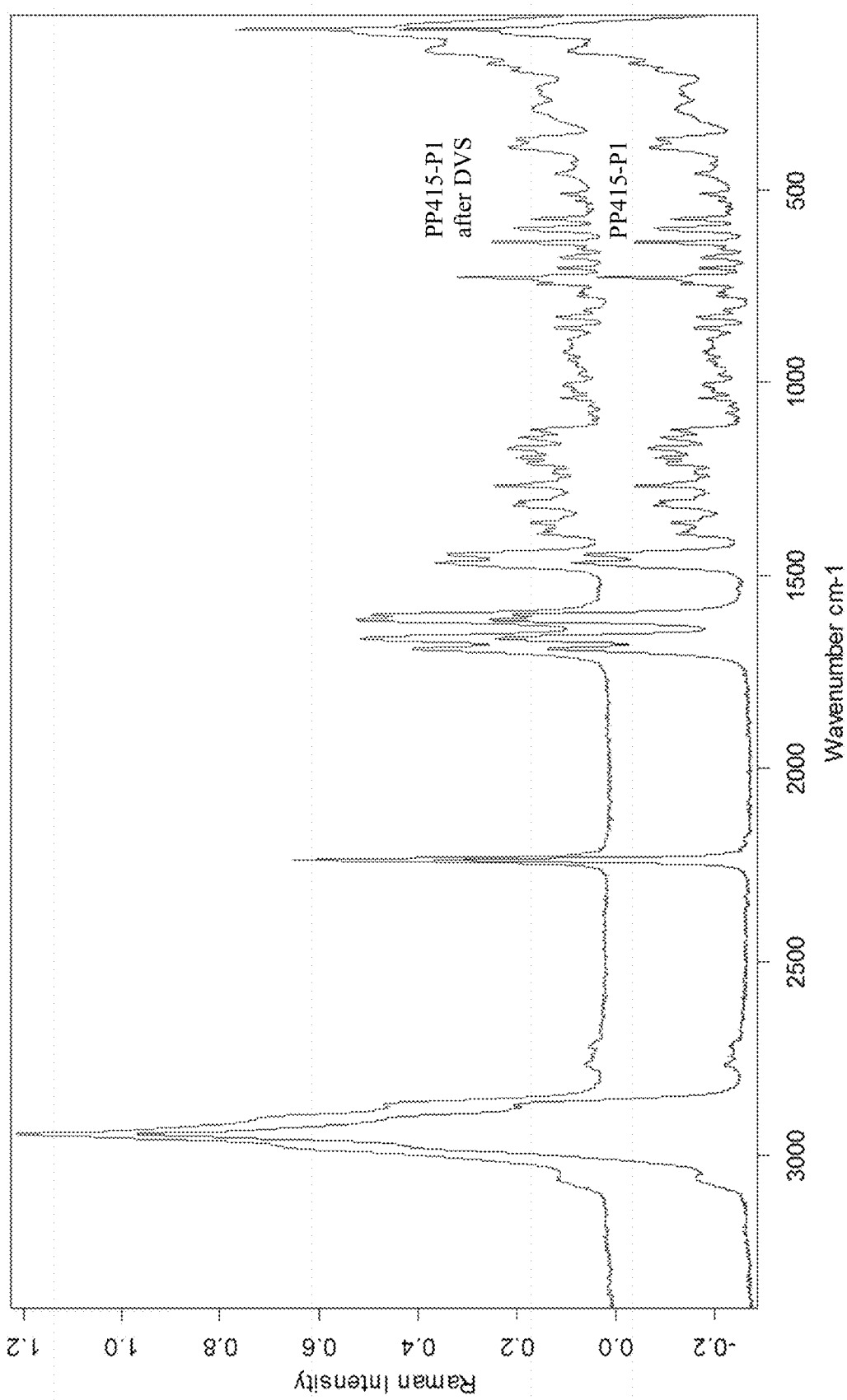
FIG. 64—FT-Raman spectrum of the sample PP415-P1, which corresponds to the amorphous form (Class 1), after DVS measurement (top) is unchanged compared to the material before the DVS measurement (bottom). The spectra have been scaled and offset in the y-direction for the purpose of comparison.
Figure 65:
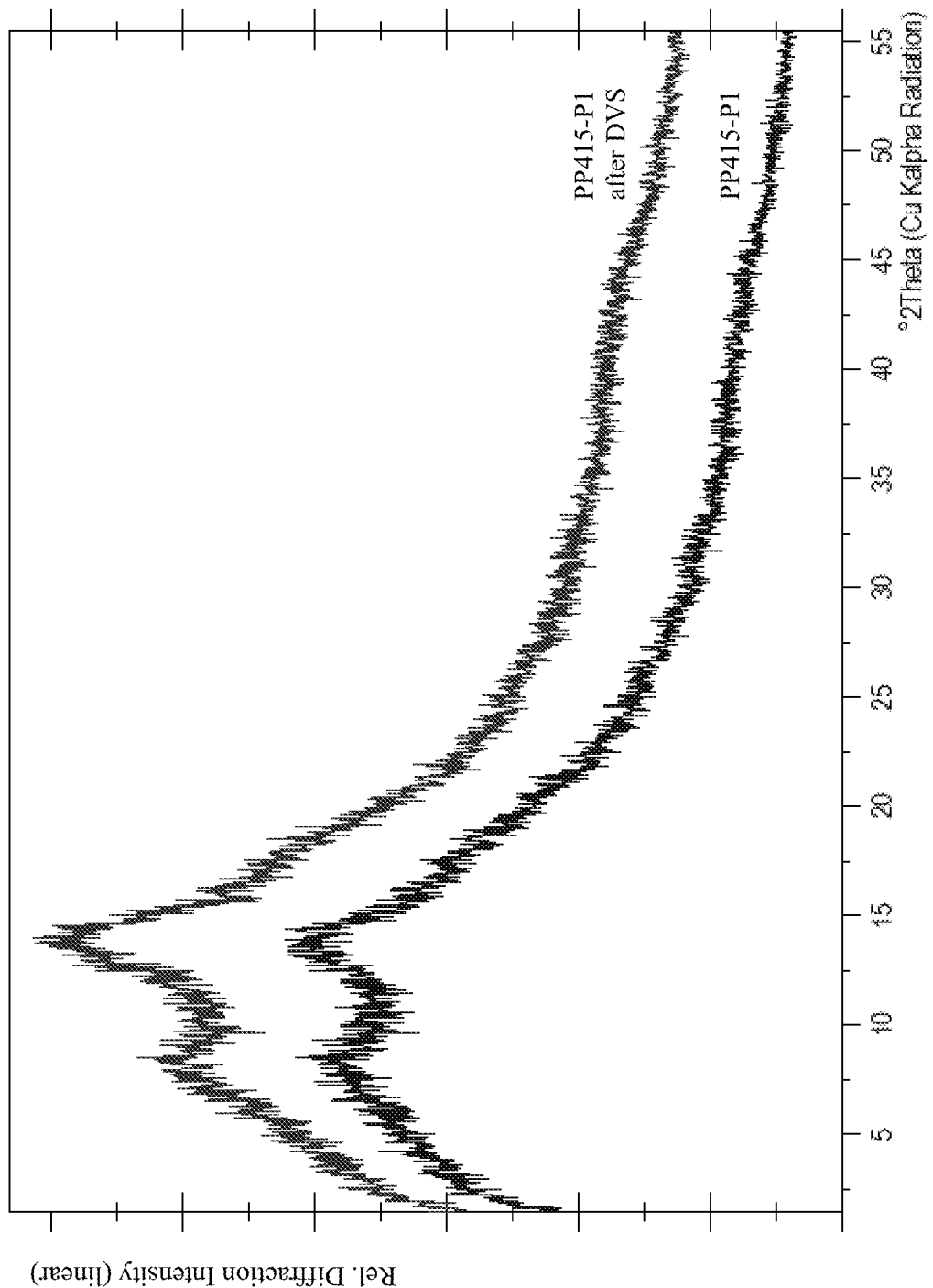
FIG. 65—PXRD pattern of the sample PP415-P1, which corresponds to the amorphous form (Class 1), after DVS measurement (top) is unchanged compared to the material before the DVS measurement (bottom). The patterns have not been scaled but are offset in the y-direction for the purpose of comparison.

The FT-Raman spectrum (FIG. 64) and PXRD pattern (FIG. 65) of the sample after the DVS measurement are unchanged compared to the spectrum and pattern of the sample before the measurement.

The approximate solubility of the PP415-P1 starting material was measured in twelve solvents and four solvent mixtures at r.t. by manual dilution combined with visual observation (Table 10). Due to the experimental error inherent in this method, the solubility values are intended to be regarded as rough estimates and are to be used solely for the design of crystallization experiments. All solvent mixtures are listed as ratios by volume (v/v).

TABLE 10

Approximate solubility of the PP415-P1 (amorphous) starting material

| Solvent | Solubility S [mg/mL] |
|---|---|
| toluene | S > 200 |
| DCM | S > 200 |
| EtOAc | S > 210 |
| acetone | S > 230 |
| MeCN | S > 230 |
| DMF | S > 210 |
| MeOH | S < 210 |
| EtOH[a] | 105 < S < 210 |
| 2PrOH | 16 < S < 19 |
| DEE | S ≥ 1[d] |
| heptane | S < 1 |
| H$_2$O | S < 1 |
| 2PrOH/H$_2$O (9:1)[b] | 7.9 < S < 8.5 |
| MeCN/H$_2$O (2:3)[c] | S < 1 |

TABLE 10-continued

Approximate solubility of the PP415-P1 (amorphous) starting material

| Solvent | Solubility S [mg/mL] |
|---|---|
| EtOAc/heptane (1:1)[a] | 100 < S < 200 |
| toluene/DEE (1:1)[a] | S > 220 |

[a]observed precipitation after~1 d;
[b]water activity a(H$_2$O)~0.7 at 25° C.;
[c]water activity a(H$_2$O) > 0.9 at 50° C.;
[d]incomplete dissolution at first (S < 1), but solid residue dissolved completely overnight (S > 1).

3. Compound 63415, Batch #2083-69-DC (PP415-P40): Class 2

Figure 66:
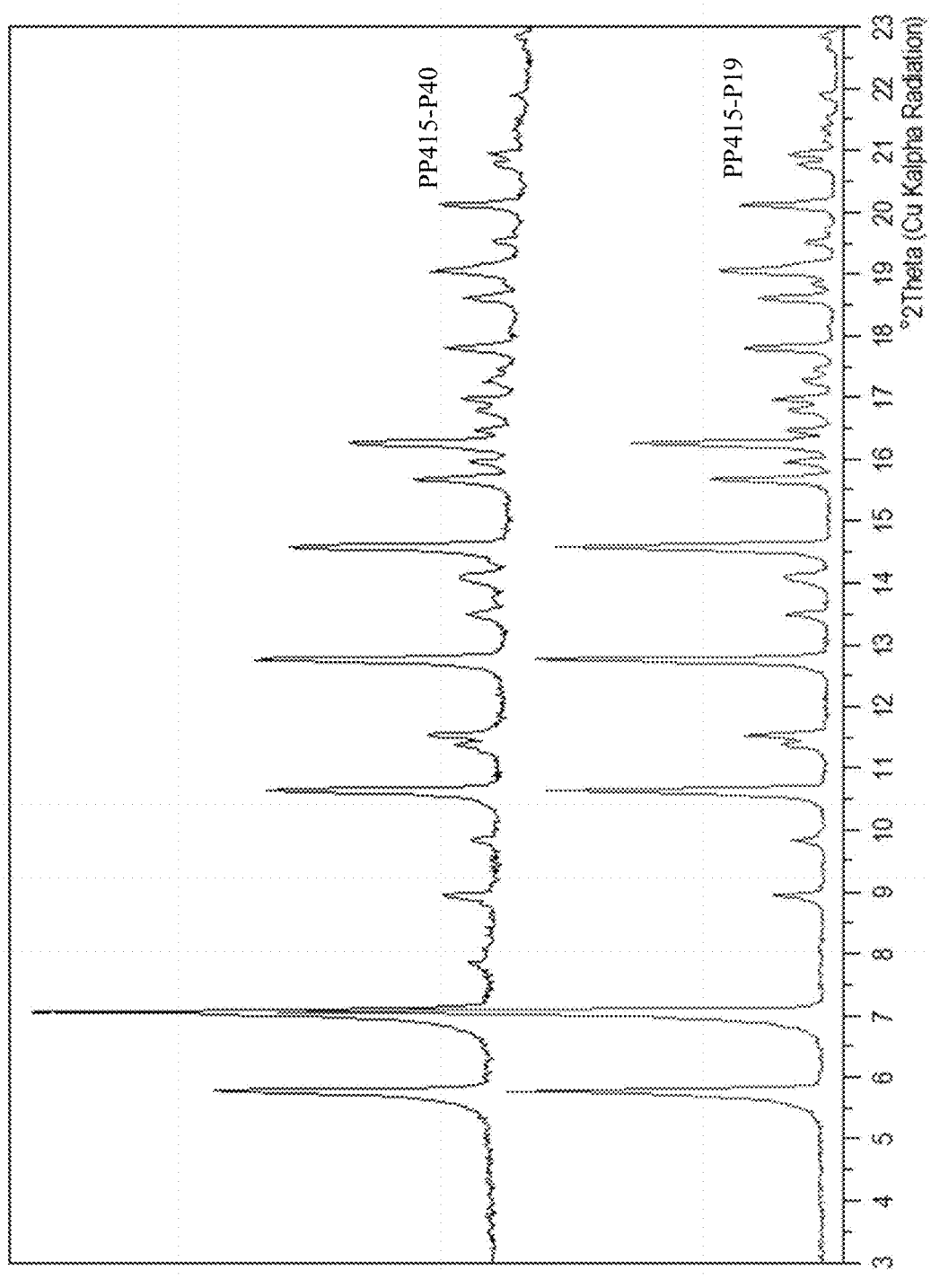
FIG. 66—PXRD pattern of the sample PP415-P40 (top) corresponds to the pattern of the solvate form (Class 2) (bottom, sample PP415-P19). The patterns have been scaled and offset in the y-direction for the purpose of comparison.

63415, batch #2083-69-DC, is a heptane solvate. This material (PP415-P40) was characterized by PXRD and found to correspond to class 2 (FIG. 66).

Class 2 likely corresponds to isostructural, non-stoichiometric (<0.5 eq.) solvates (of heptane, cyclohexane, isopropyl ether, 1-butanol, triethyl amine, and possibly other solvents, such as hexane and other ethers) with tightly bound solvent.

The small peaks visible in the pattern of PP415-P40 at 7.9° 2θ and 13.8° 2θ do not correspond to peaks of classes 3, 4, or 5. Their origin is not clear at this point.

4. Chemical Stability of the Amorphous Form

The chemical stability of the amorphous form was investigated in different solvents over the course of seven days.

Solutions/suspensions with a concentration of 1 mg/mL were prepared in four organic solvents (acetone, MeOH, MeCN, EtOAc) and three aqueous surfactant media (1% aq. SDS, 1% aq. Tween 80, 1% aq. CTAB).

Four separate solutions/suspensions were prepared for each solvent, equilibrated for 6 h, 24 h, 2 d, and 7 d and subsequently analyzed by HPLC.

The relative area-% obtained from the HPLC chromatograms are given in Table 11. The compound seems to be somewhat unstable in the diluent (0.1% formic acid in MeCN); over the course of the sequence (i.e., within ~24 hours) the area-% of a reference sample (PP415-P1, ran at the beginning and the end of the sequence) decreased from 99.9% to 99.3% at 254 nm and from 99.9% to 99.5% at 242 nm. Due to this effect, the samples measured towards the end of the sequence (set up in the following order: 7 d, 2 d, 24 h, 6 h), might be affected and the obtained area-% might be underestimated.

TABLE 11

Chemical stability experiments with the amorphous form of 63415 (PP415-P1)[a]

| | at 254 nm | | | | at 242 nm | | | |
|---|---|---|---|---|---|---|---|---|
| Solvent | 7 d | 2 d | 24 h | 6 h | 7 d | 2 d | 24 h | 6 h |
| acetone | 99.6% | 99.6% | 99.6% | 99.6% | 99.7% | 99.7% | 99.6% | 99.6% |
| EtOAc | 99.8% | 99.8% | 99.8% | 99.7% | 99.8% | 99.9% | 99.8% | 99.7% |
| MeOH | 99.8% | 99.8% | 99.7% | 99.8% | 99.8% | 99.9% | 99.7% | 99.8% |
| MeCN | 97.7% | 99.5% | 99.3% | 99.4% | 97.4% | 99.5% | 99.3% | 99.3% |
| Tween 1%[b] | 97.7% | 97.1% | 95.1% | 97.6% | 98.7% | 98.7% | 96.2% | 99.1% |
| SDS 1%[c] | 99.7% | 99.6% | 99.7% | 99.7% | 99.8% | 99.7% | 99.7% | 99.7% |
| CTAB 1% | 99.3% | 99.4% | 99.4% | 99.6% | 99.3% | 99.4% | 99.4% | 99.7% |

[a]at the third wavelength (210 nm), the signal intensity was weak and the signal-to-noise ratio large, thus integration was not carried out
[b]suspensions, not all material dissolved for all time points
[c]suspensions, not all solid dissolved for time points 24 h and 6 h Decomposition ≥1% was observed for solutions in MeCN after seven days and for suspensions in the 1% aqueous Tween 80 media (at all time points at 254 nm and after 24 h, 2 d, and 7 d at 242 nm).

5. Storage Stability of the Amorphous Form

To learn more about its fundamental properties and physical stability, the amorphous form of 63415 was stressed by storage at elevated temperatures and relative humidities.

Samples of the amorphous form (the PP415-P1 starting material) were stored open at 25° C./~62% r.h. (over saturated aqueous solution of $NH_4NO_3$) and 40° C./~75% r.h. (over saturated aqueous solution of NaCl) and closed at 60° C. and 80° C. (Table 12). At time points 0 w, 1 w, 2 w, and 4 w the samples were examined by PXRD and compared to the starting material, PP415-P1.

TABLE 12

Storage stability experiments with the amorphous form of 63415 (PP415-P1)

| Sample | Conditions | Time Point | PXRD Result |
|---|---|---|---|
| PP415-P2a | open, 25° C./~62% r.h. | 1 w | amorphous |
| PP415-P2b | open, 25° C./~62% r.h. | 2 w | amorphous |
| PP415-P2c | open, 25° C./~62% r.h. | 4 w | amorphous |
| PP415-P3a | open, 40° C./~75% r.h. | 1 w | amorphous |
| PP415-P3b | open, 40° C./~75% r.h. | 2 w | amorphous |
| PP415-P3c | open, 40° C./~75% r.h. | 4 w | amorphous |
| PP415-P4a | closed, 60° C. | 1 w | amorphous |
| PP415-P4b | closed, 60° C. | 2 w | amorphous |
| PP415-P4c | closed, 60° C. | 4 w | amorphous |
| PP415-P5a | closed, 80° C. | 1 w | amorphous |
| PP415-P5b | closed, 80° C. | 2 w | amorphous |
| PP415-P5c | closed, 80° C. | 4 w | amorphous |

Figure 67:
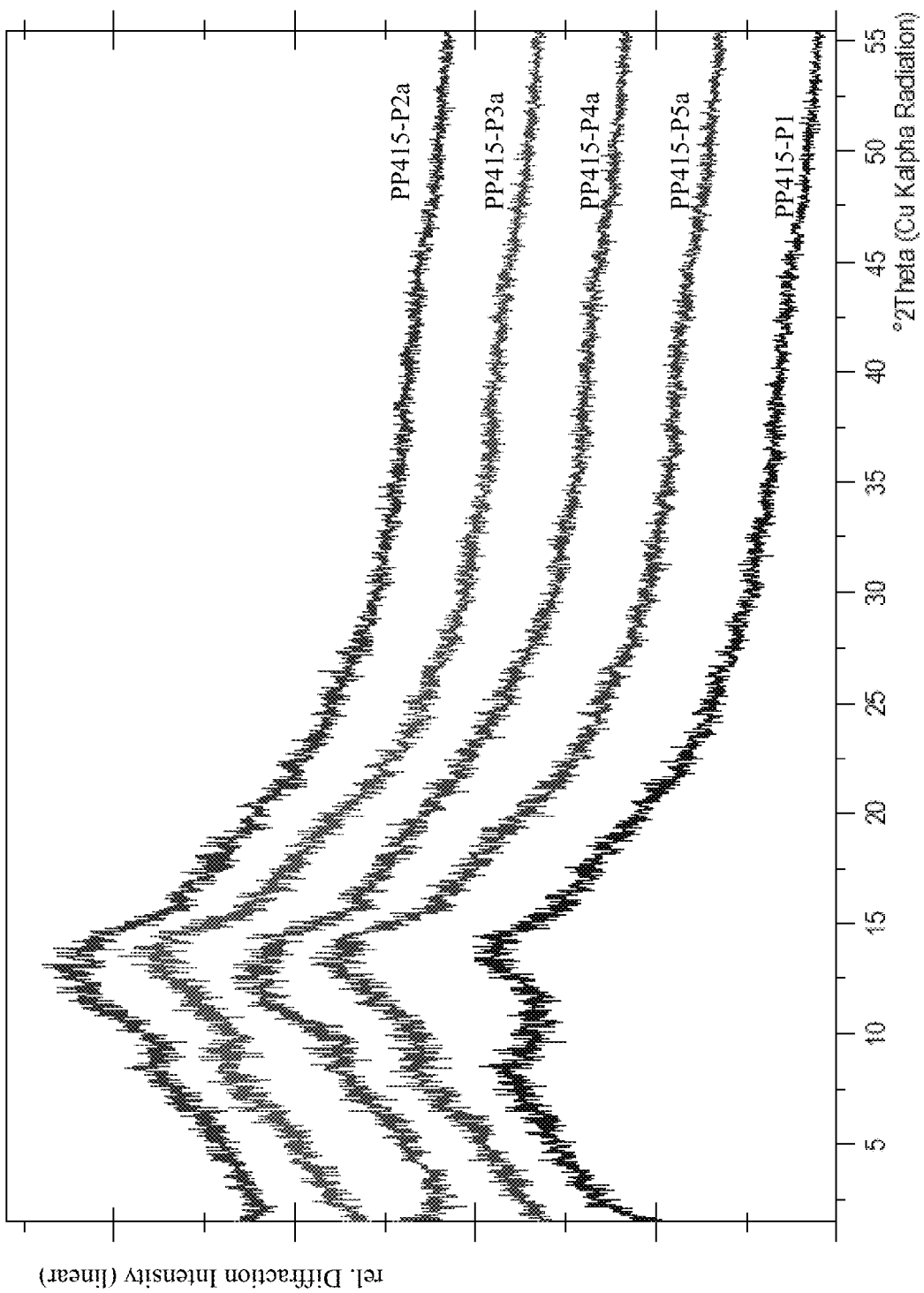
FIG. 67—PXRD patterns of the stability samples PP415-P2a (top), PP415-P3a ($2^{nd}$ from top), PP415-P4a (middle), and PP415-P5a ($2^{nd}$ from bottom), which corresponds to the amorphous form (Class 1), after one week show no differences compared to the starting material at time point to (bottom, sample PP415-P1). The patterns are not scaled but are offset in the y-direction for the purpose of comparison.
Figure 68:
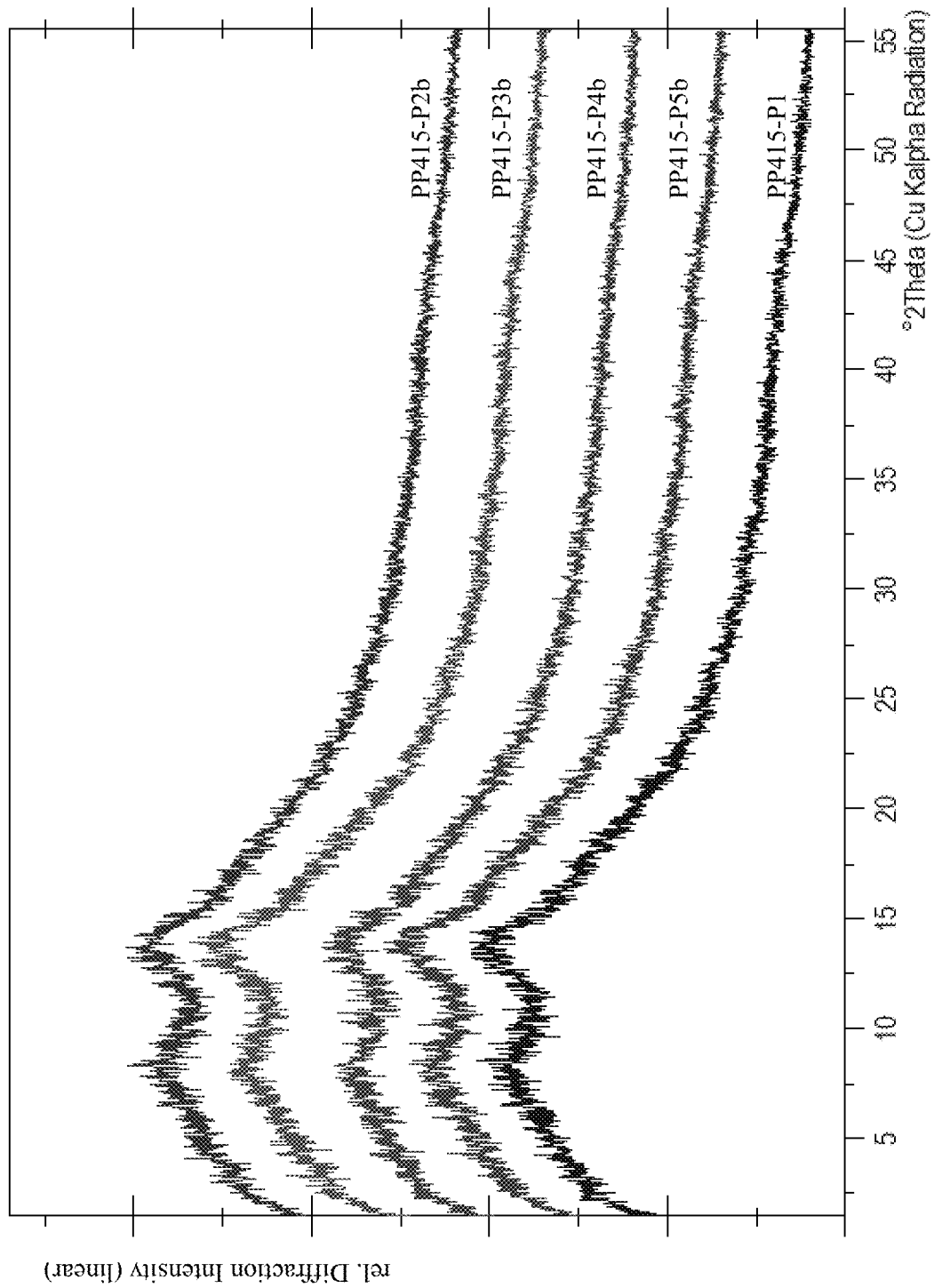
FIG. 68—PXRD patterns of the stability samples PP415-P2b (top), PP415-P3b ($2^{nd}$ from stop), PP415-P4b (middle), and PP415-P5b ($2^{nd}$ from bottom), which corresponds to the amorphous form (Class 1), after two weeks show no differences compared to the starting material at time point to (bottom, sample PP415-P1). The patterns are not scaled but are offset in the y-direction for the purpose of comparison.
Figure 69:
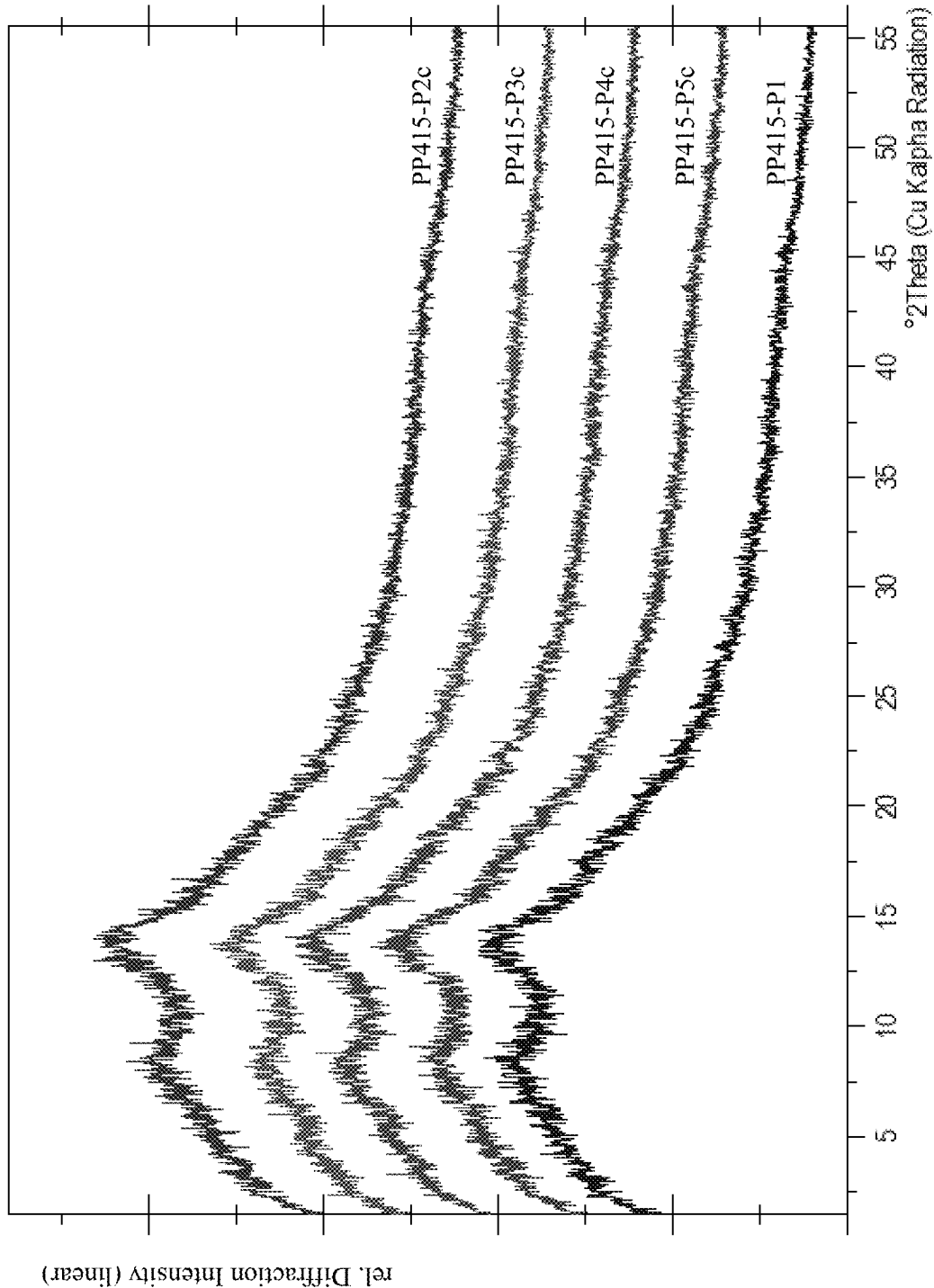
FIG. 69—PXRD patterns of the stability samples PP415-P2c (top), PP415-P3c ($2^{nd}$ from top), PP415-P4c (middle), and PP415-P5c ($2^{nd}$ from bottom), which corresponds to the amorphous form (Class 1), after four weeks show no differences compared to the starting material at time point to (bottom, sample PP415-P1). The patterns are not scaled but are offset in the y-direction for the purpose of comparison.

After one week (time point 1 w, FIG. 67), two weeks (time point 2 w, FIG. 68), and four weeks (time point 4 w, FIG. 69) all four samples were still amorphous, as the powder X-ray diffractograms show no differences compared to the starting material at time point 0 w.

6. Crystallization and Drying Experiments a. Crystallization Experiments

Phase equilibrations, crystallizations from hot solutions, and evaporation experiments were carried out starting from the amorphous form in order to identify with reasonably high probability the most stable anhydrous form at r.t. and possible hydrates. All obtained materials were characterized by FT-Raman spectroscopy; selected samples were also characterized by PXRD.

The FT-Raman spectra were grouped into classes according to the similarity of their peak positions. The original sample (PP415-P1, see Table 8) was classified along with the crystallization products. The spectra within a class, however, are not strictly identical, but similar. Small differences and peak shifts might exist. Considering the FT-Raman spectra alone, it is difficult to determine if the spectra of one class belong to the same polymorphic form.

The peaks in the PXRD patterns were determined and the patterns then classified into clusters using the PANalytical X'Pert (Highscore Plus) software. These clusters identify patterns of a high similarity. However, small but significant differences exist within a cluster. Thus, the patterns within a cluster do not necessarily correspond to the same polymorphs, but represent different forms with very similar molecular structures. The FT-Raman classes correspond in all cases to the PXRD clusters.

b. Suspension Equilibration Experiments

Suspension equilibration experiments were carried out in one solvent and eleven solvent mixtures (Table 13). Suspensions of ~100 mg of PP415-P1 in 0.2-2.0 mL of the selected solvents were prepared and shaken for 4-15 days at 22-24° C. The solids were recovered and characterized by FT-Raman spectroscopy; most were characterized also by PXRD.

TABLE 13

Suspension equilibration experiments starting from the amorphous form (PP415-P1)

| Sample | Solvent/Mixture | FT-Raman class | PXRD cluster |
|---|---|---|---|
| PP415-P6 | 2PrOH | 3 | 3 |
| PP415-P7 | 1:2 EtOAc/heptane | 2 | 2 |
| PP415-P8 | 1:2 acetone/hexane | 2 | 2 |
| PP415-P9 | 1:3 toluene/DEE | $2^d$ | — |
| PP415-P10 | 1:3 MeOH/TBME | 2 | 2 |
| PP415-P11 | 1:2 MEK/cyclohexane | $2^d$ | — |
| PP415-P12 | 9:1 EtOH/$H_2O^a$ | 3 | 3 |
| PP415-P13 | 7:3 MeCN/$H_2O^b$ | $4^d$ | 4 |
| PP415-P14 | ~1:1 THF/$H_2O^c$ | $5^d$ | 5 |
| PP415-P29 | 1:2 EtOAc/TEA | 2 | 2 |
| PP415-P31 | 9:1 PEG/$H_2O$ | 1 | 1 |
| PP415-P35 | 7:3 MeCN/$H_2O^b$ | $4^d$ | 4 | water activities: $^a$a($H_2O$)~0.5 at 50° C.; $^b$a($H_2O$)~0.85 at 50° C.; $^c$a($H_2O$) > 0.99 at 64° C.; $^d$the spectrum contains solvent signals c. Crystallizations from Hot Solutions Hot solutions of PP415-P1 were prepared in one solvent and four solvent mixtures (Table 14). Upon slow cooling to 5° C. at a rate of ~0.2 K/min, precipitation was observed in three cases (-P20, -P21, -P24). In two cases (-P22, -P23) no solid precipitated, even after storage at 4-5° C. for two days. Here, the solvent was evaporated under $N_2$ flow at r.t. The solids were recovered and characterized by FT-Raman spectroscopy and for those with spectra different from the amorphous starting material, FT-Raman class 1, also by PXRD.

TABLE 14

Slow cooling experiments starting from the amorphous form (PP415-P1)

| Sample | Solvent/Mixture | Conditions | FT-Raman class | PXRD cluster |
|---|---|---|---|---|
| PP415-P20 | ~2:1 acetone/$H_2O$ | 55° C. → 5° C. | $3^b$ | 3 |
| PP415-P21 | ~1:5 EtOH/cyclohexane | 75° C. → 5° C. | 2 | 2 |
| PP415-P22 | ~1:3 MeCN/toluene | 75° C. → 5° C.$^a$ | $1^b$ | — |
| PP415-P23 | 1:3 EtOAc/dioxane | 75° C. → 5° C.$^a$ | $1^b$ | — |
| PP415-P24 | 1BuOH | 75° C. → 5° C. | $2^b$ | 2 |

$^a$no precipitation after slow cooling and stirring at 5° C. for 2 days; evaporated solvent under $N_2$ flow at r.t.
$^b$the spectrum contains solvent signals d. Evaporation/Precipitation Experiments Clear solutions of PP415-P1 were prepared in three solvent mixtures (Table 15). The solvents were then slowly evaporated at r.t. under ambient conditions. However, in two of the three experiments (-P15 and -P17) white solid precipitated before evaporation began. The obtained solids were examined by FT-Raman spectroscopy and PXRD.

TABLE 15

Slow evaporation experiments with the amorphous form (PP415-P1)

| Sample | Solvent/Mixture | FT-Raman class | PXRD cluster |
|---|---|---|---|
| PP415-P15 | 1:2 DCM/IPE | 2[a] | 2 |
| PP415-P16 | 1:2 MeOH/toluene | 1[a] | — |
| PP415-P17 | 1:3 EtOAc/heptane | 2[a] | 2 |

[a] the spectrum contains solvent signals e. Drying Experiments

At least one sample of each class was dried under vacuum with the aim to desolvate the solvates and to obtain non-solvated crystalline forms of 63415 (Table 16). The dried materials were characterized further by FT-Raman, PXRD, and TG-FTIR.

TABLE 16

Drying experiments carried out on samples obtained from the crystallization experiments

| Sample | Starting Material (Class) | Conditions | Result |
|---|---|---|---|
| PP415-P18 | PP415-P15 (2) | r.t., 2-10 mbar, ~2 h | 2 |
| PP415-P19 | PP415-P17 (2) | r.t., 2-10 mbar, ~2 h | 2 |
| PP415-P25 | PP415-P6 (3) | r.t., ~3 mbar, ~5 d; 60° C., 5-10 mbar, 2 × 1 h; 40-50° C., 5-20 mbar, ~1 d | 3 |
| PP415-P26 | PP415-P13 (4) | r.t., ~3 mbar, ~5 d; 60° C., 5-10 mbar, 2 × 1 h; 40-50° C., 5-20 mbar, ~1 d | 4 |
| PP415-P27 | PP415-P14 (5) | r.t., ~3 mbar, ~5 d; 60° C., 5-10 mbar, 2 × 1 h; 40-50° C., 5-20 mbar, ~1 d | 1[a] |
| PP415-P28 | PP415-P21 (2) | r.t., ~3 mbar, ~5 d; 60° C., 5-10 mbar, 2 × 1 h; 40-50° C., 5-20 mbar, ~1 d | 2[b] |
| PP415-P30 | PP415-P7 (2) | 50-70° C., 1-10 mbar, 3 d | 2 |
| PP415-P32 | PP415-P19 (2) | 80° C., <1 × $10^{-3}$ mbar, 3 d | 2[b] |
| PP415-P33 | PP415-P25 (3) | 80° C., <1 × $10^{-3}$ mbar, 3 d | 3 |
| PP415-P34 | PP415-P28 (2) | 80° C., <1 × $10^{-3}$ mbar, 3 d | 2[b] |
| PP415-P36 | PP415-P35 (4) | 80° C., <1 × $10^{-3}$ mbar, 3 d | 4[c] |
| PP415-P37 | PP415-P35 (4) | 80° C., $N_2$ flow, 3 d | 4[c] |
| PP415-P44a | PP415-P41 (5) | 80° C., 100 mbar, 2 d | 1[a] |
| PP415-P46a | PP415-P45 (6) | 80° C., 100 mbar, 4 d | 1[a] |

[a] desolvation successful, significant reduction of solvent content, sample mainly amorphous; only few, broad peaks in PXRD
[b] sample less crystalline, as indicated by broader peaks in PXRD
[c] desolvation successful, significant reduction of solvent content, sample still crystalline; no change in structure 7. Characterization of New Forms (Classes)
a. Summary of New Classes In addition to the amorphous form of 63415, four new crystalline forms were obtained in this study (Table 17).

TABLE 17

Summary of obtained classes

| Class | Characteristics | Result of Drying Experiments |
|---|---|---|
| Class 1 | amorphous form | — |
| Class 2 | isostructural solvates (e.g., heptane) | drying unsuccessful |
| Class 3 | isostructural solvates (e.g., ethanol) | drying unsuccessful |
| Class 4 | MeCN solvate & desolvated solvate | drying successful, structure unchanged |
| Class 5 | THF solvate | drying resulted in amorphous form |

Class 2: Most crystallization experiments resulted in solid material of class 2. These samples likely correspond to isostructural, non-stoichiometric (<0.5 eq.) solvates (of heptane, cyclohexane, isopropyl ether, 1-butanol, triethylamine, and possibly hexane and other ethers, etc.) with tightly bound solvent molecules. The Raman spectra and PXRD patterns within this class are very similar to each other, thus the structures might be essentially identical with only small differences due to the different solvents that were incorporated.

Drying experiments on class 2 samples have not resulted in a crystalline, non-solvated form. Even elevated temperatures (80° C.) and a high vacuum (<1×$10^{-3}$ mbar) could not remove the tightly bound solvent molecules completely; a solvent content of >2 wt.-% always remained. The crystallinity of these samples is reduced, but neither transformation into a different structure nor substantial amorphization was observed.

Class 3: Solid material of class 3 was obtained from several crystallization experiments. The samples of class 3 are likely isostructural solvates of 2PrOH, EtOH, and probably acetone with tightly bound solvent molecules. They could correspond to either stoichiometric hemisolvates or non-stoichiometric solvates with a solvent content of ~0.5 eq. As with class 2, the Raman spectra and PXRD patterns within this class are very similar to each other, indicating similar structures that incorporate different solvents.

Similar to class 2, drying experiments were also unsuccessful. The very tightly bound solvent molecules could only partially be removed (~5.4 wt.-% to ~4.8 wt.-%, up to 3 d at 1×$10^{-3}$ mbar and 80° C.). The PXRD pattern remained unchanged.

Class 4: Material of class 4 was only obtained from a 7:3 MeCN/$H_2O$ solvent system. It most likely corresponds to a crystalline acetonitrile hemisolvate.

By drying (under vacuum or $N_2$ flow at elevated temperatures) most of the solvent could be removed without changing or destroying the crystal structure (PXRD remained unchanged). Thus, a crystalline, non-solvated form (or rather desolvated solvate) was obtained. It is slightly hygroscopic (mass gain of ~0.7 wt.-% from 50% r.h. to 85% r.h.) and has a possible melting point at 196.1° C. (ΔH=29.31 J/g).

Class 5: Class 5 was also obtained from only one solvent system (~1:1 THF/$H_2O$) and contains bound THF (and may be $H_2O$). As the content of the two components cannot be quantified separately, the exact nature of this crystalline solvate cannot be determined.

Drying of class 5 resulted in complete desolvation and transformation into the amorphous form (class 1). One possible process to prepare the amorphous form from class 2 material is a transformation of class 2 to class 5, followed by drying and amorphization.

b. Class 1—The Amorphous Form

Class 1, the amorphous form of 63415, was obtained from a few crystallization experiments (Table 18). Most crystallization experiments resulted in crystalline material of classes 2, 3, 4, or 5.

The starting material, PP415-P1, is amorphous and belongs to class 1. Further experiments, exclusively aimed at preparing the amorphous form (class 1), were carried out.

TABLE 18

Crystallization experiments resulting in solid material of class 1

| Sample | Method | Solvent | Characterization | Drying |
|---|---|---|---|---|
| PP415-P31 | susp. equil. | 9:1 PEG/$H_2O$ | Raman, PXRD | — |
| PP415-P22 | slow cooling[a] | ~1:3 MeCN/toluene | vis. obs., Raman | — |

TABLE 18-continued

Crystallization experiments resulting in solid material of class 1

| Sample | Method | Solvent | Characterization | Drying |
|---|---|---|---|---|
| PP415-P23 | slow cooling | 1:3 EtOAc/dioxane | vis. obs., Raman | — |
| PP415-P16 | evap./precip. | 1:2 MeOH/toluene | vis. obs., Raman | — |

[a] no precipitation after slow cooling and stirring at 5° C. for 2 days; evaporated solvent under N₂ flow at r.t.

c. Class 2—Isostructural Solvates (e.g., Heptane)

Most crystallization experiments resulted in solid material of class 2 (Table 19). In addition, one batch of a class 2 heptane solvate, PP415-P40, was used as starting material (see Table 8).

Figure 70:
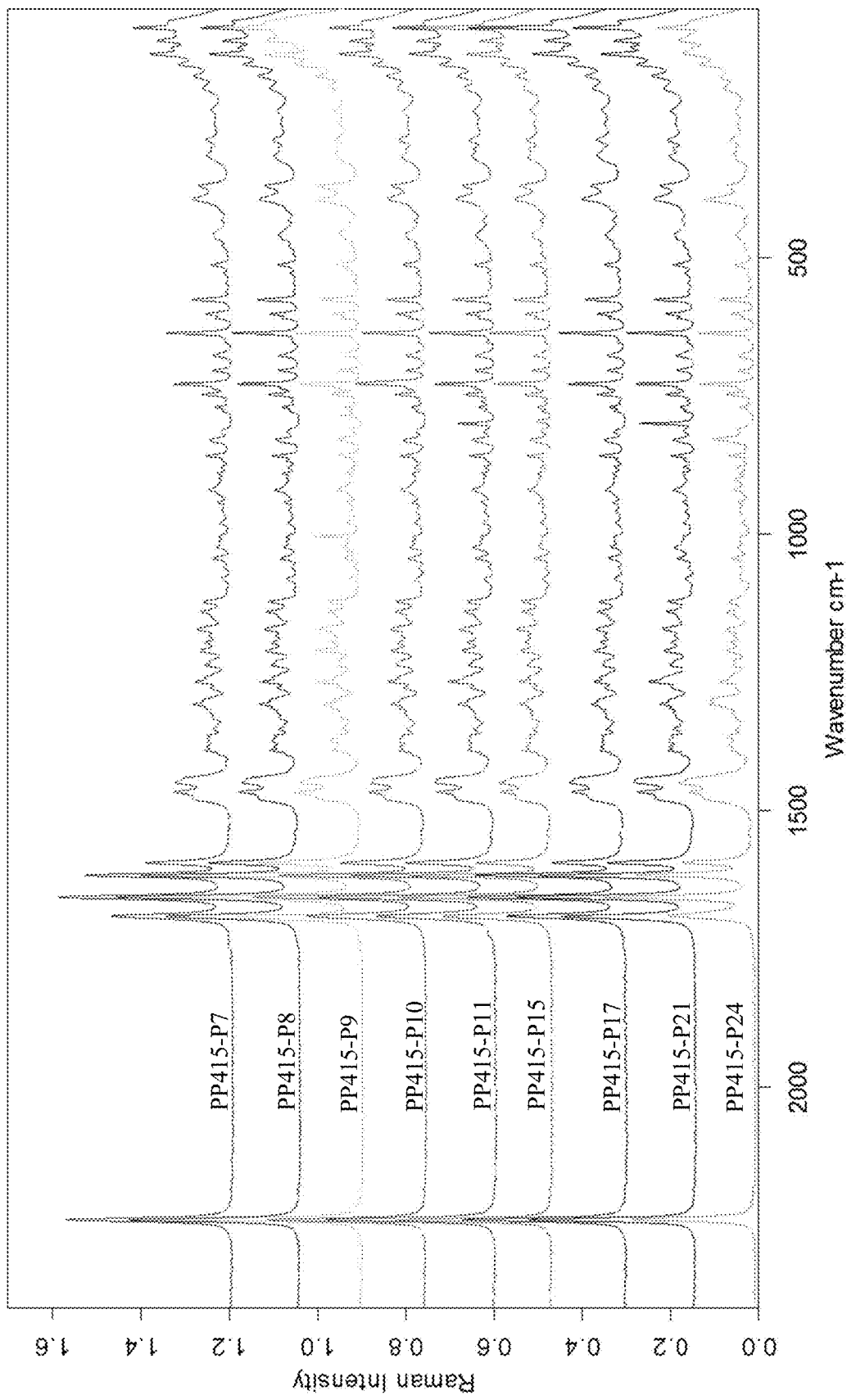
FIG. 70—FT-Raman spectra (2400-50 $cm^{-1}$) of samples of the solvate form (Class 2) (PP415-P7: top; PP415-P8: $2^{nd}$ from top; PP415-P9: $3^{rd}$ from top; PP415-P10: $4^{th}$ from top; PP415-P11: middle; PP415-P15: $4^{th}$ from bottom; PP415-P17: $3^{rd}$ from bottom; PP415-P21: $2^{nd}$ from bottom; PP415-P24: bottom). The spectra have been scaled and offset in the y-direction for the purpose of comparison.
Figure 71:
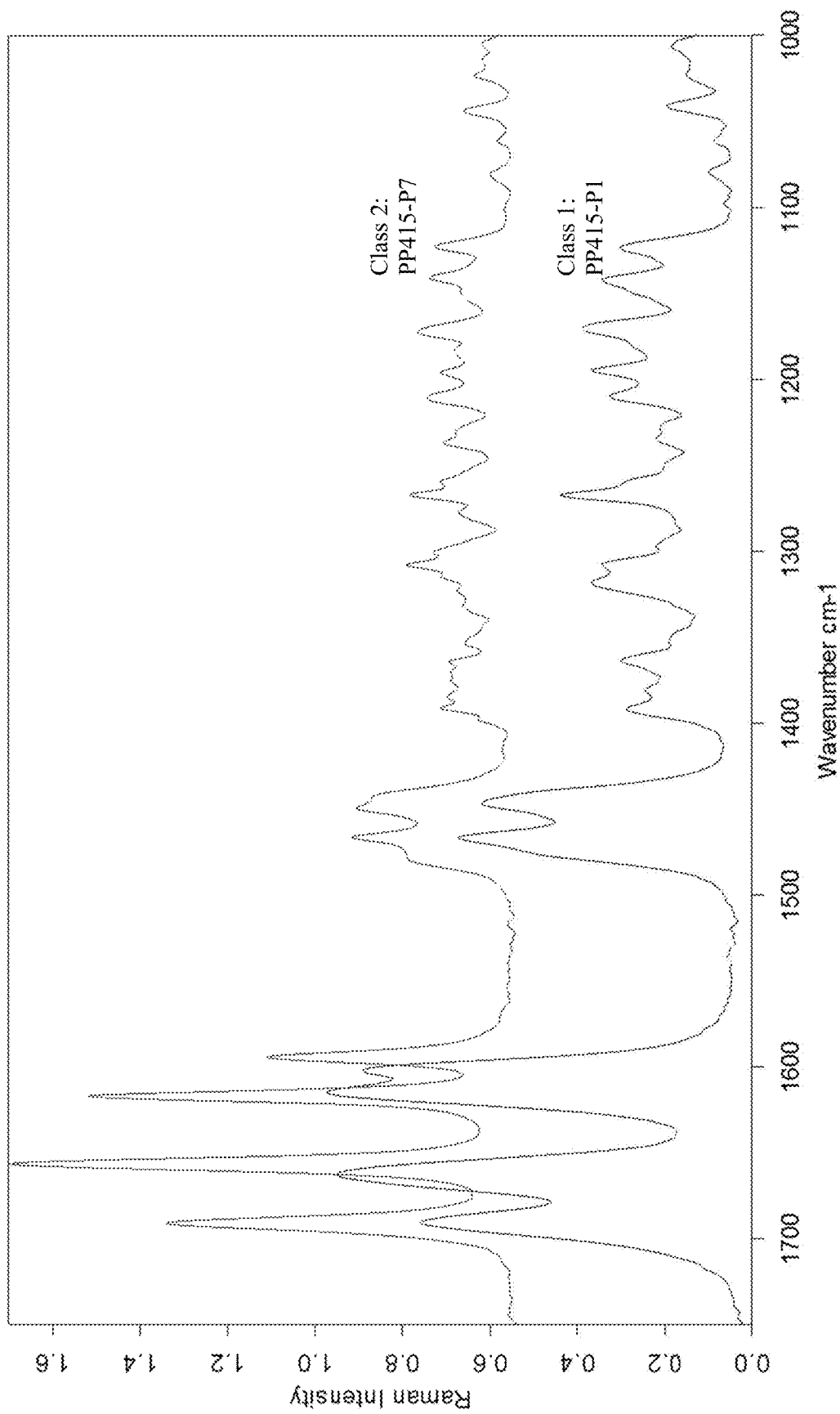
FIG. 71—FT-Raman spectrum (1750-1000 $cm^{-1}$) of the solvate form (Class 2) (PP415-P7: top) clearly differs from the spectrum of the amorphous form (Class 1) (PP415-P1: bottom). The spectra have been scaled and offset in the y-direction for the purpose of comparison.
Figure 72:
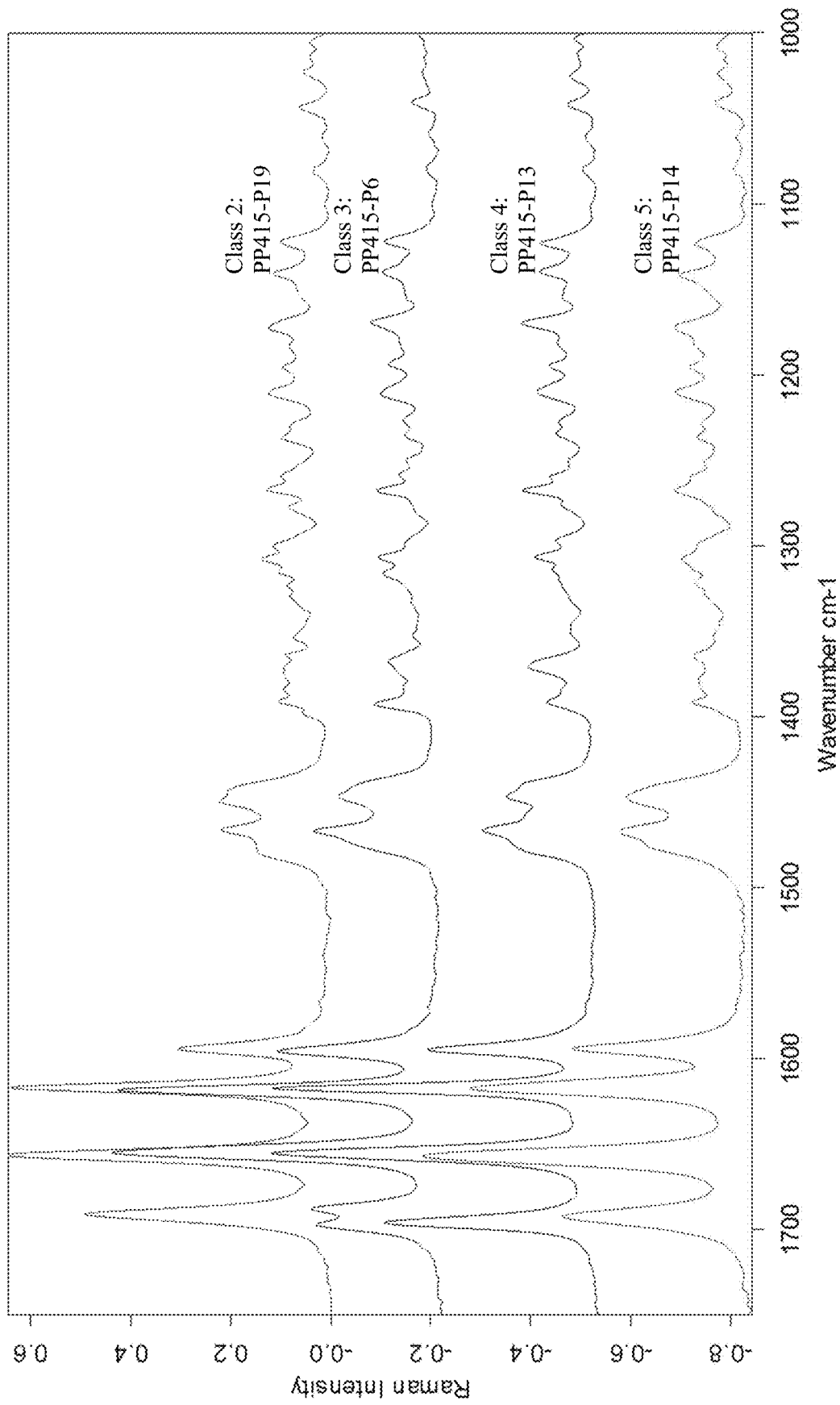
FIG. 72—FT-Raman spectra (1750-1000 $cm^{-1}$) of class 2 (sample PP415-P19: top), class 3 (sample PP415-P6: $2^{nd}$ from top), class 4 (sample PP415-P13: $2^{nd}$ from bottom), and class 5 (sample PP415-P14: bottom) differ significantly from each other. The spectra have been scaled and offset in the y-direction for the purpose of comparison.

The FT-Raman spectra of class 2 are clearly similar to each other (FIG. 70) but show small differences. They differ significantly from the spectrum of the amorphous starting material, class 1 (FIG. 71) and from the spectra of classes 3, 4, and 5 (FIG. 72).

Figure 73:
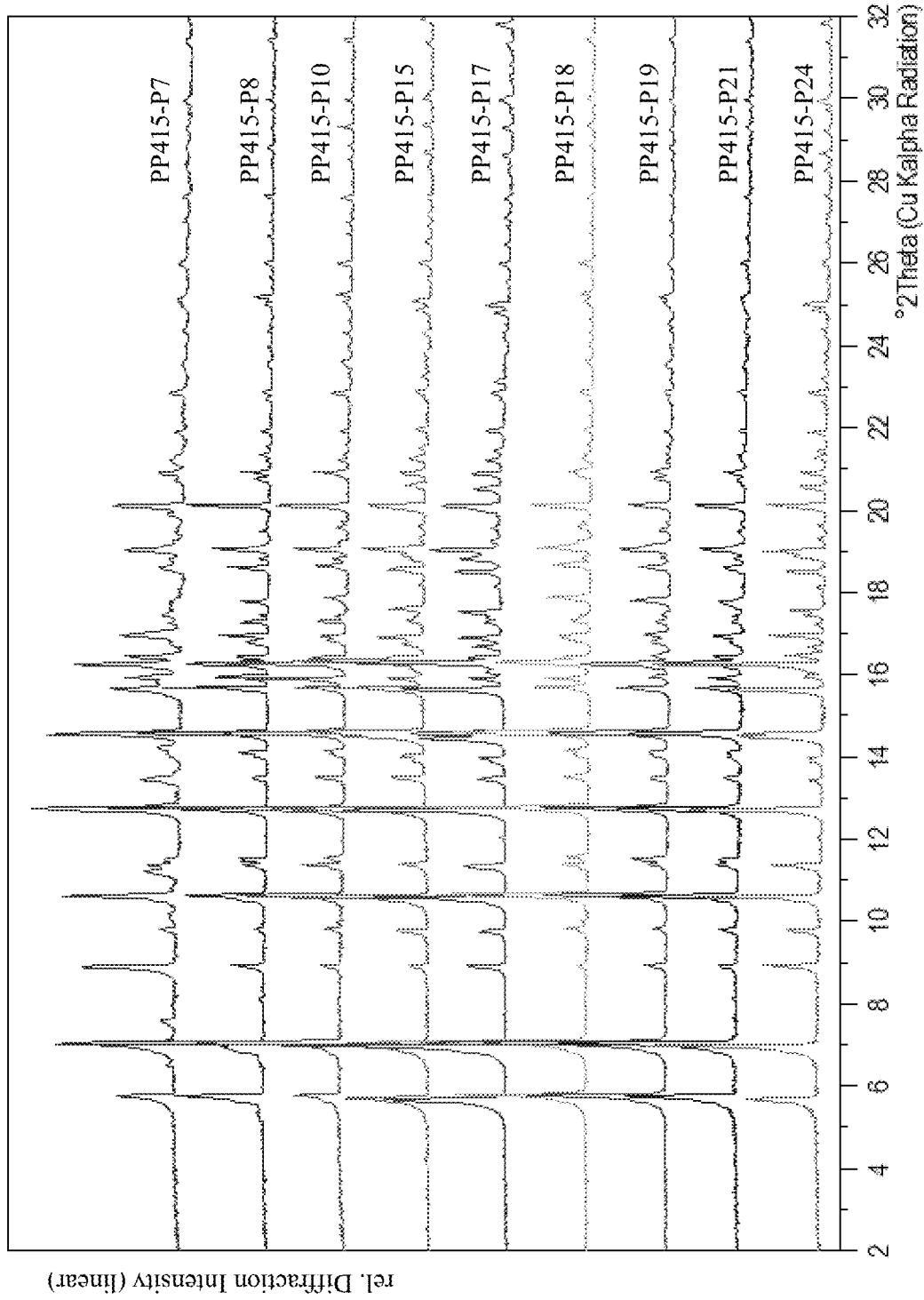
FIG. 73—PXRD patterns (2-32° 2θ) of samples of the solvate form (Class 2) (PP415-P7: top; PP415-P8: $2^{nd}$ from top; PP415-P10: $3^{rd}$ from top; PP415-P15: $4^{th}$ from top; PP415-P17: middle; PP415-P18: $4^{th}$ from bottom; PP415-P19: $3^{rd}$ from bottom; PP415-P21: $2^{nd}$ from bottom; PP415-P24: bottom). The patterns have been scaled and offset in the y-direction for the purpose of comparison.
Figure 74:
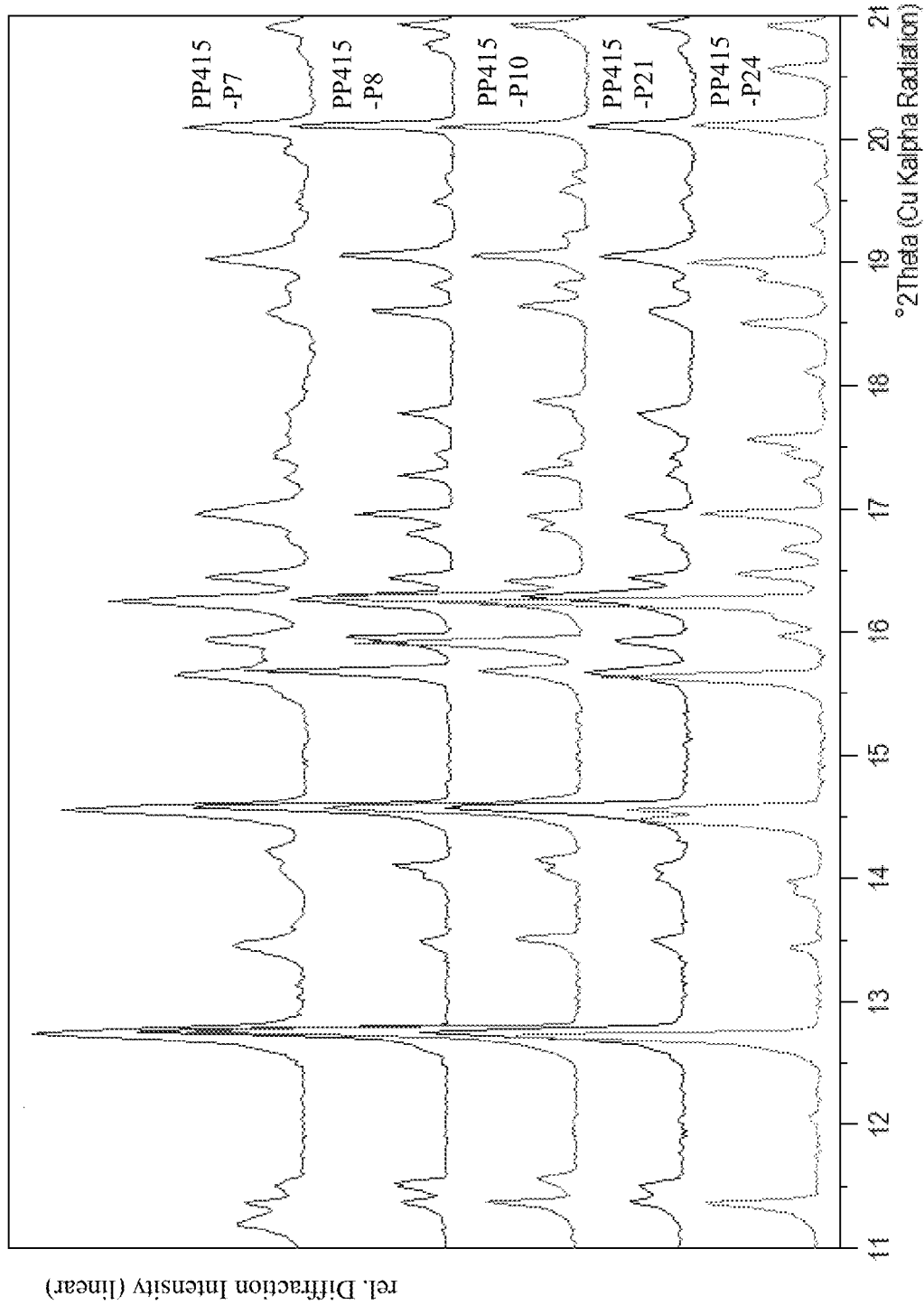
FIG. 74—PXRD patterns (11-21° 2θ) of some samples of the solvate form (Class 2) (PP415-P7: top; PP415-P8: $2^{nd}$ from top; PP415-P10: middle; PP415-P21: $2^{nd}$ from bottom; PP415-P24: bottom). The patterns have been scaled and offset in the y-direction for the purpose of comparison.
Figure 75:
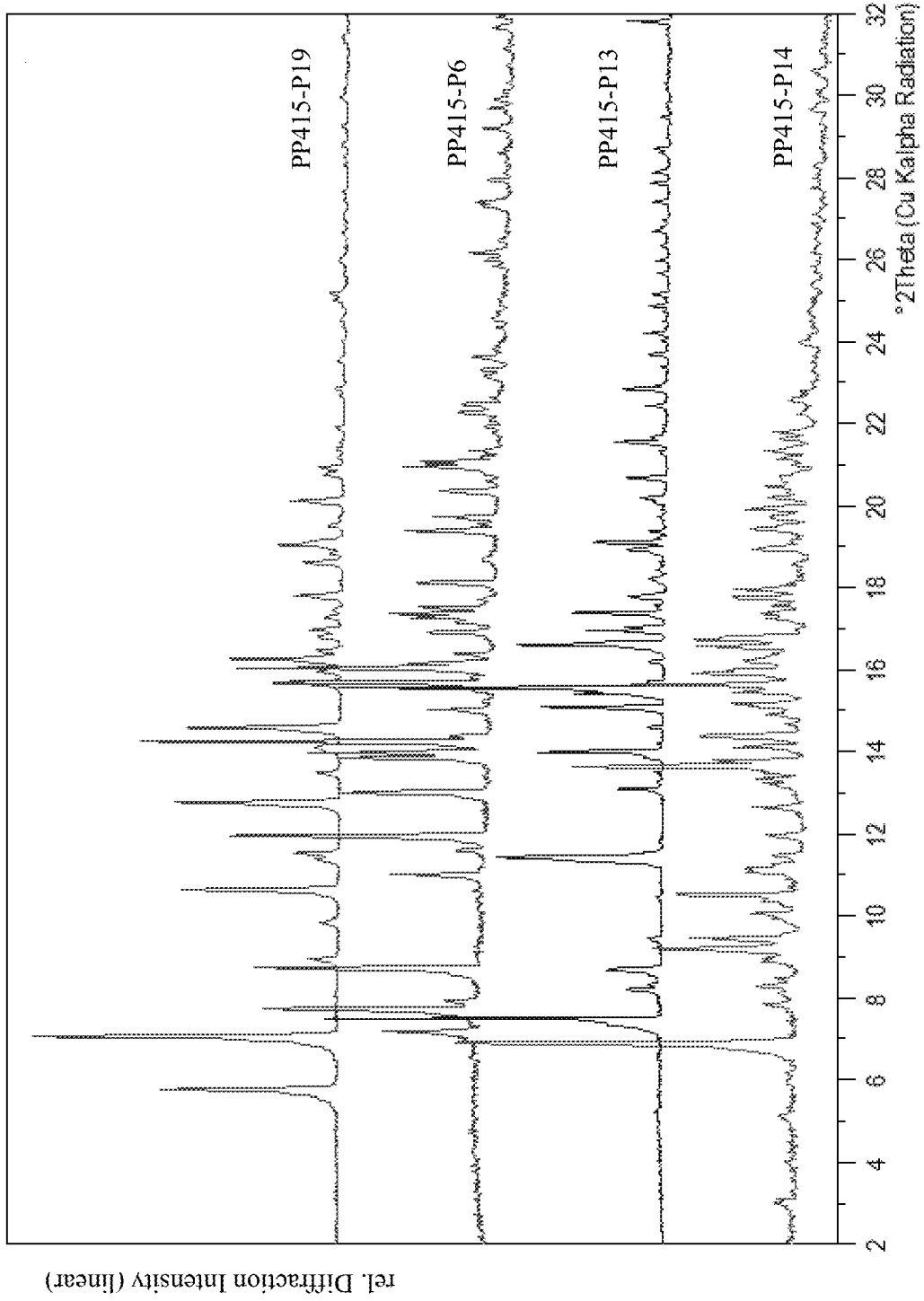
FIG. 75—PXRD patterns (2-32° 2θ) of class 2 (sample PP415-P19: top), class 3 (sample PP415-P6: $2^{nd}$ from top), class 4 (sample PP415-P13: $2^{nd}$ from bottom), and class 5 (sample PP415-P14: bottom) are distinctly different. The patterns have been scaled and offset in the y-direction for the purpose of comparison.

The PXRD patterns of class 2 (FIG. 73) confirm the crystallinity of the materials. The patterns of the samples are very similar to each other but show small differences (FIG. 74). The class 2 patterns differ clearly from the patterns of classes 3, 4, and 5 (FIG. 75).

Figure 76:
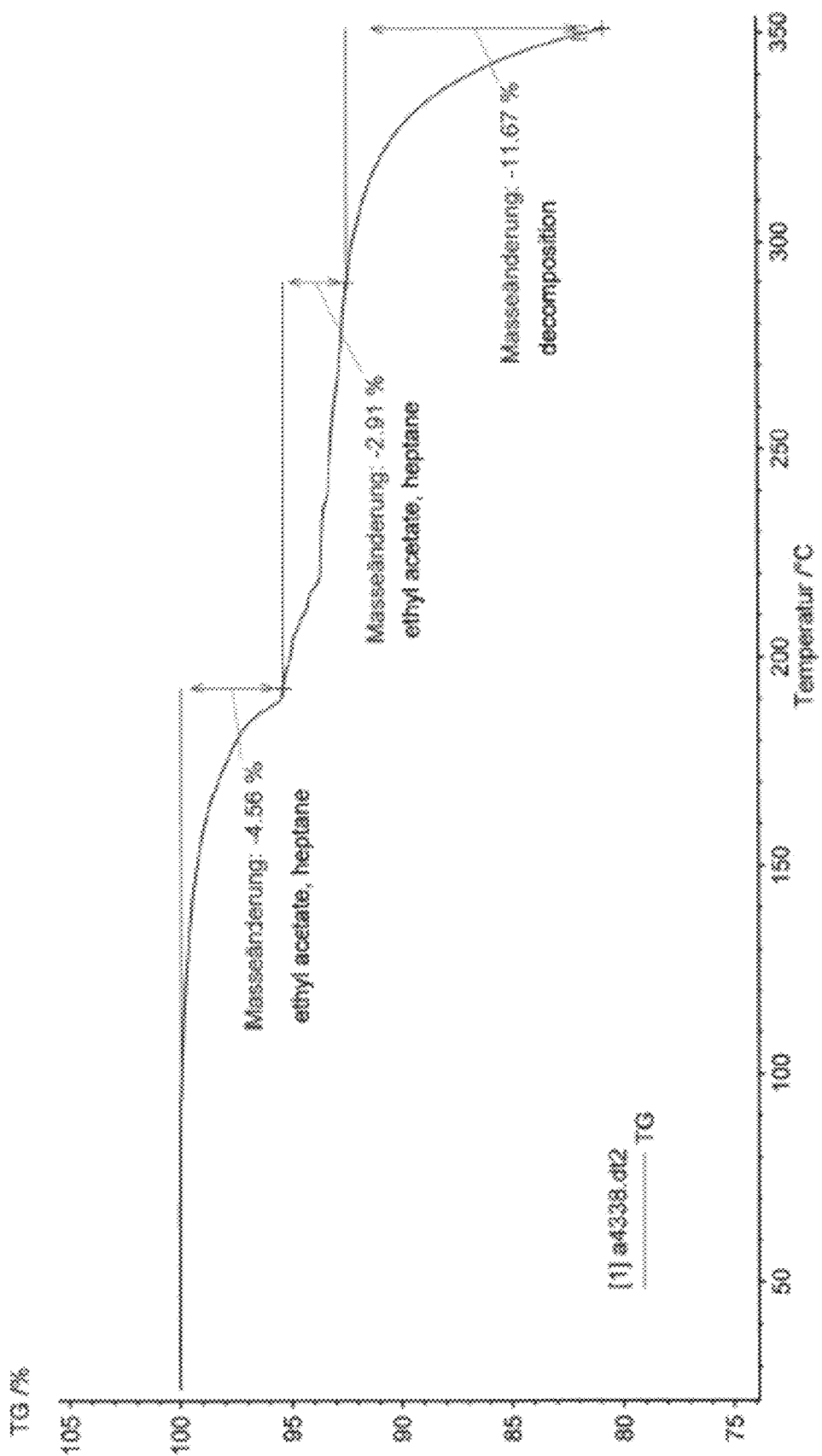
FIG. 76—TG-FTIR thermogram of the sample PP415-P7, which corresponds to a solvate form (Class 2).

The TG-FTIR thermogram of sample PP415-P7 (FIG. 76) shows the loss of ~7.5 wt.-% EtOAc and heptane in two steps from ~100° C. to 290° C. and decomposition at temperatures T>290° C. Before the TG-FTIR experiments, the samples were dried briefly (for ~5 min) under vacuum (10-20 mbar) to remove excess, unbound solvent. The loss of both EtOAc and heptane occur together in the same temperature range; both solvents seem tightly bound within the structure. The theoretical EtOAc content (b.p.=76° C.) of a hemisolvate is 7.4 wt.-%, the theoretical heptane content (b.p.=98° C.) of a hemisolvate is 8.3 wt.-%. Unfortunately, the content of the two components cannot be quantified separately.

Figure 77:
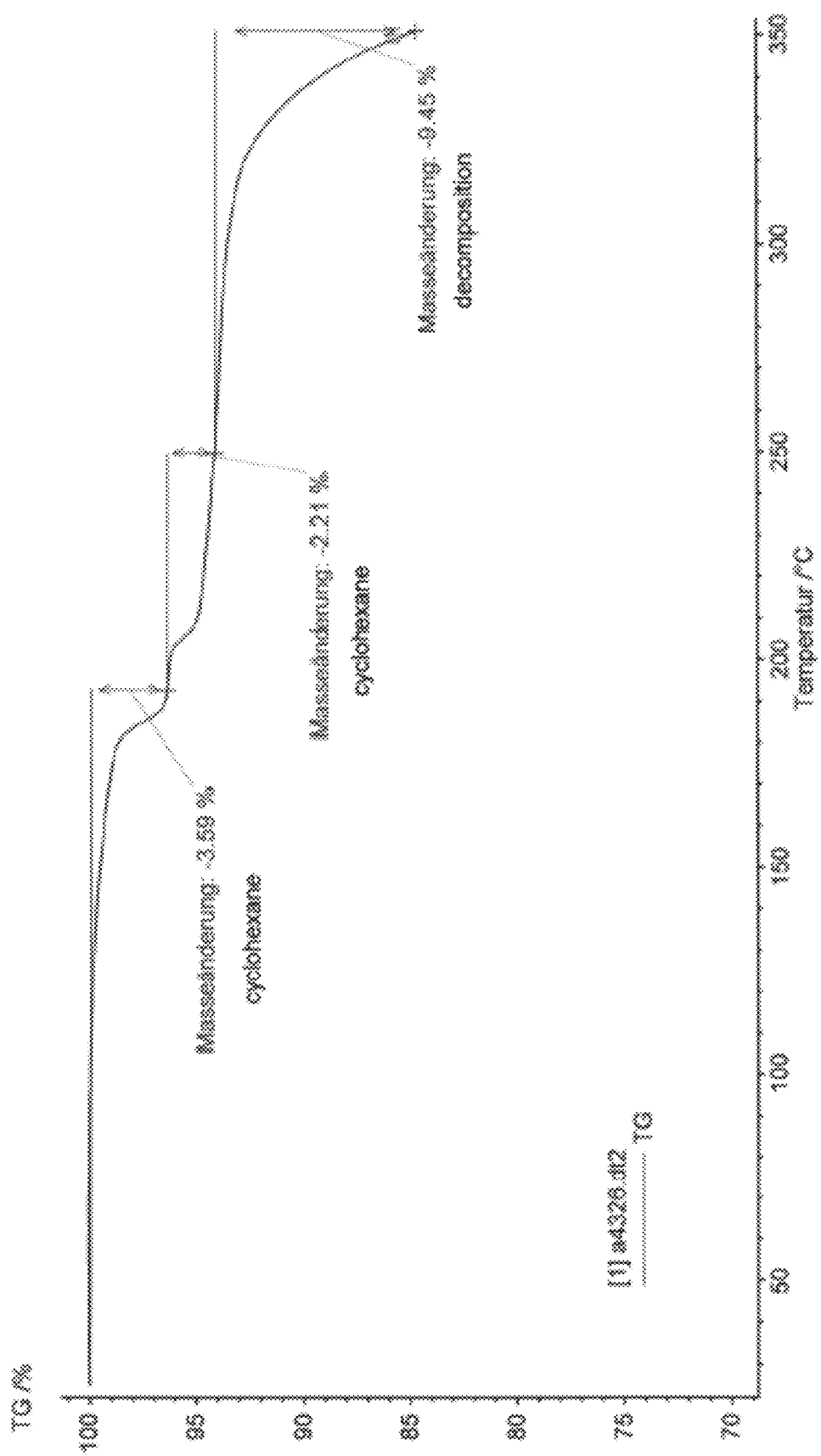
FIG. 77—TG-FTIR thermogram of the sample PP415-P21, which corresponds to a solvate form (Class 2).

The TG-FTIR thermogram of sample PP415-P21 (FIG. 77) shows the loss of ~5.8 wt.-% cyclohexane in two steps from ~140° C. to ~250° C. and decomposition at temperatures T>250° C. With the boiling point of cyclohexane at 81° C., the solvent seems tightly bound within the structure. The theoretical cyclohexane content of a hemisolvate is 7.1 wt.-%. Thus, sample PP415-P18 possibly corresponds to a non-stoichiometric cyclohexane solvate (with <0.5 eq. solvent content).

Figure 78:
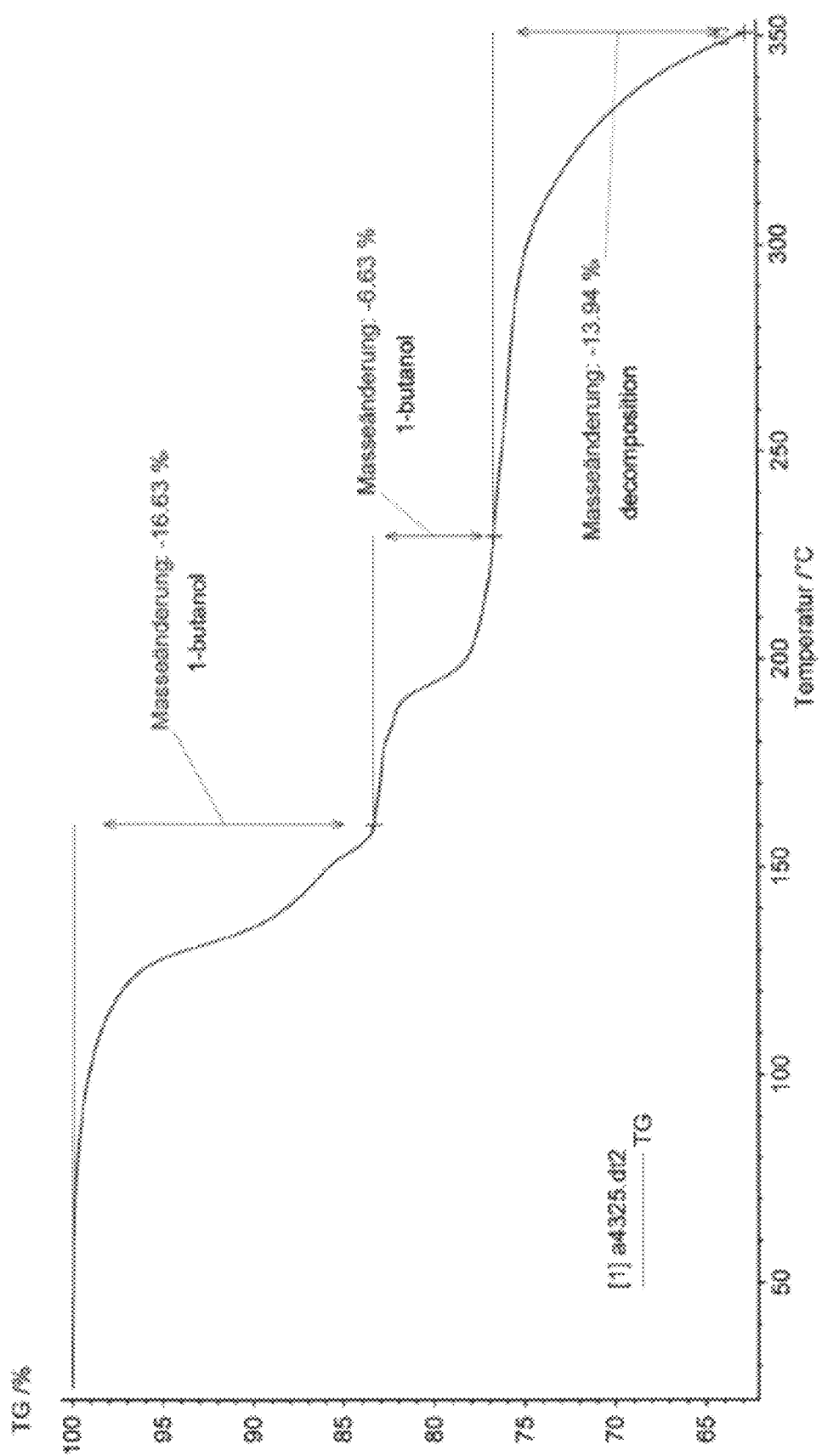
FIG. 78—TG-FTIR thermogram of the sample PP415-P24, which corresponds to a solvate form (Class 2).

The TG-FTIR thermogram of sample PP415-P24 (FIG. 78) shows the loss of ~16.6 wt.-% 1BuOH in a step from ~50° C. to ~160° C., further loss of 1BuOH (6.6 wt.-%) in a second step from 160° C. to 230° C. and decomposition at temperatures T>230° C. With the boiling point of 1BuOH at 117° C., the solvent of at least the second step seems tightly bound within the structure. The theoretical 1BuOH content of a hemisolvate is 6.3 wt.-%.

Figure 79:
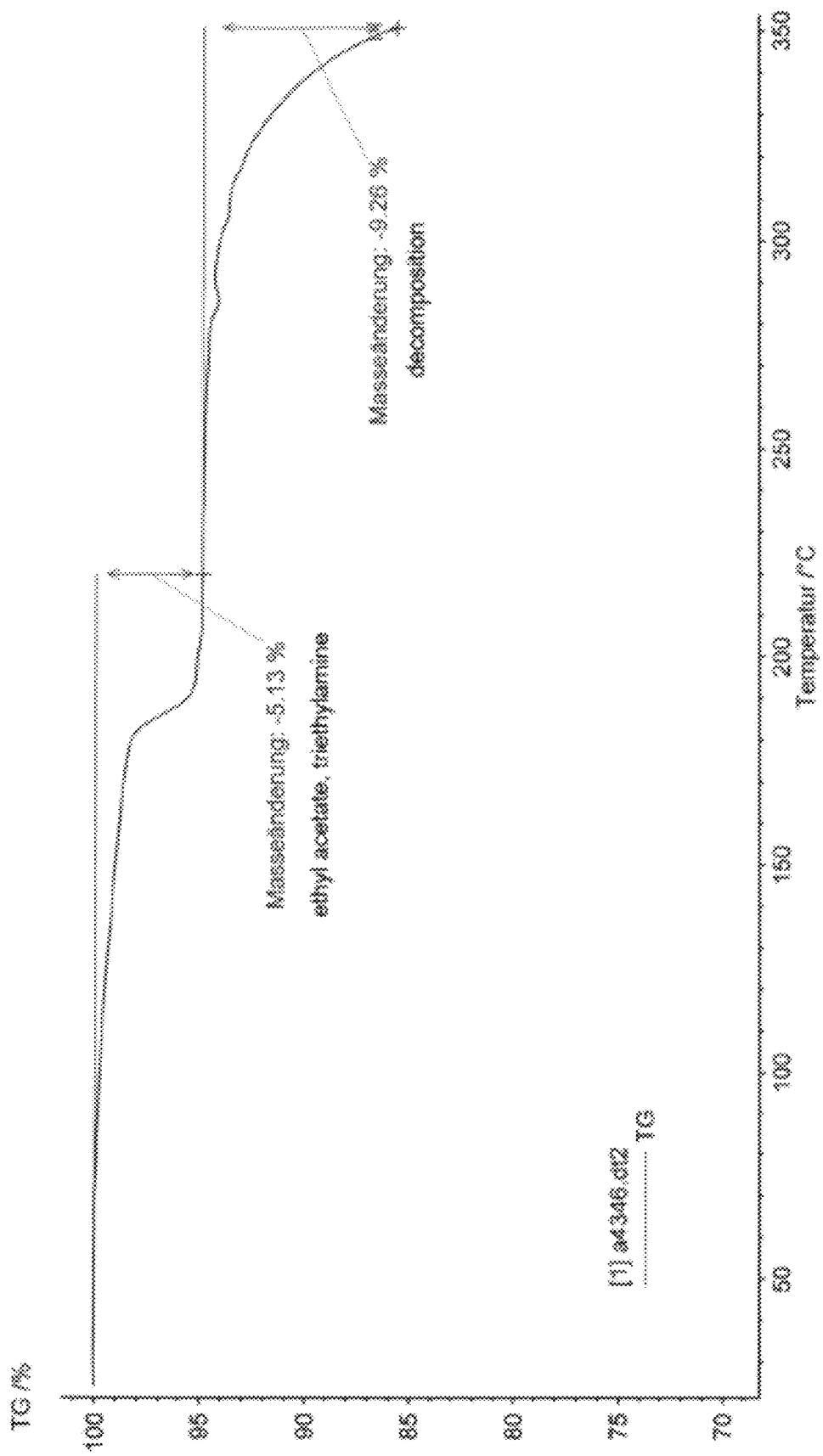
FIG. 79—TG-FTIR thermogram of the sample PP415-P29, which corresponds to a solvate form (Class 2).

The TG-FTIR thermogram of sample PP415-P29 (FIG. 79) shows the loss of ~5.1 wt.-% EtOAc and TEA from ~50° C. to ~220° C., most of it in a step from 180° C. to 210° C. Decomposition occurs at temperatures T>220° C. The loss of both EtOAc and TEA occur together in the same temperature range; both solvents seem tightly bound within the structure (with the boiling point of EtOAc at 77° C. and of TEA at 89° C.).

Figure 80:
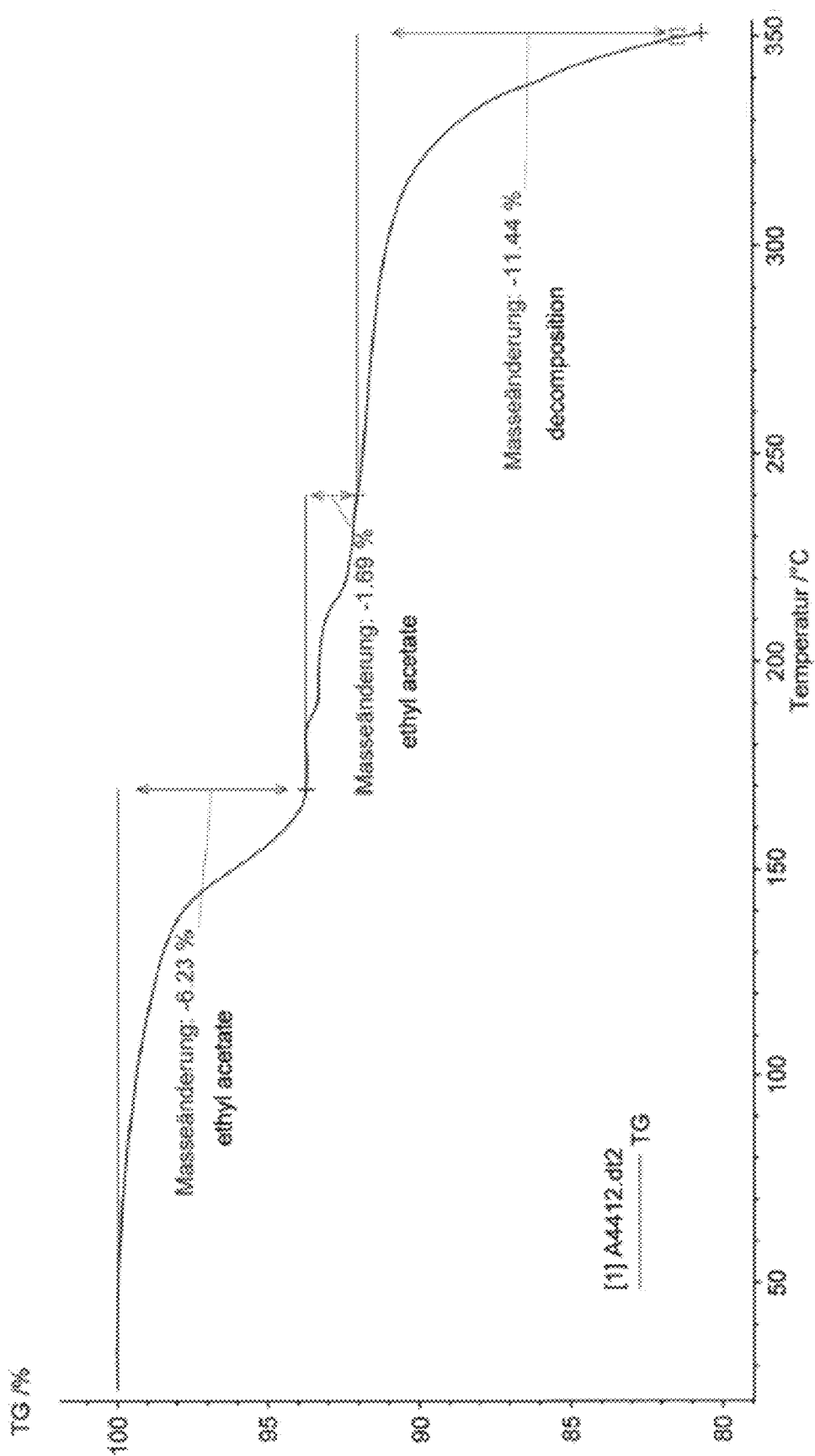
FIG. 80—TG-FTIR thermogram of the sample PP415-P47, which corresponds to a solvate form (Class 2).

The TG-FTIR thermogram of sample PP415-P47 (FIG. 80) shows the typical two-step mass loss for class 2 (total of ~7.9 wt.-% EtOAc) at temperatures up to 240° C., indicating very tightly bound solvent molecules.

Figure 81:
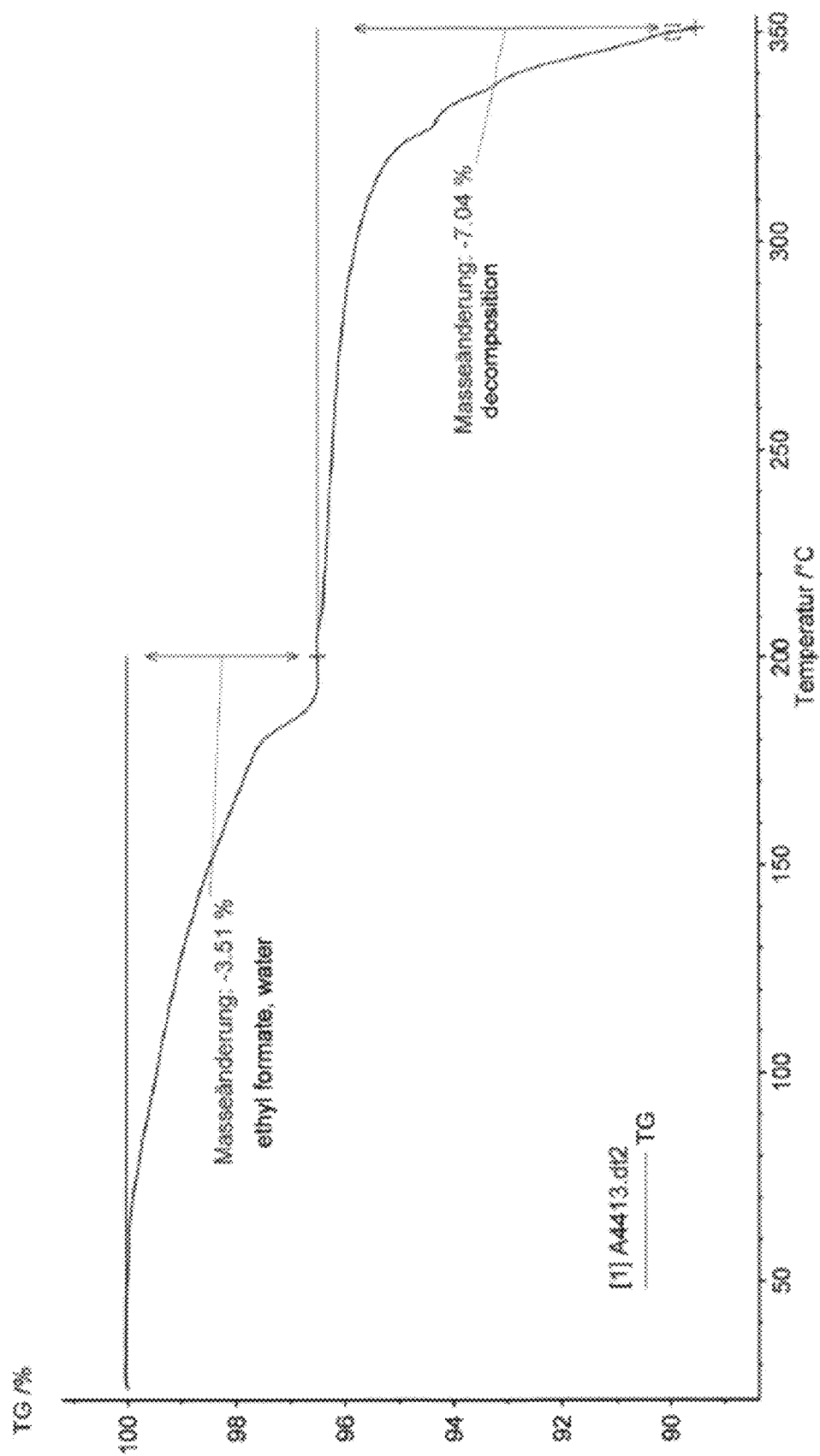
FIG. 81—TG-FTIR thermogram of the sample PP415-P48, which corresponds to a solvate form (Class 2).

The TG-FTIR thermogram of sample PP415-P48 (FIG. 81) shows the mass loss of ~3.5 wt.-% ethyl formate and water, at first gradually and then in a clear step between 180° C. and 200° C. There might be further loss of ethyl formate concomitant with the decomposition at T>240° C.

Thus, the samples of class 2 might all correspond to non-stoichiometric (<0.5 eq.), isostructural solvates with tightly bound solvent molecules. As the Raman spectra and PXRD patterns within this class are very similar to each other, the structures might be essentially identical to each other with only small distortions of the unit cell dimensions or small changes of atomic positions within the unit cell, due to the different sizes and shapes of the incorporated solvent molecules.

TABLE 19

Crystallization experiments resulting in solid material of class 2

| Sample | Method | Solvent | Characterization | Drying |
|---|---|---|---|---|
| PP415-P7 | susp. equil. | 1:2 EtOAc/heptane | Raman, PXRD, TG-FTIR | x |
| PP415-P8 | susp. equil. | 1:2 acetone/hexane | Raman, PXRD | — |
| PP415-P9 | susp. equil. | 1:3 toluene/DEE | Raman, PXRD | — |
| PP415-P10 | susp. equil. | 1:3 MeOH/TBME | Raman, PXRD | — |
| PP415-P11 | susp. equil. | 1:2 MEK/cyclohexane | Raman | — |
| PP415-P29 | susp. equil. | EtOAc/TEA | Raman, PXRD, TG-FTIR | — |
| PP415-P15 | evap./precip. | 1:2 DCM/IPE | Raman, PXRD | x |
| PP415-P17 | evap./precip. | 1:3 EtOAc/heptane | Raman, PXRD | x |
| PP415-P21 | slow cooling | ~1:5 EtOH/cyclohexane | Raman, PXRD, TG-FTIR | x |
| PP415-P24 | evap./precip. | 1BuOH | Raman, PXRD, TG-FTIR | — |
| PP415-P43[a] | evaporation | (8:2) THF/hexane | PXRD | — |
| PP415-P47[a] | evaporation | EtOAc | PXRD, TG-FTIR | — |
| PP415-P48[a] | evaporation | ethyl formate | PXRD, TG-FTIR | — |

[a] starting material: PP415-P40, class 2; in all other experiments PP415-P1, class 1, was used as starting material.

d. Drying Experiments on Samples of Class 2

Several samples of class 2 were dried under vacuum (and some at elevated temperatures) and in an attempt to desolvate them with the aim to obtain an anhydrous form of 63415. Details and characterizations of the dried samples are provided below in Table 20.

However, even drying for three days at 80° C. and a vacuum <1×10⁻³ mbar could not remove the tightly bound solvent molecules completely; a solvent content of >2 wt.-% remained (see samples -P32 and -P34). The PXRD patterns show a reduced crystallinity of these samples, but no transformation into a different structure was observed.

TABLE 20

Drying experiments on class 2 samples

| Starting Material | | Drying | Dried Material | | |
|---|---|---|---|---|---|
| Sample | Solvent Content | Conditions | Sample | Solvent Content | Class |
| PP415-P7 | EtOAc/heptane (~7.5%) | 50-70° C., 1-10 mbar, 3 d | PP415-P30 | heptane (~2.5%) | 2 |
| PP415-P15 | IPE (unknown) | r.t., 2-10 mbar, ~2 h | PP415-P18 | IPE (~7.0%) | 2 |
| PP415-P17 | EtOAc(?)/ heptane (unknown) | r.t., 2-10 mbar, ~2 h | PP415-P19 | heptane (~7.6%) | 2 |
| PP415-P19 | heptane (~7.6%) | 80° C., <1 × 10⁻³ mbar, 3 d | PP415-P32 | heptane (~2.2%) | 2[a] |

TABLE 20-continued

Drying experiments on class 2 samples

| Starting Material | | Drying | Dried Material | | |
|---|---|---|---|---|---|
| Sample | Solvent Content | Conditions | Sample | Solvent Content | Class |
| PP415-P21 | cyclohexane (~5.8%) | r.t., ~3 mbar, ~5 d; 60° C., 5-10 mbar, 2 × 1 h; 40-50° C., 5-20 mbar, ~1 d | PP415-P28 | cyclohexane (~3.0%) | 2[a] |
| PP415-P28[a] | cyclohexane (~3.0%) | 80° C., <1 × 10$^{-3}$ mbar, 3 d | PP415-P34 | cyclohexane (~2.3%) | 2[a] |

[a]according to PXRD somewhat less crystalline

Thus, the class 2 solvates seem to have very tightly bound solvent molecules. They are difficult to desolvate or transform/amorphize.

e. Pp415-P7→Pp415-P30

The solid material of sample PP415-P7, class 2, obtained from a suspension equilibration experiment in 1:2 EtOAc/heptane was dried (as PP415-P30) under vacuum for several days (1-10 mbar, 50-70° C.).

Figure 82:
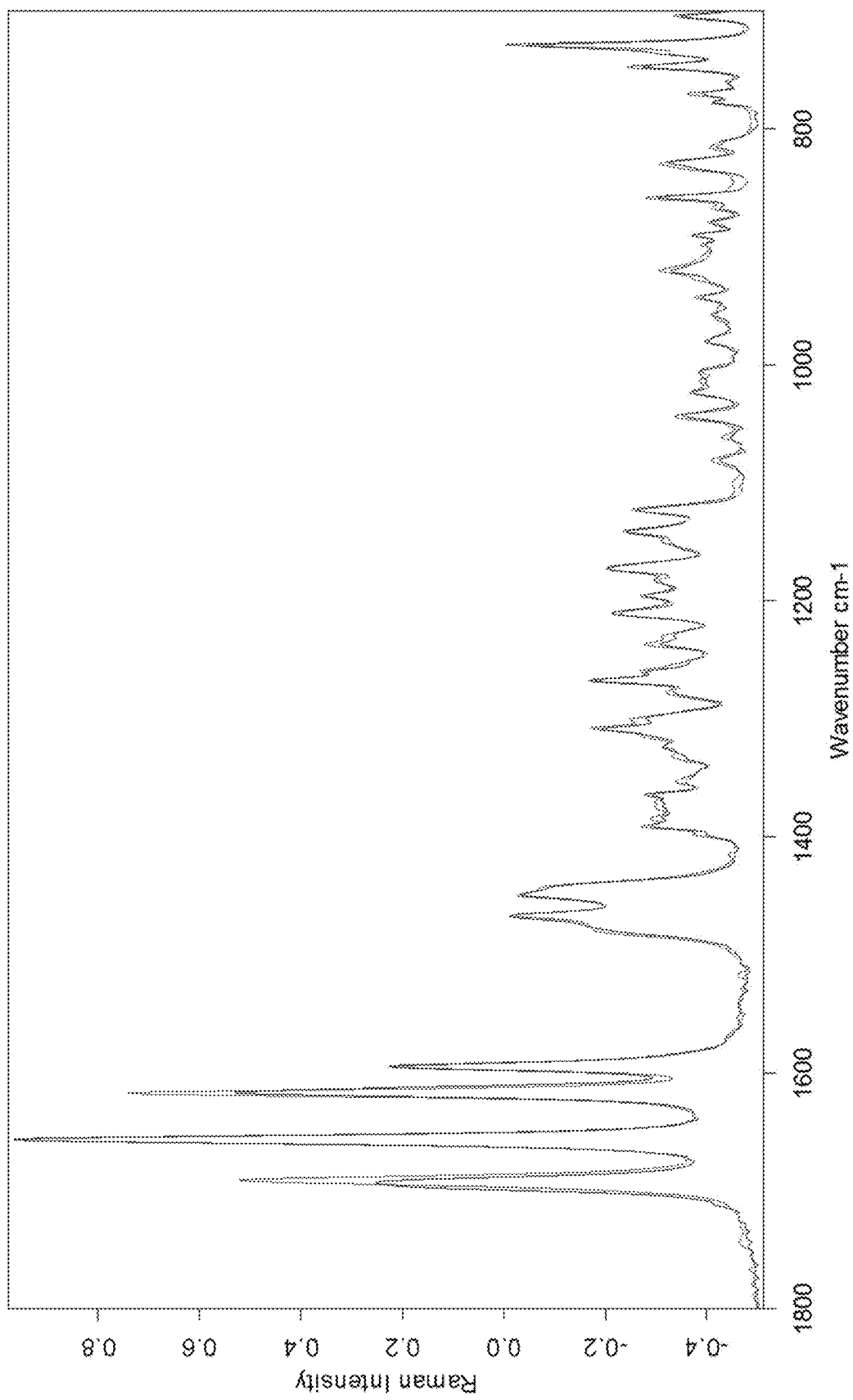
FIG. 82—FT-Raman spectra (1800-700 $cm^1$) of the solvate form (Class 2) (bottom, sample PP415-P7) and of the dried solvate form (Class 2) (top, sample PP415-P30) are similar and show only small differences which can hardly be distinguished within the graph. The spectra are scaled for the purpose of comparison.

The FT-Raman spectrum of the dried class 2 material (PP415-P30) shows small differences from the original spectrum (sample PP415-P7, FIG. 82) but still corresponds to class 2.

Figure 83:
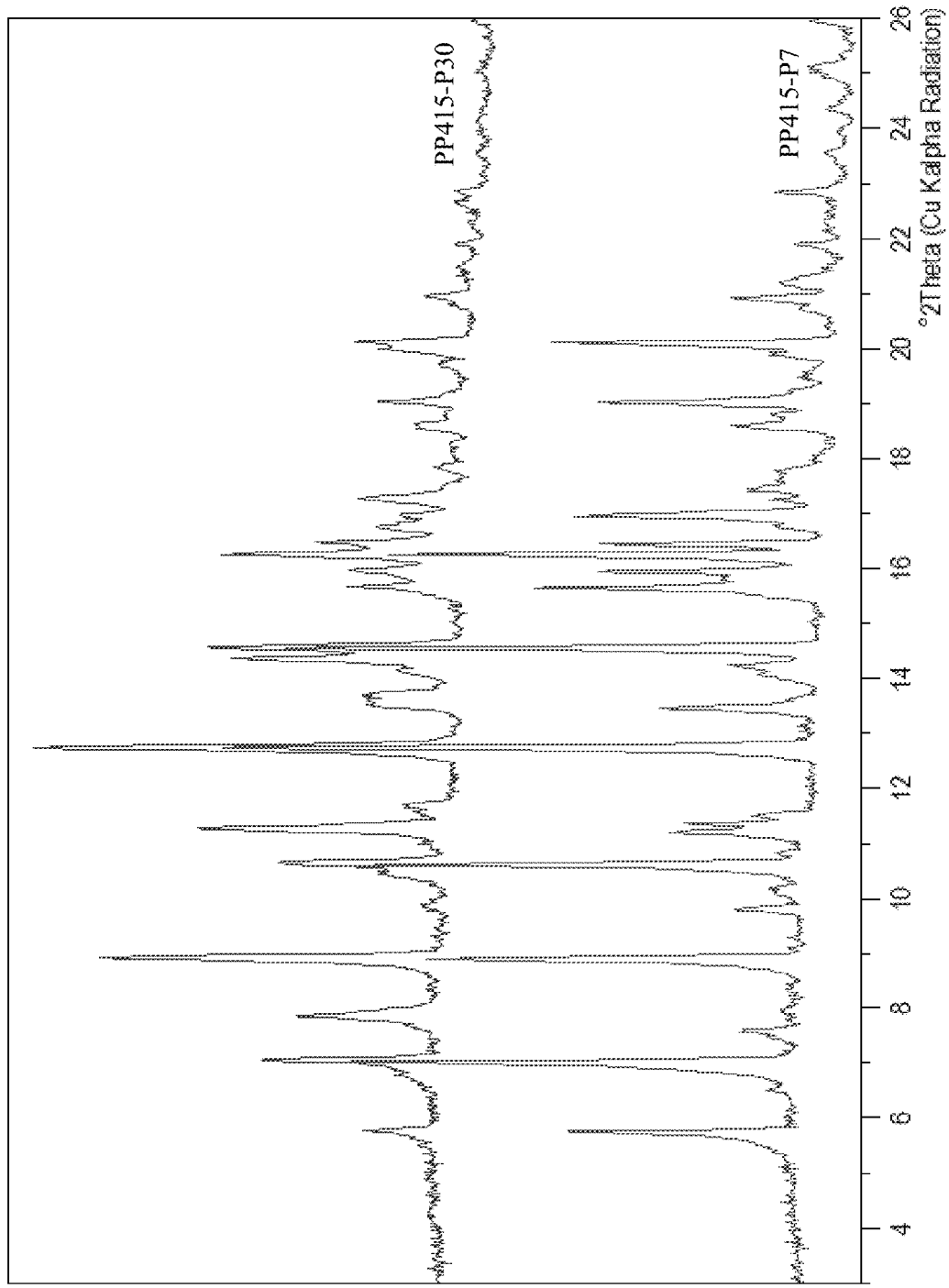
FIG. 83—PXRD pattern of the dried solvate form (Class 2), sample PP415-P30 (top) in comparison to the pattern of the solvate form (Class 2), sample PP415-P7 (bottom). The patterns are not scaled but are offset in the y-direction for the purpose of comparison.

The PXRD pattern of the dried class 2 material (PP415-P30) shows slightly broader, less intense peaks (FIG. 83) but still corresponds to class 2.

Figure 84:
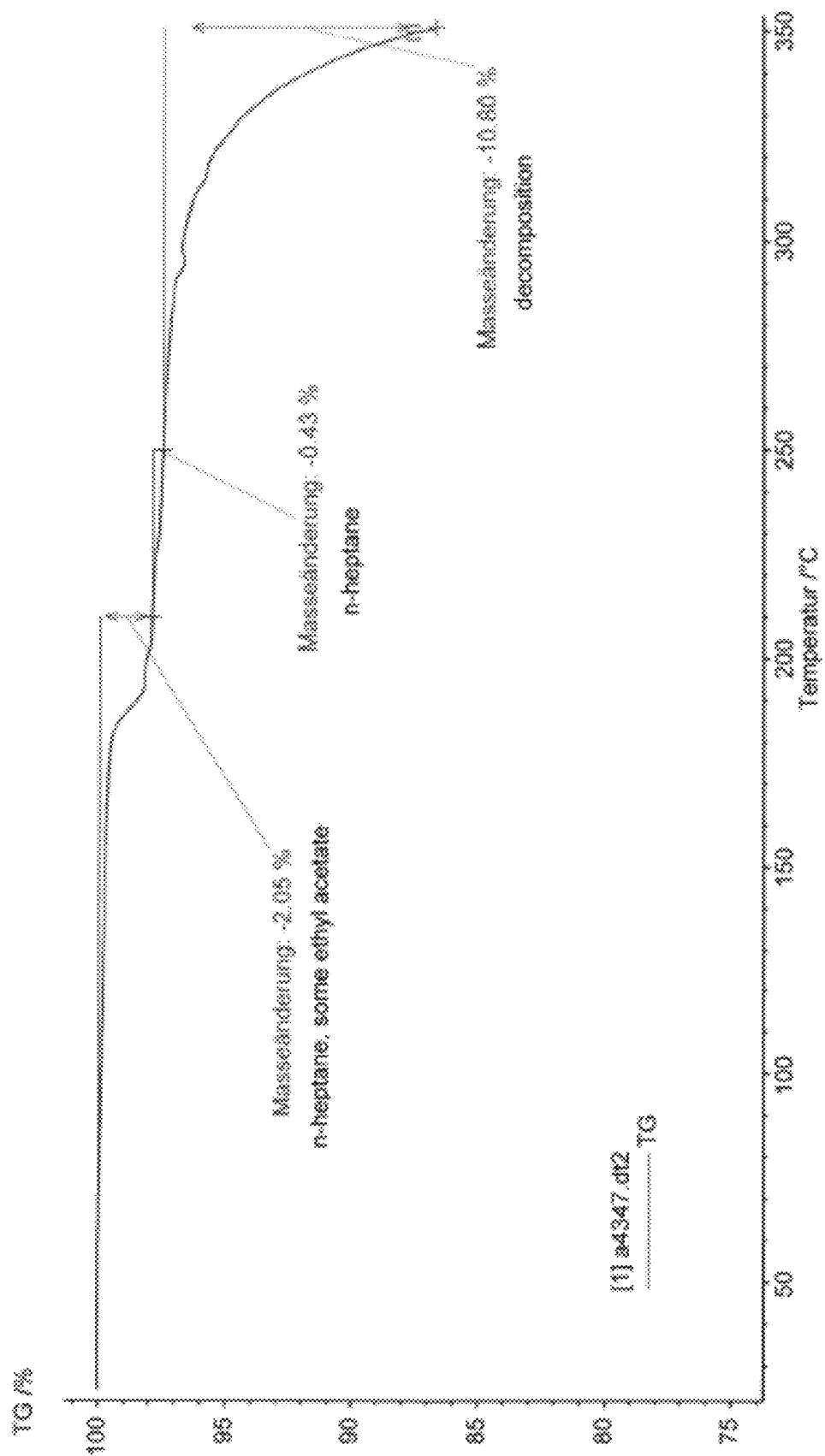
FIG. 84—TG-FTIR thermogram of the dried sample PP415-P30, which corresponds to a solvate form (Class 2).

The TG-FTIR thermogram of the dried sample PP415-P30 (FIG. 84) shows the loss of ~2.5 wt.-% heptane (and some EtOAc) in two steps from ~50° C. to ~250° C. and decomposition at temperatures T>250° C. Compared to the TG-FTIR of sample PP415-P7 (FIG. 76), the two steps of solvent loss are preserved, but the total amount of solvent in the sample has decreased from ~7.5 wt.-% in PP415-P7 to ~2.5 wt.-% in PP415-P30.

Thus, the attempt to desolvate this solvate at elevated temperatures (50-70° C.) and a vacuum of 1-10 mbar) has caused only a partial loss of solvent.

f. Pp415-P15→Pp415-P18

The solid material of sample PP415-P15, class 2, obtained from a precipitation experiment in 1:2 DCM/IPE was dried (as PP415-P18) under vacuum (~2-20 mbar) at r.t. for ~2 h.

Figure 85:
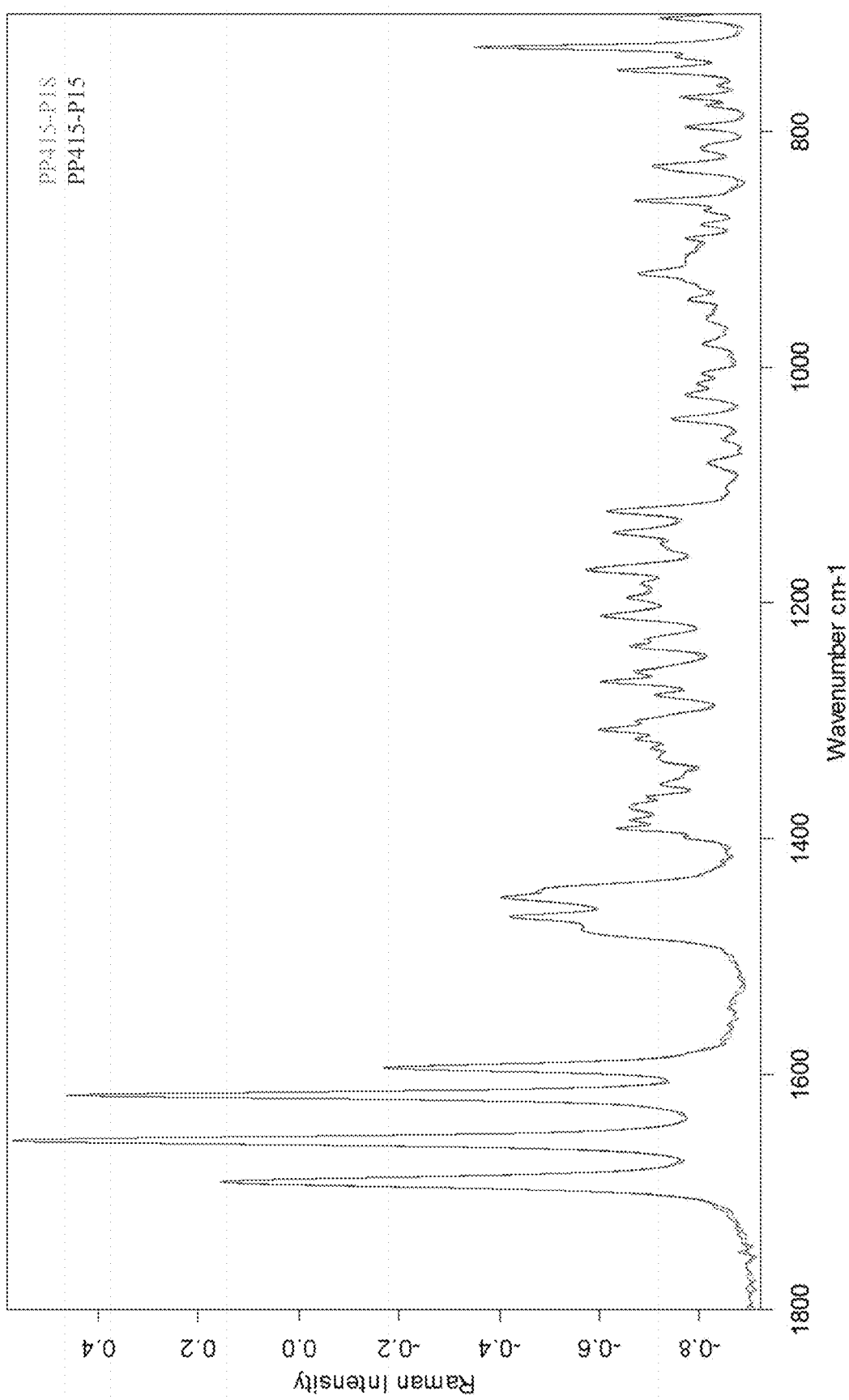
FIG. 85—FT-Raman spectrum of the dried sample PP415-P18 (light grey) is identical to the spectrum of the original sample PP415-P15 (dark grey) are similar and show only small differences which can hardly be distinguished within the graph. The spectra have been scaled for the purpose of comparison.

The FT-Raman spectrum of PP415-P18 is identical to the spectrum of sample PP415-P15 (FIG. 85), both correspond to class 2.

Figure 86:
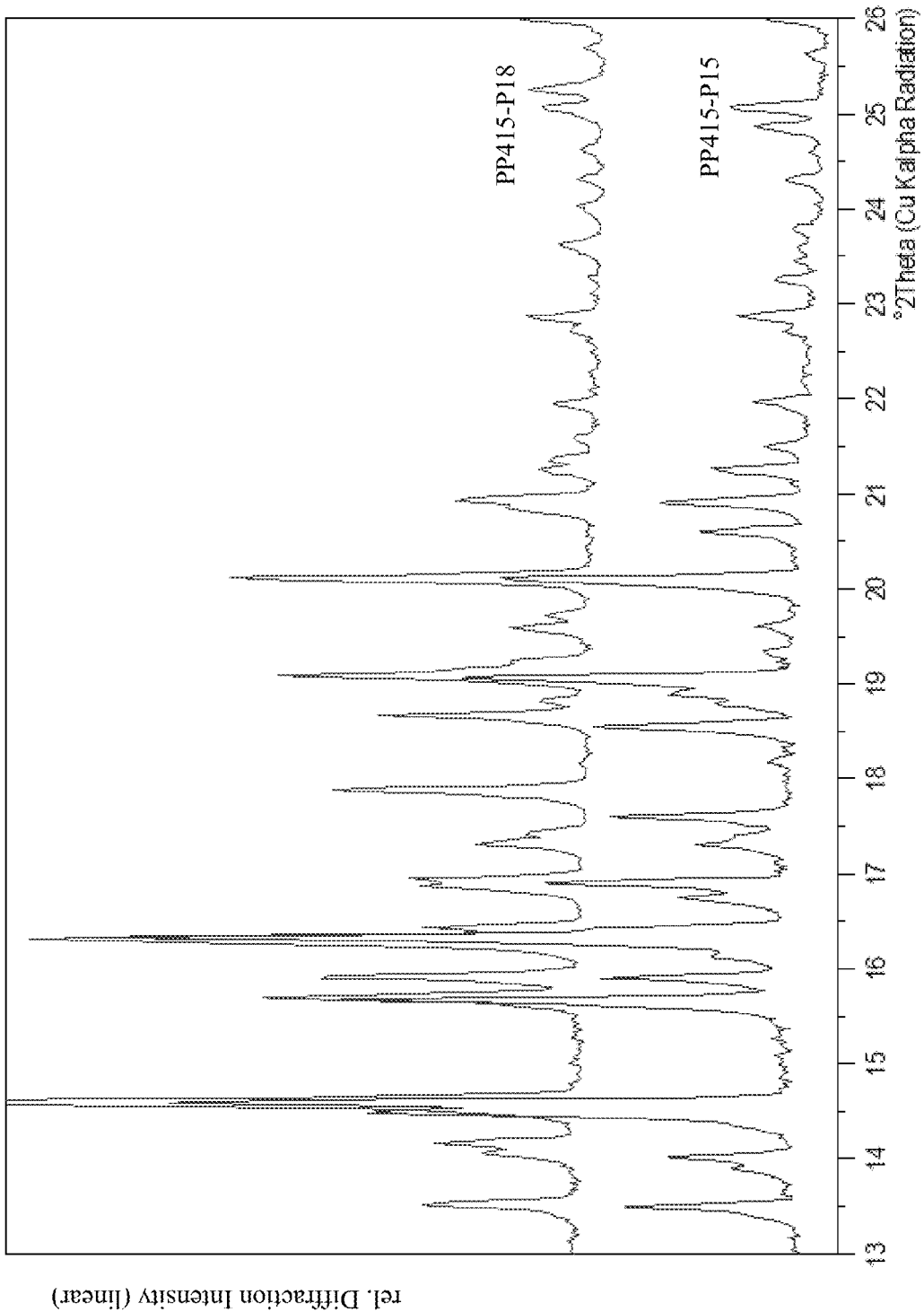
FIG. 86—PXRD pattern of the dried sample PP415-P18 (top) shows small differences from the pattern of the original sample PP415-P15 (bottom), although both solvate forms (Class 2). The patterns have been scaled and offset in the y-direction for the purpose of comparison.

The PXRD pattern of PP415-P18 shows small differences to the pattern of PP415-P15 (FIG. 86). PP415-P18 still corresponds to class 2.

Figure 87:
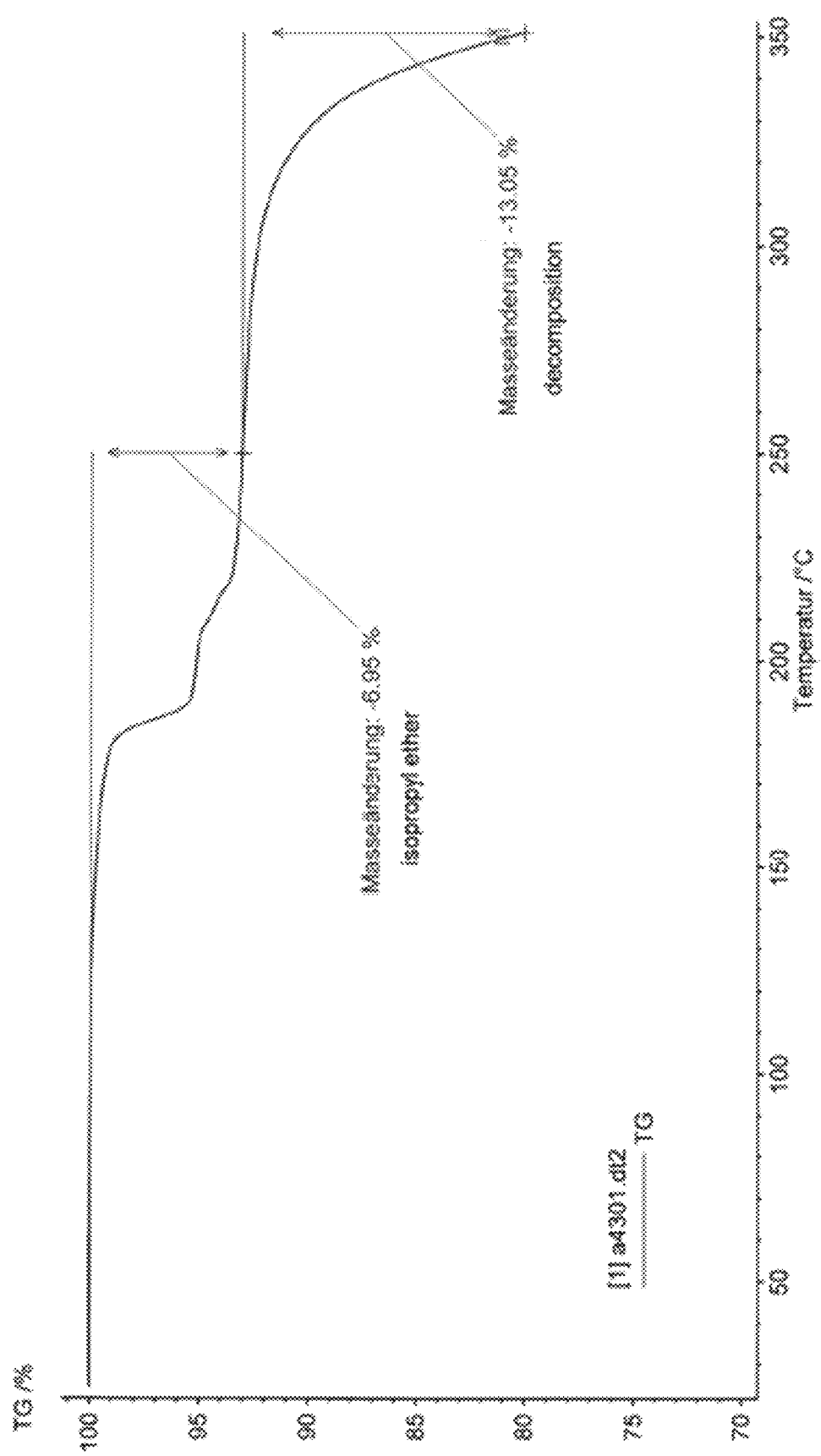
FIG. 87—TG-FTIR thermogram of the sample PP415-P18, which corresponds to a solvate form (Class 2).

The TG-FTIR thermogram (FIG. 87) shows the loss of ~7.0 wt.-% IPE in two steps from ~140° C. to ~250° C. and decomposition at temperatures T>250° C. With the boiling point of IPE being 67° C., the solvent seems tightly bound within the structure. The theoretical IPE content of a hemisolvate is 8.4 wt.-%.

Unfortunately, no TG-FTIR was recorded of the material before the drying step. However, as the solvent seems so tightly bound into the structure and no (or only small) changes are observed in the FT-Raman spectra and PXRD patterns, it is assumed that the drying has had no significant effect on structure or solvent content.

g. Pp415-P17→Pp415-P19→Pp415-P32

The solid material of sample PP415-P17, class 2, obtained from a precipitation experiment in 1:3 EtOAc/heptane was dried (as PP415-P19) under vacuum (~2-20 mbar) at r.t. for ~2 h.

The FT-Raman spectrum of PP415-P19 is identical to the spectrum of sample PP415-P17 (FIG. 88); no changes can be observed, and both correspond to class 2.

Figure 89:
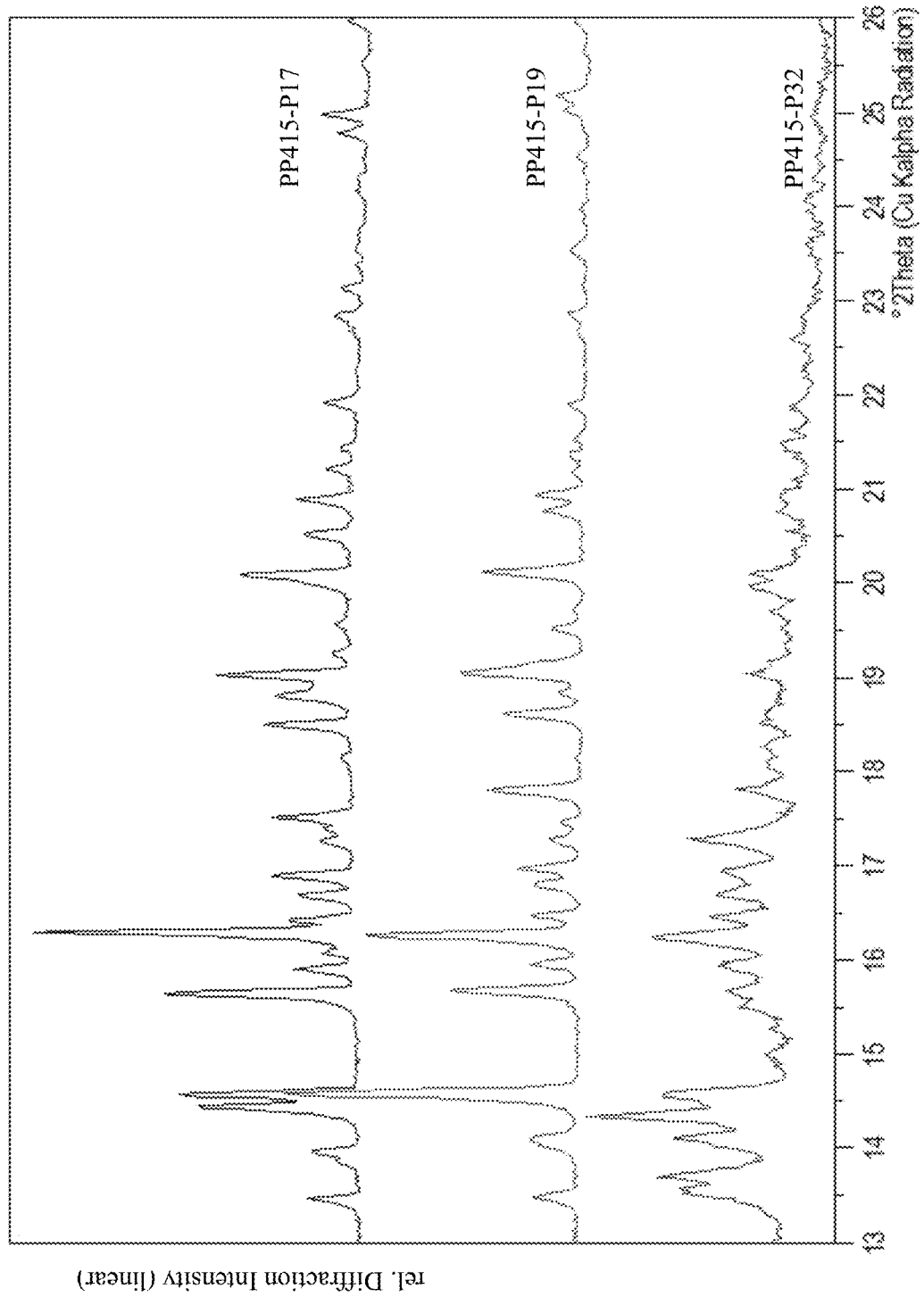
FIG. 89—PXRD pattern of the dried sample PP415-P19 (middle) is different from the pattern of the original sample PP415-P17 (top) but still corresponds to class 2 form. The pattern of the further dried sample PP415-P32 (bottom) shows broader peaks with a lower S/N ratio. The material is less crystalline, but still corresponds to class 2 form. The patterns have been scaled and offset in the y-direction for the purpose of comparison.

The PXRD pattern of PP415-P19 differs slightly from the pattern of PP415-P17 (FIG. 89) but still corresponds to class 2.

Figure 90:
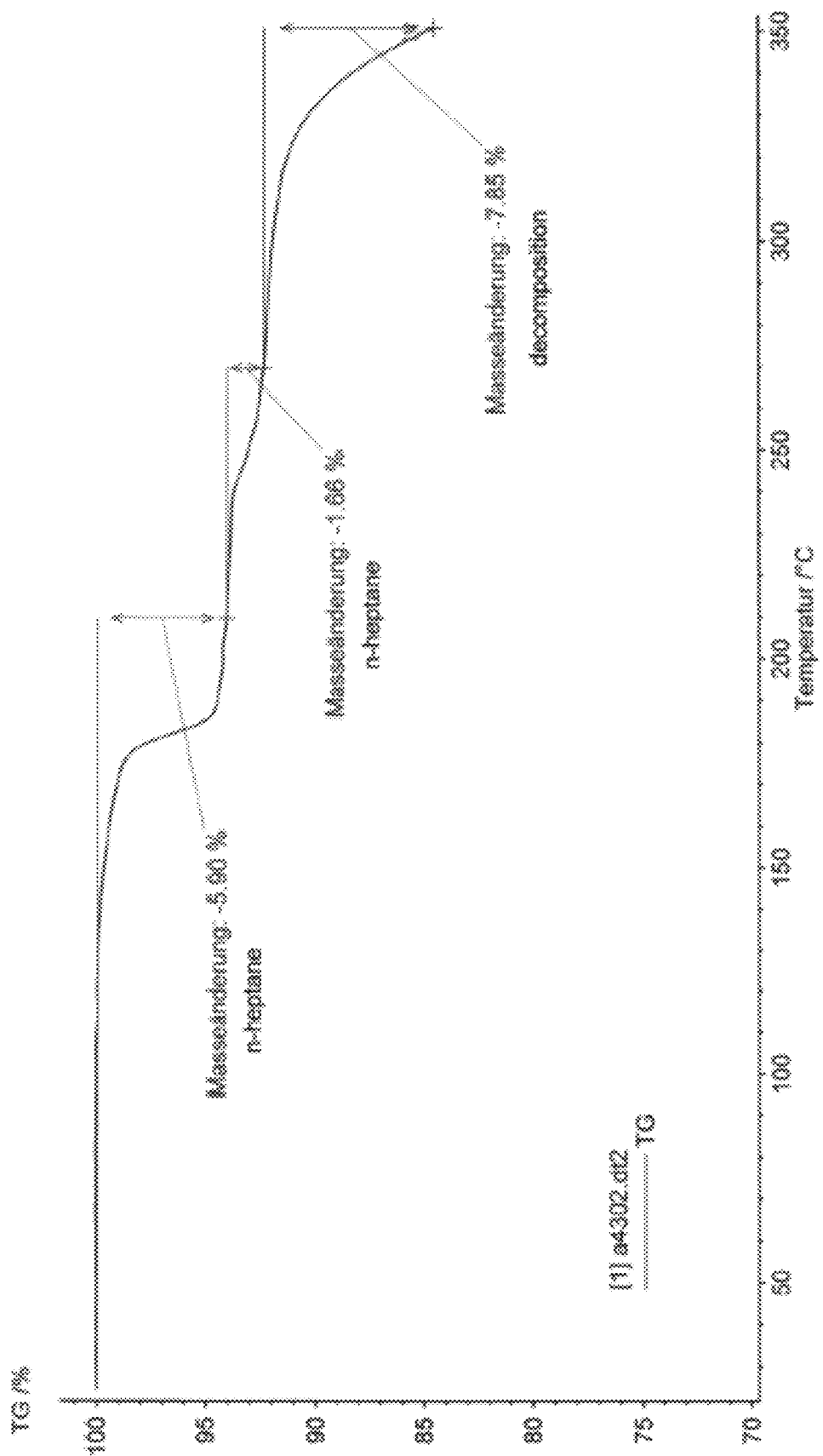
FIG. 90—TG-FTIR thermogram of the sample PP415-P19, which corresponds to a solvate form (Class 2).
Figure 91:
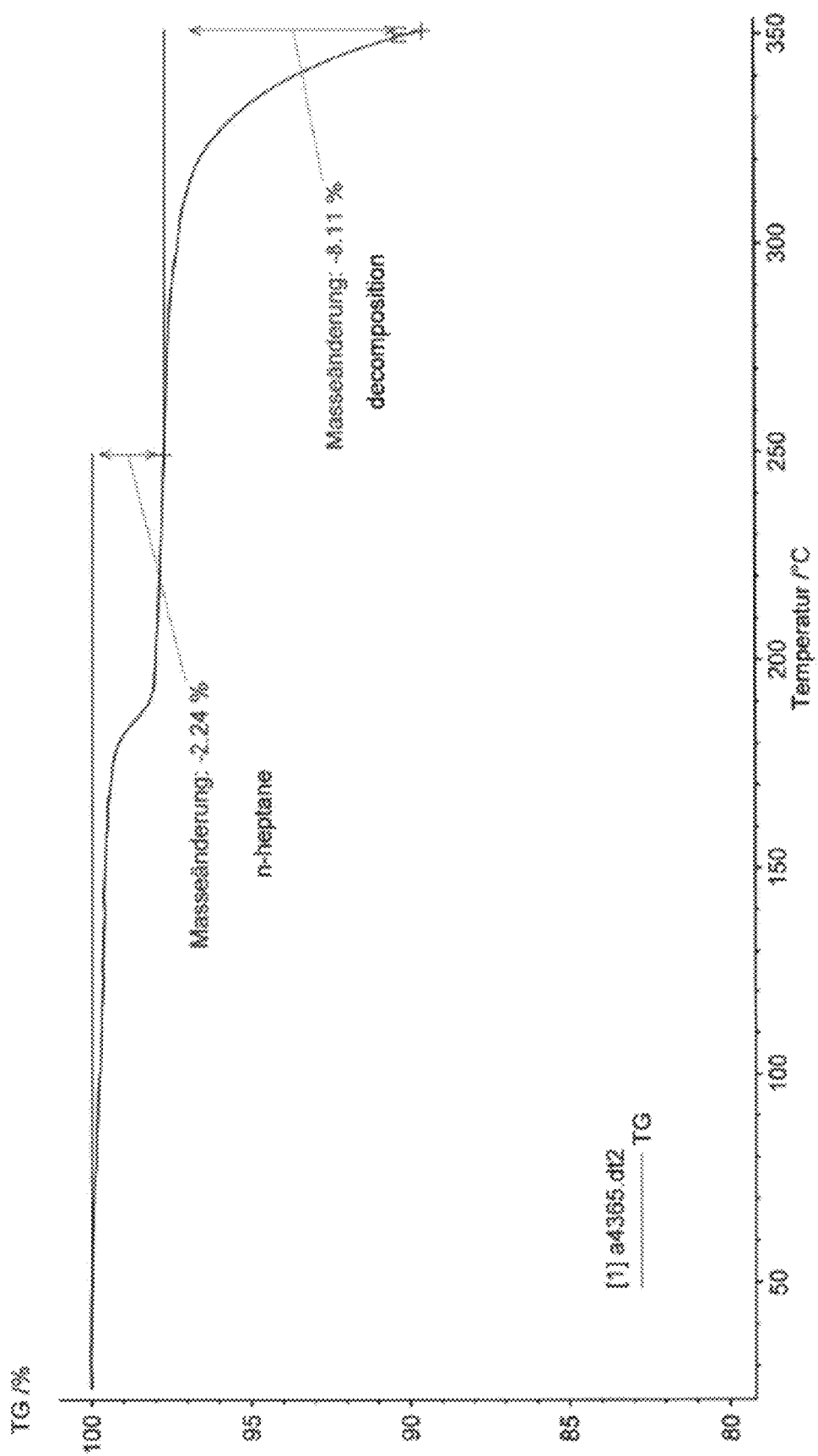
FIG. 91—TG-FTIR thermogram of the sample PP415-P32A, which corresponds to a solvate form (Class 2).

The TG-FTIR thermogram (FIG. 90) shows the loss of ~7.6 wt.-% heptane in two steps from ~140° C. to ~270° C. and decomposition at temperatures T>270° C. With the boiling point of heptane being 98° C., the solvent seems tightly bound in the structure. The theoretical heptane content of a hemisolvate is 8.3 wt.-%.

A further drying experiment (80° C., <1×10$^{-3}$ mbar, 3 days) was carried out on the same sample as PP415-P32.

Figure 88:
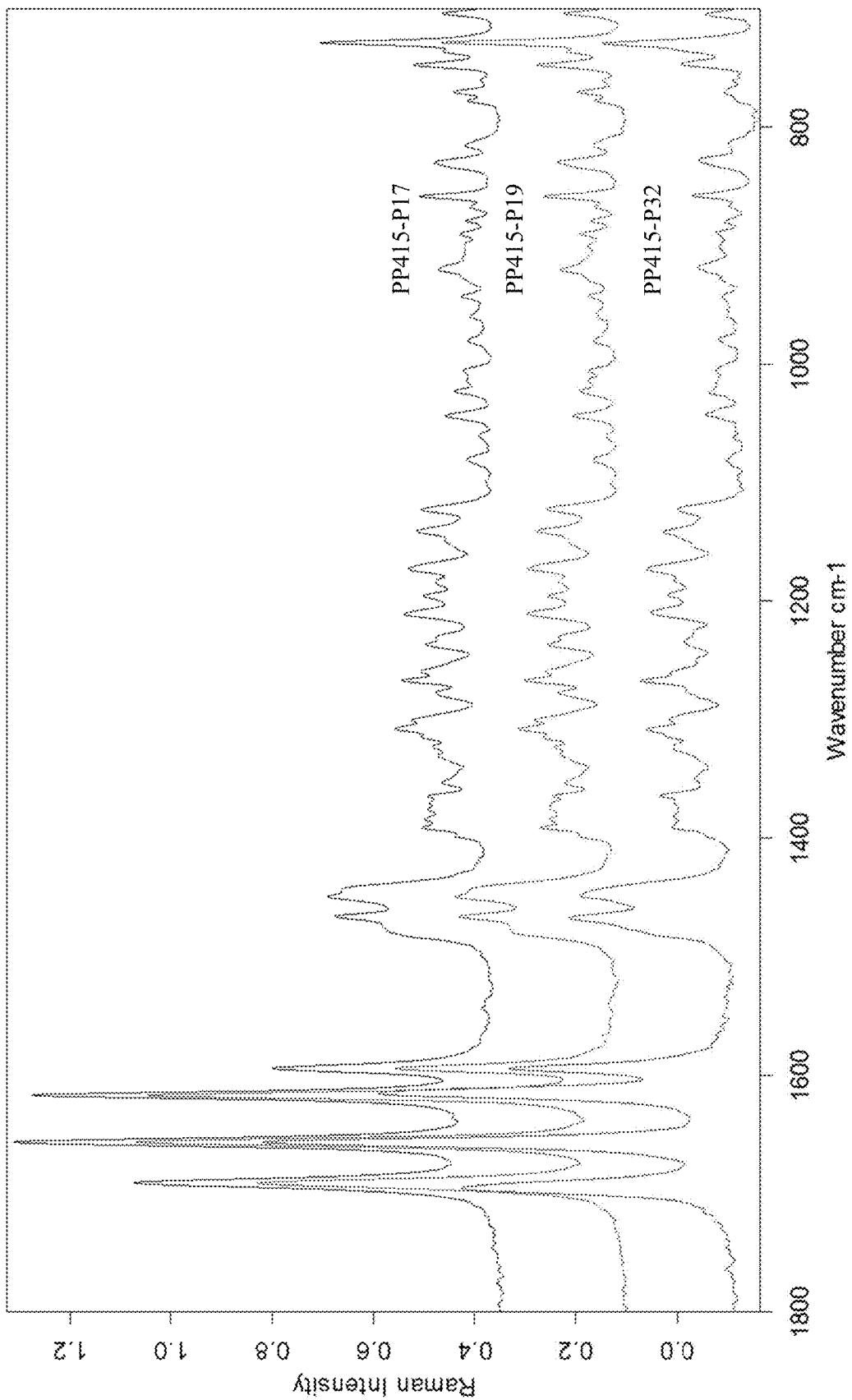
FIG. 88—FT-Raman spectrum of the sample PP415-P17 (top) is nearly identical to the spectra of the dried samples PP415-P19 (middle) and PP415-P32 (bottom) and show only small differences which can hardly be distinguished within the graph. The spectra have been scaled and offset in the y-direction for the purpose of comparison.

The FT-Raman spectrum remained unchanged (FIG. 88). The PXRD pattern still corresponded to class 2 (FIG. 89), but the sample was less crystalline (as the peaks were broader and had a lower S/N ratio).

The TG-FTIR thermogram (FIG. 90) shows the loss of ~2.2 wt.-% heptane, most of it in a step from 170° C. to 200° C. and decomposition at temperatures T>250° C.

Thus, the heptane content was reduced only from 7.6 wt.-% to 2.2 wt.-%, confirming the tight binding of the solvent molecules.

h. PP415-P21→PP415-P28→PP415-P34

The solid material of sample PP415-P21, class 2, obtained from a slow cooling experiment in ~1:5 EtOH/cyclohexane was dried (as PP415-P28) under vacuum for several days (2-20 mbar, r.t. to 60° C.).

The FT-Raman spectrum of the dried class 2 material (PP415-P28) shows small differences to the spectrum of class 2 (sample PP415-P21, FIG. 92), but still corresponds to class 2.

Figure 93:
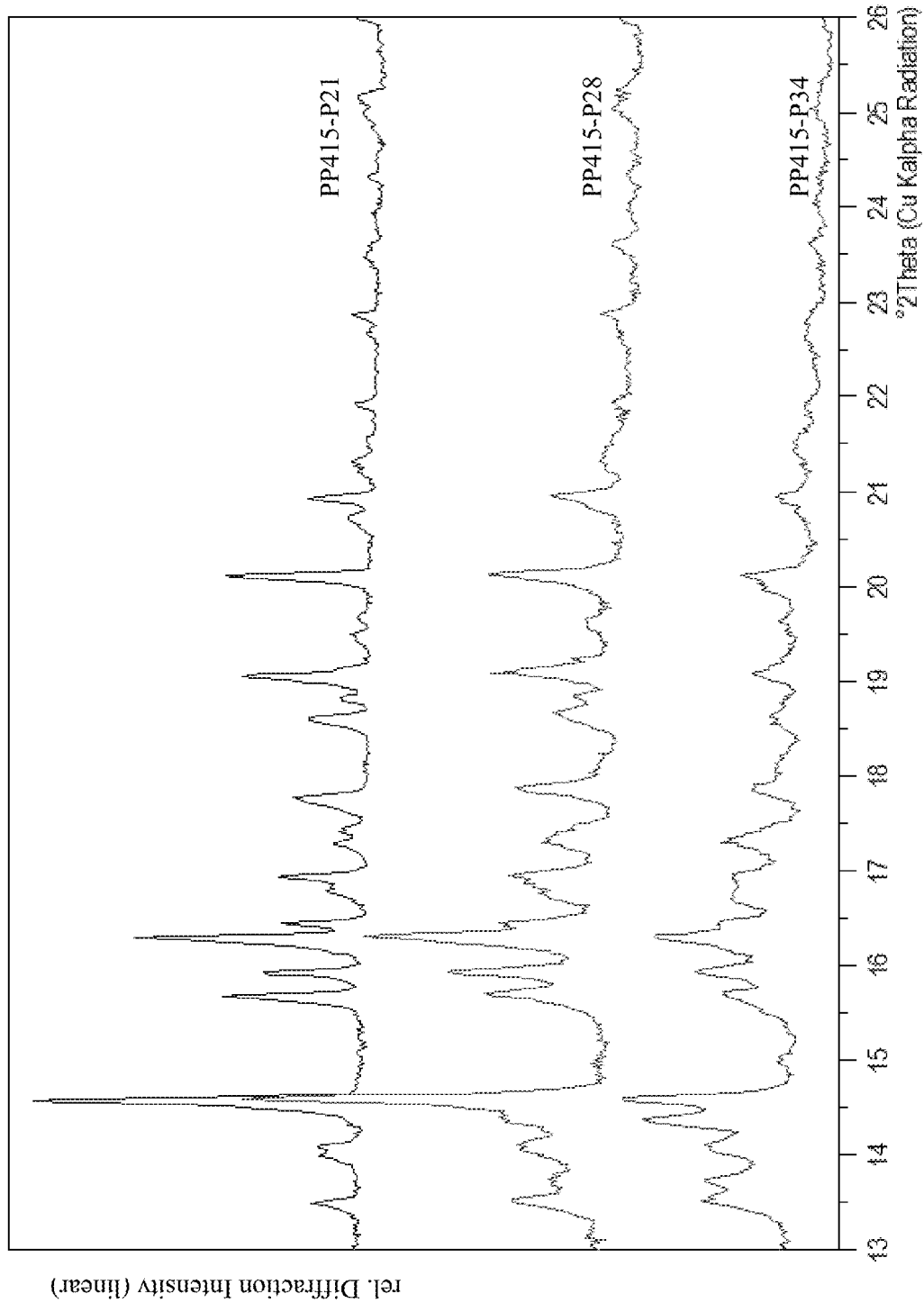
FIG. 93—PXRD patterns of the dried samples PP415-P28 (middle) and PP415-P34 (bottom) show broader peaks with a lower S/N ratio, indicating a lower crystallinity of the samples compared to the pattern of the original sample PP415-P21 (top). The patterns are somewhat different but still correspond to class 2 form. They have been scaled and offset in the y-direction for the purpose of comparison.

The PXRD pattern of the dried class 2 material (PP415-P28) shows broader, less intense peaks compared to the pattern of PP415-P21 (FIG. 93), indicating that the dried sample is less crystalline. However, the pattern still corresponds to class 2.

Figure 94:
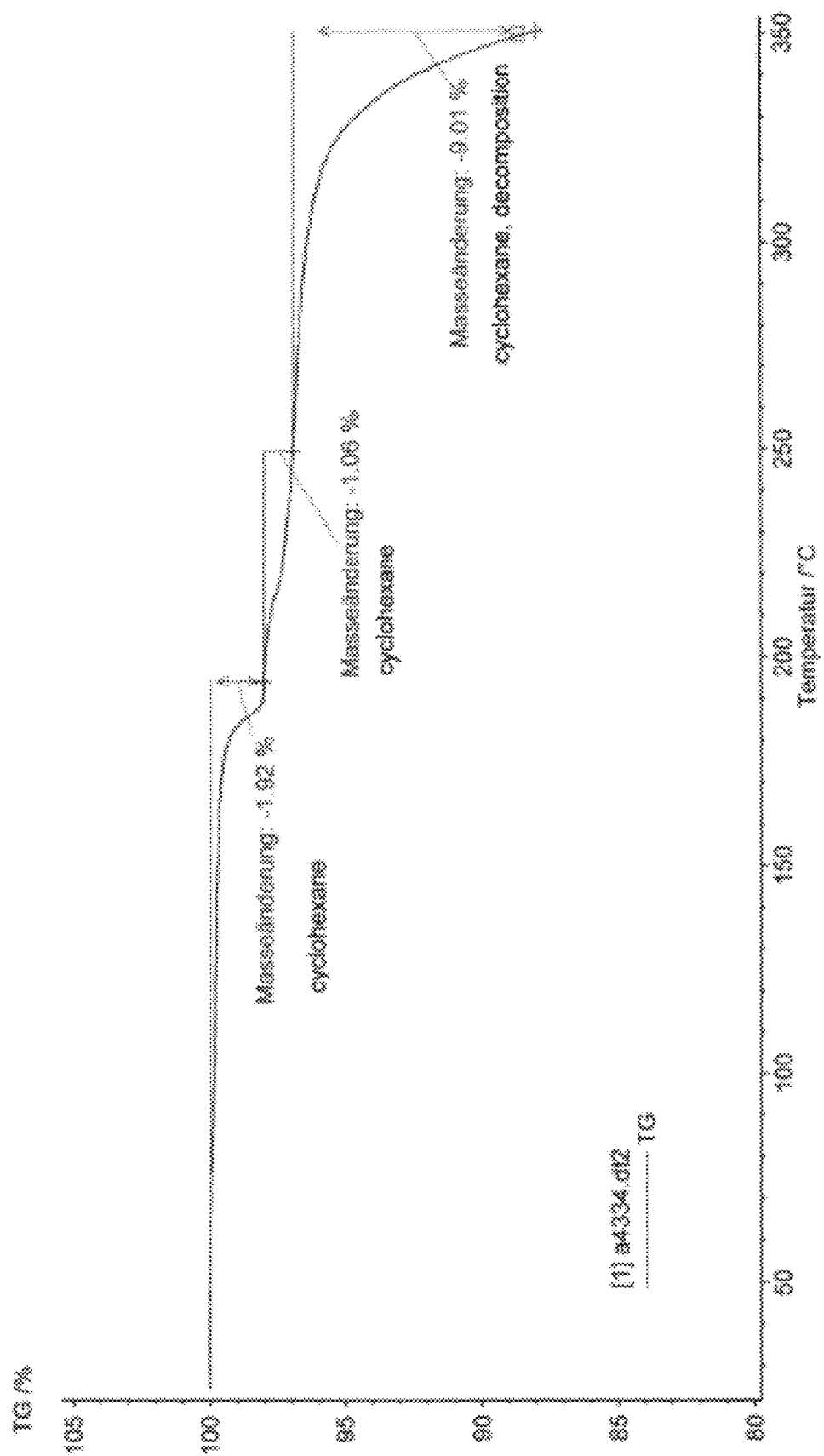
FIG. 94—TG-FTIR thermogram of the dried sample PP415-P28, which corresponds to a solvate form (Class 2).

The TG-FTIR thermogram of the dried sample PP415-P28 (FIG. 94) shows the loss of ~3.0 wt.-% cyclohexane in two steps from ~140° C. to ~250° C. and decomposition at temperatures T>250° C. Compared to the TG-FTIR of sample PP415-P21 (FIG. 77), the two steps of solvent loss are preserved, but the total amount of solvent in the sample has decreased from ~5.8 wt.-% in PP415-P21 to ~3.0 wt.-% in PP415-P28.

Thus, the desolvation of this solvate seems to have caused only a partial loss of solvent, parallel to a partial loss of crystallinity.

Further drying of this sample (at 80° C., <1×10$^{-3}$ mbar, 3 days) was carried out as PP415-P34.

Figure 92:
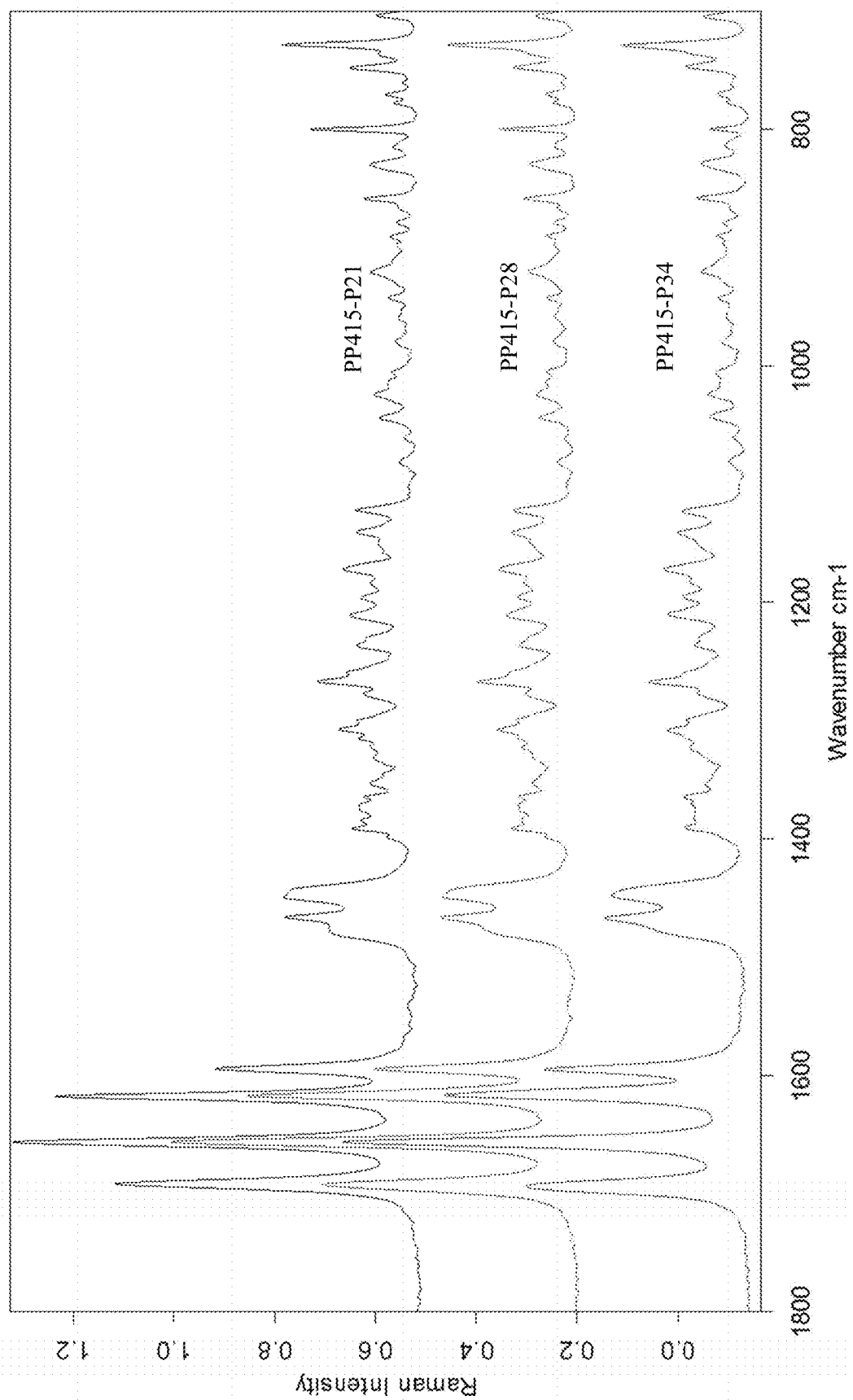
FIG. 92—FT-Raman spectrum of the sample PP415-P21 (top) is identical to the spectra of the dried samples PP415-P28 (middle) and PP415-P34 (bottom). The spectra have been scaled and offset in the y-direction for the purpose of comparison.

The FT-Raman spectrum remained unchanged (FIG. 92). The PXRD pattern still corresponded to class 2 (FIG. 93), but the sample was less crystalline (as the peaks were broader and had a lower S/N ratio).

Figure 95:
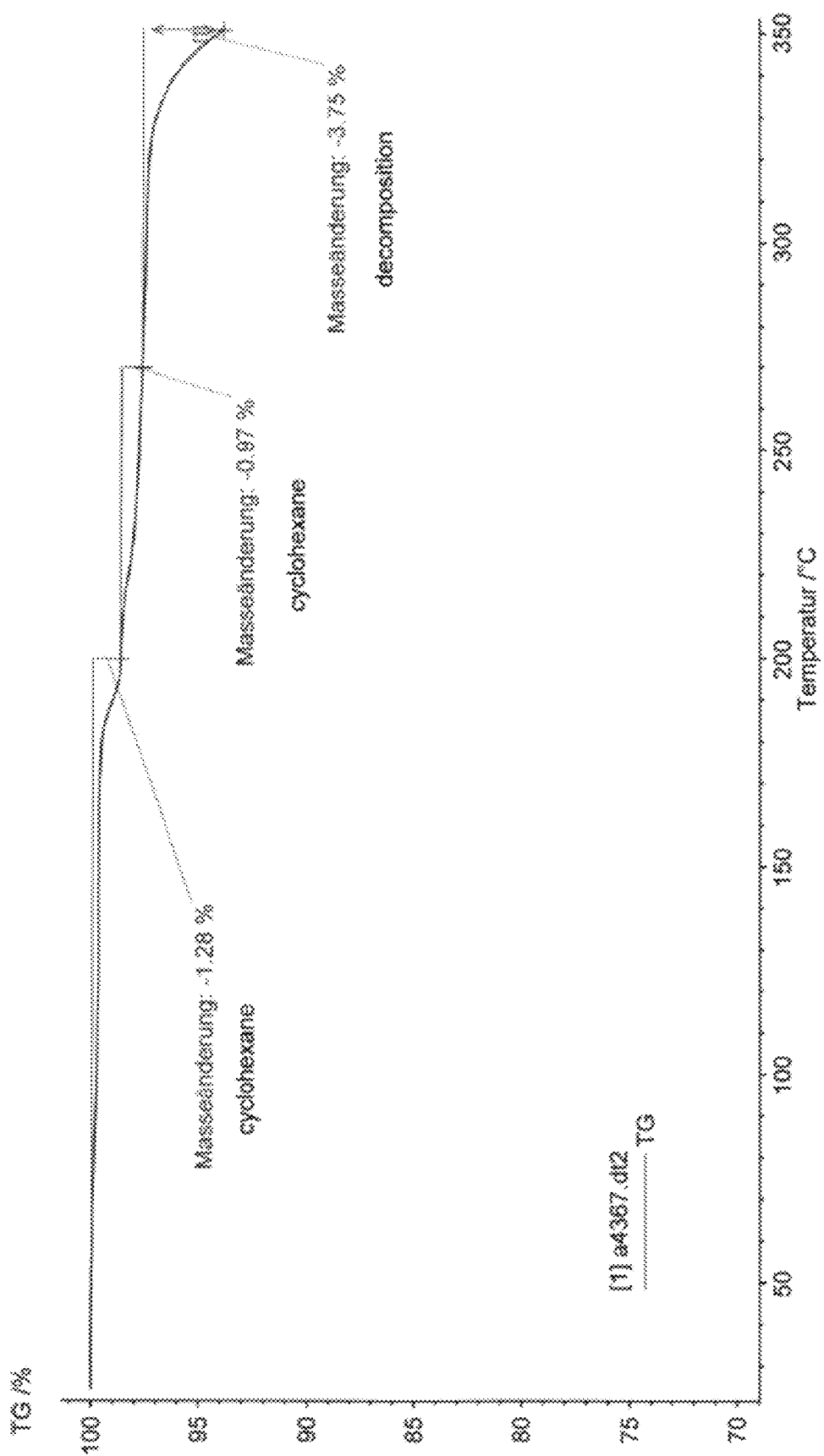
FIG. 95—TG-FTIR thermogram of the dried sample PP415-P34, which corresponds to a solvate form (Class 2).

The TG-FTIR thermogram (FIG. 95) shows the loss of ~2.3 wt.-% cyclohexane, in two steps from 25° C. to 270° C. and decomposition at temperatures T>270° C.

Thus, the cyclohexane content was reduced only from 3.0 wt.-% to 2.3 wt.-% confirming the tight binding of the solvent molecules.

i. Class 3—Isostructural Solvates (e.g., Ethanol)

Several crystallization experiments resulted in solid material of class 3 and were characterized by FT-Raman spectroscopy, PXRD, and TG-FTIR (Table 21).

Figure 96:
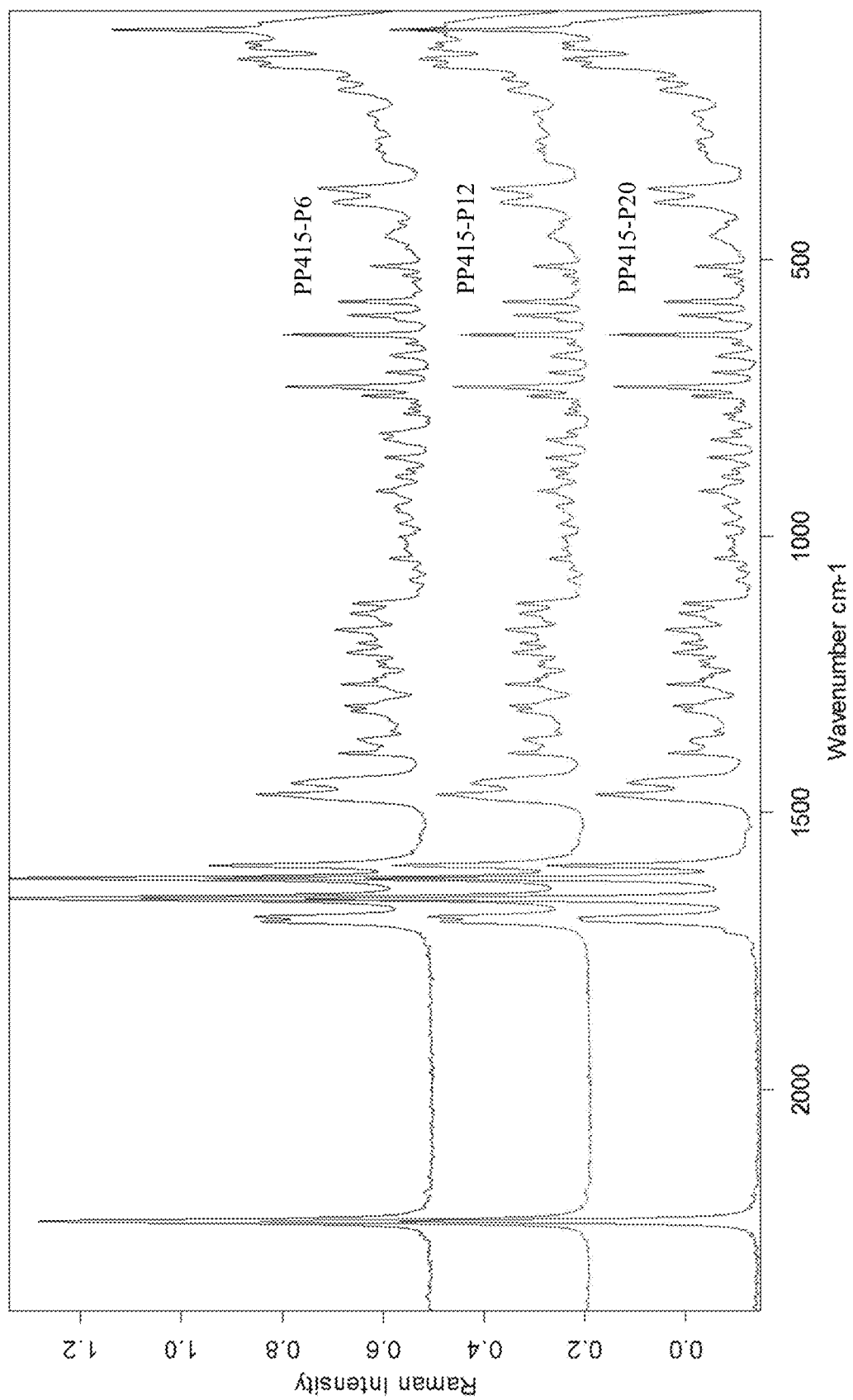
FIG. 96—FT-Raman spectra (2400-50 $cm^{-1}$) of the samples of the solvate form (Class 3) (PP415-P6: top; PP415-P12: middle; PP415-P20: bottom). The spectra have been scaled and offset in the y-direction for the purpose of comparison.
Figure 97:
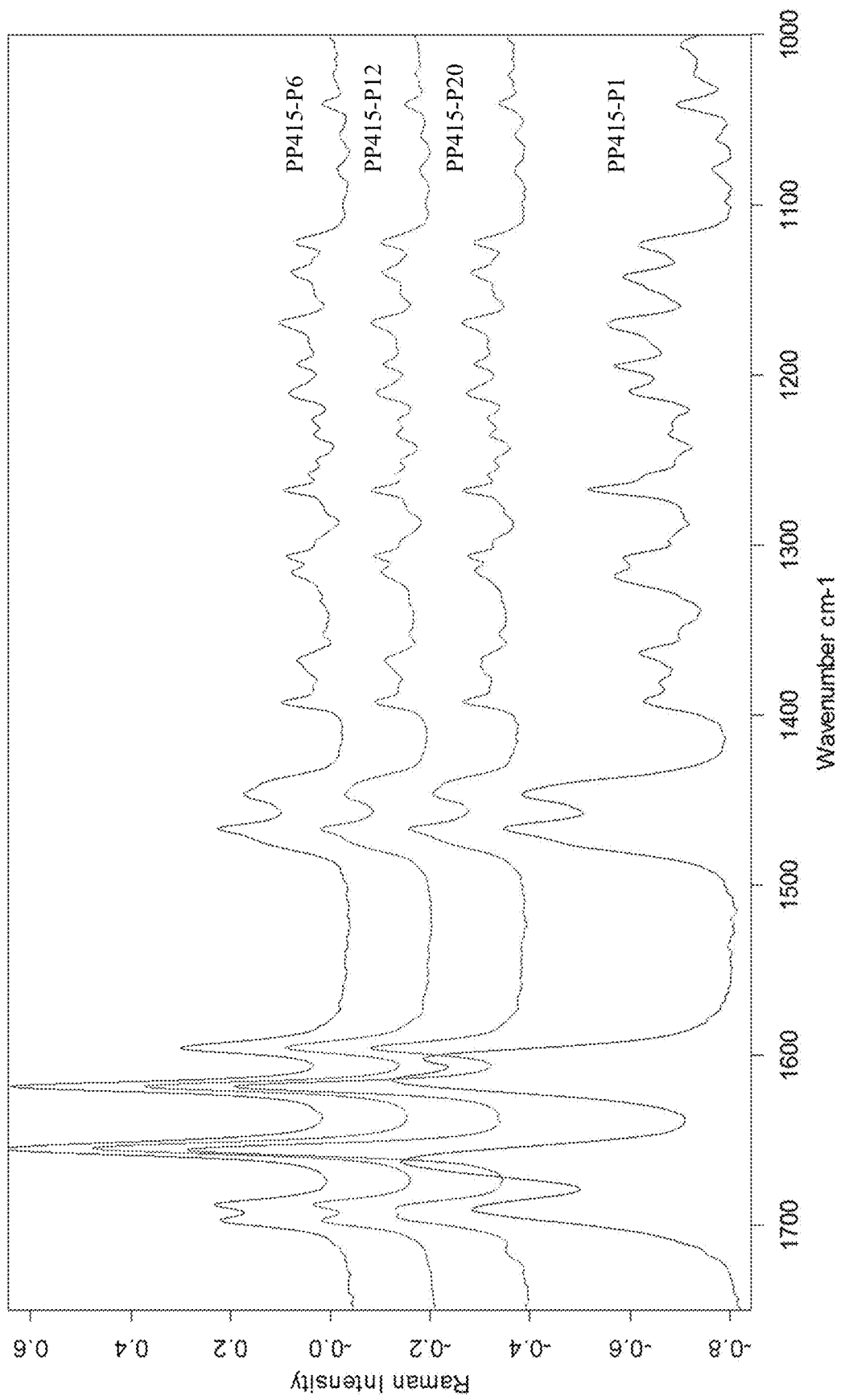
FIG. 97—FT-Raman spectra (1750-1000 cm$^{-1}$) of the samples of the solvate form (Class 3) (PP415-P6: top; PP415-P12: 2"d from top; PP415-P20: 2"d from bottom) are very similar to each other with only small differences, e.g., at ~1690 cm$^{-1}$, but are clearly different from class 1 (PP415-P1: bottom). The spectra have been scaled and offset in the y-direction for the purpose of comparison.
Figure 98:
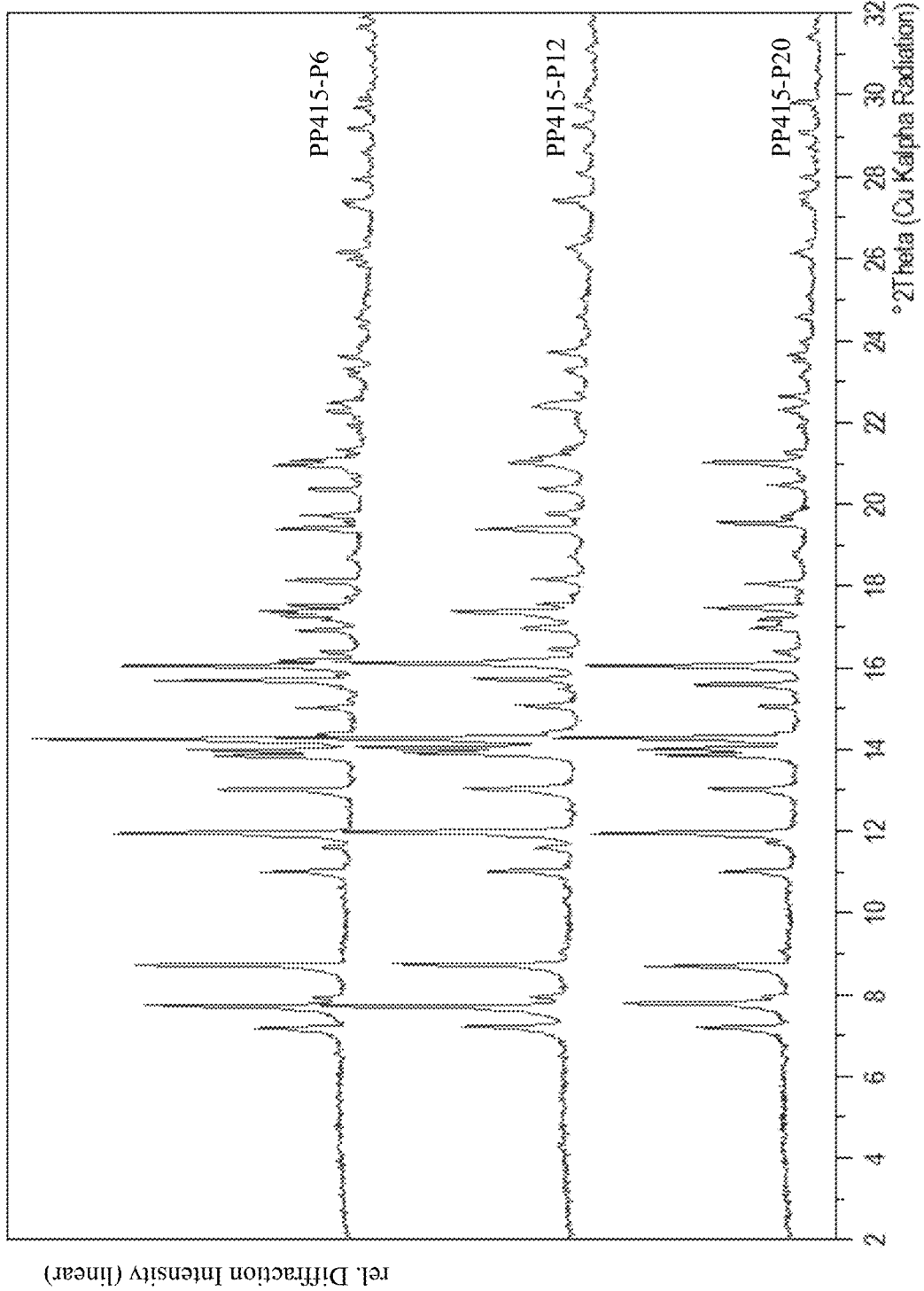
FIG. 98—PXRD patterns (2-32° 2θ) of the samples of the solvate form (Class 3) (PP415-P6: top; PP415-P12: middle; PP415-P20: bottom). The patterns have been scaled and offset in the y-direction for the purpose of comparison.

The FT-Raman spectra of class 3 are clearly similar to each other (FIG. 96) but show small differences (FIG. 97). The spectra of class 3 differ significantly from the spectrum of the amorphous starting material, class 1 (FIG. 98), and from the spectra of classes 2, 4, and 5 (FIG. 72).

Figure 99:
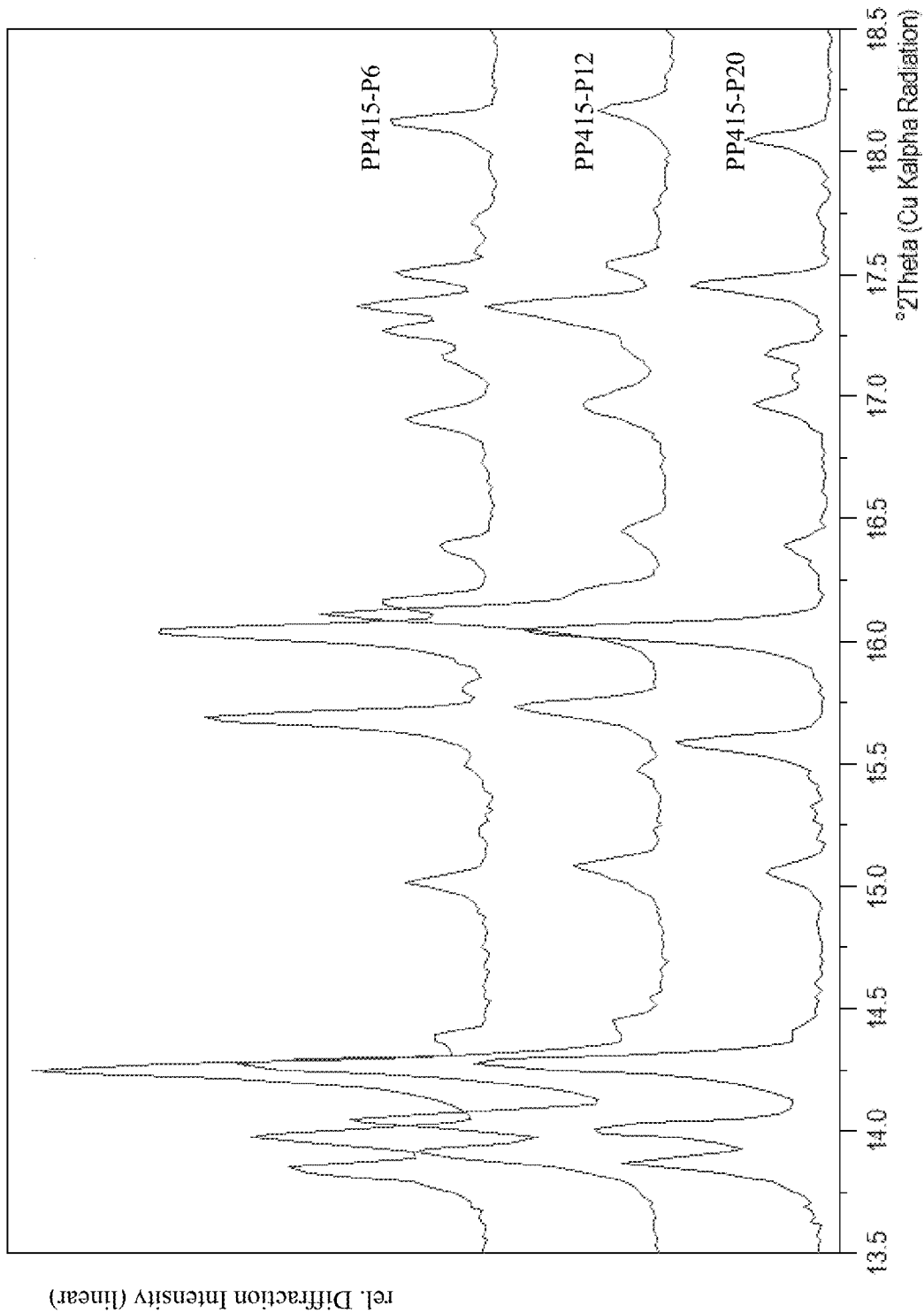
FIG. 99—PXRD patterns (13.5-18.5° 2θ) of the samples of solvate form (Class 3) (PP415-P6: top; PP415-P12: middle; PP415-P20: bottom) show small differences. The patterns have been scaled and offset in the y-direction for the purpose of comparison.
Figure 100:
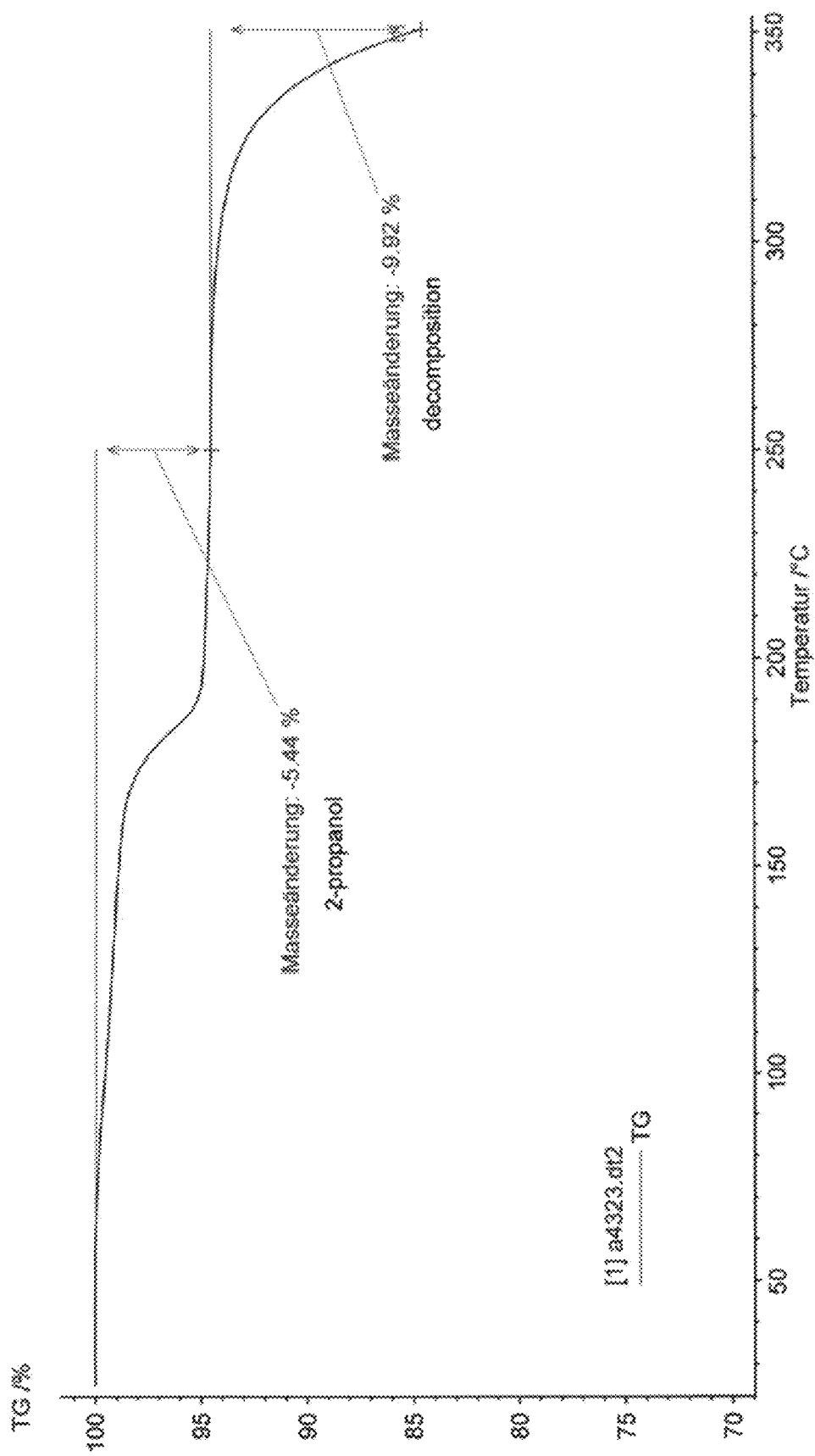
FIG. 100—TG-FTIR thermogram of the sample PP415-P6, which corresponds to the solvate form (Class 3).

The PXRD patterns of class 3 (FIG. 99) confirm the crystallinity of the materials. The patterns of the three samples are similar to each other but show small but significant differences (FIG. 100). The class 3 pattern clearly differs from the crystalline patterns of classes 2, 4, and 5 (FIG. 75).

The TG-FTIR thermogram of sample PP415-P6 (FIG. 100) shows the loss of ~5.4 wt.-% 2PrOH from 25° C. to 250° C., most of it in a step from ~170° C. to 190° C. Decomposition starts at temperatures T>250° C. Before the TG-FTIR experiments, the samples were dried briefly (for ~5 min) under vacuum (10-20 mbar) to remove excess, unbound solvent. The theoretical 2PrOH (b.p.=82° C.) content of a hemisolvate is 5.1 wt.-%.

Figure 101:
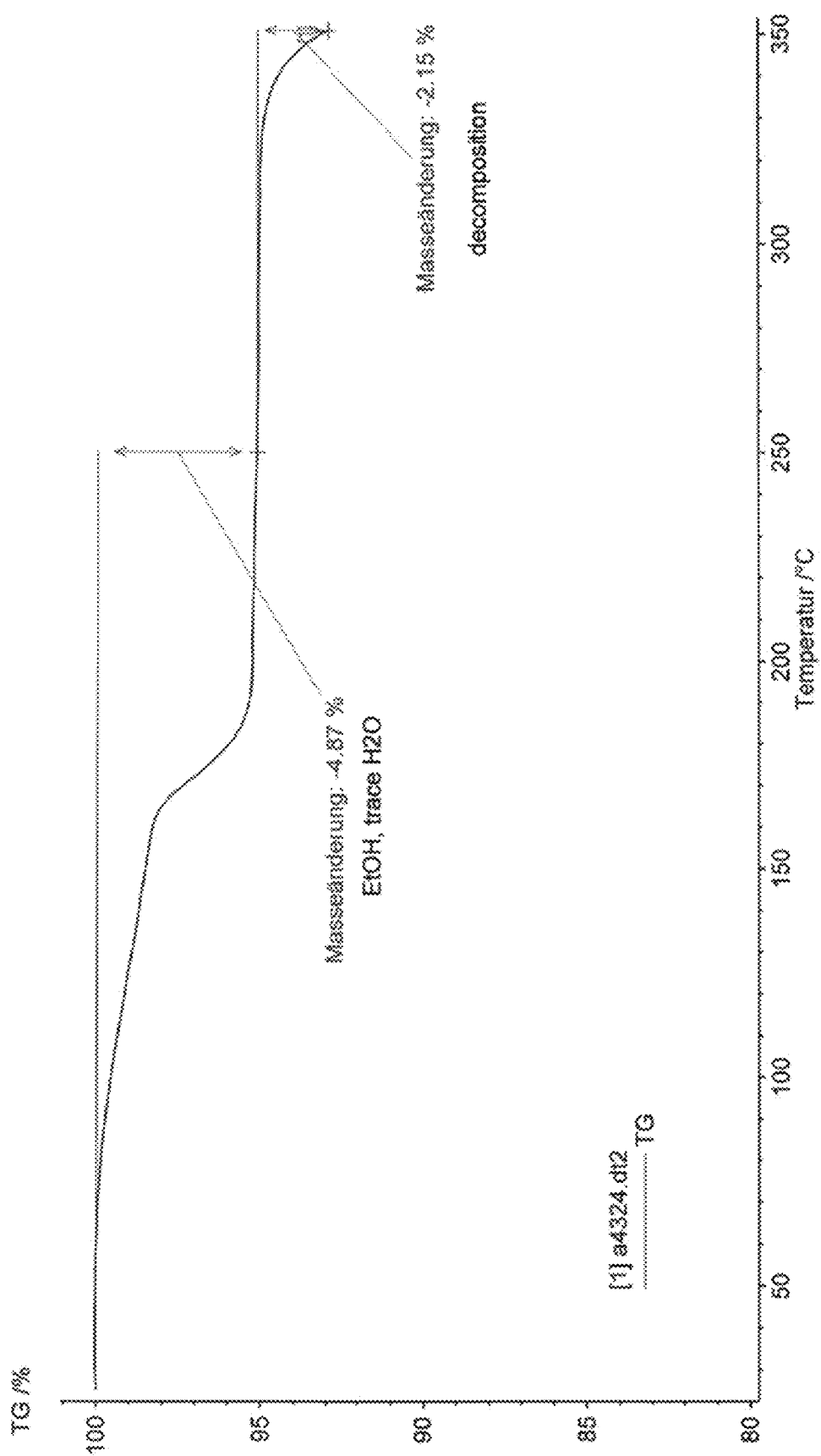
FIG. 101—TG-FTIR thermogram of the sample PP415-P12, which corresponds to the solvate form (Class 3).

The TG-FTIR thermogram of sample PP415-P12 (FIG. 101) shows the loss of ~4.9 wt.-% EtOH (with traces of water) from 25° C. to 250° C., most of it in a step from ~160° C. to 190° C. Decomposition starts at temperatures T>250° C. The theoretical EtOH (b.p.=78° C.) content of a hemisolvate is 4.0 wt.-%.

Thus, the samples of class 3 seem to be isostructural solvates of 2PrOH, EtOH, and probably acetone with tightly bound solvent content. They could correspond to stoichiometric hemisolvates. It cannot be ruled out, however, that these forms are non-stoichiometric solvates.

As the Raman spectra and PXRD patterns within this class are very similar to each other, the structures might be essentially identical with only small distortions of the unit cell dimensions or small changes of atomic positions within the unit cell due to the incorporation of different solvent molecules.

TABLE 21

Crystallization experiments resulting in solid material of class 3

| Sample | Method | Solvent/Mixture | Characterization | Drying |
|---|---|---|---|---|
| PP415-P6 | suspension equil. | 2PrOH | Raman, PXRD, TG-FTIR | X |
| PP415-P12 | suspension equil. | 9:1 EtOH/H$_2$O | Raman, PXRD, TG-FTIR | — |
| PP415-P20 | slow cooling | ~2:1 acetone/H$_2$O | Raman, PXRD | — | j. Drying Experiments on Samples of Class 3

One of the samples of class 3 (PP415-P6), obtained from a suspension equilibration experiment in 2PrOH, was dried (as PP415-P25) under vacuum for several days (2-20 mbar, r.t. to 60° C., Table 22).

Figure 102:
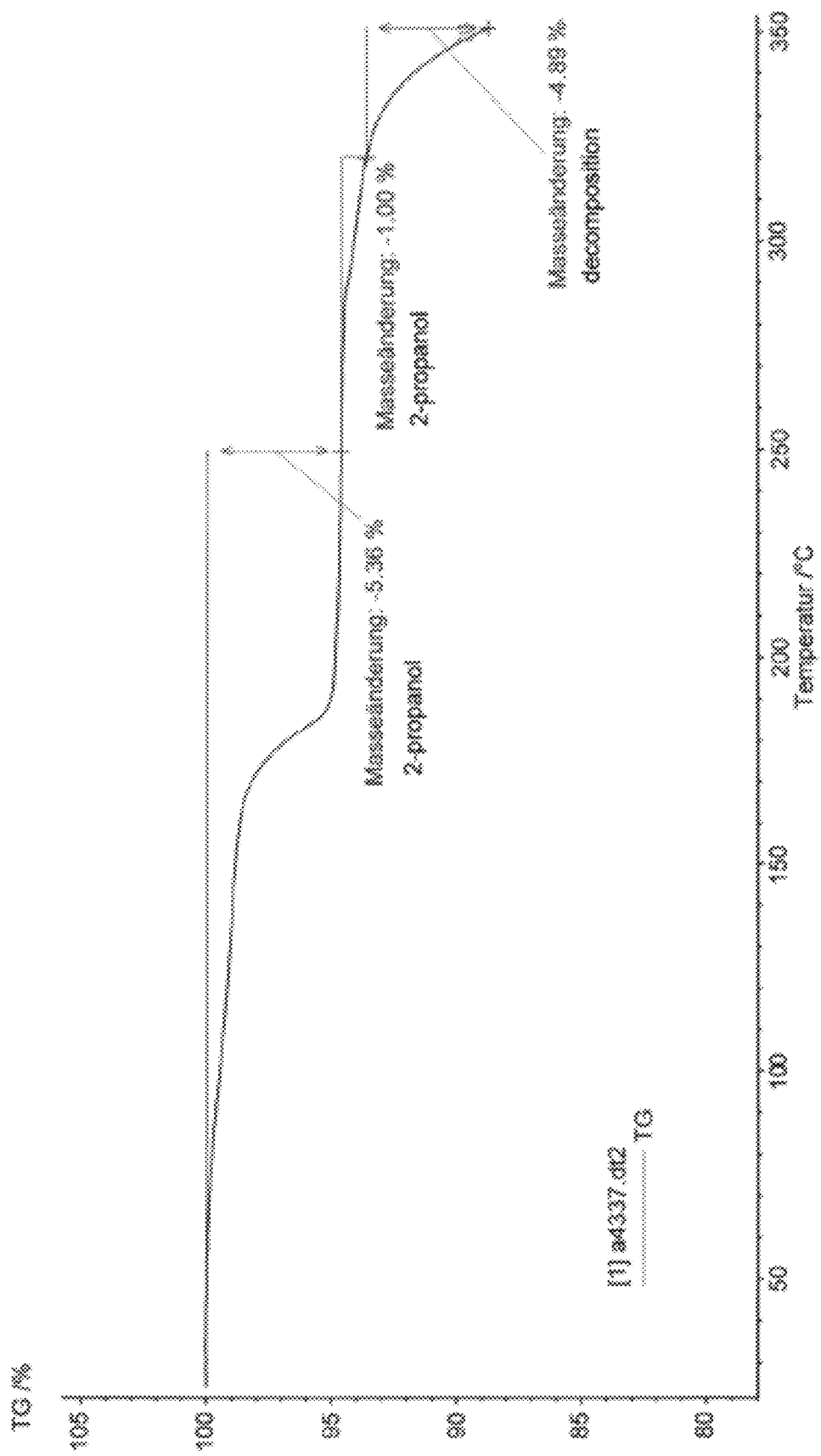
FIG. 102—TG-FTIR thermogram of the dried solvate form (Class 3), sample PP415-P25.
Figure 103:
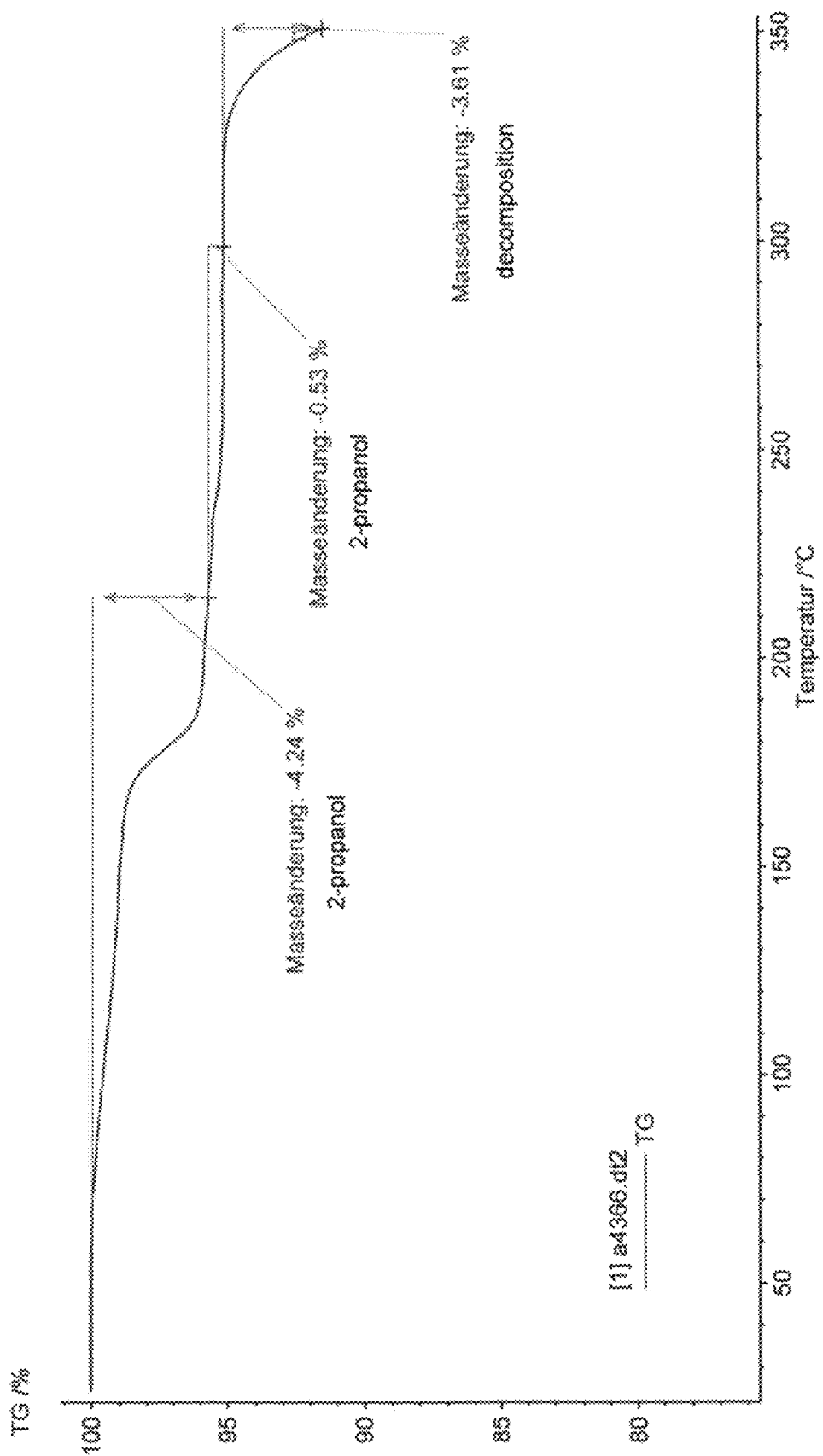
FIG. 103—TG-FTIR thermogram of the further dried solvate form (Class 3), sample PP415-P33.

The TG-FTIR thermogram of this dried class 3 material, sample PP415-P25 (FIG. 102), shows the loss of ~5.4 wt.-% 2PrOH from 50° C. to 250° C., most of it in a step from 170° C. to 190° C., another loss of ~1.0 wt.-% 2PrOH from 290° C. to 320° C., and decomposition at temperatures T>320° C. Compared to the TG-FTIR of the original class 3 sample PP415-P6 (FIG. 103), with a solvent content of ~5.4 wt.-% 2PrOH, the solvent content does not seem to have decreased significantly.

This material was dried further (as PP415-P33, Table 22) for three days under high vacuum and elevated temperatures (<1×10$^{-3}$ mbar, 80° C.) with the aim to desolvate the solvate and to obtain a non-solvated, anhydrous form of 63415.

The TG-FTIR thermogram of this further dried class 3 material, sample PP415-P33 (FIG. 103) shows the loss of ~4.2 wt.-% 2PrOH from 50° C. to 210° C., most of it in a step from 160° C. to 190° C., another loss of ~0.5 wt.-% 2PrOH from 210° C. to 290° C., and decomposition at temperatures T>290° C.

Compared to the solvent content of the samples PP415-P6 and PP415-P25, the solvent content has decreased only from ~5.4 wt.-% to ~4.8 wt.-%.

TABLE 22

Drying experiments on samples of class 3

| Starting Material | | Drying | Dried Material | | |
|---|---|---|---|---|---|
| Sample | Solvent Content | Conditions | Sample | Solvent Content | Class |
| PP415-P6 | 2PrOH (~5.4%) | r.t., ~3 mbar, ~5 d; 60° C., 5-10 mbar, 2 × 1 h; 40-50° C., 5-20 mbar, ~1 d | PP415-P25 | 2PrOH (~5.4%) | 3 |
| PP415-P25 | 2PrOH (~5.4%) | 80° C., <1 × 10$^{-3}$ mbar, 3 d | PP415-P33 | 2PrOH (~4.8%) | 3 |

Figure 104:
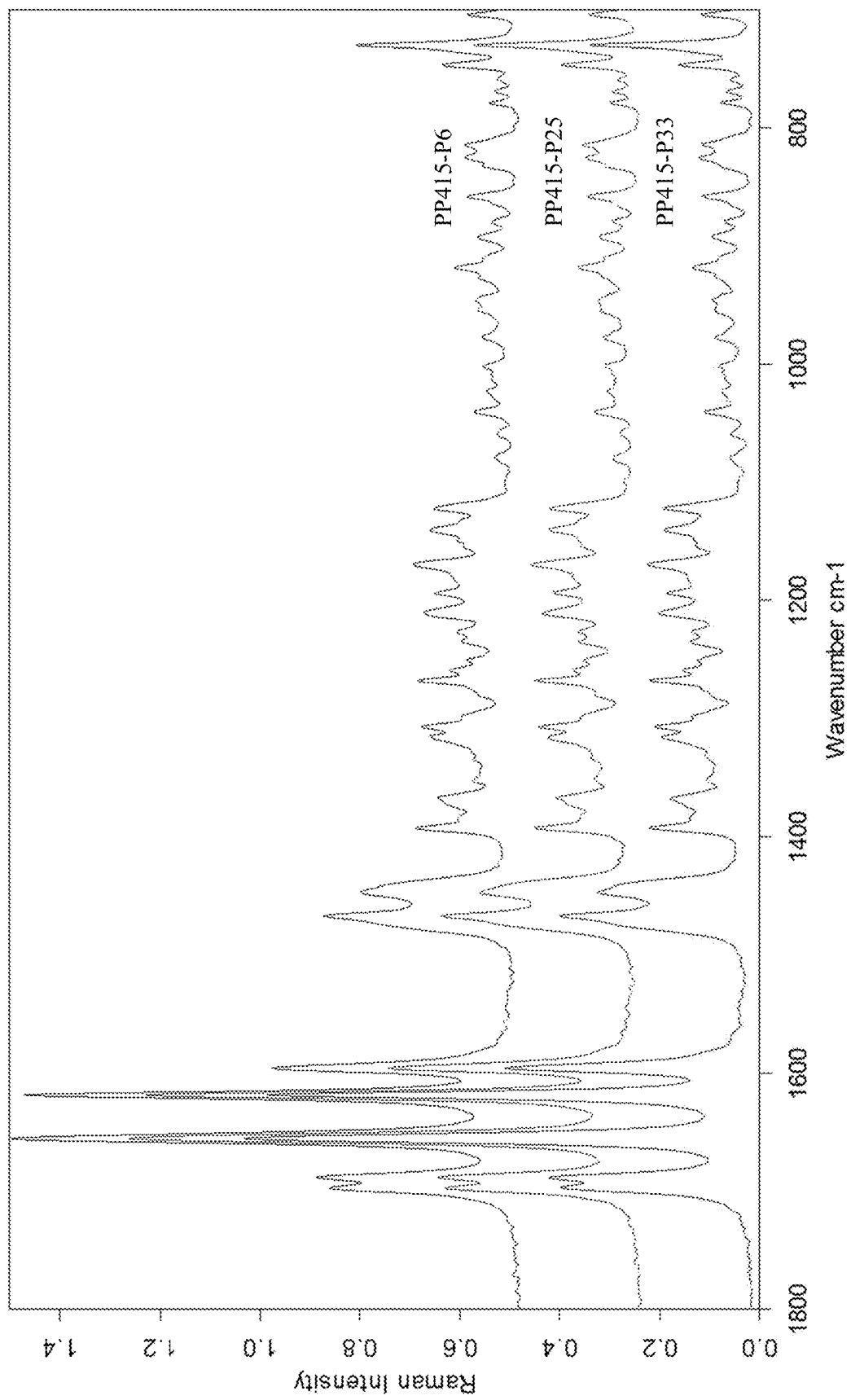
FIG. 104—FT-Raman spectra (1800-700 cm$^{-1}$) of the solvate form (Class 3) (top, sample PP415-P6), of the dried solvate form (Class 3) (middle, sample PP415-P25), and of the further dried solvate form (Class 3) (bottom, sample PP415-P33) are identical. The spectra have been scaled and offset in the y-direction for the purpose of comparison.

The FT-Raman spectra of class 3 (sample PP415-P6), of the dried material of class 3 (sample PP415-P25), and of the further dried material of class 3 (sample PP415-P33) are identical and show no changes (FIG. 104).

Figure 105:
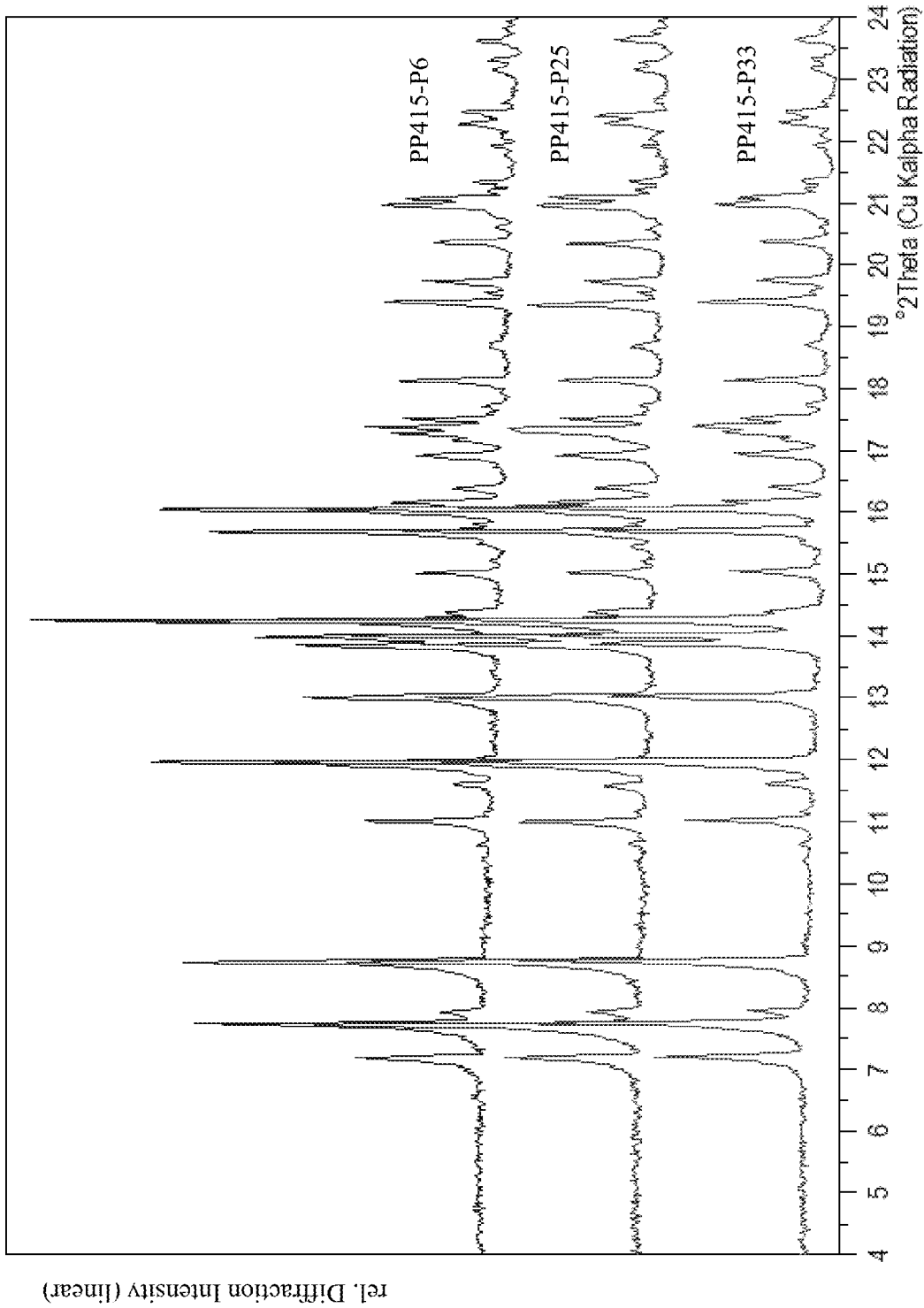
FIG. 105—PXRD patterns (4-24° 2θ) of the solvate form (Class 3) (top, sample PP415-P6), of the dried solvate form (Class 3) (middle, sample PP415-P25), and of the further dried solvate form (Class 3) (bottom, sample PP415-P33). The patterns have been scaled and offset in the y-direction for the purpose of comparison.

The PXRD patterns of class 3 (sample PP415-P6) and of the further dried material of class 3 (sample PP415-P33) do not show any significant differences, while there are few small shifts and differences from the pattern of the initially dried material of class 3 (sample PP415-P25, FIG. 105). All patterns correspond to class 3.

As the drying had no major effect on the solvent content, it is not surprising that the FT-Raman spectra and PXRD patterns of the dried materials do not show differences compared to the non-dried material.

Thus, class 3 is a class of isostructural solvates (2PrOH, EtOH, and probably acetone) with very tightly bound solvent molecules that could be removed only partially (~5.4 wt.-% to ~4.8 wt.-%) by the drying conditions applied here (up to 3 d at 1×10$^{-3}$ mbar and 80° C.).

k. Class 4—Acetonitrile Solvate

Class 4 was obtained only from a 7:3 MeCN/H$_2$O solvent mixture (Table 23). The experiment resulting in class 4 (PP415-P13) was repeated as PP415-P35 to prepare more material for further drying studies.

The FT-Raman spectrum (FIG. 72) and PXRD pattern (FIG. 75) of class 4 (sample PP415-P13) differ significantly from the spectra and patterns of classes 2, 3, and 5.

Figure 106:
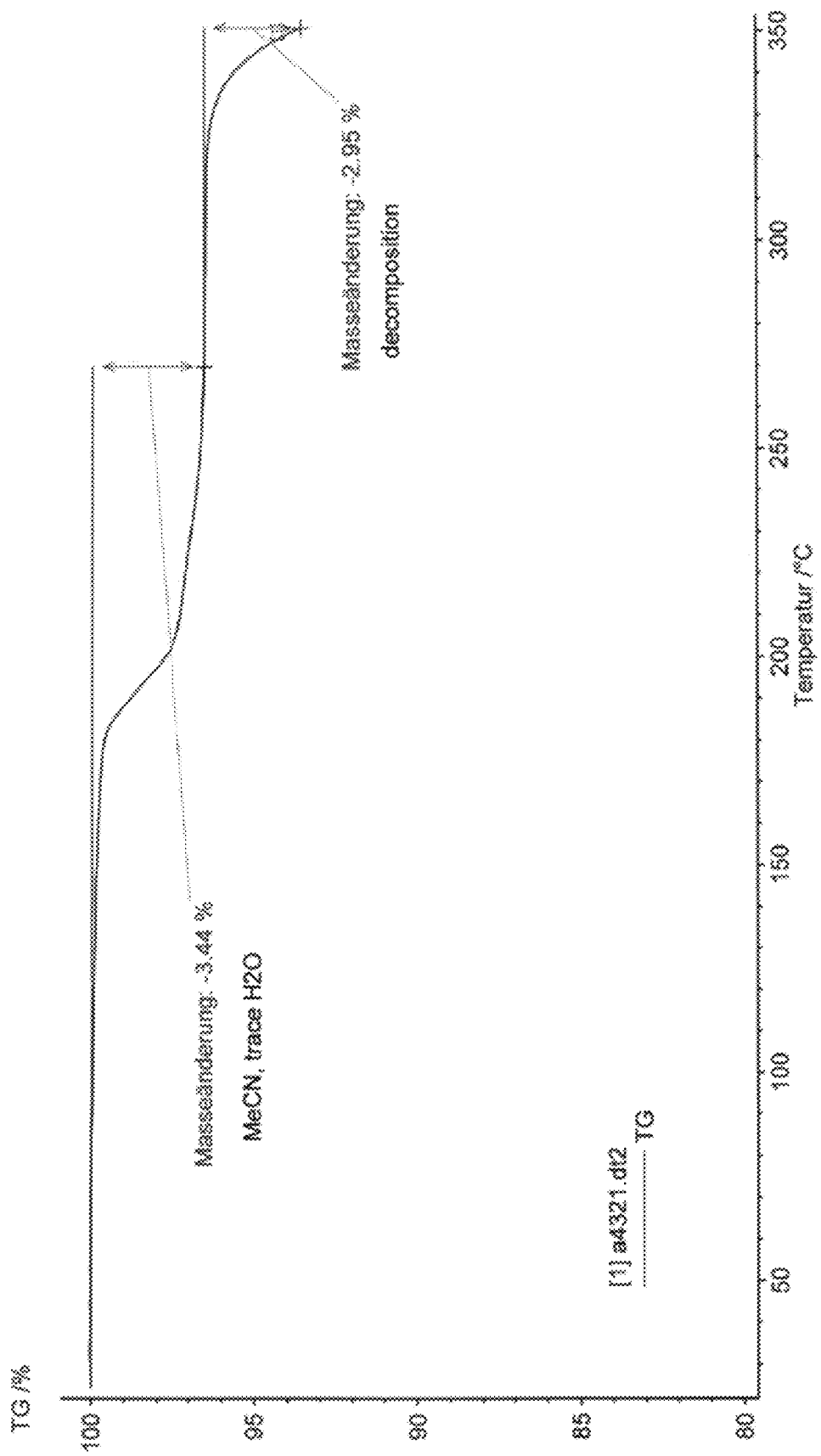
FIG. 106—TG-FTIR thermogram of the sample PP415-P13, which corresponds to an acetonitrile solvate form (Class 4).

The TG-FTIR thermogram of class 4 (sample PP415-P13, FIG. 106) shows the loss of ~3.4 wt.-% MeCN (with traces of water) from 25° C. to 270° C., most of it in a step from ~180° C. to 210° C. Decomposition starts at temperatures T>270° C. Before the TG-FTIR experiments, the samples were dried briefly (for ~5 min) under vacuum (10-20 mbar) to remove excess, unbound solvent. The theoretical MeCN (b.p.=81° C.) content of a hemisolvate is 3.6 wt.-%.

TABLE 23

Crystallization experiments resulting in solid material of class 4

| Sample | Method | Solvent | Characterization | Drying |
|---|---|---|---|---|
| PP415-P13 | suspension equilibration | 7:3 MeCN/H$_2$O | Raman, PXRD, TG-FTIR | X |
| PP415-P35 | suspension equilibration | 7:3 MeCN/H$_2$O | Raman, PXRD, TG-FTIR | X | l. Drying Experiments on Class 4

The samples of class 4 obtained from suspension equilibration experiments in ~7:3 MeCN/H$_2$O were dried under vacuum for several days or under N$_2$ flow (Table 24).

TABLE 24

Drying experiments on samples of class 4

| Starting Material | | | Dried Material | | |
|---|---|---|---|---|---|
| Sample | Solvent Content | Drying Conditions | Sample | Solvent Content | Class |
| PP415-P13 | MeCN (~3.4%) | r.t., ~3 mbar, ~5 d; 60° C., 5-10 mbar, 2 × 1 h; 40-50° C., 5-20 mbar, ~1 d | PP415-P26 | MeCN (~2.8%) | 4 |
| PP415-P35 | MeCN (~2.9%) | 80° C., <1 × 10$^{-3}$ mbar, 3 d | PP415-P36 | MeCN/H$_2$O$^a$ (~0.6%) | 4 |
| PP415-P35 | MeCN (~2.9%) | 80° C., N$_2$ flow, 3 d | PP415-P37 | MeCN/H$_2$O$^a$ (~0.9%) | 4 |

Figure 107:
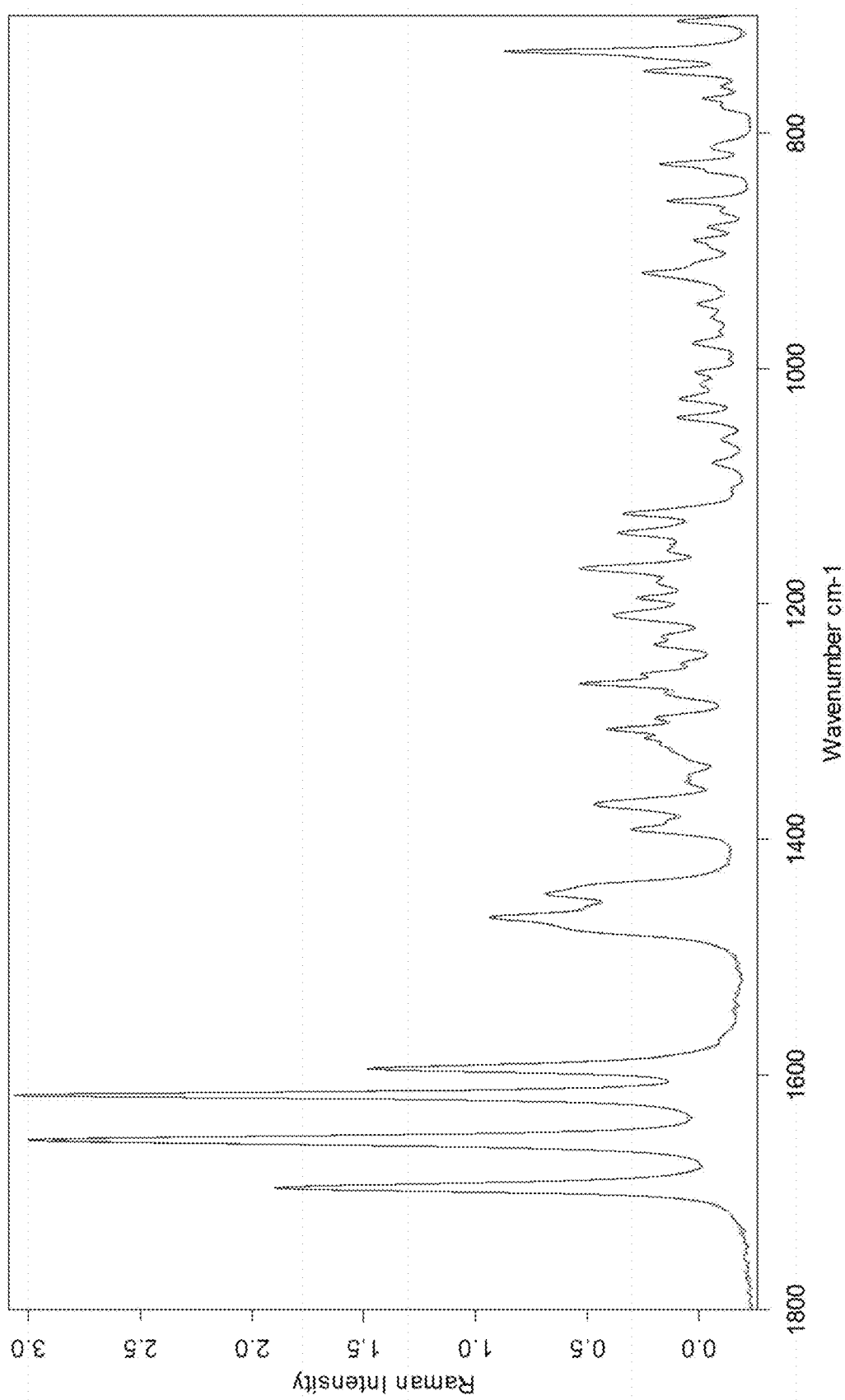
FIG. 107—FT-Raman spectra (1800-700 cm$^{-1}$) of the acetonitrile solvate form (Class 4) (dark grey, sample PP415-P13) and of the dried material of an acetonitrile solvate form (Class 4) (light grey, sample PP415-P26) are identical and overlay perfectly. The spectra have been scaled for purposes of comparison.

$^a$solvent content possibly MeCN and H$_2$O, but difficult to determine as amounts are small The FT-Raman spectrum of the dried class 4 material (PP415-P26) is identical to the spectrum of class 4 (PP415-P13, FIG. 107).

Figure 108:
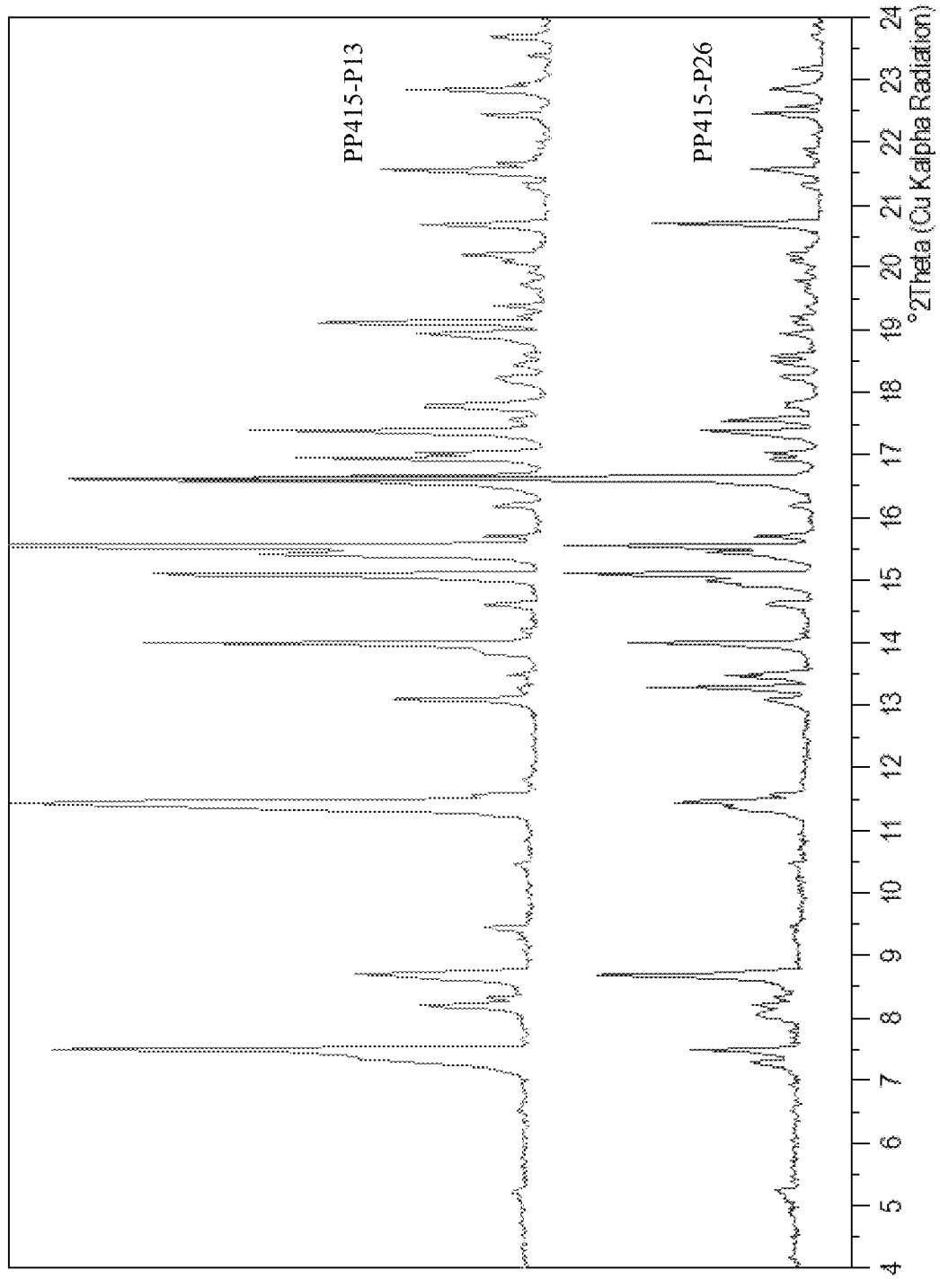
FIG. 108—PXRD pattern of the dried acetonitrile solvate form (Class 4), sample PP415-P26 (bottom), in comparison to the reference pattern of the acetonitrile solvate form (Class 4), sample PP415-P13 (top). The patterns have not been scaled but were offset in the y-direction for purposes of comparison.

The PXRD pattern of the dried class 4 material (PP415-P26) shows only very small differences from the pattern of class 4, sample PP415-P13 (FIG. 108). Some peaks seem better resolved, and peak intensities have shifted. No amorphization is observed. The pattern of PP415-P26 corresponds to class 4.

Figure 109:
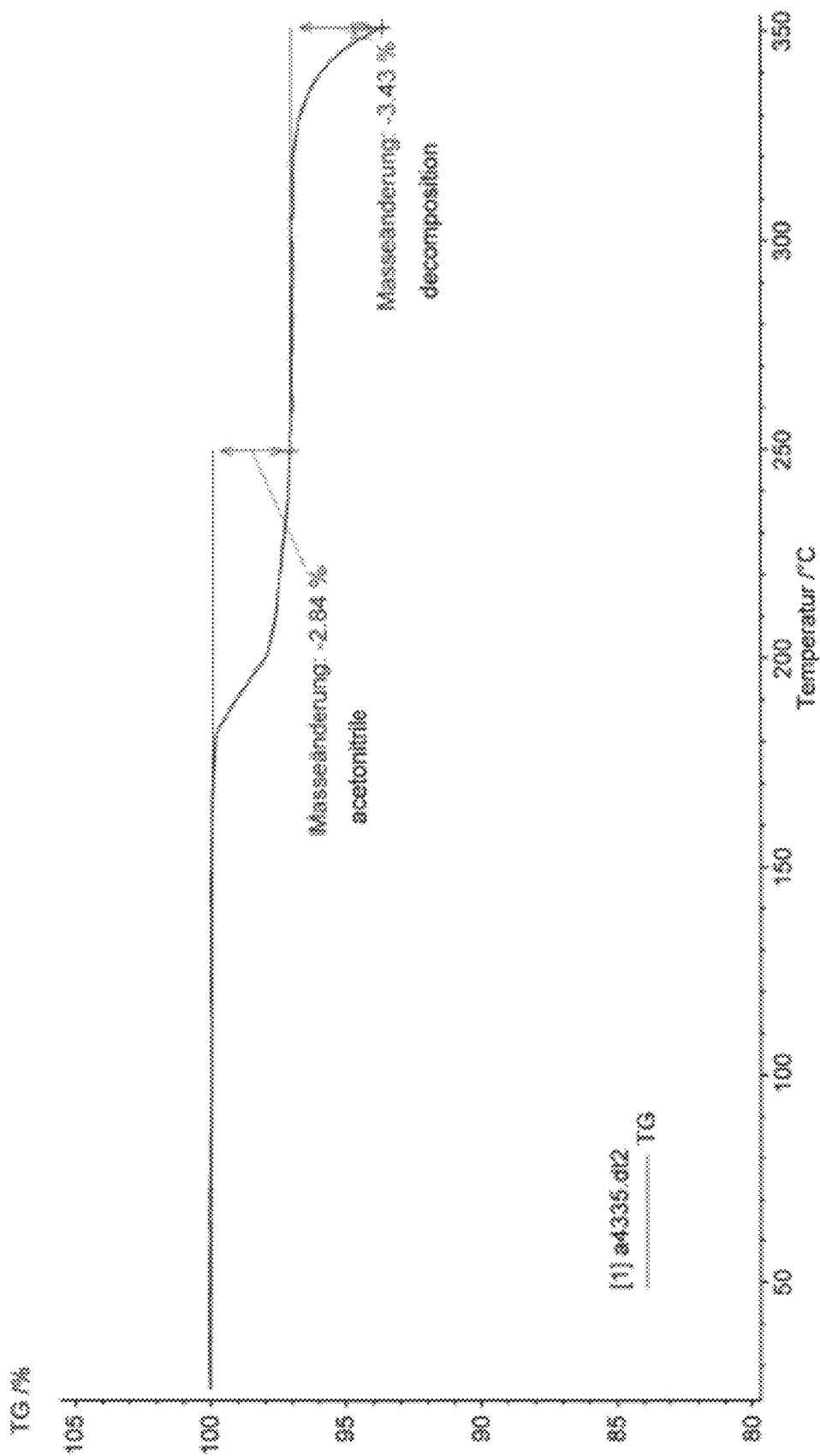
FIG. 109—TG-FTIR thermogram of the dried acetonitrile solvate form (Class 4), sample PP415-P26.

The TG-FTIR thermogram of the dried class 4 material, sample PP415-P26 (FIG. 109) shows the loss of ~2.8 wt.-% MeCN from 170° C. to 250° C. and decomposition at temperatures T>300° C. Compared to the TG-FTIR of sample PP415-P13 (FIG. 106), the solvent content of the sample has decreased from 3.4 wt.-% to 2.8 wt.-%.

Thus, the sample seems to be a partially desolvated solvate. As not sufficient material remained for a second drying experiment with subsequent characterization, experiment PP415-P13 was repeated (as PP415-P35). More material of class 4 was prepared and two drying experiments were carried out with this freshly prepared material:

PP415-P36: drying under vacuum (<1×10$^{-3}$ mbar) at 80° C. for three days

PP415-P37: drying under N$_2$ flow at 80° C. for three days

Figure 110:
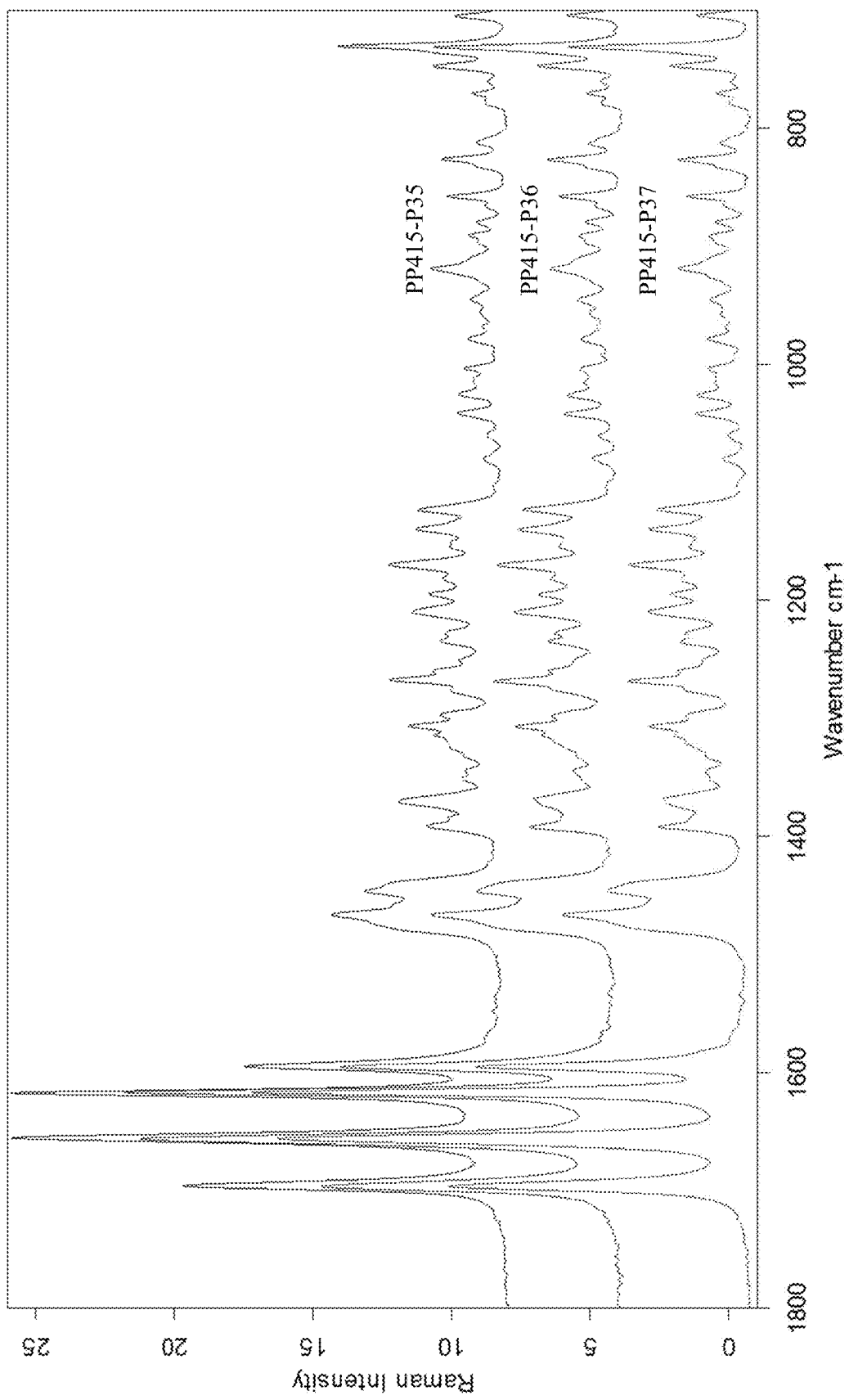
FIG. 110—FT-Raman spectra (1800-700 cm$^{-1}$) of the acetonitrile solvate form (Class 4) (top, sample PP415-P35), and of the dried acetonitrile solvate form (Class 4) (middle, sample PP415-P36 and bottom, sample PP415-P37) correspond to each other. The spectra have been scaled and offset in the y-direction for purposes of comparison.

The FT-Raman spectra of these dried class 4 samples (PP415-P36 and -P37) correspond to the spectrum of class 4 (i.e., PP415-P35, FIG. 110).

Figure 111:
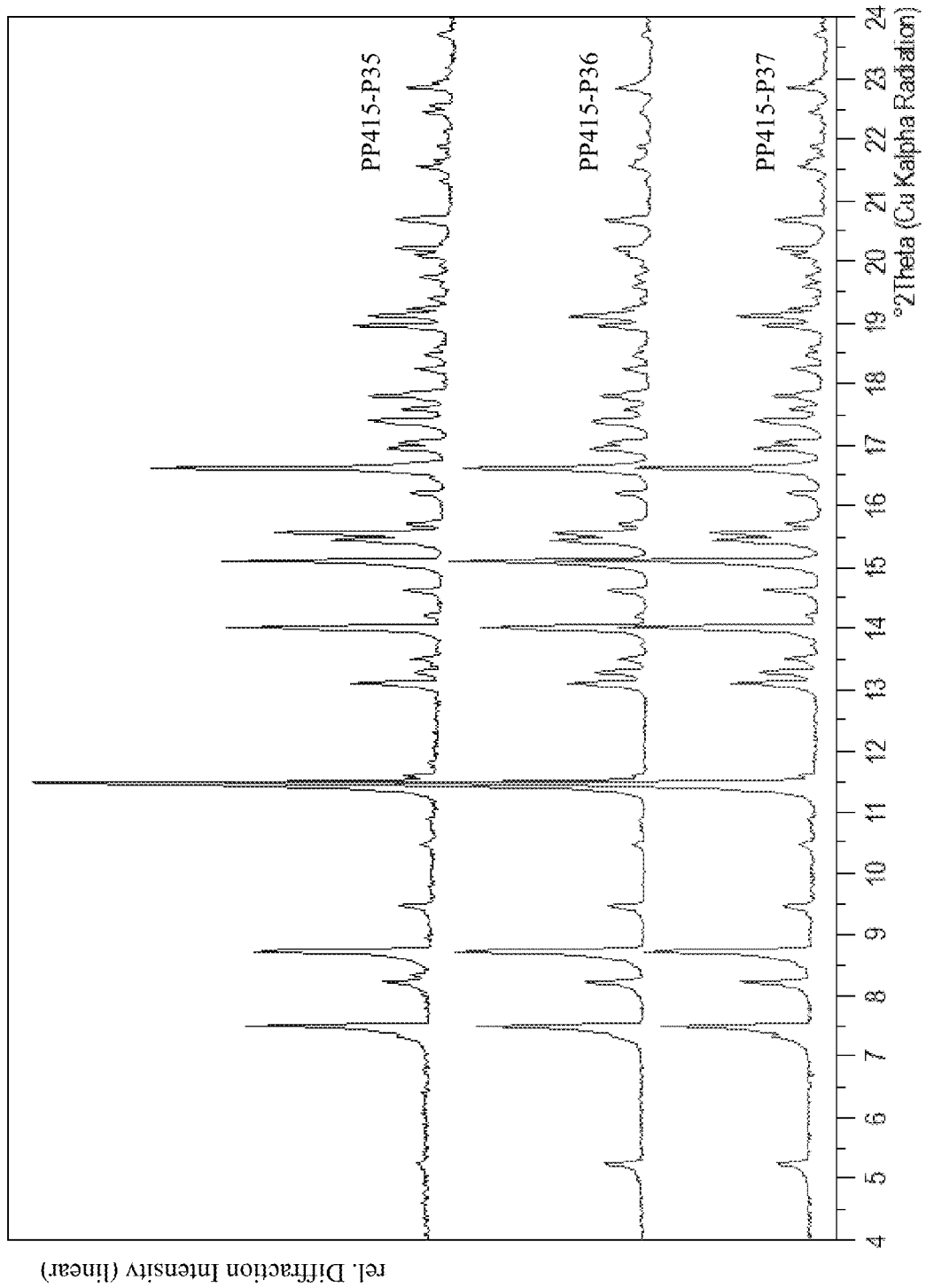
FIG. 111—PXRD patterns (4-24° 2θ) of the acetonitrile solvate form (Class 4) (top, sample PP415-P35) and of the dried acetonitrile solvate form (Class 4) (middle, sample PP415-P36 and bottom, sample PP415-P37) agree with each other. The patterns have been scaled and offset in the y-direction for the purpose of comparison.

The PXRD patterns (FIG. 111) of the class 4 material (sample PP415-P35) and the dried samples of class 4 (samples PP415-P36 and PP415-P37) are identical. The dried samples are crystalline.

Figure 112:
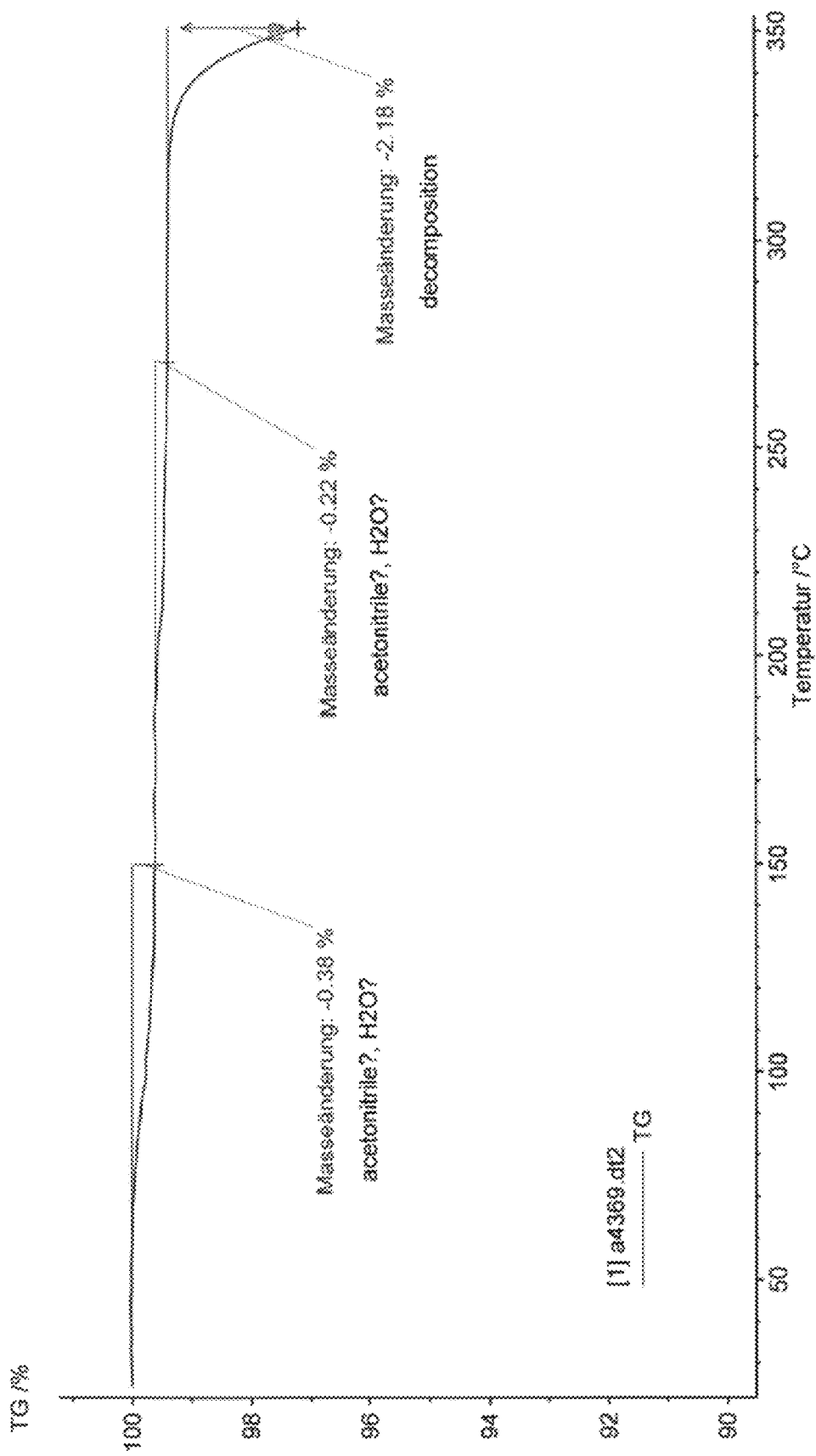
FIG. 112—TG-FTIR thermogram of the dried acetonitrile solvate form (Class 4), sample PP415-P36.
Figure 113:
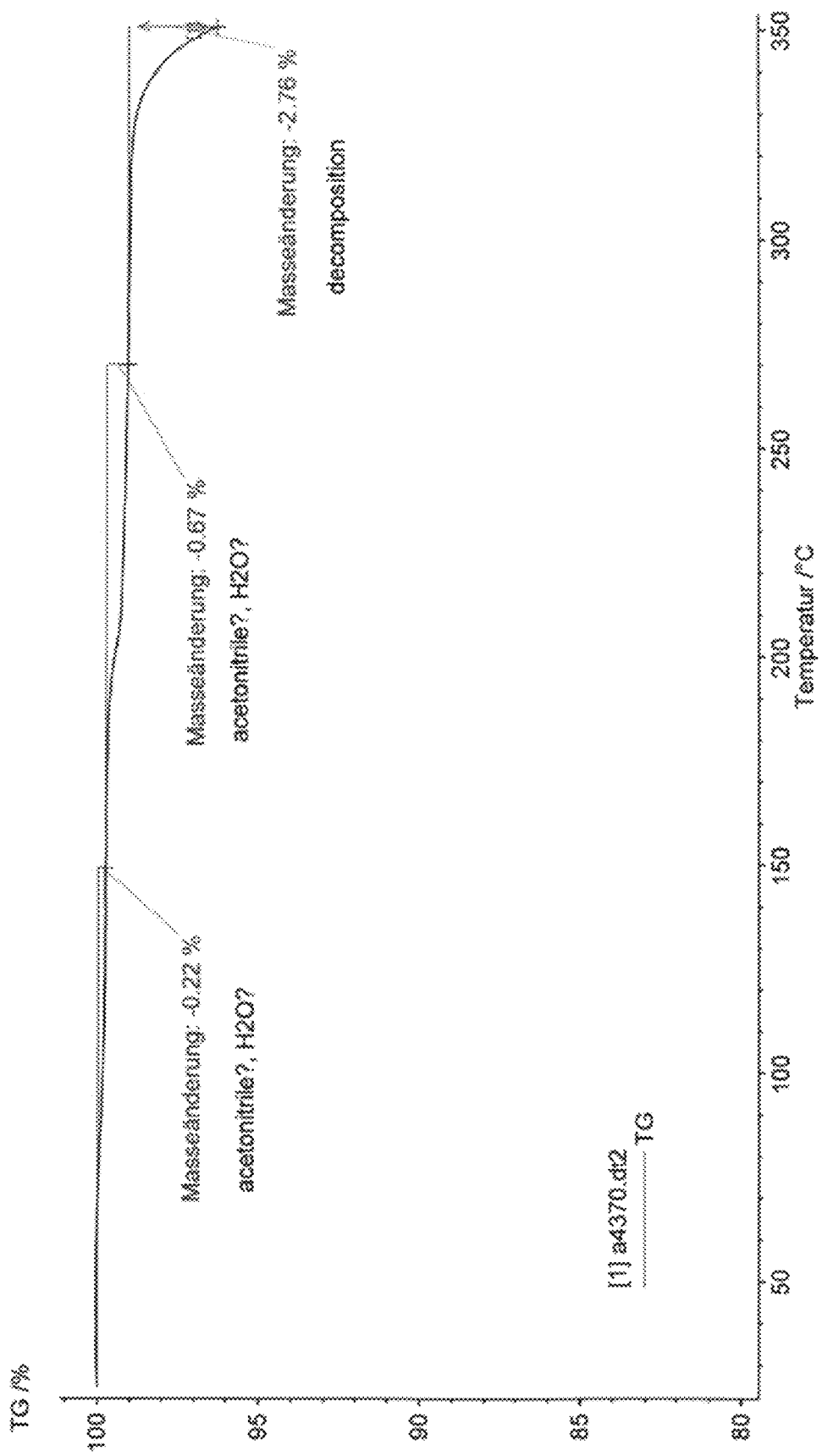
FIG. 113—TG-FTIR thermogram of the dried acetonitrile solvate form (Class 4), sample PP415-P37.

The TG-FTIR thermograms of these dried samples of class 4 (FIG. 112 for PP415-P36 and FIG. 113 for PP415-P37) show only a small solvent content (MeCN and/or H$_2$O) of ~0.6 wt.-% and ~0.9 wt.-% for PP415-P36 and PP415-P37, respectively, in two steps from 25° C. to 280° C. Solvent content is possibly MeCN and H$_2$O, but is difficult to determine as amounts are small. Decomposition starts at temperatures T>280° C.

Thus, most of the solvent of this solvate could be removed without destroying the crystal structure. A crystalline, non-solvated form (or rather desolvated solvate) was obtained.

m. Further Characterization of the Dried and Desolvated Class 4

Drying of class 4 (MeCN solvate) resulted in a desolvated solvate with the solvent content reduced to <1 wt.-% (TG-FTIR).

No change in the structure occurred upon desolvation (FT-Raman and PXRD). No significant loss of the crystallinity was observed.

Thus, a non-solvated, crystalline form of 63415 was obtained, the only one known to date.

This desolvated class 4 material was characterized further by DVS and DSC.

Figure 114:
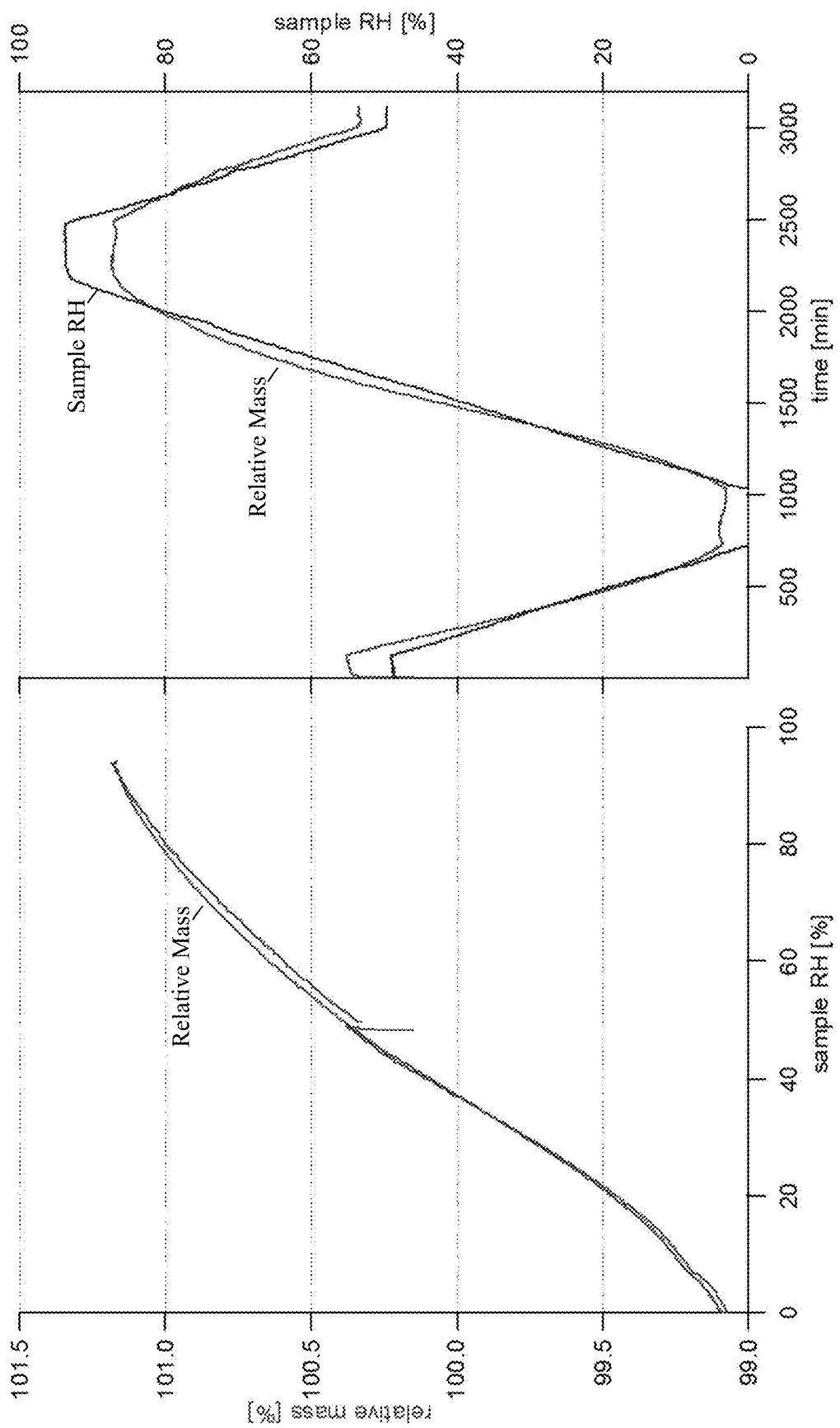
FIG. 114—DVS isotherm of the desolvated acetonitrile solvate form (Class 4), sample PP415-P37.

The DVS isotherm (FIG. 114) shows that during initial equilibration time at 50% r.h. a mass gain of ~0.4 wt.-% occurred. During the measurement, a gradual, reversible mass loss of ~1.3 wt.-% occurred upon lowering the relative humidity from 50% r.h. to 0% r.h. Equilibrium was reached. Upon increasing the relative humidity to 95% r.h., a gradual mass gain of ~0.8 wt.-% was observed (relative to the equilibration mass at 50% r.h.). Equilibrium was reached. After lowering the relative humidity to 50% r.h., the final mass remained 0.1 wt.-% below the equilibrated starting mass. The mass gain of ~0.7 wt.-% upon increasing the relative humidity from 50% r.h. to 85% r.h. classified the sample as slightly hygroscopic.

Figure 115:
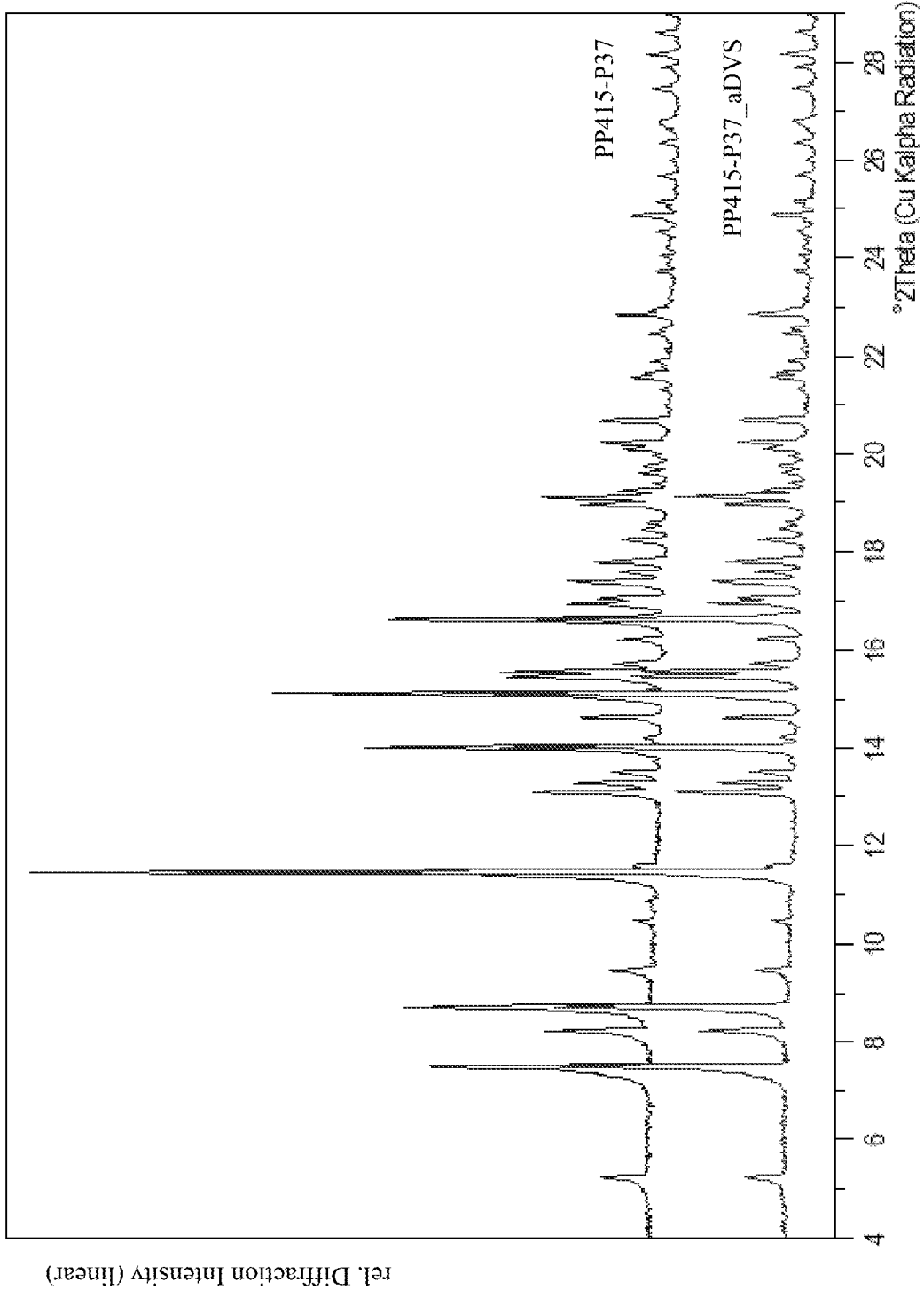
FIG. 115—PXRD pattern of the sample PP415-P37, an acetonitrile solvate form (Class 4) after the DVS measurement (bottom) is unchanged compared to the material before the DVS measurement (top). The patterns have not been scaled but are offset in the y-direction for the purpose of comparison.

The PXRD pattern of the sample after the measurement is unchanged compared to the pattern before the measurement (FIG. 115).

The DSC thermogram of a sample of desolvated class 4 material (FIG. 116) shows no glass transition attributable to the amorphous form, which would have been expected at ~150° C., but instead a sharp endothermic peak with a maximum at T=196.1° C. (ΔH=29.31 J/g), probably corresponding to melting, and no decomposition up to 270° C.

In addition, a DSC experiment was carried out with a ~1:1 mixture of the amorphous material, class 1, with the desolvated class 4 material to investigate if the amorphous material would transform and crystallize into the desolvated class 4, an event expected to occur (if at all) above the glass transition temperature of the amorphous form (T$_g$≈150° C.) and below the melting of the desolvated class 4 (T$_m$≈196° C.).

Figure 117:
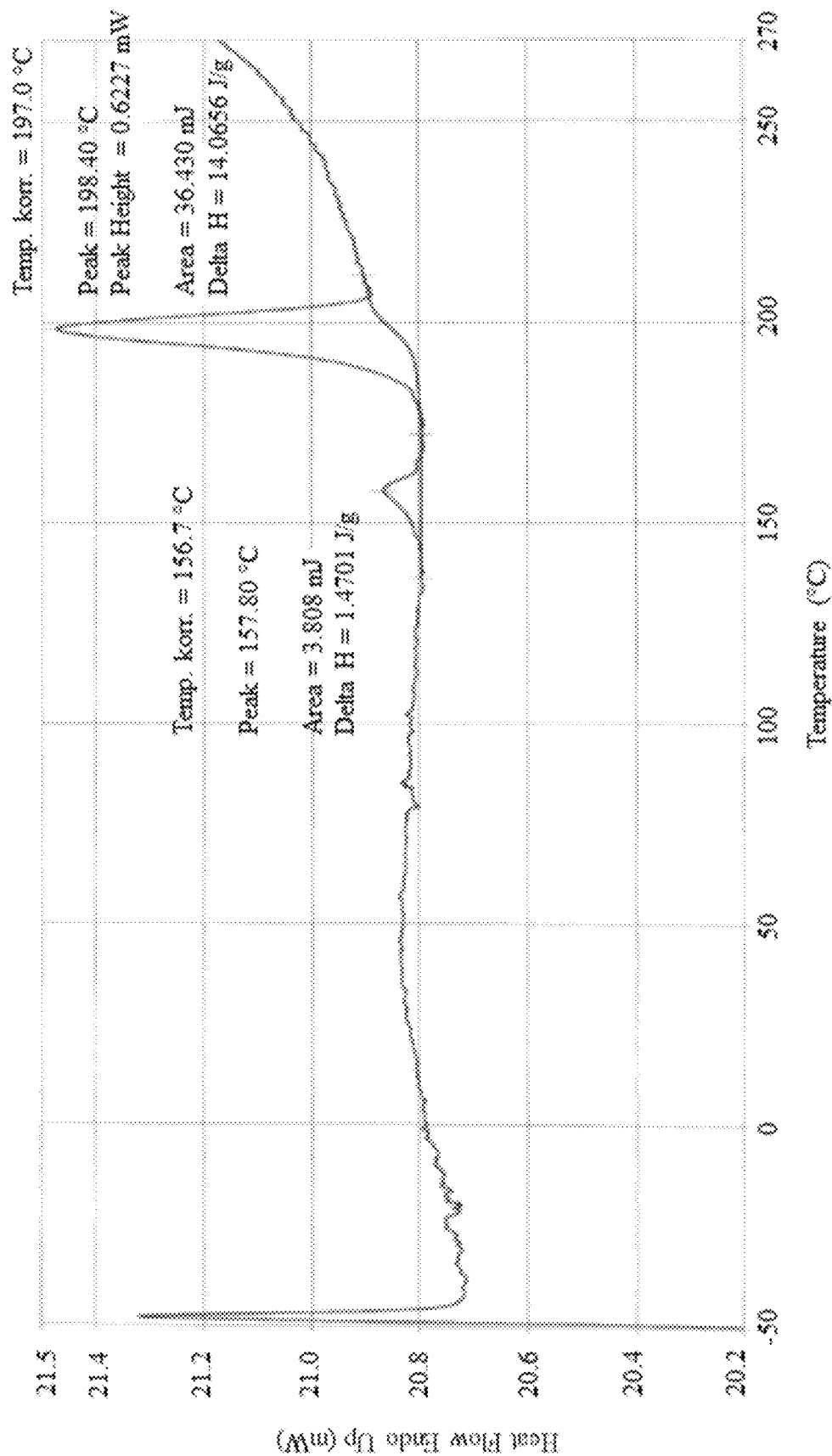
FIG. 117—DSC thermogram of a ~1:1 mixture of the amorphous form (Class 1), sample PP415-P1, with the desolvated acetonitrile solvate form (Class 4), sample PP415-P36.

The DSC thermogram of the mixture (FIG. 117) shows an endothermic event with a peak at T=156.7° C. (ΔH=1.47 J/g) and a second endothermic event with a peak at 197.0° C. (ΔH=14.1 J/g). The first event could be attributable to the amorphous material (glass transition at T$_g$≈150° C.). The second event could correspond to the melting of the desolvated class 4 at T$_m$≈196° C. The heat of fusion (ΔH=14.1 J/g) of the mixture correlates well to half of the heat of fusion (ΔH=29.3 J/g) of the pure desolvated class 4.

No exothermic event in the temperature range between the glass transition and the melting corresponding to a possible crystallization of the amorphous material can be observed. Thus, no transformation of the amorphous form into the desolvated class 4 form seemed to have occurred on this timescale.

In yet another DSC experiment with a ~1:1 mixture of the amorphous material, class 1, with the desolvated class 4 material, the heating was stopped at 173° C. (in between the glass transition and the melting) to allow time for a possible crystallization.

Figure 118:
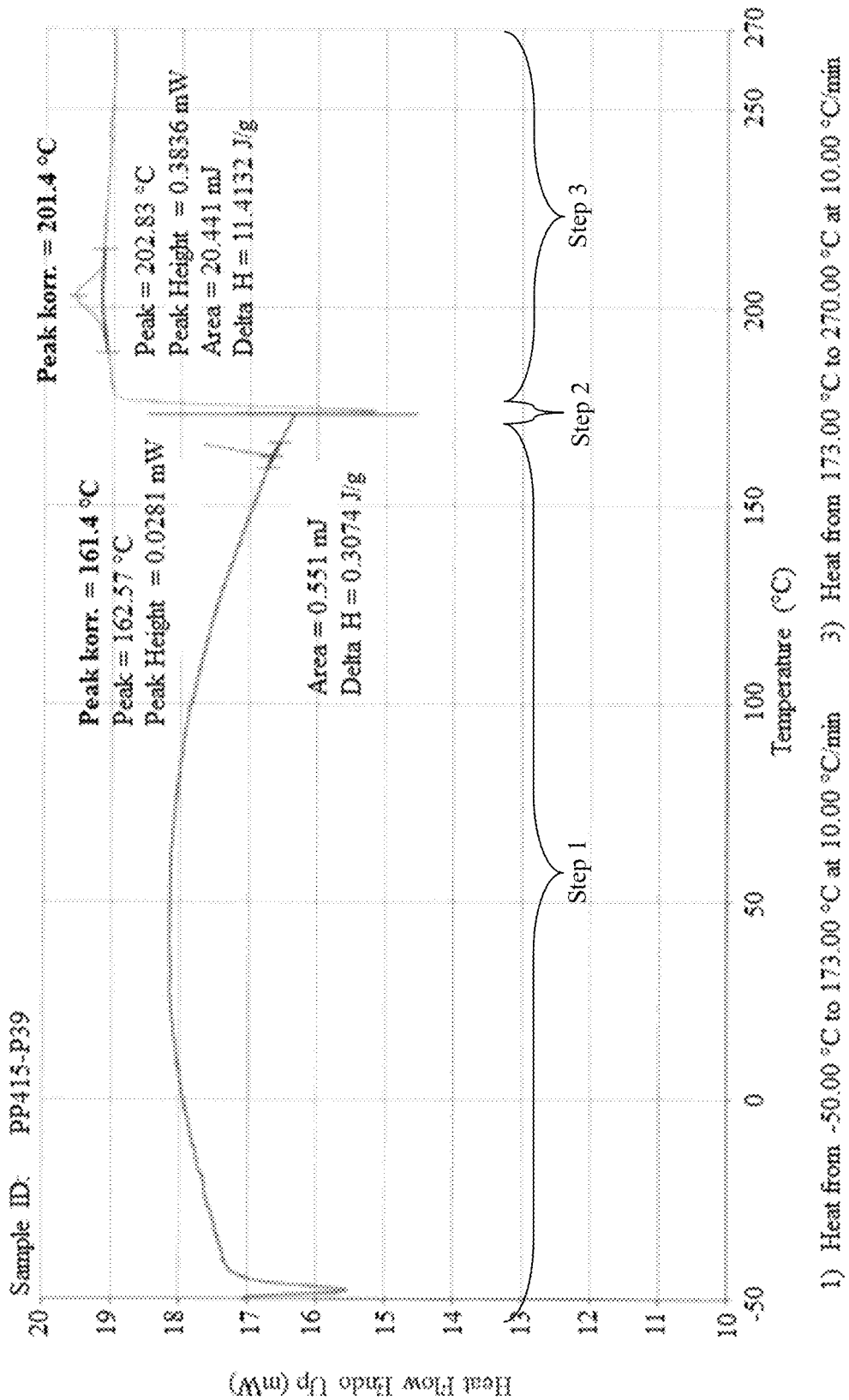
FIG. 118—DSC thermogram of a ~1:1 mixture of the amorphous form (Class 1), sample PP415-P1, with the desolvated acetonitrile solvate form (Class 4), sample PP415-P36 (experiment number: PP415-P39). The heating scan (Step 1) was stopped for 30 min at 173° C. (Step 2) and then resumed (Step 3).

The DSC thermogram of the mixture (FIG. 118) shows an endothermic event with a peak at T=161.4° C. ($\Delta H$=0.31 J/g) and a second endothermic event with a peak at 201.4° C. ($\Delta H$=11.4 J/g). As in the first experiment, the heat of fusion of the second peak did not increase; no indications for a transformation of the amorphous form into the desolvated class 4 form are visible.

The curved baseline (−50° C. to 150° C.) is most likely an artifact (due to a bent sample holder lid).

n. Class 5—THF Solvate

Class 5 was obtained only from a 1:1 THF/H$_2$O solvent mixture (Table 25).

The FT-Raman spectrum (FIG. 71) and PXRD pattern (FIG. 75) of class 5 differs significantly from the spectra and patterns of classes 2, 3, and 4.

The TG-FTIR thermogram of class 5 (sample PP415-P14, FIG. 119) shows the loss of ~36.1 wt.-% THF and H$_2$O from 25 to 200° C., most of it in a step from ~100° C. to 130° C. Before the TG-FTIR experiments, the samples were dried briefly (for ~5 min) under vacuum (10-20 mbar) to remove excess, unbound solvent. The loss of both THF and H$_2$O occur together in the same temperature range. Decomposition starts at temperatures T>300° C. The theoretical THF (b.p.=66° C.) content of a trisolvate is 28.1 wt.-%. Unfortunately, as the content of the two components cannot be quantified separately, the exact solvation state cannot be determined.

Details on the experiments and characterizations of samples PP415-P41 and PP415-P45 are provided.

TABLE 25

Crystallization experiments resulting in solid material of class 5

| Sample | Method | Solvent | Characterization | Drying |
|---|---|---|---|---|
| PP415-P14 | suspension equilibration | 1:1 THF/H$_2$O | Raman, PXRD, TG-FTIR | X |
| PP415-P41[b] | suspension equilibration | 1:1 THF/H$_2$O | PXRD | X |
| PP415-P45[b,c] | suspension equilibration | 1:1 THF/H$_2$O | PXRD | X |

[b]starting material: PP415-P40, class 2; in all other experiments in this table PP415-P1, class 1, was used as the starting material
[c]3-g scale experiment instead of 100-mg scale o. Drying Experiments on Samples of Class 5

The sample of class 5 (PP415-P14), obtained from a suspension equilibration experiment in ~1:1 THF/H$_2$O, was dried (as PP415-P27) under vacuum for several days (2-20 mbar, r.t. to 60° C., Table 26).

TABLE 26

Drying experiments of samples of Class 5

| Starting Material | | | Dried Material | | |
|---|---|---|---|---|---|
| Sample | Solvent Content | Drying Conditions | Sample | Solvent Content | Class |
| PP415-P14 | THF & H$_2$O (~36 wt.%) | r.t., ~3 mbar, ~5 d; 60° C., 5-10 mbar, 2 × 1 h; 40-50° C., 5-20 mbar, ~1 d | PP415-P27 | --(~0.3 wt.-%) | 1 (+5)[a] |

[a]mainly amorphous, only few broad peaks with low S/N ratio

The FT-Raman spectrum of the dried material (PP415-P27) is different from the spectrum of class 5 (PP415-P14, FIG. 120) and, with its broadened peaks, resembles more the spectrum of class 1, the amorphous starting material, PP415-P1.

The PXRD pattern of the dried class 5 material (PP415-P27) shows only some broad, low intensity peaks with a low S/N ratio, indicating the poor crystallinity of the sample (FIG. 121). Some of the peaks could correspond to class 5, while others, i.e., at 7.35° 2θ, are new or shifted.

The TG-FTIR thermogram of the dried class 5 material (FIG. 122) shows a mass loss of ~0.3 wt.-% from 25° C. to 290° C. and decomposition at temperatures T>290° C. The sample is anhydrous.

Thus, by drying under vacuum, the material has lost its solvent content and also much of its crystallinity.

8. Experiments to Prepare the Amorphous Form

Experiments with the aim to prepare the amorphous form, class 1, were carried out using class 2 material (PP415-P40, Table 8) as the starting material. Several strategies and methods were attempted:

Transformation of class 2 into class 5, followed by drying of class 5 to obtain the amorphous form, class 1.

Preparation of the amorphous form, class 1, directly from class 2, if possible using ICH class 3 solvents.

Mainly amorphous material was prepared starting from class 2 material in a two-step process via class 5 on a 100-mg and 3-g scale.

Further experiments were carried out with the aim to simplify the procedure to a one-step process, to avoid the ICH class 2 solvent THF, and to obtain fully amorphous material. The most promising method was found to be the precipitation from an acetone solution in a cold water bath. This direct method gives much better results than the two-step method via class 5.

a. Preparation of the Amorphous Form Via Class 5

Crystallization experiments using class 2, PP415-P40, as the starting material were carried out with the aim to transform this heptane solvate into class 5 (likely THF solvate), followed by drying of class 5 to obtain the amorphous material (Table 27).

Class 5 is thought to be a good intermediate step, as it is easier to desolvate and amorphize than classes 2 or 3.

TABLE 27

Summary of experiments aimed at preparation of amorphous form, class 1, via class 5 material

| Step | Sample | Method | Conditions | Results |
|---|---|---|---|---|
| 1 | PP415-P41 | suspension equil. | 1:1 THF/H$_2$O, 24° C., 3 d | class 5 |
| " | PP415-P45 | suspension equil. | 1:1 THF/H$_2$O, r.t. 1 d | class 5 |
| 2 | PP415-P44a | drying | 100 mbar, 80° C., 2 d | class 1[a]; 0.9 wt.-% THF |
| " | PP415-P46a | drying | 100 mbar, 80° C., 4 d | class 1[a]; 0.4 wt.-% H$_2$O |

[a]mainly amorphous, only few broad peaks with low S/N ratio b. Step 1: Transformation of Class 2 into Class 5

Transformation of the heptane solvate, class 2, into the THF solvate, class 5, was successfully carried out by suspending the PP415-P40 (heptane solvate) material in a (1:1) THF/H$_2$O mixture and equilibrating the suspension at r.t. (PP415-P41, 100 mg-scale). The resulting solid material corresponds to the THF solvate, class 5 (FIG. 123).

A first scale-up experiment from the mg-scale to the g-scale (×30, i.e., 3-g scale) was carried out analogous to PP415-P41: the class 2 heptane solvate starting material (PP415-P40) was equilibrated in THF/H$_2$O (1:1) for one day and successfully transformed into class 5, the THF solvate (PP415-P45, FIG. 124).

c. Step 2: Amorphization of Class 5 Material by Drying

The class 5 material (THF solvate) was dried at elevated temperature (80° C.) under vacuum (~100 mbar) taking into account the conditions that can be used at the API MFG site.

After drying the material of the 100-mg scale experiment, PP415-P41, for one day at 80° C. and 100 mbar it transformed into mainly amorphous material (PP415-P44, FIG. 125). The PXRD pattern shows only some broad peaks with low intensity. After additional drying (80° C., 100 mbar) overnight, the intensity of these broad peaks is further reduced (PP415-P44a). The TG-FTIR of this material shows the loss of ~0.9 wt.-% THF (with traces of water) gradually from 25° C. to 280° C. and decomposition at temperatures T>300° C. (FIG. 126).

The material of the 3-g scale experiment, PP415-P45, was also dried at 80° C. and 100 mbar (as PP415-P46). It transformed overnight into mainly amorphous material with only some broad peaks with low intensity (FIG. 127). After a total of four days of drying (80° C., 100 mbar), these broad peaks are still present (-P46a, FIG. 128). The TG-FTIR of this material shows no THF content, but the loss of ~0.4 wt.-% water gradually from 25° C. to 250° C. and decomposition at temperatures T>250° C. (FIG. 129).

d. Obtaining the Amorphous Form Directly

The preparation of the amorphous form starting from class 2 material in the two-step process via class 5 was largely, but not fully, successful. Thus, further experiments were carried out with the aim to simplify the procedure to a one-step process, to avoid the use of ICH class 2 solvent THF, and to obtain fully amorphous material (Table 28).

The amorphous form, class 1, was prepared directly from the class 2 material in an evaporation experiment of a class 2 solution in THF under N$_2$ flow (PP415-P42, FIG. 129).

In an attempt to simulate an incompletely dried heptane/hexane solvate with a significant amount of remaining solvent, an evaporation of a class 2 solution in an 8:2 THF/hexane solution was carried out (hexane was used instead of heptane in order to have similar boiling points in the solvent mixture). However, the resulting solid corresponds to class 2, the class of the isostructural solvates, not to class 5 (PP415-P43, FIG. 130).

In order to avoid the ICH class 2 solvent THF, evaporation experiments were carried out in ICH class 3 solvents.

Evaporation of a class 2 solution in EtOAc under N$_2$ flow resulted in crystalline material with a PXRD pattern corresponding to class 2 (PP415-P47, FIG. 130). The TG-FTIR (FIG. 80) shows the class 2-typical two-step mass loss (total of ~7.9 wt.-% EtOAc) at temperatures up to 240° C., indicating very tightly bound solvent molecules.

Evaporation in ethyl formate also gave crystalline class 2 material and not the amorphous form (PP415-P48, FIG. 131). The TG-FTIR (FIG. 78) shows the mass loss of ~3.5 wt.-% ethyl formate, at first gradually and then in a clear step between 180° C. and 200° C. There might be further loss of ethyl formate concomitant with the decomposition at T>240° C.

However, class 2 material was successfully transformed into the amorphous form, class 1, by adding an acetone solution to a cold (5° C.) water bath (PP415-P49, FIG. 132).

This direct method for the preparation of the amorphous form gives better results and is a more promising route than the two-step process.

TABLE 28

Summary experiments aimed at obtaining the amorphous form directly from class 2 starting material

| Sample | Method | Solvent | Condition | Result |
|---|---|---|---|---|
| PP415-P42 | evaporation | THF | N$_2$ flow, 1 d | class 1 |
| PP415-P43 | evaporation | 8:2 THF/hexane | N$_2$ flow, 1 d | class 2 |
| PP415-P47 | evaporation | EtOAc | N$_2$ flow, 1 d | class 2 |
| PP415-P48 | evaporation | ethyl formate | N$_2$ flow, 1 d | class 2 |
| PP415-P49 | precipitation | acetone | H$_2$O bath at 5° C. | class 1 |

9. Instrumental—Typical Measurement Conditions

FT-Raman Spectroscopy: Bruker RFS100 with OPUS 6.5 software; Nd:YAG 1064-nm excitation, Ge detector, 3500-100 cm$^{-1}$ range; typical measurement conditions: 100-300 mW nominal laser power, 64-128 scans, 2 cm$^{-1}$ resolution.

PXRD: Stoe Stadi P; Mythen1K Detector; Cu-Kα radiation; standard measurement conditions: transmission; 40 kV and 40 mA tube power; curved Ge monochromator; 0.02° 2θ step size, 12 s or 60 s step time, 1.5-50.5° 2θ or 1.0-55° 2θ scanning range; detector mode: step scan; 1° 2θ or 6° 2θ detector step; standard sample preparation: 10 to 20 mg sample was placed between two acetate foils; sample holder: Stoe transmission sample holder; the sample was rotated during the measurement.

TG-FTIR: Netzsch Thermo-Microbalance TG 209 with Bruker FT-IR Spectrometer Vector 22; aluminum crucible (with microhole), N$_2$ atmosphere, 10 K/min heating rate, 25-250° C. or 25-350° C. range.

DSC: Perkin Elmer DSC 7; gold crucibles (closed or with microhole), sample filled in an N$_2$ environment, 10 K/min heating rate, −50 to 250° C. or 350° C. range, at times quench cooling (at ~200 K/min) to −50° C. between scans.

DVS: Projekt Messtechnik Sorptions Prufsystem SPS 11—100n or Surface Measurement Systems DVS-1. The sample was placed on an aluminum or platinum holder on top of a microbalance and allowed to equilibrate for 2 h at 50% r.h. before starting the pre-defined humidity program:
(1) 50→0% r.h. (5%/h); 5 h at 0% r.h.
(2) 0→95% r.h. (5%/h); 5 h at 95% r.h.
(3) 95→50% r.h. (5%/h); 2 h at 50% r.h.

The hygroscopicity was classified based on the mass gain at 85% r.h. relative to the initial mass as follows: deliquescent (sufficient water adsorbed to form a liquid), very hygroscopic (mass increase of ≥15%), hygroscopic (mass increase <15% but ≥2%), slightly hygroscopic (mass increase <2% but ≥0.2%), or non-hygroscopic (mass increase <0.2%).

Solvents: For all experiments, Fluka, Merck, or ABCR analytical grade solvents were used.

Approximate Solubility Determination: Approximate solubilities were determined by a stepwise dilution of a suspension of about 10 mg of substance in 0.05 mL of solvent. If the substance was not dissolved by addition of a total of >10 mL solvent, the solubility is indicated as <1 mg/mL. Due to the experimental error inherent in this method, the solubility values are intended to be regarded as rough estimates and are to be used solely for the design of crystallization experiments.

Chemical Stability Determination: Four samples of 1.0 mg of the PP415-P1 material in 1.0 mL of the respective solvent were prepared. The resulting suspensions/solutions were equilibrated in a temperature-controlled Eppendorf Thermomixer Comfort shaker for 7 d, 2 d, 24 h, and 6 h at 25° C. at a shaking rate of 500 rpm. If necessary, the solid phase was separated by filter centrifugation (0.5-μm PVDF membrane). The filtrates were diluted in the diluent (0.1% formic acid in MeCN) to concentrations ≤0.2 mg/mL (unknown and likely lower for suspensions) and examined using the HPLC method given in Table 29. As reference, the PP415-P1 material was diluted in the diluent to a concentration of 0.25 mg/mL and added to the beginning and end of the HPLC sequence.

HPLC Results

TABLE 29

HPLC method used for chemical stability determinations

| Column | Zorbax Eclipse XDB-C18, 3 × 150 mm, 5 μm (CC19) | | |
|---|---|---|---|
| Eluent A | $H_2O$ + 0.1% formic acid | | |
| Eluent B | MeCN + 0.1% formic acid | | |
| Gradient | 0 min | 50% A | 50% B |
| | 10.0 min | 10% A | 90% B |
| | 15.0 min | 0% A | 100% B |
| | 15.1 min | 50% A | 50% B |
| | 20.0 min | 50% A | 50% B |
| Flow | 0.75 mL/min | | |
| Injection Volume | 10 μL | | |
| Wavelength | 254 nm, 242 nm, 210 nm | | |
| Acquisition time | 20 min | | |
| Run time | 20 min | | |
| Column temperature | 25° C. | | |
| Retention time | 8.9-9.0 min | | |

10. Abbreviations

Methods:
 AUC area under the curve analysis
 DSC differential scanning calorimetry
 DVS dynamic vapor sorption
 FT Raman Fourier-transform Raman spectroscopy
 $^1$H-NMR proton nuclear magnetic resonance spectroscopy
 HPLC high-performance liquid chromatography
 PXRD powder X-ray diffraction
 TG-FTIR thermogravimetry coupled to Fourier transform infrared spectroscopy Chemicals:
 1BuOH 1-butanol
 CTAB cetyl trimethylammonium bromide
 DCM dichloromethane
 DEE diethyl ether
 DMF N,N-dimethylformamide
 EtOAc ethyl acetate
 EtOH ethanol
 IPE isopropyl ether
 MeCN acetonitrile
 MEK methyl ethyl ketone
 MeOH methanol
 PEG propylene glycol
 PTFE polytetrafluoroethylene, Teflon
 2PrOH 2-propanol, isopropanol
 SDS sodium dodecyl sulfate
 TBME tert-butyl methyl ether
 TEA triethylamine
 THF tetrahydrofuran
 Tween 80 polyoxyethylene (80) sorbitan monooleate or polysorbate 80

Genes, Proteins, and Biological Parameters:
 AIM antioxidant inflammation modulator
 Akr1c1 aldo-keto reductase family 1, member c1
 ALP alkaline phosphatase
 ALT alanine transaminase
 ARE antioxidant response element
 AST aspartate transaminase
 AUC area under the curve
 BAL bronchoalveolar lavage
 BALF bronchoalveolar lavage fluid
 Bil bilirubin
 BUN blood urea nitrogen
 COPD chronic obstructive pulmonary disease
 COX-2 cyclooxygenase-2
 Cr creatine
 CYP450 cytochrome P450
 Eh-1 epoxide hydrolase 1
 G6PD glucose-6 phosphate dehydrogenase
 Gclc glutamate-cysteine ligase, catalytic subunit
 Gclm glutamate-cysteine ligase, modifier subunit
 Ggt1 gamma-glutamyltransferase
 Glrx glutaredoxin-1
 Glu glucose
 GOT glutamic-oxaloacetic transaminase
 GPT1 glutamic-pyruvate transaminase
 Gpx3 glutathione peroxidase 3
 GSH glutathione
 GSR glutathione reductase
 GSs glutathione synthetase
 GST glutathione S-transferase
 GSTa1 glutathione S-transferase alpha 1
 GSTp1 glutathione S-transferase pi 1
 Gy Gray
 H6PD hexose-6-phosphate dehydrogenase
 hERG human ether a-go-go-related gene
 HMOX1 heme oxygenase (decycling) 1
 HO-1 heme oxygenase
 IFNγ interferon-gamma
 IL interleukin
 iNOS inducible nitric oxide synthase
 IκBα nuclear factor of kappa light polypeptide gene enhancer in B-cells inhibitor, alpha
 KC mouse IL-8 related protein
 Keap1 Kelch-like ECH associated protein-1
 LPS lipopolysaccharide
 ME1 malic enzyme 1

MPCE micronucleated polychromatic erythrocytes
Mrp metG-related protein
Mrps multidrug resistance-related proteins
NADPH nicotinamide adenine dinucleotide phosphate, reduced
NFκB nuclear factor of kappa-light-chain-enhancer of activated B cells
NO nitric oxide
NQO1 NAD(P)H quinone oxidoreductase 1
Nrf2 nuclear factor (erythroid-derived)-like 2
p-IκBa phosphorylated IκBa
PBMC peripheral blood mononuclear cell
PCE polychromatic erythrocytes
PGD phosphogluconate dehydrogenase
PMN polymorphonuclear
RANTES regulated and normal T cell expressed and secreted
SOD1 superoxide dismutase 1
SRXN1 sulfiredoxin-1
TG total glycerides
TKT transketolase
TNFα tumor necrosis factor alpha
Txn thioredoxin
TXNRD1 thioredoxin reductase 1
xCT solute carrier family 7, member 11

Misc:
API active pharmaceutical ingredient
aq. aqueous
b.p. boiling point
cryst. crystalline
decomp. decomposition
d day(s)
eq. equivalent
equil. equilibration
evap. evaporation
h hour(s)
mat. material
min minute(s)
m.p. melting point
MS molecular sieves
part. partially
precip. precipitation
r.h. relative humidity
rpm revolutions per minute
r.t. room temperature (~25° C.)
S/N signal-to-noise (ratio)
solv. solvent
susp. suspension
T temperature
$T_g$ glass transition temperature
theo. theoretical
vis. obs. visual observation
w week(s)
wt.-% weight percent K. Further Tables

TABLE 30

List of Samples and Performed Experiments

| Sample | Experimental Description | Test Methods | Result/Remarks |
|---|---|---|---|
| PP415-P1 | received ~5 g of 63415, batch # 0141-66-1, on Mar. 25, 2011; MW = 554.7 g/mol, $C_{33}H_{44}F_2N_2O_3$ | FT-Raman: PP415P1.0 PP415P1.1 PXRD: 117a TG-FTIR: a4285 $^1$H-NMR: Mar. 30, 2011-ktr/30 DSC: d_9840 DVS: #0305_02 post-DVS Raman: PP415P1_aDVS post-DVS PXRD: 179a | FT-Raman: used as reference for P1 PXRD: amorphous, no crystalline peak pattern TG-FTIR: loss of ~0.9 wt-% (~0.1 eq) EtOH with traces of $H_2O$ from 25° C. to 200° C., decomposition at T >290° C. $^1$H-NMR: agrees with structure, ~0.08 eq. EtOH DSC: 1$^{st}$ scan: Tg = 152.7° C. (ΔCp = 0.72 J/g ° C.); 2nd scan: Tg = 149.7° C. (ΔCp = 0.45 J/g° C.) DVS: slightly hygroscopic; Δm = +0.4% (50%→85% r.h.); total mass gain of 2.1 wt.-% from 0% r.h. to 95% r.h. post-DVS Raman and PXRD: unchanged |
| PP415-P2 | stored material of PP415-P1 at 25° C. open over a saturated solution of $NH_4NO_3$ (i.e., at ~62% r.h.); examined samples after 1 w (PP415-P2a), 2 w (PP415-P2b), and 4 w (PP415-P2c). | PXRD: 132a (-P2a) 191a (-P2b) 262a (-P2c) | PXRD: all amorphous, correspond to P1 |
| PP415-P3 | stored material of PP415-P1 at 40° C. open over a saturated solution of NaCl (i.e., at ~75% r.h.); examined samples after 1 w (PP415-P3a), 2 w (PP415-P3b), and 4 w (PP415-P3c). | PXRD: 133a (-P3a) 192a (-P3b) 263a (-P3c) | PXRD: all amorphous, correspond to P1 |
| PP415-P4 | stored material of PP415-P1 at 60° C. in a closed container; examined samples after 1 w (PP415-P4a), 2 w (PP415-P4b), and 4 w (PP415-P4c). | PXRD: 134a (-P4a) 193a (-P4b) 264a (-P4c) | PXRD: all amorphous, correspond to P1 |
| PP415-P5 | stored material of PP415-P1 at 80° C. in a closed container; examined samples after 1 w (PP415-P5a), 2 w (PP415-P5b), and 4 w (PP415-P5c). | PXRD: 135a (-P5a) 194a (-P5b) 265a (-P5c) | PXRD: all amorphous, correspond to P1 |
| PP415-P6 | suspended 97.7 mg of PP415-P1 in 0.4 mL of 2PrOH; obtained white suspension; equilibrated suspension at 22° C. shaking at 400 rpm; added stepwise a total of 0.5 mL of the solvent over the next couple of days; after 15 d recovered solid material by filter centrifugation (0.20-μm PTFE membrane); examined material by FT-Raman spectroscopy and PXRD; dried material for 5 min under vacuum (10-20 mbar); examined material by TG-FTIR. | FT-Raman: PP415P6.0 PXRD: 225a TG-FTIR: a4323 | Raman: corresponds to class 3 PXRD: corresponds to class 3 TG-FTIR: loss of ~5.4 wt.-% 2PrOH from 25° C. to 250° C., most of it in a step from ~170° C. to 190° C.; decomposition starts at T >250° C. |

TABLE 30-continued

List of Samples and Performed Experiments

| Sample | Experimental Description | Test Methods | Result/Remarks |
|---|---|---|---|
| PP415-P7 | suspended 104.3 mg of PP415-P1 in 0.6 mL of 1:2 EtOAc/heptane; obtained white suspension; equilibrated suspension at 22° C. shaking at 400 rpm; added stepwise a total of 0.2 mL of the solvent mixture over the next couple of days; after 15 d recovered solid material by filter centrifugation (0.20-μm PTFE membrane); examined material by FT-Raman spectroscopy and PXRD; dried material for 5 min under vacuum (10-20 mbar); examined material by TG-FTIR. | FT-Raman: PP415P7.0 PXRD: 227a TG-FTIR: a4338 | Raman: corresponds to class 2 PXRD: corresponds to class 2 TG-FTIR: loss of ~7.5 wt.-% EtOAc and heptane in two steps from ~100° C. to 290° C.; decomposition starts at T >290° C. |
| PP415-P8 | suspended 102.0 mg of PP415-P1 in 0.4 mL of 1:2 acetone/hexane; obtained white suspension; equilibrated suspension at 22° C. shaking at 400 rpm; added stepwise a total of 0.2 mL of the solvent mixture over the next couple of days; after 15 d recovered solid material by filter centrifugation (0.20-μm PTFE membrane); examined material by FT-Raman spectroscopy and PXRD. | FT-Raman: PP415P8.0 PXRD: 228a | Raman: corresponds to class 2 PXRD: corresponds to class 2 |
| PP415-P9 | suspended 102.6 mg of PP415-P1 in 0.4 mL of 1:3 toluene/diethyl ether; obtained white suspension; equilibrated suspension at 22° C. shaking at 400 rpm; added stepwise a total of 0.2 mL of the solvent mixture over the next couple of days; after 15 d recovered solid material by filter centrifugation (0.20-μm PTFE membrane); examined material by FT-Raman spectroscopy. | FT-Raman: PP415P9.0 | Raman: corresponds to class 2, contains solvent signals |
| PP415-P10 | suspended 102.5 mg of PP415-P1 in 0.2 mL of 1:3 MeOH/TBME; obtained clear solution; equilibrated solution at 22° C. shaking at 400 rpm; after 1 d observed thick suspension; added 0.2 mL of the solvent mixture; continued equilibration of suspension at 22° C. shaking at 400 rpm; after a total of 15 d recovered solid material by filter centrifugation (0.20-μm PTFE membrane); examined material by FT-Raman spectroscopy and PXRD. | FT-Raman: PP415P10.0 PXRD: 229a | Raman: corresponds to class 2 PXRD: corresponds to class 2 |
| PP415-P11 | suspended 97.1 mg of PP415-P1 in 0.4 mL of 1:2 MEK/cyclohexane; obtained white suspension; equilibrated suspension at 22° C. shaking at 400 rpm; after 15 d recovered solid material by filter centrifugation (0.20-μm PTFE membrane); examined material by FT-Raman spectroscopy. | FT-Raman: PP415P11.0 | Raman: corresponds to class 2, contains solvent signals |
| PP415-P12 | suspended 98.6 mg of PP415-P1 in 0.2 mL of 9:1 EtOH/H$_2$O; obtained white suspension; equilibrated suspension at 22° C. shaking at 400 rpm; added stepwise a total of 0.2 mL of the solvent mixture over the next couple of days; after 15 d recovered solid material by filter centrifugation (0.20-μm PTFE membrane); examined material by FT-Raman spectroscopy and PXRD; dried material for 5 min under vacuum (10-20 mbar); examined material by TG-FTIR. | FT-Raman: PP415P12.0 PXRD: 230a TG-FTIR: a4324 | Raman: corresponds to class 3 PXRD: corresponds to class 3 TG-FTIR: loss of ~4.9 wt.-% EtOH (with traces of water) from 25° C. to 250° C., most of it in a step from ~160° C. to 190° C.; decomposition starts at T >250° C. |
| PP415-P13 | suspended 95.9 mg of PP415-P1 in 0.2 mL of 7:3 MeCN/H$_2$O; obtained two clear, separated phases; equilibrated solution at 22° C. shaking at 400 rpm; after 1 d observed thick suspension; added 0.2 mL of the solvent mixture; continued equilibration of suspension at 22° C. shaking at 400 rpm; after a total of 15 d recovered solid material by filter centrifugation (0.20-μm PTFE membrane); examined material by FT-Raman spectroscopy and PXRD; dried material for 5 min under vacuum (10-20 mbar); examined material by TG-FTIR. | FT-Raman: PP415P13.0 PXRD: 231a TG-FTIR: a4321 | Raman: corresponds to class 4, contains solvent signals PXRD: corresponds to class 4 TG-FTIR: loss of ~3.4 wt.-% MeCN (with traces of water) from 25° C. to 270° C., most of it in a step from ~180° C. to 210° C.; decomposition starts at T >270° C. |
| PP415-P14 | suspended 95.8 mg of PP415-P1 in 0.2 mL of 9:1 THF/H$_2$O; obtained two clear, separated phases; equilibrated solution at 22° C. shaking at 400 rpm; after 1 d observed one clear phase; added 0.2 mL of H$_2$O; observed white precipitate; equilibrated suspension at 22° C. shaking at 400 rpm; after a total of 15 d recovered solid material by filter centrifugation (0.20-μm PTFE membrane); examined material by FT-Raman spectroscopy and PXRD; dried material for 5 min under vacuum (10-20 mbar); examined material by TG-FTIR. | FT-Raman: PP415P14.0 PXRD: 232a TG-FTIR: a4322 | Raman: corresponds to class 5, contains solvent signals PXRD: corresponds to class 5 TG-FTIR: loss of ~36.1 wt-% and H$_2$O from 25° C. to 200° C., most of it in a step from ~100° C. to 130° C.; decomposition starts at T >300° C. |
| PP415-P15 | dissolved 100.6 mg of PP415-P1 in 0.2 mL of 1:2 DCM/IPE; obtained clear solution; observed precipitation of white solid in <1 min; added 0.2 mL of solvent mixture; covered vial with single-layer tissue and let solvent evaporate under ambient conditions; obtained wet, white solid material after several hours; examined solid by FT-Raman spectroscopy and PXRD. | FT-Raman: PP415P15.0 PXRD: 137a | Raman: corresponds to class 2, contains solvent signals PXRD: corresponds to class 2 |

TABLE 30-continued

List of Samples and Performed Experiments

| Sample | Experimental Description | Test Methods | Result/Remarks |
|---|---|---|---|
| PP415-P16 | dissolved 100.3 mg of PP415-P1 in 0.2 mL of 1:2 MeOH/toluene; obtained clear solution; covered vial with single-layer tissue and let solvent evaporate under ambient conditions; obtained glassy material after several days; examined material by FT-Raman spectroscopy. | FT-Raman: PP415P16.0 | FT-Raman: corresponds to class 1, contains toluene solvent peaks |
| PP415-P17 | dissolved 101.0 mg of PP415-P1 in 0.3 mL of 1:3 EtOAc/heptane; obtained clear solution; observed precipitation of white solid in <1 min; added 0.2 mL of solvent mixture; covered vial with single-layer tissue and let solvent evaporate under ambient conditions; obtained wet, white solid material after several hours; examined solid by FT-Raman spectroscopy and PXRD. | FT-Raman: PP415P17.0 PXRD: 138a | Raman: corresponds to class 2, contains solvent signals PXRD: corresponds to class 2 |
| PP415-P18 | dried material of PP415-P15 under vacuum (2-20 mbar) at r.t. for ~2 h; examined dry, white solid by FT-Raman spectroscopy, PXRD, and TG-FTIR. | FT-Raman: PP415P18.0 PXRD: 149a TG-FTIR: a4301 | Raman: corresponds to class 2 PXRD: corresponds to class 2 TG-FTIR: loss of ~7.0 wt.% IPE in two steps from ~140° C. to ~250° C.; decomposition at T >250° C. |
| PP415-P19 | dried material of PP415-P17 under vacuum (2-20 mbar) at r.t. for ~2 h; examined dry, white solid by FT-Raman spectroscopy, PXRD, and TG-FTIR. | FT-Raman: PP415P19.0 PXRD: 150a TG-FTIR: a4302 | Raman: corresponds to class 2 PXRD: corresponds to class 2 TG-FTIR: loss of ~7.6 wt.-% heptane in two steps from ~140° C. to ~270° C.; decomposition at T >270° C. |
| PP415-P20 | suspended 98.8 mg of PP415-P1 in 2.0 mL of $H_2O$; heated suspension to 50° C.; added slowly and stepwise 4.0 mL of acetone; obtained clear solution; heated solution to 55° C. and held at 55° C. for 30 min; slowly cooled in 4 h 10 min to 5° C. (at ~0.2 K/min); recovered solid by vacuum filtration (P4 pore size); examined solid by FT-Raman spectroscopy and PXRD. | FT-Raman: PP415P20.0 PXRD: 226a | Raman: corresponds to class 3, contains solvent signals PXRD: corresponds to class 3 |
| PP415-P21 | suspended 100.9 mg of PP415-P1 in 2.0 mL of cyclohexane; heated suspension to 70° C.; added slowly and stepwise 0.5 mL of cyclohexane and 0.5 mL of EtOH; thin suspension became thicker due to additional precipitation over course of solvent addition; heated suspension to 75° C. and held at 75° C. for 30 min; slowly cooled in 5 h to 5° C. (at ~0.23 K/min); recoverd solid by vacuum filtration (P4 pore size); examined solid by FT-Raman spectroscopy and PXRD; dried material for 5 min under vacuum (10-20 mbar); examined material by TG-FTIR. | FT-Raman: PP415P21.0 PXRD: 218a TG-FTIR: a4326 | Raman: corresponds to class 2 PXRD: corresponds to class 2 TG-FTIR: loss of ~5.8 wt.-% cyclohexane in two steps from ~140° C. to ~250° C.; decomposition at T >250° C. |
| PP415-P22 | suspended 151.1 mg of PP415-P1 in 1.5 mL of toluene; heated suspension to 70° C.; obtained clear solution; added 0.5 mL of MeCN; heated solution to 75° C. and held at 75° C. for 30 min; slowly cooled in 5 h to 5° C. (at ~0.23 K/min); observed clear solution and no precipitation; stirred clear solution at 5° C. for 2 d; observed no precipitation; evaporated solvent under $N_2$ flow at r.t.; obtained glassy substance; examined it by FT-Raman spectroscopy. | FT-Raman: PP415P22.0 | Raman: corresponds to class 1, contains solvent signals |
| PP415-P23 | suspended 150.6 mg of PP415-P1 in 1.5 mL of dioxane; heated suspension to 70° C.; added 0.5 mL of EtOAc; heated solution to 75° C. and held at 75° C. for 30 min; slowly cooled in 5 h to 5° C. (at ~0.23 K/min); observed clear solution and no precipitation; stirred clear solution at 5° C. for 2 d; observed no precipitation; evaporated solvent under $N_2$ flow at r.t.; obtained glassy substance; examined it by FT-Raman spectroscopy. | FT-Raman: PP415P23.0 | Raman: corresponds to class 1, contains solvent signals |
| PP415-P24 | suspended 99.4 mg of PP415-P1 in 0.3 mL of 1BuOH; heated suspension to 70° C.; obtained clear solution; observed shortly thereafter precipitation of white solid; added 0.5 mL 1BuOH; still suspension; heated suspension to 75° C. and held at 75° C. for 30 min; slowly cooled in 5 h to 5° C. (at ~0.23 K/min); recovered solid by vacuum filtration (P4 pore size); examined solid by FT-Raman spectroscopy and PXRD; dried material for 5 min under vacuum (10-20 mbar); examined material by TG-FTIR. | FT-Raman: PP415P24.0 PXRD: 219a TG-FTIR: a4325 | Raman: corresponds to class 2, contains solvent signals PXRD: corresponds to class 2 TG-FTIR: loss of ~16.6 wt.-% 1BuOH in a step from ~50° C. to ~160° C., further loss of 1BuOH (6.6 wt.-%) in a second step from 160° C. to 230° C.; decomposition at T >230° C. |
| PP415-P25 | dried material of PP415-P25 under vacuum: at 60° C. and ~5 mbar for ~1 h; at r.t. and ~3 mbar for 4.5 d; at 60° C. and ~10 mbar for 1 h; at 40-50° C. and 5-20 mbar for ~20 h, examined solid by FT-Raman spectroscopy, PXRD, and TG-FTIR. | FT-Raman: PP415P25.0 PXRD: 258a TG-FTIR: a4337 | Raman: corresponds to class 3 PXRD: corresponds to class 3 TG-FTIR: loss of ~5.4 wt.-% 2PrOH from 50° C. to 250° C., most of it in a step from 170° C. to 190° C., another loss of ~1.0 wt.-% from 290° C. to 320° C.; decomposition at T >320° C. |
| PP415-P26 | dried material of PP415-P13 under vacuum: at 60° C. and ~5 mbar for ~1 h; at r.t. and 3 mbar for 4.5 d; at 60° C. and ~10 mbar for 1 h; at 40-50° C. and 5-20 mbar for ~20 h, examined solid by FT-Raman spectroscopy, PXRD, and TG-FTIR. | FT-Raman: PP415P26.0 PXRD: 259a TG-FTIR: a4335 | Raman: corresponds to class 4 PXRD: corresponds to class 4 TG-FTIR: loss of ~2.8 wt.-% MeCN from 170° C. to 250° C.; decomposition at T >300° C. |

TABLE 30-continued

List of Samples and Performed Experiments

| Sample | Experimental Description | Test Methods | Result/Remarks |
|---|---|---|---|
| PP415-P27 | dried material of PP415-P14 under vacuum: at 60° C. and ~5 mbar for ~1 h; at r.t. and ~3 mbar for 4.5 d; at 60° C. and ~10 mbar for 1 h; at 40-50° C. and 5-20 mbar for ~20 h, examined solid by FT-Raman spectroscopy, PXRD, and TG-FTIR. | FT-Raman: PP415P27.0 PXRD: 260a TG-FTIR: a4336 | Raman: seems to corresponds to a mixture of class 1 and class 5 PXRD: sample is only partially crystalline; the few, broad peaks correspond to class 5; thus corresponds to a mixture of the amorphous class 1 and class 5 TG-FTIR: loss of ~0.3 wt.-% from 25° C. to 290° C.; decomposition at T >290° C. |
| PP415-P28 | dried material of PP415-P21 under vacuum: at 60° C. and ~5 mbar for 1 h; at r.t. and ~3 mbar for 4.5 d; at 60° C. and ~10 mbar for 1 h; at 40-50° C. and 5-20 mbar for ~20 h, examined solid by FT-Raman spectroscopy, PXRD, and TG-FTIR. | FT-Raman: PP415P28.0 PXRD: 261a TG-FTIR: a4334 | Raman: corresponds to class 2 PXRD: corresponds to class 2, sample less crystalline, as indicated by broader peaks TG-FTIR: loss of ~3.0 wt.-% cyclohexane in two steps from ~140° C. to ~250° C.; decomposition at T >250° C. |
| PP415-P29 | suspended 132.2 mg of PP415-P1 in 0.8 mL of 1:2 EtOAc/TEA; observed change in appearance of solid phase; agitated and sonicated; equilibrated suspension at 24° C. shaking at 500 rpm; after 4 d recovered solid material by filter centrifugation (0.20-μm PTFE membrane); examined material by FT-Raman spectroscopy and PXRD; dried material for 5 min under vacuum (10-20 mbar); examined material by TG-FTIR. | FT-Raman: PP415P29.0 PXRD: 282a TG-FTIR: a4346 | Raman: corresponds to class 2 PXRD: corresponds to class 2 TG-FTIR: loss of ~5.1 wt.-% EtOAc and TEA from ~50° C. to ~220° C., most of it in a step from 180° C. to 210° C.; decomposition at T >220° C. |
| PP415-P30 | dried material of PP415-P7 under vacuum at 50-70° C. and 1-10 mbar for 3 days; examined solid by FT-Raman spectroscopy, PXRD, and TG-FTIR. | FT-Raman: PP415P30.0 PXRD: 290a TG-FTIR: a4347 | Raman: corresponds to class 2 PXRD: corresponds to class 2 TG-FTIR: loss of ~2.1 wt.-% heptane (and some EtOAc) in two steps from ~50° C. to ~250° C.; decomposition at T >250° C. |
| PP415-P31 | suspended 137.6 mg of PP415-P1 in 2 mL of 9:1 $H_2O$/PEG 400; obtained white suspension; equilibrated suspension at 24° C. shaking at 400 rpm; after 5 d recovered solid material by vacuum filtration; washed solid three times with small amount of H2O; examined material by FT-Raman spectroscopy and PXRD. | FT-Raman: PP415P31.0 PXRD: 320a | Raman: corresponds to class 1 PXRD: amorphous, corresponds to class 1 |
| PP415-P32 | dried material of PP415-P19 under vacuum at 80° C. and <1 × 10-3 mbar; after 1 d examined material by TG-FTIR (a4362); continued drying; after a total of 3 d examined material by TG-FTIR (a4365), FT-Raman spectroscopy, and PXRD as P32A. | FT-Raman: PP415P32.0 PXRD: 331a (P32A) TG-FTIR: a4362(P32) a4365 (P32A) | Raman: corresponds to class 2 PXRD: corresponds to class 2, less crystalline TG-FTIR P32: loss of 2.8 wt.-% heptane (25-250° C.), most of it in a step from 170° C. to 200° C.; decomposition at T >250° C. TG-FTIR P32A: loss of 2.2 wt.-% heptane (25-250° C.), most of it in a step from 170° C. to 200° C.; decomposition at T >250° C. |
| PP415-P33 | dried material of PP415-P19 under vacuum at 80° C. and <1×10-3 mbar; after 3 d examined material by FT-Raman spectroscopy, PXRD and TG-FTIR. | FT-Raman: PP415P33.0 PXRD: 332a TG-FTIR: a4366 | Raman: corresponds to class 3 PXRD: corresponds to class 3 TG-FTIR: loss of ~4.2 wt.-% 2PrOH (50-210° C.), most of it in a step from 160° C. to 190° C., another loss of ~0.5 wt.-% 2PrOH (210° C. to 290° C.); decomposition at T >290° C. |
| PP415-P34 | dried material of PP415-P19 under vacuum at 80° C. and <1×10-3 mbar; after 3 d examined material by FT-Raman spectroscopy, PXRD and TG-FTIR. | FT-Raman: PP415P34.0 PXRD: 333a TG-FTIR: a4367 | Raman: corresponds to class 2 PXRD: corresponds to class 2, less crystalline TG-FTIR: loss of ~2.3 wt.-% cyclohexane in two steps from 25° C. to 270° C.; decomposition at T >270° C. |
| PP415-P35 | suspended 158.4 mg of PP415-P1 in 0.2 mL of MeCN/$H_2O$ obtained two clear, separated phases; equilibrated solution at 24° C. shaking at 400 rpm; after 3 d observed thick suspension; added 0.1 mL of the solvent mixture; continued equilibration of suspension at 24° C. shaking at 400 rpm; after a total of 5 d recovered solid material by filter centrifugation (0.20-μm PTFE membrane); examined material by FT-Raman spectroscopy; dried material for 10 min under vacuum (10-20 mbar); examined material by PXRD and TG-FTIR. | FT-Raman: PP415P35.0 PXRD: 326a TG-FTIR: a4363 | Raman: corresponds to class 4, contains solvent signals PXRD: corresponds to class 4 TG-FTIR: loss of 2.9 wt.-% MeCN from 25° C. to 250° C.; decomposition at T >250° C. |
| PP415-P36 | dried material of PP415-P35 under vacuum at 80° C. and <1 × 10-3 mbar; after 3 d examined material by FT-Raman spectroscopy, PXRD and TG-FTIR. | FT-Raman: PP415P36.0 PXRD: 339a TG-FTIR: a4369 | Raman: corresponds to class 4 PXRD: corresponds to class 4 TG-FTIR: loss of ~0.6 wt.-% (probably $H_2O$ and/or MeCN) in two steps from 25° C. to 280° C.; decomposition at T >280° C. |

TABLE 30-continued

List of Samples and Performed Experiments

| Sample | Experimental Description | Test Methods | Result/Remarks |
| --- | --- | --- | --- |
| PP415-P37 | dried material of PP415-P35 under $N_2$ flow at 80° C.; after 3 d examined material by FT-Raman spectroscopy, PXRD, TG-FTIR, DSC, and DVS. | FT-Raman: PP415P37.0 PXRD: 340a TG-FTIR: a4370 DSC: d_9907 DVS: dvs1176 post-DVS PXRD: 363a | Raman: corresponds to class 4 PXRD: corresponds to class 4 TG-FTIR: loss of ~0.9 wt.-% (probably H2O and/or MeCN) in two steps from 25° C. to 280° C.; decomposition at T >280° C. DSC: sharp endothermic peak at T = 196.1° C. ($\Delta H$ = 29.31 J/g); no decomposition up to 270° C. DVS: slightly hygroscopic; $\Delta m$ =+0.7% (50%→85% r.h.); total mass gain of 2.1 wt.-% from 0% r.h. to 95% r.h. post-DVS PXRD: corresponds to class 4 |
| PP415-P38 | DSC experiment: combined 1.275 mg of PP415-P1 and 1.344 mg of PP415-P36; equilibrated for 3 min under $N_2$; heated sample from −50° C. to 270° C. at 10 K/min. | DSC: d_9917 | DSC |
| PP415-P39 | DSC experiment: combined 2.17 mg of PP415-P1 and 2.20 mg of PP415-P36; mixed solids using a spatula; equilibrated for 3 min under $N_2$; heated sample from −50° C. to 173° C. at 10 K/min; held at 173° C. for 30 min; heated from 173° C. to 270° C. at 10 K/min. | DSC: d_9923 | DSC |
| PP415-P40 | received ~5 g of 63415, batch #: 2083-69-DC on May 27, 2011; MW = 554.7 g/mol, $C_{33}H_{44}F_2N_2O_3$ | PXRD: 390a | PXRD: corresponds to class 2 |
| PP415-P41 | suspended 101.3 mg of PP415-P40 in 0.20 mL of THF/$H_2O$ (1:1); obtained white suspension; equilibrated suspension at 24° C.; after 3 days recovered solid by filter centrifugation (0.2-µm PTFE membrane); dried solid material under vacuum for 5 min; examined solid by PXRD. | PXRD: 400a | PXRD: corresponds to class 5 |
| PP415-P42 | dissolved 104.6 mg of PP415-P40 in 0.20 mL of THF; obtained clear solution; evaporated solvent under $N_2$ flow overnight; obtained white solid; examined solid by PXRD. | PXRD: 405a | PXRD: amorphous (class 1) |
| PP415-P43 | dissolved 101.8 mg of PP415-P40 in 0.20 mL of THF/hexane (8:2); obtained clear solution; evaporated solvent under N2 flow overnight; obtained white solid; examined solid by PXRD. | PXRD: 429a | PXRD: corresponds to class 2 |
| PP415-P44 | dried material of PP415-P41 under vacuum (~100 mbar) at 80° C.; examined solid after 1 day by PXRD (474a); continued drying overnight; examined solid again by PXRD (482a) and TG-FTIR. | PXRD: 474a, 482a TG-FTIR: a4401 | PXRD: both mainly amorphous (class 1), some broad peaks with low intensity TG-FTIR: ~0.9 wt.-% THF 25-280° C., decomposition at T >300° C. |
| PP415-P45 | suspended 3.03 g of PP415-P40 in 6.0 mL of THF/H2O (1:1); obtained white suspension; equilibrated suspension at r.t.; after 1 day recovered small aliquot by filter centrifugation and examined it by PXRD; recovered solid of whole sample by vacuum filtration; dried sample for 10 min under vacuum (~10 mbar). | PXRD: 471a | PXRD: corresponds to class 5 |
| PP415-P46 | dried material of PP415-P45 under vacuum (~100 mbar) at 80° C.; examined solid after drying overnight by PXRD (481a); continued drying; after 4 days examine solid as PP415-P46a by PXRD (496a) and TG-FTIR. | PXRD: 481a, 496a TG-FTIR: a4410 | PXRD: both mainly amorphous (class 1), some broad peaks with low intensity TG-FTIR: ~0.4 wt.-% $H_2O$ 25-250° C., decomposition at T >250° C. |
| PP415-P47 | dissolved 101.8 mg of PP415-P40 in 0.4 mL of EtOAc; obtained clear solution; evaporated solvent under $N_2$ flow overnight; obtained white solid; examined solid by PXRD and TG-FTIR. | PXRD: 492a TG-FTIR: a4412 | PXRD: corresponds to class 2 TG-FTIR: ~6.2 wt.-% EtOAc 25-170° C., 1.7 wt.-% EtOAc 170-240° C., decomposition at T >240° C. |
| PP415-P48 | dissolved 101.1 mg of PP415-P40 in 0.4 mL of ethyl formate; obtained clear solution; evaporated solvent under $N_2$ flow overnight; obtained white solid; examined solid by PXRD and TG-FTIR. | PXRD: 493a TG-FTIR: a4413 | PXRD: corresponds to class 2 TG-FTIR: ~3.5 wt.-% ethyl formate 25-200° C., decompostion at T >200° C. |
| PP415-P49 | dissolved 205.3 mg of PP415-P40 in 0.3 mL of acetone; obtained clear solution; added dropwise to 30.0 mL of $H_2O$ (pre-cooled to 5° C.); obtained thin white suspension; stirred thin suspension at 5° C. overnight; obtained thicker white suspension; recovered solid by vacuum filtration (pore size P4); obtained 188.3 mg of white solid; examined solid by PXRD. | PXRD: 593a | PXRD: amorphous (class 1) |

TABLE 31

Figure 51:
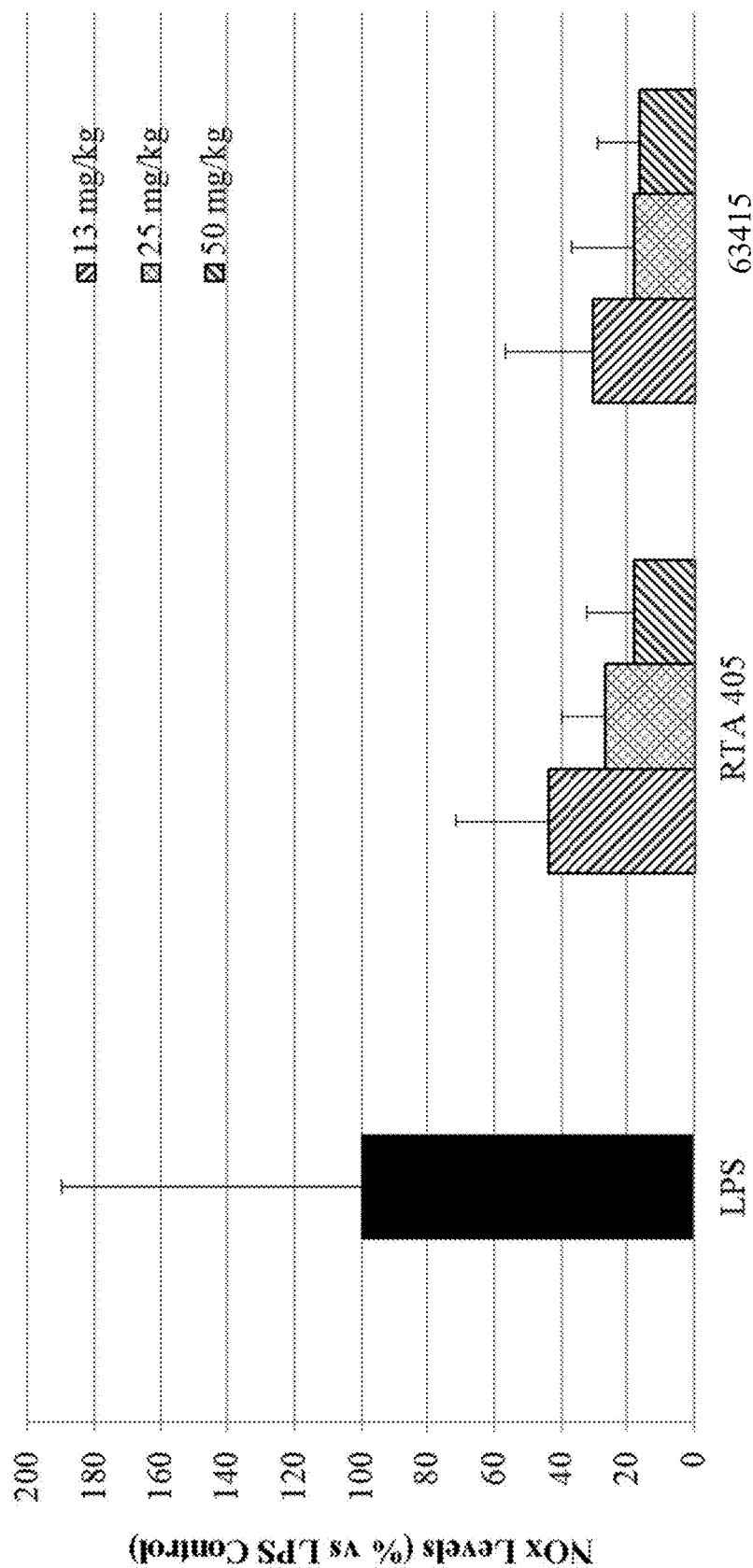
FIG. 51—Dose-dependent suppression of NO in vivo by 63415. CD-1 mice (n=6) were dosed with DMSO or AIM by oral gavage. LPS (5 mg/kg) was administered 24 h later. Twenty-four hours after LPS administration, whole blood was collected for NO assay. NO inhibition was determined by Griess Reaction from reduced, de-proteinated plasma.

Parameters of FIG. 51

| Compound | NOx Levels (% vs LPS Controls) | | |
|---|---|---|---|
| | 13 mg/kg | 25 mg/kg | 50 mg/kg |
| RTA 405 * | 44% | 26% | 18% |
| 63415 | 30% | 18% | 16% |

TABLE 32

63415: Primary In Vivo ADMET-Key Primary ADMET Assays and Endpoints

| Assay | Key Endpoints |
|---|---|
| 14-day mouse toxicity | Tolerability, body weight, clinical chemistry<br>Tissue distribution<br>Nrf2 target gene mRNA expression & enzyme activation in liver |
| 14-day rat toxicity | Tolerability, body weight, clinical chemistry, & limited histopathology<br>Tissue distribution and plasma TK<br>Nrf2 target gene mRNA expression & enzyme activation in liver |
| 14-day monkey toxicity | Tolerability, body weight, clinical chemistry, & limited histopathology<br>Tissue distribution and plasma TK<br>Nrf2 target gene mRNA expression and enzyme activation in multiple tissues & PBMCs |

TABLE 33

Figure 54:
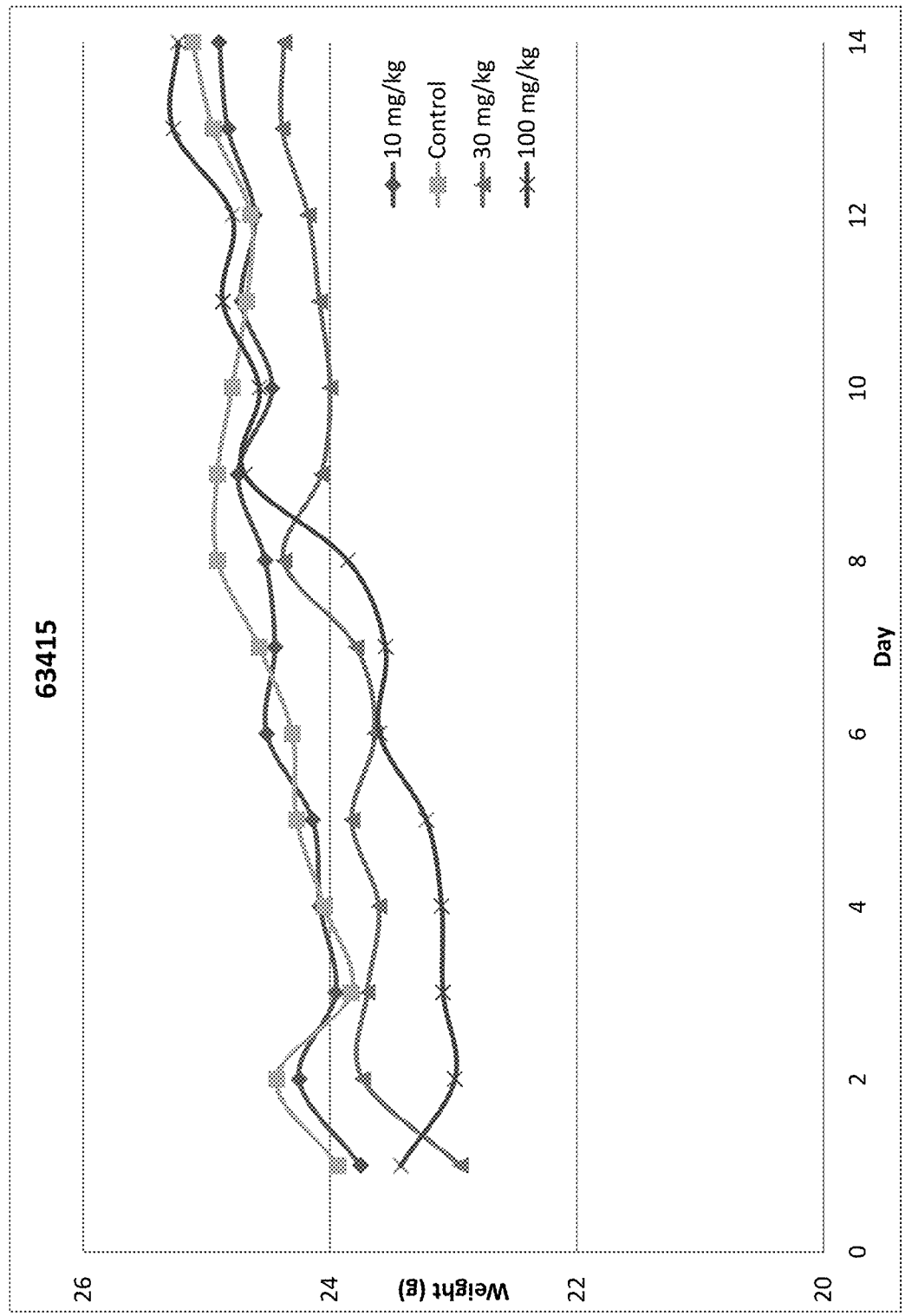
FIG. 54—Summary of 63415 14-day mouse toxicity study. C57BL/6 mice were dosed PO QD×14. Endpoints included survival, weight, and clinical chemistries. All animals survived to day 14. No significant weight changes occurred compared to the vehicle group, and there was no evidence of toxicity at any dose based on clinical chemistries.
Figure 55:
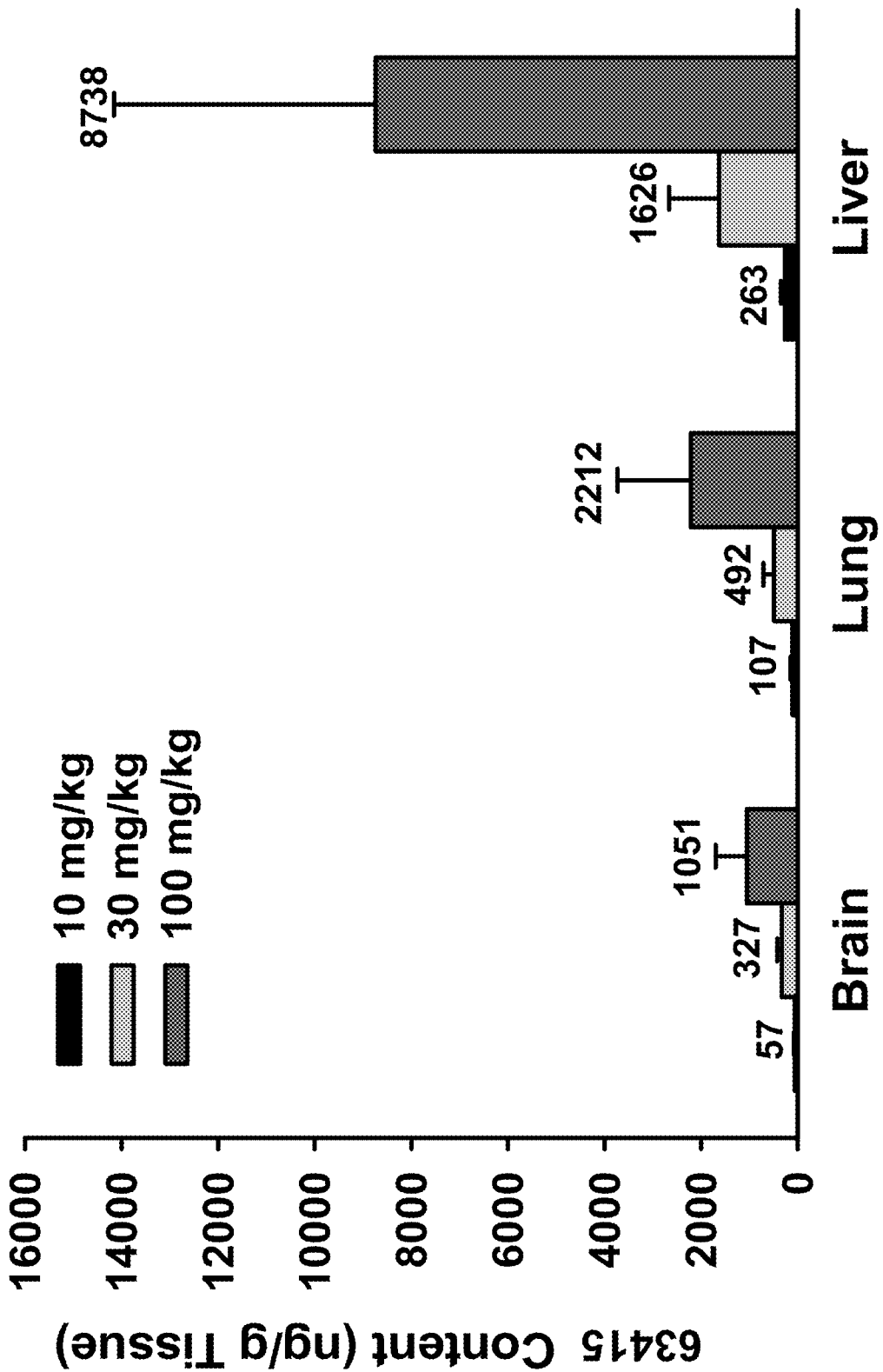
FIG. 55—Tissue distribution of 63415 from 14-day mouse toxicity study in C57BL/6 mice. Brain, lung, and liver samples were collected 4 h after final dose and quantified for 63415 content using sensitive LC/MS/MS method. Exposures at 10 and 100 mg/kg in lung exceeded the in vitro $IC_{50}$ for NO induction by 55- and 1138-fold, respectively. Exposure at 10 and 100 mg/kg in brain exceeded the in vitro $IC_{50}$ for NO induction by 29- and 541-fold, respectively.
Figure 56:
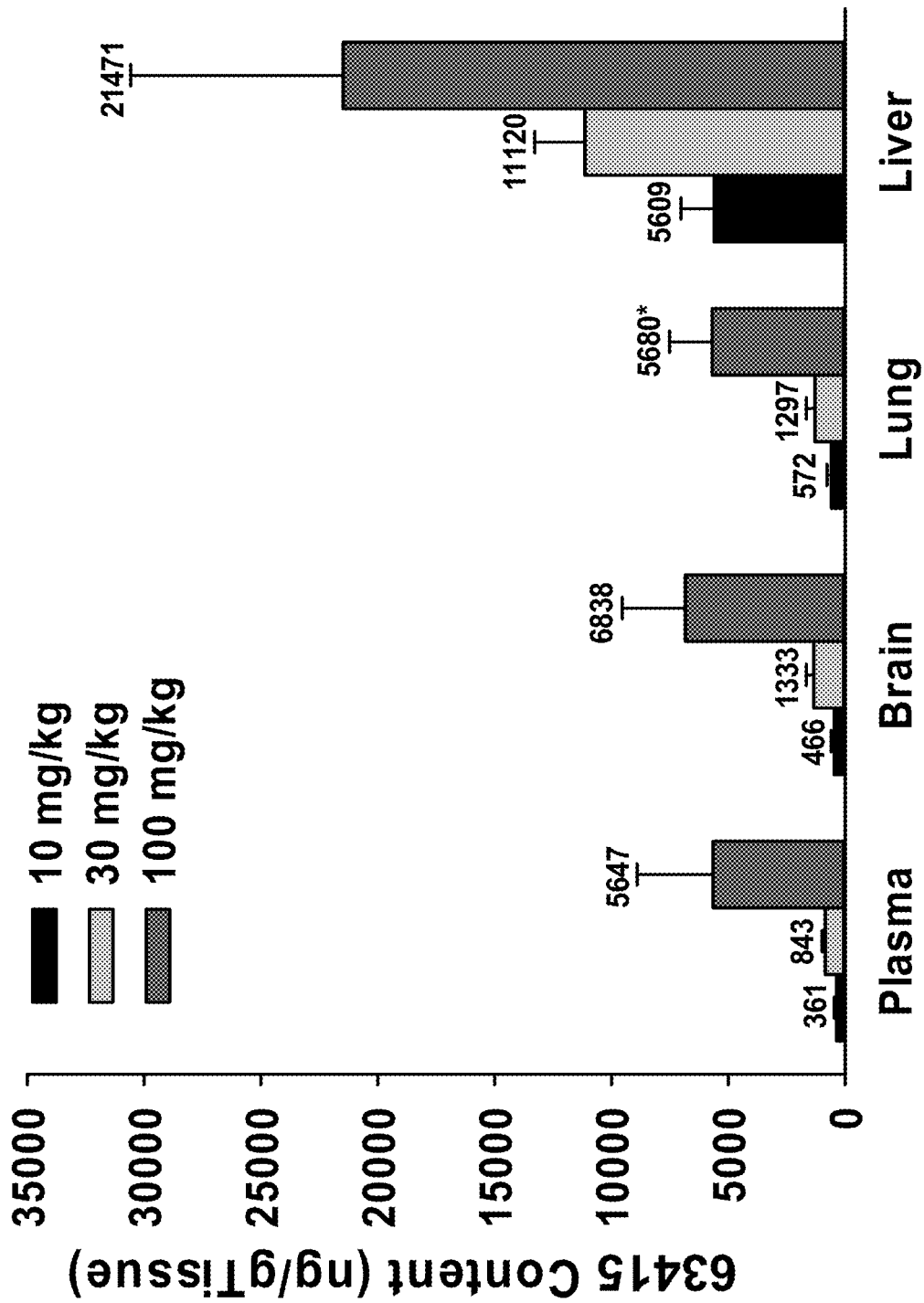
FIG. 56—Tissue distribution of 63415 in Sprague Dawley rats. Tissues were collected four hours after final dosing on Day 14 or Day 6 (100 mg/kg), extracted, and quantified for 63415 content using a sensitive LC/MS/MS method. Compound 63415 distributes well into target tissues. Exposures at 10 mg/kg in lung and brain exceed the in vitro $IC_{50}$ for NO inhibition by 294- and 240-fold, respectively.
Figure 57:
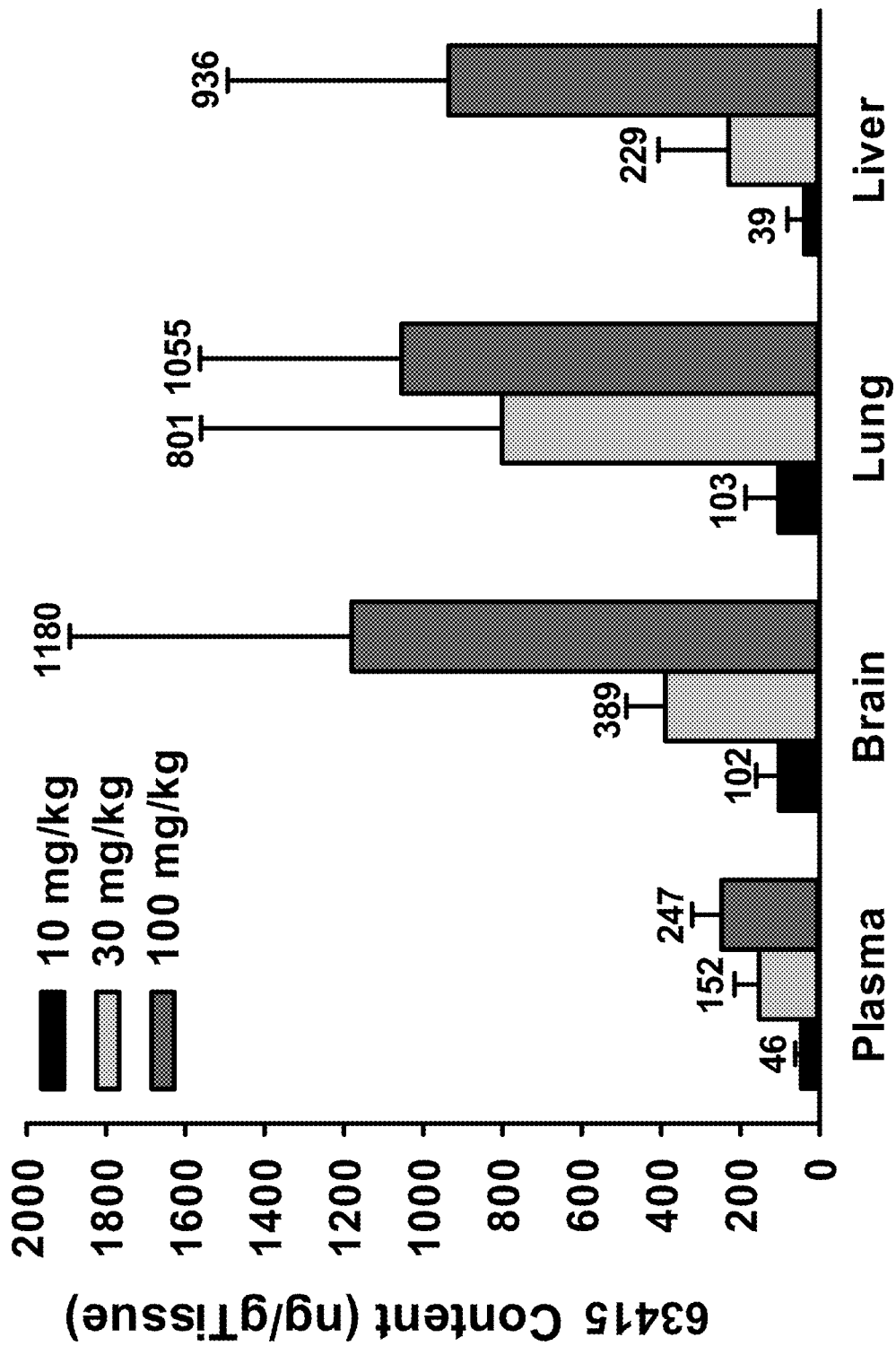
FIG. 57—Target tissue distribution of compound 63415 in cynomolgus monkeys. Tissues were collected four hours after final dosing on Day 14. Compound 63415 content was extracted and quantified using a sensitive LC/MS/MS method.

Parameters of FIG. 54

| | Vehicle | 63415 | | |
|---|---|---|---|---|
| Dose (mg/kg) | 0 | 10 | 30 | 100 |
| ALT (U/L) | 100 | 39 | 63 | 91 |
| AST (U/L) | 156 | 98 | 147 | 167 |
| ALP (U/L) | 120 | 131 | 110 | 98 |
| Tot Bil (mg/dL) | <0.2 | <0.2 | <0.2 | <0.2 |
| BUN (mg/dL) | 17 | 15 | 15 | 15 |
| Cr (mg/dL) | <0.2 | <0.2 | <0.2 | <0.2 |
| Glu (mg/dL) | 288 | 307 | 285 | 273 |

TABLE 34

63415 is Negative for Genotoxicity in the In Vivo Micronucleus Study

| Treatment (n = 5/group) | PCE/Total Erythrocytes (Mean +/− SD) | Change from Control (%) | Number of MPCE/1000 PCE (Mean +/− SD) | Number of MPCE/PCE Scored |
|---|---|---|---|---|
| 24-h timepoint | | | | |
| Sesame Oil | 0.588 ± 0.04 | — | 0.2 ± 0.27 | 2/10000 |
| 125 mg/kg | 0.543 ± 0.03 | −8 | 0.3 ± 0.27 | 3/10000 |
| 250 mg/kg | 0.520 ± 0.06 | −12 | 0.3 ± 0.27 | 3/10000 |
| 500 mg/kg | 0.426 ± 0.07 | −28 | 0.0 ± 0.00 | 0/10000 |
| 1000 mg/kg | 0.498 ± 0.05 | −15 | 0.2 ± 0.27 | 2/10000 |
| 1500 mg/kg | 0.499 ± 0.06 | −15 | 0.4 ± 0.22 | 4/10000 |
| 2000 mg/kg | 0.531 ± 0.05 | −10 | 0.2 ± 0.27 | 2/10000 |
| 48-h timepoint | | | | |
| Sesame Oil | 0.526 ± 0.05 | — | 0.3 ± 0.27 | 3/10000 |
| 125 mg/kg | 0.453 ± 0.03 | −14 | 0.2 ± 0.27 | 2/10000 |
| 250 mg/kg | 0.391 ± 0.02 | −26 | 0.2 ± 0.27 | 2/10000 |
| 500 mg/kg | 0.339 ± 0.05 | −36 | 0.3 ± 0.45 | 3/10000 |
| 1000 mg/kg | 0.344 ± 0.04 | −35 | 0.1 ± 0.22 | 1/10000 |
| 1500 mg/kg | 0.376 ± 0.05 | −39 | 0.4 ± 0.42 | 4/10000 |
| 2000 mg/kg | 0.360 ± 0.03 | −32 | 0.1 ± 0.22 | 1/10000 |

TABLE 35

Parameters of FIG. 35

| Treatment | Day | ALT (U/L) | AST (U/L) | ALP (U/L) | Tot Bil (mg/dL) | BUN (mg/dL) | Cr (mg/dL) | Tot Prot (g/dL) | Albumin (g/dL) | Glucose (mg/dL) | Chol (mg/dL) | TG (mg/dL) |
|---|---|---|---|---|---|---|---|---|---|---|---|---|
| Vehicle | BL | 30 | 29 | 320 | 0.15 | 23 | 0.63 | 7.2 | 4.1 | 87 | 124 | 52 |
| | Day 14 | 37 | 37 | 345 | 0.23 | 18 | 0.63 | 6.9 | 4.1 | 63 | 130 | 64 |
| 10 mg/kg | BL | 46 | 32 | 351 | 0.18 | 35 | 0.78 | 7.4 | 4 | 74 | 146 | 51 |
| | Day 14 | 46 | 38 | 382 | 0.23 | 27 | 0.68 | 7.2 | 4 | 39 | 144 | 82 |
| 30 mg/kg | BL | 32 | 32 | 409 | 0.18 | 23 | 0.7 | 7.3 | 4.2 | 85 | 125 | 47 |
| | Day 14 | 47 | 43 | 416 | 0.2 | 20 | 0.58 | 7.2 | 4 | 53 | 122 | 64 |
| 100 mg/kg | BL | 32 | 35 | 381 | 0.15 | 24 | 0.7 | 6.9 | 4 | 96 | 137 | 37 |
| | Day 14 | 43 | 37 | 390 | 0.18 | 24 | 0.55 | 6 | 3.2 | 32 | 93 | 61 |

TABLE 36

In Vitro Activity of 63415 and 63355

| | 63415 | 63355 |
|---|---|---|
| NO $IC_{50}$ (nM), RAW264.7 | 4.0 ± 1 | 0.63 ± 0.06 |
| WST-1 $IC_{50}$ (nM), RAW264.7 | 125 | 150 |
| NQO1-ARE (fold at 62.5 nM in HuH7) | 5.3 ± 1.0 | 6.5 ± 0.9 |

TABLE 37

Figure 52:
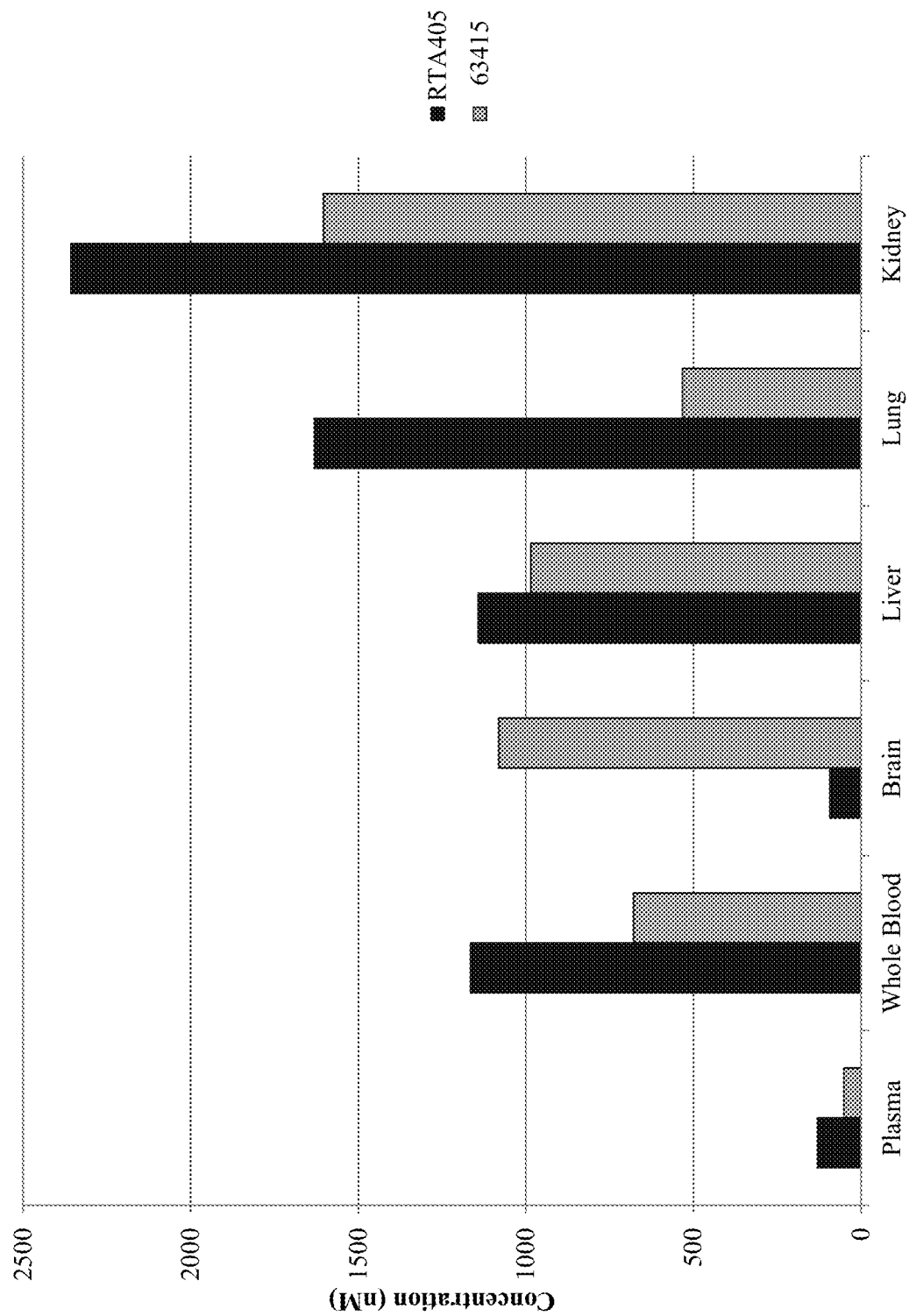
FIG. 52—Extensive distribution of 63415 (RTA 408) into mouse tissues. Mice were dosed PO QD×3 with either 25 mg/kg 63415 (RTA 408) or 25 mg/kg RTA 405. Blood (plasma and whole blood) and tissues (brain, liver, lung, and kidney) were collected 6 h after the last dose. Semi-quantitative analysis of drug content was performed. Notable levels were observed in the CNS.

Parameters of FIG. 52

| Compound | Plasma | Whole Blood | Brain | Liver | Lung | Kidney |
|---|---|---|---|---|---|---|
| RTA 405 (nM) | 130 | 1165 | 93 | 1143 | 1631 | 2357 |
| 63415 (nM) | 51 | 679 | 1081 | 985 | 533 | 1604 |

TABLE 38

Figure 53:
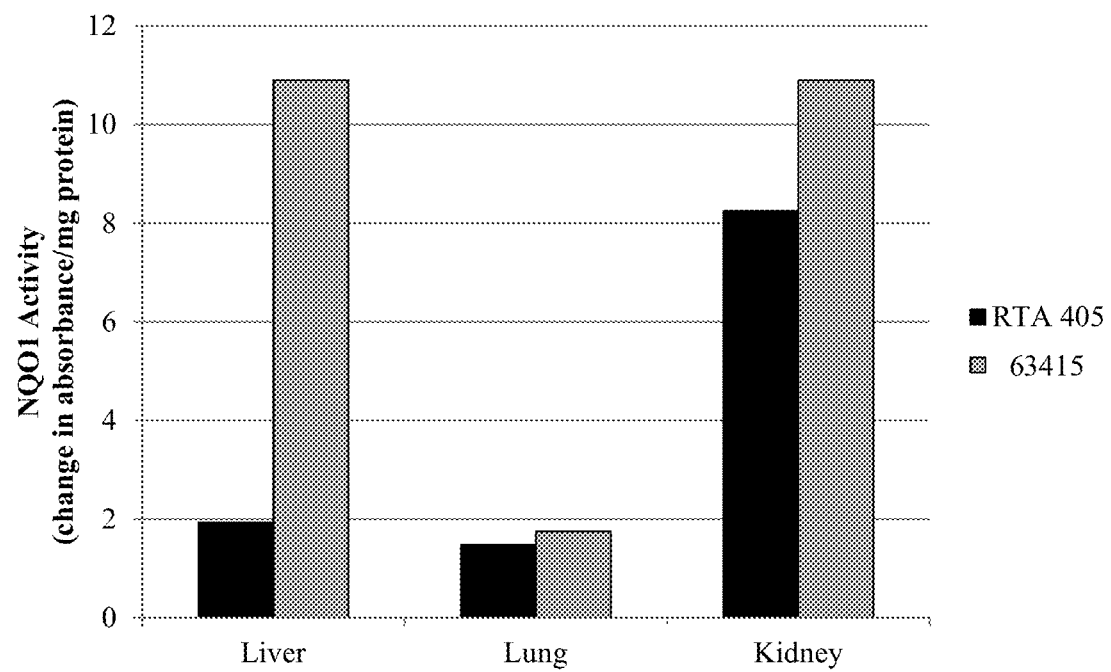
FIG. 53—NQO1 activity induction in mouse liver, lung, and kidney by 63415. Mice were dosed PO QD×3 with 25 mg/kg. Tissues were collected 6 h after the last dose, and analysis of NQO1 activity was performed. Meaningful activation of NQO1 was observed in multiple tissues.

Parameters of FIG. 53

| Compound | Liver | Lung | Kidney |
|---|---|---|---|
| RTA 405 | 1.93 | 1.48 | 8.25 |
| 63415 | 10.9 | 1.75 | 10.9 |

All of the compounds, polymorphs, formulations, and methods disclosed and claimed herein can be made and executed without undue experimentation in light of the present disclosure. While the compounds, polymorphs, formulations, and methods of this invention have been described in terms of preferred embodiments, it will be apparent to those of skill in the art that variations may be applied to the compounds, polymorphs, formulations, and methods, as well as in the steps or in the sequence of steps of the method described herein without departing from the concept, spirit, and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references to the extent that they provide exemplary procedural or other details supplementary to those set forth herein, are specifically incorporated herein by reference.

U.S. Pat. No. 6,326,507
U.S. Pat. No. 6,974,801
U.S. Pat. No. 7,915,402
U.S. Pat. No. 7,943,778
U.S. Pat. No. 8,124,799
U.S. Pat. No. 8,129,429
U.S. Patent Publication 2009/0060873
Abraham and Kappas, *Free Radical Biol. Med.*, 39:1-25, 2005.
Aghajan et al., *J Gastroenterol Hepatol.*, Suppl 2:10-14, 2012.
Ahmad et. al., *Cancer Res.*, 68:2920-2926, 2008.
Ahmad et. al., *J. Biol. Chem.*, 281:35764-9, 2006.
Angulo et al., *Eur. J Immunol.*, 30:1263-1271, 2000.
Araujo et. al., *J. Immunol.*, 171(3):1572-1580, 2003.
Arend and Dayer, *Arthritis Rheum.*, 38:151-160, 1995.
Bach, *Hum. Immunol.*, 67(6):430-432, 2006.
Bagasra et al., *Proc. Natl. Acad. Sci. USA*, 92:12041-12045, 1995.
Blake et. al. *Am J Respir Cell Mol Biol*, 42:524-36, 2010.
Berridge et al., *Biochemica*, 4: 14-19, 1996.
Botoman et al., *Am. Fam. Physician*, 57(1):57-68, 1998.
Brandt et al., *Arthritis Rheum.*, 43:1346-1352, 2000.
Brewerton et al., *Lancet.*, 1:904-907, 1973a.
Brewerton et al., *Lancet.*, 1:956-957, 1973b.
Bronte et al., *Trends Immunol.*, 24:302-306, 2003.
Brown and DuBois *J. Clin. Oncol.*, 23:2840-2855, 2005.
Brynskov et al., *N. Engl. J. Med.*, 321(13):845-850, 1989.
Cantin et. al., *J Clin Invest*, 79:1665-73, 1987.
Cai et al., *Nat. Med.*, 11(2):183-190, 2005.
Calin and Taurog, In: *The Spondylarthritides*, Calin et al. (Eds.), Oxford, UK. Oxford University Press, 179, 1998.
Car et. al., *Am J Respir Crit Care Med*, 149:655-9, 1994.
Cernuda-Morollon et. al., *J Biol Chem*, 276:35530-6, 2001.
Chan and Kan, *Proc Natl Acad Sci USA*, 96:12731-6, 1999.
Chauhan and Chauhan, *Pathophysiology*, 13(3):171-181. 2006.
Chen and Kunsch, *Curr Pharm Des*, 10:879-91, 2004.
Cho et. al., *Am J Respir Cell Mol Biol*, 26:175-82, 2002.
Crowell et al., *Mol. Cancer Ther.*, 2:815-823, 2003.
Cuzzocrea et. al., *Mol Pharmacol*, 61:997-1007, 2002.
Dickerson et. al., *Prog Neuropsychopharmacol Biol. Psychiatry*, Mar. 6, 2007.
Dinarello, *Int. Rev. Immunol.*, 16:457-499, 1998.
Dinkova-Kostova et. al., *Proc. Natl. Acad. Sci. USA*, 102(12):4584-4589, 2005.
Dionne et al., *Clin. Exp. Imunol.*, 112(3):435-442, 1998.
Douglas et. al., *Am J Respir Crit Care Med*, 158:220-5, 1998.
Dudhgaonkar et. al., *Eur. J. Pain*, 10(7):573-9, 2006.
Eastgate et al., *Lancet*, 2(8613):706-9, 1988.
Eikelenboom et al., *Glia*, 40(2):232-239, 2002.
Ettehadi et al., *Clin. Exp. Immunol.*, 96(1):146-151, 1994.
Fischer et. al., *Int J Chron Obstruct Pulmon Dis*, 6:413-21, 2011.
Forstermann, *Biol. Chem.*, 387:1521, 2006.
Funakoshi et al., *Digestion*, 59(1):73-78, 1998.
Gebel et. al., *Toxicol Sci*, 115:238-52, 2010.
Gehrmann et al., *Glia*, 15(2):141-151, 1995.
Genain and Nauser, *J. Mol. Med.*, 75:187-197, 1997.
Goodman et al., *Kidney Int.*, 72(8):945-953, 2007.
Graeber et al., *Glia*, 40(2):252-259, 2002.
Greten et al., *Cell*, 118:285-296, 2004.
Grivennikov and Karin, *Cytokine Growth Factor Rev.*, 21(1):11-19, 2010.
Guilherme et al., *Nat. Rev. Mol. Cell Biol.*, 9(5):367-77, 2008.
Gwee et al., *Gut.*, 44(3):400-406., 1999.
Hallgren et. al., *Am Rev Respir Dis*, 139:373-7, 1989.
Hahn and Tsao, In: *Dubois' Lupus Erythematosus*, 4th Ed, Wallace and Hahn (Eds.), Lea and Febiger, Philadelphia, 195-201, 1993.
*Handbook of Pharmaceutical Salts: Properties, and Use*, Stahl and Wermuth Eds.), *Verlag Helvetica Chimica Acta*, 2002.
Hanson et. al., *BMC Medical Genetics*, 6(7), 2005.
Hansson et al., *Annu. Rev. Pathol. Mech. Dis.*, 1:297-329, 2006.
Hayden and Ghosh, *Cell*, 132:344-62, 2008.

He and Karin, *Cell Res.,* 21(1):159-168, 2011.
Honda et. al. *Bioorg. Med. Chem. Lett.,* 12:1027-1030, 2002.
Honda et. al., *Bioorg. Med. Chem. Lett.,* 16(24):6306-6309, 2006.
Honda et. al., *Bioorg. Med. Chem. Lett.,* 7:1623-1628, 1997.
Honda et. al., *Bioorg. Med. Chem. Lett.,* 8(19):2711-2714, 1998.
Honda et. al., *Bioorg. Med. Chem. Lett.,* 9(24):3429-3434, 1999.
Honda et. al., *J. Med. Chem.,* 43:4233-4246, 2000a.
Honda et. al., *J. Med. Chem.,* 43:1866-1877, 2000b.
Hotamisligil, *Nature,* 444(7121):860-7, 2006.
Iizuka et. al., *Genes Cells,* 10:1113-25, 2005.
Ikezaki et. al., *Food Chem Toxicol,* 34:327-35, 1996.
Ishii et. al., *J Immunol,* 175:6968-75, 2005.
Ishikawa et. al., *Circulation,* 104(15):1831-1836, 2001.
Ishizawa and Dickson, *J. Neuropathol. Exp. Neurol.,* 60(6): 647-657, 2001.
Jarvis, *Curr. Opin. Rheumatol.,* 10(5):459-467, 1998.
Jarvis, *Pediatr. Ann.,* 31(7):437-446, 2002.
Jonsson et al., *Oral Dis.,* 8(3):130-140, 2002.
Jonsson et al., *Trends Immunol.,* 22(12):653-654, 2001.
Kahle et al., *Ann. Rheum. Dis.,* 51:731-734, 1992.
Kaltschmidt et al., *Proc. Natl. Acad. Sci. USA,* 94:2642-2647, 1997.
Karin, *Nature,* 441(7092):431-436, 2006.
Kawakami et. al., *Brain Dev.,* 28(4):243-246, 2006.
Kawamoto et. al., *J Biol Chem,* 275:11291-9, 2000.
Kendall-Tackett, *Trauma Violence Abuse,* 8(2):117-126, 2007.
Kensler et. al., *Annu Rev Pharmacol Toxicol,* 47:89-116, 2007.
Kikuchi et. al., *Respir Res,* 11:31, 2010.
Kim et. al., *Mutat Res,* 690:12-23, 2010.
King et. al., *Am J Respir Crit Care Med,* 184:92-99, 2011.
Kinnula et. al., *Am J Respir Crit Care Med,* 172:417-22, 2005.
Klingsberg et. al., *Respirology,* 15:19-31, 2010.
Kortylewski et al., *Nat. Med.,* 11:1314-1321, 2005.
Kotzin and O'Dell, In: *Samler's Immunologic Diseases,* 5th Ed., Frank et al. (Eds.), Little Brown & Co., Boston, 667-697, 1995.
Kotzin, *Cell,* 85:303-306, 1996.
Kruger et. al., *J. Pharmacol. Exp. Ther.,* 319(3):1144-1152, 2006.
Kuboyama, *Kurume Med. J.,* 45(1):33-37, 1998.
Lee et. al., *Mol Cell,* 36:131-40, 2009.
Lee et. al., *Glia.,* 55(7):712-22, 2007.
Lencz et. al., *Mol. Psychiatry,* 12(6):572-80, 2007.
Levonen et. al., *Biochem J,* 378:373-82, 2004.
Li and Kong, *Mol Carcinog,* 48:91-104, 2009.
Liby et. al., *Cancer Res.,* 65(11):4789-4798, 2005.
Liby et. al., *Mol. Cancer Ther.,* 6(7):2113-9, 2007b.
Liby et. al., *Nat. Rev. Cancer,* 7(5):357-356, 2007a.
Lipsky, In: *Harrison's principles of internal medicine,* Fauci et al. (Eds.), 14th Ed., NY, McGraw-Hill, 1880-1888, 1998.
Liu et. al., *FASEB J.,* 20(2):207-216, 2006.
Lu et. al., *J. Clin. Invest.,* 121(10):4015-29, 2011.
Lugering et al., *Ital. J. Gastroenterol. Hepatol.,* 30(3):338-344, 1998.
Malhotra et. al., *Am J Respir Crit Care Med,* 178:592-604, 2008.
*March's Advanced Organic Chemistry: Reactions,* Mechanisms, and Structure, 2007.
Mazur et al., *Cell Microbiol.,* 9(7):1683-94, 2007.
Mazzoni et al., *J Immunol.,* 168:689-695, 2002.
McAlindon et al., *Gut,* 42(2):214-219, 1998.
McGeer and McGeer, *Brain Res. Brain Res.* Rev., 21:195-218, 1995.
McGeer et al., *Neurology,* 19:331-338, 1996.
McGonagle et al., *Arthritis Rheum.,* 41:694-700, 1998.
McGonagle et al., *Curr. Opin. Rheumatol.,* 11:244-250, 1999.
McIver et. al., *Pain,* 120(1-2):161-9, 2005.
Mease et al., *Lancet,* 356:385-390, 2000.
Merrill and Benvenist, *Trends Neurosci.,* 19:331-338, 1996.
Mochizuki et. al., *Am J Respir Crit Care Med,* 171:1260-6, 2005.
Morbidity & Mortality: 2009 Chart Book on Cardiovascular, Lung, and Blood Diseases. National Heart, Lung, and Blood Institute, 2009.
Morris et. al., *J. Mol. Med.,* 80(2):96-104, 2002.
Morse and Choi, *Am. J. Respir. Crit. Care Med.,* 172(6): 660-670, 2005.
Morse and Choi, *Am. J. Respir. Crit. Care Med.,* 27(1):8-16, 2002.
Nath et al., *Neurology,* 66(1):149-150, 2006.
Neal et al., *BMJ.,* 314(7083):779-782, 1997.
Nichols, *Drug News Perspect.,* 17(2):99-104, 2004.
Ohnishi et. al., *Int. Immunol.,* 6:817-830, 1994.
Ogushi et. al., *J Med Invest,* 44:53-8, 1997.
Pall, *Med. Hypoth.,* 69:821-825, 2007.
Parambil et. al., *Chest,* 128:3310-5, 2005.
Partsch et al., *Br. J. Rheumatol.,* 24:518-523, 1997.
Pergola et. al., *N Engl J Med,* 365:327-336, 2011.
Pica et al., *Antimicrob Agents Chemother.,* 44(1):200-4, 2000.
Pimentel et al., *Am. J. Gastroenterol.,* 95(12):3503-3506, 2000.
Place et. al., *Clin. Cancer Res.,* 9(7):2798-806, 2003.
Prochaska and Santamaria, *Anal Biochem.,* 169:328-336, 1988.
Rajakariar et. al., *Proc. Natl. Acad. Sci. USA,* 104(52): 20979-84, 2007.
Rangasamy et. al., *J Clin Invest,* 114:1248-59, 2004.
Rangasamy et. al., *J Exp Med,* 202:47-59, 2005.
Reimund et al., *Eur. J. Clin. Invest.,* 28(2):145-150, 1998.
Renauld, *J Clin Pathol,* 54:577-89, 2001.
Rogler and Andus, *World J. Surg.,* 22(4):382-389, 1998.
Rooney et al., *Rheumatol. Int.,* 10:217-219, 1990.
Ross et. al., *Am. J. Clin. Pathol.,* 120(Suppl):S53-71, 2003.
Ross et. al., *Expert Rev. Mol. Diagn.,* 3(5):573-585, 2003.
Rossi et. al., *Nature,* 403:103-8, 2000.
Rostom et al., *Ann. Intern. Med.,* 146, 376-389, 2007.
Ruster et. al., *Scand. J. Rheumatol.,* 34(6):460-3, 2005.
Sacerdoti et. al., *Curr Neurovasc Res.,* 2(2):103-111, 2005.
Saha et. al., *J Biol Chem,* 285:40581-92, 2010.
Saiki et al., *Scand. J Gastroenterol.,* 33(6):616-622, 1998.
Salomonsson et al., *Scand. J. Immunol.,* 55(4):336-342, 2002.
Salvemini et. al., *J. Clin. Invest.,* 93(5):1940-1947, 1994.
Sarchielli et. al., *Cephalalgia,* 26(9):1071-1079, 2006.
Satoh et. al., *Proc. Natl. Acad. Sci. USA,* 103(3):768-773, 2006.
Schlosstein et al., *NE J. Medicine,* 288:704-706, 1973.
Schulz et. al., *Antioxid. Redox. Sig.,* 10:115, 2008.
Selman et. al., *Ann Intern Med,* 134:136-51, 2001.
Sheppard, *J Clin Invest,* 107:1501-2, 2001.
Shishodia et. al., *Clin Cancer Res,* 12:1828-38, 2006.
Simonian and Coyle, *Annu. Rev. Pharmacol. Toxicol.,* 36:83-106, 1996.
Singh et. al., *Free Rad Biol Med,* 46:376-386, 2009.
Sinha et al., *Cancer Res.,* 67:4507-4513, 2007.

Sporn et. al., *J Nat Prod*, 74:537-45, 2011.
Sriram et. al., *Pulm Pharmacol Ther*, 22:221-36, 2009.
Stack et al., *Lancet*, 349(9051):521-524, 1997.
Standiford et. al., *Chest*, 103:121S, 1993.
Standiford et. al., *J Immunol*, 151:2852-63, 1993.
Stewart et al., *Neurology*, 48:626-632, 1997.
Straus et. al., *Proc Natl Acad Sci USA*, 97:4844-9, 2000.
Strejan et. al., *J. Neuroimmunol.*, 7:27, 1984.
Strieter, *Am J Respir Crit Care Med*, 165:1206-7, 2002.
Suh et. al., *Cancer Res.*, 58:717-723, 1998.
Suh et. al., *Cancer Res.*, 59(2):336-341, 1999.
Sussan et al., *Proc Natl Acad Sci USA*, 106:250-5, 2009.
Szabo et. al., *Nature Rev. Drug Disc.*, 6:662-680, 2007.
Takahashi et. al., *Cancer Res.*, 57:1233-1237, 1997.
Tamir and Tannebaum, *Biochim. Biophys. Acta*, 1288:F31-F36, 1996.
Taniguchi et. al., *Eur Respir J*, 35:821-9, 2010.
Targan et al., *N. Engl. J. Med.*, 337(15):1029-1035, 1997.
Thimmulappa et al., *Cancer Research*, 62: 5196-5203, 2002.
Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670.
Touzani et al., *J. Neuroimmunol.*, 100(1-2):203-215, 1999.
Tumlin et al., *Am. J Cardiol.*, 98(6A):14K-20K, 2006.
van den Berg, *Semin. Arthritis Rheum.*, 30(5S-2):7-16, 2001.
van Dullemen et al., *Gastroenterol.*, 109(1):129-135, 1995.
van Hogezand and Verspaget, *Drugs*, 56(3):299-305, 1998.
Vazquez et al., *J. Virol.*, 79(7):4479-91, 2005.
Wakabayashi, et. al., *Antioxid Redox Signal*, 13:1649-63, 2010.
Wang et al., *Cancer Res.*, 66:10983-10994, 2006.
Wardle, *Nephrol. Dial. Transplant.*, 16(9):1764-8, 2001.
Weyand and Goronzy, *Ann. NY Acad. Sci.*, 987:140-149, 2003.
Williams et al., *Clin. Neurosci.*, 2(3-4):229-245, 1994.
Wordsworth, In: *Genes and Arthritis*, Brit. Medical Bulletin, 51:249-266, 1995.
Wright, *Clin. Orthop. Related Res.*, 143:8-14, 1979.
Wu et. al., *Toxicol Sci*, 123:590-600, 2011.
Xie et. al., *J. Biol. Chem.*, 270(12):6894-6900, 1995.
Yates et al., *Mol. Cancer Ther*, 6(1):154-162, 2007.
Yore et. al., *Mol Cancer Ther*, 5:3232-9, 2006.
Yoh et al., *Kidney Int.*, 60(4):1343-1353, 2001.
Yu et al., *Nat. Rev. Immunol.*, 7:41-51, 2007.
Zhou et al., *Am. J. Pathol.*, 166(1):27-37, 2005.
Zhou et al., *Cancer Sci.*, 98:882-889, 2007.
Zingarelli et al., *J. Immunol.*, 171(12):6827-6837, 2003.

What is claimed is:

1. An in vitro method of activating the antioxidant/anti-inflammatory Keap1/Nrf2/ARE pathway in a cell, the method comprising contacting the cell with an effective amount of

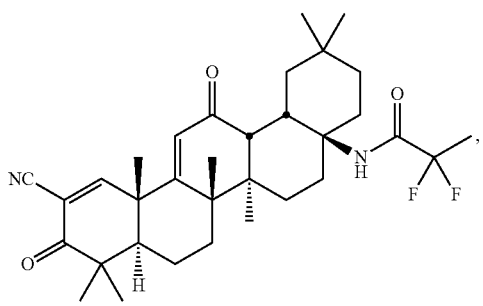

a compound of the formula or a pharmaceutically acceptable salt thereof.

2. The method of claim 1, wherein the compound is a polymorphic form having an X-ray powder diffraction pattern (CuKα) comprising a halo peak at about 14° 2θ.

3. The method of claim 2, wherein the X-ray powder diffraction pattern (CuKα) further comprises a shoulder peak at about 8° 2θ.

Figure 59:
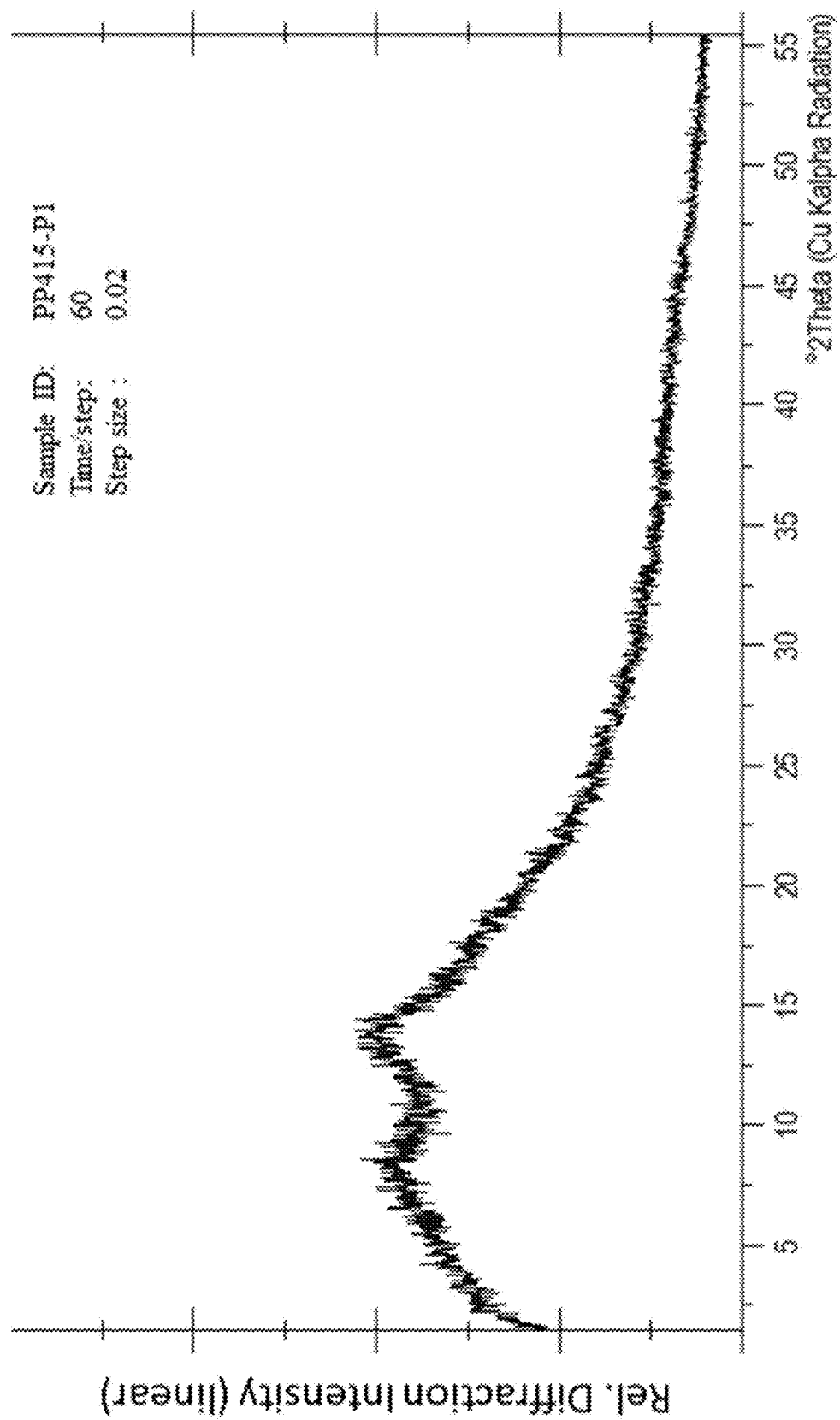
FIG. 59—PXRD (1.5-55.5° 2θ) pattern of the sample PP415-P1, which corresponds to the amorphous form (Class 1).

4. The method of claim 2, wherein the X-ray powder diffraction pattern (CuKα) is substantially as shown in FIG. 59.

5. The method of claim 2, further having a Tg from about 150° C. to about 155° C.

6. The method of claim 2, further having a differential scanning calorimetry (DSC) curve comprising an endotherm centered from about 150° C. to about 155° C.

Figure 62:
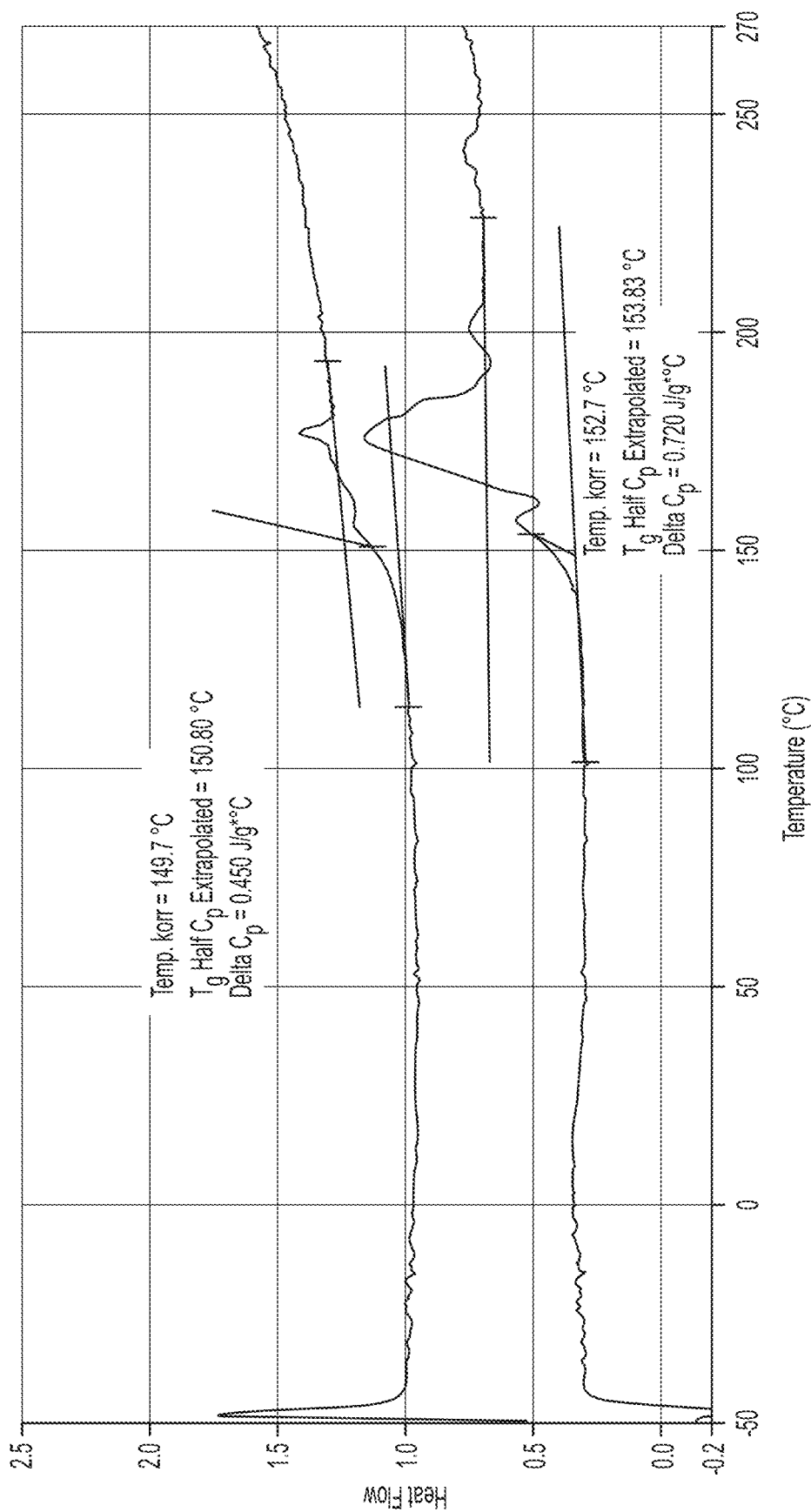
FIG. 62—DSC thermogram of the sample PP415-P1, which corresponds to the amorphous form (Class 1).

7. The method of claim 2, having a differential scanning calorimetry (DSC) curve substantially as shown in FIG. 62.

8. The method of claim 1, wherein the compound is a solvate having an X-ray powder diffraction pattern (CuKα) comprising significant peaks at about 5.6, 7.0, 10.6, 12.7, and 14.6° 2θ.

9. The method of claim 8, wherein the X-ray powder diffraction pattern (CuKα) is substantially as shown in FIG. 75, top pattern.

10. The method of claim 1, wherein the compound is a solvate having an X-ray powder diffraction pattern (CuKα) comprising significant peaks at about 7.0, 7.8, 8.6, 11.9, 13.9 (double peak), 14.2, and 16.0° 2θ.

11. The method of claim 10, wherein the X-ray powder diffraction pattern (CuKα) is substantially as shown in FIG. 75, second pattern from top.

12. The method of claim 1, wherein the compound is an acetonitrile hemisolvate having an X-ray powder diffraction pattern (CuKα) comprising significant peaks at about 7.5, 11.4, 15.6, and 16.6 2θ.

13. The method of claim 12, wherein the X-ray powder diffraction pattern (CuKα) is substantially as shown in FIG. 75, second pattern from bottom.

14. The method of claim 12, further having a Tg of about 196° C.

15. The method of claim 12, further having a differential scanning calorimetry (DSC) curve comprising an endotherm centered at about 196° C.

Figure 116:
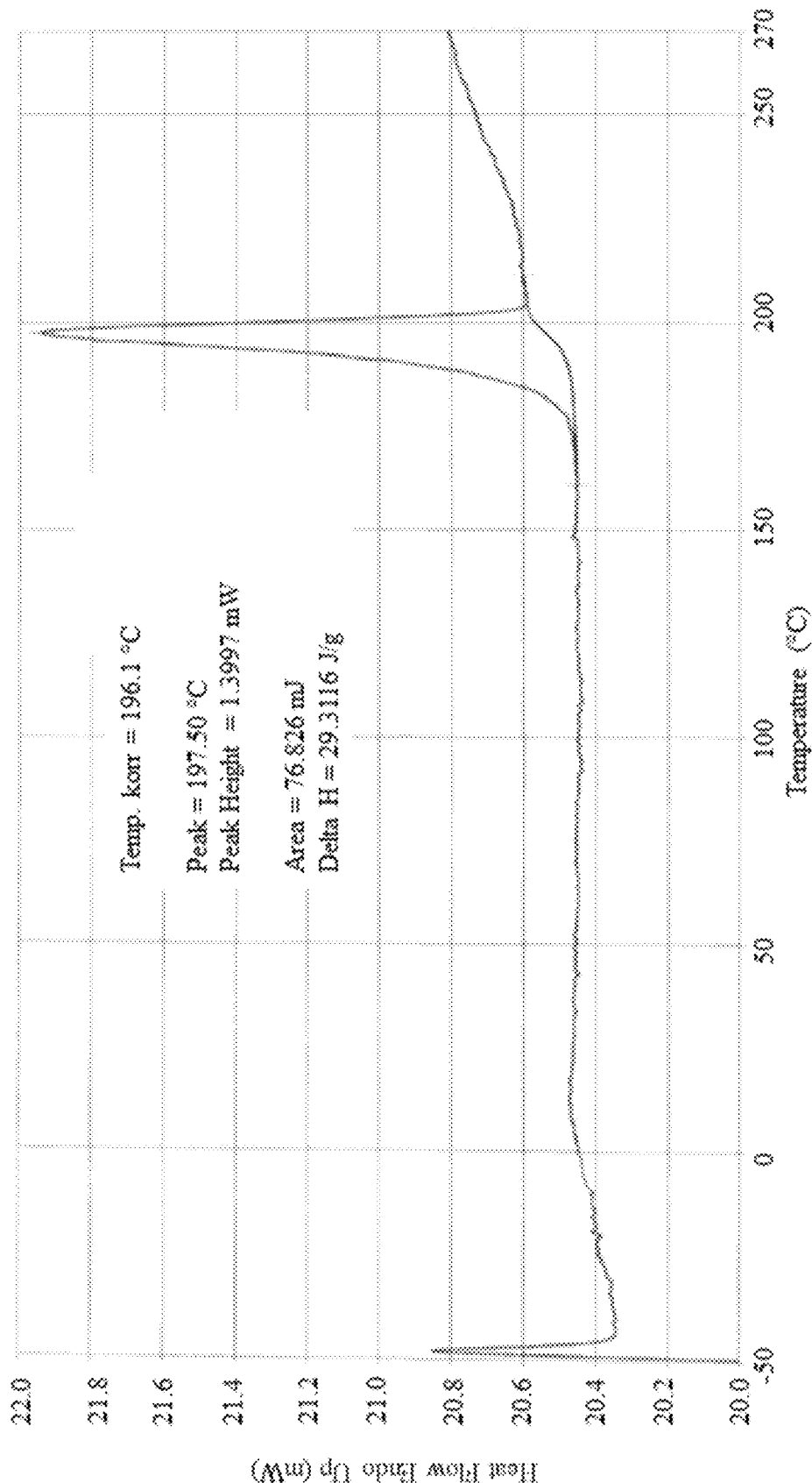
FIG. 116—DSC thermogram of the desolvated acetonitrile solvate form (Class 4) (sample PP415-P37).

16. The method of claim 12, having a differential scanning calorimetry (DSC) curve substantially as shown in FIG. 116.

17. The method of claim 1, wherein the compound is a solvate having an X-ray powder diffraction pattern (CuKα) comprising significant peaks at about 6.8, 9.3, 9.5, 10.5, 13.6, and 15.6° 2θ.

18. The method of claim 17, wherein the X-ray powder diffraction pattern (CuKα) is substantially as shown in FIG. 75, bottom pattern.

* * * * *

UNITED STATES PATENT AND TRADEMARK OFFICE
CERTIFICATE OF CORRECTION

PATENT NO. : 12,065,464 B2
APPLICATION NO. : 17/304778
DATED : August 20, 2024
INVENTOR(S) : Eric Anderson, Xiaofeng Liu and Andrea Decker It is certified that error appears in the above-identified patent and that said Letters Patent is hereby corrected as shown below:

In the Claims

Claim 1, Column 117, Line 15, delete "amount of" and insert --amount of a compound of the formula:-- therefor.

Claim 1, Column 117, Line 31, delete "of a compound of the formula or" and insert --or-- therefor.

Claim 5, Column 117, Line 42, delete "Tg" and insert --$T_g$-- therefor.

Claim 12, Column 118, Line 29, delete "20" and insert --2θ-- therefor.

Claim 14, Column 118, Line 33, delete "Tg" and insert --$T_g$-- therefor.

Signed and Sealed this
Twenty-eighth Day of January, 2025

Coke Morgan Stewart
*Acting Director of the United States Patent and Trademark Office*

SEQUENCE LISTING

```
<160> NUMBER OF SEQ ID NOS: 31

<210> SEQ ID NO 1
<211> LENGTH: 20
<212> TYPE: DNA
<213> ORGANISM: Artificial Sequence
<220> FEATURE:
<223> OTHER INFORMATION: Synthetic primer

<400> SEQUENCE: 1
gctgtggcta ctgcggtatt                                              20

<210> SEQ ID NO 2
<211> LENGTH: 20
<212> TYPE: DNA
<213> ORGANISM: Artificial Sequence
<220> FEATURE:
<223> OTHER INFORMATION: Synthetic primer

<400> SEQUENCE: 2
atctgcctca atgacaccat                                              20

<210> SEQ ID NO 3
<211> LENGTH: 20
<212> TYPE: DNA
<213> ORGANISM: Artificial Sequence
<220> FEATURE:
<223> OTHER INFORMATION: Synthetic primer

<400> SEQUENCE: 3
tccgatgggt ccttacactc                                              20

<210> SEQ ID NO 4
<211> LENGTH: 20
<212> TYPE: DNA
<213> ORGANISM: Artificial Sequence
<220> FEATURE:
<223> OTHER INFORMATION: Synthetic primer

<400> SEQUENCE: 4
```
taggctcctt cctcctttcc                                               20

<210> SEQ ID NO 5
<211> LENGTH: 20
<212> TYPE: DNA
<213> ORGANISM: Artificial Sequence
<220> FEATURE:
<223> OTHER INFORMATION: Synthetic primer

<400> SEQUENCE: 5
aaaacactgc cctcttgtgg                                               20

<210> SEQ ID NO 6
<211> LENGTH: 20
<212> TYPE: DNA
<213> ORGANISM: Artificial Sequence
<220> FEATURE:
<223> OTHER INFORMATION: Synthetic primer

<400> SEQUENCE: 6
gtgccagtca gcatctggta                                               20

<210> SEQ ID NO 7
<211> LENGTH: 25
<212> TYPE: DNA
<213> ORGANISM: Artificial Sequence
<220> FEATURE:
<223> OTHER INFORMATION: Synthetic primer

<400> SEQUENCE: 7
gatgagaagg accccacggc gtctg                                         25

<210> SEQ ID NO 8
<211> LENGTH: 25
<212> TYPE: DNA
<213> ORGANISM: Artificial Sequence
<220> FEATURE:
<223> OTHER INFORMATION: Synthetic primer

<400> SEQUENCE: 8
gagacaatcc agcagcccag gaggg                                         25

<210> SEQ ID NO 9
<211> LENGTH: 20
<212> TYPE: DNA
<213> ORGANISM: Artificial Sequence
<220> FEATURE:
<223> OTHER INFORMATION: Synthetic primer

<400> SEQUENCE: 9
attgccactg gtgaaagacc                                               20

<210> SEQ ID NO 10
<211> LENGTH: 20
<212> TYPE: DNA
<213> ORGANISM: Artificial Sequence
<220> FEATURE:
<223> OTHER INFORMATION: Synthetic primer

<400> SEQUENCE: 10
accaattttg ttggccatgt                                               20

<210> SEQ ID NO 11
<211> LENGTH: 20
<212> TYPE: DNA

```
<213> ORGANISM: Artificial Sequence
<220> FEATURE:
<223> OTHER INFORMATION: Synthetic primer

<400> SEQUENCE: 11
gaggccgtgt acaccaagat                                               20

<210> SEQ ID NO 12
<211> LENGTH: 20
<212> TYPE: DNA
<213> ORGANISM: Artificial Sequence
<220> FEATURE:
<223> OTHER INFORMATION: Synthetic primer

<400> SEQUENCE: 12
agcagtgggg tgaaaatacg                                               20

<210> SEQ ID NO 13
<211> LENGTH: 20
<212> TYPE: DNA
<213> ORGANISM: Artificial Sequence
<220> FEATURE:
<223> OTHER INFORMATION: Synthetic primer

<400> SEQUENCE: 13
aaggcactct acgcttccaa                                               20

<210> SEQ ID NO 14
<211> LENGTH: 20
<212> TYPE: DNA
<213> ORGANISM: Artificial Sequence
<220> FEATURE:
<223> OTHER INFORMATION: Synthetic primer

<400> SEQUENCE: 14
aggagtcctg gcagttttca                                               20

<210> SEQ ID NO 15
<211> LENGTH: 20
<212> TYPE: DNA
<213> ORGANISM: Artificial Sequence
<220> FEATURE:
<223> OTHER INFORMATION: Synthetic primer

<400> SEQUENCE: 15
catctccgag agcaacatca                                               20

<210> SEQ ID NO 16
<211> LENGTH: 20
<212> TYPE: DNA
<213> ORGANISM: Artificial Sequence
<220> FEATURE:
<223> OTHER INFORMATION: Synthetic primer

<400> SEQUENCE: 16
ttgtattggc ggctagttcc                                               20

<210> SEQ ID NO 17
<211> LENGTH: 20
<212> TYPE: DNA
<213> ORGANISM: Artificial Sequence
<220> FEATURE:
<223> OTHER INFORMATION: Synthetic primer

<400> SEQUENCE: 17
tatatcctgg ccaaggcaac                                               20
```

<210> SEQ ID NO 18
<211> LENGTH: 20
<212> TYPE: DNA
<213> ORGANISM: Artificial Sequence
<220> FEATURE:
<223> OTHER INFORMATION: Synthetic primer

<400> SEQUENCE: 18
ggataaagcc gaccctcttc                                               20

<210> SEQ ID NO 19
<211> LENGTH: 22
<212> TYPE: DNA
<213> ORGANISM: Artificial Sequence
<220> FEATURE:
<223> OTHER INFORMATION: Synthetic primer

<400> SEQUENCE: 19
tcaggctaca gaagaggctt gc                                            22

<210> SEQ ID NO 20
<211> LENGTH: 21
<212> TYPE: DNA
<213> ORGANISM: Artificial Sequence
<220> FEATURE:
<223> OTHER INFORMATION: Synthetic primer

<400> SEQUENCE: 20
acagtcacag gcttgcggat g                                             21

<210> SEQ ID NO 21
<211> LENGTH: 20
<212> TYPE: DNA
<213> ORGANISM: Artificial Sequence
<220> FEATURE:
<223> OTHER INFORMATION: Synthetic primer

<400> SEQUENCE: 21
tcgggctagt cccagttaga                                               20

<210> SEQ ID NO 22
<211> LENGTH: 20
<212> TYPE: DNA
<213> ORGANISM: Artificial Sequence
<220> FEATURE:
<223> OTHER INFORMATION: Synthetic primer

<400> SEQUENCE: 22
aaagagctgg agagccaacc                                               20

<210> SEQ ID NO 23
<211> LENGTH: 20
<212> TYPE: DNA
<213> ORGANISM: Artificial Sequence
<220> FEATURE:
<223> OTHER INFORMATION: Synthetic primer

<400> SEQUENCE: 23
cacggagcag gtcttcaacg                                               20

<210> SEQ ID NO 24
<211> LENGTH: 20
<212> TYPE: DNA
<213> ORGANISM: Artificial Sequence
<220> FEATURE:

```
<223> OTHER INFORMATION: Synthetic primer

<400> SEQUENCE: 24
agaatggtca tccggaaatg                                          20

<210> SEQ ID NO 25
<211> LENGTH: 20
<212> TYPE: DNA
<213> ORGANISM: Artificial Sequence
<220> FEATURE:
<223> OTHER INFORMATION: Synthetic primer

<400> SEQUENCE: 25
cgcggtgcag gtcaactact                                          20

<210> SEQ ID NO 26
<211> LENGTH: 20
<212> TYPE: DNA
<213> ORGANISM: Artificial Sequence
<220> FEATURE:
<223> OTHER INFORMATION: Synthetic primer

<400> SEQUENCE: 26
cctcatcagc caggagaaaa                                          20

<210> SEQ ID NO 27
<211> LENGTH: 20
<212> TYPE: DNA
<213> ORGANISM: Artificial Sequence
<220> FEATURE:
<223> OTHER INFORMATION: Synthetic primer

<400> SEQUENCE: 27
ggctattcgc tattttgtgt                                          20

<210> SEQ ID NO 28
<211> LENGTH: 20
<212> TYPE: DNA
<213> ORGANISM: Artificial Sequence
<220> FEATURE:
<223> OTHER INFORMATION: Synthetic primer

<400> SEQUENCE: 28
gaccaggtga ttcgtacaat                                          20

<210> SEQ ID NO 29
<211> LENGTH: 20
<212> TYPE: DNA
<213> ORGANISM: Artificial Sequence
<220> FEATURE:
<223> OTHER INFORMATION: Synthetic primer

<400> SEQUENCE: 29
agagtcctct tcagtcattg                                          20

<210> SEQ ID NO 30
<211> LENGTH: 20
<212> TYPE: DNA
<213> ORGANISM: Artificial Sequence
<220> FEATURE:
<223> OTHER INFORMATION: Synthetic primer

<400> SEQUENCE: 30
atgattagag cagatggtgg                                          20
```

```
<210> SEQ ID NO 31
<211> LENGTH: 26
<212> TYPE: DNA
<213> ORGANISM: Homo sapiens

<400> SEQUENCE: 31
cagtcacagt gactcagcag aatctg                                        26
```